US012617839B2

(12) United States Patent
Chhabra et al.

(10) Patent No.: US 12,617,839 B2
(45) Date of Patent: May 5, 2026

(54) FACTOR VIII CHIMERIC PROTEINS AND USES THEREOF

(71) Applicant: Bioverativ Therapeutics Inc., Waltham, MA (US)

(72) Inventors: Ekta Seth Chhabra, Framingham, MA (US); Tongyao Liu, Lexington, MA (US); Robert T. Peters, Needham, MA (US); John Kulman, Belmont, MA (US)

(73) Assignee: BIOVERATIV THERAPEUTICS INC., Waltham, MA (US)

( * ) Notice: Subject to any disclaimer, the term of this patent is extended or adjusted under 35 U.S.C. 154(b) by 164 days.

(21) Appl. No.: 17/519,719

(22) Filed: Nov. 5, 2021

(65) Prior Publication Data

US 2022/0275057 A1 Sep. 1, 2022

Related U.S. Application Data

(62) Division of application No. 15/110,673, filed as application No. PCT/US2015/010738 on Jan. 9, 2015, now Pat. No. 11,192,936.

(60) Provisional application No. 61/988,104, filed on May 2, 2014, provisional application No. 61/926,226, filed on Jan. 10, 2014.

(51) Int. Cl.

*C07K 14/755* (2006.01)
*C07K 16/00* (2006.01)
*A61K 38/00* (2006.01)

(52) U.S. Cl.

CPC ............ *C07K 14/755* (2013.01); *C07K 16/00* (2013.01); *A61K 38/00* (2013.01); *C07K 2319/00* (2013.01); *C07K 2319/30* (2013.01); *C07K 2319/31* (2013.01)

(58) Field of Classification Search

None
See application file for complete search history.

(56) References Cited

U.S. PATENT DOCUMENTS

| | | | |
|---|---|---|---|
| 836,805 | A | 11/1906 | Dozier |
| 3,992,518 | A | 11/1976 | Chien et al. |
| 4,088,864 | A | 5/1978 | Theeuwes et al. |
| 4,179,337 | A | 12/1979 | Davis et al. |
| 4,200,098 | A | 4/1980 | Ayer et al. |
| 4,200,984 | A | 5/1980 | Fink |
| 4,215,051 | A | 7/1980 | Schroeder et al. |
| 4,235,881 | A | 11/1980 | Cort |
| 4,284,444 | A | 8/1981 | Bernstein et al. |
| 4,398,908 | A | 8/1983 | Siposs |
| 4,435,173 | A | 3/1984 | Siposs et al. |
| 4,456,591 | A | 6/1984 | Thomas |
| 4,542,025 | A | 9/1985 | Tice et al. |
| 4,599,311 | A | 7/1986 | Kawasaki |
| 4,683,195 | A | 7/1987 | Mullis et al. |
| 4,683,202 | A | 7/1987 | Mullis |
| 4,684,479 | A | 8/1987 | D'Arrigo |
| 4,704,362 | A | 11/1987 | Itakura et al. |
| 4,713,339 | A | 12/1987 | Levinson et al. |
| 4,757,006 | A | 7/1988 | Toole et al. |
| 4,770,999 | A | 9/1988 | Kaufman et al. |
| 4,784,950 | A | 11/1988 | Hagen et al. |
| 4,800,159 | A | 1/1989 | Mullis et al. |
| 4,845,075 | A | 7/1989 | Murray et al. |
| 4,861,800 | A | 8/1989 | Buyske |
| 4,868,112 | A | 9/1989 | Toole, Jr. |
| 4,870,008 | A | 9/1989 | Brake |
| 4,882,279 | A | 11/1989 | Cregg |
| 4,897,268 | A | 1/1990 | Tice et al. |
| 4,931,373 | A | 6/1990 | Kawasaki et al. |
| 4,933,185 | A | 6/1990 | Wheatley et al. |
| 4,965,188 | A | 10/1990 | Mullis et al. |
| 4,965,199 | A | 10/1990 | Capon et al. |
| 4,970,300 | A | 11/1990 | Fulton et al. |
| 4,976,696 | A | 12/1990 | Sanderson et al. |
| 4,988,337 | A | 1/1991 | Ito |
| 4,994,371 | A | 2/1991 | Davie et al. |
| 5,004,803 | A | 4/1991 | Kaufman et al. |
| 5,004,804 | A | 4/1991 | Kuo et al. |

(Continued)

FOREIGN PATENT DOCUMENTS

| | | | |
|---|---|---|---|
| AU | 609829 | B2 | 5/1991 |
| AU | 2016213822 | B2 | 8/2017 |

(Continued)

OTHER PUBLICATIONS

Sxhramm, W. Thromb Res. Nov. 2014;134 Suppl 1:S4-9. doi: 10.1016/j.thromres.2013.10.020. Epub Feb. 7, 2014. PMID: 24513149.*
Bobrow R.S., J Am Board Fam Pract. Mar.-Apr. 2005; 18(2):147-9.*
Van Hylckama Vlieg et al., Blood. Jun. 15, 2000;95(12):3678-82.*
"Report of Expert Meeting on FVIII Products and Inhibitor Development", European Medicines Agency, (Feb. 28, 2006-Mar. 2, 2006), 32 Pages.
(Dec. 12, 2014) "Approval Letter—NovoSeven", U.S. Food and Drug Administration, Department of Health and Human Services, FDA Reference No. 96-0597, accessed at http://www.fda.gov/BiologicsBloodVaccines/BloodBloodProducts/ApprovedProducts/LicensedProductsBLAs/FractionatedPlasmaProducts/ucm056916.htm#, 2 Pages.

(Continued)

*Primary Examiner* — Michael Szperka
(74) *Attorney, Agent, or Firm* — LATHROP GPM LLP; James H. Velema, Esq.; James V. DeGiulio, Esq.

(57) ABSTRACT

The present invention provides a chimeric protein comprising a first polypeptide which comprises a FVIII protein and a first Ig constant region or a portion thereof and a second polypeptide which comprises a VWF protein comprising the D' domain and D3 domain of VWF, a XTEN sequence having less than 288 amino acids in length, and a second Ig constant region or a portion thereof, wherein the first polypeptide and the second polypeptide are associated with each other. The invention also includes nucleotides, vectors, host cells, methods of using the chimeric proteins.

161 Claims, 14 Drawing Sheets

Figure 1:
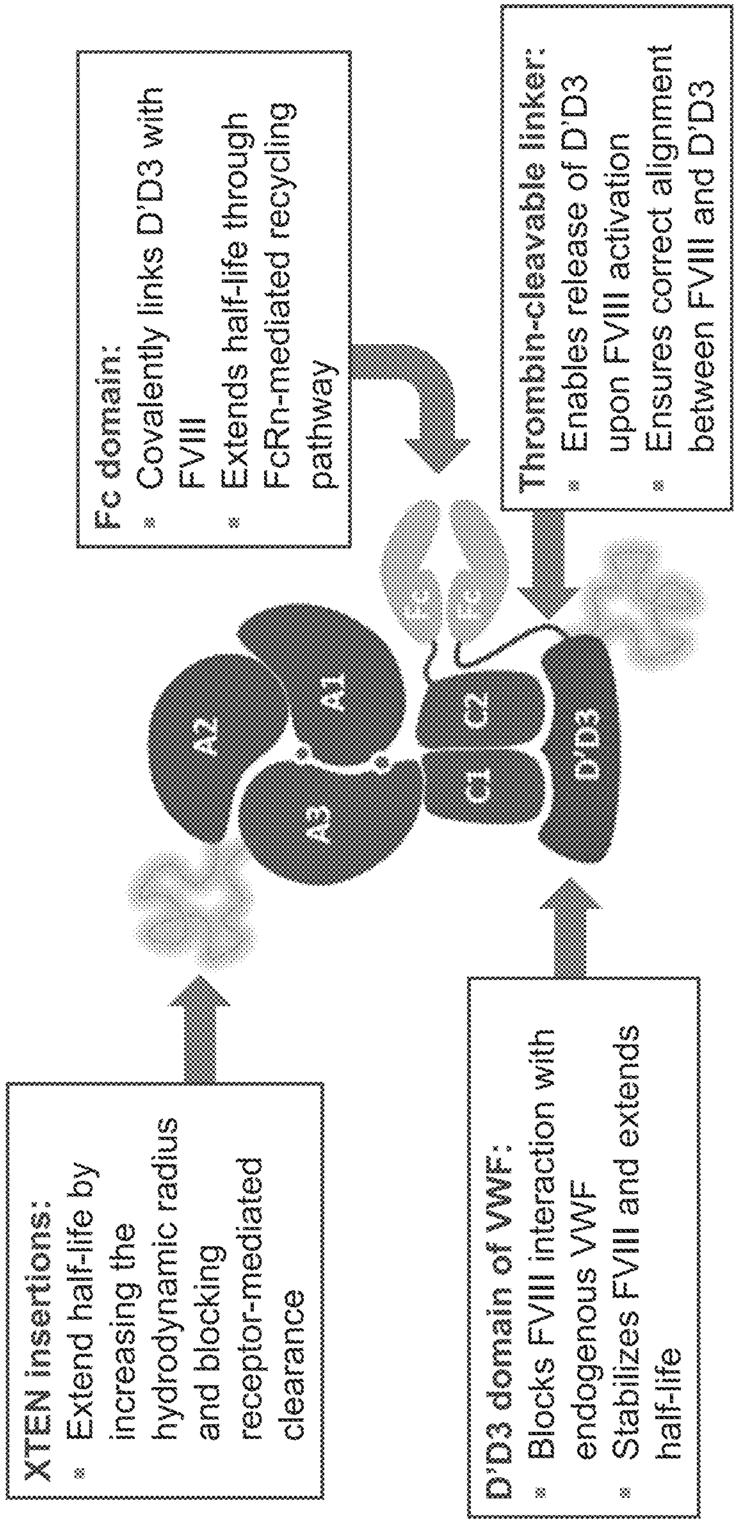

Specification includes a Sequence Listing.

(56) References Cited

U.S. PATENT DOCUMENTS

| | | | |
|---|---|---|---|
| 5,017,378 | A | 5/1991 | Turner et al. |
| 5,037,743 | A | 8/1991 | Welch et al. |
| 5,089,474 | A | 2/1992 | Castro et al. |
| 5,112,950 | A | 5/1992 | Meulien et al. |
| 5,171,844 | A | 12/1992 | Van Ooyen et al. |
| 5,176,502 | A | 1/1993 | Sanderson et al. |
| 5,186,938 | A | 2/1993 | Sablotsky et al. |
| 5,198,349 | A | 3/1993 | Kaufman |
| 5,215,680 | A | 6/1993 | D'Arrigo |
| 5,223,409 | A | 6/1993 | Ladner et al. |
| 5,250,421 | A | 10/1993 | Kaufman et al. |
| 5,260,274 | A | 11/1993 | Zimmerman et al. |
| 5,270,176 | A | 12/1993 | Dorschug et al. |
| 5,298,022 | A | 3/1994 | Bernardi |
| 5,318,540 | A | 6/1994 | Athayde et al. |
| 5,364,771 | A | 11/1994 | Lollar et al. |
| 5,364,934 | A | 11/1994 | Drayna et al. |
| 5,407,609 | A | 4/1995 | Tice et al. |
| 5,422,260 | A | 6/1995 | Kaufman et al. |
| 5,424,199 | A | 6/1995 | Goeddel et al. |
| 5,492,534 | A | 2/1996 | Athayde et al. |
| 5,534,617 | A | 7/1996 | Cunningham et al. |
| 5,543,502 | A | 8/1996 | Nordfang et al. |
| 5,554,730 | A | 9/1996 | Woiszwillo et al. |
| 5,573,776 | A | 11/1996 | Harrison et al. |
| 5,576,291 | A | 11/1996 | Curtis et al. |
| 5,578,709 | A | 11/1996 | Woiszwillo |
| 5,595,886 | A | 1/1997 | Chapman et al. |
| 5,599,907 | A | 2/1997 | Anderson et al. |
| 5,610,278 | A | 3/1997 | Nordfang et al. |
| 5,643,575 | A | 7/1997 | Martinez et al. |
| 5,648,260 | A | 7/1997 | Winter et al. |
| 5,658,570 | A | 8/1997 | Newman et al. |
| 5,660,848 | A | 8/1997 | Moo-Young |
| 5,693,499 | A | 12/1997 | Yonemura et al. |
| 5,712,122 | A | 1/1998 | Boime et al. |
| 5,733,873 | A | 3/1998 | Oesterberg et al. |
| 5,739,277 | A | 4/1998 | Presta et al. |
| 5,756,115 | A | 5/1998 | Moo-Young et al. |
| 5,789,203 | A | 8/1998 | Chapman et al. |
| 5,833,982 | A | 11/1998 | Berkner et al. |
| 5,834,250 | A | 11/1998 | Wells et al. |
| 5,837,679 | A | 11/1998 | Wolf et al. |
| 5,846,951 | A | 12/1998 | Gregoriadis |
| 5,859,204 | A | 1/1999 | Lollar |
| 5,869,046 | A | 2/1999 | Presta et al. |
| 5,874,104 | A | 2/1999 | Adler-Moore et al. |
| 5,916,588 | A | 6/1999 | Popescu et al. |
| 5,919,766 | A | 7/1999 | Osterberg et al. |
| 5,942,252 | A | 8/1999 | Tice et al. |
| 5,965,156 | A | 10/1999 | Proffitt et al. |
| 5,972,885 | A | 10/1999 | Spira et al. |
| 5,981,216 | A | 11/1999 | Kenten et al. |
| 5,981,719 | A | 11/1999 | Woiszwillo et al. |
| 6,005,082 | A | 12/1999 | Smeds |
| 6,024,983 | A | 2/2000 | Tice et al. |
| 6,030,613 | A | 2/2000 | Blumberg et al. |
| 6,037,452 | A | 3/2000 | Minamino et al. |
| 6,043,094 | A | 3/2000 | Martin et al. |
| 6,048,720 | A | 4/2000 | Dalborg et al. |
| 6,056,973 | A | 5/2000 | Allen et al. |
| 6,060,447 | A | 5/2000 | Chapman et al. |
| 6,086,875 | A | 7/2000 | Blumberg et al. |
| 6,090,925 | A | 7/2000 | Woiszwillo et al. |
| 6,096,871 | A | 8/2000 | Presta et al. |
| 6,110,498 | A | 8/2000 | Rudnic et al. |
| 6,121,022 | A | 9/2000 | Presta et al. |
| 6,126,966 | A | 10/2000 | Abra et al. |
| 6,159,730 | A | 12/2000 | Reff |
| 6,183,770 | B1 | 2/2001 | Muchin et al. |
| 6,194,551 | B1 | 2/2001 | Idusogie et al. |
| 6,228,620 | B1 | 5/2001 | Chapman et al. |
| 6,242,195 | B1 | 6/2001 | Idusogie et al. |
| 6,251,632 | B1 | 6/2001 | Lillicrap et al. |
| 6,254,573 | B1 | 7/2001 | Haim et al. |
| 6,268,053 | B1 | 7/2001 | Woiszwillo et al. |
| 6,277,375 | B1 | 8/2001 | Ward |
| 6,284,276 | B1 | 9/2001 | Rudnic et al. |
| 6,294,170 | B1 | 9/2001 | Boone et al. |
| 6,294,191 | B1 | 9/2001 | Meers et al. |
| 6,294,201 | B1 | 9/2001 | Kettelhoit et al. |
| 6,303,148 | B1 | 10/2001 | Hennink et al. |
| 6,309,370 | B1 | 10/2001 | Haim et al. |
| 6,310,183 | B1 | 10/2001 | Johannessen et al. |
| 6,316,024 | B1 | 11/2001 | Allen et al. |
| 6,316,226 | B1 | 11/2001 | Van Ooyen et al. |
| 6,329,186 | B1 | 12/2001 | Nielsen et al. |
| 6,346,513 | B1 | 2/2002 | Van Ooyen et al. |
| 6,352,716 | B1 | 3/2002 | Janoff et al. |
| 6,352,721 | B1 | 3/2002 | Faour |
| 6,358,703 | B1 | 3/2002 | Cho et al. |
| 6,361,796 | B1 | 3/2002 | Rudnic et al. |
| 6,376,463 | B1 | 4/2002 | Lollar |
| 6,395,302 | B1 | 5/2002 | Hennink et al. |
| 6,406,632 | B1 | 6/2002 | Safir et al. |
| 6,406,713 | B1 | 6/2002 | Janoff et al. |
| 6,413,777 | B1 | 7/2002 | Reff et al. |
| 6,458,387 | B1 | 10/2002 | Scott et al. |
| 6,458,563 | B1 | 10/2002 | Lollar |
| 6,485,726 | B1 | 11/2002 | Blumberg et al. |
| 6,514,532 | B2 | 2/2003 | Rudnic et al. |
| 6,517,859 | B1 | 2/2003 | Tice et al. |
| 6,528,624 | B1 | 3/2003 | Idusogie et al. |
| 6,530,648 | B2 | 3/2003 | Leu et al. |
| 6,534,090 | B2 | 3/2003 | Puthli et al. |
| 6,538,124 | B1 | 3/2003 | Idusogie et al. |
| 6,572,585 | B2 | 6/2003 | Choi |
| 6,669,961 | B2 | 12/2003 | Kim et al. |
| 6,686,179 | B2 | 2/2004 | Fleer et al. |
| 6,696,245 | B2 | 2/2004 | Winter et al. |
| 6,713,086 | B2 | 3/2004 | Qiu et al. |
| 6,715,485 | B1 | 4/2004 | Djupesland |
| 6,733,753 | B2 | 5/2004 | Boone et al. |
| 6,737,056 | B1 | 5/2004 | Presta |
| 6,743,211 | B1 | 6/2004 | Prausnitz et al. |
| 6,759,057 | B1 | 7/2004 | Weiner et al. |
| 6,770,744 | B2 | 8/2004 | Lollar |
| 6,814,979 | B2 | 11/2004 | Rudnic et al. |
| 6,818,439 | B1 | 11/2004 | Jolly et al. |
| 6,821,505 | B2 | 11/2004 | Ward |
| 6,833,352 | B2 | 12/2004 | Johannessen et al. |
| 6,838,093 | B2 | 1/2005 | Flanner et al. |
| 6,887,852 | B1 | 5/2005 | Paik et al. |
| 6,890,918 | B2 | 5/2005 | Burnside et al. |
| 6,905,688 | B2 | 6/2005 | Rosen et al. |
| 6,911,323 | B2 | 6/2005 | Persson et al. |
| 6,919,311 | B2 | 7/2005 | Lenting et al. |
| 6,945,952 | B2 | 9/2005 | Kwon |
| 6,960,657 | B2 | 11/2005 | Persson et al. |
| 6,998,253 | B1 | 2/2006 | Presta et al. |
| 7,026,524 | B2 | 4/2006 | Persson et al. |
| 7,041,635 | B2 | 5/2006 | Kim et al. |
| 7,045,318 | B2 | 5/2006 | Balance |
| 7,083,784 | B2 | 8/2006 | Dall'Acqua et al. |
| 7,091,321 | B2 | 8/2006 | Gillies et al. |
| 7,125,841 | B2 | 10/2006 | Sheehan |
| 7,138,505 | B1 | 11/2006 | Kuo et al. |
| 7,176,288 | B2 | 2/2007 | Persson et al. |
| 7,199,223 | B2 | 4/2007 | Bossard et al. |
| 7,211,559 | B2 | 5/2007 | Saenko et al. |
| 7,276,475 | B2 | 10/2007 | DeFrees et al. |
| 7,276,593 | B2 | 10/2007 | Vernet et al. |
| 7,294,513 | B2 | 11/2007 | Wyatt |
| 7,317,091 | B2 | 1/2008 | Lazar et al. |
| 7,329,640 | B2 | 2/2008 | Vlasuk |
| 7,348,004 | B2 | 3/2008 | Peters et al. |
| 7,381,408 | B2 | 6/2008 | Mezo et al. |
| 7,404,956 | B2 | 7/2008 | Peters et al. |
| 7,413,537 | B2 | 8/2008 | Ladner et al. |
| 7,414,022 | B2 | 8/2008 | Pedersen et al. |
| 7,442,778 | B2 | 10/2008 | Gegg et al. |
| 7,452,967 | B2 | 11/2008 | Bertin |
| 7,507,406 | B2 | 3/2009 | Gillies et al. |
| 7,511,024 | B2 | 3/2009 | Pedersen et al. |

(56) References Cited

U.S. PATENT DOCUMENTS 7,514,257 B2 4/2009 Lee et al.
7,528,242 B2 5/2009 Anderson et al.
7,560,107 B2 7/2009 Lollar
7,566,565 B2 7/2009 Peters et al.
7,566,701 B2 7/2009 Diener et al.
7,592,010 B2 9/2009 Rosen et al.
7,620,601 B2 11/2009 Miyawaki et al.
7,632,921 B2 12/2009 Pan et al.
7,645,860 B2 1/2010 Turecek et al.
7,683,158 B2 3/2010 Siekmann et al.
7,700,733 B2 4/2010 Haaning et al.
7,700,734 B2 4/2010 Lin et al.
7,786,070 B2 8/2010 Johannessen et al.
7,790,415 B2 9/2010 Gillies et al.
7,820,162 B2 10/2010 Mezo et al.
7,846,445 B2 12/2010 Schellenberger et al.
7,846,455 B2 12/2010 Collins et al.
7,855,279 B2 12/2010 Schellenberger et al.
7,862,820 B2 1/2011 Peters et al.
7,884,075 B2 2/2011 Scheiflinger et al.
7,939,632 B2 5/2011 Metzner et al.
8,021,880 B2 9/2011 Peters et al.
8,329,182 B2 12/2012 Peters et al.
8,357,779 B2 1/2013 Scheiflinger et al.
8,367,805 B2 2/2013 Chamberlain et al.
8,492,530 B2 7/2013 Schellenberger et al.
8,563,521 B2 10/2013 Skerra et al.
8,575,104 B2 11/2013 Weimer et al.
8,673,860 B2 3/2014 Schellenberger et al.
8,680,050 B2 3/2014 Schellenberger et al.
8,703,717 B2 4/2014 Schellenberger et al.
8,716,448 B2 5/2014 Schellenberger et al.
8,754,194 B2 6/2014 Schulte et al.
8,835,388 B2 9/2014 Scheiflinger et al.
8,932,830 B2 1/2015 Peters et al.
8,933,197 B2 1/2015 Stemmer et al.
9,050,318 B2 6/2015 Dumont et al.
9,107,902 B2 8/2015 Kronthaler
9,168,312 B2 10/2015 Schellenberger et al.
9,233,145 B2 1/2016 Pierce et al.
9,241,978 B2 1/2016 Dumont et al.
9,376,672 B2 6/2016 Schellenberger et al.
9,458,223 B2 10/2016 Schulte et al.
9,486,507 B2 11/2016 Thorn et al.
9,623,091 B2 4/2017 Pierce et al.
9,629,903 B2 4/2017 Pierce et al.
9,670,475 B2 6/2017 Pierce et al.
9,675,676 B2 6/2017 Pierce et al.
9,867,873 B2 1/2018 Pierce et al.
9,878,017 B2 1/2018 Metzner et al.
9,956,269 B2 5/2018 Horn et al.
9,958,572 B2 5/2018 Chang et al.
10,138,291 B2 11/2018 Chaabra et al.
10,221,455 B2 3/2019 Jiang et al.
10,325,687 B2 6/2019 Jiang et al.
10,370,430 B2 8/2019 Kulman
10,391,152 B2 8/2019 Jiang et al.
10,421,798 B2 9/2019 Schellenberger et al.
10,537,616 B2 1/2020 Horn et al.
10,548,954 B2 2/2020 Pierce et al.
10,561,714 B2 2/2020 Pierce et al.
10,568,943 B2 2/2020 Pierce et al.
10,584,147 B2 3/2020 Thorn et al.
10,588,949 B2 3/2020 Brader
10,772,942 B2 9/2020 Thome et al.
10,786,554 B2 9/2020 Maloney et al.
10,881,717 B2 1/2021 Horn et al.
10,898,554 B1 1/2021 Pierce et al.
10,927,362 B2 2/2021 Salas et al.
11,091,534 B2 8/2021 Chhabra et al.
11,192,936 B2 * 12/2021 Chhabra .................. A61P 7/04
11,225,650 B2 1/2022 Pierce et al.
11,266,720 B2 3/2022 Dumont et al.
11,370,827 B2 6/2022 Chaabra et al.
12,030,925 B2 7/2024 Chhabra et al.
12,161,696 B2 12/2024 Dumont et al.
12,186,375 B2 1/2025 Dumont et al.
2002/0019036 A1 2/2002 Schwarz et al.
2002/0042079 A1 4/2002 Simon et al.
2002/0150881 A1 10/2002 Ladner et al.
2003/0049689 A1 3/2003 Edwards et al.
2003/0065787 A1 4/2003 Osafune et al.
2003/0069395 A1 4/2003 Sato et al.
2003/0143697 A1 7/2003 Stahl et al.
2003/0181381 A1 9/2003 Himmelspach et al.
2003/0190740 A1 10/2003 Altman
2003/0199444 A1 10/2003 Knudsen et al.
2003/0228309 A1 12/2003 Salcedo et al.
2003/0235536 A1 12/2003 Blumberg et al.
2004/0029207 A1 2/2004 Marnett et al.
2004/0043446 A1 3/2004 DeFrees et al.
2004/0101740 A1 5/2004 Sanders
2004/0106118 A1 6/2004 Kolmar et al.
2004/0147436 A1 7/2004 Kim et al.
2004/0192599 A1 9/2004 Schuh et al.
2004/0203107 A1 10/2004 Murray
2004/0259780 A1 12/2004 Glasebrook et al.
2005/0042721 A1 2/2005 Fang et al.
2005/0048512 A1 3/2005 Kolkman et al.
2005/0100990 A1 5/2005 Saenko et al.
2005/0118136 A1 6/2005 Leung et al.
2005/0123997 A1 6/2005 Lollar
2005/0147618 A1 * 7/2005 Rivera .................. A61K 45/06
530/391.1
2005/0260194 A1 11/2005 Peters et al.
2005/0260605 A1 11/2005 Punnonen et al.
2005/0266533 A1 12/2005 Ballance et al.
2005/0287153 A1 12/2005 Dennis
2006/0026719 A1 2/2006 Kieliszewski et al.
2006/0040856 A1 2/2006 DeFrees et al.
2006/0074199 A1 4/2006 Hirata et al.
2006/0084113 A1 4/2006 Ladner et al.
2006/0115876 A1 6/2006 Pan et al.
2006/0122376 A1 6/2006 Chapman et al.
2006/0159675 A1 7/2006 Jiao et al.
2006/0160948 A1 7/2006 Scheiflinger et al.
2006/0205036 A1 9/2006 Ostergaard et al.
2006/0211621 A1 9/2006 Knudsen et al.
2006/0287220 A1 12/2006 Li et al.
2006/0293232 A1 12/2006 Levy et al.
2006/0293238 A1 12/2006 Kaufman et al.
2007/0021494 A1 1/2007 Taveras et al.
2007/0048282 A1 3/2007 Rosen et al.
2007/0161087 A1 7/2007 Glaesner et al.
2007/0191272 A1 8/2007 Stemmer et al.
2007/0191597 A1 8/2007 Jain et al.
2007/0203058 A1 8/2007 Lau et al.
2007/0212703 A1 9/2007 Stemmer et al.
2007/0231329 A1 10/2007 Lazar et al.
2007/0237765 A1 10/2007 Lazar et al.
2007/0237766 A1 10/2007 Lazar et al.
2007/0237767 A1 10/2007 Lazar et al.
2007/0243188 A1 10/2007 Lazar et al.
2007/0244301 A1 10/2007 Siekmann et al.
2007/0248603 A1 10/2007 Lazar et al.
2007/0286859 A1 12/2007 Lazar et al.
2008/0004206 A1 1/2008 Rosen et al.
2008/0033413 A1 2/2008 Inochkin et al.
2008/0039341 A1 2/2008 Schellenberger et al.
2008/0057056 A1 3/2008 Lazar et al.
2008/0146782 A1 6/2008 DeFrees et al.
2008/0153751 A1 6/2008 Rosen et al.
2008/0161243 A1 7/2008 Rosen et al.
2008/0167219 A1 7/2008 Lin et al.
2008/0167238 A1 7/2008 Rosen et al.
2008/0176288 A1 7/2008 Leung et al.
2008/0193441 A1 8/2008 Trown et al.
2008/0194481 A1 8/2008 Rosen et al.
2008/0214462 A1 9/2008 Dockal et al.
2008/0227691 A1 9/2008 Ostergaard et al.
2008/0233100 A1 9/2008 Chen et al.
2008/0234193 A1 9/2008 Bossard et al.
2008/0255040 A1 10/2008 DeFrees
2008/0260755 A1 10/2008 Metzner et al.

(56) References Cited

U.S. PATENT DOCUMENTS

| | | | |
|---|---|---|---|
| 2008/0261877 | A1 | 10/2008 | Ballance et al. |
| 2008/0269125 | A1 | 10/2008 | Ballance et al. |
| 2008/0286808 | A1 | 11/2008 | Schellenberger et al. |
| 2008/0312157 | A1 | 12/2008 | Levy et al. |
| 2009/0011992 | A1 | 1/2009 | Olsen et al. |
| 2009/0042787 | A1 | 2/2009 | Metzner et al. |
| 2009/0058322 | A1 | 3/2009 | Toma et al. |
| 2009/0060862 | A1 | 3/2009 | Chang et al. |
| 2009/0087411 | A1 | 4/2009 | Fares et al. |
| 2009/0092582 | A1 | 4/2009 | Bogin et al. |
| 2009/0099031 | A1 | 4/2009 | Stemmer et al. |
| 2009/0117104 | A1 | 5/2009 | Baker et al. |
| 2009/0118185 | A1 | 5/2009 | Fay et al. |
| 2009/0169553 | A1 | 7/2009 | Day |
| 2009/0192076 | A1 | 7/2009 | Matthiessen et al. |
| 2009/0247459 | A1 | 10/2009 | Schwarz et al. |
| 2009/0250598 | A1 | 10/2009 | Hamada et al. |
| 2009/0263380 | A1 | 10/2009 | Gilles et al. |
| 2010/0022445 | A1 | 1/2010 | Scheiflinger et al. |
| 2010/0081187 | A1 | 4/2010 | Griffith et al. |
| 2010/0081615 | A1 | 4/2010 | Pan et al. |
| 2010/0120664 | A1 | 5/2010 | Schulte et al. |
| 2010/0130427 | A1 | 5/2010 | Bossard et al. |
| 2010/0143326 | A1 | 6/2010 | Rischel et al. |
| 2010/0183556 | A1 | 7/2010 | Choi et al. |
| 2010/0189682 | A1 | 7/2010 | Schellenberger et al. |
| 2010/0239554 | A1 | 9/2010 | Schellenberger et al. |
| 2010/0260706 | A1 | 10/2010 | Bogin et al. |
| 2010/0285021 | A1 | 11/2010 | Jacquemin et al. |
| 2010/0292130 | A1 | 11/2010 | Skerra et al. |
| 2010/0323956 | A1 | 12/2010 | Schellenberger et al. |
| 2011/0046060 | A1 | 2/2011 | Schellenberger et al. |
| 2011/0046061 | A1 | 2/2011 | Schellenberger et al. |
| 2011/0069164 | A1 | 3/2011 | Satoshi et al. |
| 2011/0077199 | A1 | 3/2011 | Schellenberger et al. |
| 2011/0124656 | A1 | 5/2011 | Hauser et al. |
| 2011/0151433 | A1 | 6/2011 | Schellenberger et al. |
| 2011/0172146 | A1 | 7/2011 | Schellenberger et al. |
| 2011/0183907 | A1 | 7/2011 | Weimer et al. |
| 2011/0263595 | A1 | 10/2011 | Zhang et al. |
| 2011/0286988 | A1 | 11/2011 | Jiang et al. |
| 2011/0287041 | A1 | 11/2011 | Carrico et al. |
| 2011/0287517 | A1 | 11/2011 | Steward et al. |
| 2011/0288005 | A1 | 11/2011 | Silverman et al. |
| 2011/0312881 | A1 | 12/2011 | Silverman et al. |
| 2012/0065077 | A1 | 3/2012 | Astermark et al. |
| 2012/0121706 | A1 | 5/2012 | Kuliopulos et al. |
| 2012/0142593 | A1 | 6/2012 | Zhao et al. |
| 2012/0178691 | A1 | 7/2012 | Schellenberger et al. |
| 2012/0220011 | A1 | 8/2012 | Schellenberger et al. |
| 2012/0230947 | A1 | 9/2012 | Schellenberger et al. |
| 2012/0263701 | A1 | 10/2012 | Schellenberger et al. |
| 2012/0263703 | A1 | 10/2012 | Schellenberger et al. |
| 2012/0289468 | A1 | 11/2012 | Barnett |
| 2012/0308641 | A1 | 12/2012 | Arruda et al. |
| 2013/0001799 | A1 | 1/2013 | Chang et al. |
| 2013/0017997 | A1 | 1/2013 | Schellenberger et al. |
| 2013/0039884 | A1 | 2/2013 | Bogin et al. |
| 2013/0108629 | A1 | 5/2013 | Dumont et al. |
| 2013/0165389 | A1 | 6/2013 | Schellenberger et al. |
| 2013/0171138 | A1 | 7/2013 | Peters et al. |
| 2013/0171175 | A1 | 7/2013 | Pierce et al. |
| 2013/0172274 | A1 | 7/2013 | Chilkoti |
| 2013/0183280 | A1 | 7/2013 | Oestergaard et al. |
| 2013/0274194 | A1 | 10/2013 | Dumont et al. |
| 2014/0018297 | A1 | 1/2014 | Bolt et al. |
| 2014/0050693 | A1 | 2/2014 | Skerra et al. |
| 2014/0072561 | A1 | 3/2014 | Weimer et al. |
| 2014/0186327 | A1 | 7/2014 | Schellenberger et al. |
| 2014/0273096 | A1 | 9/2014 | Schulte et al. |
| 2014/0294821 | A1 | 10/2014 | Dumont et al. |
| 2014/0301974 | A1 | 10/2014 | Schellenberger et al. |
| 2014/0308280 | A1 | 10/2014 | Maloney et al. |
| 2014/0328819 | A1 | 11/2014 | Schellenberger et al. |
| 2014/0356326 | A1 | 12/2014 | Schellenberger et al. |
| 2014/0370035 | A1 | 12/2014 | Jiang et al. |
| 2014/0371136 | A1 | 12/2014 | Schellenberger et al. |
| 2015/0023959 | A1 | 1/2015 | Chhabra et al. |
| 2015/0038421 | A1 | 2/2015 | Schellenberger et al. |
| 2015/0158929 | A1 | 6/2015 | Schellenberger et al. |
| 2015/0175503 | A1 | 6/2015 | Marks et al. |
| 2015/0252345 | A1 | 9/2015 | Pierce et al. |
| 2015/0259431 | A1 | 9/2015 | Stemmer et al. |
| 2015/0266943 | A1 | 9/2015 | Chhabra et al. |
| 2015/0328819 | A1 | 11/2015 | Tom et al. |
| 2015/0344862 | A1 | 12/2015 | Schellenberger et al. |
| 2016/0115467 | A1 | 4/2016 | Salas |
| 2016/0199454 | A1 | 7/2016 | Liu et al. |
| 2016/0199455 | A1 | 7/2016 | Dumont et al. |
| 2016/0200794 | A1 | 7/2016 | Metzner et al. |
| 2016/0229903 | A1 | 8/2016 | Chhabra et al. |
| 2016/0251408 | A1 | 9/2016 | Chhabra et al. |
| 2016/0306945 | A1 | 10/2016 | Jiang |
| 2016/0355568 | A1 | 12/2016 | Kulman |
| 2016/0376344 | A1 | 12/2016 | Schellenberger et al. |
| 2017/0073393 | A1 | 3/2017 | Chhabra et al. |
| 2017/0152300 | A1 | 6/2017 | Wilson et al. |
| 2017/0209546 | A1 | 7/2017 | Schmidbauer et al. |
| 2018/0002684 | A1 | 1/2018 | Pierce et al. |
| 2018/0051067 | A1 | 2/2018 | Moses et al. |
| 2018/0161402 | A1 | 6/2018 | Schulte et al. |
| 2018/0185455 | A1 | 7/2018 | Kannicht et al. |
| 2018/0207244 | A1 | 7/2018 | Pierce et al. |
| 2018/0228879 | A1 | 8/2018 | Pierce et al. |
| 2019/0169267 | A1 | 6/2019 | Chhabra et al. |
| 2019/0262429 | A1 | 8/2019 | Dumont et al. |
| 2019/0315835 | A1 | 10/2019 | Schellenberger et al. |
| 2019/0375822 | A1 | 12/2019 | Chhabra et al. |
| 2019/0381149 | A1 | 12/2019 | Dumont et al. |
| 2020/0087379 | A1 | 3/2020 | Schellenberger et al. |
| 2020/0095567 | A1 | 3/2020 | Metzner et al. |
| 2020/0261554 | A1 | 8/2020 | Brader |
| 2021/0008178 | A1 | 1/2021 | Pierce et al. |
| 2021/0032616 | A1 | 2/2021 | Liu et al. |
| 2021/0069307 | A1 | 3/2021 | Thome et al. |
| 2022/0010347 | A1 | 1/2022 | Strack-Logue et al. |
| 2022/0056108 | A1 | 2/2022 | Chhabra et al. |
| 2022/0064622 | A1 | 3/2022 | Pierce et al. |
| 2022/0106383 | A1 | 4/2022 | Chhabra et al. |
| 2022/0265780 | A1 | 8/2022 | Dumont et al. |
| 2022/0275057 | A1 | 9/2022 | Chhabra et al. |
| 2023/0011438 | A1 | 1/2023 | Chhabra et al. |
| 2023/0019286 | A1 | 1/2023 | Schellenberger et al. |
| 2023/0322900 | A1 | 10/2023 | Schellenberger et al. |
| 2024/0083875 | A1 | 3/2024 | Chhabra et al. |
| 2024/0287158 | A1 | 8/2024 | Carlage et al. |
| 2024/0358800 | A1 | 10/2024 | Carlage et al. |
| 2024/0400645 | A1 | 12/2024 | Chhabra et al. |
| 2025/0092117 | A1 | 3/2025 | Benson et al. |
| 2025/0121036 | A1 | 4/2025 | Dumont et al. |

FOREIGN PATENT DOCUMENTS

| | | | |
|---|---|---|---|
| BR | 112015000267 | A2 | 3/2018 |
| CA | 2728012 | A1 | 12/2009 |
| CA | 2780542 | A1 | 5/2011 |
| CA | 2804280 | A1 | 1/2012 |
| CL | 2011001856 | A1 | 3/2011 |
| CN | 1761684 | A | 4/2006 |
| CN | 1863556 | A | 11/2006 |
| CN | 1871252 | A | 11/2006 |
| CN | 101190945 | A | 6/2008 |
| CN | 101743309 | A | 6/2010 |
| CN | 102076855 | A | 5/2011 |
| CN | 102348715 | A | 2/2012 |
| CN | 102648212 | A | 8/2012 |
| CN | 102741422 | A | 10/2012 |
| CN | 103796670 | A | 5/2014 |
| CN | 104271150 | A | 1/2015 |
| CN | 104411716 | A | 3/2015 |
| CN | 104487452 | A | 4/2015 |
| CN | 104661674 | A | 5/2015 |
| CN | 106456718 | A | 2/2017 |
| EA | 200501756 | A1 | 8/2006 |

(56) References Cited

FOREIGN PATENT DOCUMENTS

| | | | |
|---|---|---|---|
| EA | 201590198 | A1 | 6/2015 |
| EA | 201792485 | A2 | 8/2018 |
| EP | 0036776 | A3 | 10/1982 |
| EP | 0154316 | A2 | 9/1985 |
| EP | 0184438 | A3 | 1/1988 |
| EP | 0272277 | A1 | 6/1988 |
| EP | 0244234 | A3 | 10/1988 |
| EP | 0295597 | A2 | 12/1988 |
| EP | 0238023 | A3 | 2/1989 |
| EP | 0401384 | A1 | 12/1990 |
| EP | 0272277 | B1 | 9/1993 |
| EP | 1444986 | A1 | 8/2004 |
| EP | 1203014 | B1 | 10/2004 |
| EP | 0506757 | B2 | 10/2005 |
| EP | 1252192 | B1 | 8/2006 |
| EP | 1935430 | A1 | 6/2008 |
| EP | 2256135 | A1 | 12/2010 |
| EP | 2173890 | B1 | 3/2011 |
| EP | 2371856 | A2 | 10/2011 |
| EP | 2506868 | A2 | 10/2012 |
| EP | 2032607 | B1 | 1/2014 |
| EP | 2796145 | A1 | 10/2014 |
| EP | 2804623 | A1 | 11/2014 |
| EP | 2814840 | A1 | 12/2014 |
| EP | 2882450 | A2 | 6/2015 |
| EP | 3013358 | A1 | 5/2016 |
| EP | 3091997 | A1 | 11/2016 |
| EP | 3326643 | A1 | 5/2018 |
| EP | 3505179 | A1 | 7/2019 |
| EP | 3564260 | A1 | 11/2019 |
| EP | 3674410 | A1 | 7/2020 |
| EP | 3793588 | A1 | 3/2021 |
| JP | 2006-518985 | A | 8/2006 |
| JP | 2007-500744 | A | 1/2007 |
| JP | 2008-508871 | A | 3/2008 |
| JP | 2008-520208 | A | 6/2008 |
| JP | 2008-524117 | A | 7/2008 |
| JP | 2008-525491 | A | 7/2008 |
| JP | 2009-505964 | A | 2/2009 |
| JP | 2009-534392 | A | 9/2009 |
| JP | 2010-512768 | A | 4/2010 |
| JP | 2010-531135 | A | 9/2010 |
| JP | 2011-503101 | A | 1/2011 |
| JP | 2011-519898 | A | 7/2011 |
| JP | 2011-525363 | A | 9/2011 |
| JP | 2011-526151 | A | 10/2011 |
| JP | 2011-528562 | A | 11/2011 |
| JP | 2012-219022 | A | 11/2012 |
| JP | 2013-510581 | A | 3/2013 |
| JP | 2013-512678 | A | 4/2013 |
| JP | 2013-525363 | A | 6/2013 |
| JP | 2013-534427 | A | 9/2013 |
| JP | 2013-545457 | A | 12/2013 |
| JP | 2015-527882 | A | 9/2015 |
| JP | 63-85410 | B2 | 8/2016 |
| JP | 2016-523919 | A | 8/2016 |
| JP | 60-62459 | B2 | 12/2016 |
| JP | 2017-503509 | A | 2/2017 |
| JP | 2020-115424 | A | 7/2020 |
| TW | 201605889 | A | 2/2016 |
| WO | WO 1987/004187 | A1 | 7/1987 |
| WO | WO 1988/000831 | A1 | 5/1988 |
| WO | WO 1988/003558 | A1 | 5/1988 |
| WO | WO 1988/007089 | A1 | 9/1988 |
| WO | WO 1988/007220 | A1 | 9/1988 |
| WO | WO 1988/008035 | A1 | 10/1988 |
| WO | WO 1989/009051 | A1 | 10/1989 |
| WO | WO 1991/009122 | A1 | 6/1991 |
| WO | WO 1992/010576 | A1 | 6/1992 |
| WO | WO 1992/016221 | A1 | 10/1992 |
| WO | WO 1993/020093 | A1 | 10/1993 |
| WO | WO 1994/011503 | A2 | 5/1994 |
| WO | WO 1995/034326 | A1 | 12/1995 |
| WO | WO 1996/014339 | A1 | 5/1996 |
| WO | WO 1997/033552 | A1 | 9/1997 |
| WO | WO 1998/005787 | A1 | 2/1998 |
| WO | WO 1998/022577 | A1 | 5/1998 |
| WO | WO 1998/023289 | A1 | 6/1998 |
| WO | WO 1998/052976 | A1 | 11/1998 |
| WO | WO 1999/041383 | A1 | 8/1999 |
| WO | WO 1999/049901 | A1 | 10/1999 |
| WO | WO 1999/051642 | A1 | 10/1999 |
| WO | WO 1999/058572 | A1 | 11/1999 |
| WO | WO 2000/003317 | A1 | 1/2000 |
| WO | WO 2000/009560 | A2 | 2/2000 |
| WO | WO 2000/032767 | A1 | 6/2000 |
| WO | WO 2000/042072 | A2 | 7/2000 |
| WO | WO 2001/007072 | A1 | 2/2001 |
| WO | WO 2001/187922 | A2 | 11/2001 |
| WO | WO 2002/044215 | A2 | 6/2002 |
| WO | WO 2002/060919 | A2 | 8/2002 |
| WO | WO 2002/077036 | A2 | 10/2002 |
| WO | WO 2002/079232 | A2 | 10/2002 |
| WO | WO 2003/074569 | A2 | 9/2003 |
| WO | WO 2003/077834 | A2 | 9/2003 |
| WO | WO 2004/016750 | A2 | 2/2004 |
| WO | WO 2004/029207 | A2 | 4/2004 |
| WO | WO 2004/035752 | A2 | 4/2004 |
| WO | WO 2004/044859 | A1 | 5/2004 |
| WO | WO 2004/063351 | A2 | 7/2004 |
| WO | WO 2004/067566 | A1 | 8/2004 |
| WO | WO 2004/074455 | A2 | 9/2004 |
| WO | WO 2004/076484 | A1 | 10/2004 |
| WO | WO 2004/099249 | A2 | 11/2004 |
| WO | WO 2004/101739 | A2 | 11/2004 |
| WO | WO 2004/101740 | A2 | 11/2004 |
| WO | WO 2005/001025 | A2 | 1/2005 |
| WO | WO 2005/016455 | A2 | 2/2005 |
| WO | WO 2005/025499 | A2 | 3/2005 |
| WO | WO 2005/040217 | A2 | 5/2005 |
| WO | WO 2005/047327 | A2 | 5/2005 |
| WO | WO 2005/069845 | A2 | 8/2005 |
| WO | WO 2005/070963 | A1 | 8/2005 |
| WO | WO 2005/077981 | A2 | 8/2005 |
| WO | WO 2005/092925 | A2 | 10/2005 |
| WO | WO 2005/123780 | A2 | 12/2005 |
| WO | WO 2006/015879 | A1 | 2/2006 |
| WO | WO 2006/019447 | A1 | 2/2006 |
| WO | WO 2006/047350 | A2 | 5/2006 |
| WO | WO 2006/053299 | A2 | 5/2006 |
| WO | WO 2006/071801 | A2 | 7/2006 |
| WO | WO 2006/074199 | A1 | 7/2006 |
| WO | WO 2006/085967 | A2 | 8/2006 |
| WO | WO 2006/127040 | A2 | 11/2006 |
| WO | WO 2006/081249 | A3 | 2/2007 |
| WO | WO 2007/015107 | A2 | 2/2007 |
| WO | WO 2007/021494 | A2 | 2/2007 |
| WO | WO 2007/073486 | A2 | 6/2007 |
| WO | WO 2007/090584 | A1 | 8/2007 |
| WO | WO 2007/103455 | A2 | 9/2007 |
| WO | WO 2007/103515 | A2 | 9/2007 |
| WO | WO 2007/124090 | A2 | 11/2007 |
| WO | WO 2007/144173 | A1 | 12/2007 |
| WO | WO 2008/033413 | A2 | 3/2008 |
| WO | WO 2008/049931 | A1 | 5/2008 |
| WO | WO 2008/057683 | A2 | 5/2008 |
| WO | WO 2008/077616 | A1 | 7/2008 |
| WO | WO 2008/151258 | A2 | 12/2008 |
| WO | WO 2008/155134 | A1 | 12/2008 |
| WO | WO 2009/023270 | A2 | 2/2009 |
| WO | WO 2009/023270 | A3 | 5/2009 |
| WO | WO 2009/058322 | A1 | 5/2009 |
| WO | WO 2009/062100 | A1 | 5/2009 |
| WO | WO 2009/135888 | A2 | 11/2009 |
| WO | WO 2009/149303 | A1 | 12/2009 |
| WO | WO 2009/156137 | A1 | 12/2009 |
| WO | WO 2009/158511 | A1 | 12/2009 |
| WO | WO 2010/009122 | A1 | 1/2010 |
| WO | WO 2010/010051 | A1 | 1/2010 |
| WO | WO 2010/060081 | A1 | 5/2010 |
| WO | WO 2010/062768 | A1 | 6/2010 |
| WO | WO 2010/091122 | A1 | 8/2010 |
| WO | WO 2010/111414 | A1 | 9/2010 |
| WO | WO 2010/133834 | A2 | 11/2010 |

(56) References Cited

FOREIGN PATENT DOCUMENTS

| | | | | |
|---|---|---|---|---|
| WO | WO 2010/144502 A2 | 12/2010 | | |
| WO | WO 2010/144508 A1 | 12/2010 | | |
| WO | WO 2011/020866 A2 | 2/2011 | | |
| WO | WO 2011/028228 A1 | 3/2011 | | |
| WO | WO 2011/028229 A1 | 3/2011 | | |
| WO | WO 2011/028344 A2 | 3/2011 | | |
| WO | WO 2011/041770 A1 | 4/2011 | | |
| WO | WO 2011/043568 A2 | 4/2011 | | |
| WO | WO 2011/060242 A2 | 5/2011 | | |
| WO | WO 2011/069164 A2 | 6/2011 | | |
| WO | WO 2011/084808 A2 | 7/2011 | | |
| WO | WO 2011/101242 A1 | 8/2011 | | |
| WO | WO 2011/101267 A1 | 8/2011 | | |
| WO | WO 2011/101284 A1 | 8/2011 | | |
| WO | WO 2011/123813 A2 | 10/2011 | | |
| WO | WO 2011/133637 A2 | 10/2011 | | |
| WO | WO 2012/006623 A1 | 1/2012 | | |
| WO | WO 2012/006624 A2 | 1/2012 | | |
| WO | WO 2012/006633 A1 | 1/2012 | | |
| WO | WO 2012/006635 A1 | 1/2012 | | |
| WO | WO 2012/007324 A2 | 1/2012 | | |
| WO | WO 2012/061654 A1 | 5/2012 | | |
| WO | WO 2012/170969 A2 | 12/2012 | | |
| WO | WO 2013/009627 A2 | 1/2013 | | |
| WO | WO 2013/083858 A1 | 6/2013 | | |
| WO | WO 2013/106786 A2 | 7/2013 | | |
| WO | WO-2013106787 A1 * | 7/2013 | ............. | A61K 38/37 |
| WO | WO 2013/123457 A1 | 8/2013 | | |
| WO | WO-2013122617 A1 * | 8/2013 | ................ | A61P 7/00 |
| WO | WO 2013/160005 A1 | 10/2013 | | |
| WO | WO 2013/189827 A2 | 12/2013 | | |
| WO | WO 2014/011819 A2 | 1/2014 | | |
| WO | WO 2014/052490 A1 | 4/2014 | | |
| WO | WO 2014/070953 A1 | 5/2014 | | |
| WO | WO 2014/101287 A1 | 7/2014 | | |
| WO | WO 2014/173873 A1 | 10/2014 | | |
| WO | WO 2014/194282 A2 | 12/2014 | | |
| WO | WO 2014/198699 A2 | 12/2014 | | |
| WO | WO 2014/210448 A1 | 12/2014 | | |
| WO | WO 2014/210547 A1 | 12/2014 | | |
| WO | WO 2014/210558 A1 | 12/2014 | | |
| WO | WO 2015/021423 A2 | 2/2015 | | |
| WO | WO 2015/023891 A2 | 2/2015 | | |
| WO | WO 2015/106052 A1 | 7/2015 | | |
| WO | WO 2015/185758 A2 | 12/2015 | | |
| WO | WO 2016/025764 A2 | 2/2016 | | |
| WO | WO 2017/117630 A1 | 7/2017 | | |
| WO | WO 2017/117631 A1 | 7/2017 | | |
| WO | WO 2017/222337 A1 | 12/2017 | | |
| WO | WO 2018/087271 A1 | 5/2018 | | |
| WO | WO 2019/222682 A1 | 11/2019 | | |
| WO | WO 2021/257899 A1 | 12/2021 | | |
| WO | WO 2022/271962 A1 | 12/2022 | | |

OTHER PUBLICATIONS

Abraham et al. Outcome of Immune Tolerance Induction Using an Extended Half-Life Clotting Factor Concentrate—Recombinant Factor VIII Fc (Eloctate T'•')—a Report from India. Blood. 2018:132(S1):2494.

Abstracts, Haemophilia, Jul. 11, 2016, 22 (Suppl. 4): 3-138, Konkle et al. "Dosing regimens before and following long-term treatment with recombinant factor VIII Fc fusion protein (rFVIIIFc) in adults and adolescents with severe hemophilia A".

Ackerman, et al. (1997) "Ion Channels—Basic Science and Clinical Disease", the New England Journal of Medicine, vol. 336, No. 22, pp. 1575-1586.

Adams, et al. (1998) "Increased Affinity Leads to Improved Selective Tumor Delivery of Single-Chain Fv Antibodies", Cancer Research, vol. 58, No. 3, pp. 485-490.

Adams, et al. (2001) "High Affinity Restricts the Localization and Tumor Penetration of Single-Chain Fv Antibody Molecules", Cancer Research, vol. 61, No. 12, pp. 4750-4755.

Advate, United States Prescribing Information [USPI], May 2015, Baxter International Inc., The most recent version is available at: http://www.shirecontent.com/PI/PDFs/ADVATE_USA_ENG.pdf.

Adynovate, United States Prescribing Information [USPI], Dec. 2016, Baxalta US Inc., The most recent version is available at: http://www.shirecontent.com/PI/PDFs/ADYNOVATE_USA_ENG.pdf.

Agarwal et al., Retroviral gene therapy with an immunoglobulin-antigen fusion construct protects from experimental autoimmune uveitis, J Clin Invest., 2000, 106(2):245-252.

Agersoe, et al. (Jul. 2011) "Prolonged effect of N8-Gp In Haemophilia a Dogs Supports Less Frequent Dosing", Journal of Thrombosis and Haemostasis, vol. 9, Supplement 2, P-MO-181, ISTH Meeting, International Society on Thrombosis and Haemostasis, United States.

Ahmad, et al. (May 1, 2004) "ASA View: Database and tool for Solvent Accessibility Representation in Proteins", BMC Bioinformatics, vol. 5, No. 51, pp. 1-5.

Ahnstrom et al., "A 6-year follow-up of dosing, coagulation factor levels and bleedings in relation to joint status in the prophylactic treatment of haemophilia", Haemophilia, Nov. 2004, 10(6): 689-697.

Alam, et al. (1998) "Expression and Purification of a Mutant Human Growth Hormone That Is Resistant to Proteolytic Cleavage by Thrombin, Plasmin and Human Plasma In Vitro", Journal of Biotechnology, vol. 65, No. 2-3, Elsevier Science Publishers, Netherlands, pp. 183-190.

Alber, et al. (1982) "Nucleotide Sequence of the Triose Phosphate Isomerase Gene of *Saccharomyces cerevisiae*", Journal of Molecular and Applied Genetics, vol. 1.5, pp. 419-434.

Aledort et al., A longitudinal study of orthopaedic outcomes for severe factor-VIII-deficient haemophiliacs, The Orthopaedic Outcome Study Group, J Intern Med. 1994, 236(4): 391-399.

Aleman et al., "Recombinant FVIIIFc-VWF-XTEN (BIVV001) promotes normal fibrin formation, structure and stability", International Society on Thrombosis and Haemostasis (ISTH) Congress, Jul. 8-13, 2017, Berlin Germany, 1 page.

Algiman, et al. (1992) "Natural Antibodies to Factor VIII (Anti-Hemophilic Factor) In Healthy Individuals", Proceedings of the National Academy of Sciences, vol. 89, No. 9, pp. 3795-3799.

Altuviiio [package insert], Waltham, MA: Bioverativ Therapeutics Inc., 2023.

Alvarez, et al. (Jan. 30, 2003) "Improving Protein Pharmacokinetics by Genetic Fusion to Simple Amino Acid Sequences", Journal of Biological Chemistry, vol. 279, No. 5, pp. 3375-3381.

Amin, et al. (2004) "Construction of Stabilized Proteins by Combinatorial Consensus Mutagenesis", Protein Engineering, Design & Selection: PEDS, vol. 17, No. 11, pp. 787-793.

Amunix, "Bioverativ announces FDA acceptance of IND Application for BIVV001 a novel, long-acting FVIII hemophilia therapeutic utilizing Amunix XTEN® half-life extension technology", Jun. 14, 2017, retrieved from: https://www.amunix.com/newsroom/press-releases/2017/061417, 2 pages.

Amy et al., Hemophilia A, in Transfusion Medicine and Hemostasis (2nd Ed.) 2013, Clinical and Laboratory Aspects, Chapter 106, pp. 699-704.

Ansong, et al. (2006) "Epitope Mapping Factor VIII A2 Domain by Affinity-Directed Mass Spectrometry: Residues 497-510 and 584-593 Comprise a Discontinuous Epitope for the Monoclonal Antibody R8B 12", Journal of Thrombosis and Haemostasis, vol. 4, No. 4, pp. 842-847.

Antcheva (2001) "Proteins of Circularly Permuted Sequence Present within the Same Organism: The Major Serine Proteinase inhibitor from Capsicum Annuum Seeds", Protein Science, vol. 10, No. 11, pp. 2280-2290.

Appa, R, et al. (Aug. 2010) "Investigating Clearance Mechanisms for Recombinant Activated Factor VII in a Perfused Liver Model", Journal of Thrombosis and Haemostasis, vol. 104, No. 2, pp. 243-251.

Araki, et al. (1990) "Four Disulfide Bonds' Allocation of Na+, K+-ATPase Inhibitor (SPAI)", Biochemical and Biophysical Research Communications, vol. 172, No. 1, pp. 42-46.

Arap, et al. (2002) "Steps Toward Mapping the Human Vasculature by Phage Display", Nature Medicine, vol. 8, No. 2, pp. 121-127.

(56) References Cited

OTHER PUBLICATIONS

Armour, et al. (Aug. 1999) "Recombinant Human IgG Molecules Lacking Fcgamma Receptor I Binding and Monocyte Triggering Activities", European Journal of Immunology, vol. 29, No. 8, pp. 2613-2624.

Arnau, et al. (Jul. 2006) "Current Strategies for the Use of Affinity Tags and Tag Removal for the Purification of Recombinant Proteins", Protein Expression and Purification, vol. 48, No. 1, pp. 1-13.

Arndt, et al. (1998) "Factors Influencing the Dimer to Monomer Transition of an Antibody Single-Chain Fv Fragment", Biochemistry, vol. 37, pp. 12918-12926.

Arruda, et al. (Jan. 1, 2001) "Posttranslational Modifications of Recombinant Myotube-Synthesized Human Factor Ix", Blood, vol. 97, No. 1, pp. 130-138.

Ashkenazi, et al., "Immunoadhesins", International Reviews of Immunology, vol. 10, Issue 2-3, Harwood Academic Publishers GmbH, United States, pp. 219-227, Jan. 1, 1993.

Assadi-Porter, et al. (2000) "Sweetness Determinant Sites of Brazzein, a Small, Heat-Stable, Sweet-Tasting Protein", Archives of Biochemistry and Biophysics, vol. 376, No. 2, pp. 259-265.

Aster, et al. (Apr. 13, 1999) "the Folding and Structural Integrity of the First LIN-12 Module of Human Notch1 Are Calcium-Dependent", Biochemistry, vol. 38, No. 15, pp. 4736-4742.

Astermark et al., The Malmo International Brother Study (MIBS), Genetic defects and inhibitor development in siblings with severe hemophilia A, Haematologica, 2005, 90(7): 924-931.

Astermark, et al. (Dec. 1, 2006) "Polymorphisms in the TNFA Gene and the Risk of Inhibitor Development in Patients with Hemophilia A", Hemostasis, Thrombosis, and Vascular Biology, Blood, vol. 108, No. 12, pp. 3739-3745.

Aznar et al., Haemophilia in Spain, Haemophilia, 2009, 15(3): 665-675.

Bachmann, et al. (1995) "T Helper Cell-Independent Neutralizing B Cell Response Against Vesicular Stomatitis Virus: Role of Antigen Patterns in B Cell Induction", European Journal of Immunology, vol. 25, No. 12, pp. 3445-3451.

Bai, et al. (May 17, 2005) "Recombinant Granulocyte Colony-Stimulating Factor-Transferrin Fusion Protein as an oral Myelopoietic Agent", Proceedings of the National Academy of Sciences of the United States of America, vol. 102, No. 20, pp. 7292-7296.

Bailon, et al. (2001) "Rational Design of a Potent, Long-Lasting form of Interferon: a 40 kDa Branched Polyethylene Glycol-Conjugated Interferon α-2a for the Treatment of Hepatitis C", Bioconjugate Chemistry, vol. 12, No. 2, pp. 195-202.

Bajaj, et al. (1993) "Human Factor IX and Factor IXa", Methods in Enzymology, vol. 222, pp. 96-128.

Baneyx, et al. (2004) "Recombinant Protein Folding and Misfolding in *Escherichia coli*", Nature Biotechnology, vol. 22, No. 11, pp. 1399-1408.

Baron, et al. (1990) "From Cloning to a Commercial Realization: Human Alpha Interferon", Critical Reviews in Biotechnology, vol. 10, No. 3, pp. 179-190.

Barrowcliffe, et al. (Jun. 2002) "Coagulation and Chromogenic Assays of Factor VIII Activity: General Aspects, Standardization, and Recommendations", Seminars in Thrombosis and Hemostasis, vol. 28, No. 3, pp. 247-256.

Barta, et al. (2002) "Repeats with Variations: Accelerated Evolution of the Pin2 Family of Proteinase Inhibitors", Trends in Genetics, vol. 18, No. 12, pp. 600-603.

Baskin et al., Management of occlusion and thrombosis associated with longterm indwelling central venous catheters, Lancet. 2009, 374(9684): 159-169.

Bateman, et al. (1998) "Granulins: The Structure and Function of An Emerging Family of Growth Factors,", the Journal of Endocrinology, vol. 158, No. 2, pp. 145-151.

Batorova et al., "Expert opinion on current and future prophylaxis therapies aimed at improving protection for people with hemophilia A", Journal of Medicine and Life, Apr. 4, 2022, 15(4): 570-578.

Batsuli et al. Immune tolerance induction in paediatric patients with haemophilia A and inhibitors receiving emicizumab prophylaxis. Haemophilia. 2019;25(5):789-796.

Baxevanis et al., Evidence for distinct epitopes on human IgG with T cell proliferative and suppressor function, Eur J Immunol., 1986, 16(8): 1013-1016.

Beissinger, et al. (1998) "How Chaperones Fold Proteins", Biological Chemistry, vol. 379, No. 3, pp. 245-259.

Belaaouaj, et al. (2000) "Matrix Metalloproteinases Cleave Tissue Factor Pathway Inhibitor Effects on Coagulation", Journal of Biological Chemistry, vol. 275, No. 35, pp. 27123-27128.

Belew, et al. (1994) "Purification of Recombinant Human Granulocyte-Macrophage Colony-Stimulating Factor from the Inclusion Bodies Produced by Transformed *Escherichia coli* Cells", Journal of Chromatography A, vol. 679, No. 1, pp. 67-83.

Benhar, et al. (Dec. 1994) "Cloning, Expression and Characterization of the Fv Fragments of the Anti-Carbohydrate mAbs B1 and B5 As Single-Chain Immunotoxins", Protein Engineering, Design and Selection, vol. 7, No. 12, pp. 1509-1515.

Bensch, et al. (1995) "Hbd-1: A Novel Beta-Defensin from Human Plasma", FEBS Letters, vol. 368, No. 2, pp. 331-335.

Berger, et al. (1993) "Phoenix Mutagenesis: one-Step Reassembly of Multiply Cleaved Plasmids with Mixtures of Mutant and Wild-Type Fragments", Analytical Biochemistry, vol. 214, No. 2, pp. 571-579.

Berkner, et al., "Expression of Recombinant Vitamin K-Dependent Proteins in Mammalian Cells: Factors IX and VII", Methods in Enzymology, vol. 222, Academic Press, United States, pp. 450-477, Jan. 1, 1993.

Berntorp et al., Consensus perspectives on prophylactic therapy for haemophilia: summary statement, Haemophilia, 2003, 9(Suppl 1): 1-4.

Berntorp et al., Modern treatment of haemophilia, Bull World Health Organ., 1995, 73(5): 691-701.

Berntrop et al., "dosing regimens, FVIII levels and estimated haemostatic protection with special focus on rFVIIIFc", Haemophilia, May 2016, 22(3): 389-396.

Beste, et al. (1999) "Small Antibody-like Proteins with Prescribed Ligand Specificities Derived from the Lipocalin Fold", Proceedings of the National Academy of Sciences, vol. 96, No. 5, pp. 1898-1903.

Bhagunde et al., "A Population Pharmacokinetic (PopPK) Model to Characterize Efanesoctocog Alfa (BIVV001) Factor VIII (FVIII) Activity Levels in Patients With Severe Hemophilia A", Abstract, HTRS Mar. 10-12, 2023, Orlando, Florida.

Bhagunde et al., "A Population Pharmacokinetic (PopPK) Model to Characterize Efanesoctocog Alfa (BIVV001) Factor VIII (FVIII) Activity Levels in Patients with Severe Hemophilia A", Abstract, Blood, Nov. 15, 2022, 140 (Supplement 1): 8449-8450.

Bhagunde et al., "A Population Pharmacokinetic (PopPK) Model to Characterize Efanesoctocog Alfa (BIVV001) Factor VIII (FVIII) Activity Levels in Patients with Severe Hemophilia A", Poster, Blood, Nov. 15, 2022.

Bhagunde et al., "A Repeated Time to Event (RTTE) Model to Characterize Bleed Risk in Patients with Severe Hemophilia A Treated with Efanesoctocog Alfa", Abstract, Haemophilia, 2023.

Bhagunde et al., "A Repeated Time to Event (RTTE) Model to Characterize Bleed Risk in Patients with Severe Hemophilia A Treated with Efanesoctocog Alfa", Poster, 16th Annual Congress of the European Association for Haemophilia and Allied Disorders, Feb. 7-10, 2023.

Bhagunde et al., "A Population Pharmacokinetic (PopPK) Model to Characterize Efanesoctocog Alfa (BIVV001) Factor VIII (FVIII) Activity Levels in Patients With Severe Hemophilia", Poster, HTRS Mar. 10-12, 2023, Orlando, Florida.

Bharmal et al., Validation of an abbreviated Treatment Satisfaction Questionnaire for Medication (TSQM-9) among patients on anti-hypertensive medications, 2009, Health Qual Life Outcomes, 7: 36.

Bi, et al., "Targeted Disruption of The Mouse Factor VIII Gene Produces A Model Of Haemophilia A", Nature Genetics, vol. 10, No. 1, pp. 119-121, May 1, 1995.

Bihoreau et al., "Structural and functional characterization of Factor VIII-ΔII, a new recombinant Factor VIII lacking most of the B-domain", Biochem. J. vol. 277, 1991, pp. 23-31.

(56) References Cited

OTHER PUBLICATIONS

Binz, et al. (2005) "Engineering Novel Binding Proteins from Nonimmunoglobulin Domains", Nature Biotechnology, vol. 23, No. 10, pp. 1257-1268.
Bioverativ Investor Day, Jan. 6, 2017.
Bioverativ Therapeutics Inc., "A Phase 1/2a, Open-Label, Dose-Escalation Study to Determine the Safety, Tolerability, and Pharmacokinetics of a Single Intravenous Injection of rFVIIIFc-VWF-XTEN (BIVV001) in Previously Treated Adults with Severe Hemophilia A", Study Results, NCT03205163, Eudra CT No. 2017-001140-34, Version 6.0, Jan. 4, 2018.
Bioverativ Therapeutics Inc., "A Phase 1/2a, Open-Label, Dose-Escalation Study to Determine the Safety, Tolerability, and Pharmacokinetics of a Single Intravenous Injection of rFVIIIFc-VWF-XTEN (BIVV001) in Previously Treated Adults with Severe Hemophilia A", Statistical Analysis Plan, Version 1.0, NCT03205163, Eudra CT No. 2017-001140-34, Protocol 242HA101, Apr. 13, 2018.
Bioverativ Therapeutics Inc., "A Phase 1, Open-Label, Single-Site, Safety, Tolerability, and Pharmacokinetics Study of Repeat Doses of BIVV001", Patient Information Sheet and Informed Consent Form, Protocol No. 242HA101, Final Form for Bulgaria, Version 2.0, Nov. 15, 2018.
Bioverativ Therapeutics Inc., "A Phase 1, Open-Label, Single-Site, Safety, Tolerability, and Pharmacokinetics Study of Repeat Doses of BIVV001", Investigator and Sponsor's Agreement and Brochure, Protocol No. 242HA102, EudraCT No. 2018-001535-51, Final, Version 3.0, Oct. 25, 2018.
Bioverativ, a Sanofi company, "A Phase 3 Open-label Interventional Study of Intravenous Recombinant Coagulation Factor VIII Fc-von Willebrand Factor-XTEN Fusion Protein, Efanesoctocog Alfa (BIVV001), in Patients With Severe Hemophilia A (XTEND-1)", Study Record, NCT04161495, May 24, 2023.
Bioverativ, a Sanofi company, "A Phase 3 Open-Label, Multicenter Study of the Safety, Efficacy, and Pharmacokinetics of Intravenous Recombinant Coagulation Factor VIII Fc-von Willebrand Factor-XTEN Fusion Protein (rFVIIIFc-VWF-XTEN; BIVV001) in Previously Treated Patients ≥12 Years of Age With Severe Hemophilia A", Amended Clinical Trial Protocol 05, Protocol No. EFC16293, Version No. 1, Aug. 20, 2021.
Bioverativ, a Sanofi company, "A Phase 3 Open-Label, Multicenter Study of the Safety, Efficacy, and Pharmacokinetics of Intravenous Recombinant Coagulation Factor VIII Fc-von Willebrand Factor-XTEN Fusion Protein (rFVIIIFc-VWF-XTEN; BIVV001) in Previously Treated Patients ≥12 Years of Age With Severe Hemophilia A", Statistical Analysis Plan, NCT04161495, Protocol No. EFC16293, EudraCT: 2019-002023-15, Version No. 8.0, Jun. 16, 2020.
Bioverativ, a Sanofi company, "A Safety, Tolerability, and Pharmacokinetics Study of a Single Intravenous Injection of Recombinant Coagulation Factor VIII Fc-Von Willebrand Factor-XTEN Fusion Protein (rFVIIIFc-VWF-XTEN) (BIVV001) in Previously Treated Adults With Severe Hemophilia A (EXTEN-A)", Study Record, Protocol No. 242HA101, Apr. 19, 2022.
Bioverativ, Summary Basis for Regulatory Action of ALTUVIIIO, Feb. 21, 2023.
Bird, et al. (Oct. 21, 1988) "Single-Chain Antigen-Binding Proteins", Science, vol. 242, No. 4877, pp. 423-426.
Bitonti, et al., "Pulmonary Administration of Therapeutic Proteins using an Immunoglobulin Transport Pathway", Advanced Drug Delivery Reviews, vol. 58, Issues 9-10, pp. 1106-1118, Oct. 31, 2006.
Bittner, et al. (1998) "Recombinant Human Erythropoietin (rhEPO) Loaded Poly (Lactide-Co-Glycolide) Microspheres: influence of the Encapsulation Technique and Polymer Purity on Micro Sphere Characteristics", European Journal of Pharmaceutics and Biopharmaceutics vol. 45, No. 3, pp. 295-305.
Bjoern, S., et al. (Sep. 1986) "Activation of Coagulation Factor VII to VIIa", Research Disclosure, vol. 269, pp. 564-565.
Bjorkman, et al. (Nov. 1, 2001) "Pharmacokinetics of Coagulation Factors: Clinical Relevance for Patients with Haemophilia", Clinical Pharmacokinetics, vol. 40, No. 11, Adis International Ltd., New Zealand, pp. 815-832.
Blanchette et al., "For the Subcommittee on Factor VIII, Factor IX, and Rare Coagulation Disorders. Definitions in hemophilia: communication from the SSC of the IST", J Thromb Haemost. 2014; 12(11):1935-1939.
Blanchette et al., Plasma and albumin-free recombinant factor VIII: pharmacokinetics, efficacy, and safety in previously treated pediatric patients. J Thromb Haemost. 2008;6(8):1319-26.
Blanchette, et al. (2004) "Principles of Transmucosal Delivery of therapeutic Agents", Biomedicine & Pharmacotherapy, vol. 58, No. 3, pp. 142-151.
Blanchette, et al., "A Survey of Factor Prophylaxis in the Canadian Haemophilia A Population", Haemophilia, vol. 10, Issue 6, Blackwell Publishing, England, pp. 679-683, Nov. 1, 2004.
Bloch, et al. (1998) "1H NMR Structure of An Antifungal Gannna-Thionin Protein Sialpha1: Similarity to Scorpion toxins", Proteins, vol. 32, No. 3, pp. 334-349.
Blumberg, Tolerogenic properties of the Fc portion of IgG and its relevance to the treatment and management of hemophilia. Blood. 2018;131(20):2205-2214.
Bobrow, R. S. (2005) "Excess Factor VIII: A Common Cause of Hypercoagulability", American Board of Family Medicine, United States, pp. 147-149.
Bodenmuller, et al. (1986) "the Neuropeptide Head Activator Loses Its Biological Acitivity by Dimerization", the EMBO Journal vol. 5, No. 8, pp. 1825-1829.
Boder, et al. (Sep. 26, 2000) "Directed Evolution of Antibody Fragments with Monovalent Femtomolar Antigen-Binding Affinity", Proceedings of the National Academy of Sciences, vol. 97, No. 20, pp. 10701-10705.
Borel et al., Prevention of Murine Lupus Nephritis by Carrier-Dependent Induction of Immunologic Tolerance to Denatured DNA, Science, 1973, 182(4107): 76-78.
Boshart, et al. (1985) "A Very Strong Enhancer Is Located Upstream of An Immediate Early Gene of Human Cytomegalovirus", Cell, vol. 41, No. 2, pp. 521-530.
Bovenschen (2010) "LDL Receptor Polymorphisms Revisited", Blood, vol. 116, No. 25, pp. 5439-5440.
Bovenschen, et al. (2005) "LDL receptor cooperates with LDL receptor-related protein in regulating plasma levels of coagulation factor VIII in vivo", Blood, vol. 106, pp. 906-912.
Brandsma, et al. (Mar.-Apr. 2011) "Recombinant Human Transferrin: Beyond Iron Binding and Transport", Biotechnology Advances, vol. 29, No. 2, pp. 230-238.
Briet, et al. (1994) "High Titer Inhibitors in Severe Haemophilia A: A Meta-Analysis Based on Eight Long-term Follow-up Studies concerning Inhibitors Associated with Crude or Intermediate Purity Factor VIII Products", Journal of Thrombosis and Haemostasis, vol. 72, No. 1, pp. 162-164.
Brinkhous, et al., "Preclinical Pharmacology of Albumin-Free B-Domain Deleted Recombinant Factor VIII", Seminars in Thrombosis and Hemostasis, Thieme Medical Publishers, vol. 28, No. 3, pp. 269-272, Jun. 1, 2002.
Brooks, et al. (Oct. 2002) "Evolution of Amino Acid Frequencies in Proteins Over Deep Time: Inferred order of Introduction of Amino Acids into the Genetic Code", Molecular Biology and Evolution, vol. 19, No. 10, pp. 1645-1655.
Brutlag, et al., "Improved Sensitivity of Biological Sequence Database Searches", Computer Applications in the Biosciences: CABIOS, vol. 6, No. 3, pp. 237-245, Aug. 1, 1990.
Buchner, J. (1996) "Supervising the Fold: Functional Principles of Molecular Chaperones", F ASEB Journal, vol. 10, No. 1, pp. 10-19.
Bulaj, et al. (2003) "Efficient Oxidative Folding of Conotoxins and the Radiation of Venomous Cone Snails", Proceedings of the National Academy of Sciences of the United States of America, vol. 100, Supplement 2, pp. 14562-14568.
Bullinger et al., Pilot testing of the 'Haemo-QoL' quality of life questionnaire for haemophiliac children in six European countries. Haemophilia, Mar. 8, 2002, Suppl 2: 47-54.

(56) References Cited

OTHER PUBLICATIONS

Burmeister, et al. (Nov. 24, 1994) "Crystal Structure of the Complex of Rat Neonatal Fc Receptor with Fc", Nature, vol. 372, No. 6504, pp. 379-383.
Buscaglia, et al. (1999) "Tandem Amino Acid Repeats from Trypanosoma Cruzi Shed Antigens Increase the Half-Life of Proteins in Blood", Blood, vol. 93, No. 6, pp. 2025-2032.
Byetta United States Prescribing Information [USPI], Feb. 2015, AstraZeneca Pharmaceuticals LP. The most recent version is available at: https://www.azpicentral.com/byetta/pi_byetta.pdf.
Calabrese, et al. (2004) "Crystal Structure of Phenylalanine Ammonia Lyase: Multiple Helix Dipoles Implicated in Catalysis", Biochemistry, vol. 43, No. 36, pp. 11403-11416.
Caliceti, et al. (1999) "Biopharmaceutical Properties of Uricase Conjugated to Neutral and Amphiphilic Polymers", Bioconjugate Chemistry, vol. 10, No. 4, pp. 638-646.
Caliceti, et al. (2003) "Pharmacokinetic and Biodistribution Properties of Poly (Ethylene Glycol)—Protein Conjugates", Advanced Drug Delivery Reviews, vol. 55, No. 10, pp. 1261-1277.
Calvete, et al. (2000) "Disulphide-Bond Pattern and Molecular Modelling of the Dimeric Disintegrin Emf-10, A Potent and Selective integrin Alpha5Beta1 Antagonist from Eristocophis Macmahoni Venom", the Biochemical Journal, vol. 345, Part 3, pp. 573-581.
Calvete, et al. (2003) "Snake Venom Disintegrins: Novel Dimeric Disintegrins and Structural Diversification by Disulphide Bond Engineering", the Biochemical Journal, vol. 372, Part 3, pp. 725-734.
Calvete, et al. (2005) "Snake Venom Disintegrins: Evolution of Structure and Function", Toxicon, vol. 45, No. 8, pp. 1063-1074.
Cameron, et al. (Feb. 1998) "The Canine Factor VIII cDNA and 5' Flanking Sequence", Journal of Thrombosis and Haemostasis, vol. 79, No. 2, pp. 317-322.
Cao, et al. (2006) "Development of a Compact Anti-Baff Antibody in *Escherichia coli*", Applied Microbiology and Biotechnology, vol. 73, No. 1, pp. 151-157.
Capon, et al. (Feb. 9, 1989) "Designing CD4 Immunoadhesins for AIDS therapy", Nature, vol. 337, No. 6207, pp. 525-531.
Carcao et al., Inhibitors in Hemophilia: a primer. 5 ed: World Federation of Hemophilia; 2018.
Carcao M, et al. Real-world data of immune tolerance induction using recombinant factor VIII Fc fusion protein in patients with severe haemophilia A with inhibitors at high risk for immune tolerance induction failure: A follow-up retrospective analysis. Haemophilia. 2020: 27(1):19-25.
Carcao M, et al. The changing face of immune tolerance induction in haemophilia A with the advent of emicizumab. Haemophilia. 2019:25(4):676-684.
Carcao M, et al., Recombinant factor VIII Fc fusion protein for immune tolerance induction in patients with severe haemophilia A with inhibitors—A retrospective analysis, Haemophilia, 2018, 24(2): 245-252.
Carlsson et al., "Pain, deperssion and anxiety in people with haemophilia from three Nordic countries: Cross-sectional survey data from the MIND study", Haemophilia, 2022, 28: 557-567.
Carlsson et al., On-demand vs. prophylactic treatment for severe haemophilia in Norway and Sweden: differences in treatment characteristics and outcome, Haemophilia, 2003,9(5): 555-566.
Carpenter et al. Increased prevalence of inhibitors in Hispanic patients with severe haemophilia A enrolled in the Universal Data Collection database. Haemophilia. 2012;18(3):e260-5.
Carr, et al. (1994) "Solution Structure of a Trefoil-Motif-Containing Cell Growth Factor, Porcine Spasmolytic Protein", Proceedings of the National Academy of Sciences of the United States of America, vol. 91, No. 6, pp. 2206-2210.
Castor, et al. (1994) "Septic Cutaneous Lesions Caused by *Mycobacterium malmoense* in A Patient with Hairy Cell Leukemia", European Journal of Clinical Microbiology & infectious Diseases, vol. 13, No. 2, pp. 145-148.
Cella et al., The Patient-Reported Outcomes Measurement Information System (PROMIS): Progress of an NIH Roadmap Cooperative Group During Its First Two Years, Medical Care, 45(5 Suppl 1), 2007, S3-S11.
Centers for Disease Control and Prevention (CDC), Summary Report of UDC Activity National, Patient Demographics (Hemophilia) 2017. Available at: https://www2a.cdc.gov/ncbddd/htcweb/UDC_Report/UDC_Report.asp.
Chamow at al., Immunoadhesins: principles and applications, Trends Biotechnol., 1996, 14(2): 52-60.
Chang, et al. (1978) "Phenotypic Expression in *E. coli* of A DNA Sequence Coding for Mouse Dihydrofolate Reductase", Nature, vol. 275, No. 5681, pp. 617-624.
Chang, et al., "Replacing the First Epidermal Growth Factor-like Domain of Factor IX with That of Factor VII Enhances Activity In Vitro and in Canine Hemophilia B", The Journal of Clinical Investigation, vol. 100, No. 4, The American Society for Clinical Investigation, Inc., pp. 886-892, Aug. 15, 1997.
Chaudhury, et al., "Albumin Binding to FcRn: Distinct from the FcRn-IgG Interaction", Biochemistry, vol. 45, No. 15, pp. 4983-4990, Apr. 18, 2006.
Chen et al., "Fusion protein linkers: Property, design and functionality", Advanced Drug Delivery Reviews, Oct. 2013, 65(10): 1357-1369.
Chen, et al. (1991) "Crystal Structure of a Bovine Neurophysin li Dipeptide Complex at 2", Proceedings of the National Academy of Sciences of the United States of America vol. 88, No. 10, pp. 4240-4244.
Chen, et al. (1993) "Site-Directed Mutations in a Highly Conserved Region of Bacillus Thuringiensis Delta-Endotoxin Affect inhibition of Short Circuit Current Across Bombyx Mori Midguts", Proceedings of the National Academy of Sciences of the United States of America vol. 90, No. 19, pp. 9041-9045.
Chen, et al. (2006) "Expression, Purification, and in Vitro Refolding of a Humanized Single-Chain Fv Antibody Against Human Ctla4 (Cd152)", Protein Expression and Purification, vol. 46, No. 2, pp. 495-502.
Chhabra et al., "BIVV001, a new class of factor VIII replacement for hemophilia A that is independent of von Willebrand factor in primates and mice", Blood, Apr. 23, 2020, 135(17): 1484-1496.
Chhabra et al., Application of in silico antigenicity prediction methods to avoid neo-epitopes during the designing of BIIB073, a next-generation long-acting recombinant Factor VIII (rFVIII) molecule, Haemophilia, 2016, 22(Suppl 4): 18.
Chirino, et al. (2004) "Minimizing the Immunogenicity of Protein therapeutics", Drug Discovery Today, vol. 9, No. 2, pp. 82-90.
Cho, et al. (Nov. 22, 1994) "Polysialic Acid Engineering: Synthesis of Polysialylated Neoglycosphingolipids by Using the Polysialyltransferase From Neuroinvasive *Escherichia coli* K1", Proceedings of the National Academy of Sciences of the United States of America, vol. 91, No. 24, pp. 11427-11431.
Chong, et al. (2001) "Determination of Disulfide Bond assignments and NGlycosylation Sites of the Human Gastrointestinal Carcinoma Antigen Ga733-2 (Co17-1A, EGP, Ks1-4, KSA, and Ep-Cam)", The Journal of Biological Chemistry, vol. 276, No. 8, pp. 5804-5813.
Chong, et al. (2002) "Disulfide Bond Assignments of Secreted Frizzled-Related Protein-1 Provide Insights About Frizzled Homology and Netrin Modules", the Journal of Biological Chemistry, vol. 277, No. 7, pp. 5134-5144.
Choo, et al. (1982) "Molecular Cloning of the Gene for Human Anti-Haemophilic Factor IX", Nature, vol. 299, No. 5879, pp. 178-180.
Chou, et al. (1974) "Prediction of Protein Conformation", Biochemistry, vol. 13, No. 2, pp. 222-245.
Chowdary et al., "Managing surgery in hemophilia with recombinant factor VIII Fc and factor IX Fc: Data on safety and effectiveness from phase 3 pivotal studies", Res Pract Thromb Haemost., Jul. 2022, 6(5): E12760, 1-15.
Chowdhury, et al. (1999) "Improving Antibody Affinity by Mimicking Somatic Hypermutation In Vitro", Nature Biotechnology, vol. 17, No. 6, pp. 568-572.
Christmann, et al. (1999) "The Cystine Knot of a Squash-Type Protease Inhibitor as A Structural Scaffold for *Escherichia coli* Cell

(56) References Cited

OTHER PUBLICATIONS

Surface Display of Conformationally Constrained Peptides", Protein Engineering, vol. 12, No. 9, pp. 797-806.
Clark, et al. (1996) "Long-Acting Growth Hormones Produced by Conjugation with Polyethylene Glycol", Journal of Biological Chemistry, vol. 271, No. 36, pp. 21969-21977.
Clark, et al. (1996) "Recombinant Human Growth Hormone (GH)-Binding Protein Enhances the Growth-Promoting Activity of Human GH in the Rat", Endocrinology, vol. 137, No. 10, pp. 4308-4315.
Cleland, et al. (2001) "Emerging Protein Delivery Methods", Current Opinion in Biotechnology, vol. 12, No. 2, pp. 212-219.
Cleland, et al. (2009) "An Extended Half-life Exenatide Construct for Weekly Administration in the Treatment of Diabetes Mellitus", Diabetes, vol. 58, pp. A511-A512.
clinicaltrials.gov, (Apr. 13, 2018) Bioverativ Therapeutics, Inc., NCT03205163, Statistical Analysis Plan: Protocol Title: A Phase 1/2a, Open-Label, Dose-Escalation Study to Determine the Safety, Tolerability, and Pharmacokinetics of a Single Intravenous Injection of rFVIIIFc-VWF-XTEN (BIVV001) in Previously Treated Adults With Severe Hemophilia A, Protocol No. 242HA101, Version 1.0 dated Apr. 13, 2018, based on Protocol Version 6.0, dated Jan. 2, 2018.
clinicaltrials.gov, (Apr. 7, 2023) "A Safety, Tolerability, and Pharmacokinetics Study of a Single Intravenous Injection of Recombinant Coagulation Factor VIII Fc-Von Willebrand Factor-XTEN Fusion Protein (rFVIIIFc-VWF-XTEN) (BIVV001) in Previously Treated Adults with Severe Hemophilia A (EXTEN-A)", Study Details, ClinicalTrials.gov Identifier: NCT03205163, https://clinicaltrials.gov/archive/NCT03205163.
clinicaltrials.gov, (Apr. 7, 2023) "A Safety, Tolerability, and Pharmacokinetics Study of a Single Intravenous Injection of Recombinant Coagulation Factor VIII Fc-Von Willebrand Factor-XTEN Fusion Protein (rFVIIIFc-VWF-XTEN) (BIVV001) in Previously Treated Adults with Severe Hemophilia A (EXTEN-A)", Study Results, ClinicalTrials.gov Identifier: NCT03205163, https://clinicaltrials.gov/archive/NCT03205163.
clinicaltrials.gov, (Apr. 7, 2023) "A Safety, Tolerability, and Pharmacokinetics Study of a Single Intravenous Injection of Recombinant Coagulation Factor VIII Fc-Von Willebrand Factor-XTEN Fusion Protein (rFVIIIFc-VWF-XTEN) (BIVV001) in Previously Treated Adults with Severe Hemophilia A (EXTEN-A)", Tabular View, ClinicalTrials.gov Identifier: NCT03205163, https://clinicaltrials.gov/archive/NCT03205163.
clinicaltrials.gov, (Dec. 4, 2009) "Study of Recombinant Factor VIII Fc Fusion Protein (rFVIIIFc) in Subjects with Severe Hemophilia A", ClinicalTrials.gov Identifier: NCT01027377, 3 Pages.
clinicaltrials.gov, (Feb. 23, 2023) "A Phase 3, Open-label Interventional Study of an Intravenous Recombinant Coagulation Factor VIII Fc-von Willebrand Factor-XTEN Fusion Protein, Efanesoctocog Alfa (BIVV001), in Patients with Severe Hemophilia (XTEND-1)", History of Changes, ClinicalTrials.gov Identifier: NCT04161495, https://clinicaltrials.gov/archive/NCT04161495.
clinicaltrials.gov, (Jan. 4, 2018) Bioverativ Therapeutics, Inc., NCT03205163, Protocol Title: A Phase 1/2a, Open-Label, Dose-Escalation Study to Determine the Safety, Tolerability, and Pharmacokinetics of a Single Intravenous Injection of rFVIIIFc-VWF-XTEN (BIVV001) in Previously Treated Adults With Severe Hemophilia A, Protocol No. 242HA 101, Phase of Development: 1/2a, Eudra CT No. 2017-001140-34, Version 6.0.
clinicaltrials.gov, (Jan. 23, 2023) "Safety, Efficacy and PK of BIVV 001 in Pediatric Patients with Hemophilia A (XTEND-Kids)", Study Details, ClinicalTrials.gov Identifier: NCT04759131, https://clinicaltrials.gov/archive/NCT04759131.
clinicaltrials.gov, (Jan. 23, 2023) "Safety, Efficacy and PK of BIVV 001 in Pediatric Patients with Hemophilia A (XTEND-Kids)", Tabular View, ClinicalTrials.gov Identifier: NCT04759131, https://clinicaltrials.gov/archive/NCT04759131.
clinicaltrials.gov, (Jul. 19, 2022) "A Phase 3, Open-label Interventional Study of an Intravenous Recombinant Coagulation Factor VIII Fc-von Willebrand Factor-XTEN Fusion Protein, Efanesoctocog Alfa (BIVV001), in Patients with Severe Hemophilia (XTEND-1)", Tabular View, ClinicalTrials.gov Identifier: NCT04161495, https://clinicaltrials.gov/archive/NCT04161495.
clinicaltrials.gov, (Jul. 19, 2022) "A Phase 3, Open-label Interventional Study of an Intravenous Recombinant Coagulation Factor VIII Fc-von Willebrand Factor-XTEN Fusion Protein, Efanesoctocog Alfa (BIVV001), in Patients with Severe Hemophilia (XTEND-1)", Study Details, ClinicalTrials.gov Identifier: NCT04161495, https://clinicaltrials.gov/archive/NCT04161495.
Coia, et al. (1997) "Use of Mutator Cells as a Means for increasing Production Levels of a Recombinant Antibody Directed Against Hepatitis B", Gene, vol. 201, No. 1-2, pp. 203-209.
Collen, et al. (Oct. 10, 2000) "Polyethylene Glycol-Derivatized Cysteine-Substitution Variants of Recombinant Staphylokinase for Single-Bolus Treatment of Acute Myocardial Infarction", Circulation, vol. 102, Issue 15, pp. 1766-1772.
Collins et al., Break-through bleeding in relation to predicted factor VIII levels in patients receiving prophylactic treatment for severe hemophilia A, J Thromb Haemost, Mar. 2009,7(3): 413-420.
Collins et al., Factor VIII requirement to maintain a target plasma level in the prophylactic treatment of severe hemophilia A: influences of variance in pharmacokinetics and treatment regimens, J Thromb Haemost., 2009, 8(2): 269-275.
Collins et al., Recombinant long-acting glycoPEGylated factor IX in hemophilia B: a multinational randomized phase 3 trial, Blood, 2014, 124(26): 3880-3886.
Collins, "Personalized prophylaxis", Haemophilia, 2012, 18(Suppl. 4): 131-135.
Conticello, et al. (Feb. 2001) "Mechanisms for Evolving Hypervariability: The Case of Conopeptides", Molecular Biology and Evolution, Oxford University Press, United States, vol. 18, Issue 2, pp. 120-131.
Coppola, et al. (Feb. 2012) "Prophylaxis in Children with Hemophilia: Evidence-Based Achievements, Old and New Challenges", Seminars in Thrombosis and Hemostasis, vol. 38, No. 1, pp. 79-94.
Corisdeo, et al. (Apr. 2004) "Functional Expression and Display of An Antibody Fab Fragment in *Escherichia coli*: Study of Vector Designs and Culture Conditions", Protein Expression and Purification, vol. 34, Issue 2, pp. 270-279.
Corsaro, et al. (1981) "Enhancing the Efficiency of DNA-Mediated Gene Transfer in Mammalian Cells", Somatic Cell Genetics, vol. 7, No. 5, pp. 603-616.
Counts, et al. (Sep. 1978) "Disulfide Bonds and the Quaternary Structure of Factor VIII/von Willebrand Factor", Journal of Clinical Investigation, vol. 62, No. 3, pp. 702-709.
Coyle et al., Phase 1 study of BAY 94-9027, a PEGylated B-domain-deleted recombinant factor VIII with an extended half-life, in subjects with hemophilia A, J Thromb Haemost., 2014, 12(4): 488-496.
Craik, et al. (Dec. 17, 1999) "Plant cyclotides: A Unique Family of Cyclic and Knotted Proteins that Defines the Cyclic Cystine Knot Structural Motif", Journal of Molecular Biology, vol. 294, Issue 5, Dec. 17, 1999, pp. 1327-1336.
Crameri, et al. (Apr. 1996) "Improved Green Fluorescent Protein by Molecular Evolution Using DNA Shuffling", Nature Biotechnology, vol. 14, No. 3, pp. 315-319.
Cull, et al. (Mar. 1, 1992) "Screening for Receptor Ligands Using Large Libraries of Peptides Linked to the C Terminus of the Lac Repressor", Proceedings of the National Academy of Sciences, vol. 89, No. 5, pp. 1865-1869.
Cutler, et al. (2002) "the Identification and Classification of 41 Novel Mutations in the Factor VIII Gene (F8c)", Human Mutation, vol. 19, No. 3, pp. 274-278.
Daley, et al. (Apr. 30, 2002) "Structure and Dynamics of a Beta-Helical Antifreeze Protein", Biochemistry, vol. 41, No. 17, pp. 5515-5525.
Daniel, et al. (May 1991) "Screening for Potassium Channel Modulators by a High Through-Put 86-Rubidium Efflux Assay in a 96-Well Microtiter Plate", Journal of Pharmacological Methods, vol. 25, Issue 3, pp. 185-193.
Danner, et al. (Nov. 6, 2001) "T7 Phage Display: A Novel Genetic Selection System for Cloning RNA-Binding Proteins From cDNA

(56) References Cited

OTHER PUBLICATIONS

Libraries", Proceedings of the National Academy of Sciences of the United States of America, vol. 98, No. 23, pp. 12954-12959.
D'Aquino, et al. (Jun. 1996) "the Magnitude of the Backbone Conformational Entropy Change in Protein Folding", Proteins, vol. 25, Issue 2, pp. 143-156.
Darby et al., The incidence of factor VIII and factor IX inhibitors in the hemophilia population of the UK and their effect on subsequent mortality, 1977-99, J Thromb Haemost., 2004, 2(7): 1047-1054.
Database Geneseq [Online] (Sep. 8, 2020) "dTDP-4-dehydrorhamnose reductase [Entomomonas moraniae]", GenBank Accession No. AZS50750.1.
Dattani, et al. (1996) "An Investigation into the Lability of the Bioactivity of Human Growth Hormone Using the ESTA Bioassay", Hormone Research, vol. 46, No. 2, pp. 64-73.
Dauplais, et al. (Feb. 14, 1997) "on the Convergent Evolution of Animal Toxins", the Journal of Biological Chemistry, vol. 272, No. 7, pp. 4302-4309.
Davidson, M. W. (2009) "Engineered Fluorescent Proteins: Innovations and Applications", Nature Methods, vol. 6, No. 10, pp. 713-717.
De Boer, et al. (1983) "the Tac Promoter: A Functional Hybrid Derived from the Trp and Lac Promoters", Proceedings of the National Academy of Sciences, vol. 80, No. 1, pp. 21-25.
De Groot et al., Activation of natural regulatory T cells by IgG Fc-derived peptide "Tregitopes", Blood, 2008, 112: 3303-3311.
De Kruif, et al. (Apr. 21, 1995) "Selection and Application of Human Single Chain Fv Antibody Fragments from A Semi-Synthetic Phage Antibody Display Library with Designed CDR3 Regions", Journal of Molecular Biology, vol. 248, No. 1, pp. 97-105.
De, et al. (1994) "Crystal Structure of a Disulfide-Linked"Trefoil" Motif Found in a Large Family of Putative Growth Factors", Proceedings of the National Academy of Sciences, vol. 91, No. 3, pp. 1084-1088.
Decision to Grant Received for European Patent Application No. 10835255.0, mailed on Oct. 19, 2017, 3 Pages.
Decision to Grant Received for European Patent Application No. 17194648.6, mailed on Mar. 12, 2021, 3 Pages.
Deckert, et al. (2000) "Pharmacokinetics and Microdistribution of Polyethylene Glycol-Modified Humanized A33 Antibody Targeting Colon Cancer Xenografts", International Journal of Cancer, vol. 87, No. 3, pp. 382-390.
Delgado, et al. (1992) "The Uses and Properties of PEG-Linked Proteins", Critical Reviews in therapeutic Drug Carrier Systems, vol. 9, No. 3-4, pp. 249-304.
Delignat et al., "Immunoprotective effect of von Willebrand factor towards therapeutic factor VIII in experimental haemophilia A", Haemophilia, Mar. 2012, 18(2): 248-254.
Demers et al., "Efanesoctocog alfa elicits functional clot formation that is indistinguishable to that of recombinant factor VIII", Journal of Thrombosis and Haemostasis, Jul. 2022, 20(7): 1674-1583.
Demers et al., "rFVIIIFc-VWF-XTEN (BIVV001) demonstrates comparable efficacy to recombinant human FVIII in mice by acute bleeding and intravital microscopy models", International Society on Thrombosis and Haemostasis (ISTH) Congress, Jul. 8-13, 2017, Berlin, Germany, 1 page.
Den Uijl et al., "Analysis of low frequency bleeding data: the association of joint bleeds according to baseline FVIII activity levels". Haemophilia, Jan. 2011, 17(1):41-44.
Den Uijl et al., Clinical severity of hemophilia A: does the classification of the 1950s still stand?, Hemophilia, 17: 849-853.
Dennis, et al. (Sep. 20, 2002) "Albumin Binding as a General Strategy for Improving the Pharmacokinetics of Proteins", Journal of Biological Chemistry, vol. 277, No. 38, pp. 35035-35043.
Denoto, et al. (1981) "Human Growth Hormone DNA Sequence and mRNA Structure: Possible Alternative Splicing", Nucleic Acids Research, vol. 9, No. 15, pp. 3719-3730.
Der Maur, et al. (2002) "Direct in Vivo Screening of intrabody Libraries Constructed on A Highly Stable Single-Chain Framework", The Journal of Biological Chemistry, vol. 277, No. 47, pp. 45075-45085.
Desplancq, et al. (1994) "Multimerization Behaviour of Single Chain Fv Variants for the Tumour-Binding Antibody B72.3,", Protein Engineering, vol. 7, No. 8, pp. 1027-1033.
Dhalluin, et al. (2005) "Structural and Biophysical Characterization of the 40 kDa Peg-Interferon-a2a and Its Individual Positional Isomers", Bioconjugate Chemistry, vol. 16, No. 3, pp. 504-517.
Di Lullo, et al. (2002) "Mapping the Ligand-Binding Sites and Disease-associated Mutations on the Most Abundant Protein in the Human, Type I Collagen", the Journal of Biological Chemistry, vol. 277, No. 6, pp. 4223-4231.
Di Michele et al., "Severe and moderate haemophilia A and B in US females". Haemophilia, Feb. 2014, 20: 136-143.
Diaz-Collier, et al. (1994) "Refold and Characterization of Recombinant Tissue Factor Pathway Inhibitor Expressed in *Escherichia coli*", Thrombosis and Haemostasis, vol. 71, No. 03, pp. 339-346.
Dietrich, et al. (2003) "ABC of Oral Bioavailability: Transporters as Gatekeepers in the Gut", Gut, vol. 52, No. 12, pp. 1788-1795.
Ding et al., Multivalent antiviral XTEN-peptide conjugates with long in vivo half-life and enhanced solubility, Bioconjugate Chem., 2014, 25: 1351-1359.
Dobeli, et al., "Role of the Carboxy-Terminal Sequence on the Biological Activity of Human Immune Interferon (IFN-y)", Journal of Biotechnology, vol. 7, No. 3, pp. 199-216, Jan. 1, 1988.
Dolezal, et al. (2000) "ScFv Multimers of the Anti-Neuraminidase Antibody Nc10: Shortening of the Linker in Single-Chain Fv Fragment assembled in V(L) to V(H) orientation Drives the formation of Dimers, Trimers, Tetramers and Higher Molecular Mass Multimers", Protein Engineering, vol. 13, No. 8, pp. 565-574.
Donath et al., "Characterization of des-(741-1668)-factor VIII. A single-chain factor VIII variant with a fusion site susceptible to proteolysis by thrombin and factor Xa", Biochem J., 1995, vol. 312, pp. 49-55.
Dooley, et al. (1998) "Stabilization of Antibody Fragments in Adverse Environments", Biotechnology and Applied Biochemistry, vol. 28, Part 1, pp. 77-83.
Doyle, et al. (1996) "Crystal Structures of a Complexed and Peptide-Free Membrane Protein-Binding Domain: Molecular Basis of Peptide Recognition by PDZ", Cell, vol. 85, No. 7, pp. 1067-1076.
Drager et al., "Paper: Recombinant FVIIIFc-VWF-XTEN Demonstrates Significant Bioavailability Following Subcutaneous Administration in Hemophilia A Mice", Blood, vol. 126, Issue 23, Dec. 7, 2015.
Duan et al., "Recombinant factor VIII Fc fusion protein engages monocytes via Fc and FVIII domains to reduce monocyte differentiation into osteoclasts", Frontier in Hematology, Nov. 3, 2022, 1-13.
Dufton, M. J. (1984) "Classification of Elapid Snake Neurotoxins and Cytotoxins According to Chain Length: Evolutionary Implications", Journal of Molecular Evolution, vol. 20, No. 2, pp. 128-134.
Dumont et al., Prolonged activity of a recombinant factor VIII-Fc fusion protein in hemophilia A mice and dogs, Blood, Mar. 29, 2012, 119(13): 3024-3030.
Dumont, et al., "Delivery of an Erythropoietin-Fc Fusion Protein by Inhalation in Humans Through an Immunoglobulin Transport Pathway", Journal of Aerosol Medicine, vol. 18, No. 3, pp. 294-303, Sep. 23, 2005.
Dumont, et al., "Factor VIII-Fc Fusion Protein Shows Extended Half-Life and Hemostatic Activity in Hemophilia A Dogs", Abstract 545, Blood, vol. 114, No. 22, 51st Annual Meeting of the American Society of Hematology, 1 Page, Nov. 20, 2009.
Dumont, J A., "Monomeric Fc Fusions: Impact on Pharmacokinetic and Biological Activity of Protein Therapeutics", BioDrugs, vol. 20, No. 3, pp. 151-160, May 1, 2006.
Dumont, The Evolving Science of Fc Fusion Proteins for the Treatment of Hemophilia, 2nd Fc Receptor & IgG Targeted Therapies Summit, Apr. 27, 2022, Boston, MA.

(56) References Cited

OTHER PUBLICATIONS

Dumoulin, et al. (Mar. 2002) "Single-Domain Antibody Fragments with High Conformational Stability", Protein Science, vol. 11, No. 3, pp. 500-515.
Dutton, et al. (2002) "A New Level of Conotoxin Diversity, A Non-Native Disulfide Bond Connectivity in Alpha-Conotoxin AuIB Reduces Structural Definition But increases Biological Activity", The Journal of Biological Chemistry, vol. 277, No. 50, pp. 48849-48857.
Dyson, et al. (2004) "Production of Soluble Mammalian Proteins in *Escherichia coli*: Identification of Protein Features That Correlate with Successful Expression," BMC Biotechnology 4:32, American Society for Biochemistry and Molecular Biology, United States, BMC Biotechnology, vol. 4, No. 32.
Eaton, et al. (Dec. 1986) "Construction and Characterization of An Active Factor VIII Variant Lacking the Central One-Third of The Molecule", Biochemistry, vol. 25, No. 26, pp. 8343-8347.
Ellis, et al. (1994) "Valid and Invalid Implementations of GOR Secondary Structure Predictions", Computer Applications in Biosciences, vol. 10, No. 3, pp. 341-348.
Ellis, et al., "Treatment of Chronic Plaque Psoriasis by Selective Targeting of Memory Effector T Lymphocytes", The New England Journal of Medicine, vol. 345, No. 4, Massachusetts Medical Society, pp. 248-255, Jul. 26, 2001.
Eloctate United States Prescribing Information [USPI], Jan. 2017, Biogen Inc., The most recent version is available at: https://www.eloctate.com/pdfs/full-prescribing-information.pdf.
Engels, et al. (Jun. 1989) "Gene Synthesis", Angewandte Chemie International Edition, vol. 28, No. 6, pp. 716-734.
English language Abstract of European Patent Publication No. EP0295597 A2, European Patent office, Espacenet database-worldwide, Dec. 21, 1988.
European Medicines Agency (EMA), Committee for Medicinal Products for Human Use (CHMP), Guideline on the clinical investigation of recombinant and human plasma-derived factor VIII products, London, Jul. 21, 2011., EMA/CHMP/BPWP/144533/2009 rev. 1, Available from: http://www.ema.europa.eu/docs/en_GB/document_library/Scientificguideline/2011/08/WC500109692.pdf.
European Medicines Agency. Elocta (rFVIIIFc) Summary of Product Characteristics. https://www.ema.europa.eu/en/ documents/product-information/elocta-epar-product-information_ en.pdf. Published 2019. Accessed May 2020.
European Search Report and opinion for European Application No. 08795371, mailed on Jan. 27, 2011.
Extended European Search report received for European Application No. 13735649.9, mailed on Nov. 3, 2015.
Extended European Search Report received for European Application No. 13816031.2, mailed on May 20, 2016, 7 Pages.
Extended European Search Report received for European Application No. 19210390.1, mailed on May 27, 2020, 11 Pages.
Extended European Search report received for European Application No. 22181403.1, mailed on Mar. 31, 2023.
Extended European Search Report received for European Patent Application No. 06804210, mailed on Feb. 4, 2010.
Extended European Search Report received for European Patent Application No. 07752549.1, dated Mar. 5, 2009.
Extended European Search Report received for European Patent Application No. 07752636.6, mailed on Mar. 26, 2009.
Extended European Search Report received for European Patent Application No. 10835255.0, mailed on Jun. 20, 2013, 8 Pages.
Extended European Search Report received for European Patent Application No. 12868427.1, mailed on Jan. 29, 2016.
Extended European Search Report received for European Patent Application No. 14817900.5, mailed on Feb. 21, 2017.
Extended European Search Report received for European Patent Application No. 15735473.9, mailed on Jun. 26, 2017.
Extended European Search Report received for European Patent Application No. 17194648.6, mailed on Apr. 4, 2018, 6 Pages.
Extended European Search Report received for European Patent Application No. 18211179.9, mailed on Mar. 22, 2019.
Extended European Search Report received for European Patent Application No. 19165518.2, mailed on Oct. 7, 2019.
Extended European Search Report received for European Patent Application No. 23179872.9 mailed on Sep. 28, 2023.
Fair, et al. (1984) "Human Hepatoma Cells Secrete Single Chain Factor X, Prothrombin, and Antithrombin III", Blood, vol. 64, No. 1, pp. 194-204.
Fajloun, et al. (2000) "Maurotoxin Versus Pi1/Hstx1 Scorpion Toxins", the Journal of Biological Chemistry, vol. 275, No. 50, American Society for Biochemistry and Molecular Biology, pp. 39394-39402.
Fang, et al. (2007) "the Protein Structure and Effect of Factor VIII", Thrombosis Research, vol. 119, No. 1, pp. 1-13.
Fares, F. A. (1992) "Design of a Long-Acting Follitropin Agonist by Fusing the C-Terminal Sequence of the Chorionic Gonadotropin Beta Subunit to the Follitropin Beta Subunit", Proceedings of the National Academy of Sciences, vol. 89, No. 10, pp. 4304-4308.
Fay, Philip J., "Factor VIII Structure and Function", International Journal of Hematology, vol. 83, No. 2, pp. 103-108, Feb. 1, 2006.
FDA, BLA Approval Letter ALTUVIIIO to Bioverativ Therapeutics, Inc., Feb. 22, 2023.
Felici, et al. (1991) "Selection of Antibody Ligands from a Large Library of Oligopeptides Expressed on a Multivalent Exposition Vector", Journal of Molecular Biology, vol. 222, No. 2, pp. 301-310.
Final Office Action Received for U.S. Appl. No. 13/513,424, mailed on Oct. 1, 2014, 17 Pages.
Fisher, et al. (2006) "Genetic Selection for Protein Solubility Enabled by the Folding Quality Control Feature of the Twin-Arginine Translocation Pathway", Protein Science, vol. 15, No. 3, pp. 449-458.
Fisher, et al., "Treatment of Septic Shock with the Tumor Necrosis Factor Receptor: Fc Fusion Protein", The New England Journal of Medicine, vol. 334, No. 26, Massachusetts Medical Society, United States, pp. 1697-1702, Jun. 27, 1996.
Fitzgerald, et al. (1995) "Interchangeability of Caenorhabditis Elegans DSL Proteins and Intrinsic Signalling Activity of their Extracellular Domains In Vivo", Development, vol. 121, No. 12, pp. 4275-4282.
Fraczkiewicz, et al. (1998) "Exact and Efficient Analytical Calculation of the Accessible Surface Areas and their Gradients for Macromolecules", Journal of Computational Chemistry, vol. 19, pp. 319-333.
Frampton, Efmoroctocog alfa: A Review in Haemophilia A. Drugs, 2016, Abstract, 76: 1281-1291.
Francis, G E. (1992) "Protein Modification and Fusion Proteins", Focus on Growth Factors, vol. 3, No. 2, Mediscript, England, pp. 4-10.
Franz, T. J. (1975) "Percutaneous Absorption on the Relevance of in Vitro Data", Journal of Investigative Dermatology, vol. 64, No. 3, pp. 190-195.
Fraternale et al., Polarization and Repolarization of Macrophages, J Clin Cell Immunol, 2015, 6(2): 1-10.
Frenal, et al. (2004) "Exploring Structural Features of the interaction Between the Scorpion toxincnerg1 and Erg K+ Channels", Proteins, vol. 56, No. 2, pp. 367-375.
Friend, et al. (Dec. 15, 1999) "Phase I Study of An Engineered Aglycosylated Humanized Cd3 Antibody in Renal Transplant Rejection1", Transplantation, vol. 68, Issue 11, pp. 1632-1637.
Fulcher, et al. (1985) "Localization of Human Factor FVIII Inhibitor Epitopes to Two Polypeptide Fragments", Proceedings of the National Academy of Sciences, vol. 82, No. 22, pp. 7728-7732.
Furie, Molecular basis of hemophilia, Semin Hematol, 1990, 27(3): 270-285.
Gamez, et al. (2005) "Development of Pegylated forms of Recombinant Rhodosporidium Toruloides Phenylalanine Ammonia-Lyase for the Treatment of Classical Phenylketonuria", The Journal of the American Society of Gene, Therapy 11, No. 6, pp. 986-989.
Garnier, et al. (1996) "GOR Method for Predicting Protein Secondary Structure from Amino Acid Sequence", Methods in Enzymology. vol. 266, Academic Press, pp. 540-553.

(56) References Cited

OTHER PUBLICATIONS

Gayle, et al., "Identification of Regions in Interleukin-1 Alpha Important for Activity", Journal of Biological Chemistry, vol. 268, No. 29, pp. 22105-22111, Oct. 15, 1993.
Geething, et al. (2010) "Gcg-XTEN: An Improved Glucagon Capable of Preventing Hypoglycemia without Increasing Baseline Blood Glucose", PLoS One, vol. 5, No. 4, e10175 Page.
GenBank (Jan. 14, 1995) "Human Transferrin mRNA, Complete cds", GenBank Accession No. M12530.1, Available at http://www.ncbi.nlm.nih.gov/nuccore/M1253014, 2 pages.
GenBank (Jun. 11, 2015) "Hypothetical Protein TRAVEDRAFT_138159", EIW63862.1, Trametes versicolor FP-10 1664 SS1. Available at URL: http://www.ncbi.nlm.nih.gov/protein/392570690?report=genbank&log$=protalign&blast_rank=1&RID=3ERSOM7501R, 3 Pages.
GenBank (May 7, 1993) "Transferrin [human, liver, mRNA, 2347 nt]", Accession No. S95936.1, accessed at http://www.ncbi.nlm.nih.gov/nuccore/S95936, 2 pages.
GenBank Database (Jan. 14, 1995) "Transferrin Precursor [*Homo sapiens*]", Accession No. AAA61140.1, accessed at http://www.ncbi.nlm.nih.gov/protein/AAA61140.1, 1 Page.
GenBank Database (Jul. 16, 2001) "*Homo sapiens* Transferrin (TF), mRNA", GenBank accession No. XM039845, accessed at https://www.ncbi.nlm.nih.gov/nuccore/XM_039845.1?report=genbank, 2 Pages.
GenBank Database (Jul. 16, 2001) "*Homo sapiens* Transferrin (TF), mRNA", GenBank accession No. XM039847, accessed at https://www.ncbi.nlm.nih.gov/nuccore/XM_039847.1?report=genbank, accessed on Sep. 24, 2014, 2 pages.
GenBank Database (Mar. 29, 2016) "*Homo sapiens* von Willebrand Factor (VWF), mRNA", NCBI Reference Sequence: NM_000552.3, accessed at https://www.ncbi.nlm.nih.gov/nuccore/NM_000552.3, 10 Pages.
GenBank Database (Mar. 29, 2016) "Von Willebrand Factor Preproprotein [*Homo sapiens*]", NCBI Reference Sequence: NP_000543.2, accessed at http://www.ncbi.nlm.nih.gov/protein/NP_000543.2, 8 Pages.
GenBank Database (May 13, 2002) "*Homo sapiens* Transferrin (TF), mRNA", GenBank accession No. XM002793, accessed at https://www.ncbi.nlm.nih.gov/nuccore/XM_002793.7?report=genbank, accessed on Sep. 24, 2014, 2 Pages.
GenBank Database (May 25, 2014) "*Homo sapiens* Transferrin (TF), Transcript Variant 1, mRNA", Accession No. NM001063.3, accessed at http://www.ncbi.nlm.nih.gov/nuccore/NM_001063, 5 Pages.
GeneBank (2008) "*Homo sapiens* Coagulation Factor VIII, Procoagulant Component (F8), Transcript Variant 1, mRNA", Accession No. NM_000132.3, accessed at http://www.ncbi.nlm.nih.gov/nuccore/NM_000132.3, 12 Pages.
George, et al. (2003) "An Analysis of Protein Domain Linkers: their Classification and Role in Protein Folding", Protein Engineering Design, vol. 15, No. 11, pp. 871-879.
Ghetie, et al., "Multiple Roles for The Major Histocompatibility Complex Class I-Related Receptor FcRn", Annual Review of Immunology, vol. 18, pp. 739-766., Jan. 1, 2000.
Giangrande et al., Clinical evaluation of glycoPEGylated recombinant FVIII: Efficacy and safety in severe haemophilia A., Thromb Haemost., Jan. 26, 2017, 117(2):252-261.
Gilkes, et al. (1991) "Domains in Microbial Beta-1, 4-Glycanases: Sequence Conservation, Function, and Enzyme Families", Microbiological Reviews, vol. 55, No. 2, pp. 303-315.
Gilles, et al. (1993) "Anti-Factor VIII Antibodies of Hemophiliac Patients Are Frequently Directed Towards Nonfunctional Determinants and Do Not Exhibit Isotypic Restriction", Blood, vol. 82, No. 8, pp. 2452-2461.
Gitschier, et al. (Nov. 22-28, 1984) "Characterization of the Human Factor VIII Gene", Nature, vol. 312, No. 5992, pp. 326-330.
Gleeson, et al. (1986) "Transformation of the Methylotrophic Yeast *Hansenula polymorpha*", Microbiology. vol. 132, No. 12, pp. 3459-3465.
Goeddel, et al. (1980) "Synthesis of Human Fibroblast Interferon by *E. coli*", Nucleic Acids Research, vol. 8, No. 18, pp. 4057-4074.
Goeddel, et al. (Oct. 18, 1979) "Direct Expression in *Escherichia coli* of a DNA Sequence Coding for Human Growth Hormone", Nature, vol. 281, No. 5732, pp. 544-548.
Gomez-Duarte, et al. (1995) "Expression of Fragment C of Tetanus Toxin Fused to A Carboxyl-Terminal Fragment of Diphtheria toxin in *Salmonella typhi* CVD 908 Vaccine Strain", Vaccine, vol. 13, No. 16, pp. 1596-1602.
Goudemand, et al. (Oct. 2005) "Pharmacokinetic Studies on Wilfactin®, a von Willebrand Factor Concentrate with a Low Factor VIII Content Treated with Three Virus-Inactivation/Removal Methods", Journal of Thrombosis and Haemostasis, vol. 3, No. 10, pp. 2219-2227.
Gouw et al., Treatment characteristics and the risk of inhibitor development: a multicenter cohort study among previously untreated patients with severe hemophilia A, J Thromb Haemost., 2007, 5(7): 1383-1390.
Gouw, et al. (Nov. 2009) "the Multifactorial Etiology of Inhibitor Development in Hemophilia: Genetics and Environment", Seminars in Thrombosis and Hemostasis, vol. 35, No. 8, pp. 723-734.
Graff, et al. (2003) "theoretical Analysis of Antibody Targeting of Tumor Spheroids: Importance of Dosage for Penetration, and Affinity for Retention", Cancer Research, vol. 63, No. 6, pp. 1288-1296.
Graham, et al. (Apr. 1, 1973) "a New Technique for the Assay of Infectivity of Human Adenovirus 5 DNA", Virology, vol. 52, No. 2, pp. 456-467.
Graham, et al. (Jul. 1, 1977) "Characteristics of a Human Cell Line Transformed by DNA From Human Adenovirus Type 5", Journal of General Virology, vol. 36, No. 1, pp. 59-72.
Graham, et al., "Canine Hemophilia: Observations on the Course, the Clotting Anomaly", and the Effect of Blood Transfusions, Journal of Experimental Medicine, vol. 90, No. 2, pp. 97-111, Aug. 1, 1949.
Graw et al., Haemophilia A: from mutation analysis to new therapies, Nat Rev Genet. 2005, 6(6): 488-501.
Gray, et al. (1988) "Peptide Toxins from Venomous Conus Snails", Annual Review of Biochemistry, vol. 57, pp. 665-700.
Greenwald, et al. (2003) "Effective Drug Delivery by PEGylated Drug Conjugates", Advanced Drug Delivery Reviews, vol. 55, No. 2, pp. 217-250.
Gringeri et al., A randomized clinical trial of prophylaxis in children with hemophilia A (the ESPRIT Study), J Thromb Haemost., 2011, 9(4): 700-710.
Groomes et al. Reduction of Factor VIII Inhibitor Titers During Immune Tolerance Induction With Recombinant Factor VIII-Fc Fusion Protein. Pediatr Blood Cancer. 2016;63(5): 922-924.
Gruppo, et al. (May 2003) "Comparative Effectiveness of Full-Length and B-Domain Deleted Factor VIII for Prophylaxis-a Meta-Analysis", Haemophilia, vol. 9, No. 3, pp. 251-260.
Guncar, et al. (1999) "Crystal Structure of MHC Class li-associated P41 li Fragment Bound to Cathepsin L Reveals the Structural Basis for Differentiation Between Cathepsins L and S", The EMBO Journal, vol. 18, No. 4, pp. 793-803.
Guo, et al. (2005) "Crystal Structure of the Cysteine-Rich Secretory Protein Stecrisp Reveals That the Cysteine-Rich Domain Has A K + Channel inhibitor-Like Fold", he Journal of Biological Chemistry, vol. 280, No. 13, pp. 12405-12412.
Gupta et al., Regulation of immune responses to protein therapeutics by transplacental induction of T cell tolerance, Sci Transl Med., 2015, 7(275): 275ra21.
Gupta, et al. (2004) "Classification of Disulfide Patterns and Its Relationship to Protein Structure and Function", Protein Science: A Publication of the Protein Society, vol. 13, No. 8, pp. 2045-2058.
Gustafsson, et al. (2004) "Codon Bias and Heterologous Protein Expression", Trends in Biotechnology, vol. 22, No. 7, pp. 346-353.
Haberichter et al., "Regulated Release of VWF and FVIII and the Biologic Implications", Pediatric Blood Cancer, May 2006, 46(5): 547-553.
Hacker et al., "Barriers to compliance with prophylaxis therapy in haemophilia", Haemophilia, 2001 7: 392-396.

(56) References Cited

OTHER PUBLICATIONS

Hamers-Casterman, et al. (Jun. 3, 1993) "Naturally Occurring Antibodies Devoid of Light Chains", Nature, vol. 363, No. 6428, pp. 446-448.
Hammer, J. (1995) "New Methods to Predict MHC-Binding Sequences within Protein Antigens", Current Opinion in Immunology, vol. 7, No. 2, pp. 263-269.
Harlow, et al. (1988) "Cell Staining", Cold Spring Harbor Laboratory, pp. 359-420.
Harris, et al. (2000) "Rapid and General Profiling of Protease Specificity by Using Combinatorial Fluorogenic Substrate Libraries", Proceedings of the National Academy of Sciences, vol. 97, No. 14, pp. 7754-7759.
Harris, et al. (2003) "Effect of Pegylation on Pharmaceuticals", Nature Reviews Drug Discovery, vol. 2, No. 3, pp. 214-221.
Hay et al. The principal results of the International Immune Tolerance Study: a randomized dose comparison. Blood. 2012:119(6):1335-1344.
Healey, et al. (Dec. 1, 1996) "The cDNA and Derived Amino Acid Sequence of Porcine Factor VIII", Blood, vol. 88, No. 11, pp. 4209-4214.
Hedner, et al. (1983) "Use of Human Factor VIIa in The Treatment of Two Hemophilia a Patients with High-Titer inhibitors", The Journal of Clinical Investigation vol. 71, No. 6, pp. 1836-1841.
Hedner, U. (2000) "NovoSeven® as a Universal Haemostatic Agent", Blood Coagulation & Fibrinolysis II, Supplement 1, pp. S107-S111.
Heinz et al. (Nov. 2009) "Factor VIII-eGFP Fusion Proteins with Preserved Functional Activity for the Analysis of the Early Secretory Pathway of Factor VIII", Thrombosis and Haemostasis, vol. 102, No. 5, pp. 925-935.
Hennighausen et al., "Mouse Whey Acidic Protein is A Novel Member of the Family of Four-Disulfide Core' Proteins", Nucleic Acids Research, Apr. 1982, vol. 10, No. 8, pp. 2677-2684.
Hermans et al. Recombinant factor VIII Fc for the treatment of haemophilia A. Eur J Haematot 2021;106(6):745-761.
Hermans et al., Pharmacokinetics in routine haemophilia clinical practice: rationale and modalities—a practical review, Therapeutic Advances in Hematology, 2020, 11:1-15.
Hermeling, et al. (2004) "Structure-Immunogenicity Relationships of therapeutic Proteins", Pharmaceutical Research, vol. 21, No. 6, pp. 897-903.
Higgins, et al. (1995) "Characterization of Mutant forms of Recombinant Human Properdin Lacking NPL177 Single Thrombospondin Type I Repeats", Journal of Immunology, vol. 155, No. 12, pp. 5777-5785.
Higgins, et al. (1995) "Polyclonal and Clonal Analysis of Human Cd4+ T-Lymphocyte Responses to Nut Extracts", Immunology, vol. 84, No. 1, pp. 91-97.
Hill, et al. (2000) "Conotoxin TVIIA, A Novel Peptide from the Venom of Conus Tulipa 1", European NPL178 Journal of Biochemistry/FEBS, vol. 267, No. 15, pp. 4642-4648.
Hinds, et al. (2005) "PEGylated insulin in PLGA Microparticles. in Vivo and in Vitro Analysis", Journal of Controlled Release, vol. 104, No. 3, pp. 447-460.
Hirel, et al. (1989) "Extent of N-Terminal Methionine Excision from *Escherichia coli* Proteins is Governed by the Side-Chain Length of the Penultimate Amino Acid", Proceedings of the National Academy of Sciences of the United States of America, vol. 86, No. 21, pp. 8247-8251.
Ho, et al. (Apr. 15, 1989) "Site-Directed Mutagenesis by Overlap Extension Using the Polymerase Chain Reaction", Gene, vol. 77, No. 1, pp. 51-59.
Hoeben, et al. (1990) "Expression of Functional Factor Viii in Primary Human Skin Fibroblasts After Retrovirus-Mediated Gene Transfer", Journal of Biological Chemistry, vol. 265, No. 13, pp. 7318-7323.
Hogg, P. J. (2003) "Disulfide Bonds as Switches for Protein Function", Trends in Biochemical Sciences, vol. 28, No. 4, pp. 210-214.
Holevinsky, et al. (1994) "ATP-Sensitive K+ Channel Opener Acts as A Potent CI-Channel inhibitor in Vascular Smooth Muscle Cells", The Journal of Membrane Biology 137, No. 1, pp. 59-70.
Holt, et al. (May 2008) "Anti-Serum Albumin Domain Antibodies for Extending the Half-Lives of Short Lived Drugs", Protein Engineering, Design and Selection, vol. 21, No. 5, pp. 283-288.
Hopp, et al. (1981) "Prediction of Protein Antigenic Determinants from Amino Acid Sequences", Proceedings of the National Academy of Sciences, vol. 78, No. 6, pp. 3824-3828.
Horton, et al. (1993) "Gene Splicing by Overlap Extension", Methods in Enzymology, vol. 217, pp. 270-279.
Horvais et al., "rFVIII-Fc in severe haemophilia A: The incentive switch in case of high risk of joint bleedings", Eur J Clin Invest., Oct. 2022, 52(10): e13824, 11 pages.
Hsu, et al. (2000) "Vaccination Against Gonadotropin-Releasing Hormone (GnRH) Using toxin Receptor-Binding Domain-Conjugated GnRH Repeats", Cancer Research, vol. 60, No. 14, pp. 3701-3705.
Hubbard, et al. (May 2013) "Recommendations on The Potency Labelling of Factor VIII and Factor IX Concentrates.", Journal of thrombosis and Haemostasis, vol. 11, Issue 5, pp. 988-989.
Hudson, et al. (1999) "High Avidity ScFv Multimers; Diabodies and Triabodies", Journal of Immunological Methods, vol. 231, No. 1-2, pp. 177-189.
Hugli, T. E. (1990) "Structure and Function of C3A Anaphylatoxin", Current topics in Microbiology and Immunology, vol. 153, pp. 181-208. Hugli, T. E. (1990) "Structure and Function of C3A Anaphylatoxin", Current topics in Microbiology and Immunology, vol. 153, pp. 181-208.
Huston, et al. (Aug. 1988) "Protein Engineering of Antibody Binding Sites: Recovery of Specific Activity in an Anti-Digoxin Single-Chain Fv Analogue Produced in *Escherichia coli*", Proceedings of the National Academy of Sciences of the United States of America, vol. 85, No. 16, pp. 5879-5883.
Intention to Grant Received for European Patent Application No. 10835255.0, mailed on Jun. 8, 2017, 6 Pages.
Intention to Grant Received for European Patent Application No. 17194648.6, mailed on Oct. 28, 2020, 6 Pages.
International Preliminary Report on Patentability for PCT International Patent Application No. PCT/US2013/021330, ISA/US, dated Jul. 15, 2014, 5 pages.
International Preliminary Report on Patentability for PCT International Patent Application No. PCT/US2013/049989, ISA/US, dated Jan. 13, 2015, 10 pages.
International Preliminary Report on Patentability for PCT International Patent Application No. PCT/US2014/044718, ISA/US, dated Dec. 29, 2015, 7 pages.
International Preliminary Report on Patentability for PCT International Patent Application No. PCT/US2014/044731, ISA/US, dated Dec. 29, 2015, 8 pages.
International Preliminary Report on Patentability for PCT International Patent Application No. PCT/US2015/010738, International Bureau of WIPO, Geneva, Switzerland, mailed on Jul. 12, 2016.
International Search Report and Written Opinion in related PCT Application No. PCT/US2019/032956 mailed Oct. 4, 2019 (13 pages).
International Search Report and Written Opinion received for PCT Patent Application No. PCT/US2006/037713, mailed on Jan. 17, 2008.
International Search Report and Written Opinion received for PCT Patent Application No. PCT/US2007/005857, mailed on Sep. 26, 2007.
International Search Report and Written Opinion received for PCT Patent Application No. PCT/US2007/005952, mailed on Dec. 26, 2007.
International Search Report and Written Opinion received for PCT Patent Application No. PCT/US2008/009787, mailed on Mar. 16, 2009.
International Search Report and Written Opinion received for PCT Patent Application No. PCT/US2010/002147, mailed on Dec. 20, 2010.

(56) References Cited

OTHER PUBLICATIONS

International Search Report and Written Opinion received for PCT Patent Application No. PCT/US2010/002148, mailed on Dec. 1, 2010.
International Search Report and Written Opinion received for PCT Patent Application No. PCT/US2010/023106, mailed on Apr. 20, 2010.
International Search Report and Written Opinion received for PCT Patent Application No. PCT/US2010/037855, mailed on Oct. 29, 2010.
International Search Report and Written Opinion received for PCT Patent Application No. PCT/US2010/061590, mailed on Jul. 12, 2011.
International Search Report and Written Opinion received for PCT Patent Application No. PCT/US2010/059136, mailed on Jun. 2, 2011, 11 Pages.
International Search Report and Written Opinion received for PCT Patent Application No. PCT/US2011/043568, mailed on Nov. 25, 2011.
International Search Report and Written Opinion received for PCT Patent Application No. PCT/US2011/048517, mailed on Mar. 14, 2012.
International Search Report and Written Opinion received for PCT Patent Application No. PCT/US2012/046326, mailed on Jan. 25, 2013.
International Search Report and Written Opinion received for PCT Patent Application No. PCT/US2013/021330, mailed on Apr. 29, 2013.
International Search Report and Written Opinion received for PCT Patent Application No. PCT/US2013/026521, mailed on Apr. 24, 2013.
International Search Report and Written Opinion received for PCT Patent Application No. PCT/US2013/049989, mailed on Dec. 16, 2013.
International Search Report and Written Opinion received for PCT Patent Application No. PCT/US2014/040370, mailed on Jan. 9, 2015.
International Search Report and Written Opinion received for PCT Patent Application No. PCT/US2014/044718, mailed on Nov. 4, 2014.
International Search Report and Written Opinion received for PCT Patent Application No. PCT/US2014/044731, mailed on Nov. 4, 2014.
International Search Report and Written Opinion received for PCT Patent Application No. PCT/US2014/051144, mailed on Feb. 10, 2015.
International Search Report and Written Opinion received for PCT Patent Application No. PCT/US2015/010738, mailed on May 15, 2015.
International Search Report and Written Opinion received for PCT Patent Application No. PCT/US2021/037926, mailed on Nov. 9, 2021.
Irani et al., Molecular properties of human IgG subclasses and their implications for designing therapeutic monoclonal antibodies against infectious diseases, Mol Immunol., 2015, 67: 171-182.
Israel, et al. (Sep. 1997) "Expression of the Neonatal Fc Receptor, FcRn, on Human Intestinal Epithelial Cells", Immunology, vol. 92, No. 1, pp. 69-74.
Iwasaki, et al. (1997) "Solution Structure of Midkine, a New Heparin-Binding Growth Factor", the EMBO Journal, vol. 16, No. 23, pp. 6936-6946.
Jackson, et al. (2007) "The Characterization of Paclitaxel-Loaded Micro Spheres Manufactured from Blends of Poly (Lactic-Co-Glycolic Acid) (PLGA) and Low Molecular Weight Diblock Copolymers", International Journal of Pharmaceutics, vol. 342, No. 1-2, pp. 6-17.
Jacquemin, et al. (2000) "A Human Antibody Directed to The Factor VIII C1 Domain inhibits Factor VIII Cofactor Activity and Binding to Von Willebrand Factor", Blood, vol. 95, No. 1, pp. 156-163.
Janbain M, Pipe S. What is the role of an extended half-life product in immune tolerance induction in a patient with severe hemophilia A and high-titer inhibitors? Hematology Am Soc Hematol Educ Program. 2016;2016(1):648-649.
Jazayeri et al., Half-Life Extension by Fusion to the Fc Region, Therapeutic Proteins: Strategies to Modulate Their Plasma Half-Live, Wiley-VCH Verlag GmbH & Co., KGaA, 2012, pp. 157-188.
Jenkins et al., Elevated factor VIII levels and risk of venous thrombosis, Brit J Haematology. 2012, 157: 653-663.
Jimenez-Yuste et al., Achieving and maintaining an optimal trough level for prophylaxis in haemophilia: the past, the present and the future, Blood Transfus., 2014, 12: 314-319.
JIVI [package insert], Whippany, NJ: Bayer HealthCare LLC, 2018.
Johansson, et al. (2007) "Modifications Increasing the Efficacy of Recombinant Vaccines; Marked Increase in Antibody Titers with Moderately Repetitive Variants of a Therapeutic Allergy Vaccine", Vaccine, vol. 25, No. 9, pp. 1676-1682.
Jonassen, et al. (1995) "Finding Flexible Patterns in Unaligned Protein Sequences", Protein Science, vol. 4, No. 8, pp. 1587-1595.
Jones, et al. (1997) "Determination of Tumor Necrosis Factor Binding Protein Disulfide Structure: Deviation of the Fourth Domain Structure from the TNFR/NGFR Family Cysteine-Rich Region Signature", Biochemistry, vol. 36, No. 48, pp. 14914-14923.
Jones, et al. (May 29, 1986) "Replacing the Complementarity-Determining Regions in a Human Antibody with Those from a Mouse", Nature, vol. 321, No. 6069, pp. 522-525.
Jonsson, et al. (1993) "Quantitative Sequence-Activity Models (QSAM)—Tools for Sequence Design", Nucleic Acids Research, vol. 21, No. 3, pp. 733-739.
Joosten, et al. (2011) "A Series of PDB Related Databases for Everyday Needs", Nucleic Acids D Research, vol. 39, pp. D411-D419.
Jung, et al. (1997) "Improving In Vivo Folding and Stability of a Single-Chain Fv Antibody Fragment by Loop Grafting", Protein Engineering, vol. 10, No. 8, pp. 959-966.
Kabsch, et al. (1983) "Dictionary of Protein Secondary Structure: Pattern Recognition of Hydrogen-Bonded and Geometrical Features", Biopolymers, vol. 22, No. 12, pp. 2577-2637.
Kamal (Jul. 2007) "How to Interpret and Pursue an Abnormal Prothrombin Time, Activated Partial Thromboplastin Time, and Bleeding Time in Adults", Mayo Clinic Proceedings, vol. 87, No. 7, pp. 863-874.
Kamikubo, et al. (2004) "Disulfide Bonding Arrangements in Active forms of the Somatomedin B Domain of Human Vitronectin", Biochemistry, vol. 43, No. 21, pp. 6519-6534.
Kasper, CK, et al. (Nov. 15, 1975) "Proceedings: A More Uniform Measurement of Factor VIII Inhibitors", Thrombosis et diathesis haemorrhagica, vol. 34, No. 2, 612 Page.
Kasuda, et al. (Aug. 2008) "Establishment of Embryonic Stem Cells Secreting Human Factor VIII for Cell-Based Treatment of Hemophilia A", Journal of Thrombosis and Haemostasis, vol. 6, No. 8, pp. 1352-1359.
Katragadda et al., "Population pharmacokinetic (PK) analysis of bivv001 (rFVIIIFc-VWF-xten), a new class of factor VIII (FVIII) replacement", Research and Practice in Thrombosis and Haemostasis, Jul. 2020, 4(Suppl 1): 474.
Kaufman, et al. (1982) "Amplification and Expression of Sequences Cotransfected with a Modular Dihydrofolate Reductase Complementary DNA Gene", Journal of Molecular Biology, vol. 159, No. 4, pp. 601-621.
Kaufman, et al. (1982) "Construction of a Modular Dihydrofolate Reductase cDNA Gene: Analysis of Signals Utilized for Efficient Expression", Molecular and Cellular Biology, vol. 2, No. 11, pp. 1304-1319.
Kavakli et al., Prophylaxis vs. on-demand treatment with BAY 81-8973, a full-length plasma protein-free recombinant factor VIII product: results from a randomized trial (Leopold II), J Thromb Haemost., Mar. 13, 2015, 13(3): 360-369.
Kay, et al. (1993) "An M13 Phage Library Displaying Random 38-Amino-Acid Peptides as a Source of Novel Sequences with Affinity to Selected Targets", Gene, vol. 128, No. 1, pp. 59-65.
Kazatchkine, et al. (1980) "Circulating Immune Complexes Containing Anti-VIII Antibodies in Multi-Transfused Patients with

(56) References Cited

OTHER PUBLICATIONS

Haemophilia A", American Journal of Clinical and Experimental Immunology, vol. 39, No. 2, pp. 315-320.
Kelly, et al. (2003) "Isolation of a Colon Tumor Specific Binding Peptide Using Phage Display Selection", Neoplasia, vol. 5, No. 5, pp. 437-444.
Kemball-Cook, et al. (1998) "the factor VIII Structure and Mutation Resource Site: HAMSTeRS Version 4", Nucleic Acids Research, vol. 26, No. 1, pp. 216-219.
Khan, et al. (1998) "Solubilization of Recombinant Ovine Growth Hormone with Retention of Native-Like Secondary Structure and Its Refolding from the Inclusion Bodies of *Escherichia coli*", Biotechnology Progress, vol. 14, No. 5, pp. 722-728.
Kim, et al. (1995) "Three-Dimensional Solution Structure of the Calcium Channel Antagonist Omega-Agatoxin Iva: Consensus Molecular Folding of Calcium Channel Blockers", Journal of Molecular Biology, vol. 250, No. 5, pp. 659-671.
Kim, et al. (Sep. 2010) "Transferrin Fusion Technology: A Novel Approach to Prolonging Biological Half-Life of Insulinotropic Peptides", Journal of Pharmacology and Experimental therapeutics, vol. 334, No. 3, pp. 682-692.
Kimble, et al. (1997) "the Lin-12/Notch Signaling Pathway and Its Regulation", Annual Review of Cell and Developmental Biology, pp. 333-361.
Kingdon et al., An adventure in biotechnology: the development of haemophilia A therapeutics from whole blood transfusion to recombinant DNA to gene therapy, Biotechnol Appl Biochem., 2002, 35(Pt 2): 141-148.
Kisiel, et al. (1983) "Enzymological Aspects of Blood Coagulation", Behring Institute Mitteilungen, vol. 73, pp. 29-42.
Kissel, et al. (2002) "Aba-Triblock Copolymers from Biodegradable Polyester A-Blocks and Hydrophilic Poly (Ethylene Oxide) B-Blocks as a Candidate for In Situ forming Hydrogel Delivery Systems for Proteins", Advanced Drug Delivery Reviews, vol. 54, No. 1, pp. 99-134.
Kis-Toth et al. Recombinant factor VIII Fc fusion protein drives regulatory macrophage polarization. Blood Adv. 2018;2(21):2904-2916.
Kis-Toth, et al., Recombinant Factor Viii Fc Fusion Protein Exhibits Immunomodulatory Effects On Antigen-Presenting Cells, 9th BIC Int'l Conference Presentation, 2017.
Klamroth al., Results from a phase 3, randomize, multicenter study of rurioctocog alfa pegol PK-guided prophylaxis targeting 2 FVIII trough levels in patients with severe hemophilia A (propel study), Poster P255 presented at: European Association for Haemophilia and Allied Disorders (EAHAD), Feb. 6-9, 2019, Prague, Czech Republic.
Klamroth et al., "Perioperative Management with Efanesoctocog Alfa in Patients with Hemophilia A in the Phase 3 XTEND-1 Study", Abstract, Haemophilia, 87-88.
Klamroth et al., "Perioperative Management with Efanesoctocog Alfa in Patients with Hemophilia A in the Phase 3 XTEND-1 Study", Poster, 16th Annual Congress of the European Association for Haemophilia and Allied Disorders, Feb. 7-10, 2023.
Klitgaard, et al. (2008) "Overview of the Human Pharmacokinetics of Recombinant Activated Factor VII", British Journal of Clinical Pharmacology, vol. 65, No. 1, pp. 3-11.
Kobayashi, et al. (Feb. 2002) "FcRn-Mediated Transcytosis of Immunoglobulin G in Human Renal Proximal Tubular Epithelial Cells", American Journal of Physiology—Renal Physiology, vol. 282, No. 2, pp. F358-F365.
Kochendoerfer, G. "Chemical and Biological Properties of Polymer-Modified Proteins", Expert Opinion on Biological therapy, vol. 3, No. 8, pp. 1253-1261.
Kogenate [package insert], Whippany, NJ: Bayer HealthCare LLC, 2016.
Kohn, et al. (2004) "Random-Coil Behavior and the Dimensions of Chemically Unfolded Proteins", Proceedings of the National Academy of Sciences, vol. 101, No. 34, pp. 12491-14296.
Koide, et al. (1998) "the Fibronectin Type III Domain as a Scaffold for Novel Binding Proteins", Journal of Molecular Biology, vol. 284, No. 4, pp. 1141-1151.
Konig, et al. (Sep. 1, 1998) "Use of an Albumin-Binding Domain for the Selective Immobilisation of Recombinant Capture Antibody Fragments on ELISA Plates", Journal of Immunological Methods, vol. 218, No. 1-2, pp. 73-83.
Konigs C, et al. Final results of PUPs A-LONG study: evaluating safety and efficacy of rFVIIIFc in previously untreated patients with haemophilia A. Res Pract Thromb Haemost. 2020;4 S1:8 (Abstract OC 03.02).
Konigs C, et al. Final Results of ReITIrate—A Prospective Study of Rescue Immune Tolerance Induction (ITI) with Recombinant Factor VIII Fc (rFVIIIFc) in Patients Who Have Failed Previous ITI Attempts. Poster PB0522 presented at the International Society on Thrombosis and Haemostasis (ISTH) 2021 Virtual Congress, Jul. 17-21, 2021, Philadelphia, PA, USA.
Konigs et al., "First study of extended half-life rFVIIIFc in previously untreated patients with hemophilia A: PUPs A-LONG final results", Blood, Jun. 30, 2022, 139(26): 3699-3707.
Konkle et al. "BIVV001 Fusion Protein as Factor VIII Replacement Therapy for Hemophilia A", NEJM, 2020, 383: 1018-1027.
Konkle et al., "BIVV001: The First Investigational Factor VIII Therapy to Break Through the VWF Ceiling in Hemophilia A, with Potential for Extended Protection for One Week or Longer", Blood, Amer Soc of Hematology US, Nov. 29, 2018, 132: 636.
Konkle et al., "Pegylated, full-length, recombinant factor VIII for prophylactic and on-demand treatment of severe hemophilia A", Blood, Aug. 2015, 126(9): 1078-1085.
Kornblatt, et al. (1980) "Cross-Linking of Cytochrome Oxidase Subunits with Difluorodinitrobenzene", Canadian Journal of Biochemistry, vol. 58, No. 3, pp. 219-224.
Kortt, et al. (1997) "Single-Chain Fv Fragments of Anti-Neuraminidase Antibody Nc10 Containing Five- and Ten-Residue Linkers Form Dimers and with Zero-Residue Linker a Trimer", Protein Engineering, vol. 10, No. 4, pp. 423-433.
Kou, et al. (2007) "Preparation and Characterization of Recombinant Protein ScFv(Cd11C)-Trp2 for Tumor therapy from inclusion Bodies in *Escherichia coli*", Protein Expression and Purification, vol. 52, No. 1, pp. 131-138.
Kratzner, et al. (2005) "Structure of Ecballium Elaterium Trypsin inhibitor li (EETI-li): A Rigid Molecular Scaffold", Acta Crystallographica, vol. 61, Part 9, pp. 1255-1262.
Kraulis, et al. (Jan. 8, 1996) "The Serum Albumin-Binding Domain of Streptococcal Protein G Is A Three-Helical Bundle: A Heteronuclear NMR Study", FEBS Letters, vol. 378, Issue 2, pp. 190-194.
Krishnamoorthy et al., Recombinant factor VIII Fc (rFVIIIFc) fusion protein reduces immunogenicity and induces tolerance in hemophilia A mice, Cell Immunol., 2016, 301: 30-39.
Krishnan et al., "Thrombin cleavage analysis of a novel antihaemophilic factor variant, factor VIII ΔII", Eur. J. Biochem. Vol. 195, 1991, pp. 637-644.
Kristensen, et al. (1998) "Proteolytic Selection for Protein Folding Using Filamentous Bacteriophages", Folding & Design, vol. 3, No. 5, pp. 321-328.
Kronek et al., Biocompatibility and Immunocompatibility Assessment of Poly(2-Oxazolines), in Andrade et al. eds Practical Applications in Biomedical Engineering 2013.
Kubetzko, et al. (Nov. 1, 2005) "Protein PEGylation Decreases Observed Target Association Rates Via A Dual Blocking Mechanism", Molecular Pharmacology vol. 68, No. 5, The American Society for Pharmacology and Experimental Therapeutics, United States, pp. 1439-1454.
Kulkarni et al. Improved hemostasis and joint health over time in a subset of patients who did not reach optimal hemostatic control in the first year of recombinant factor VIII Fc fusion protein (rFVIIIFc) therapy. Research and Practice in Thrombosis and Haemostasis. 2019;3(S1):262.
Kulkarni et al., "Clinical Development of Efanesoctocog Alfa (BIV001), A New Class of Factor VIII (FVIII) Replacement Therapy Designed to Provide High Sustained Factor Activity", Abstract, THSNA 2022 Summit Abstract Proceedings, American Journal of Hematology, E601-E61.

(56) References Cited

OTHER PUBLICATIONS

Kulkarni et al., "Clinical Development of Efanesoctocog Alfa (BIV001), A New Class of Factor VIII (FVIII) Replacement Therapy Designed to Provide High Sustained Factor Activity", Poster, THSNA 2022 Summit of North America, Aug. 16-18, 2022.
Kulman, et al. (2007) "A Versatile System for Site-Specific Enzymatic Biotinylation and Regulated Expression of Proteins in Cultured Mammalian Cells", Protein Expression and Purification, vol. 52, No. 2, pp. 320-328.
Kurachi, et al. (1982) "Isolation and Characterization of A cDNA Coding for Human Factor IX", Proceedings of the National Academy of Sciences, pp. 6461-6464.
Kwon, et al. (Feb. 2004) "Biodegradable Triblock Copolymer Microspheres Based on thermosensitive Sol-Gel Transition", Pharmaceutical Research, vol. 21, Issue 2, pp. 339-343.
LaCroix-Desmazes et al., Fc-fusion technology beyond half-life extension—review of potential immunomodulatory and anti-inflammatory effects of rFVIIIFc in haemophilia A, WFH 2022 World Congress, Montreal and virtual, May 8-11, 2022.
Lambert et al., "Practical aspects of extended half-life products for the treatment of haemophilia", Therapeutic Advances in Hematology, 2018; 295-308.
Lane, et al. (Jan. 3, 2006) "Influence of Post-Emulsification Drying Processes on the Microencapsulation of Human Serum Albumin", International Journal of Pharmaceutics, vol. 307, No. 1, pp. 16-22.
Langner, et al. (Apr. 1988) "Synthesis of Biologically Active Deletion Mutants of Human Factor VIII:C", Behring Institute Mitteilungen, No. 82, pp. 16-25.
Lapatto, et al. "X-ray Structure of Antistasin at 1.9 Å Resolution and Its Modelled Complex with Blood Coagulation Factor Xa", the EMBO Journal, Sep. 1997, vol. 16, No. 17, Wiley Blackwell, England, pp. 5151-5161.
Larrick, et al. (1989) "Rapid Cloning of Rearranged Immunoglobulin Genes from Human Hybridoma Cells using Mixed Primers and the Polymerase Chain Reaction", Biochemical and Biophysical Research Communications, vol. 160, No. 3, pp. 1250-1256.
Lauber, et al. (Apr. 18, 2003) "Homologous Proteins with Different Folds: The Three-Dimensional Structures of Domains 1 and 6 of the Multiple Kazal-Type inhibitor LEKTI", Journal of Molecular Biology, vol. 328, No. 1, pp. 205-219.
Lavigne-Lissalde, et al. (Oct. 2009) "Characteristics, mechanisms of action, and epitope mapping of anti-factor VIII antibodies", Clinical Reviews in Allergy & Immunology, vol. 37, No. 2, pp. 67-79.
Le Gall, et al. (Jun. 1999) "Di-, Tri- and Tetrameric Single Chain Fv Antibody Fragments Against Human Cd19: Effect of Valency on Cell Binding", FEBS letters, vol. 453, No. 1-2, pp. 164-168.
Lee et al. A crucial role for reactive oxygen species in RANKL-induced osteoclast differentiation. Blood. 2005;106(3):852-859.
Lee et al., Utilization patterns of coagulation factor consumption for patients with hemophilia, J Korean Med Sci., 2010, 31(1): 33-38.
Lee, et al. (Aug. 31, 2001) "Disorders of Coagulation", Pediatric Hematology Secrets, Weiner M.A. and Cario, M.S., eds., Hanley & Belfus, United States, pp. 47-52.
Lee, et al. (Dec. 1999) "Pharmacokinetics of Recombinant Factor VIII (Recombinate) Using One-Stage Clotting and Chromogenic Factor VIII Assay", Journal of Thrombosis and Haemostasis, vol. 82, No. 6, pp. 1644-1647.
Lee, et al. "A recombinant human G-CSF/GM-CSF fusion protein from *E. coli* showing colony stimulating activity on human bone marrow cells", Biotechnology Letters, Feb. 2003, vol. 25, No. 3, pp. 205-211.
Lee, Vincent H. (2001) "Mucosal Drug Delivery", Journal of the National Cancer Institute Monographs, vol. 29, pp. 41-44.
Lehtinen et al., "Surgical outcomes in patients with haemophilia A or B receiving extended half-life recombinant factor VIII and IX Fc fusion proteins: Real-world eperience in the Nordic countries", Haemophilia, Sep. 2022, 28(5): 713-719.
Lei et al., Induction of tolerance to factor VIII inhibitors by gene therapy with immunodominant A2 and C2 domains presented by B cells as Ig fusion proteins, Blood, 2005, 105(12): 4865-4670.
Lenting et al., Von Willebrand factor interaction with FVIII: development of long-acting FVIII therapies, Blood, 2016, 128: SCI-8.
Lenting, et al. (Aug. 20, 1999) "the light chain of factor VIII comprises a binding site for low density lipoprotein receptor-related protein", the Journal of Biological Chemistry, vol. 274, No. 34, pp. 23734-23739.
Lenting, et al. (Dec. 1, 1998) "the Life Cycle of Coagulation Factor VIII in View of its Structure and Function", Blood, vol. 92, No. 11, pp. 3983-3996.
Lenting, et al. (Jul. 2007) "Clearance Mechanisms of von Willebrand Factor and Factor VIII", Journal of Thrombosis and Haemostasis, vol. 5, No. 7, pp. 1353-1360.
Lenting, et al. (May 2010) "The disappearing act of factor VIII", Haemophilia, vol. 16, No. 102, pp. 6-15.
Lentz et al., Results from a large multinational clinical trial (guardian 1) using prophylactic treatment with turocotocog alfa in adolescent and adult patients with severe haemophilia A: safety and efficacy., Haeomophilia. 2013, 691-697.
Leong, et al. (Feb. 4, 2003) "Optimized Expression and Specific Activity of 11-12 by Directed Molecular Evolution", Proceedings of the National Academy of Sciences of the United States of America, vol. 100, No. 3, pp. 1163-1168.
Leong, et al. (Nov. 2001) "Adapting Pharmacokinetic Properties of a Humanized Anti-Interleukin-8 Antibody for therapeutic Applications Using Site-Specific Pegylation", Cytokine, vol. 16, Issue 3, pp. 106-119.
Lethagen, et al. (Nov. 1986) "Clinical Application of the Chromogenic Assay of Factor VIII in Haemophilia A, and Different Variants of von Willebrand's Disease", Scandinavian Journal of Haematology, vol. 37, No. 5, pp. 448-453.
Leung, et al. (1989) "A Method for Random Mutagenesis of a Defined DNA Segment Using a modified Polymerase Chain Reaction", Technique, vol. 1, pp. 11-15.
Leung-Hagesteijn, et al. (1992) "Unc-5, A Transmembrane Protein with Immunoglobulin and Thrombospondin Type 1 Domains, Guides Cell and Pioneer Axon Migrations in C", Cell, vol. 71, No. 2, pp. 289-299.
Levitt, et al. (1976) "A Simplified Representation of Protein Conformations for Rapid Simulation of Protein Folding", Journal of Molecular Biology, vol. 104, No. 1, pp. 59-107.
Levy, et al. (2007) "Isolation of Trans-Acting Genes That Enhance Soluble Expression of ScFv Antibodies in the E", Journal of Immunological Methods, vol. 321, No. 1-2, pp. 164-173.
Leyte et al., "Sulfation of $Tyr^{1680}$ of Human Blood Coagulation Factor VII Is Essential for the Interaction of Factor with von Willebrand Factor", The Journal of Biological Chemistry, Jan. 15, 1991, vol. 266, No. 2, pp. 740-746.
Leyte, et al. (1989) "The Interaction Between Human Blood-Coagulation Factor VIII and Von Willebrand Factor: Characterization of a High-Affinity Binding Site on Factor VIII", Biochemical, Journal 257, No. 3, pp. 679-683.
Li, et al. (1997) "The Physical Exchange of Factor VIII (FVIII) between von Willebrand Factor and Activated Platelets and the Effect of the FVIII B-Domain on Platelet Binding", Biochemistry, vol. 36, pp. 10760-10767.
Li, H, et al. (May 2002) "The Role of the Transferrin-Transferrin-Receptor System in Drug Delivery and Targeting", Trends in Pharmacological Sciences, vol. 23, No. 5, pp. 206-209.
Lillicrap, D. (2008) "Extending Half-Life in Coagulation Factors: Where Do We Stand?", Thrombosis Research, vol. 122, Supplement 4, pp. S2-S8.
Lin, et al. (2007) "Metal-Chelating Affinity Hydrogels for Sustained Protein Release", Journal of Biomedical Materials Research, Part A, vol. 83, No. 4, pp. 954-964.
Linhult, et al. (Feb. 2002) "Mutational Analysis of the Interaction Between Albumin-Binding Domain from Streptococcal Protein G and Human Serum Albumin", Protein Science, vol. 11, No. 2, pp. 206-213.

(56) References Cited

OTHER PUBLICATIONS

Lippi, et al. (2007) "Diagnostic Approach to Inherited Bleeding Disorders", Clinical Chemistry and Laboratory Medicine, vol. 45, No. 1, pp. 2-12.
Lirazan, et al. (2000) "the Spasmodic Peptide Defines a New Conotoxin Superfamily", Biochemistry, vol. 39, No. 7, pp. 1583-1588.
Lissitchkov et al., "A Phase 1 Sequential Pharmacokinetic (PK) Evaluation of Octocog Alfa, Rurioctocog Alfa Pegol, ad Efanesoctocog Alfa in Severe Hemophilia A", Abstract, Haemophilia, 107-108, NHF 2022 Congress: Aug. 25-27, 2022.
Lissitchkov et al., "A Phase 1 Sequential Pharmacokinetic (PK) Evaluation of Octocog Alfa, Rurioctocog Alfa Pegol, ad Efanesoctocog Alfa in Severe Hemophilia A", Presentation slides, World Federation of Hemophilia, NHF 2022 Congress: Aug. 25-27, 2022.
Lissitchkov et al., "A Phase 1 Sequential Pharmacokinetic (PK) Evaluation of Octocog Alfa, Rurioctocog Alfa Pegol, and Efanesoctocog Alfa in Severe Hemophilia A", Efanesoctocog alfa Phase 1 PK Abstract—Encore, NHF 2022 Congress: Aug. 25-27, 2022.
Lissitchkov et al., "A Phase 1 Sequential Pharmacokinetic (PK) Evaluation of Octocog Alfa, Rurioctocog Alfa Pegol, and Efanesoctocog Alfa in Severe Hemophilia A", Poster, Blood 2022 Congress: Sep. 11-14, 2022, Sydney.
Lissitchkov et al., "A Phase 1 Sequential Pharmacokinetic (PK) Evaluation of Octocog Alfa, Rurioctocog Alfa Pegol, and Efanesoctocog Alfa in Severe Hemophilia A", Poster, NHF 74th Annual Bleeding Disorders Conference (BDC) 2022, Aug. 25-27, 2022.
Lissitchkov et al., "Efanesoctocog alfa for hemophilia A: results from a phase 1 repeat-dose study", Blood Advances, Feb. 11, 2022, 6(4): 1089-1094.
Lissitchkov et al., "Efanesoctocog alfa Phase 1 PK" Abstract Encore, Blood 2022 Congress: Sep. 11-14, 2022, Sydney.
Lissitchkov et al., "Phase 1 Repeat Dosing with BIVV001: The First Investigational Factor VIII Product to Break through the Von Willebrand Factor-Imposed Half-Life Ceiling", Blood, Amer Soc of Hematology US, Nov. 13, 2019, 134: 625.
Liu et al., "Evaluation of Antibody Responses to rFVIIIFc compared to Xyntha® and Advate® in Hemophilia A Mice", Haemophilia, 2012, vol. 18, Suppl. 3.
Liu, et al. (1997) "the Human Beta-Defensin-1 and Alpha-Defensins are Encoded by Adjacent Genes: Two Peptide Families with Differing Disulfide Topology Share a Common Ancestry", Genomics, vol. 43, No. 3, pp. 316-320.
Liu, et al. (2007) "Evaluation of PEG-FVIII Molecules with Prolonged Half-lives in a Murine FVIII Dependent Bleeding Model", Journal of Thrombosis and Haemostasis, vol. 9, Suppl. 2: P-M-035, ISTH Meeting, Abstract: Factor VIII, Factor V, Exhibition Area, International Society on Thrombosis and Haemostasis, United States, 1 page.
Liu, et al. (2011) "Recombinant FVIII Fe Fusion Protein Is Fully Active in Treating Acute Injury and Demonstrates Prolonged Prophylactic Efficacy in Hemophilia a Mice", Journal of Thrombosis and Haemostasis vol. 9, Suppl. 2: P-WE-131, ISTH Meeting, International Society on Thrombosis and Haemostasis, United States.
Logan, et al. (Jun. 1984) "Adenovirus Tripartite Leader Sequence Enhances Translation of mRNAs Late After Infection", Proceedings of the National Academy of Sciences, vol. 81, No. 12, pp. 3655-3659.
Lollar, et al. (Jun. 1994) "Inhibition of Human Factor VIIIa by Anti-A2 Subunit Antibodies", the Journal of Clinical Investigation, vol. 93, No. 6, pp. 2497-2504.
Lollar, et al., "Coagulant Properties of Hybrid Human/Porcine Factor VIII Molecules", Journal of Biological Chemistry, vol. 267, pp. 23652-23657, Nov. 25, 1992.
Lollar, et al., "Structural Basis for The Deceased Procoagulant Activity of Human Factor VIII Compared to The Porcine Homolog", Journal of Biological Chemistry, vol. 266, No., pp. 12481-12486, Jul. 5, 1991.
London, et al. (Jul. 20, 2000) "Zymogen Factor IX Potentiates Factor IXa-Catalyzed Factor X Activation", Biochemistry, vol. 39, No. 32, pp. 9850-9858.
Low, et al., "Oral and Pulmonary Delivery of FSH-Fc Fusion Proteins via Neonatal Fc Receptor-Mediated Transcytosis", Human Reproduction, vol. 20, No. 7, Oxford University Press, pp. 1805-1813, Jul. 1, 2005.
Lowman, et al. (Nov. 12, 1991) "Selecting High-Affinity Binding Proteins by Monovalent Phage Display", Biochemistry, vol. 30, No. 45, pp. 10832-10838.
Loyter, et al. (Jan. 1982) "Mechanisms of DNA Uptake by Mammalian Cells: Fate of Exogenously Added DNA Monitored by the Use of Fluorescent Dyes", Proceedings of the National Academy of Sciences, vol. 79, No. 2, pp. 422-426.
Lozier, et al. (2002) "the Chapel Hill Hemophilia a Dog Colony Exhibits a Factor VIII Gene Inversion", Proceedings of the National Academy of Sciences USA, vol. 99, No. 20, pp. 12991-12996.
Lusher, Hemophilia: From plasma to recombinant factors, 2008, In: 50 Years in Hematology Research That Revolutionized Patient Care. Washington, DC: American Society of Hematology, pp. 25-27. Available from: http://www.hematology.org/Publications/50 Years in Hematology/4323.aspx.
Mackett, et al. (Dec. 1982) "Vaccinia Virus: A Selectable Eukaryotic Cloning and Expression Vector", Proceedings of the National Academy of Sciences of the United States of America, vol. 79, No. 23, pp. 7415-7419.
Mackett, et al. (Mar. 1984) "General Method for Production and Selection of Infectious Vaccinia Virus Recombinants Expressing Foreign Genes", Journal of Virology, vol. 49, No. 3, pp. 857-864.
Maggio (2006) "A Renaissance in Peptide therapeutics is Underway", Drug Delivery Reports, pp. 23-26.
Maggio, Edward (Jul. 2006) "Intravail: Highly Effective Intranasal Delivery of Peptide and Protein Drugs", Expert Opinion on Drug Delivery, vol. 3, No. 4, pp. 529-539.
Mahlangu et al., Efficacy and safety of rVIII-SingleChain: results of a phase 1/3 multicenter clinical trial in severe hemophilia A, Blood, Aug. 2016, 128(5): 630-637.
Mahlangu et al., Emicizumab Prophylaxis in Patients Who Have Hemophilia A without Inhibitors, The New England Journal of Medicine, 2018, 811-822.
Mahlangu J, et al. Phase 3 study of recombinant factor VIII Fc fusion protein in severe hemophilia A. Blood. 2014;123(3): 317-325.
Maillere (Jun. 15, 1993) "Role of Thiols in the Presentation of a Snake Toxin to Murine T Cells", Journal of Immunology, vol. 150, No. 12, pp. 5270-5280.
Maillere, et al. (Apr. 1995) "Immunogenicity of a Disulphide-Containing Neurotoxin: Presentation to T-Cells Requires a Reduction Step", Toxicon, vol. 33, No. 4, pp. 475-482.
Mair et al., Thinking about the burden of treatment, BMJ, 2014, 349.
Malardier, et al. (May 15, 1989) "Cloning of the Nitrate Reductase Gene (niaD) of Aspergillus Nidulans and its Use for Transformation of Fusarium Oxysporum", Gene, vol. 78, No. 1, pp. 147-156.
Malec et al. Extended half-life factor VIII for immune tolerance induction in haemophilia. Haemophilia. 2016;22(6):e552-e554.
Malec L, et al. LBA-5 Efficacy of rFVIIIFc for first-time immune tolerance induction (ITI) therapy: Final results from the Global, Prospective VerITI-8 Study. Presented at ASH 2021.
Malik, et al. (Sep. 1992) "Polyethylene Glycol (PEG)-Modified Granulocyte-Macrophage Colony-Stimulating Factor (GM-CSF) with Conserved Biological Activity", Experimental Hematology, vol. 20, No. 8, pp. 1028-1035.
Manco-Johnson et al., Prophylaxis usage, bleeding rates, and joint outcomes of hemophilia, 1999 to 2010: a surveillance project, Blood, 2017, 2368-2374.
Manco-Johnson et al., Prophylaxis versus episodic treatment to prevent joint disease in boys with severe hemophilia, N Engl J Med., 2007, 357(6): 535-544.
Manco-Johnson, M., "Comparing Prophylaxis with Episodic Treatment in Haemophilia A: Implications for Clinical Practice", Haemophilia., vol. 13, Supplement 2, Blackwell Publishing Ltd., England, pp. 4-9, Sep. 1, 2007.

(56) References Cited

OTHER PUBLICATIONS

Manco-Johson et al., Randomized, controlled, parallel-group trial of routine prophylaxis vs. on-demand treatment with sucrose-formulated recombinant factor VIII in adults with severe hemophilia A (SPINART), J Thromb Haemost., Jun. 2013,11(6):1119-1127.

Mannucci, et al. (Jun. 1, 2001) "the Hemophilias—From Royal Genes to Gene therapy", New England Journal of Medicine, vol. 344, No. 23, pp. 1773-1779.

Marshall, et al. (Aug. 25, 2004) "Enhancing the Activity of a Beta-Helical Antifreeze Protein by the Engineered Addition of Coils", Biochemistry, vol. 43, No. 37, pp. 11637-11646.

Martin, et al. (Apr. 1999) "Evaluation of a Novel ELISA Screening Test for Detection of Factor VIII Inhibitory Antibodies in Haemophiliacs", Clinical & Laboratory Haematology, vol. 21, No. 2, pp. 125-128.

Martin, et al. (Jan. 2003) "Rational Design of a CD4 Mimic that Inhibits HIV-1 Entry and Exposes Cryptic Neutralization Epitopes", Nature Biotechnology, vol. 21, No. 1, pp. 71-76.

Martineau, et al. (Jul. 3, 1998) "Expression of an Antibody Fragment at High Levels in the Bacterial Cytoplasm", Journal of Molecular Biology, vol. 280, No. 1, pp. 117-127.

Martinelli, et al. (2010) "Polymorphisms at LDLR Locus May Be Associated with Coronary Artery Disease Through Modulation of Coagulation Factor VIII Activity and Independently from Lipid Profile", Blood, vol. 116, pp. 5688-5697.

Matsumoto, et al. (2006) "the Measurement of Low Levels of Factor Viii or Factor IX in Hemophilia A and Hemophilia B Plasma by Clot Waveform Analysis and Thrombin Generation Assay", Journal of Thrombosis and Haemostasis, vol. 4, No. 2, pp. 377-384.

Matthews, et al. (May 21, 1993) "Substrate Phage: Selection of Protease Substrates by Monovalent Phage Display", Science, vol. 260, No. 5111, pp. 1113-1117.

Mazepa et al., Men with severe hemophilia in the United States: birth cohort analysis of a large national database, Blood, 2016, 127: 3073-3081.

McCue, et al. (Nov. 6, 2009) "Application of a Novel Affinity Adsorbent for the Capture and Purification of Recombinant Factor VIII Compounds", Journal of Chromatography A, vol. 1216, No. 45, pp. 7824-7830.

McDonald, et al. (Sep. 15, 2002) "Significance of Blood Vessel Leakiness in Cancer", Cancer Research, vol. 62, No. 18, pp. 5381-5385.

McEneny-King et al., "Development and evaluation of a generic population pharmacokinetic model for standard half-life factor VIII for use in dose individualization", Journ Pharmacokinet Pharmacodyn., Oct. 2019, 46(5): 411-426.

McKnight, et al. (Aug. 1, 1985) "Identification and Molecular Analysis of a Third Aspergillus Nidulans Alcohol Dehydrogenase Gene", the EMBO Journal, vol. 4, No. 8, pp. 2093-2099.

McNulty, et al. (Nov. 29, 2001) "High-Resolution NMR Structure of the Chemically-Synthesized Melanocortin Receptor Binding Domain AGRP (87-132) of the Agouti-Related Protein", Biochemistry, vol. 40, No. 51, pp. 15520-15527.

Meeks et al. (Apr. 2009) "Non-Classical Anti-Factor VIII C2 Domain Antibodies are Pathogenic in a Murine In vivo Bleeding Model", Journal of Thrombosis and Haemostasis, vol. 7, No. 4, pp. 658-664.

Meeks et al., Emerging benefits of Fc fusion technology in the context of recombinant factor VIII replacement therapy, Haemophilia, 2020, 26(6): 958-965.

Meeks, et al. (Dec. 15, 2007) "Antihuman Factor VIII C2 Domain Antibodies in Hemophilia a Mice Recognize a Functionally Complex Continuous Spectrum of Epitopes Dominated by Inhibitors of Factor VIII Activation", Blood, vol. 110, No. 13, pp. 4234-4242.

Mei, et al. (Jul. 15, 2010) "Rational Design of a Fully Active, Long-Acting PEGylated Factor VIII for Hemophilia A Treatment", Blood, vol. 116, No. 2, pp. 270-279.

Mei, et al. (Oct. 2006) "Expression of Human Coagulation Factor VIII in a Human Hybrid Cell Line, HKB11", Molecular Biotechnology, vol. 34, No. 2, Humana Press Inc., pp. 165-178.

Meier, et al. (Jul. 2, 2004) "Determination of a High-Precision NMR Structure of the Minicollagen Cysteine Rich Domain from Hydra and Characterization of Its Disulfide Bond formation", FEBS Letters, vol. 569, No. 1-3, pp. 112-116.

Meloun, et al. (Oct. 15, 1975) "Complete Amino Acid Sequence of Human Serum Albumin", FEBS Letters, vol. 58, No. 1, pp. 134-137.

Meulien, et al. (1988) "A New Recombinant Procoagulant Protein Derived From the cDNA Encoding Human Factor VIII", Protein Engineering, Design and Selection, vol. 2, No. 4, pp. 301-306.

Mi et al., Targeting the Neonatal Fc Receptor for Antigen Delivery Using Engineered Fc Fragments, J Immunol., 2008, 181(11): 7550-7561.

Miao, et al. (May 1, 2004) "Bioengineering of Coagulation Factor Viii for Improved Secretion", Blood, vol. 103, No. 9, pp. 3412-3419.

Miljanich, G. P., et al. (Jan. 2004) "Ziconotide: Neuronal Calcium Channel Blocker for Treating Severe Chronic Pain", Current Medicinal Chemistry, vol. 11, No. 23, pp. 3029-3040.

Misenheimer, et al. (Dec. 16, 2005) "Biophysical Characterization of the Signature Domains of Thrombospondin-4 and Thrombospondin-2", Journal of Biological Chemistry, vol. 280, No. 40, pp. 41229-41235.

Misenheimer, et al. (Oct. 4, 2001) "Disulfide Connectivity of Recombinant C-terminal Region of Human Thrombospondin 2", the Journal of Biological Chemistry, vol. 276, No. 49, pp. 45882-45887.

Mitraki, et al. (1989) "Protein Folding Intermediates and Inclusion Body formation", Nature Biotechnology, vol. 7, pp. 690-697.

Mize, et al. (2008) "Regulated Expression of Active Biotinylated G-Protein Coupled Receptors in Mammalian Cells", Protein Expression and Purification, vol. 57, No. 2, pp. 280-289.

Mogk, et al. (Sep. 2, 2002) "Mechanisms of Protein Folding: Molecular Chaperones and their Application in Biotechnology", ChemBioChem, vol. 3, Issue 9, pp. 807-814.

Moore et al., A Randomized Safety and Efficacy Study of Somavaratan (VRS-317), a Long-Acting rhGH, in Pediatric Growth Hormone Deficiency, J Clin Endocrinol Metab., 2016, 101(3): 1091-1097.

Morfini, M., "Pharmacokinetics of Factor VIII and Factor IX", Haemophilia, vol. 9, No. 1, pp. 94-99, May 1, 2003.

Morfini, Massimo (2008) "Secondary Prophylaxis with Factor IX Concentrates: Continuous Infusion", Blood Transfusion, vol. 6, Supplement 2, pp. s21-s25.

Morpurgo, et al. (Jan. 1996) "Covalent Modification of Mushroom Tyrosinase with Different Amphiphic Polymers for Pharmaceutical and Biocatalysis Applications", Applied Biochemistry and Biotechnology, vol. 56, No. 1, pp. 59-72.

Mount, et al. (Apr. 15, 2002) "Sustained Phenotypic Correction of Hemophilia B Dogs with a Factor IX Null Mutation by Liver-Directed Gene therapy", Blood, vol. 99, No. 8, pp. 2670-2676.

Mrsny, et al. (Feb. 15, 2002) "Bacterial Toxins as Tools for Mucosal Vaccination", Drug Discovery Today, vol. 7, Issue 4, pp. 247-258.

Muller, et al. (Aug. 2007) "Recombinant Bispecific Antibodies for Cellular Cancer Immunotherapy", Current opinion in molecular therapeutics, vol. 9, No. 4, pp. 319-326.

Murtuza, et al. (Mar. 23, 2004) "Transplantation of Skeletal Myoblasts Secreting An IL-1 Inhibitor Modulates Adverse Remodeling in Infarcted Murine Myocardium", Proceedings of the National Academy of Sciences of the United States of America, vol. 101, No. 12, pp. 4216-4221.

Nagao et al., PB0277 Real-world Data of Immune Tolerance Induction Using Recombinant Factor VIII Fc Fusion Protein for Hemophilia A Patients with Inhibitors in Japan: Observational Fc Adolescent and Children Treatment Study (FACTs) First Interim Reports, Res Pract Thromb Haemost., 2019, 3(S1): 290.

Narita, et al. (1998) "the Low-Density Lipoprotein Receptor-Related Protein (LRP) Mediates Clearance of Coagulation Factor Xa In Vivo", Blood, vol. 91, No. 2, pp. 555-560.

Narmoneva, et al. (Aug. 2005) "Self-Assembling Short Oligopeptides and the Promotion of Angiogenesis", Biomaterials, vol. 26, Issue 23, pp. 4837-4846.

(56) References Cited

OTHER PUBLICATIONS

National Heart Lung and Blood Institution, (Oct. 22, 2011), The Diagnosis, Evaluation and Management of von Willebrand Disease Scientific Overview, accessed at http://www.nhlbi.nih.gov/guidelines/vwd/2scientificoverview.htm.
National Hemophilia Foundation (NHF). Medical and Scientific Advisory Council (MASAC). MASAC Document #241: MASAC Recommendation Concerning Prophylaxis, Feb. 28, 2016.
NCBI (Jun. 11, 2015) "Serine Phosphatase RsbU, Regulator of Sigma Subunit [Amycolatopsis azurea]", Reference Sequence: WP_005158338.1, Available at URL: http://www.ncbi.nlm.nih.gov/protein/491300334?report=genbank&log$=protalign&blast_rank=1&RID=3ERSOM7501R, 2 Pages.
NCBI "Probable Electron Transfer Flavoprotein Subunit Alpha, Mitochondrial [Galendromus Occidentalis]", NCBI Reference Sequence: XP_003746909.1 Retrieved at URL: https://www.ncbi.nlm.nih.gov/protein/391345263?report=genbank&log$=protalign&blast_rank=1&RID=3ERSOM7501R, 3 pages.
Needleman, et al. (Mar. 1970) "A General Method Applicable to the Search for Similarities in the Amino Acid Sequence of Two Proteins", Journal of Molecular Biology, vol. 48, No. 3, pp. 443-453.
Neumann, et al. (1982) "Gene Transfer into Mouse Lyoma Cells by Electroporation in High Electric Fields", the EMBO Journal, vol. 1, No. 7, pp. 841-845.
Newell et al., Acidic Residues C-Terminal to the A2 Domain Facilitate Thrombin-Catalyzed Activation of Factor VIII, 2008, pp. 8786-8795.
Newell et al., Residues Surrounding Arg372, Arg740, and Arg 1689 Contribute to the Rates of Thrombin-Catalyzed Cleavage of Factor VIII, 2009, p. 349.
Newman et al., "Primatization" Of Recombinant Antibodies For Immunotherapy Of Human Diseases: A Macaque/Human Chimeric Antibody Against Human CD4, 1992, pp. 1455-1460.
Ngo, et al. (Apr. 2008) "Crystal Structure of Human Factor VIII: Implications for the formation of the Factor IXa-Factor VIIIa Complex", Structure, vol. 16, No. 4, pp. 597-606.
Nielsen, et al. (Jul. 2003) "Di/Tri-Peptide Transporters as Drug Delivery Targets: Regulation of Transport Under Physiological and Patho-Physiological Conditions", Current Drug Targets, vol. 4, Issue 5, pp. 373-388.
Nielsen, et al. (Jul. 26, 2002) "Solution Structure of μ-Conotoxin PIIIA, a Preferential Inhibitor of Persistent Tetrodotoxin-sensitive Sodium Channels", the Journal of Biological Chemistry, vol. 277, pp. 27247-27255.
Nieman, et al. (Jul. 24, 2007) "Interaction of Thrombin with PAR1 and PAR4 at the Thrombin Cleavage Site", Biochemistry, vol. 46, No. 29, pp. 8603-8610.
Nilsson et al., Twenty-five years' experience of prophylactic treatment in severe haemophilia A and B, J Intern Med., 1992, 232(1): 25-32.
Nimmerjahn et al., Fcgamma receptors as regulators of immune responses, Nat Rev Immunol., 2008, 8(1): 34-47.
Nimmerjahn F., Molecular and Cellular Pathways of Immunoglobulin G Activity In Vivo, ISRN Immunology, 2014, Article ID 524081.
Noe, D A., et al. (Nov.-Dec. 1996) "A Mathematical Model of Coagulation Factor VIII Kinetics", Haemostasis, vol. 26, No. 6, pp. 289-303.
Nogami, et al. (Jun. 1, 2002) "A novel mechanism of factor VIII protection by von Willebrand factor from activated protein C-Catalyzed inactivation", Blood, vol. 99, No. 11, pp. 3993-3998.
Nogami, et al. (May 2007) "Relationship Between the Binding Sites for von Willebrand Factor, Phospholipid, and Human Factor VIII C2 Inhibitor Alloantibodies within the Factor VIII C2 Domain", International Journal of Hematology, vol. 85, No. 4, pp. 317-322.
Nolan et al. Recombinant factor VIII Fc fusion protein for the treatment of severe haemophilia A: final results from the ASPIRE extension study. Haemophilia 2020:26(3):494-502.
Non-Final Office Action received for U.S. Appl. No. 14/894,108, mailed on May 21, 2020.
Non-Final Office Action Received for U.S. Appl. No. 13/513,424, mailed on May 5, 2014, 11 Pages.
Non-Final Office Action Received for U.S. Appl. No. 13/793,783, mailed on Mar. 11, 2015, 11 Pages.
Non-Final Office Action Received for U.S. Appl. No. 14/964,289, mailed on Apr. 10, 2018, 11 Pages.
Non-Final Office Action Received for U.S. Appl. No. 16/270,302, mailed on Feb. 18, 2021, 12 Pages.
Nord, et al. (Aug. 1997) "Binding Proteins Selected from Combinatorial Libraries of an α-Helical Bacterial Receptor Domain", Nature Biotechnology, vol. 15, Issue 8, pp. 772-777.
Notice of Allowance Received for U.S. Appl. No. 13/513,424, mailed on Feb. 3, 2015, 16 Pages.
Notice of Allowance Received for U.S. Appl. No. 13/793,783, mailed on Sep. 9, 2015, 12 Pages.
Notice of Allowance Received for U.S. Appl. No. 14/964,289, mailed on Nov. 8, 2018, 9 Pages.
NUWIQ [package insert], SE-112 75, Sweden: Octapharma, 2017.
O'Hara et al., "New challenges for an expanding generation of older persons with haemophilia", J Haem Pract 2022, 9(1), 13 pages.
O'Brien, et al. (Apr. 15, 1990) "Purification and Characterization of Factor VIII 372-Cys: A Hypofunctional Cofactor from A Patient with Moderately Severe Hemophilia A", Blood, vol. 75, No. 8, pp. 1664-1672.
O'Connell, et al. (Aug. 2, 2002) "Phage versus Phagemid Libraries for Generation of Human Monoclonal Antibodies", Journal of Molecular Biology, vol. 321, Issue 1, pp. 49-56.
Office Action mailed Apr. 16, 2013, in U.S. Appl. No. 12/806,005, Schellenberger, et al., filed Aug. 2, 2010.
Office Action mailed Apr. 17, 2019, for U.S. Appl. No. 15/110,673, inventor Ekta Seth Chhabra, filed Jul. 8, 2016.
Office Action mailed Apr. 30, 2018, in United States U.S. Appl. No. 14/379,196 inventor Ekta Seth Chhabra, filed Aug. 15, 2014.
Office Action mailed Aug. 23, 2012, in United States U.S. Appl. No. 12/848,984, Schellenberger, et al., filed Aug. 2, 2010.
Office Action mailed Aug. 7, 2018, for U.S. Appl. No. 14/379,192, inventor Ekta Seth Chhabra, filed Feb. 20, 2015.
Office Action mailed Dec. 12, 2017 in U.S. Appl. No. 14/371,948, inventor Ekta Seth Chhabra, filed Jul. 11, 2014, 21 pages.
Office Action mailed Feb. 25, 2014, in United States U.S. Appl. No. 13/392,509, Schellenberger, et al., filed Feb. 24, 2012.
Office Action mailed Jan. 14, 2014, in U.S. Appl. No. 12/796,650, Schellenberger, et al., filed Jun. 8, 2010.
Office Action mailed Jan. 26, 2018, in U.S. Appl. No. 14/895,264 inventor Ekta Seth Chhabra, filed Dec. 2, 2015.
Office Action mailed Jul. 2, 2013 in U.S. Appl. No. 13/392,511, Schellenberger, V. et al., filed Jun. 27, 2012.
Office Action mailed Jul. 21, 2017, in U.S. Appl. No. 14/413,765, inventor Ekta Seth Chhabra, filed Jan. 9, 2015.
Office Action mailed Jun. 17, 2015, in U.S. Appl. No. 14/317,888, Schellenberger, et al., filed Jun. 27, 2014.
Office Action mailed Jun. 18, 2020, for U.S. Appl. No. 16/154,310, inventor Ekta Seth Chhabra, filed Oct. 8, 2018.
Office Action mailed Jun. 21, 2013, in U.S. Appl. No. 12/806,004, Schellenberger, et al., filed Aug. 2, 2010.
Office Action mailed Jun. 25, 2018 in U.S. Appl. No. 14/371,948 inventor Ekta Seth Chhabra, filed Jul. 11, 2014.
Office Action mailed Mar. 16, 2018, for U.S. Appl. No. 14/379,192, inventor Ekta Seth Chhabra, filed Feb. 20, 2015.
Office Action mailed Mar. 22, 2013, in U.S. Appl. No. 12/796,650, Schellenberger, et al., filed Jun. 8, 2010.
Office Action mailed Mar. 29, 2017, in U.S. Appl. No. 14/413,765 inventor Ekta Seth Chhabra, filed Jan. 9, 2015.
Office Action mailed Mar. 9, 2016 in U.S. Appl. No. 14/218,524, filed Mar. 18, 2014.
Office Action mailed Mar. 9, 2020, for U.S. Appl. No. 14/371,948, inventor Ekta Seth Chhabra, filed Jul. 11, 2014.
Office Action mailed May 7, 2013, in U.S. Appl. No. 12/699,761, Schellenberger, et al., filed Feb. 3, 2010.
Office Action mailed May 17, 2017, in U.S. Appl. No. 14/371,948, inventor Ekta Seth Chhabra, filed Jul. 11, 2014.
Office Action mailed May 20, 2014 in U.S. Appl. No. 13/392,511, Schellenberger, V. et al., filed Jun. 27, 2012.

(56) References Cited

OTHER PUBLICATIONS

Office action mailed May 23, 2017, in U.S. Appl. No. 14/894,108, inventor Ekta Seth Chhabra, filed May 3, 2016.
Office Action mailed May 30, 2017, in U.S. Appl. No. 14/379,192, inventor Ekta Seth Chhabra, filed Feb. 20, 2015.
Office Action mailed Nov. 1, 2016, in U.S. Appl. No. 14/379,192, inventor Ekta Seth Chhabra, filed Feb. 20, 2015.
Office Action mailed Nov. 18, 2019, for U.S. Appl. No. 14/895,264, inventor Ekta Seth Chhabra, filed Dec. 2, 2015.
Office Action mailed Nov. 24, 2015 in U.S. Appl. No. 14/317,888, filed Jun. 27, 2014.
Office Action mailed Oct. 5, 2012, in U.S. Appl. No. 12/806,004, Schellenberger, et al., filed Aug. 2, 2010.
Office Action mailed Oct. 20, 2014 in U.S. Appl. No. 13/392,511, Schellenberger, V. et al., filed Jun. 27, 2012.
Office Action mailed Sep. 11, 2013, in U.S. Appl. No. 12/848,984, Schellenberger, et al., filed Aug. 2, 2010.
Office Action mailed Sep. 19, 2019, for U.S. Appl. No. 14/371,948, inventor Ekta Seth Chhabra, filed Jul. 11, 2014.
Office Action mailed Sep. 25, 2017, in U.S. Appl. No. 14/379,196, Kulman, filed Feb. 15, 2013.
Office Action mailed Sep. 27, 2017, in U.S. Appl. No. 14/379,192, inventor Ekta Seth Chhabra, filed Feb. 20, 2015.
Office Action mailed Sep. 5, 2018, in U.S. Appl. No. 14,379,196, inventor Kulman, J., et al., filed Aug. 15, 2014.
Office Action mailed Sep. 7, 2018, in U.S. Appl. No. 14/895,264 inventor Ekta Seth Chhabra, filed Dec. 2, 2015.
Office Action mailed, Oct. 29, 2019 in U.S. Appl. No. 15/110,673 inventor Ekta Seth Chhabra, filed Jul. 8, 2016.
Office Action Received for European Patent Application No. 10835255.0, mailed on Aug. 6, 2015, 4 Pages.
Office Action Received for European Patent Application No. 10835255.0, mailed on Feb. 7, 2017, 4 Pages.
Office Action Received for European Patent Application No. 10835255.0, mailed on Jun. 3, 2016, 3 Pages.
Office Action Received for European Patent Application No. 17194648.6, mailed on Jul. 10, 2019, 4 Pages.
Office Action Received for European Patent Application No. 17194648.6, mailed on Mar. 18, 2020, 4 Pages.
Ofir, et al. (May 2005) "Versatile Protein Microarray Based on Carbohydrate-Binding Modules", Proteomics, vol. 5, No. 7, pp. 1806-1814.
Oganesyan, et al., "Structural Characterization of a Human Fc Fragment Engineered for Extended Serum Half-Life", Molecular Immunology, vol. 46, No. 8-9, pp. 1750-1755, May 1, 2009.
Ökten, et al. (Aug. 1, 2004) "Myosin VI Walks Hand-Over-Hand Along Actin", Nature Structural & Molecular Biology, vol. 11, pp. 884-887.
Oldenburg et al. Improved joint health in subjects with severe haemophilia A treated prophylactically with recombinant factor VIII Fc fusion protein. Haemophilia. 2018:24(1):77-84.
Oldenburg et al., Controlled, cross-sectional MRI evaluation of joint status in severe haemophilia A patients treated with prophylaxis vs on demand, Haemophilia, 2015, 21:171-179.
Oldenburg et al., Genetic risk factors for inhibitors to factors VIII and IX, Haemophilia, 2006,12(6): 15-22.
Oldenburg et al., Prophylaxis in adult patients with severe haemophilia A., Thrombosis Research, 2014, s33-s37.
Oldenburg, Optimal treatment strategies for hemophilia: achievements and limitations of current prophylactic regimens, Blood, 2015, 125: 2038-2044.
O'Leary, et al. (Jan. 2005) "Solution Structure and Dynamics of a Prototypical Chordin-like Cysteine-rich Repeat (von Willebrand Factor Type C Module) from Collagen IIA", Journal of Biological Chemistry, vol. 279, No. 51, pp. 53857-53866.
Orlova, et al. (Apr.-Jun. 2013) "Blood Clotting Factor VIII: From Evolution to therapy", Acta Naturae, vol. 5, No. 2, pp. 19-39.
Ormo, et al. (1996) "Crystal Structure of the Aequorea Victoria Green Fluorescent Protein", Science, vol. 273, No. 5280, pp. 1392-1395.
Osterud, et al. (Jul. 18, 1972) "Activation of the Coagulation Factor VII by Tissue Thromboplastin and Calcium", Biochemistry, vol. 11, No. 15, pp. 2853-2857.
Padiolleau-LeFevre, et al. (Mar. 2007) "Expression and Detection Strategies for an ScFv Fragment Retaining the Same High Affinity than Fab and Whole Antibody: Implications for therapeutic Use in Prion Diseases", Molecular Immunology, vol. 44, Issue 8, pp. 1888-1896.
Pallaghy, et al. (Nov. 20, 1993) "Three-dimensional Structure in Solution of the Calcium Channel Blocker ω-Conotoxin", Journal of Molecular Biology, vol. 234, Issue 2, pp. 405-420.
Pallaghy, et al. (Oct. 1994) "A Common Structural Motif Incorporating a Cystine Knot and a Triple-Stranded β-sheet in Toxic and Inhibitory Polypeptides", Protein Science, vol. 3, Issue 10, pp. 1833-1839.
Palmiter, et al. (1983) "Metallothionein-Human GH Fusion Genes Stimulate Growth of Mice", Science, vol. 222, No. 4625, pp. 809-814.
Pan, et al. (Dec. 1993) "Structure and Expression of Fibulin-2, A Novel Extracellular Matrix Protein with Multiple EGF-Like Repeats and Consensus Motifs for Calcium Binding", Journal of Cell Biology, vol. 123, Issue 5, pp. 1269-1277.
Pan, et al., "Enhanced efficacy of recombinant FVIII in noncovalent complex with PEGylated liposome in hemophilia A mice", Blood Journal, vol. 114, No. 13, pp. 2802-2811, Sep. 24, 2009.
Panda, et al. (2003) "Bioprocessing of therapeutic Proteins from the Inclusion Bodies of *Escherichia coli*", Advances in Biochemical Engineering / Biotechnology, vol. 85, pp. 43-93.
Panicali, et al. (Aug. 1982) "Construction of Poxviruses as Cloning Vectors: Insertion of the Thymidine Kinase Gene from Herpes Simplex Virus into the DNA of Infectious Vaccinia Virus", Proceedings of the National Academy of Sciences of the United States of America, vol. 79, No. 16, pp. 4927-4931.
Park, et al. (2010) "A Diagnostic Challenge: Mild Hemophilia B with Normal Activated Partial Thromboplastin Time", Blood Coagulation & Fibrinolysis, vol. 21, No. 4, pp. 368-371.
Partial European Search Report received for European Patent Application No. 12868427.1, mailed on Sep. 18, 2015, 7 Pages.
Pasi et al. Improvement in pain-related quality of life in patients with hemophilia A treated with rFVIIIFc individualized prophylaxis: post hoc analysis from the A-LONG study. Therapeutic Advances in Hematology. 2022.
Patarroyo-White et al., "A FVIII/VWF Chimeric Protein with VWF Independent Pharmacokinetic Properties", XXV Congress of the International Society of Thrombosis and Haemostasis (ISTH), Jun. 20-25, 2015, Toronto, Canada.
Patra, et al. (Mar. 2000) "Optimization of Inclusion Body Solubilization and Renaturation of Recombinant Human Growth Hormone from *Escherichia coli*", Protein Expression and Purification, vol. 18, Issue 2, pp. 182-192.
Pelegrini (Nov. 2005) "Plant Gamma-Thionins: Novel insights on The Mechanism of Action of a Multi-Functional Class of Defense Proteins", The International Journal of Biochemistry & Cell Biology, vol. 37, No. 11, pp. 2239-2253.
Pepinsky, et al. (Jun. 2001) "Improved Pharmacokinetic Properties of a Polyethylene Glycol-Modified form of Interferon-β-1a with Preserved In vitro Bioactivity", Journal of Pharmacology and Experimental therapeutics, vol. 297, vol. 3, pp. 1059-1066.
Peters et al., Biochemical and functional characterization of a recombinant monomeric factor VIII-Fc fusion protein, J Thromb Haemost., 2013, 11(1): 132-141.
Peters RT, et al., Prolonged activity of factor IX as a monomeric Fo fusion protein, Blood, 2010, 115(10): 2057-2064.
Petersen, et al. (Nov. 25, 2003) "the Dual Nature of Human Extracellular Superoxide Dismutase: one Sequence and Two Structures", Proceedings of the National Academy of Sciences of the United States of America, vol. 100, No. 24, pp. 13875-13880.
Peyvandi, et al., "Genetic Diagnosis of Haemophilia and Other Inherited Bleeding Disorders", Haemophilia, vol. 12, Suppl 3, pp. 82-89, Jul. 1, 2006.
Pi, et al. (Feb. 2006) "Analysis of Expressed Sequence Tags from the Venom Ducts of Conus Striatus: Focusing on the Expression Profile of Conotoxins", Biochimie, vol. 88, Issue 2, pp. 131-140.

(56) References Cited

OTHER PUBLICATIONS

Pierce, Glenn, MD, Ph.D., "Innovation in Hemophilia: From Blood to Genes, and the Unintended Consequences Along the Way", ISPE Annual Meeting & Expo, Oct. 29 -Nov. 1, 2017, https://www2.ispe.org/imis/conference-handouts/NA17CEOCT1/Pierce_NA17CEOCT1_Innovation-in-Hemophilia-From-Blood-to-Genes-and-the-Unintended-Consequences-Along-the-Way.pdf.
Pimanda, et al. (Nov. 2002) "the von Willebrand Factor-Reducing Activity of Thrombospondin-1 is Located in the Calcium-Binding/C-Terminal Sequence and Requires a Free Thiol at Position 974", Blood, vol. 100, No. 8, pp. 2832-2838.
Pipe et al., "A global comparative field study to evaluate the factor VIII activity of efanesoctocog alfa by one-stage clotting and chromogenic substrate assays at clinical haemostasis laboratories", Haemophilia, Oct. 30, 2023, 1-10.
Pipe et al., "Efanesoctocog Alfa Activity Assessment with One-Stage Clotting (OSA) and Chromogenic Substrate (CSA) Factor VIII Assays", Abstract, Haemophilia, Feb. 5, 2023.
Pipe et al., "Efanesoctocog Alfa Activity Assessment with One-Stage Clotting (OSA) and Chromogenic Substrate (CSA) Factor VIII Assays", Poster, 16th Annual Congress of the European Association for Haemophilia and Allied Disorders, Feb. 7-10, 2023.
Pipe et al., "Characterization of a Genetically Engineered Inactivation-Resistant Coagulation Factor VIIIa", PNAS USA, Oct. 1997, vol. 94, pp. 11851-11856.
Pipe et al., Life in the shadow of a dominant partner: the FVIII-VWF association and its clinical implications for hemophilia A, Blood, 2016, 128(16): 2007-2016.
Pipe, et al. (2011) "Functional Factor VIII Made with Von Willebrand Factor at High Levels in Transgenic Milk", Journal of Thrombosis and Haemostasis, vol. 9, No. 11, pp. 2235-2242.
Pipe, S.W., "Functional roles of the factor VIII B domain", Haemophilia, vol. 15, 2009, pp. 1187-1196.
Pipe, Stewen W. (2005) "the Promise and Challenges of Bioengineered Recombinant Clotting Factors", Journal of Thrombosis and Haemostasis, vol. 3, No. 8, pp. 1692-1701.
Pittman, et al., "Biochemical, Immunological, and in Vivo Functional Characterization of B-Domain-Deleted Factor VIII", Blood, vol. 81, pp. 29252935, Jan. 1, 1993.
Podust et al. Extension of in vivo half-life of biologically active molecules by XTEN protein polymers. J Control Release. 2016; 240:52-66.
Pokidysheva, et al. (2004) "the Structure of the Cys-Rich Terminal Domain of Hydra Minicollagen, Which Is Involved in Disulfide Networks of the Nematocyst Wall", the Journal of Biological Chemistry, vol. 279, No. 29, pp. 30395-30401.
Pool et al., High potency antihaemophilic factor concentrate prepared from cryoglobulin precipitate, Nature, 1964,203: 312.
Pool, et al. (Sep. 8, 1966) "Ineffectiveness of intramuscularly injected Factor 8 concentrate in two Hemophilic patients", the New England Journal of Medicine, vol. 275, No. 10, pp. 547-548.
Popkov, et al. (2004) "Isolation of Human Prostate Cancer Cell Reactive Antibodies Using Phage Display Technology", Journal of Immunological Methods, vol. 291, No. 1-2, pp. 137-151.
Powell et al., Safety and prolonged activity of recombinant factor VIII Fc fusion protein in hemophilia A patients, Blood, 2012, 119(13): 3031-3037.
Powell JS, et al., Phase 3 Study of Recombinant Factor IX Fc Fusion Protein in Hemophilia B, N Engl J Med., 2013, 369(24): 2313-2323.
Prilusky, et al. (2005) "FoldIndex@: A Simple tool to Predict Whether A Given Protein Sequence is intrinsically Unfolded", Bioinformatics, vol. 21, No. 16, pp. 3435-3438.
Prinz, et al. (1997) "the Role of the Thioredoxin and Glutaredoxin Pathways in Reducing Protein Disulfide Bonds in the *Escherichia coli* Cytoplasm", the Journal of Biological Chemistry, vol. 272, No. 25, pp. 15661-15667.
Proft, T. (Jan. 2010) "Sortase-Mediated Protein Ligation: An Emerging Biotechnology Tool for Protein Modification and Immobilisation", Biotechnology Letters, vol. 32, No. 1, pp. 1-10.
Purvis et al, "Two Cys Residues Essential for Von Willebrand Factor Multimer Assembly in the Golgi", Proc Natl Acad Sci U S A, vol. 104 (40), pp. 15647-15652.
Puthenveetil, et al. (Nov. 2009) "Yeast Display Evolution of a Kinetically Efficient 13-Arnino Acid Substrate for Lipoic Acid Ligase", Journal of the American Chemical Society, vol. 131, No. 45, pp. 16430-16438.
Qi, et al. (2005) "Structural Features and Molecular Evolution of Bowman-Birk Protease Inhibitors and their Potential Application", Acta Biochimica Et Biophysica Sinica, vol. 37, No. 5, pp. 283-292.
Rajani et al., OC 75.5 Recombinant Factor VIII Fc Fusion Protein Inhibits Inflammatory Osteoclast Formation in vitro, Research and Practice In Thrombosis and Haemostasis, 2019, 3(S1): 126.
Ramgren., A clinical and medico-social study of haemophilia in Sweden, Acta Med Scand Suppl., 1962,379: 111-190.
Rao, et al. (1985) "Activation of Human Factor VII During Clotting In Vitro", Blood, vol. 65, No. 1, pp. 218-226.
Rao, et al. (1998) "Molecular and Biotechnological aspects of Microbial Proteases", Microbiology and Molecular Biology Reviews: MMBR, vol. 62, No. 3, pp. 597-635.
Rasmussen, et al. (2002) "Tumor Cell-Targeting by Phage-Displayed Peptides", Cancer Gene therapy, vol. 9, No. 7, pp. 606-612.
Rath T, et al., Fc-fusion proteins and FcRn: structural insights for longer-lasting and more effective therapeutics, Crit Rev Biotechnol., 2015, 35(2): 235-254.
Raut, et al., "Phospholipid Binding of Factor VIII in Different Therapeutic Concentrates", British Journal of Haematology, vol. 107, No. 2, Blackwell Science Ltd, pp. 323-329, Nov. 1, 1999.
Rawlings, et al. (2004) "Evolutionary Families of Peptidase Inhibitors", the Biochemical Journal, vol. 378, Part 3, pp. 705-716.
Rawlings, et al. (2008) "MEROPS: The Peptidase Database", Nucleic Acids Research vol. 36, Supplement 1, pp. D320-D325.
Rebay, et al. (1991) "Specific EGF Repeats of Notch Mediate Interactions with Delta and Serrate Implications for Notch as a Multifunctional Receptor", Cell, vol. 67, No. 4, pp. 687-699.
Recht, et al., "Clinical Evaluation of Moroctocog Alfa(AF-CC), A New Generation of B-Domain Deleted Recombinant Factor VIII (BDDrFVIII) for Treatment of Haemophilia A: Demonstration of Safety, Efficacy, and Pharmacokinetic Equivalence to Full-Length Recombinant Factor VIII", Haemophilia, vol. 15, No. 4, pp. 869-880, Jul. 1, 2009.
Reding et al., Safety and efficacy of BAY 94-9027, a prolonged-half-life factor VIII. J Thromb Haemost., Mar. 2017,15(3): 411-419.
Restriction Requirement received for U.S. Appl. No. 13/513,424, mailed on Dec. 16, 2013, 8 Pages.
Restriction Requirement received for U.S. Appl. No. 13/793,783, mailed on Oct. 21, 2014, 6 Pages.
Restriction Requirement received for U.S. Appl. No. 16/270,302, mailed on Aug. 20, 2020, 8 Pages.
Rizzo, et al. (2010) "Fluorescent Protein Tracking and Detection", in Live Cell Imaging: A Laboratory Manual, pp. 3-34.
Roberge, et al. (2006) "Construction and Optimization of a Cc49-Based ScFv-Beta-Lactamase Fusion", Protein Engineering, Design & Selection: PEDS, vol. 19, No. 4, pp. 141-145.
Rodriguez-Merchan, Carlos E. (2003) "Management of Musculo-skeletal Complications of Hemophilia", Seminars in Thrombosis and Hemostasis., vol. 29, No. 01, pp. 87-96.
Rodriguez-Santana et al., "Differential humanistic and economic burden of mild, moderate and severe haemophilia in european adults: a regression analysis of the CHESS II study", Orphanet Journal of Rare Diseases. 2022, 17(148), 10 pages.
Rodriguez-Santana et al., "Health-related quality of life, direct medical and societal costs among children with moderate or severe haemophilia in Europe: multivariable models of the CHESS-PAEDs study", Orphanet Journal of Rare Diseases, 2022, 17(150), 9 pages.
Ron, et al., "Expression of Biologically Active Recombinant Keratinocyte Growth Factor—Structure/Function Analysis of Amino-Terminal Truncation Mutants", Journal of Biological Chemistry, vol. 268, No. 4, pp. 2984-2988, Jan. 1, 1993.
Roopenian et al., FcRn: the neonatal Fc receptor comes of age, Nat Rev Immunol., 2007, 7(9): 715-725.

(56) References Cited

OTHER PUBLICATIONS

Roosendaal et al., Blood-induced joint damage in hemophilia, Semin Thromb Haemost., 2003, 29(1): 37-42.
Roovers, et al. (Mar. 2007) "Efficient Inhibition of EGFR Signaling and of Tumour Growth by Antagonistic anti-EFGR Nanobodies", Cancer Immunology, Immunotherapy, vol. 56, No. 3, pp. 303-317.
Rosa, et al. (2000) "Influence of the Co-Encapsulation of Different Non-Ionic Surfactants on the Properties of PLGA insulin-Loaded Micro spheres", Journal of Controlled Release, vol. 69, No. 2, pp. 283-295.
Rosen (1984) "Assay of Factor VIII:C with a chromogenic substrate", Scandinavian Journal of Haematology, vol. 33, Supplement 40, pp. 139-145.
Rosen, et al. (1985) "Clinical Application of a Chromogenic Substrate Method", Thrombosis and Haemostasis, vol. 54, No. 4, pp. 818-823.
Rosenfeld, et al. (1998) "Biochemical, Biophysical, and Pharmacological Characterization of Bacterially Expressed Human Agouti-Related Protein", Biochemistry, vol. 37, No. 46, pp. 16041-16052.
Rostin, et al., "B-Domain Deleted Recombinant Coagulation Factor VIII Modified with Monomethoxy Polyethylene Glycol", Bioconjugate Chemistry, vol. 11, No. 3, pp. 387-396, May 15, 2000.
Roth, et al. (1993) "Expression of Polysialic Acid in Human Tumors and Its Significance for Tumor Growth", From microbes to man: Polysialic Acid, pp. 335-348.
Roussel, et al. (2001) "Complexation of Two Proteic insect inhibitors to the Active Site of Chymotrypsin Suggests Decoupled Roles for Binding and Selectivity", The Journal of Biological Chemistry, vol. 276, No. 42, pp. 38893-38898.
Routledge, et al. (Oct. 1, 1995) "The Effect of Aglycosylation on The Immunogenicity of a Humanized Therapeutic CD3 Monoclonal Antibody", Transplantation, vol. 60, No. 8, pp. 847-853.
Ruberti, et al. (Jul. 12, 1994) "The Use of The RACE Method to Clone Hybridoma cDNA When V Region Primers Fail", Journal of Immunological Methods, vol. 173, No. 1, pp. 33-39.
Ruther, et al. (Oct. 1983) "Easy Identification of cDNA Clones", The EMBO Journal, vol. 2, No. 10, pp. 1791-1794.
Rychkov, et al. (2007) "Joint Neighbors Approximation of Macromolecular Solvent Accessible Surface Area", Journal of Computational Chemistry, vol. 28, No. 12, pp. 1974-1989.
Saenko et al., A mechanism of inhibition of factor VIII binding to phospholipid by von Willebrand factor, J Biol Chem, 1995, 270(23): 13826-13833.
Saenko, et al. (1997) "the Acidic Region of the Factor VIII Light Chain and the C2 Domain Together form the High Affinity Binding Site for Von Willebrand Factor", Journal of Biological Chemistry, vol. 272, No. 29, pp. 18007-18014.
Saenko, et al. (1999) "Role of The Low-Density Lipoprotein-Related Protein Receptor in Mediation of Factor VIII Catabolism", The Journal of Biological Chemistry, vol. 274, No. 53, pp. 37685-37692.
Saenko, et al. (2005) "the Future of Recombinant Coagulation Factors", Journal of Thrombosis and Haemostasis, vol. 1, pp. 922-930.
Saenko, et al. (Apr. 15, 1994) "A Role for The C2 Domain of Factor VIII in Binding to von Willebrand Factor", Journal of Biological Chemistry, vol. 269, No. 15, pp. 11601-11605.
Saenko, et al. (Jul. 2006) "Strategies Towards a Longer Acting Factor VIII", Haemophilia, vol. 12, Supplement 3, pp. 42-51.
Sahdev, et al. (Jan. 2008) "Production of Active Eukaryotic Proteins Through Bacterial Expression Systems: A Review of the Existing Biotechnology Strategies", Molecular and Cellular Biochemistry, vol. 307, No. 1-2, pp. 249-264.
Sakata, PAR-1 Thrombin Receptor Antagonist, 2012, pp. 47-50.
Salloum, et al. (Apr. 2009) "Anakinra in Experimental Acute Myocardial Infarction—Does Dosage or Duration of Treatment Matter?", Cardiovascular Drugs and therapy Sponsored by the International, Society of Cardiovascular Pharmacotherapy, vol. 23, No. 2, pp. 129-135.
Sambrook et al., Molecular Cloning: A Laboratory Manual, 1989, Second Edition, Cold Spring Harbor Laboratory Press, United States.
Sandberg et al., "Structural and Functional Characterization of B-Domain Deleted Recombinant Factor VIII", Seminars in Hematology, Apr. 2001, vol. 38, No. 2, Suppl. 4, pp. 4-12.
Sanofi, "Capital Markets Day, Play to Win", Presentation Slides, Dec. 10, 2019.
Sanofi, "Press Release: Efanesoctocog alfa met primary and key secondary endpoints in pivotal study in hemophilia A, demonstrating superiority to prior factor prophylaxis treatment", Mar. 9, 2022, 3 pages.
Sanofi, "Press Release: FDA approves once-weekly aLTUVIIIO™, a new class of factor VIII therapy for hemophilia A that offers signiciant bleed protection. This positive event triggers impairment erversal, impacting 2022 IFRS net income; No. change on business net income (non-IFRS)", Feb. 24, 2023, 2 pages.
Sanofi, "Press Release: FDA grants priority review to efanesoctocof alfa for people with hemophilia A", Aug. 30, 2022, 3 pages.
Sanofi, "FDA grants efanesoctocog alfa Breakthrough Therapy designation for hemophilia A", Press Release, Jun. 1, 2022.
Sanofi, A Phase 1/2a, Open-Label, Dose-Escalation Study to Determine the Safety, Tolerability, and Pharmacokinetic of a Single Intravenous Injection of rFVIIIFc-VWF-XTEN (BIVV001) in Previously Treated Adults with Severe Hemophilia A, Model Patient Information Sheet and Informed Consent Form, Protocol No. 242HA101, EudraCT No. 2017-001140-34, Version 3, Jun. 13, 2017, 12 pages.
Sanofi, A Phase 3 Open-Label Multicenter Study of the Safety, Efficacy, and Pharmacokinetics of Intravenous Recombinant Coagulation Factor VIII Fc-von Willebrand Factor-XTEN Fusion Protein (rFVIIIFc-VWF-XTEN; BIVV001) in Previously Treated Patients under 12 Years of Age With Severe Hemophilia A, Core Study Information and Informed Consent Form, Protocol No. EFC16293, Nov. 6, 2019.
Sanofi, Hemophilia Investor Event Presentation slides, Jul. 13, 2022, 48 pages.
Sanofi, Media Update: Sanofi to present new clinical data reinforcing novel therapies across rare blood disorders at ASH 2022, Nov. 30, 2022, 4 pages.
Sanofi, R&D Investor Event: Lead with innovation, Presentation slides, Jun. 23, 2020, 82 pages.
Saqib U, et al. Phytochemicals as modulators of M1-M2 macrophages in inflammation. Oncotarget. 2018;9(25): 17937-17950.
Sarver, et al. (Dec. 1987) "Stable Expression of Recombinant Factor Viii Molecules Using a Bovine Papillomavirus Vector", DNA, vol. 6, No. 6, pp. 553-564.
Scandella, et al. (1989) "Localization of Epitopes for Human Factor VIII Inhibitor Antibodies by Immunoblotting and Antibody Neutralization", Blood, vol. 74, No. 5, pp. 1618-1626.
Scandella, et al. (Aug. 1, 1988) "Epitope Mapping of Human Factor VIII Inhibitor Antibodies by Deletion Analysis of Factor VIII Fragments Expressed in *Escherichia coli*", Proceedings of the National Academy of Sciences, vol. 85, No. 16, pp. 6152-6156.
Schatz, P. J. (1993) "Use of Peptide Libraries to Map the Substrate Specificity of a Peptide-Modifying Enzyme: A 13 Residue Consensus Peptide Specifies Biotinylation In *Escherichia coli*", Biotechnology, vol. 11, No. 10, pp. 1138-1143.
Schellenberger et al., A recombinant polypeptide extends the in vivo half-life of peptides and proteins in a tunable manner, Nat Biotechnol., 2009, 27(12): 1186-1190.
Schellenberger, et al. (1993) "Analysis of Enzyme Specificity by Multiple Substrate Kinetics", Biochemistry, vol. 32, No. 16, pp. 4344-4348.
Schlapschy, et al. (Jun. 1, 2007) "Fusion of a Recombinant Antibody Fragment with a Homo-Amino-Acid Polymer: Effects on Biophysical Properties and Prolonged Plasma Half-Life", Protein Engineering, Design and Selection, vol. 20, No. 6, pp. 273-284.
Schmidt, et al. (2003) "Structure-Function Relationships in Factor IX and Factor IXa", Trends in Cardiovascular Medicine, vol. 13, No. 1, pp. 39-45.

(56) References Cited

OTHER PUBLICATIONS

Scholle, et al. (2005) "Efficient Construction of a Large Collection of Phage-Displayed Combinatorial Peptide Libraries", Combinatorial Chemistry High Throughput Screening, vol. 8. No. 6, pp. 545-551.
Schulte, et al., "Prolonged In-Vivo Half-Life of FVIIa by Fusion to Albumin", Blood, 2007, vol. 110, No. 11, Abstract 3142, American Society of Hematology.
Schulte, S (2011) "Pioneering Designs for Recombinant Coagulation Factors", Thrombosis Research, vol. 128, Supplement 1, pp. S9-S12.
Schulte, Stefan (Dec. 2008) "Use of Albumin Fusion Technology to Prolong the Half-Life of Recombinant Factor", Thrombosis Research, vol. 122, Supplement 4, pp. S14-S19.
Schulte, Stefan, "Half-Life Extension Through Albumin Fusion Technologies", Thrombosis Research, vol. 124, Supplement 2, pp. S6-S8, Dec. 1, 2009.
Schultz-Cherry, et al. (1994) "The Type 1 Repeats of Thrombospondin 1 Activate Latent Transforming Growth Factor-Beta", the Journal of Biological Chemistry, vol. 269, No. 43, pp. 26783-26788.
Schultz-Cherry, et al. (1995) "Regulation of Transforming Growth Factor-Beta Activation by Discrete Sequences of Thrombospondin 1", Journal of Biological Chemistry, vol. 270, No. 13, pp. 7304-7310.
Schulz, et al. (2005) "Potential of Nir-Ft-Raman Spectroscopy in Natural Carotenoid Analysis", Biopolymers, vol. 77, No. 4, pp. 212-221.
Schwab et al., Intravenous immunoglobulin therapy: how does IgG modulate the immune system?, Nat Rev Immunol., 2013, 13(3): 176-189.
Scott et al., Factor VIII: Perspectives on Immunogenicity and Tolerogenic Strategies. Front Immunol. 2020, 10: 3078.
Shaikh, et al. "Examining the impact of haemophilia treatment on health-related quality of life", Haemophilia, 2022, 28(5): 796-805.
Shapiro et al., "Recombinant factor VIII Fc fusion protein: extended-interval dosing maintains low bleeding rates and correlates with von Willebrand factor levels", Journal of Thrombosis and Haemostasis, Nov. 2014, 12(11): 1788-1800.
Shapiro et al., Recombinant factor IX-Fc fusion protein (rFIXFc) demonstrates safety and prolonged activity in a phase 1/2a study in hemophilia B patients, Blood, 2012, 119(3): 666-672.
Sheffield, et al. (2004) "Effects of Genetic Fusion of Factor IX to Albumin on In Vivo Clearance in Mice and Rabbits", British Journal of Haematology, vol. 126, No. 4, pp. 565-573.
Shen, et al. (1998) "A Type I Peritrophic Matrix Protein from the Malaria Vector Anopheles Gambiae Binds to Chitin Cloning, Expression, and Characterization", Journal of Biological Chemistry, vol. 273, No. 28, pp. 17665-17670.
Shen, et al. (Feb. 1, 2008) "The Tertiary Structure and Domain organization of Coagulation Factor VIII", Blood, vol. 111, No. 3, pp. 1240-1247.
Shields, et al. (Mar. 2, 2001) "High Resolution Mapping of the Binding Site on Human IgG1 for Fc Gamma RI, Fc Gamma RII, Fc Gamma RIII, and FcRn and Design of IgG1 Variants with Improved Binding to the Fc Gamma R", Journal of Biological Chemistry, vol. 276, No. 9, pp. 6591-6604.
Shima, et al. (1993) "A Factor VIII Neutralizing Monoclonal Antibody and A Human Inhibitor Alloantibody Recognizing Epitopes in The C2 Domain inhibit Factor VIII Binding to Von Willebrand Factor and to Phosphatidylserine", Journal of Thrombosis and Haemostasis, vol. 69, No. 3, pp. 240-246.
Shimomura, et al. (1962) "Extraction, Purification and Properties of Aequorin, a Bioluminescent Protein from the Luminous Hydromedusan, Aequorea", Journal of Cellular and Comparative Physiology, vol. 59, pp. 223-239.
Shukla et al., "Interaction of Arginine with Proteins and the Mechanism by Which It Inhibits Aggression", J Phys Chem B., 2010, 114: 13426-13438.
Sidhu, et al. (2000) "Phage Display for Selection of Novel Binding Peptides", Methods in Enzymology, vol. 328, No., pp. 333-363.
Silverman, et al. (2005) "Multivalent Avimer Proteins Evolved by Exon Shuffling of a Family of Human Receptor Domains", Nature Biotechnology, vol. 23, No. 12, pp. 1556-1561.
Simonet, et al. (2002) "Structural and Functional Properties of a Novel Serine Protease Inhibiting Peptide Family in Arthropods", Comparative Biochemistry and Physiology. Part B, Biochemistry & Molecular Biology, vol. 132, No. 1, pp. 247-255.
Simonsen, et al. (May 1983) "Isolation and Expression of An Altered Mouse Dihydrofolate Reductase cDNA", Proceedings of the National Academy of Sciences of the United States of America, vol. 80, No. 9, pp. 2495-2499.
Singh, et al. (Dec. 2001) "ProPred: Prediction of HLA-DR Binding Sites", Bioinformatics, vol. 17, No. 12, pp. 1236-1237.
Skinner et al. "WFH: Closing the global gap—achieving optimal care", Haemophilia, 2012, 18(Suppl. 4): 1-12.
Skinner, et al. (1989) "Purification and Characterization of Two Classes of Neurotoxins from the Funnel Web Spider, Agelenopsis Aperta", the Journal of Biological Chemistry, vol. 264, No. 4, pp. 2150-2155.
Skotnicki et al., Efficacy, safety, and pharmacokinetic profiles of a plasma-derived VWF/FVIII concentrate (Voncento®) in subjects with haemophilia A (SWIFT-HA study). Thrombosis Resarch, Jan. 2016, 137: 119-125.
Smith, et al. (1988) "Single-Step Purification of Polypeptides Expressed in *Escherichia coli* as Fusions with Glutathione S-Transferase", Gene, vol. 67, No. 1, pp. 31-40.
Smith, et al. (1997) "Phage Display", Chemical Reviews, vol. 97, vol. 2, pp. 391-410.
Smith, et al. (Dec. 1981) "Comparison of Biosequences", Advances in Applied Mathematics, vol. 2, No. 4, pp. 482-489.
Smith, et al. (May 1983) "Molecular Engineering of the Autographa Californica Nuclear Polyhedrosis Virus Genome: Deletion Mutations within the Polyhedrin Gene", Journal of Virology, vol. 46, No. 2, pp. 584-593.
So, et al. (2001) "Contribution of Conformational Stability of Hen Lysozyme to Induction of Type 2 T-Helper Immune Responses", Immunology, vol. 104, No. 3, pp. 259-268.
Sommermeyer, et al. (1987) "Klinisch verwendete Hydroxyethylstärke: physikalisch chemische Charakterisierung", Krankenhauspharmazie, vol. 8, No. 8, Deutscher Apotheker Verlag, Birkenwaldstr, Germany, pp. 271-278.
Soucie et al., The frequency of joint hemorrhages and procedures in nonsevere hemophilia A vs B, Blood Adv., 2018,2: 2136-2144.
Southern, et al. (1982) "Transformation of Mammalian Cells to Antibiotic Resistance with a Bacterial Gene Under Control of the Sv40 Early Region Promoter", Journal of Molecular and Applied Genetics 1, No. 4, pp. 327-341.
Spencer, et al. (2011) "Lentiviral Vector Platform for Production of Bioengineered Recombinant Coagulation Factor VIII", Molecular therapy, vol. 19, No. 2, pp. 302-309.
Spira, et al., "Evaluation of Liposomal Dose in Recombinant Factor VIII Reconstituted with Pegylated Liposomes for the Treatment of Patients with Severe Haemophilia A", Thrombosis and Haemostasis, vol. 100, No. 4, pp. 429434, Jan. 1, 2008.
Spira, et al., "Prolonged Bleeding-Free Period Following Prophylactic Infusion of Recombinant Factor VIII Reconstituted with Pegylated Liposomes", Blood, vol. 108, No. 12, pp. 3668-3673, Jan. 1, 2006.
Srivastava et al., Treatment Guidelines Working Group on behalf of the World Federation of Hemophilia, Guidelines for the management of hemophilia, Haemophilia, 2013, 19(1): e1-47.
Srivastava et al., WFH Guidelines for the Management of Hemophilia, 3rd edition, Haemophilia. 2020, 26 Suppl 6: 1-158.
Srivastava, et al. (2005) "Application of Self-Assembled Ultra-Thin Film Coatings to Stabilize Macromolecule Encapsulation in Alginate Micro spheres", Journal of Microencapsulation, vol. 22, No. 4, pp. 397-411.
Srour, et al., "Modified Expression of Coagulation Factor VIII by Addition of a Glycosylation Site at the N Terminus of the Protein", Annals of Hematology, vol. 87, Issue 2, pp. 107-112, Feb. 1, 2008.
Staber et al., "Efanesoctocog alfa half-life and clearance are independent of von Willebrand factor (VWF) in severe hemophilia A: a

(56) References Cited

OTHER PUBLICATIONS post hoc analysis from Phase 1/2a studies", Abstract, Blood 2022 Congress: Sep. 11-14, 2022, Sydney.
Staber et al., "Efanesoctocog alfa half-life and clearance are independent of von Willebrand factor (VWF) in severe hemophilia A: a post hoc analysis from Phase 1/2a studies", Poster, Blood 2022 Congress: Sep. 11-14, 2022, Sydney.
Staber et al., "Efanesoctocog alfa Exhibits Von Willebrand Factor-Independent Pharmacokinetics in Severe Hemophilia A: A Post Hoc Analysis From Phase 1/2a Studies", Abstract, THSNA 2022 Summit Abstract Proceedings, American Journal of Hematology, E104.
Staber et al., "Efanesoctocog alfa Exhibits Von Willebrand Factor-Independent Pharmacokinetics in Severe Hemophilia A: A Post Hoc Analysis From Phase 1/2a Studies", Presentation Slides, THSNA 2022 Summit Abstract Proceedings, 14 pages.
Staber et al., "Efanesoctocog Alfa Half-Life and Clearance Are Independent of von Willebrand Factor in Severe Hemophilia A: A Post Hoc Analysis From Phase 1/2a Studies", 44th Congress of the Japanese Society on Thrombosis and Hemostasis, Jun. 23-25, 2022.
Staber et al., "Efanesoctocog Alfa Half-Life and Clearance Are Independent of von Willebrand Factor in Severe Hemophilia A: A Post Hoc Analysis From Phase 1/2a Studies", Efanesoctocog alfa half-life and VWF independence Abstract—Encore, NHF 2022 Congress: Aug. 25-27, 2022, Houston & Virtual.
Staber et al., "Efanesoctocog Alfa Half-Life and Clearance Are Independent of von Willebrand Factor in Severe Hemophilia A: A Post Hoc Analysis From Phase 1/2a Studies", Presentation Slides, NHF 7th Annual Bleeding Disorders Conference (BDC) 2022, Aug. 25-27, 2022.
Staber et al., "Efanesoctocog Alfa Half-Life and Clearance Are Independent of von Willebrand Factor in Severe Hemophilia A: A Post Hoc Analysis From Phase 1/2a Studies", Presentation Slides, The 44th Congress of the Japanese Society on Thrombosis and Hemostasis, 13 pages.
Staber et al., "The 44th Congress of the Japanese Society on Thrombosis and Hemostasis: Abstract Submission Form", 2022.
Stamos, et al. (2004) "Crystal Structure of the HGF Beta-Chain in Complex with the Sema Domain of the Met Receptor", The EMBO Journal, vol. 23, No. 12, pp. 2325-2335.
Steipe, et al. (Jul. 15, 1994) "Sequence Statistics Reliably Predict Stabilizing Mutations in a Protein Domain", Journal of Molecular Biology, vol. 240, No. 3, pp. 188-192.
Stemmer, et al. (1995) "Single-Step Assembly of a Gene and Entire Plasmid from Large Numbers of Oligodeoxyribonucleotides", Gene, vol. 164, No. 1, pp. 49-53.
Stemmer, W. P. (1994) "Rapid Evolution of a Protein in Vitro by DNA Shuffling", Nature, vol. 370, No. 6488, pp. 389-0391.
Stennicke, et al., "Generation and Biochemical Characterization of Glycopegylated Factor Vila Derivatives", Thrombosis and Haemostasis, vol. 100, No. 5, pp. 920-928, Jan. 1, 2008.
Stickler, et al. (2003) "Human Population-Based Identification of CD4+ T-Cell Peptide Epitope Determinants", Journal of Immunological Methods, vol. 281, No. 1-2, pp. 95-108.
Stieltjes, et al., "Continuous Infusion of B-Domain Deleted Recombinant factor VIII ReFacto) in Patients with Haemophilia a Undergoing Surgery: Clinical Experience", Haemophilia, vol. 10, Issue 5, pp. 452-458, Sep. 1, 2004.
Stites, et al. (1995) "Empirical Evaluation of the Influence of Side Chains on the Conformational Entropy of the Polypeptide Backbone", Proteins: Structure, Function, and Bioinformatics, vol. 22, No. 2, pp. 132-140.
Stoll, et al. (2000) "Mechanistic Analysis of Carrier-Mediated Oral Delivery of Protein therapeutics", Journal of Controlled Release, vol. 64, No. 1-3, pp. 217-228.
Story, et al. (Dec. 1, 1994) "A Major Histocompatibility Complex Class I-like Fc Receptor Cloned from Human Placenta: Possible Role in Transfer of Immunoglobulin G from Mother to Fetus", Journal of Experimental Medicine, vol. 180, No. 6, pp. 2377-2381.
Strohl, Fusion Proteins for Half-Life Extension of Biologics as a Strategy to Make Biobetters. BioDrugs. 2015;29(4): 215-239.
Sturniolo, et al. (1999) "Generation of Tissue-Specific and Promiscuous HLA Ligand Database Using DNA Microarrays and Virtual HLA Class II Matrices", Nature Biotechnology, vol. 17, No. 6, pp. 555-561.
Subramani, et al. (1981) "Expression of the Mouse Dihydrofolate Reductase Complementary Deoxyribonucleic Acid in Simian Virus 40 Vectors", Molecular and Cellular Biology, vol. 1, No. 9, pp. 854-864.
Suetake, et al. (2000) "Chitin-Binding Proteins in Invertebrates and Plants Comprise a Common Chitin-Binding Structural Motif", the Journal of Biological Chemistry, vol. 275, No. 24, pp. 17929-17932.
Suetake, et al. (2002) "Production and Characterization of Recombinant Tachycitin, the Cys-Rich Chitin-Binding Protein", Protein Engineering, vol. 15, No. 9, pp. 763-769.
Summers, et al. (1978) "Baculovirus Structural Polypeptides", Virology, vol. 84, No. 2, pp. 390-402.
Supplementary European Search Report received for European Patent Application No. 12868427, mailed on Sep. 18, 2015, 8 pages.
Tagalakis et al., The epidemiology of peripheral vein infusion thrombophlebitis: A critical review, Am J Med., 2002, 113(2): 146-51.
Takahashi, et al. (2000) "Solution Structure of Hanatoxin1, a Gating Modifier of Voltage-Dependent K (+) Channels: Common Surface Features of Gating Modifier Toxins", Journal of Molecular Biology, vol. 297, No. 3, pp. 771-780.
Takenobu, et al. (2002) "Development of P53 Protein Transduction Therapy Using Membrane-Permeable Peptides and the Application to oral Cancer Cells", Molecular Cancer therapeutics, vol. 1, No. 12, pp. 1043-1049.
Tam, et al. (1998) "A Biomimetic Strategy in the Synthesis and Fragmentation of Cyclic Protein", Protein Science, vol. 7, No. 7, pp. 1583-1592.
Tavladoraki, et al. (1999) "A Single-Chain Antibody Fragment is Functionally Expressed in the Cytoplasm of Both *Escherichia coli* and Transgenic Plants", European Journal of Biochemistry/FEBS, vol. 262, No. 2, pp. 617-624.
Tax, et al. (1994) "Sequence of C. Elegans lag-2 Reveals a Cell-Signalling Domain Shared with Delta and Serrate of *Drosophila*", Nature, vol. 368, No. 6467, pp. 150-154.
Terpe, K. (2003) "Overview of Tag Protein Fusions: from Molecular and Biochemical Fundamentals to Commercial Systems", Applied Microbiology and Biotechnology, vol. 60, No. 5, pp. 523-533.
Terraube et al., "Factor VIII and Von Willebrand Factor Interaction: Biological, Clinical and Therapeutic Importance", Haemophilia, 16(1): 3-13.
Thai, et al. (2004) "Antigen Stability Controls Antigen Presentation", the Journal of Biological Chemistry, vol. 279, No. 48, pp. 50257-50266.
Thermo Scientific (2012) "Instructions: Imidoester Crosslinkers: DMA, DMP, DMS, DTBP", https://tools.thermofisher.com/content/sfs/manuals/MAN0011314_ImidoesterCrsLnk_DMA_DMP_DMS_DTBP_UG.pdf, 2 Pages.
Thomas, Patrica S. (1980) "Hybridization of Denatured RNA and Small DNA Fragments Transferred to Nitrocellulose", Proceedings of the National Academy of Sciences vol. 77, No. 9, pp. 5201-5205.
Thompson, Structure and Function of the Factor VIII Gene and Protein, Thromb and Hemost., 2003, 29(1), pp. 11-22.
Thornburg et al., Treatment adherence in hemophilia, Patient Preference and Adherence, 2017,11: 1677-1686.
Tiede et al., Enhancing the pharmacokinetic properties of recombinant factor VIII: first-in-human trial of glycoPEGylated recombinant factor VIII in patients with hemophilia A, J Thromb Haemost., 2013, 11(4): 670-678.
Toby et al., Recombinant Factor IX Fc Fusion Protein Maintains Full Procoagulant Properties and Exhibits Prolonged Efficacy in Hemophilia B Mice, PLoS One, 2016, 11(2): e0148255.
Tolkatchev, et al. (2000) "Design and Solution Structure of a Well-Folded Stack of Two Beta-Hairpins Based on the Amino-Terminal Fragment of Human Granulin A", Biochemistry, vol. 39, No. 11, pp. 2878-2886.

(56) References Cited

OTHER PUBLICATIONS

Toole, et al. (Aug. 1986) "A Large Region (Approximately Equal to 95 kDa) of Human Factor VIII Is Dispensable for In Vitro Procoagulant Activity", Proceedings of the National Academy of Sciences, vol. 83, No. 16, pp. 5939-5942.
Toole, et al. (Nov. 22-28, 1984) "Molecular Cloning of a cDNA Encoding Human Antihaemophilic Factor", Nature, vol. 312, No. 5992, pp. 342-347.
Torres, et al. (1999) "Solution Structure of a Defensin-Like Peptide from Platypus Venom", the Biochemical Journal, vol. 341, Part 3, pp. 785-794.
Towfighi, et al. (2005) "Comparative Measurement of Anti-Factor VIII Antibody by Bethesda Assay and ELISA Reveals Restricted Isotype Profile and Epitope Specificity", Acta Haematologica, vol. 4, No. 2, pp. 84-90.
Trussel, et al. (Dec. 2009) "New Strategy for the Extension of the Serum Half-Life of Antibody Fragments", Bioconjugate Chemistry, vol. 20, No. 12, pp. 2286-2292.
Tuddenham, et al. (1982) "Response to Infusions of Polyelectrolyte Fractionated Human Factor VIII Concentrate in Human Haemophilia A and Von Willebrand's Disease", British Journal of Haematology, vol. 52, No. 2, pp. 259-267.
Tur, et al. (2003) "Novel Approach for Immunization, Screening and Characterization of Selected ScFv Libraries Using Membrane Fractions of Tumor Cells", International Journal of Molecular Medicine, vol. 11, No. 4, pp. 523-527.
Turacek et al., Structure and Function of a Recombinant von Willebrand Factor Drug Candidate, Seminars in Thrombosis and Hemostasis, 2010, 36(5): 510-521.
U.S. Appl. No. 14/466,567 to Schellenberger et al., filed Aug. 22, 2014 (Not Published).
U.S. Appl. No. 14/517,680 to Schellenberger et al., filed Oct. 17, 2014 (Not Published).
UniProtKB (Dec. 16, 2014) "ELNE_Human", UniProtKB, Accession No. P08246; Retrieved from http://www.uniprot.org/uniprot/P08246, 19 Pages.
UniProtKB (Dec. 16, 2014) "FA10_Human", UniProtKB, Accession No. P00742, Retrieved from https://www.uniprot.org/uniprot/P00742, 25 Pages.
UniProtKB (Dec. 16, 2014) "FA11_Human", UniProtKB, Accession No. P03951, Retrieved from https://www.uniprot.org/uniprot/P03951, 22 Pages.
UniProtKB (Dec. 16, 2014) "FA12_Human", UniProtKB, Accession No. P00748; Retrieved from https://www.uniprot.org/uniprot/P03951, 14 Pages.
UniProtKB (Dec. 16, 2014) "FA7_Human", UniProtKB, Accession No. P08709, Retrieved from https://www.uniprot.org/uniprot/P08709, 27 Pages.
UniProtKB (Dec. 16, 2014) "FA9_Human", UniProtKB, Accession No. P00740, 26 Pages.
UniProtKB (Dec. 16, 2014) "KLKB1_Human", UniProtKB, Accession No. P03952; Retrieved from https://www.uniprot.org/uniprot/P03952, 11 Pages.
UniProtKB (Dec. 16, 2014) "MMP12_Human", UniProtKB, Accession No. P39900, Retrieved from https://www.uniprot.org/uniprot/P39900, 12 pages.
UniProtKB (Dec. 16, 2014) "MMP17_Human", UniProtKB, Accession No. Q9ULZ9, Retrieved from https://www.uniprot.org/uniprot/Q9ULZ9, 11 Pages.
UniProtKB (Dec. 16, 2014) "MMP20 Human", UniProtKB, Accession No. O60882, Retrieved from https://www.uniprot.org/uniprot/O60882, 10 pages.
UniProtKB (Dec. 16, 2014) "THRB_Human", accession No. P00734, accessed at http://www.uniprot.org/uniprot/P00734, 42 Pages.
UniProtKB (Dec. 16, 2014,) "MMP13_Human", UniProtKB, Accession No. P45452; Retrieved from https://www.uniprot.org/uniprot/P45452, 15 Pages.
United Kingdom Haemophilia Centre Doctors' Organisation (UKHCDO), UKHCDO Bleeding Disorder Statistics for 2010-2011, a report from the National Haemophila Database, 2011, Available at: http://www.ukhcdo.org/docs/AnnualReports/2011/LTKHCDO%20Bleeding%20Disorder%20Statistics%20for%202010-2011.pdf.
Urlaub, et al. (Jul. 1980) "Isolation of Chinese Hamster Cell Mutants Deficient in Dihydrofolate Reductase Activity", Proceedings of the National Academy of Sciences of the United States of America, vol. 77, No. 7, pp. 4216-4220.
Uttamapinant, et al. (Jun. 2010) "Fluorophore Ligase for Site-Specific Protein Labeling Inside Living Cells", Proceedings of the National Academy of Sciences, vol. 107, No. 24, pp. 10914-10919.
Uversky, et al. (2000) "Why Are "Natively Unfolded" Proteins Unstructured Under Physiologic Conditions?", Proteins: Structure, Function and Genetics, vol. 41, No. 3, pp. 415-427.
Vaccaro, et al., "Engineering the Fc Region of Immunoglobulin G to Modulate In Vivo Antibody Levels", Nature Biotechnology, vol. 23, No. 10, pp. 12831288, Oct. 1, 2005.
Valente, et al. (2006) "Optimization of the Primary Recovery of Human Interferon Alpha2B from *Escherichia coli* Inclusion Bodies", Protein Expression and Purification, vol. 45, No. 1, pp. 226-234.
Valentino et al., A randomized comparison of two prophylaxis regimens and a paired comparison of on-demand and prophylaxis treatments in hemophilia A management, J Thromb Haemost., 2012, 10(3):359-367.
Valjakka, et al. (1998) "Unreliability of the Chou-Fasman Parameters in Predicting Protein Secondary Structure", Protein Engineering, vol. 11, No. 5, pp. 345-348.
Van Den Hooven, et al. (2001) "Disulfide Bond Structure of the AVR9 Elicitor of the Fungal Tomato Pathogen *Cladosporium fulvum*: Evidence for a Cystine Knot", Biochemistry, vol. 40, No. 12, pp. 3458-3466.
Van Genderen et al., Measuring patients' perceptions on their functional abilities: validation of the Haemophilia Activities List, Haemophilia Jan. 2006, 12(1):36-46.
Van Vlijmen, et al. (2004) "A Novel Database of Disulfide Patterns and Its Application to the Discovery of Distantly Related Homologs", Journal of Molecular Biology, vol. 335, No. 4, pp. 1083-1092.
Vanhercke, et al. (2005) "Reducing Mutational Bias in Random Protein Libraries", Analytical Biochemistry, vol. 339, No. 1, pp. 9-14.
Vardar, et al. (2003) "Nuclear Magnetic Resonance Structure of a Prototype Lin12-Notch Repeat Module from Human Notch1", Analytical Biochemistry, vol. 339, No. 1, pp. 7061-7067.
Vehar, et al. (Nov. 1984) "Structure of Human Factor VIII", Nature, vol. 312, No. 5992, pp. 337-342.
Venkatachalam, et al. (1969) "Conformation of Polypeptide Chains", Annual Review of Biochemistry, vol. 38, pp. 45-82.
Venkateswarlu, Divi (Feb. 25, 2010) "Structural Investigation of Zymogenic and Activated forms of Human Blood Coagulation Factor VIII: A Computational Molecular Dynamics Study", BMC Structural Biology vol. 10, Article No. 7, 20 Pages.
Venkateswarlu, Structural Insights Into The Interaction Of Blood Coagulation Co-Factor VIIIa with factor IXa: A Computational Protein-Protein Docking And Molecular Dynamics, 2014, Sep. 26, pp. 408-414.
Ventura, S. (2005) "Sequence Determinants of Protein Aggregation: Tools to Increase Protein Solubility", Microbial Cell Factories, vol. 4, No. 1, 11 Pages.
Verbruggen, et al. (1995) "the Nijmegen modification of the Bethesda assay for factor VIII:C inhibitors: improved specificity and reliability", Journal of Thrombosis and Haemostasis, vol. 73, No. 2, pp. 247-251.
Verbruggen, et al. (Nov. 2009) "Improvements in Factor VIII Inhibitor Detection: From Bethesda to Nijmegen", Seminars in Thrombosis and Hemostasis, vol. 35, No. 8, pp. 752-759.
Vestergaard-Bogind, et al. (1985) "Single-File Diffusion Through the Ca2+-Activated K+ Channel of Human Red Cells", the Journal of Membrane Biology, vol. 88, No. 1, pp. 67-75.
Viel KR, Ameri A, Abshire TC, Iyer RV, Watts RG, Lutcher C, et al. Inhibitors of factor VIII in black patients with hemophilia. N Engl J Med. 2009;360(16):1618-27.

(56) References Cited

OTHER PUBLICATIONS

Voisey, et al. (2002) "Agouti: from Mouse to Man, from Skin to Fat", Pigment Cell Research Sponsored by the European Society for Pigment Cell Research and the International Pigment Cell Society, vol. 15, No. 1, pp. 10-18.
Von Drygalski et al., "Change in Hemophilia Joint Health Score (HJHS) During the Phase 3 XTEND-1 Study of Efanesoctocog Alfa in Patients with Severe Hemophilia A", Eahad Oral Presentation Script, 16th Annual Congress of the European Association for Haemophilia and Allied Disorders, Feb. 7-10, 2023.
Von Drygalski et al., "Change in Hemophilia Joint Health Score (HJHS) During the Phase 3 XTEND-1 Study of Efanesoctocog Alfa in Patients with Severe Hemophilia A", Presentation Slides, 16th Annual Congress of the European Association for Haemophilia and Allied Disorders, Feb. 7-10, 2023.
Von Drygalski et al., "Consensus on Outcomes of Physical Functional and Activites for Persons with Haemophilia: Results from the IPOP Study", Haemophilia, 2023, 14-15.
Von Drygalski et al., "Efanesoctocog Alfa Prophylaxis for Patients with Severe Hemophilia A", The New England Journal of Medicine, Jan. 26, 2023, 388(4):310-318.
Von Drygalski et al., "Efficacy, Safety, and Pharmacokinetics of Once-Weekly Efanesoctocog Alfa (BIVV001) Prophylaxis in Previously Treated Patients With Severe Hemophilia A: Results From the Phase 3 XTEND-1 Study", Abstract, ISTH 2022 Congress Meeting, 3 pages.
Von Drygalski et al., "Efficacy, Safety, and Pharmacokinetics of Once-Weekly Efanesoctocog Alfa (BIVV001) Prophylaxis in Previously Treated Patients With Severe Hemophilia A: Results From the Phase 3 XTEND-1 Study", Presentation Slides, ISTH 2022 Congress Meeting, London, England, 16 pages.
Von Mackensen S, Gringeri A & the Haem-A-QoL study Group. Health-related Quality of Life in Adult Patients with Haemophilia—Assessment with a New Disease-specific Questionnaire (Haem-A-QoL). Journal Of Thrombosis and Haemostasis. 2005;3(Sup1):P0813.
Vorobjev, et al. (Nov.-Dec. 1999) "Oligonucleotide Conjugated to Linear and Branched High Molecular Weight Polyethylene Glycol as Substrates for RNase H", Nucleosides and Nucleotides, vol. 18, No. 11-12, pp. 2745-2750.
Vranken, et al. (1999) "A 30-Residue Fragment of the Carp Granulin-1 Protein Folds into a Stack of Two Beta-Hairpins Similar to That Found in the Native Protein", the Journal of Peptide Research: official Journal of the American Peptide Society, vol. 53, No. 5, pp. 590-597.
Wagenvoord, et al. (1989) "Development of a Simple Chromogenic Factor VIII Assay for Clinical Use", Haemostasis, vol. 19, No. 4, pp. 196-204.
Walker, et al. (2003) "Using Protein-Based Motifs to Stabilize Peptides", the Journal of Peptide Research, vol. 62, No. 5, pp. 214-226.
Wang, et al. (1988) "Parenteral formulations of Proteins and Peptides: Stability and Stabilizers", Journal of Parenteral Science and Technology, vol. 42, pp. S2-S24.
Wang, et al. (1999) "Structure-Function Studies of Omega-Atracotoxin, a Potent Antagonist of Insect Voltage-Gated Calcium Channels", European Journal of Biochemistry/ FEBS, vol. 264, No. 2, pp. 488-494.
Wang, et al. (Nov. 7, 2011) "Receptor-Mediated Activation of a Proinsulin-Transferrin Fusion Protein in Hepatoma Cells", Journal of Controlled Release, vol. 155, No. 3, pp. 386-392.
Ward, et al. (Apr. 1995) "the Effector Functions of Immunoglobulins: Implications for therapy", therapeutic immunology, vol. 2, No. 2, pp. 77-94.
Ward, et al. (Oct. 12, 1989) "Binding Activities of a Repertoire of Single Immunoglobulin Variable Domains Secreted from *Escherichia coli*", Nature, vol. 341, No. 6242, pp. 544-546.
Wasley, et al. (Apr. 25, 1993) "PACE/Furin can Process the Vitamin K-Dependent Pro-Factor IX Precursor within the Secretory Pathway", the Journal of Biological Chemistry, vol. 268, No. 12, pp. 8458-8465.
Watters, et al. (1997) "An Optimized Method for Cell-Based Phage Display Panning", Immunotechnology, vol. 3, No. 1, pp. 21-29.
Weidler, et al. (May 1991) "Pharmacokinetic Parameters as Criteria for Clinical Use of Hydroxyethyl Starch Preparations", Arzneimittel-Forschung/Drug Research, vol. 41, No. 5, pp. 494-498.
Weimer, et al. (Apr. 2008) "Prolonged In-Vivo Half-Life of Factor VIIa by Fusion to Albumin", Thrombosis and Haemostasis, vol. 99, No. 04, pp. 659-667.
Weiss, et al. (1977) "Stabilization of Factor VIII in Plasma by the Von Willebrand Factor: Studies on Posttransfusion and Dissociated Factor Viii and In Patients with Von Willebrand's Disease", the Journal of Clinical Investigation, vol. 60, No. 2, pp. 390-404.
Weiss, et al. (1995) "A Cooperative Model for Receptor Recognition and Cell Adhesion: Evidence from the Molecular Packing In the 1.6-A Crystal Structure of the Pheromone Er-1 from the Ciliated Protozoan Euplotes Raikovi", Proceedings of the National Academy of Sciences of the United States of America, vol. 92, No. 22, pp. 10172-10176.
Wentzel, et al. (1999) "Sequence Requirements of the GPNG Beta-Tum of the Ecballium Elaterium Trypsin Inhibitor li Explored by Combinatorial Library Screening", the Journal of Biological Chemistry, vol. 274, No. 30, pp. 21037-21043.
Werle, et al. (2006) "the Potential of Cystine-Knot Microproteins As Novel Pharmacophoric Scaffolds in Oral Peptide Drug Delivery", Journal of Drug Targeting, vol. 14, No. 3, pp. 137-146.
Werther, et al. (1996) "Humanization of An Anti-Lymphocyte Function-associated Antigen (LFA)-1 Monoclonal Antibody and Reengineering of the Humanized Antibody for Binding to Rhesus Lfa-1", Journal of Immunology, vol. 157, No. 1, pp. 4986-4995.
Weyand et al., "Treatment of Bleeding Episodes with Efanesoctocog Alfa in Patients with Severe Haemophilia A in the Phase 3 XTEND-1 Study", Abstract, Haemophilia, 136-137.
Weyand et al., "Treatment of Bleeding Episodes with Efanesoctocog Alfa in Patients with Severe Haemophilia A in the Phase 3 XTEND-1 Study", Poster, 16th Annual Congress of the European Association for Haemophilia and Allied Disorders, Feb. 7-10, 2023.
WFH, 2012, World Federation of Hemophilia, Guidelines for the management of hemophilia, 2nd edition.
White et al., A multicenter study of recombinant factor VIII (Recombinate) in previously treated patients with hemophilia A, The Recombinate Previously Treated Patient Study Group, Thromb Haemost., 1997, 77(4): 660-667.
White, et al. (1989) "Factor VIII Gene and Hemophilia A", Blood, vol. 73, No. 1, pp. 1-12.
Whitlow, et al. (1994) "Multivalent Fvs: Characterization of Single-Chain Fv Oligomers and Preparation of a Bispecific Fv", Protein Engineering, vol. 7, No. 8, pp. 1017-1026.
Wigler, et al. (Jul. 1978) "Biochemical Transfer of Single-Copy Eucaryotic Genes Using Total Cellular DNA As Donor", Cell, vol. 14, No. 3, pp. 725-731.
Williams, What Are Platelets and Why Are They Important? Johns Hopkins Medicine, Obtained from url: https:// www.hopkinsmedicine.org/health/conditions-and-diseases/what-are-platelets-and-why-are-they-important. (Year: 2010).
Wilson et al., "Impact of Efanesoctocog Alfa Prophylaxis on Pain in Previously Treated Patients with Hemophilia A: Results from the XTEND-1 Phase 3 Study", Abstract, HTRS Mar. 10-12, 2023, Orlando, Florida.
Wilson et al., "Impact of Efanesoctocog Alfa Prophylaxis on Pain in Previously Treated Patients with Hemophilia A: Results from the XTEND-1 Phase 3 Study", Poster, HTRS Mar. 10-12, 2023, Orlando, Florida.
Wilson et al., "Efficacy of Efanesoctocog Alfa on Physical Functioning: Results From the XTEND-1 Phase 3 Clinical Trial in Previously Treated Patients With Hemophilia A", Abstract, HTRS Mar. 10-12, 2023, Orlando, Florida, 5 pages.
Wilson et al., "Efficacy of Efanesoctocog Alfa on Physical Functioning: Results From the XTEND-1 Phase 3 Clinical Trial in Previously Treated Patients With Hemophilia A", Presentation Slides, HTRS Mar. 10-12, 2023, Orlando, Florida, 14 Pages.
Winter, et al. (Jun. 1, 1993) "Humanized Antibodies", Immunology Today, vol. 14, No. 6, pp. 243-246.

(56) References Cited

OTHER PUBLICATIONS

Witmer et al., Associations between intracranial haemorrhage and prescribed prophylaxis in a large cohort of haemophilia patients in the United States, Br J Haematol., 2011, 152(2): 211-216.
Witmer et al., Factor VIII inhibitors in hemophilia A: rationale and latest evidence. TherAdv Hematol., 2013;4(1): 59-72.
Wittrup, K. D. (2001) "Protein Engineering by Cell-Surface Display", Current Opinion in Biotechnology, vol. 12, No. 4, pp. 395-399.
Wood, et al. (Nov. 22-28, 1984) "Expression of Active Human Factor VIII from Recombinant DNA Clones", Nature, vol. 312, No. 5992, pp. 330-337.
Woof, et al. (Feb. 2004) "Human Antibody-Fc Receptor Interactions Illuminated by Crystal Structures", Nature Reviews Immunology, vol. 4, pp. 89-99.
World Federation of Haemophilia (WFH), World Federation of Hemophilia Report on the Annual Global Survey 2010, Montreal, Quebec: World Federation of Hemophilia, Dec. 2011.
World Federation of Hemophilia, World Federation of Hemophilia Report on the Annual Global Survey 2017. Montreal, Quebeck: World Federation of Hemophilia, Oct. 2018. Available at: http://www1.wfh/org/publications/files/pdf-1714.pdf.
World Health Organization (WHO), WHO Handbook for Reporting Results of Cancer Treatment, Geneva, 1979, Available at: http://apps.who.int/iris/bitstream/10665/37200/1/WHO_OFFSET_48.pdf.
Worn, et al. (2000) "Correlation Between In Vitro Stability and In Vivo Performance of Anti-Gcn4 Intrabodies As Cytoplasmic Inhibitors", the Journal of Biological Chemistry, vol. 275, No. 4, pp. 2795-2803.
Worn, et al. (2001) "Stability Engineering of Antibody Single-Chain Fv Fragments", Journal of Molecular Biology, vol. 305, No. 5, pp. 989-1010.
Wrammert, et al. (May 2008) "Rapid Cloning of High-Affinity Human Monoclonal Antibodies Against Influenza Virus", Nature, vol. 453, No. 7195, pp. 667-671.
Wright, et al. (1999) "Intrinsically Unstructured Proteins: Re-Assessing the Protein Structure-Function Paradigm", Journal of Molecular Biology, vol. 293, No. 2, pp. 321-331.
Wu et al., Pharmacokinetics of Peptide-Fc fusion proteins, J Pharm Sci., 2014, 103(1): 53-64.
Xia et al., "A Physiologically Based Pharmacokinetic (PBPK) Model to Characterize BIVV001 Activity, A New Class of Factor VIII (FVIII) With High Sustained Factor Activity", Poster, 14th Annual Congress of the European Association for Haemophilia and Allied Disorders, Feb. 3-5, 2021, 4 pages.
Xiong et al., "Studies on Correlations Between Gene Mutations of Factor V, Factor VIII at Sites Cleavaged by Activated Protein C and Chinese Patients with Arterial Thrombotic Diseases", Chinese Journal of Microcirculation, 2004, 4: 49-51, 54.
Xiong, et al. (2004) "A Novel Adaptation of the Integrin Psi Domain Revealed from Its Crystal Structure", the Journal of Biological Chemistry, vol. 279, No. 39, pp. 40252-40254.
Xu, et al. (2000) "Solution Structure of Bmp02, A New Potassium Channel Blocker from the Venom of the Chinese Scorpion Buthus Martensi Karsch", Biochemistry, vol. 39, No. 45, pp. 13669-13675.
Xyntha [package insert], Philadelphia, PA: Wyeth Pharmaceuticals Inc, 2015.
Yamazaki, et al. (2003) "A Possible Physiological Function and the Tertiary Structure of a 4-Kda Peptide in Legumes", European Journal of Biochemistry / FEBS, vol. 270, No. 6, pp. 1269-1276.
Yang, et al. (1995) "CDR Walking Mutagenesis for the Affinity Maturation of a Potent Human Anti-Hiv-1 Antibody into the Picomolar Range", Journal of Molecular Biology, vol. 254, No. 3, pp. 392-403.
Yang, et al. (1999) "Intestinal Peptide Transport Systems and oral Drug Availability", Pharmaceutical Research, vol. 16, No. 9, pp. 1331-1343.
Yang, et al. (2003) "Tailoring Structure-Function and Pharmacokinetic Properties of Single-Chain Fv Proteins by Site-Specific PEGylation", Protein Engineering, vol. 16, No. 10, pp. 761-770.
Yang, et al. (2005) "RONN: The Bio-Basis Function Neural Network Technique Applied to the Detection of Natively Disordered Regions in Proteins", Bioinformatics, vol. 21, No. 16, pp. 3369-3376.
Yankai, et al. (2006) "Ten Tandem Repeats of β-hCG 109-118 Enhance Immunogenicity and Anti-Tumor Effects of β-hCG C-Terminal Peptide Carried by Mycobacterial Heat-Shock Protein HSP65", Biochemical and Biophysical Research Communications, vol. 345, No. 4, pp. 1365-1371.
Yee et al., A von Willebrand factor fragment containing the D'D3 domains is sufficient to stabilize coagulation factor VIII in mice, Blood, 2014, 124(3): 445-452.
Yoon, et al., NF-kB and STAT3 Cooperatively Induce IL6 in Starved Cancer Cells, Oncogene, vol. 31, No. 29, pp. 3467-3481, 2011.
Young G, et al. Recombinant factor VIII Fc fusion protein for the prevention and treatment of bleeding in children with severe hemophilia A. J Thromb Haemost. 2015;13(6):967-977.
Yuan, et al. (1997) "Solution Structure of the Transforming Growth Factor Beta-Binding Protein-Like Module, a Domain Associated with Matrix Fibrils", the EMBO, Journal 16, No. 22, pp. 6659-6666.
Yuen et al., A long-acting human growth hormone with delayed clearance (VRS-317): results of a double-blind, placebo-controlled, single-ascending dose study in growth hormone-deficient adults, J Clin Endocrinol Metab., 2013, 98(6): 2595-2603.
Zambidis et al., Epitope-specific tolerance induction with an engineered immunoglobulin, Proc Natl Acad Sci USA. 1996; 93(10): 5019-5024.
Zapotocka, et al. "First experience of a hemophilia monitoring platform: florio HAEMO", Thromb Haemost. 2022, 6(e12685).
Zaveckas, et al. (Jun. 1, 2007) "Effect of Surface Histidine Mutations and their Number on the Partitioning and Refolding of Recombinant Human Granulocyte-Colony Stimulating Factor (Cys17ser) in Aqueous Two-Phase Systems Containing Chelated Metal Ions", Journal of Chromatography B, vol. 852, Issues 1-2, pp. 409-419.
Zhang, Design Of FRET-Based GFP Probes For Detection Of Protease Inhibitors, 2004, Oct. 15, pp. 674-678.
Zhang, et al. (Oct. 2009) "Factor VIII Inhibitors: Risk Factors and Methods for Prevention and Immune Modulation", Clinical Reviews in Allergy & Immunology, vol. 37, Issue 2, pp. 114-124.
Zhou JY, et al. Joint Bleeding Tendencies in Adult Patients With Hemophilia: It's Not All Pharmacokinetics. Clin Appl Thromb Hemost., 2019;25:1076029619862052.
Zhou, et al. (Jul. 12, 2012) "Sequence and Structure Relationships within Von Willebrand Factor", Blood, vol. 120, No. 2, pp. 449-458.
Zhou, et al. (Jun. 2005) "Procoagulant Stimulus Processing by the Intrinsic Pathway of Blood Plasma Coagulation", Biomaterials, vol. 26, Issue 16, pp. 2965-2973.
Zhu, et al. (Sep. 1999) "Molecular Cloning and Sequencing of Two 'Short Chain' and Two 'Long Chain' K (+) Channel-Blocking Peptides from the Chinese Scorpion Buthus Martensii Karsch", FEBS Letters, vol. 457, No. 3, pp. 509-514.
Zmachinsky, "Modern approaches to treatment of hemophilia", Meditsinskie novosti (Medical news), 2013, 3: 28-30. https://cyberleninka.ru/article/n/covremennye-podhody-k-lecheniyu-gemofilii/viewer.
Zucker et al., The In Vitro Association of Antihemophilic Factor and von Willebrand Factor, Thromb Haemostas, 1983, 49(1): 37-41.
U.S. Appl. No. 18/064,571 2023/0322900, filed Dec. 12, 2022, Volker Schellen-Berger, Factor VIII Compositions And Methods Of Making And Using Same.
U.S. Appl. No. 14/895,264 2016/0229903, filed Dec. 2, 2015 Aug. 11, 2016, Ekta Seth Chhabra, Thrombin Cleavable Linker.
U.S. Appl. No. 18/358,601, filed Jul. 25, 2023, Ekta Seth Chhabra, Thrombin Cleavable Linker With XTEN And Its Uses Thereof.
Arnold et al., "Hemophilic Arthropathy—Current Concepts of Pathogenesis and Management," The Journal of Bone & Joint Surgery, Apr. 1977, vol. 59, Issue 3, pp. 287-305.
Bhat et al., "Vascular Remodeling Underlies Rebleeding in Hemophilic Arthropathy," American Journal of Hematology, Nov. 2015, vol. 90, No. 11, pp. 1027-1035.

(56) References Cited

OTHER PUBLICATIONS

ClinicalTrials.gov, NCT01027364, Study of Recombinant Factor IX Fc Fusion Protein (rFIXFc) in Subjects with Hemophilia B, Dec. 7, 2009.
ClinicalTrials.gov, NCT01181128, Study to Evaluate the Safety, Pharmacokinetics and Efficacy of Recombinant Factor VIII Fc Fusion Protein (rFVIIIFc) in Previously Treated Subjects With Severe Hemophilia A, Aug. 13, 2010.
ClinicalTrials.gov, NCT01425723, Long-Term Safety and Efficacy of Recombinant Human Coagulation Factor IX Fusion Protein (rFIXFc) in the Prevention and Treatment of Bleeding Episodes in Previously Treated Subjects with Hemophilia B, Aug. 30, 2011.
ClinicalTrials.gov, NCT01454739, Long-Term Safety and Efficacy of rFVIIIFc in the Prevention and Treatment of Bleeding Episodes in Previously Treated Participants With Hemophilia A (ASPIRE), Oct. 19, 2011.
ClinicalTrials.gov, NCT01458106, Study to Evaluate the Safety, Efficacy, and Pharmacokinetics of Recombinant Coagulation Factor VIII Fc Fusion Protein (rFVIIIFc) in Previously Treated Pediatric Subjects With Hemophilia A (Kids ALONG), Oct. 24, 2011.
Feldman et al., "Tailored Prophylaxis in Severe Hemophilia A: Interim Results From the First 5 Years of the Canadian Hemophilia Primary Prophylaxis Study," J Thromb Haemost 4:1228-1236, Feb. 23, 2006.
Fischer et al., "Prophylaxis in real life scenarios", Haemophilia, Mar. 5, 2014, 20(Suppl 4): 106-113.
Guo et al., "Contrast Clinical Efficiency Evaluation of Children and Adult Patients with Severe Hemophilia A Prevention and Treatment of Low Dose", Heilongjiang Medical Journal, Aug. 2020, 44(8): 1043-1044.
Hilgartner, "Current treatment of hemophilic arthropathy", Current Opinion in Pediatrics, Feb. 2002, 14(1): 46-49.
International Search Report and Written Opinion received for PCT Application No. PCT/US2017/064302, mailed on Mar. 28, 2018.
Kavakli et al., "Once-weekly prophylactic treatment vs. on-demand treatment with nonacog alfa in patients with moderately severe to severe haemophilia B", Haemophilia, May 2016, 22(3/4): 381-88.
Kerlin et al., "Long-Term Efficacy of rFVIIIFc Prophylaxis in Pediatric, Adolescent, and Adult Subjects with Target Joints and Severe Hemophilia A", Blood, vol. 126, No. 23, Dec. 2012; 57th Annual Meeting of the American-Society-of-Hematology; Orlando, FL, USA, Dec. 5-8, 2015 (Abstract).
Khayat, "Once-weekly prophylactic dosing of recombinant factor IX improves adherence in hemophilia B", J Blood Med., Nov. 30, 2016, 7: 275-282.
Knobe et al., "Haemophilia and Joint Disease: Pathophysiology, Evaluation, and Management," Journal of Comorbidity, Dec. 27, 2011, vol. 1, pp. 51-59.
Korea Hemophilia Foundation, Posting dated Apr. 22, 2013 (no English translation available).
Krishnamoorthy et al., "Recombinant factor VIII Fc (rFVIIIFc) fusion protein reduces immunogenicity and induces tolerance in hemophilia A mice", Cellular Immunology, vol. 301, Dec. 29, 2015.
Liu et al., "NF-kB Signaling Regulates Functional Expression of the MHC Class I-Related Neonatal Fc Receptor for IgG via Intronic Binding Sequences," J Immunol 179(5):2999-3011, 2007.
Lobet et al., "Optimal Management of Hemophilic Arthropathy and Hematomas," Journal of Blood Medicine, 2014, No. 5, pp. 207-218.
Malec et al., "Immune Tolerance Induction Using Rfviiifc (Eloctate)", Blood, vol. 126, No. 23, Dec. 2015 (Abstract).
Moffit et al., "Nonclinical Safety Assessment of BIVV001, A Next-Generation Recombinant Factor VIII Fc-VWF-XTEN Fusion Protein", Mar. 7, 2018.
Ng et al., "Role of Imaging in Management of Hemophilic Patients," American Journal of Roentgenology, 2005, vol. 184, No. 5, pp. 1619-1623.
Nolan et al., "Long-term safety and efficacy of recombinant factor VIII Fc fusion protein (rFVIIIFc) in subjects with haemophilia A", Haemophilia, Jan. 2016, 22(1): 72-80.
Oymak et al., "The effectiveness of tools for monitoring hemophilic arthropathy", J Pediatr Hematol Oncol. 2015;37(2): e80-85.
Pasi et al., "Long-term safety and efficacy of extended-interval prophylaxis with recombinant factor IX Fc fusion protein (rFIXFc) in subjects with haemophilia B", Thromb Haemost., Feb. 28, 2017, 117(3): 508-518, ePublished Dec. 22, 2016.
Polyanskaya et al., "Modern Concepts of the Pathogenesis of Hemophilic Arthropathy", Issues of Hematology/Oncology and Immunopathology in Pediatrics, 2015, 14(3): 5-12, including English abstract.
Powell, J., et al., "Switching to recombinant factor IX Fc fusion protein prophylaxis results in fewer infusions, decreased factor IX consumption and lower bleeding rates," British Journal of Haematology 168: 113-123 (2015).
Powell, J.S., et al., "Long-Acting Recombinant Factor IX Fc Fusion Protein (rFIXFc) for Perioperative Management of Subjects with Haemophilia B in the Phase 3 B-Long Study," British Journal of Haematology, 168: 124-134 (2015).
Ragni, et al., "Use of Recombinant Factor IX in Subjects with Haemophilia B Undergoing Surgery", Haemophilia, vol. 8, No. 2, Blackwell Science, pp. 91-97. (Mar. 2002).
Rodriguez-Merchan, "Haemophilic synovitis: basic concepts", Haemophilia, 2007, 13(Suppl 3): 1-3.
Rodriguez-Merchan, et al., "General principals and indications of synoviorthesis (medical synovectomy) in haemophilia", Haemophilia, 2001, 7(Suppl 2): 6-10.
Simioni, et al. (Oct. 22, 2009) "X-Linked Thrombophilia with a Mutant Factor IX (Factor IX Padua)", The New England Journal of Medicine, vol. 361, No. 17, pp. 1671-1675.
Simpson et al., "Management of joint bleeding in hemophilia", Expert Rev Hematol., 2012, 5(4): 459-468.
Smith et al., "FcγRIIB in Autoimmunity and Infection: Evolutionary and Therapeutic Implications," Nature Reviews Immunology, 2010, vol. 10, No. 5, pp. 328-343.
Trakymiene et al., "Utility of the Haemophilia Joint Health Score in study of episodically treated boys with severe haemophilia A and B in Lithuania", Haemophilia 16(3) :479-486 (2010).
VV-TMF-68870: Model Patient Information Sheet and Informed Consent Form for Clinical Trial Identifier No. 9HB01EXT, dated Jul. 18, 2011, pp. 1-9.
WV-TMF-68872: Model Patient Information Sheet and Informed Consent Form for Clinical Trial Identifier No. 9HB01EXT, dated Jul. 18, 2011, pp. 1-8.
WV-TMF-68874: Model Patient Information Sheet and Informed Consent Form for Clinical Trial Identifier No. 9HB01EXT, dated Jul. 18, 2011, pp. 1-10.
WFH (World Federation of Hemophilia), "Hemophilia Joint Health Score (HJHS) 2.1," Feb. 7, 2011, available at https://elearning.wfh.org/resource/hemophilia-joint-health-score-hjhs/.
Wyrwich et al., "Changes in health-related quality of life with treatment of longer-acting clotting factors: results in the A-LONG and B-LONG clinical studies", Haemophilia, Nov. 2016, 22(6): 866-872.
U.S. Appl. No. 13/513,424, filed Dec. 28, 2012, 2013/0108629 May 2, 2013, U.S. Pat. No. 9,050,318 Jun. 9, 2015, Jennifer A. Dumont, Factor VIII-FC Chimeric And Hybrid Polypeptides, And Methods Of Use Thereof.
U.S. Appl. No. 13/793,783, filed Mar. 11, 2013, 2013/0274194 Oct. 17, 2013, U.S. Pat. No. 9,241,978 Jan. 26, 2016, Jennifer A. Dumont, Factor VIII-FC Chimeric And Hybrid Polypeptides, And Methods Of Use Thereof.
U.S. Appl. No. 16/270,302, filed Feb. 7, 2019, 2019/0262429 Aug. 29, 2019, U.S. Pat. No. 11,266,720 Mar. 8, 2022, Jennifer A. Dumont, Factor VIII-FC Chimeric And Hybrid Polypeptides, And Methods Of Use Thereof.
U.S. Appl. No. 17/587,941 2022/0265780, filed Jan. 28, 2022 Aug. 25, 2022, Jennifer A. Dumont, Factor VIII-FC Chimeric And Hybrid Polypeptides, And Methods Of Use Thereof.
U.S. Appl. No. 13/809,276, filed Jul. 11, 2011, 2013/0202595 Aug. 6, 2013, U.S. Pat. No. 9,670,475 Jun. 6, 2017, Glenn Pierce, Factor IX Polypeptides and Methods of Use Thereof.

(56) References Cited

OTHER PUBLICATIONS

U.S. Appl. No. 13/793,796, filed Mar. 11, 2013, 2013/0171175 Jul. 4, 2013, U.S. Pat. No. 9,233,145 Jan. 12, 2016, Glenn Pierce, Factor IX Polypeptides and Methods of Use Thereof.
U.S. Appl. No. 14/982,934, filed Dec. 29, 2015, 2016/0257943 Sep. 8, 2016, U.S. Pat. No. 9,867,973 Jan. 16, 2018, Glenn Pierce, Factor IX Polypeptides and Methods of Use Thereof.
U.S. Appl. No. 15/043,457, filed Feb. 12, 2016, 2016/0243206 Aug. 25, 2016, U.S. Pat. No. 9,629,903 Apr. 25, 2017, Glenn Pierce, Factor IX Polypeptides and Methods of Use Thereof.
U.S. Appl. No. 15/043,445, filed Feb. 12, 2016, 2016/0346365 Dec. 1, 2016, U.S. Pat. No. 9,675,676 Jun. 13, 2017, Glenn Pierce, Factor IX Polypeptides and Methods of Use Thereof.
U.S. Appl. No. 15/043,455, filed Feb. 12, 2016, 2016/0166657 Jun. 16, 2016, U.S. Pat. No. 9,623,091 Apr. 18, 2017, Glenn Pierce, Factor IX Polypeptides and Methods of Use Thereof.
U.S. Appl. No. 15/820,080, filed Nov. 21, 2017, 2018/0207244 Jul. 26, 2018, Abandoned, Glenn Pierce, Factor IX Polypeptides and Methods of Use Thereof.
U.S. Appl. No. 15/890,284, filed Feb. 6, 2018, 2018/0228878 Aug. 16, 2018, U.S. Pat. No. 10,561,714 Feb. 18, 2020, Glenn Pierce, Factor IX Polypeptides and Methods of Use Thereof.
U.S. Appl. No. 15/790,290, filed Feb. 6, 2018, 2018/0132205 May 10, 2013, Abandoned, Glenn Pierce, Factor IX Polypeptides and Methods of Use Thereof.
U.S. Appl. No. 16/271,686, filed Feb. 8, 2019, 2019/0192640 Jun. 27, 2019, U.S. Pat. No. 10,658,943 Feb. 25, 2020, Glenn Pierce, Factor IX Polypeptides and Methods of Use Thereof.
U.S. Appl. No. 16/271,689, filed Feb. 8, 2019, 2019/0192641 Jun. 27, 2019, U.S. Pat. No. 10,548,954 Feb. 4, 2020, Glenn Pierce, Factor IX Polypeptides and Methods of Use Thereof.
U.S. Appl. No. 16/907,985 2021/0008178, filed Jun. 22, 2020 Jan. 14, 2021, Glenn Pierce, Factor IX Polypeptides and Methods of Use Thereof.
U.S. Appl. No. 17/032,354, filed Sep. 25, 2020, 2021/0023185 Jan. 28, 2021, U.S. Pat. No. 10,898,554 Jan. 26, 2021, Glenn Pierce, Factor IX Polypeptides and Methods of Use Thereof.
U.S. Appl. No. 13/365,166 2013/0017997, filed Aug. 19, 2011 Jan. 17, 2013, Volker Schellen-Berger, Factor VIII Compositions And Methods Of Making And Using Same.
U.S. Appl. No. 13/423,031 2012/0178691, filed Aug. 19, 2011 Jul. 12, 2012, Volker Schellen-Berger, Factor VIII Compositions And Methods Of Making And Using Same.
U.S. Appl. No. 14/317,888 2015/0038421, filed Aug. 19, 2011 Feb. 5, 2015, Volker Schellen-Berger, Factor VIII Compositions And Methods Of Making And Using Same.
U.S. Appl. No. 15/163,561 2016/0376344, filed Aug. 19, 2011 Dec. 29, 2016, Volker Schellen-Berger, Factor VIII Compositions And Methods Of Making And Using Same.
U.S. Appl. No. 16/369,820 2019/0315835, filed Mar. 29, 2019 Oct. 17, 2019, Volker Schellen-Berger, Factor VIII Compositions And Methods Of Making And Using Same.
U.S. Appl. No. 17/097,978, filed Nov. 13, 2020, Volker Schellen-Berger, Factor VIII Compositions And Methods Of Making And Using Same.
U.S. Appl. No. 17/240,351 2023/0019286, filed Apr. 26, 2021 Jan. 19, 2023, Volker Schellen-Berger, Factor VIII Compositions And Methods Of Making And Using Same.
U.S. Appl. No. 14/371,948 2015/0023959, filed Jul. 11, 2014 Jan. 22, 2015, Ekta Seth Chhabra, Chimeric Factor VIII Polypeptides And Uses Thereof.
U.S. Appl. No. 16/357,189, filed Mar. 18, 2019, Ekta Seth Chhabra, Chimeric Factor VIII Polypeptides And Uses Thereof.
U.S. Appl. No. 17/826,932 2023/0011438, filed May 27, 2022, Ekta Seth Chhabra, Chimeric Factor VIII Polypeptides And Uses Thereof.
U.S. Appl. No. 14/379,192, filed Feb. 20, 2015, 2015/0158929 Jun. 11, 2015, U.S. Pat. No. 10,421,798 Sep. 24, 2019, Volker Schellen-Berger, Factor VIII Compositions And Methods Of Making And Using Same.
U.S. Appl. No. 16/521,789 2020/0087379, filed Jul. 25, 2019 Mar. 19, 2020, Volker Schellen-Berger, Factor VIII Compositions And Methods Of Making And Using Same.
U.S. Appl. No. 18/064,571 2023/0322900, filed Dec. 12, 2022 Oct. 12, 2023, Volker Schellen-Berger, Factor VIII Compositions And Methods Of Making And Using Same.
U.S. Appl. No. 14/413,765, filed Jan. 9, 2015, 2015/0266943 Sep. 24, 2015, U.S. Pat. No. 10,138,291 Nov. 27, 2018, Ekta Seth Chhabra, Factor VIII Complex With XTEN And Von Willebrand Factor Protein, And Uses Thereof.
U.S. Appl. No. 16/154,310, filed Oct. 8, 2018, 2019/0169267 Jun. 6, 2019, U.S. Pat. No. 11,091,534 Aug. 17, 2021, Ekta Seth Chhabra, Factor VIII Complex With XTEN And Von Willebrand Factor Protein, And Uses Thereof.
U.S. Appl. No. 17/358,142 2022/0056108, filed Jun. 25, 2021 Feb. 24, 2022, Ekta Seth Chhabra, Factor VIII Complex With XTEN And Von Willebrand Factor Protein, And Uses Thereof.
U.S. Appl. No. 14/430,848 2015/0252345, filed Sep. 25, 2013 Sep. 10, 2015, Glenn Pierce, Methods Of Using Fix Polypeptides.
U.S. Appl. No. 15/619,196, filed Jun. 9, 2017, 2018/0002684 Jan. 4, 2018, U.S. Pat. No. 11,225,650 Jan. 18, 2022, Glenn Pierce, Methods Of Using Fix Polypeptides.
U.S. Appl. No. 17/378,200 2022/0064622, filed Jul. 16, 2021 Mar. 3, 2022, Glenn Pierce, Methods Of Using Fix Polypeptides.
U.S. Appl. No. 14/895,264 2016/0229903, filed Dec. 2, 2015 Aug. 11, 2016, Ekta Seth Chhabra, Thrombin Cleaveable Linker.
U.S. Appl. No. 14/894,108 2016/0251408, filed May 3, 2016 Sep. 1, 2016, Ekta Seth Chhabra, Thrombin Cleavable Linker With XTEN And Its Uses Thereof.
U.S. Appl. No. 17/479,705 2022/0106383, filed Sep. 20, 2021 Apr. 7, 2022, Ekta Seth Chhabra, Thrombin Cleavable Linker With XTEN And Its Uses Thereof.
U.S. Appl. No. 18/358,601 2024/0083875, filed Jul. 25, 2023 Mar. 14, 2024, Ekta Seth Chhabra, Thrombin Cleavable Linker With XTEN And Its Uses Thereof.
U.S. Appl. No. 15/110,673, filed Jul. 8, 2016, 2017/0073393 Mar. 16, 2017, U.S. Pat. No. 11,192,936 Dec. 7, 2021, Ekta Seth Chhabra, Factor VIII Chimeric Proteins And Uses Thereof.
U.S. Appl. No. 17/217,752 2022/0010347, filed Mar. 30, 2021 Jan. 13, 2022, Bettina Strack-Logue, Methods Of Treating Hemophilic Arthropathy Using Chimeric Clotting Factors.
U.S. Appl. No. 16/415,893 2019/0375822, filed May 17, 2019 Dec. 12, 2019, Ekta Seth Chhabra, Methods Of Treating Hemophilia A.
U.S. Appl. No. 18/572,006, filed Jun. 23, 2022, Tyler Carlage, Formulations Of Factor VIII Chimeric Proteins And Uses Thereof.
Bray et al., "A multicenter study of recombinant factor VIII (recombinate): safety, efficacy, and inhibitor risk in previously untreated patients with hemophilia A. The Recombinate Study Group". Blood, May 1, 1994, 83(9): 2428-2435.
Dargaud et al., "Efanesoctocog alfa: the renaissance of Factor VIII replacement therapy", Haematologica, Aug. 2024, 109: 2346-2444.
Ducore et al., "Alprolix (recombinant Factor IX Fc fusion protein): extended half- life product for the prophylaxis and treatment of hemophilia B", Expert Rev Hemat., Oct. 2014, 7(5): 559-571.
Extended European Search Report received for European Patent Application No. 24150415.8 mailed on Jun. 28, 2024.
International Search Report and Written Opinion received for PCT Patent Application No. PCT/US2022/078097, mailed on Febuary 8, 2023.
International Search Report and Written Opinion received for PCT Patent Application No. PCT/US2023/063828, mailed on Sep. 25, 2023.
International Search Report and Written Opinion received for PCT Patent Application No. PCT/US2023/071400, mailed on Nov. 22, 2023.
Mceneny-King et al., "Data Analysis Protocol for the Development and Evaluation of Population Pharmacokinetic Models for Incorporation Into the Web-Accessible Population Pharmacokinetic Service - Hemophilia (WAPPS-Hemo)", JMIR Research Protocols, Dec. 7, 2016, 5(4): e232.
Roentgen Ray Reader, "Arnold-Hilgartner Staging of Hemophilic Arthropathy", Jan. 20, 2012.
Sanofi, "Appendices Research & Development", Q1, Apr. 27, 2018.

(56) References Cited

OTHER PUBLICATIONS

Sherry et al., "Avoiding the Impact of Musculoskeletal Pain on Quality of Life in Children With Hemophilia", Mar. 1, 2008, 27(2): 103-108.
Stromer et al., "Pain management in hemophilia: expert recommendations," Mar. 4, 2021, 133(19-20): 1042-1056.
Van Hlyckama Vlieg et al., "High levels of factor IX increase the risk of venous thrombosis", Blood, Jun. 15, 2000, 95(12): 3678-3682.
World Federation of Hemophilia, "WFH 2016 World Congress Abstracts", Jul. 24- 28, 2016, Orlando, Florida, USA, Haemophilia, vol. 22, Suppl. 4, pp. 3-138.
Wyseure et al., "Advances and challenges in hemophilic arthropathy", Seminars in Hematology, Jan. 2016, 53(1): 10-19.
Amunix Pharmaceuticals, Inc., "XTEN", Trademark U.S. Appl. No. 86/395,983, filed Sep. 16, 2014, Publication Date: Feb. 10, 2015, Registration Date: Dec. 15, 2015, Cancellation Date: Mar. 19, 2024.
Waugh et al., "An overview of enzymatic reagents for the removal of affinity tags", Protein Expression and Purification, Dec. 2011, 80(2): 293-293.

* cited by examiner

FVIII169/VWF057 - LVPR site in linker
FVIII169/VWF059 - a2 site in linker
FVIII169/VWF059a - truncated a2 site in linker
FVIII169/VWF073 - a2 fragment in linker ~312 kDa complex FIG. 11B
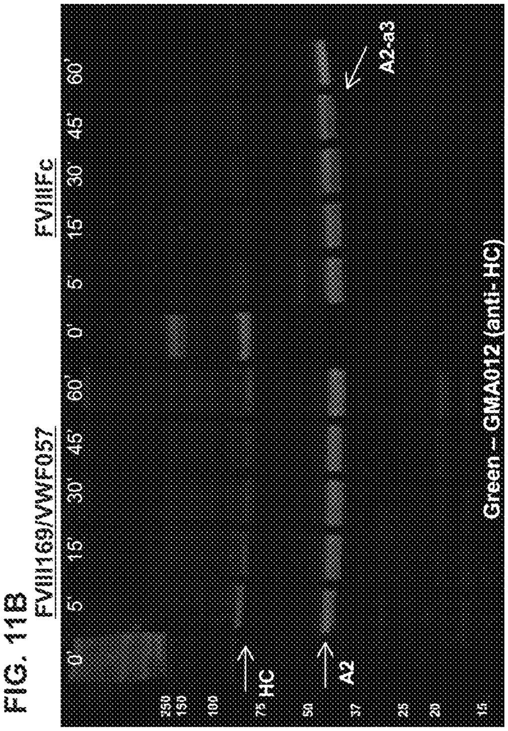
LC= light chain of FVIII
HC= Heavy chain of FVIII
A2= A2 domain of FVIII
FIG. 11A
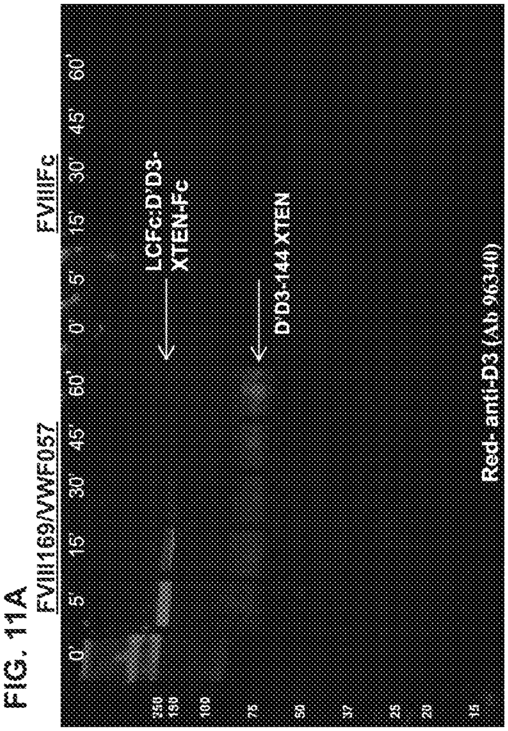
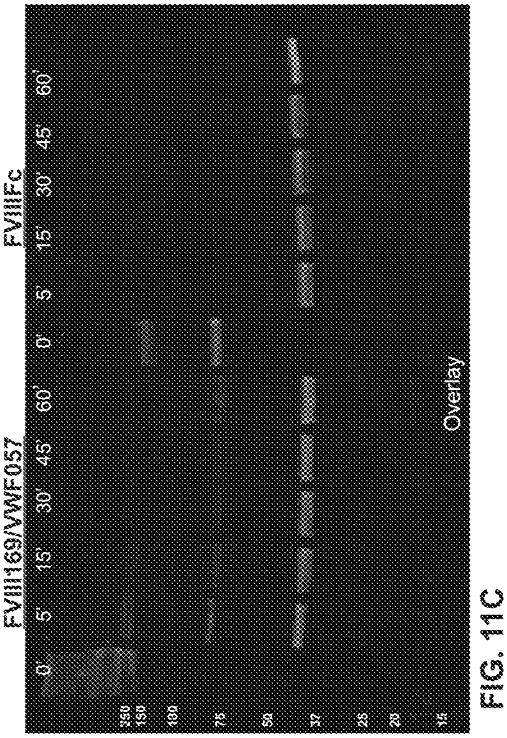
FIG. 11C

FACTOR VIII CHIMERIC PROTEINS AND USES THEREOF

CROSS-REFERENCE TO RELATED APPLICATIONS

This application is a division of U.S. patent application Ser. No. 15/110,673, filed Jul. 8, 2016, which is a 35 U.S.C. § 371 filing of International Patent Application No. PCT/US2015/010738, filed Jan. 9, 2015, which claims priority to U.S. Provisional Patent Application Ser. Nos. 61/988,104, filed May 2, 2014, and 61/926,226, filed Jan. 10, 2014, the entire disclosures of which are hereby incorporated herein by reference.

REFERENCE TO SEQUENCE LISTING SUBMITTED ELECTRONICALLY

The content of the electronically submitted sequence listing in ASCII text file (Name: 723903_SA9-448USDIV_ST25.txt; Size: 820,859 bytes; and Date of Creation: Nov. 3, 2021) is incorporated herein by reference in its entirety.

BACKGROUND OF THE INVENTION

Haemophilia A is a bleeding disorder caused by defects in the gene encoding coagulation factor VIII (FVIII) and affects 1-2 in 10,000 male births. Graw et al., *Nat. Rev. Genet.* 6(6): 488-501 (2005). Patients affected with hemophilia A can be treated with infusion of purified or recombinantly produced FVIII. All commercially available FVIII products, however, are known to have a half-life of about 8-12 hours, requiring frequent intravenous administration to the patients. See Weiner M. A. and Cairo, M. S., Pediatric Hematology Secrets, Lee, M. T., 12. Disorders of Coagulation, Elsevier Health Sciences, 2001; Lillicrap, D. Thromb. Res. 122 Suppl 4:S2-8 (2008). In addition, a number of approaches have been tried in order to extend the FVIII half-life. For example, the approaches in development to extend the half-life of clotting factors include pegylation, glycopegylation, and conjugation with albumin. See Dumont et al., Blood. 119(13): 3024-3030 (Published online Jan. 13, 2012). Regardless of the protein engineering used, however, the long acting FVIII products currently under development are reported to have limited half-lives—only to about 1.5 to 2 hours in preclinical animal models. See id. Consistent results have been demonstrated in humans, for example, rFVIIIFc was reported to improve half-life up to ~1.7 fold compared with ADVATE® in hemophilia A patients. See Id. Therefore, the half-life increases, despite minor improvements, may indicate the presence of other T½ limiting factors. See Liu, T. et al., 2007 ISTH meeting, abstract #P-M-035; Henrik, A. et al., 2011 ISTH meeting, abstract #P=MO-181; Liu, T. et al., 2011 ISTH meeting abstract #P-WE-131.

Plasma von Willebrand Factor (VWF) has a half-life of approximately 16 hours (ranging from 13 to 18 hours). Goudemand J, et al. *J Thromb Haemost* 2005; 3:2219-27. The VWF half-life may be affected by a number of factors: glycosylation pattern, ADAMTS-13 (a disintegrin and metalloprotease with thrombospondin motif-13), and various mutations in VWF.

In plasma, 95-98% of FVIII circulates in a tight non-covalent complex with full-length VWF. The formation of this complex is important for the maintenance of appropriate plasma levels of FVIII in vivo. Lenting et al., *Blood.* 92(11): 3983-96 (1998); Lenting et al., *J. Thromb. Haemost.* 5(7): 1353-60 (2007). The full-length wild-type FVIII is mostly present as a heterodimer having a heavy chain (MW 200 kD) and a light chain (MW 73 kD). When FVIII is activated due to proteolysis at positions 372 and 740 in the heavy chain and at position 1689 in the light chain, the VWF bound to FVIII is removed from the activated FVIII. The activated FVIII, together with activated factor IX, calcium, and phospholipid ("tenase complex"), induces the activation of factor X, generating large amounts of thrombin. Thrombin, in turn, then cleaves fibrinogen to form soluble fibrin monomers, which then spontaneously polymerize to form the soluble fibrin polymer. Thrombin also activates factor XIII, which, together with calcium, serves to crosslink and stabilize the soluble fibrin polymer, forming crosslinked (insoluble) fibrin. The activated FVIII is cleared fast from the circulation by proteolysis.

Due to the frequent dosing and inconvenience caused by the dosing schedule, there is still a need to develop FVIII products requiring less frequent administration, i.e., a FVIII product that has a half-life longer than the 1.5 to 2 fold half-life limitation.

BRIEF SUMMARY OF THE INVENTION

The present invention provides a chimeric protein comprising (i) a first polypeptide which comprises a Factor VIII ("FVIII") protein fused to a first immunoglobulin ("Ig") constant region or a portion thereof and (ii) a second polypeptide which comprises a von Willebrand Factor ("VWF") protein comprising a D' domain and a D3 domain of VWF fused to a second Ig constant region or a portion thereof by an XTEN sequence in-between, wherein the XTEN sequence contains less than 288 amino acid residues and wherein the first polypeptide is linked to or associated with the second polypeptide. Certain embodiments include the chimeric protein as described herein, wherein the XTEN sequence in the second polypeptide consists of an amino acid sequence having a length of between 12 amino acids and 287 amino acids.

Also disclosed is the chimeric protein as described herein, wherein the chimeric protein exhibits a longer half-life compared to a corresponding fusion protein comprising the first polypeptide and the second polypeptide wherein the second polypeptide of the fusion protein comprises an XTEN sequence containing at least 288 amino acids. Some embodiments include the XTEN sequence AE288, containing at least 288 amino acids. In some embodiments AE288 is SEQ ID NO: 8.

Also disclosed is the chimeric protein as described herein, wherein the XTEN sequence of the second polypeptide contains about 36, about 42, about 72, or about 144 amino acids. In some embodiments the XTEN sequence of the second polypeptide is selected from AE42, AE72, AE144, AG42, AG72, or AG144.

Some embodiments include the chimeric protein as described herein, wherein the XTEN sequence of the second polypeptide is selected from SEQ ID NO: 9, SEQ ID NO: 10, SEQ ID NO: 11, SEQ ID NO: 55; SEQ ID NO: 56; SEQ ID NO: 57; SEQ ID NO: 58; SEQ ID NO: 58; SEQ ID NO: 59; SEQ ID NO: 14; SEQ ID NO: 60; SEQ ID NO: 61; SEQ ID NO: 62; or SEQ ID NO: 63.

In certain embodiments the first polypeptide further comprises a second XTEN sequence which links the FVIII protein with the first Ig constant region or a portion thereof. Also disclosed is the chimeric protein as described herein, wherein the first polypeptide comprises a third XTEN sequence which is inserted at one or more insertion sites within the FVIII protein. In some embodiments the first polypeptide further comprises a second XTEN sequence which is inserted at one or more insertion sites within the FVIII protein. In certain embodiments, the first polypeptide comprises a third XTEN sequence which links the FVIII protein with the first Ig constant region or a portion thereof.

Also disclosed is the chimeric protein as described herein, wherein the second XTEN sequence, the third XTEN sequence, or the second and third XTEN sequences are each independently selected from AE42, AE72, AE864, AE576, AE288, AE144, AG864, AG576, AG288, and AG144. In some embodiments the second XTEN sequence, the third XTEN sequence, or the second and third XTEN sequences are each independently selected from SEQ ID NO: 8; SEQ ID NO: 9, SEQ ID NO: 10, SEQ ID NO: 11, SEQ ID NO: 17; SEQ ID NO: 54; SEQ ID NO: 19; SEQ ID NO: 16; SEQ ID NO: 18; SEQ ID NO: 15; SEQ ID NO: 55; SEQ ID NO: 56; SEQ ID NO: 57; SEQ ID NO: 58; SEQ ID NO: 59; SEQ ID NO: 14; SEQ ID NO: 60; SEQ ID NO: 61; SEQ ID NO: 62; or SEQ ID NO: 63. In certain embodiments the second XTEN sequence, the third XTEN sequence, or both the second and third XTEN sequences are each independently AE288 or AG288. In some embodiments the XTEN sequence in the second polypeptide is fused to the second Ig constant region or a portion thereof by a linker. In certain embodiments the linker is a cleavable linker.

Some embodiments include the chimeric protein as described herein, wherein the linker is cleavable by a protease selected from factor XIa, factor XIIa, kallikrein, factor VIIa, factor IXa, factor Xa, factor IIa (thrombin), Elastase-2, Granzyme-B, TEV, Enterokinase, Protease 3C, Sortase A, MMP-12, MMP-13, MMP-17, and MMP-20. In some embodiments the linker is cleavable by factor IIa (thrombin).

Also disclosed is the chimeric protein as described herein, wherein the linker comprises one or more cleavage sites comprising an amino acid sequence selected from RRRR (SEQ ID NO: 102), RKRRKR (SEQ ID NO: 103), RRRRS (SEQ ID NO: 104), TQSFNDFTR (SEQ ID NO: 1), SVSQTSKLTR (SEQ ID NO: 3), DFLAEGGGVR (SEQ ID NO: 4), TTKIKPR (SEQ ID NO: 5), LVPRG (SEQ ID NO: 6), ALRPR (SEQ ID NO: 7), KLTRAET (SEQ ID NO: 121), DFTRVVG (SEQ ID NO: 122), TMTRIVGG (SEQ ID NO: 123), SPFRSTGG (SEQ ID NO: 124), LQVRIVGG (SEQ ID NO: 125), PLGRIVGG (SEQ ID NO: 126), IEGRTVGG (SEQ ID NO: 127), LTPRSLLV (SEQ ID NO: 128), LGPVSGVP (SEQ ID NO: 129), VAGDSLEE (SEQ ID NO: 130), GPAGLGGA (SEQ ID NO: 131), GPAGLRGA (SEQ ID NO: 132), APLGLRLR (SEQ ID NO: 133), PALPLVAQ (SEQ ID NO: 134), ENLYFQG (SEQ ID NO: 135), DDDKIVGG (SEQ ID NO: 136), LEVLFQGP (SEQ ID NO: 137), LPKTGSES (SEQ ID NO: 138), DKNTGDYYEDSYEDISAYLLSKNNAIEPRSFS (SEQ ID NO: 88), and IEPRSFS (SEQ ID NO: 194). In some embodiments the linker comprises TLDPRSFLLRNPNDKYEPFWEDEEK (SEQ ID NO: 146). In certain embodiments the cleavage sites comprise an amino acid sequence of LVPRG (SEQ ID NO:6). In other embodiments the cleavage site comprises an amino acid sequence of IEPRSFS (SEQ ID NO: 194). In still other embodiments the cleavage site comprises an amino acid sequence of IEPRSFS (SEQ ID NO: 194), wherein the cleavage site is not the full length a2 region of FVIII. In some embodiments, the cleavage site comprises a fragment of an a2 region of FVIII comprising at least the sequence IEPR (SEQ ID NO: 200). In other embodiments, the cleavage site comprises a fragment of an a2 region of FVIII comprising at least the sequence IEPR (SEQ ID NO: 200), wherein the cleavage site is not the full length a2 region. In certain embodiments, the cleavage site is cleavable in a thrombin cleavage assay as provided herein or as known in the art.

Some embodiments include the chimeric protein as described herein, wherein the first Ig constant region or a portion thereof comprises a first Fc region and/or the second Ig constant region or a portion thereof comprises a second Fc region. In some embodiments the first Ig constant region or a portion thereof and the second Ig constant region or a portion thereof extend the half-life of the chimeric protein. In some embodiments the first polypeptide and the second polypeptide is fused by a linker. In certain embodiments the first polypeptide and the second polypeptide is fused by a processable linker. In some embodiments the first Ig constant region or a portion thereof is associated with the second Ig constant region or a portion thereof. In certain embodiments the first Ig constant region or a portion thereof is associated with the second Ig constant region or a portion thereof by a covalent bond. In some embodiments the covalent bond is a disulfide bond.

Also disclosed is the chimeric protein comprising each of the following formulae (a)-(hh):

FVIII-F1:F2-L2-X-L1-V; (a)

FVIII-F1:V-L1-X-L2-F2; (b)

F1-FVIII:F2-L2-X-L1-V; (c)

F1-FVIII:V-L1-X-L2-F2; (d)

FVIII-X2-F1:F2-L2-X1-L1-V; (e)

FVIII-X2-F1:V-L1-X1-L2-F2; (f)

FVIII(X2)-F1:F2-L2-X1-L1-V; (g)

FVIII(X2)-F1:V-L1-X1-L2-F2; (h)

F1-X2-F1:F2-L2-X1-L1-V; (i)

F1-X2-F1:V-L1-X1-L2-F2; (j)

V-L1-X-L2-F2-L3-FVIII-L4-F1; (k)

V-L1-X-L2-F2-L3-F1-L4-FVIII; (l)

F1-L4-FVIII-L3-F2-L2-X-L1-V; (m)

FVIII-L4-F1-L3-F2-L2-X-L1-V; (n)

FVIII-L4-F1-L3-V-L1-X-L2-F2; (o)

FVIII-L4-F1-L3-F2-L2-X-L1-V; (p)

F2-L2-X-L1-V-L3-F1-L4-FVIII; (q)

F2-L2-X-L1-V-L3-FVIII-L4-F1; (r)

V-L1-X1-L2-F2-L3-FVIII(X2)-L4-F1; (s)

V-L1-X1-L2-F2-L3-F1-L4-FVIII(X2); (t)

F1-L4-FVIII(X2)-L3-F2-L2-X1-L1-V; (u)

F-L4-FVIII(X2)-L3-V-L1-X1-L2-F2; (v)

FVIII(X2)-L4-F1-L3-V-L1-X1-L2-F2; (w)

FVIII(X2)-L4-F1-L3-F2-L2-X1-L1-V; (x)

F2-L2-X1-L1-V-L3-F1-L4-FVIII(X2); (y)

F2-L2-X1-L1-V-L3-FVIII(X2)-L4-F1; (z)

V-L1-X2-L2-F2-L3-FVIII-L4-X2-L5-F1; (aa)

V-L1-X2-L2-F2-L3-F1-L5-X2-L4-FVIII; (bb)

F1-L5-X2-L4-FVIII-L3-F2-L2-X2-L1-V; (cc)

F1-L5-X2-L4-FVIII-L3-V-L1-X2-L2-F2; (dd)

FVIII-L5-X2-L4-F2-L3-V-L1-X1-L2-F1; (ee)

FVIII-L5-X2-L4-F2-L3-F1-L2-X1-L1-V; (ff)

F1-L2-X1-L1-V-L3-F2-L4-X2-L5-FVIII; or (gg)

F1-L2-X1-L1-V-L3-FVIII-L5-X2-L4-F2; (hh)

wherein V is a VWF protein, which comprises a D' domain and a D3 domain, X or X1 is a first XTEN sequence that contains less than 288 amino acids, X2 is a second XTEN sequence, FVIII comprises a FVIII protein, FVIII(X2) comprises a FVIII protein having a second XTEN sequence inserted in one or more insertion sites within the FVIII protein, F1 is a first Ig constant region or a portion thereof, F2 is a second Ig constant region or a portion thereof, L1, L2, L3, L4, or L5 is an optional linker, (-) is a peptide bond; and (:) is a covalent bond or a non-covalent bond.

Some embodiments include the chimeric protein as described herein, wherein the X or X1 consists of an amino acid sequence in length between 12 amino acids and 287 amino acids.

In certain embodiments the chimeric protein as described herein exhibits a longer half-life compared to a corresponding chimeric protein comprising the formula except that the X or X1 is AE288. In some embodiments AE288 is SEQ ID NO:8.

Some embodiments include the chimeric protein as described herein, wherein the X or X1 in the formula contains about 36, about 42, about 72, or about 144 amino acids. In certain embodiments the X or X1 in the formula is selected from AE42, AE72, AE144, AG42, AG72, or AG144. In some embodiments the X or X1 in the formula is selected from SEQ ID NO: 9, SEQ ID NO: 10, SEQ ID NO: 11, SEQ ID NO: 55; SEQ ID NO: 56; SEQ ID NO: 57; SEQ ID NO: 58; SEQ ID NO: 59; SEQ ID NO: 14; SEQ ID NO: 60; SEQ ID NO: 61; SEQ ID NO: 62; or SEQ ID NO: 63. In certain embodiments the X2 comprises an amino acid sequence having a length of at least about 36 amino acids, at least about 42 amino acids, at least about 144 amino acids, at least about 288 amino acids, at least about 576 amino acids, at least about 864 amino acids. In certain embodiments the X2 is selected from AE42, AE72, AE864, AE576, AE288, AE144, AG864, AG576, AG288, and AG144. In some embodiments the X2 is selected from SEQ ID NO: 8; SEQ ID NO: 9; SEQ ID NO: 10; SEQ ID NO: 11; SEQ ID NO: 17; SEQ ID NO: 54; SEQ ID NO: 19; SEQ ID NO: 16; SEQ ID NO: 18; SEQ ID NO: 15; SEQ ID NO: 55; SEQ ID NO: 56; SEQ ID NO: 57; SEQ ID NO: 58; SEQ ID NO: 59; SEQ ID NO: 14; SEQ ID NO: 60; SEQ ID NO: 61; SEQ ID NO: 62; or SEQ ID NO: 63. In certain embodiments the X2 is AE288 or AG288.

Also disclosed is the chimeric protein as described herein, comprising X or X1 and/or X2 that exhibits a longer half-life compared to the chimeric protein not comprising X or X1 and/or X2. In some embodiments, the L1 and/or L2 is a cleavable linker. In certain embodiments the L4 and/or L5 is a cleavable linker. In certain embodiments the linker is cleavable by a protease selected from factor XIa, factor XIIa, kallikrein, factor VIIa, factor IXa, factor Xa, factor IIa (thrombin), Elastase-2, Granzyme-B, TEV, Enterokinase, Protease 3C, Sortase A, MMP-12, MMP-13, MMP-17, and MMP-20. In some embodiments the linker is cleavable by factor IIa (thrombin).

Some embodiments include the chimeric protein as described herein, wherein the linker comprises one or more cleavage sites comprising an amino acid sequence selected from RRRR (SEQ ID NO: 102), RKRRKR (SEQ ID NO: 103), RRRRS (SEQ ID NO: 104), TQSFNDFTR (SEQ ID NO: 1), SVSQTSKLTR (SEQ ID NO: 3), DFLAEGGGVR (SEQ ID NO: 4), TTKIKPR (SEQ ID NO: 5), LVPRG (SEQ ID NO: 6), ALRPR (SEQ ID NO: 7), KLTRAET (SEQ ID NO: 121), DFTRVVG (SEQ ID NO: 122), TMTRIVGG (SEQ ID NO: 123), SPFRSTGG (SEQ ID NO: 124), LQVRIVGG (SEQ ID NO: 125), PLGRIVGG (SEQ ID NO: 126), IEGRTVGG (SEQ ID NO: 127), LTPRSLLV (SEQ ID NO: 128), LGPVSGVP (SEQ ID NO: 129), VAGDSLEE (SEQ ID NO: 130), GPAGLGGA (SEQ ID NO: 131), GPAGLRGA (SEQ ID NO: 132), APLGLRLR (SEQ ID NO: 133), PALPLVAQ (SEQ ID NO: 134), ENLYFQG (SEQ ID NO: 135), DDDKIVGG (SEQ ID NO: 136), LEVLFQGP (SEQ ID NO: 137), and LPKTGSES (SEQ ID NO: 138). In some embodiments the linker comprises TLDPRSFLLRNPNDKYEPFWEDEEK (SEQ ID NO: 146). In certain embodiments the linker comprises an amino acid sequence of LVPRG (SEQ ID NO: 6). In some embodiments the linker comprises an a1 region of FVIII, an a2 region of FVIII, an a3 region of FVIII, or any combination thereof. In certain embodiments the linker comprises a fragment of the a2 region of FVIII. The fragment of the a2 region can in some cases comprise the sequence DKNTGDYYEDSYEDISAYLLSKNNAIEPRSFS (SEQ ID NO: 88). In still other embodiments a smaller fragment of the a2 region of FVIII can be used, including a fragment having the sequence of IEPRSFS (SEQ ID NO: 194). In one particular embodiment, the linker comprises the amino acid sequence of IEPRSFS (SEQ ID NO: 194). In another embodiment, the linker comprises the amino acid sequence of IEPRSFS (SEQ ID NO: 194), wherein the linker is not the full-length a2 region of FVIII.

Also disclosed is the chimeric protein as described herein, wherein the a2 region of FVIII comprises an amino acid sequence at least about 80%, about 85%, about 90%, about 95%, or 100% identical to either ISDKNTGDYYEDSYEDISAYLLSKNNAIEPRSFS (SEQ ID NO: 106) or DKNTGDYYEDSYEDISAYLLSKNNAIEPRSFS (SEQ ID NO: 88). In some embodiments the a1 region comprises an amino acid sequence at least about 80%, about 85%, about 90%, about 95%, or 100% identical to ISMKNNEEAEDYDDDLTDSEMDVVRFDDDNSPSFIQIRSV (SEQ ID NO: 107). In certain embodiments the a3 region comprises an amino acid sequence at least about 80%, about 85%, about 90%, about 95%, or 100% identical to ISEITRTTLQSDQEEIDYDDTISVEMKKEDFDIYDEDENQSPRSFQ (SEQ ID NO: 108). In some embodiments the F1 comprises a first Fc region and/or the F2 comprises a second Fc region.

Some embodiments include the chimeric protein as described herein, wherein the chimeric protein comprising the F1 and the F2 exhibits a longer half-life compared to the chimeric protein not comparing the F1 and the F2. In certain embodiments the L3 is a processable linker. In some embodiments the VWF protein is associated with the FVIII protein by a non-covalent bond. In some embodiments the half-life of the chimeric protein is extended compared to a FVIII protein without the VWF protein and/or the XTEN sequence or compared to wild type FVIII. In certain embodiments the half-life of the chimeric protein is extended at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than a FVIII protein without the VWF protein or the XTEN sequence or than wild type FVIII.

Also disclosed is the chimeric protein as described herein, wherein the half-life of the chimeric protein is at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours. In some embodiments the half-life of the chimeric protein is about 40 hours in HemA mice. In certain embodiments the VWF protein does not bind substantially to a VWF clearance receptor. In some embodiments the VWF protein is capable of protecting the FVIII protein from one or more protease cleavages, protecting the FVIII protein from activation, stabilizing the heavy chain and/or the light chain of the FVIII protein, or preventing clearance of the FVIII protein by one or more scavenger receptors.

Some embodiments include the chimeric protein as described herein, wherein the VWF protein inhibits or prevents endogenous VWF from binding to the FVIII protein by shielding or blocking a VWF binding site on the FVIII protein. In certain embodiments the VWF binding site is located in the A3 domain or the C2 domain of the FVIII protein or both the A3 domain and the C2 domain. In some embodiments the VWF binding site comprises the amino acid sequence corresponding to amino acids 1669 to 1689 and 2303 to 2332 of SEQ ID NO: 65. In some embodiments the first Ig constant region or a portion thereof and the second Ig constant region or a portion thereof are identical or different. In certain embodiments the FVIII protein is linked to and/or inserted with at least two XTEN sequences, at least three XTEN sequences, at least four XTEN sequences, at least five XTEN sequences, or at least six XTEN sequences.

Also disclosed is the chimeric protein as described herein, wherein the FVIII protein comprises one or more domains of FVIII selected from an A1 domain, a1 acidic region, an A2 domain, a2 acidic region, a B domain, an A3 domain, a3 acidic region, a C1 domain, a C2 domain, one or more fragments thereof, and any combinations thereof.

Also disclosed is the chimeric protein as described herein, wherein the one or more insertion sites in the FVIII protein is located within one or more domains of the FVIII protein selected from the A1 domain, the a1 acidic region, the A2 domain, the a2 acidic region, the A3 domain, the B domain, the C1 domain, the C2 domain, and any combinations thereof or between one or more domains of the FVIII protein selected from the group consisting of the A1 domain and a1 acidic region, the a1 acidic region and A2 domain, the A2 domain and a2 acidic region, the a2 acidic region and B domain, the B domain and A3 domain, the A3 domain and C1 domain, the C1 domain and C2 domain, and any combinations thereof or between two domains of the FVIII protein selected from the A1 domain and a1 acidic region, the a1 acidic region and A2 domain, the A2 domain and a2 acidic region, the a2 acidic region and B domain, the B domain and A3 domain, the A3 domain and C1 domain, the C1 domain and C2 domain, and any combinations thereof. In some embodiments the one or more insertion sites in the FVIII protein are one or more amino acids selected from the group consisting of the amino acid residues in Table 7, Table 8, Table 9 and Table 10. In certain embodiments the insertion sites in the FVIII protein are located immediately downstream of amino acid 745 corresponding to the mature FVIII protein (SEQ ID NO: 65). In some embodiments the insertion sites in the FVIII protein are located immediately downstream of residue 1656 and residue 1900 corresponding to the mature FVIII protein (SEQ ID NO: 65). In some embodiments the insertion sites in the FVIII protein are immediately downstream of residues 26, 1656, and 1900 corresponding to the mature FVIII protein (SEQ ID NO: 65). In certain embodiments the insertion sites in the FVIII protein are immediately downstream of residues 403 and 745 corresponding to the mature FVIII protein (SEQ ID NO: 65). In some embodiments the insertion sites in the FVIII protein are immediately downstream of residues 745 and 1900 corresponding to the mature FVIII protein (SEQ ID NO: 65). In certain embodiments the insertion sites in the FVIII protein are immediately downstream of residues 18 and 745 corresponding to the mature FVIII protein (SEQ ID NO: 65). In some embodiments the FVIII protein is a dual chain FVIII isoform. In some embodiments the FVIII protein is a single chain FVIII isoform. In certain embodiments the FVIII protein comprises B domain or a portion thereof. In some embodiments the FVIII protein is SQ B domain deleted FVIII.

Some embodiments include the chimeric protein as described herein, wherein the single chain FVIII isoform contains at least one amino acid substitution at a residue corresponding to residue 1648, residue 1645, or both residues corresponding to the full-length mature Factor VIII polypeptide (SEQ ID NO: 65) or residue 754, residue 751, or both residues of SQ BDD Factor VIII (SEQ ID NO: 67). In certain embodiments the amino acid substitution is an amino acid other than arginine. In some embodiments the dual chain FVIII isoform comprises a first chain comprising a heavy chain of FVIII and a second chain comprising a light chain of FVIII, wherein the heavy chain and the light chain are associated with each other by a metal bond. In certain embodiments the D' domain comprises an amino acid sequence at least 90%, 95%, 96%, 97%, 98%, 99%, or 100% identical to amino acids 764 to 866 of SEQ ID NO: 21. In some embodiments the D3 domain comprises an amino acid sequence at least 90%, 95%, 96%, 97%, 98%, 99%, or 100% identical to amino acids 867 to 1240 of SEQ ID NO: 21. In certain embodiments the VWF protein is a monomer.

Also disclosed is the chimeric protein as described herein, which comprises at least two VWF proteins, at least three VWF proteins, at least four VWF proteins, at least five VWF proteins, or at least six VWF proteins. In certain embodiments the VWF protein comprises an amino acid sequence at least 90%, 95%, 96%, 97%, 98%, 99%, or 100% identical to amino acids 764 to 1240 of SEQ ID NO: 21. In some embodiments the VWF protein consists essentially of or consists of amino acids 764 to 1240 of SEQ ID NO: 21. In certain embodiments the VWF protein contains at least one amino acid substitution at a residue corresponding to residue 1099, residue 1142, or both residues 1099 and 1142 of SEQ ID NO: 21. In some embodiments the VWF protein contains an amino acid other than cysteine substituted for a residue corresponding to residue 1099, residue 1142, or both residues 1099 and 1142 of SEQ ID NO: 21. In certain embodiments the VWF protein further comprises the D1 domain, the D2 domain, or the D1 and D2 domains of VWF.

Some embodiments include the chimeric protein as described herein, wherein the VWF protein further comprises a VWF domain selected from the A1 domain, the A2 domain, the A3 domain, the D4 domain, the B1 domain, the B2 domain, the B3 domain, the C1 domain, the C2 domain, the CK domain, one or more fragments thereof, and any combinations thereof.

Also disclosed is the chimeric protein as described herein, wherein the VWF protein consists essentially of or consists of: (1) the D' and D3 domains of VWF or fragments thereof; (2) the D1, D', and D3 domains of VWF or fragments thereof; (3) the D2, D', and D3 domains of VWF or fragments thereof; (4) the D1, D2, D', and D3 domains of VWF or fragments thereof; or (5) the D1, D2, D', D3, and A1 domains of VWF or fragments thereof.

Some embodiments include the chimeric protein as described herein, wherein the VWF protein further comprises a signal peptide of VWF or FVIII which is operably linked to the VWF protein.

Also disclosed is the chimeric protein as described herein, wherein one or more of the linkers have a length of at least about 10, 20, 30, 40, 50, 60, 70, 80, 90, 100, 110, 120, 130, 140, 150, 160, 170, 180, 190, 200, 210, 220, 230, 240, 250, 300, 350, 400, 450, 500, 550, 600, 650, 700, 750, 800, 850, 900, 950, 1000, 1200, 1400, 1600, 1800, or 2000 amino acid residues. In some embodiments one or more of the linkers have a length of about 1 to about 2000 amino acid residues. In certain embodiments one or more of the linkers comprise a gly/ser peptide. In some embodiments the gly/ser peptide has a formula of $(Gly_4Ser)_n$ (SEQ ID NO: 94) or $S(Gly_4Ser)_n$ (SEQ ID NO: 164), wherein n is a positive integer selected from the group consisting of 1, 2, 3, 4, 5, 6, 7, 8, 9 and 10. In certain embodiments the $(Gly_4Ser)_n$ linker is $(Gly_4Ser)_3$ (SEQ ID NO: 100) or $(Gly_4Ser)_4$ (SEQ ID NO: 165). In some embodiments the linker comprises 20 amino acids, 35 amino acids, 48 amino acids, 73 amino acids, or 95 amino acids. In certain embodiments the cleavable linker is SGGGGSGGGGSGGGGSGGGGSGGGGSLVPRGSGG (SEQ ID NO: 166).

In some embodiments, the chimeric protein as described herein is polysialylated, pegylated, or hesylated.

Also disclosed is the chimeric protein as described herein, wherein the first polypeptide comprises at least about 80%, 90%, 95%, 99%, or 100% identical to FVIII161 (SEQ ID NO: 69), FVIII169 (SEQ ID NO: 70), FVIII173 (SEQ ID NO: 72), FVIII195 (SEQ ID NO: 73), FVIII196 (SEQ ID NO: 74), FVIII199 (SEQ ID NO: 75), FVIII201 (SEQ ID NO: 76), FVIII203 (SEQ ID NO: 77), FVIII204 (SEQ ID NO: 78), FVIII205 (SEQ ID NO: 79), FVIII266 (SEQ ID NO: 80), FVIII267 (SEQ ID NO: 81), FVIII268 (SEQ ID NO: 82), FVIII269 (SEQ ID NO: 83), FVIII271 (SEQ ID NO: 84), FVIII272 (SEQ ID NO: 85), or FVIII282 (SEQ ID NO: 159), and the second polypeptide comprises at least about 80%, 90%, 95%, 99%, or 100% identical to either VWF057 (SEQ ID NO: 152) or VWF059 (SEQ ID NO: 197). In some embodiments, the first polypeptide comprises FVIII169 (SEQ ID NO: 70) and the second polypeptide comprises VWF057 (SEQ ID NO: 152). In other embodiments, the first polypeptide comprises FVIII169 (SEQ ID NO: 70) and the second polypeptide comprises VWF059 (SEQ ID NO: 197). In yet another embodiment, the first polypeptide comprises FVIII169 (SEQ ID NO: 70) and the second polypeptide comprises VWF062 (SEQ ID NO: 199). In some embodiments, the chimeric protein is efficacious in preventing and/or stopping bleeding from a subject in need thereof.

Also disclosed is a polynucleotide or a set of polynucleotides encoding the chimeric protein as described herein. In some embodiments, the polynucleotide as described herein, further comprises a polynucleotide chain, which encodes PC5 or PC7.

Some embodiments include a vector comprising the polynucleotide as described herein and one or more promoter operably linked to the polynucleotide or the set of polynucleotides.

In some embodiments the vector as described herein, further comprises an additional vector, which comprises a polynucleotide chain encoding PC5 or PC7.

Also disclosed is a host cell comprising the polynucleotide or the vector as described herein. In some embodiments the host cell is a mammalian cell. In certain embodiments the mammalian cell is selected from HEK293 cell, CHO cell, and BHK cell.

Also disclosed is a pharmaceutical composition comprising the chimeric protein, the polynucleotide, the vector, or the host cell as described herein, and a pharmaceutically acceptable carrier. In some embodiments the chimeric protein has extended half-life compared to wild type FVIII protein. In certain embodiments, the half-life of the chimeric protein is extended at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than wild type FVIII.

Some embodiments include the composition as described herein, wherein the half-life of the chimeric protein is at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours. In certain embodiments the half-life of the chimeric protein is about 40 hours in HemA mice. In some embodiments the composition as described herein is administered by a route selected from the group consisting of topical administration, intraocular administration, parenteral administration, intrathecal administration, subdural administration and oral administration. In certain embodiments the parenteral administration is intravenous or subcutaneous administration.

In some embodiments the composition as described herein is used to treat a bleeding disease or condition in a subject in need thereof. In certain embodiments the bleeding disease or condition is selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath and any combinations thereof. In some embodiments the subject is scheduled to undergo a surgery. In certain embodiments the treatment is prophylactic or on-demand.

Also disclosed is a method of extending or increasing half-life of the chimeric protein, wherein the method comprises adding an effective amount of the chimeric protein, the polynucleotide, the vector, the host cell, or the composition as described herein to a subject in need thereof, wherein the VWF protein, the XTEN sequence, the first Ig constant region or a portion thereof, and the second Ig constant region or a portion thereof increase the half-life of the chimeric protein.

Some embodiments include a method of treating a bleeding disease or disorder in a subject in need thereof comprising administering an effective amount of the chimeric protein, the polynucleotide, the vector, the host cell, or the composition as described herein, wherein the bleeding disease or disorder is selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath. In some embodiments the subject is an animal. In certain embodiments the animal is a human. In some embodiments the subject is suffering from hemophilia A. In certain embodiments the treatment is prophylactic or on-demand. In some embodiments the effective amount is 0.1 gg/kg to 500 mg/kg.

Also disclosed is a method as described herein, wherein the chimeric protein, the polynucleotide, the vector, the host cell, or the composition as described herein is administered by a route selected from the group consisting of topical administration, intraocular administration, parenteral administration, intrathecal administration, subdural administration and oral administration. In certain embodiments the parenteral administration is selected from the group consisting of intravenous administration, subcutaneous administration, intramuscular administration, and intradermal administration.

Some embodiments include a method of making a chimeric protein, comprising transfecting one or more host cell with the polynucleotide or the vector as described herein and expressing the chimeric protein in the host cell. In some embodiments, the method as described herein further comprises isolating the chimeric protein. In certain embodiments the chimeric protein is efficacious in stopping and/or preventing bleeding in the subject.

BRIEF DESCRIPTION OF THE DRAWINGS/FIGURES

FIG. 1 shows a schematic diagram of a chimeric protein comprising a first polypeptide which comprises a FVIII protein (A1-A2-partial or full B-A3-C1-C2) fused to an Fc region, wherein an XTEN is inserted at an insertion site within the FVIII protein and a second polypeptide which comprises a VWF protein comprising D'D3 domains, an XTEN having less than 288 amino acids, a thrombin cleavable linker, and a second Fc region. XTEN insertions in the FVIII protein and/or fusions to the VWF protein extend a half-life of the chimeric protein by increasing the hydrodynamic radius and by blocking receptor-mediated clearance. The D'D3 domains of VWF block FVIII interaction with endogenous VWF, stabilize the FVIII protein, and extend a half-life of the chimeric protein. The Fc domains can covalently link the D'D3 domains with the FVIII protein and extend a half-life of the chimeric protein through FcRn-mediated recycling pathway. The thrombin-cleavable linker enables a release of the D'D3 domains upon FVIII activation and ensures the correct alignment between FVIII and the D'D3 domains of VWF.

Figure 2:
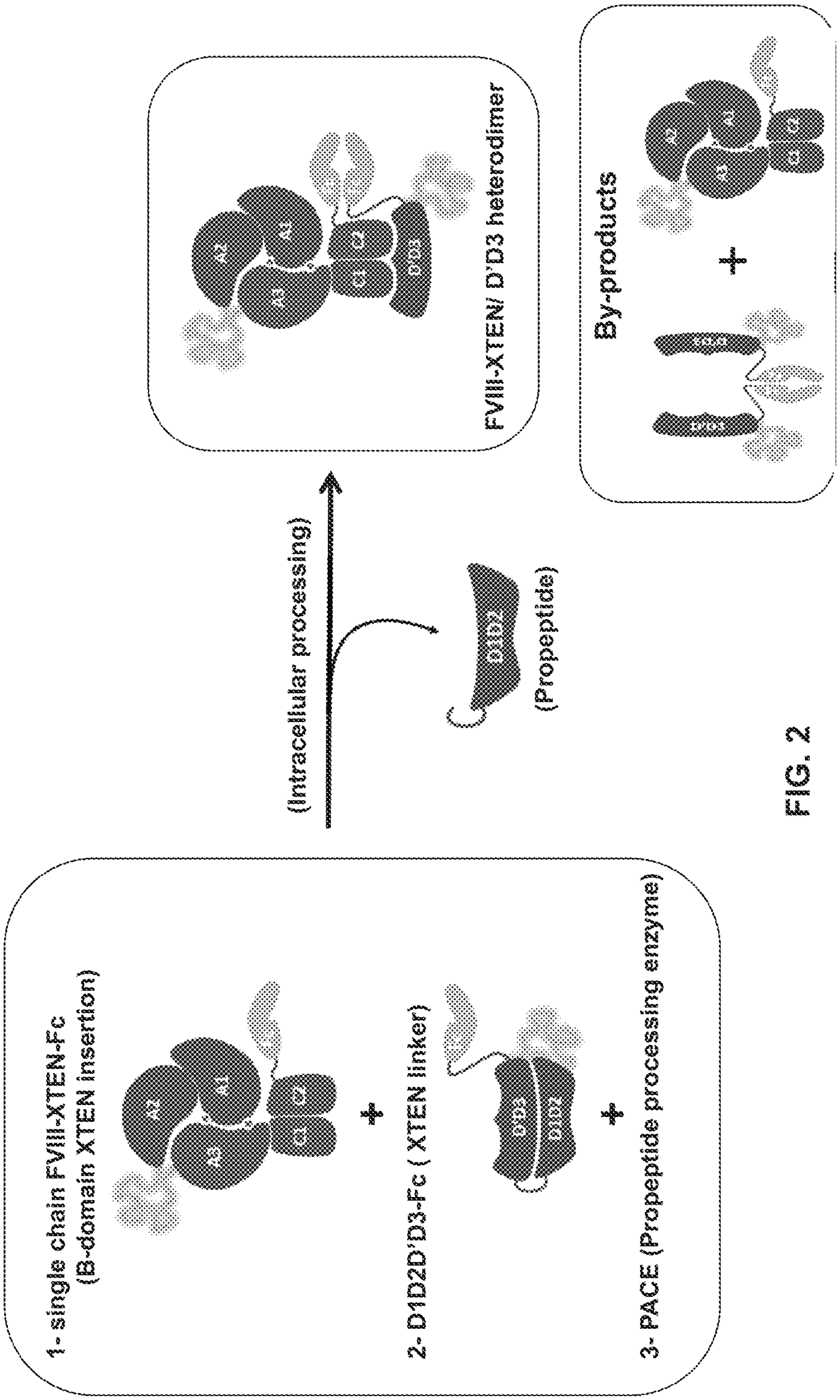

FIG. 2 shows three plasmid expression system for FVIII-XTEN-Fc:D'D3-XTEN-Fc heterodimers: a first plasmid comprising a nucleotide sequence encoding single chain FVIII-XTEN-Fc in which an XTEN is inserted in the B domain; a second plasmid comprising a nucleotide sequence encoding D1D2D'D3-XTEN-Fc, in which the XTEN sequence comprises less than 288 amino acids; and a third plasmid comprising a nucleotide sequence encoding PACE, a propeptide processing enzyme. When the three polypeptides are expressed from the three plasmids, the D1D2 propeptide domains of VWF can be processed from the D'D3 domains by intracellular processing. The resulting complex contains three products, the first molecule being FVIII-XTEN/D'D3 heterodimers, the second molecule being a by-product, homodimer of D'D3-XTEN-Fc, and the third molecule being another by-product, i.e., FVIII (XTEN)-Fc.

Figure 3:
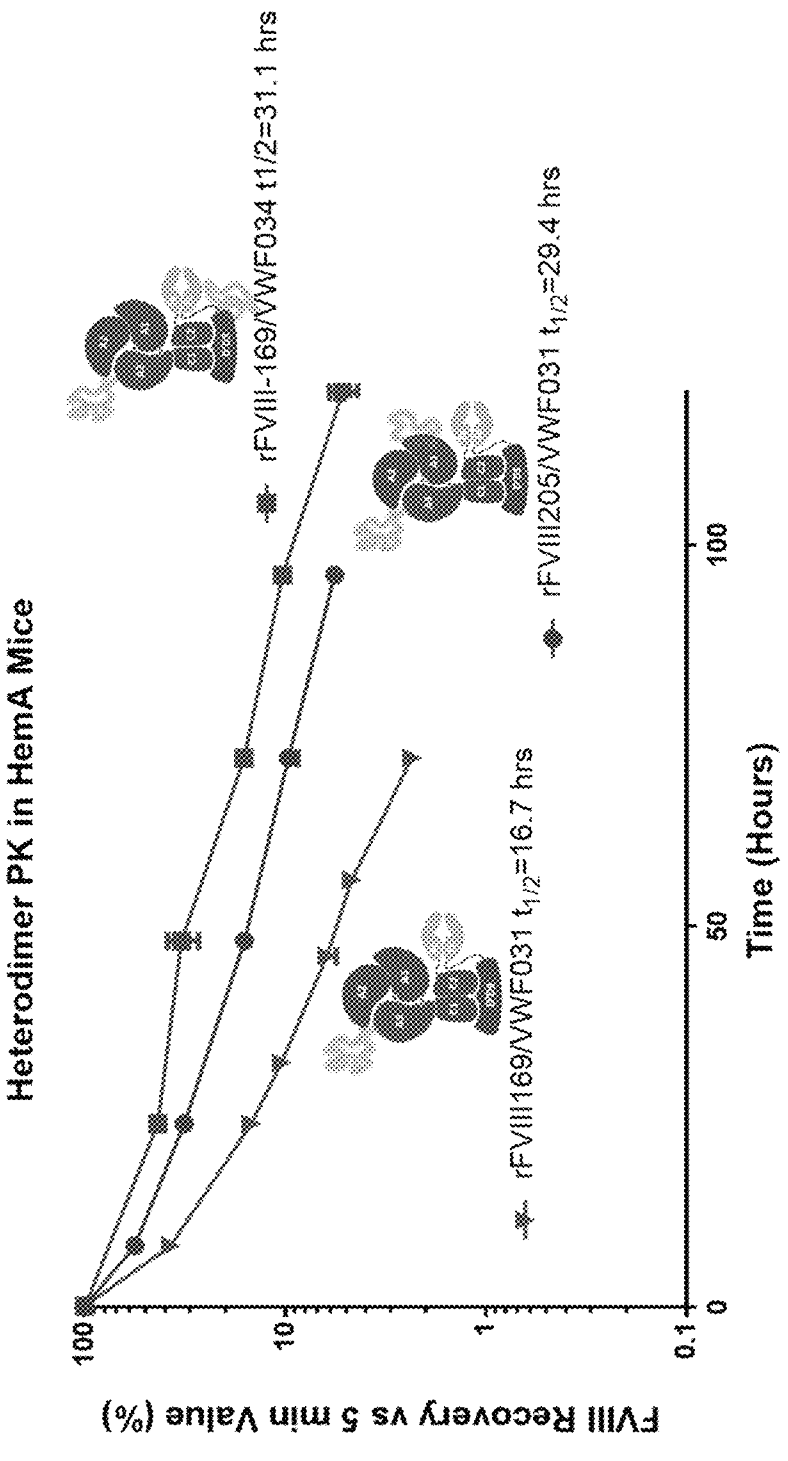

FIG. 3 shows additive effects of XTEN insertions on the half-life extension of the heterodimers. FVIII169 comprises a B domain deleted FVIII protein fused to an Fc region, wherein an XTEN sequence (e.g., AE288) is inserted at amino acid 745 corresponding to mature full length FVIII. FVIII205 comprises a B domain deleted FVIII protein fused to an Fc region, wherein an XTEN sequence (e.g., AE144) is inserted at amino acid 18 corresponding to mature full length FVIII and another XTEN sequence (e.g., AE288) is inserted at amino acid 745 corresponding to mature full length FVIII. VWF031 comprises a D' domain and a D3 domain of VWF fused to an Fc region by a thrombin cleavable linker (no XTEN). VWF034 comprises a D' domain and a D3 domain of VWF fused to AE288 and an Fc region. The half-life of FVIII169/VWF031 (inverted triangle) is 16.7 hours in HemA mice; the half-life of FVIII205/VWF031 (circle) is 29.4 hours in HemA mice; and the half-life of FVIII169/VWF034 (square) is 31.1 hours in HemA mice.

Figure 4:
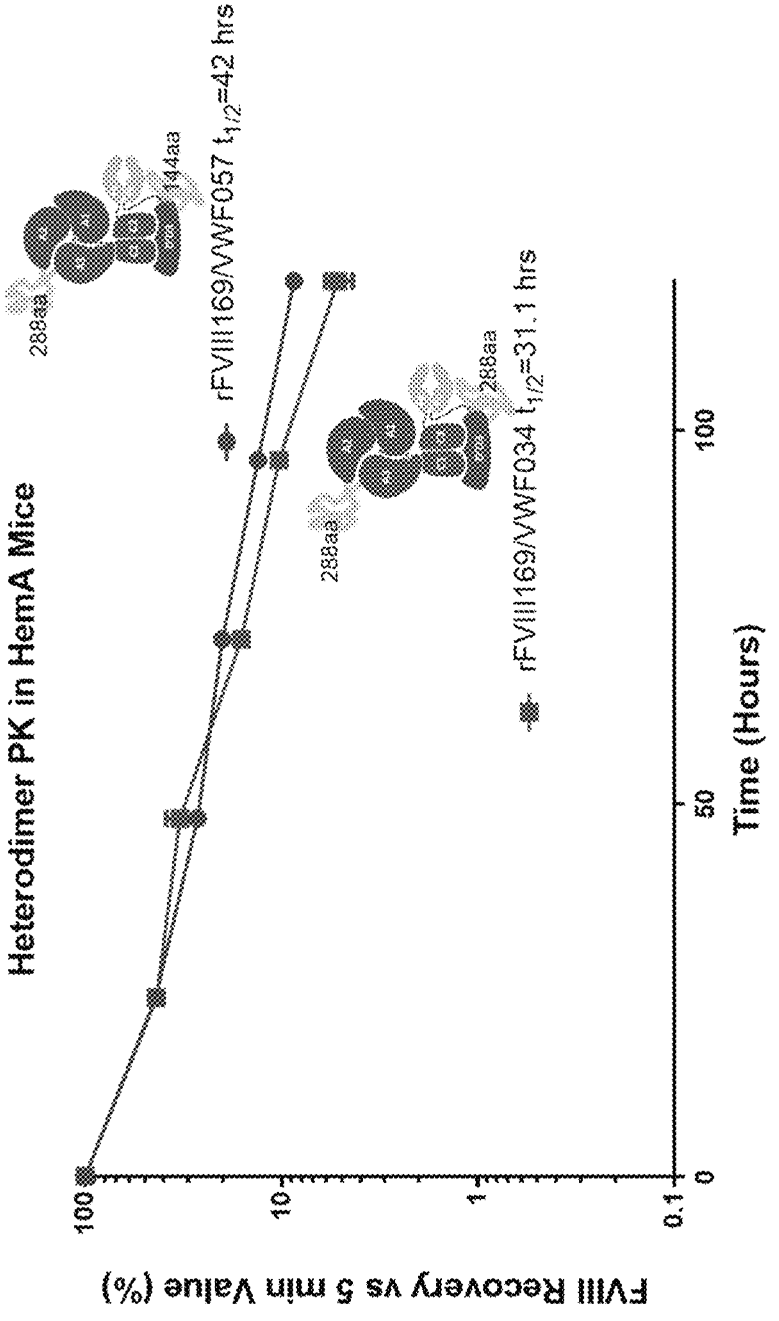

FIG. 4 shows that AE144 XTEN confers better half-life extension than AE288 XTEN when inserted between the D'D3 domains of VWF and Fc domains. For example, while the half-life of VWF169/VWF034 (square) is 31.1. hours in HemA mice, the half-life of FVIII169/VWF057 (circle) is 42 hours in HemA mice. VWF057 comprises D'D3 domains of VWF fused to AE144 and an Fc region.

Figure 5:
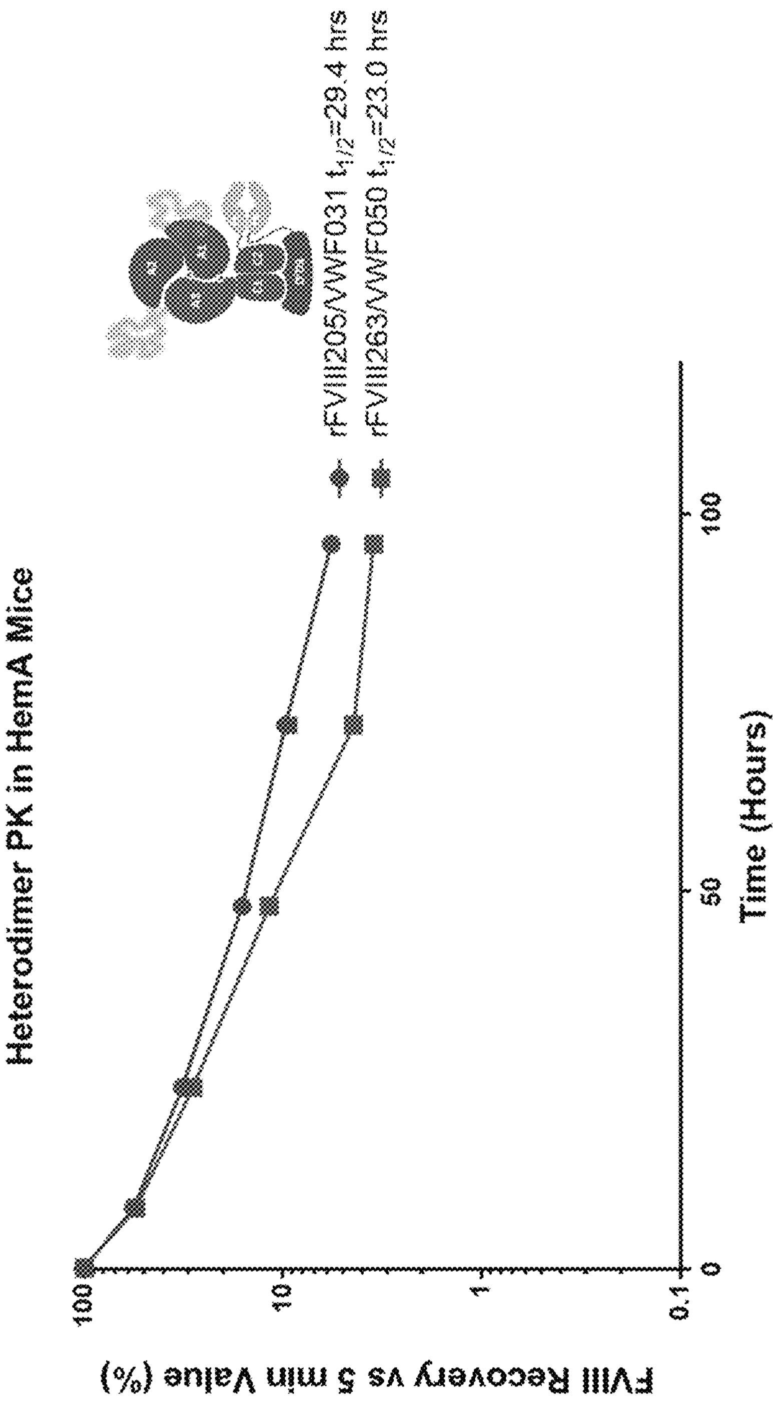

FIG. 5 shows that Fc domains are needed for half-life extension of the chimeric protein heterodimers. When the half-life of FVIII205/VWF031 (circle) was compared in HemA mice with that of FVIII263/VWF050 (square), which contains mutations at the FcRn binding sites (IHH triple mutation Fc) and thus cannot be recycled through FcRn pathway, the half-life of FVIII263/VWF050 (23 hours) is shorter than that of VWF205/VWF031 (29.4 hours). This indicates that the Fc regions are necessary for half-life extension.

Figure 6A:
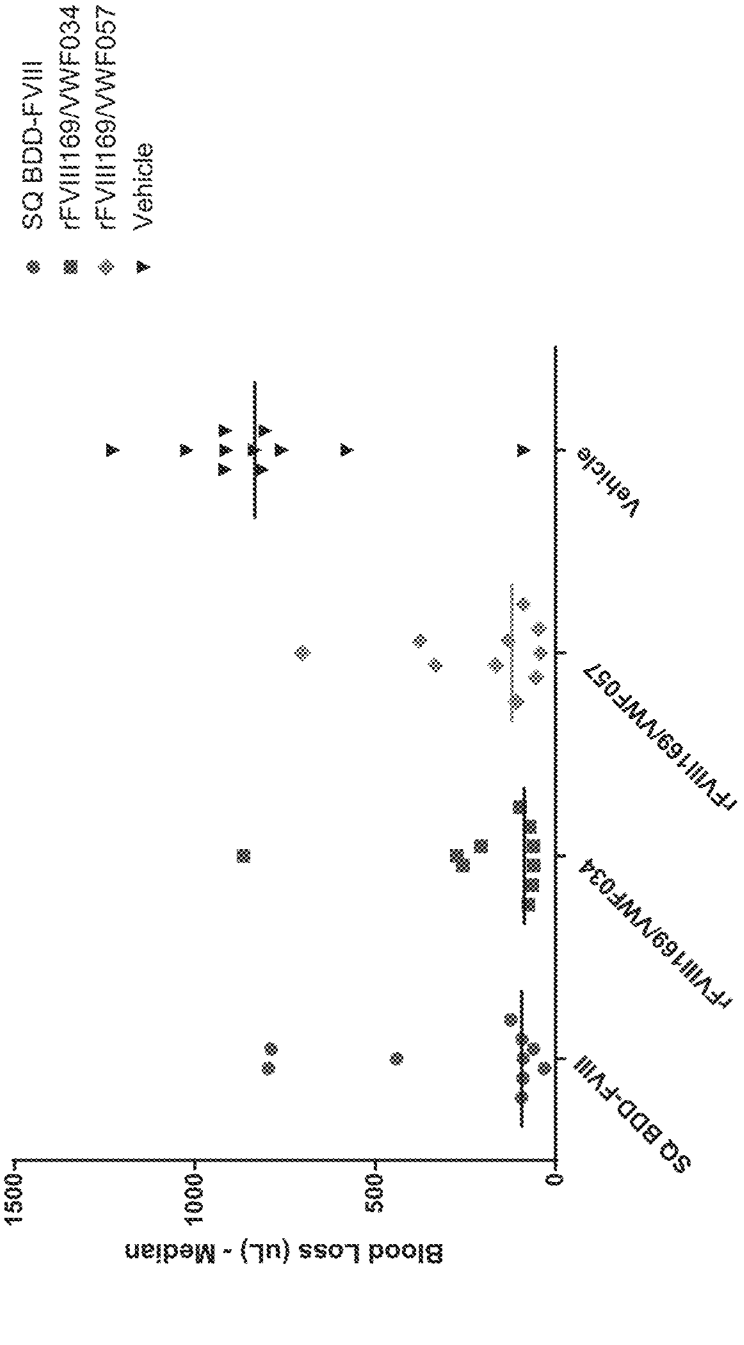
Figure 6B:
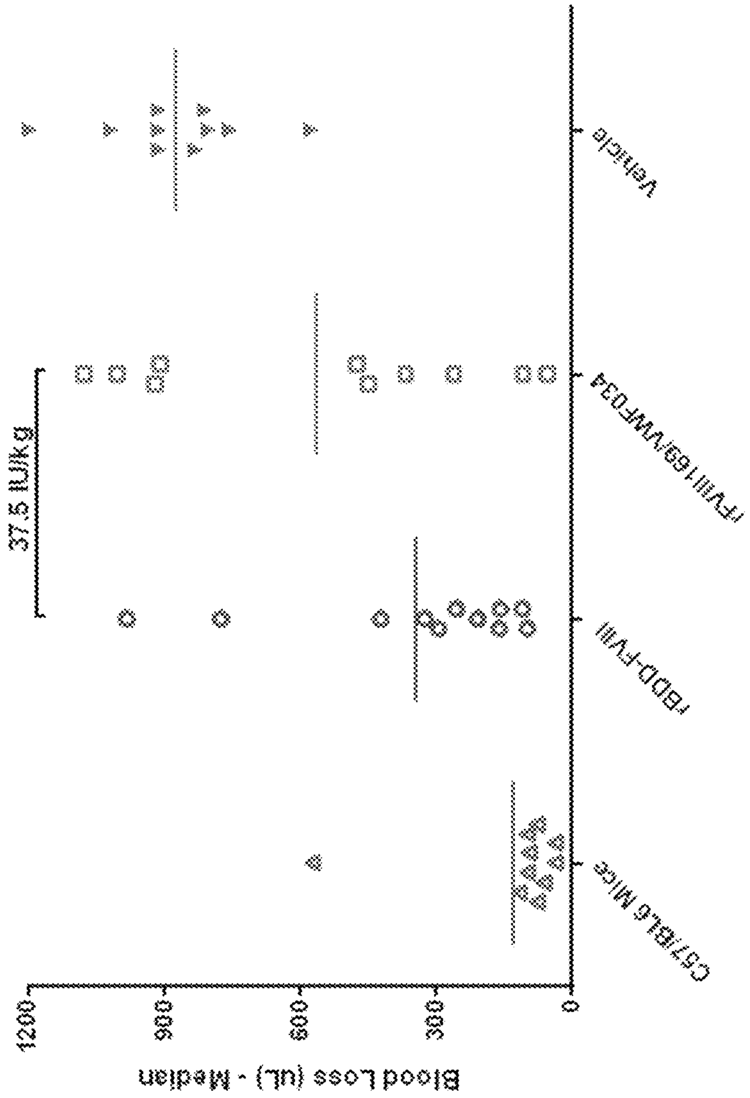

FIG. 6A shows similar acute efficacy of FVIII-XTEN-Fc/D'D3-XTEN-Fc heterodimers compared to B domain deleted FVIII (SQ BDD FVIII) in HemA mice tail clip model. Mice were dosed at 75 IU/kg, and the activity was measured by aPTT assay. SQ BDD FVIII is shown as circle while FVIII169/VWF034 is shown as square, FVIII169/VWF057 is shown as diamond, and vehicle is shown as inverted triangle. The construct details of FVIII169, VWF034, and VWF057 are shown elsewhere herein. FIG. 6B shows a comparison of the acute efficacy of FVIII169/VWF034 with B domain deleted FVIII (SQ BDD FVIII) in HemA mice at 37.5 IU/kg dose, and the activity was measured by aPTT assay. The median blood loss (uL) of mice in each treatment groups are indicated by the horizontal lines, blood loss (uL) in C57/BL6 mice is shown as hollow triangle; the blood loss (uL) after dosing of 37.5 IU/kg of rBDD-FVIII is shown as hollow circle; the blood loss (uL) after dosing of 37.5 IU/kg FVIII169/VWF034 is shown as hollow square and the blood loss (uL) after dosing of vehicle is shown as inverted triangle.

Figure 7B:
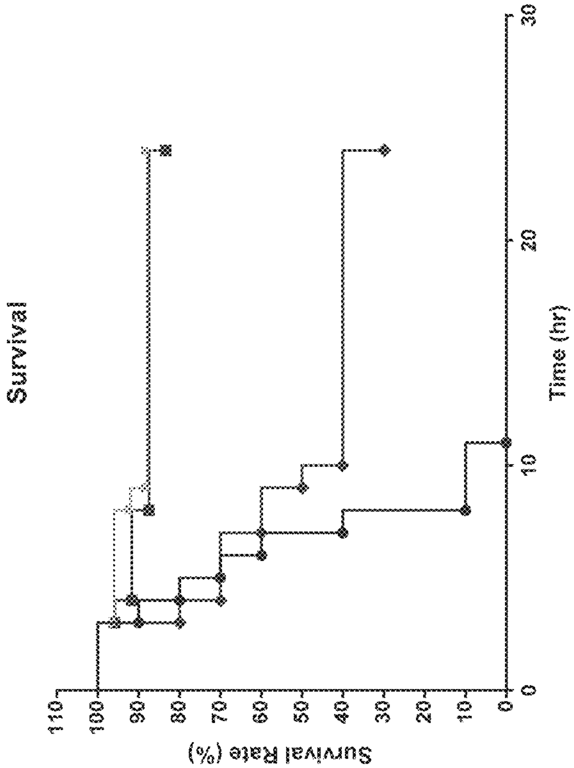
Figure 7A:
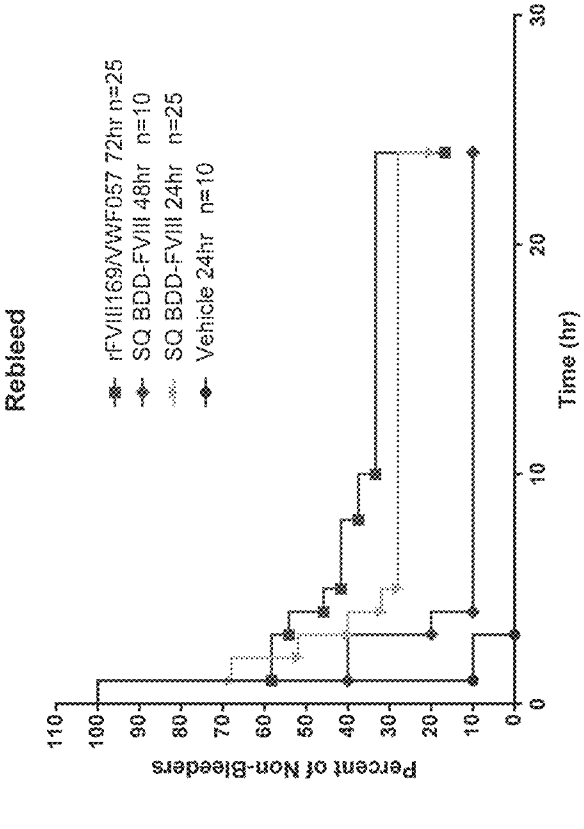

FIGS. 7A-B show that rFVIII169/VWF057 heterodimer provides longer protection to HemA mice in Tail Vein Transection Bleeding Model. FIG. 7A shows the rebleeding data in mice that received rFVIII169/VWF057 at 72 hours before tail injury (square), SQ BDD-FVIII at 48 hours before tail injury (diamond), SQ BDD FVIII at 24 hours before tail injury (inverted triangle), and vehicle (circle). The activity was measured by aPTT assay. X-axis shows time in hours, and the Y axis shows percent of Non-Bleeders. FIG. 7B shows the corresponding survival data in the four categories of the mice shown in FIG. 7A. The mice received 12 IU/kg of FVIII169/VWF057 72 hours prior to tail injury showed similar protection on re-bleeding and survival compared to the mice received SQ BDD FVIII treatment 24 hour before the tail injury.

Figure 8A:
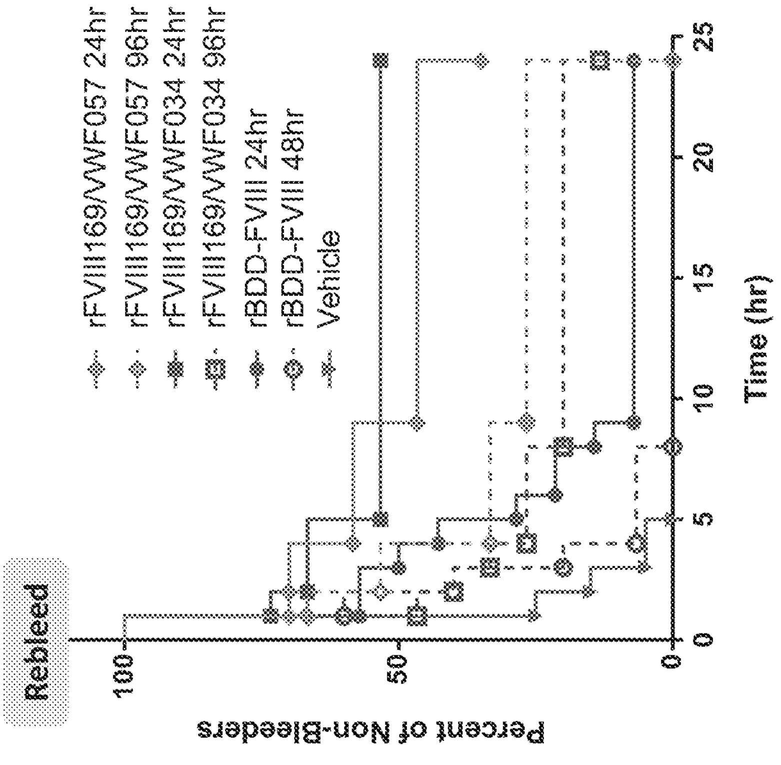
Figure 8B:
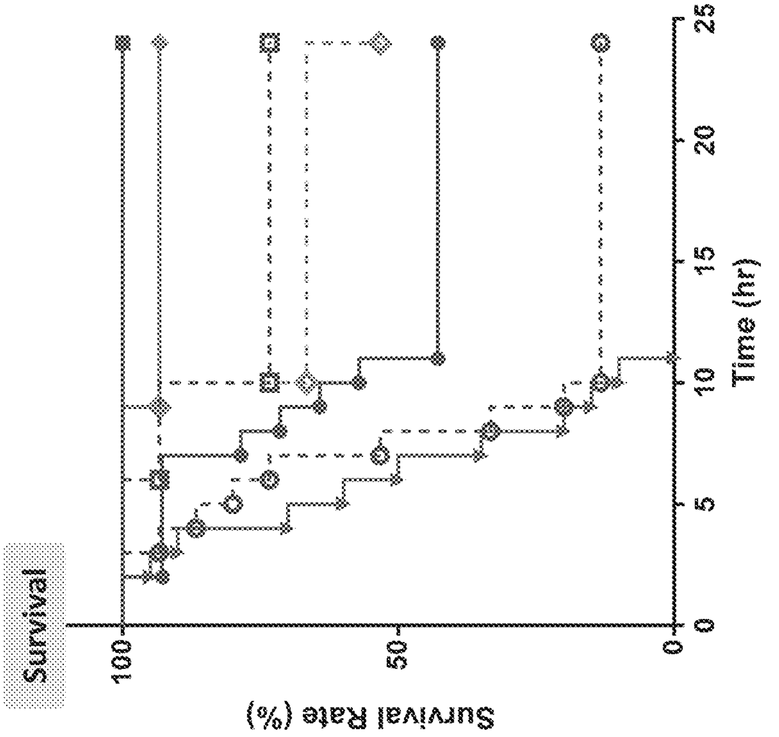

FIG. 8A shows the comparable rebleeding data in mice that received rFVIII-XTEN-Fc/D'D3-XTEN-Fc Heterodimers at 96 hours versus rBDD-FVIII at 24 hours before the injury. Filled squares show the rebleeding data in mice received FVIII169/VWF034 at 24 hours before the injury; hollow squares show the rebleeding data in mice received FVIII169/VWF034 at 96 hours before the injury; filled diamond show the rebleeding data in mice received FVIII169/VWF057 at 24 hours before the injury; hollow diamond show the rebleeding data in mice received FVIII169/VWF057 at 96 hours before the injury; filled circles show the rebleeding data in mice received rBDD-FVIII at 24 hours before the injury; hollow circles show the rebleeding data in mice received rBDD-FVIII at 48 hours before the injury; and filled triangle show the rebleeding data in mice received vehicle. X axis shows time in hours, and y axis shows percent of Non-Bleeders FIG. 8B shows the survival curve in mice that received rFVIII-XTEN-Fc/D'D3-XTEN-Fc heterodimers at 96 hours versus rBDD-FVIII at 24 hours before the injury. X axis shows time in hours, and y axis shows percent of survival. The symbols are the same as FIG. 8A.

Figure 9:
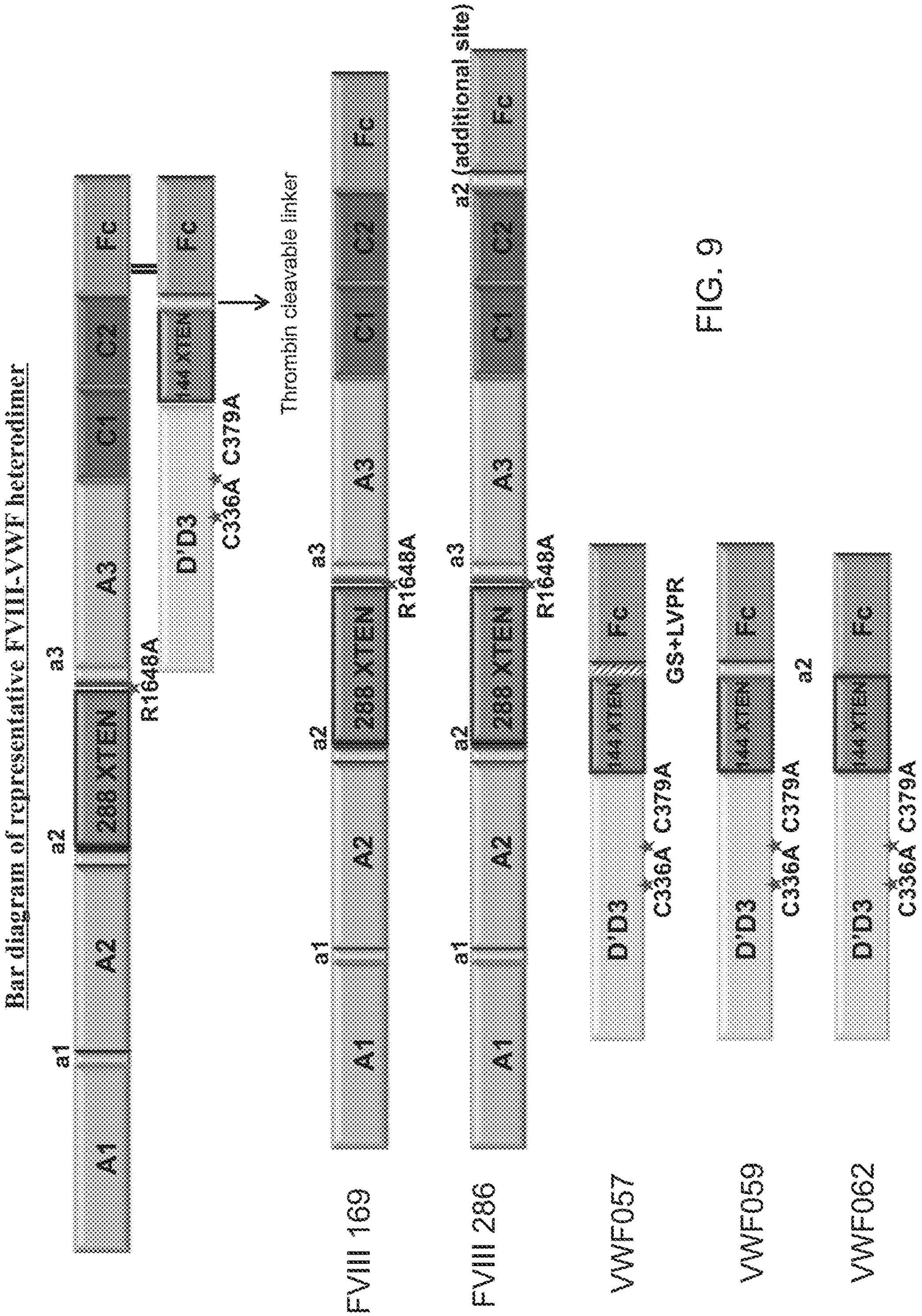

FIG. 9 shows a diagram of representative FVIII-VWF heterodimers and FVIII169, FVIII286, VWF057, VWF059, and VWF062 constructs. For example, FVIII169 construct comprises a B domain deleted FVIII protein with R1648A substitution fused to an Fc region, wherein an XTEN sequence (e.g., AE288) is inserted at amino acid 745 corresponding to mature full length FVIII (A1-a1-A2-a2-288XTEN-a3-A3-C1-C2-Fc). FVIII286 construct comprises a B domain deleted FVIII protein with R1648 substitution fused to an Fc region, wherein an XTEN sequence (e.g., AE288) is inserted at amino acid 745 corresponding to mature full length FVIII, with additional a2 region in between FVIII and Fc (A1-a1-A2-a2-288XTEN-a3-A3-C1-C2-a2-Fc). VWF057 is a VWF-Fc fusion construct that comprises D'D3 domain of the VWF protein (with two amino acid substitutions in D'D3 domain, i.e., C336A and C379A) linked to the Fc region via a VWF linker, which comprises LVPRG thrombin site ("LVPRG"; SEQ ID NO: 6) and GS linker ("GS"), wherein an XTEN sequence (i.e., AE144) is inserted between D'D3 domain and the VWF linker (D'D3-144XTEN-GS+LVPRG-Fc). VWF059 is a VWF-Fc fusion construct that comprises D'D3 domain of the VWF protein (with two amino acid substitutions in D'D3 domain, i.e., C336A and C379A) linked to the Fc region via an acidic region 2 (a2) of FVIII as a VWF linker, wherein an XTEN sequence (i.e., AE144) is inserted between D'D3 domain and the VWF linker. VWF062 is a VWF-Fc fusion construct that comprises D'D3 domain of the VWF protein (with two amino acid substitutions in D'D3 domain, i.e., C336A and C379A) linked to the Fc region, wherein an XTEN sequence (i.e., AE144) is inserted between D'D3 domain and the Fc region (D'D3-144XTEN-Fc).

Figure 10:
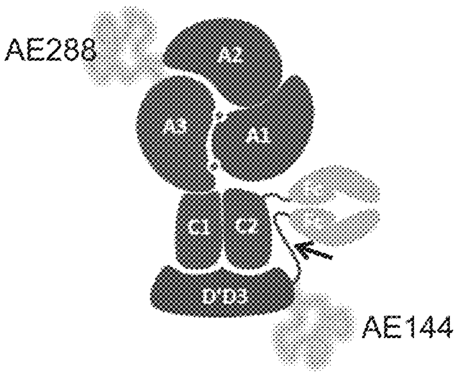

FIG. 10 shows a schematic diagram representing FVIII/VWF heterodimer constructs, for example, FVIII169/VWF057, FVIII169/VWF059, FVIII169/VWF059A, and FVIII169/VWF073. The arrow shows the site where an optional linker is added to introduce a thrombin cleavage site. FVIII169/VWF057 has a linker comprising LVPRG (SEQ ID NO: 6). FVIII169/VWF059 has a linker comprising the FVIII a2 region (i.e., IS LLSKNNAIEPRSFS DKTH (SEQ ID NO: 106)). FVIII169/VWF059A has a linker comprising a truncated FVIII a2 region (i.e., DKNTGDYYEDSYEDISAYL LSKNNAIEPRSFS DKTH (SEQ ID NO: 88)). FVIII169/VWF073 has a linker within the VWF073 construct (SEQ ID NO: 175) comprising a fragment of the FVIII a2 region consisting of IEPRSFS (SEQ ID NO: 194).

FIGS. 11A-C show SDS-PAGE images following thrombin digestion of FVIII169/VWF057 and a FVIII-Fc control. FIG. 11A shows staining of the SDS-PAGE gel with an anti-D3 antibody (AB 96340). Arrows highlight "LCFc: D'D3-XTEN-Fc," which is the un-cleaved, full-length FVIII169/VWF057; and "D'D3-144 XTEN," which is the resulting fragment following cleavage by thrombin. FIG. 11B shows staining of the SDS-PAGE gel with an anti-HC antibody (GMA012). Arrows highlight the FVIII heavy chain ("HC") and FVIII A2 domain. FIG. 11C shows the overlay of panels A and B. Samples were collected at the time points indicated at the top of each panel. Arrows point to the relevant proteins.

Figure 12A:
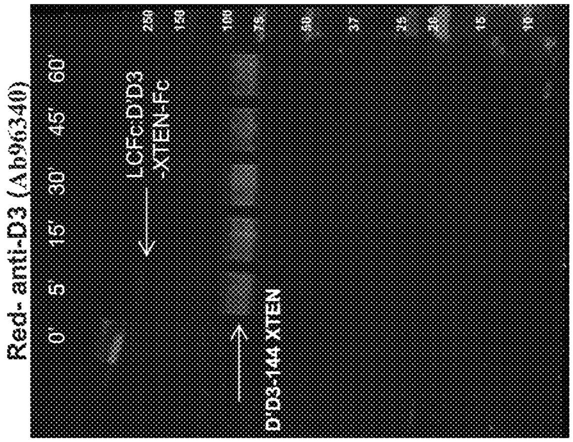
Figure 12B:
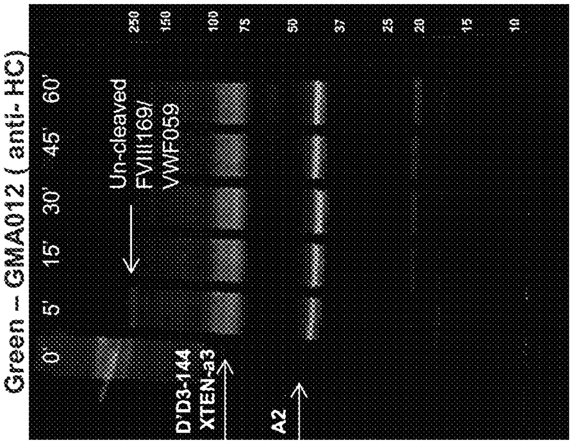
Figure 12C:
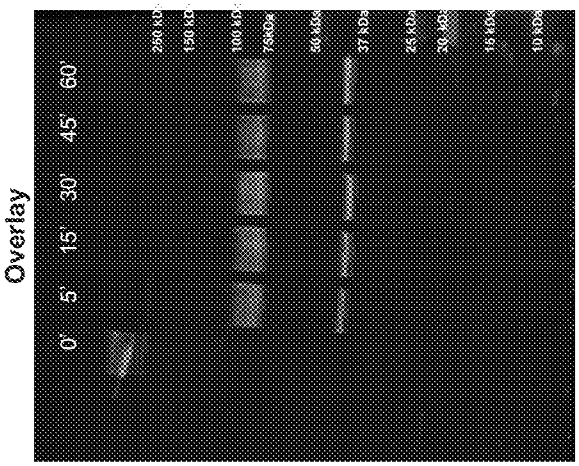
Figure 13:
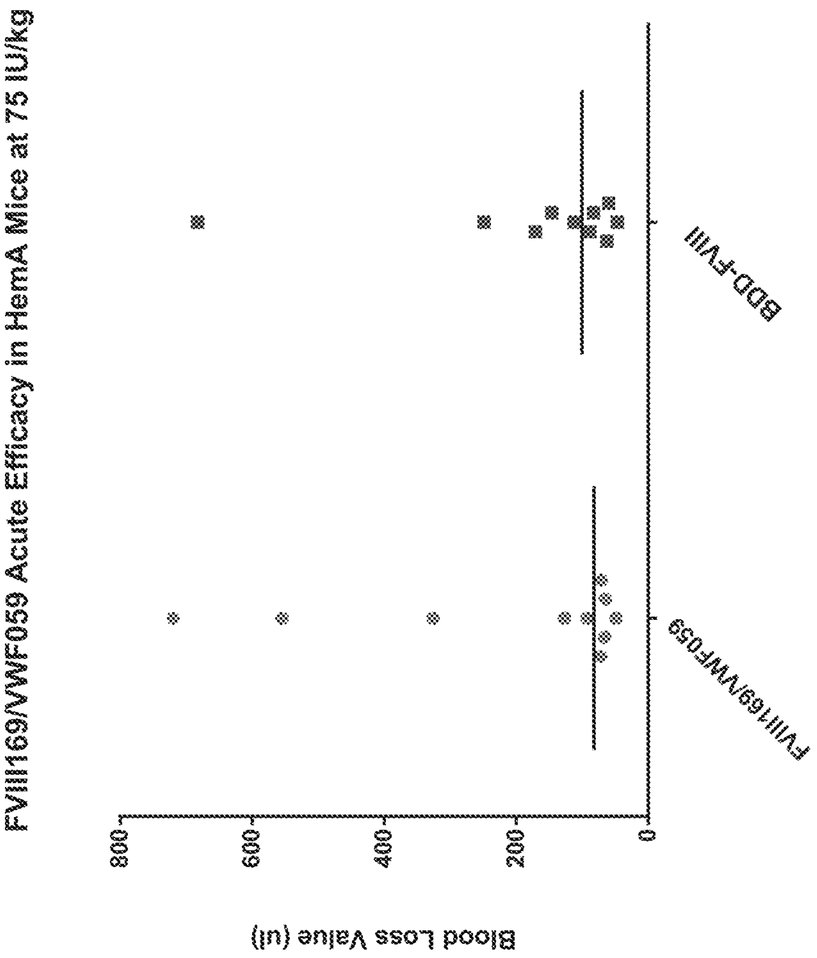

FIGS. 12A-C shows SDS-PAGE images following thrombin digestion of FVIII169/VWF059. FIG. 12A shows staining of the SDS-PAGE gel with an anti-D3 antibody (AB 96340). Arrows highlight "LCFc:D'D3-XTEN-Fc," which is the un-cleaved, full-length FVIII169/VWF059; and "D'D3-144 XTEN," which is the resulting fragment following cleavage by thrombin. FIG. 12B shows staining of the SDS-PAGE gel with an anti-HC antibody (GMA012). Arrows highlight the un-cleaved, full length FVIII169/VWF059; D'D3-144 XTEN-a3, which is the resulting fragment following cleavage by thrombin; and "A2," which is the A2 domain of FVIII. FIG. 12C shows the overlay of panels A and B. Samples were collected at the time points indicated at the top of each panel FIG. 13 shows acute efficacy data of HemA mice treated with FVIII169/VWF059 (circle) as compared to HemA mice treated with a BDD-FVIII control (Square). Blood loss value was measured following tail clip. p=0.9883.

DETAILED DESCRIPTION OF THE INVENTION

The present invention is directed to a chimeric protein comprising two polypeptides, a first polypeptide comprising a FVIII protein fused to a first Ig constant region and a second polypeptide comprising a VWF protein fused to a second Ig constant region or a portion thereof by an XTEN sequence, wherein the XTEN sequence contains less than 288 amino acids.

I. Definitions

It is to be noted that the term “a” or “an” entity refers to one or more of that entity; for example, “a nucleotide sequence,” is understood to represent one or more nucleotide sequences. As such, the terms “a” (or “an”), “one or more,” and “at least one” can be used interchangeably herein.

Furthermore, “and/or” where used herein is to be taken as specific disclosure of each of the two specified features or components with or without the other. Thus, the term “and/or” as used in a phrase such as “A and/or B” herein is intended to include “A and B,” “A or B,” “A” (alone), and “B” (alone). Likewise, the term “and/or” as used in a phrase such as “A, B, and/or C” is intended to encompass each of the following aspects: A, B, and C; A, B, or C; A or C; A or B; B or C; A and C; A and B; B and C; A (alone); B (alone); and C (alone).

It is understood that wherever aspects are described herein with the language “comprising,” otherwise analogous aspects described in terms of “consisting of” and/or “consisting essentially of” are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term “about” is used herein to mean approximately, roughly, around, or in the regions of. When the term “about” is used in conjunction with a numerical range, it modifies that range by extending the boundaries above and below the numerical values set forth. In general, the term “about” can modify a numerical value above and below the stated value by a variance of, e.g., 10 percent, up or down (higher or lower).

The term “polynucleotide” or “nucleotide” is intended to encompass a singular nucleic acid as well as plural nucleic acids, and refers to an isolated nucleic acid molecule or construct, e.g., messenger RNA (mRNA) or plasmid DNA (pDNA). In certain embodiments, a polynucleotide comprises a conventional phosphodiester bond or a non-conventional bond (e.g., an amide bond, such as found in peptide nucleic acids (PNA)). The term “nucleic acid” refers to any one or more nucleic acid segments, e.g., DNA or RNA fragments, present in a polynucleotide. By “isolated” nucleic acid or polynucleotide is intended a nucleic acid molecule, DNA or RNA, which has been removed from its native environment. For example, a recombinant polynucleotide encoding a Factor VIII polypeptide contained in a vector is considered isolated for the purposes of the present invention. Further examples of an isolated polynucleotide include recombinant polynucleotides maintained in heterologous host cells or purified (partially or substantially) from other polynucleotides in a solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid can include regulatory elements such as promoters, enhancers, ribosome binding sites, or transcription termination signals.

As used herein, a “coding region” or “coding sequence” is a portion of polynucleotide which consists of codons translatable into amino acids. Although a “stop codon” (TAG, TGA, or TAA) is typically not translated into an amino acid, it may be considered to be part of a coding region, but any flanking sequences, for example promoters, ribosome binding sites, transcriptional terminators, introns, and the like, are not part of a coding region. The boundaries of a coding region are typically determined by a start codon at the 5' terminus, encoding the amino terminus of the resultant polypeptide, and a translation stop codon at the 3' terminus, encoding the carboxyl terminus of the resulting polypeptide. Two or more coding regions of the present invention can be present in a single polynucleotide construct, e.g., on a single vector, or in separate polynucleotide constructs, e.g., on separate (different) vectors. It follows, then, that a single vector can contain just a single coding region, or comprise two or more coding regions, e.g., a single vector can separately encode a binding domain-A and a binding domain-B as described below. In addition, a vector, polynucleotide, or nucleic acid of the invention can encode heterologous coding regions, either fused or unfused to a nucleic acid encoding a binding domain of the invention. Heterologous coding regions include without limitation specialized elements or motifs, such as a secretory signal peptide or a heterologous functional domain.

Certain proteins secreted by mammalian cells are associated with a secretory signal peptide which is cleaved from the mature protein once export of the growing protein chain across the rough endoplasmic reticulum has been initiated. Those of ordinary skill in the art are aware that signal peptides are generally fused to the N-terminus of the polypeptide, and are cleaved from the complete or “full-length” polypeptide to produce a secreted or “mature” form of the polypeptide. In certain embodiments, a native signal peptide or a functional derivative of that sequence that retains the ability to direct the secretion of the polypeptide that is operably associated with it. Alternatively, a heterologous mammalian signal peptide, e.g., a human tissue plasminogen activator (TPA) or mouse ß-glucuronidase signal peptide, or a functional derivative thereof, can be used.

The term “downstream,” when refers to a nucleotide sequence, means that a nucleic acid or a nucleotide sequence is located 3' to a reference nucleotide sequence. In certain embodiments, downstream nucleotide sequences relate to sequences that follow the starting point of transcription. For example, the translation initiation codon of a gene is located downstream of the start site of transcription. The term “downstream,” when refers to a polypeptide sequence, means that the amino acid or an amino acid insertion site is located at the C-terminus of the reference amino acids. For example, an insertion site immediately downstream of amino acid 745 corresponding to the mature wild type FVIII protein means that the insertion site is between amino acid 745 and amino acid 746 corresponding to the mature wild type FVIII protein.

The term "upstream" refers to a nucleotide sequence that is located 5' to a reference nucleotide sequence. In certain embodiments, upstream nucleotide sequences relate to sequences that are located on the 5' side of a coding region or starting point of transcription. For example, most promoters are located upstream of the start site of transcription.

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions may include promoters, translation leader sequences, introns, polyadenylation recognition sequences, RNA processing sites, effector binding sites and stem-loop structures. If a coding region is intended for expression in a eukaryotic cell, a polyadenylation signal and transcription termination sequence will usually be located 3' to the coding sequence.

A polynucleotide which encodes a gene product, e.g., a polypeptide, can include a promoter and/or other transcription or translation control elements operably associated with one or more coding regions. In an operable association a coding region for a gene product, e.g., a polypeptide, is associated with one or more regulatory regions in such a way as to place expression of the gene product under the influence or control of the regulatory region(s). For example, a coding region and a promoter are "operably associated" if induction of promoter function results in the transcription of mRNA encoding the gene product encoded by the coding region, and if the nature of the linkage between the promoter and the coding region does not interfere with the ability of the promoter to direct the expression of the gene product or interfere with the ability of the DNA template to be transcribed. Other transcription control elements, besides a promoter, for example enhancers, operators, repressors, and transcription termination signals, can also be operably associated with a coding region to direct gene product expression.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit ß-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

The term "expression" as used herein refers to a process by which a polynucleotide produces a gene product, for example, an RNA or a polypeptide. It includes without limitation transcription of the polynucleotide into messenger RNA (mRNA), transfer RNA (tRNA), small hairpin RNA (shRNA), small interfering RNA (siRNA) or any other RNA product, and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage.

A "vector" refers to any vehicle for the cloning of and/or transfer of a nucleic acid into a host cell. A vector may be a replicon to which another nucleic acid segment may be attached so as to bring about the replication of the attached segment. A "replicon" refers to any genetic element (e.g., plasmid, phage, cosmid, chromosome, virus) that functions as an autonomous unit of replication in vivo, i.e., capable of replication under its own control. The term "vector" includes both viral and nonviral vehicles for introducing the nucleic acid into a cell in vitro, ex vivo or in vivo. A large number of vectors are known and used in the art including, for example, plasmids, modified eukaryotic viruses, or modified bacterial viruses. Insertion of a polynucleotide into a suitable vector can be accomplished by ligating the appropriate polynucleotide fragments into a chosen vector that has complementary cohesive termini.

Vectors may be engineered to encode selectable markers or reporters that provide for the selection or identification of cells that have incorporated the vector. Expression of selectable markers or reporters allows identification and/or selection of host cells that incorporate and express other coding regions contained on the vector. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like. Examples of reporters known and used in the art include: luciferase (Luc), green fluorescent protein (GFP), chloramphenicol acetyltransferase (CAT), -galactosidase (LacZ), -glucuronidase (Gus), and the like. Selectable markers may also be considered to be reporters.

The term "plasmid" refers to an extra-chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Eukaryotic viral vectors that can be used include, but are not limited to, adenovirus vectors, retrovirus vectors, adeno-associated virus vectors, and poxvirus, e.g., vaccinia virus vectors, baculovirus vectors, or herpesvirus vectors. Non-viral vectors include plasmids, liposomes, electrically charged lipids (cytofectins), DNA-protein complexes, and biopolymers.

A "cloning vector" refers to a "replicon," which is a unit length of a nucleic acid that replicates sequentially and which comprises an origin of replication, such as a plasmid, phage or cosmid, to which another nucleic acid segment may be attached so as to bring about the replication of the attached segment. Certain cloning vectors are capable of replication in one cell type, e.g., bacteria and expression in another, e.g., eukaryotic cells. Cloning vectors typically comprise one or more sequences that can be used for selection of cells comprising the vector and/or one or more multiple cloning sites for insertion of nucleic acid sequences of interest.

The term "expression vector" refers to a vehicle designed to enable the expression of an inserted nucleic acid sequence following insertion into a host cell. The inserted nucleic acid sequence is placed in operable association with regulatory regions as described above.

Vectors are introduced into host cells by methods well known in the art, e.g., transfection, electroporation, microinjection, transduction, cell fusion, DEAE dextran, calcium phosphate precipitation, lipofection (lysosome fusion), use of a gene gun, or a DNA vector transporter.

"Culture," "to culture" and "culturing," as used herein, means to incubate cells under in vitro conditions that allow for cell growth or division or to maintain cells in a living state. "Cultured cells," as used herein, means cells that are propagated in vitro.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced recombinant technology, but is not necessarily translated from a designated nucleic acid sequence. It can be generated in any manner, including by chemical synthesis.

An "isolated" polypeptide or a fragment, variant, or derivative thereof refers to a polypeptide that is not in its natural milieu. No particular level of purification is required. For example, an isolated polypeptide can simply be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

Also included in the present invention are fragments or variants of polypeptides, and any combination thereof. The term "fragment" or "variant" when referring to polypeptide binding domains or binding molecules of the present invention include any polypeptides which retain at least some of the properties (e.g., FcRn binding affinity for an FcRn binding domain or Fc variant, coagulation activity for an FVIII variant, or FVIII binding activity for the VWF fragment) of the reference polypeptide. Fragments of polypeptides include proteolytic fragments, as well as deletion fragments, in addition to specific antibody fragments discussed elsewhere herein, but do not include the naturally occurring full-length polypeptide (or mature polypeptide). Variants of polypeptide binding domains or binding molecules of the present invention include fragments as described above, and also polypeptides with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions.

The term "VWF protein" or "VWF proteins" used herein means any VWF fragments that interact with FVIII and retain at least one or more properties that are normally provided to FVIII by full-length VWF, e.g., preventing premature activation to FVIIIa, preventing premature proteolysis, preventing association with phospholipid membranes that could lead to premature clearance, preventing binding to FVIII clearance receptors that can bind naked FVIII but not VWF-bound FVIII, and/or stabilizing the FVIII heavy chain and light chain interactions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another embodiment, a string of amino acids can be conservatively replaced with a structurally similar string that differs in order and/or composition of side chain family members.

As known in the art, "sequence identity" between two polypeptides is determined by comparing the amino acid sequence of one polypeptide to the sequence of a second polypeptide. When discussed herein, whether any particular polypeptide is at least about 50%, 60%, 70%, 75%, 80%, 85%, 90%, 95%, 99%, or 100% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, WI 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full-length of the reference polypeptide sequence and that gaps in homology of up to 5% of the total number of amino acids in the reference sequence are allowed.

As used herein, an "amino acid corresponding to" or an "equivalent amino acid" in a VWF sequence or a FVIII protein sequence is identified by alignment to maximize the identity or similarity between a first VWF or FVIII sequence and a second VWF or FVIII sequence. The number used to identify an equivalent amino acid in a second VWF or FVIII sequence is based on the number used to identify the corresponding amino acid in the first VWF or FVIII sequence.

As used herein, the term "insertion site" refers to a position in a FVIII polypeptide, or fragment, variant, or derivative thereof, which is immediately upstream of the position at which a heterologous moiety can be inserted. An "insertion site" is specified as a number, the number being the number of the amino acid in mature native FVIII (SEQ ID NO: 65) to which the insertion site corresponds, which is immediately N-terminal to the position of the insertion. For example, the phrase "a3 comprises an XTEN at an insertion site which corresponds to amino acid 1656 of SEQ ID NO: 65" indicates that the heterologous moiety is located between two amino acids corresponding to amino acid 1656 and amino acid 1657 of SEQ ID NO: 65.

The phrase "immediately downstream of an amino acid" as used herein refers to position right next to the terminal carboxyl group of the amino acid. Similarly, the phrase "immediately upstream of an amino acid" refers to the position right next to the terminal amine group of the amino acid. Therefore, the phrase "between two amino acids of an insertion site" as used herein refers to a position in which an XTEN or any other polypeptide is inserted between two adjacent amino acids. Thus, the phrases "inserted immediately downstream of an amino acid" and "inserted between two amino acids of an insertion site" are used synonymously with "inserted at an insertion site."

The terms "inserted," "is inserted," "inserted into" or grammatically related terms, as used herein refers to the position of an XTEN in a chimeric polypeptide relative to the analogous position in native mature human FVIII. As used herein the terms refer to the characteristics of the recombinant FVIII polypeptide relative to native mature human FVIII, and do not indicate, imply or infer any methods or process by which the chimeric polypeptide was made. For example, in reference to a chimeric polypeptide provided herein, the phrase "an XTEN is inserted into immediately downstream of residue 745 of the FVIII polypeptide" means that the chimeric polypeptide comprises an XTEN immediately downstream of an amino acid which corresponds to amino acid 745 in native mature human FVIII, e.g., bounded by amino acids corresponding to amino acids 745 and 746 of native mature human FVIII.

A "fusion" or "chimeric" protein comprises a first amino acid sequence linked to a second amino acid sequence with which it is not naturally linked in nature. The amino acid sequences which normally exist in separate proteins can be brought together in the fusion polypeptide, or the amino acid sequences which normally exist in the same protein can be placed in a new arrangement in the fusion polypeptide, e.g., fusion of a Factor VIII domain of the invention with an Ig Fc domain. A fusion protein is created, for example, by chemical synthesis, or by creating and translating a polynucleotide in which the peptide regions are encoded in the desired relationship. A chimeric protein can further comprises a second amino acid sequence associated with the first amino acid sequence by a covalent, non-peptide bond or a non-covalent bond.

As used herein, the term "half-life" refers to a biological half-life of a particular polypeptide in vivo. Half-life may be represented by the time required for half the quantity administered to a subject to be cleared from the circulation and/or other tissues in the animal. When a clearance curve of a given polypeptide is constructed as a function of time, the curve is usually biphasic with a rapid α-phase and longer β-phase. The α-phase typically represents an equilibration of the administered Fc polypeptide between the intra- and extra-vascular space and is, in part, determined by the size of the polypeptide. The β-phase typically represents the catabolism of the polypeptide in the intravascular space. In some embodiments, FVIII and chimeric proteins comprising FVIII are monophasic, and thus do not have an alpha phase, but just the single beta phase. Therefore, in certain embodiments, the term half-life as used herein refers to the half-life of the polypeptide in the β-phase. The typical β phase half-life of a human antibody in humans is 21 days.

The term "linked" as used herein refers to a first amino acid sequence or nucleotide sequence covalently or non-covalently joined to a second amino acid sequence or nucleotide sequence, respectively. The first amino acid or nucleotide sequence can be directly joined or juxtaposed to the second amino acid or nucleotide sequence or alternatively an intervening sequence can covalently join the first sequence to the second sequence. The term "linked" means not only a fusion of a first amino acid sequence to a second amino acid sequence at the C-terminus or the N-terminus, but also includes insertion of the whole first amino acid sequence (or the second amino acid sequence) into any two amino acids in the second amino acid sequence (or the first amino acid sequence, respectively). In one embodiment, the first amino acid sequence can be linked to a second amino acid sequence by a peptide bond or a linker. The first nucleotide sequence can be linked to a second nucleotide sequence by a phosphodiester bond or a linker. The linker can be a peptide or a polypeptide (for polypeptide chains) or a nucleotide or a nucleotide chain (for nucleotide chains) or any chemical moiety (for both polypeptide and polynucleotide chains). The term "linked" is also indicated by a hyphen (-).

As used herein the term "associated with" refers to a covalent or non-covalent bond formed between a first amino acid chain and a second amino acid chain. In one embodiment, the term "associated with" means a covalent, non-peptide bond or a non-covalent bond. This association can be indicated by a colon, i.e., (:). In another embodiment, it means a covalent bond except a peptide bond. For example, the amino acid cysteine comprises a thiol group that can form a disulfide bond or bridge with a thiol group on a second cysteine residue. In most naturally occurring IgG molecules, the CH1 and CL regions are associated by a disulfide bond and the two heavy chains are associated by two disulfide bonds at positions corresponding to 239 and 242 using the Kabat numbering system (position 226 or 229, EU numbering system). Examples of covalent bonds include, but are not limited to, a peptide bond, a metal bond, a hydrogen bond, a disulfide bond, a sigma bond, a pi bond, a delta bond, a glycosidic bond, an agnostic bond, a bent bond, a dipolar bond, a Pi backbond, a double bond, a triple bond, a quadruple bond, a quintuple bond, a sextuple bond, conjugation, hyperconjugation, aromaticity, hapticity, or antibonding. Non-limiting examples of non-covalent bond include an ionic bond (e.g., cation-pi bond or salt bond), a metal bond, an hydrogen bond (e.g., dihydrogen bond, dihydrogen complex, low-barrier hydrogen bond, or symmetric hydrogen bond), van der Walls force, London dispersion force, a mechanical bond, a halogen bond, aurophilicity, intercalation, stacking, entropic force, or chemical polarity.

The term "monomer-dimer hybrid" used herein refers to a chimeric protein comprising a first polypeptide chain and a second polypeptide chain, which are associated with each other by a disulfide bond, wherein the first chain comprises a clotting factor, e.g., Factor VIII, and a first Fc region and the second chain comprises, consists essentially of, or consists of a second Fc region without the clotting factor. The monomer-dimer hybrid construct thus is a hybrid comprising a monomer aspect having only one clotting factor and a dimer aspect having two Fc regions.

As used herein, the term "cleavage site" or "enzymatic cleavage site" refers to a site recognized by an enzyme. Certain enzymatic cleavage sites comprise an intracellular processing site. In one embodiment, a polypeptide has an enzymatic cleavage site cleaved by an enzyme that is activated during the clotting cascade, such that cleavage of such sites occurs at the site of clot formation. Exemplary such sites include, e.g., those recognized by thrombin, Factor XIa or Factor Xa. Exemplary FXIa cleavage sites include, e.g., TQSFNDFTR (SEQ ID NO: 1) and SVSQTSKLTR (SEQ ID NO: 3). Exemplary thrombin cleavage sites include, e.g., DFLAEGGGVR (SEQ ID NO: 4), TTKIKPR (SEQ ID NO: 5), LVPRG (SEQ ID NO: 6), ALRPR (SEQ ID NO: 7), ISDKNTGDYYEDSYEDISAYLLSKNNAIEPRSFS (SEQ ID NO: 106), DKNTGDYYEDSYEDISAYLLSKNNAIEPRSFS (SEQ ID NO: 88), and IEPRSFS (SEQ ID NO: 194). Other enzymatic cleavage sites are known in the art and described in elsewhere herein.

As used herein, the term "processing site" or "intracellular processing site" refers to a type of enzymatic cleavage site in a polypeptide which is a target for enzymes that function after translation of the polypeptide. In one embodiment, such enzymes function during transport from the Golgi lumen to the trans-Golgi compartment. Intracellular processing enzymes cleave polypeptides prior to secretion of the protein from the cell. Examples of such processing sites include, e.g., those targeted by the PACE/furin (where PACE is an acronym for Paired basic Amino acid Cleaving Enzyme) family of endopeptidases. These enzymes are localized to the Golgi membrane and cleave proteins on the carboxyterminal side of the sequence motif Arg-[any residue]-(Lys or Arg)-Arg. As used herein the "furin" family of enzymes includes, e.g., PCSK1 (also known as PC1/Pc3), PCSK2 (also known as PC2), PCSK3 (also known as furin or PACE), PCSK4 (also known as PC4), PCSK5 (also known as PC5 or PC6), PCSK6 (also known as PACE4), or PCSK7 (also known as PC7/LPC, PC8, or SPC7). Other processing sites are known in the art.

In constructs that include more than one processing or cleavage site, it will be understood that such sites may be the same or different.

The term "Furin" refers to the enzymes corresponding to EC No. 3.4.21.75. Furin is subtilisin-like proprotein convertase, which is also known as PACE (Paired basic Amino acid Cleaving Enzyme). Furin deletes sections of inactive precursor proteins to convert them into biologically active proteins. During its intracellular transport, pro-peptide of VWF can be cleaved from mature VWF molecule by a Furin enzyme. In some embodiments, Furin cleaves the D1D2 from the D'D3 of VWF. In other embodiments, a nucleotide sequence encoding Furin can be expressed together with the nucleotide sequence encoding a VWF fragment so that D1D2 domains can be cleaved off intracellularly by Furin.

In constructs that include more than one processing or cleavage site, it will be understood that such sites may be the same or different.

A "processable linker" as used herein refers to a linker comprising at least one intracellular processing site, which are described elsewhere herein.

Hemostatic disorder, as used herein, means a genetically inherited or acquired condition characterized by a tendency to hemorrhage, either spontaneously or as a result of trauma, due to an impaired ability or inability to form a fibrin clot. Examples of such disorders include the hemophilias. The three main forms are hemophilia A (factor VIII deficiency), hemophilia B (factor IX deficiency or "Christmas disease") and hemophilia C (factor X1 deficiency, mild bleeding tendency). Other hemostatic disorders include, e.g., Von Willebrand disease, Factor X1 deficiency (PTA deficiency), Factor XII deficiency, deficiencies or structural abnormalities in fibrinogen, prothrombin, Factor V, Factor VII, Factor X or factor XIII, Bernard-Soulier syndrome, which is a defect or deficiency in GPIb. GPIb, the receptor for VWF, can be defective and lead to lack of primary clot formation (primary hemostasis) and increased bleeding tendency), and thrombasthenia of Glanzman and Naegeli (Glanzmann thrombasthenia). In liver failure (acute and chronic forms), there is insufficient production of coagulation factors by the liver; this may increase bleeding risk.

The chimeric molecules of the invention can be used prophylactically. As used herein the term "prophylactic treatment" refers to the administration of a molecule prior to a bleeding episode. In one embodiment, the subject in need of a general hemostatic agent is undergoing, or is about to undergo, surgery. The chimeric protein of the invention can be administered prior to or after surgery as a prophylactic. The chimeric protein of the invention can be administered during or after surgery to control an acute bleeding episode. The surgery can include, but is not limited to, liver transplantation, liver resection, dental procedures, or stem cell transplantation.

The chimeric protein of the invention is also used for on-demand treatment. The term "on-demand treatment" refers to the administration of a chimeric molecule in response to symptoms of a bleeding episode or before an activity that may cause bleeding. In one aspect, the on-demand treatment can be given to a subject when bleeding starts, such as after an injury, or when bleeding is expected, such as before surgery. In another aspect, the on-demand treatment can be given prior to activities that increase the risk of bleeding, such as contact sports.

As used herein the term "acute bleeding" refers to a bleeding episode regardless of the underlying cause. For example, a subject may have trauma, uremia, a hereditary bleeding disorder (e.g., factor VII deficiency) a platelet disorder, or resistance owing to the development of antibodies to clotting factors.

Treat, treatment, treating, as used herein refers to, e.g., the reduction in severity of a disease or condition; the reduction in the duration of a disease course; the amelioration of one or more symptoms associated with a disease or condition; the provision of beneficial effects to a subject with a disease or condition, without necessarily curing the disease or condition, or the prophylaxis of one or more symptoms associated with a disease or condition. In one embodiment, the term "treating" or "treatment" means maintaining a FVIII trough level at least about 1 IU/dL, 2 IU/dL, 3 IU/dL, 4 IU/dL, 5 IU/dL, 6 IU/dL, 7 IU/dL, 8 IU/dL, 9 IU/dL, 10 IU/dL, 11 IU/dL, 12 IU/dL, 13 IU/dL, 14 IU/dL, 15 IU/dL, 16 IU/dL, 17 IU/dL, 18 IU/dL, 19 IU/dL, or 20 IU/dL in a subject by administering a chimeric protein or a VWF fragment of the invention. In another embodiment, treating or treatment means maintaining a FVIII trough level between about 1 and about 20 IU/dL, about 2 and about 20 IU/dL, about 3 and about 20 IU/dL, about 4 and about 20 IU/dL, about 5 and about 20 IU/dL, about 6 and about 20 IU/dL, about 7 and about 20 IU/dL, about 8 and about 20 IU/dL, about 9 and about 20 IU/dL, or about 10 and about 20 IU/dL. Treatment or treating of a disease or condition can also include maintaining FVIII activity in a subject at a level comparable to at least about 1%, 2%, 3%, 4%, 5%, 6%, 7%, 8%, 9%, 10%, 11%, 12%, 13%, 14%, 15%, 16%, 17%, 18%, 19%, or 20% of the FVIII activity in a non-hemophiliac subject. The minimum trough level required for treatment can be measured by one or more known methods and can be adjusted (increased or decreased) for each person.

II. Chimeric Proteins

The present invention is directed to extending a half-life of a chimeric protein using a VWF protein fused to an XTEN sequence by preventing or inhibiting a FVIII half-life limiting factor, i.e., endogenous VWF, from associating with the FVIII protein. Endogenous VWF associates with about 95% to about 98% of FVIII in non-covalent complexes. While endogenous VWF is a FVIII half-life limiting factor, endogenous VWF bound to a FVIII protein is also known to protect FVIII in various ways. For example, full length VWF (as a multimer having about 250 kDa) can protect FVIII from protease cleavage and FVIII activation, stabilize the FVIII heavy chain and/or light chain, and prevent clearance of FVIII by scavenger receptors. But, at the same time, endogenous VWF limits the FVIII half-life by preventing pinocytosis and by clearing FVIII-VWF complex from the system through the VWF clearance pathway. It is believed, while not bound by a theory, that endogenous VWF is a half-life limiting factor that prevents the half-life of a chimeric protein fused to a half-life extender from being longer than about two-fold that of wild-type FVIII. Therefore, the present invention is directed to preventing or inhibiting interaction between endogenous VWF and a FVIII protein using a VWF protein comprising a D' domain and a D3 domain (e.g., a VWF fragment) and at the same time to increasing a half-life of resulting FVIII protein(s) by using an XTEN sequence in combination with an Ig constant region or a portion thereof. In particular, the present invention shows that a shorter XTEN sequence (i.e., XTEN that contains less than 288 amino acids in length, i.e., XTEN that is shorter than 288 amino acids) is better in extending a half-life of the chimeric protein.

In one embodiment, the invention is directed to a chimeric protein comprising (i) a first polypeptide which comprises a FVIII protein fused to a first Ig constant region or a portion thereof and (ii) a second polypeptide which comprises a VWF protein comprising a D' domain and a D3 domain of VWF fused to a second Ig constant region or a portion thereof by an XTEN sequence in-between, wherein the XTEN sequence contains less than 288 amino acid residues and wherein the first polypeptide is linked to or associated with the second polypeptide. In another embodiment, the XTEN sequence in the second polypeptide consists of an amino acid sequence having a length of between 12 amino acids and 287 amino acids. In other embodiments, the chimeric protein exhibits a longer half-life compared to a corresponding fusion protein comprising the first polypeptide and the second polypeptide, wherein the second polypeptide comprises an XTEN sequence containing at least 288 amino acids, e.g., AE288, e.g., SEQ ID NO: 8. In still other embodiments, the XTEN sequence in the second polypeptide contains at least about 36, at least about 42, at least about 72, or at least about 144 amino acids, but less than 288 amino acids, e.g., AE42, AE72, AE144 (AE144, AE144_2A, AE144_3B, AE144_4A, AE144_5A, AE144_6B), AG42, AG72, or AG144 (AG144, AG144_A, AG144_B, AG144_C, AG144_F), e.g., SEQ ID NO: 9, SEQ ID NO: 10, SEQ ID NO: 11, SEQ ID NO: 55; SEQ ID NO: 56; SEQ ID NO: 57; SEQ ID NO: 58; SEQ ID NO: 59; SEQ ID NO: 14; SEQ ID NO: 60; SEQ ID NO: 61; SEQ ID NO: 62; or SEQ ID NO: 63.

The chimeric protein of the invention can further comprise a second XTEN sequence which links the FVIII protein with the first Ig constant region or a portion thereof.

In certain embodiments, the invention is directed to a chimeric protein comprising (i) a first polypeptide which comprises a FVIII protein fused to a first Ig constant region or a portion thereof and (ii) a second polypeptide which comprises a VWF protein comprising a D' domain and a D3 domain of VWF fused to a second Ig constant region or a portion thereof by a first XTEN sequence in-between, wherein the XTEN sequence contains less than 288 amino acid residues and wherein the first polypeptide are linked to or associated with the second polypeptide, and wherein the first polypeptide further comprises a second XTEN sequence which is inserted at one or more insertion sites within the FVIII protein or which is fused to the FVIII protein and/or the first Ig constant region or a portion thereof. Therefore, in one embodiment, a second XTEN sequence is inserted at one or more insertion sites within the FVIII protein. In another embodiment, a second XTEN sequence is fused to the FVIII protein and/or the first Ig constant region or a portion thereof. In other embodiments, a second XTEN sequence is inserted at one or more insertion sites within the FVIII protein and a third XTEN sequence is fused to the FVIII protein and/or the first Ig constant region or a portion thereof.

The second and/or third XTEN sequences can be any length of XTEN amino acids. For example, the second and/or third XTEN sequences are disclosed elsewhere herein, e.g., AE42, AE72, AE864, AE576, AE288, AE144, AG864, AG576, AG288, and AG144, e.g., SEQ ID NO: 8; SEQ ID NO: 9, SEQ ID NO: 10, SEQ ID NO: 11, SEQ ID NO: 17; SEQ ID NO: 54; SEQ ID NO: 19; SEQ ID NO: 16; SEQ ID NO: 18; SEQ ID NO: 15; SEQ ID NO: 55; SEQ ID NO: 56; SEQ ID NO: 57; SEQ ID NO: 58; SEQ ID NO: 59; SEQ ID NO: 14; SEQ ID NO: 60; SEQ ID NO: 61; SEQ ID NO: 62; or SEQ ID NO: 63. In a particular embodiment, the second and/or third XTEN sequence is AE288 or AG288, e.g., SEQ ID NO: 8 or 19.

In certain embodiments, the invention is directed to a chimeric protein comprising (i) a first polypeptide which comprises a FVIII protein fused to a first Ig constant region or a portion thereof by an optional linker, wherein an optional XTEN sequence (X2) is inserted at one or more insertion sites within the FVIII protein or is fused to the FVIII protein or to the first Ig constant region or a portion thereof, and (ii) a second polypeptide which comprises a VWF protein comprising a D' domain and a D3 domain of VWF fused to a second Ig constant region or a portion thereof by an XTEN sequence (X1) between the VWF protein and the second Ig constant region or a portion thereof, wherein the XTEN sequence (X1) contains less than 288 amino acid residues and is fused to the VWF protein by a linker and wherein the first polypeptide and the second polypeptide are associated. In some embodiments, the invention is directed to a chimeric protein comprising (i) a first polypeptide which comprises a FVIII protein fused to a first Ig constant region or a portion thereof by an optional linker, wherein an optional XTEN sequence (X2) is inserted at one or more insertion sites within the FVIII protein or is fused to the FVIII protein or to the first Ig constant region or a portion thereof, and (ii) a second polypeptide which comprises a VWF protein comprising a D' domain and a D3 domain of VWF fused to a second Ig constant region or a portion thereof by an XTEN sequence (X1) between the VWF protein and the second Ig constant region or a portion thereof, wherein the XTEN sequence (X1) contains less than 288 amino acid residues and is fused to the second Ig constant region or a portion thereof by a linker and wherein the first polypeptide and the second polypeptide are associated. In other embodiments, the linker fusing the XTEN sequence (X1) with the VWF protein or the second Ig constant region or a portion thereof is a cleavable linker. Non-limiting examples of the cleavable linkers are shown elsewhere herein. In a particular embodiment, the linker is a thrombin cleavable linker.

In some embodiments, the chimeric protein is two polypeptide chains, the first chain comprising the first polypeptide described above and the second chain comprising the second polypeptide described above. For example, the two polypeptide chains comprise (i) a first chain comprising a single chain FVIII protein, a first Ig constant region or a portion thereof, and an optional XTEN sequence which is inserted at one or more insertion sites within the FVIII protein or is fused to the FVIII protein or to the first Ig constant region or a portion thereof, and (ii) a second chain comprising a VWF protein fused to a second Ig constant region or a portion thereof by an XTEN sequence (X1) in-between, wherein the XTEN sequence (X1) contains less than 288 amino acids.

In certain embodiments, the chimeric protein is two polypeptide chains, a first chain comprising a heavy chain of a FVIII protein and a second chain comprising, from N-terminus to C-terminus, a light chain of a FVIII protein, an optional XTEN sequence which is inserted at one or more insertion sites within the FVIII protein or is fused to the FVIII protein or to the first Ig constant region or a portion thereof, and a first Ig constant region or a portion thereof, an optional linker (e.g., a processable linker), a VWF protein, an XTEN sequence (X1), a second optional linker (e.g., a cleavable linker), and a second Ig constant region or a portion thereof.

In other embodiments, the chimeric protein is three polypeptide chains, (i) a first chain comprising a heavy chain of a FVIII protein, (ii) a second chain comprising a light chain of a FVIII protein, a first Ig constant region or a portion thereof, and an optional XTEN sequence which is inserted at one or more insertion sites within the heavy chain or the light chain of the FVIII protein or is fused to the FVIII protein or to the first Ig constant region or a portion thereof, and (iii) a third chain comprising a VWF protein fused to a second Ig constant region or a portion thereof by an XTEN sequence (X1) in-between, wherein the first chain and the second chain are associated by a non-covalent bond, e.g., a metal bond, and the second chain and the third chain are associated by a covalent bond, e.g., a disulfide bond.

In still other embodiments, the chimeric protein is a single chain comprising, from N terminus to C terminus, a single chain FVIII protein, an optional XTEN sequence which is inserted at one or more insertion sites within the FVIII protein or is fused to the FVIII protein or to the first Ig constant region or a portion thereof, and a first Ig constant region or a portion thereof, an optional linker (e.g., a processable linker), a VWF protein, an XTEN sequence (X1), a second optional linker (e.g., a cleavable linker), and a second Ig constant region or a portion thereof.

In certain embodiments, a chimeric protein comprises one of the following formulae (a)-(hh):

FVIII-F1:F2-L2-X-L1-V; (a)

FVIII-F1:V-L1-X-L2-F2; (b)

F1-FVIII:F2-L2-X-L1-V; (c)

F1-FVIII:V-L1-X-L2-F2; (d)

FVIII-X2-F1:F2-L2-X1-L1-V; (e)

FVIII-X2-F1:V-L1-X1-L2-F2; (f)

FVIII(X2)-F1:F2-L2-X1-L1-V; (g)

FVIII(X2)-F1:V-L1-X1-L2-F2; (h)

F1-X2-F1:F2-L2-X1-L1-V; (i)

F1-X2-F1:V-L1-X1-L2-F2; (j)

V-L1-X-L2-F2-L3-FVIII-L4-F1; (k)

V-L1-X-L2-F2-L3-F1-L4-FVIII; (l)

F1-L4-FVIII-L3-F2-L2-X-L1-V; (m)

FVIII-L4-F1-L3-F2-L2-X-L1-V; (n)

FVIII-L4-F1-L3-V-L1-X-L2-F2; (o)

FVIII-L4-F1-L3-F2-L2-X-L1-V; (p)

F2-L2-X-L1-V-L3-F1-L4-FVIII; (q)

F2-L2-X-L1-V-L3-FVIII-L4-F1; (r)

V-L1-X1-L2-F2-L3-FVIII(X2)-L4-F1; (s)

V-L1-X1-L2-F2-L3-F1-L4-FVIII(X2); (t)

F1-L4-FVIII(X2)-L3-F2-L2-X1-L1-V; (u)

F-L4-FVIII(X2)-L3-V-L1-X1-L2-F2; (v)

FVIII(X2)-L4-F1-L3-V-L1-X1-L2-F2; (w)

FVIII(X2)-L4-F1-L3-F2-L2-X1-L1-V; (x)

F2-L2-X1-L1-V-L3-F1-L4-FVIII(X2); (y)

F2-L2-X1-L1-V-L3-FVIII(X2)-L4-F1; (z)

V-L1-X2-L2-F2-L3-FVIII-L4-X2-L5-F1; (aa)

V-L1-X2-L2-F2-L3-F1-L5-X2-L4-FVIII; (bb)

F1-L5-X2-L4-FVIII-L3-F2-L2-X2-L1-V; (cc)

F1-L5-X2-L4-FVIII-L3-V-L1-X2-L2-F2; (dd)

FVIII-L5-X2-L4-F2-L3-V-L1-X1-L2-F1; (ee)

FVIII-L5-X2-L4-F2-L3-F1-L2-X1-L1-V; (ff)

F1-L2-X1-L1-V-L3-F2-L4-X2-L5-FVIII; or (gg)

F1-L2-X1-L1-V-L3-FVIII-L5-X2-L4-F2; (hh)

wherein V is a VWF protein, which comprises a D' domain and a D3 domain,

X or X1 is a first XTEN sequence that contains less than 288 amino acids,

X2 is a second XTEN sequence,

FVIII comprises a FVIII protein,

FVIII(X2) comprises a FVIII protein having a second XTEN sequence inserted in one or more insertion sites within the FVIII protein, F1 is a first Ig constant region or a portion thereof, F2 is a second Ig constant region or a portion thereof, L1, L2, L3, L4, or L5 is an optional linker, (-) is a peptide bond; and (:) is a covalent bond or a non-covalent bond.

In one embodiment, the X or X1 consists of an amino acid sequence having a length of between 12 amino acids and 287 amino acids. In another embodiment, the chimeric protein exhibits a longer half-life compared to a corresponding fusion protein comprising a formula wherein the X or X1 is AE288, e.g., SEQ ID NO: 8.

In other embodiments, the X or X1 in the formula contains at least about 36, at least about 42, at least about 72, or at least about 144 amino acids, but less than 288 amino acids, e.g., AE42, AE72, AE144 (AE144, AE144_2A, AE144_3B, AE144_4A, AE144_5A, AE144_6B), AG42, AG72, or AG144 (AG144, AG144_A, AG144_B, AG144_C, AG144_F), e.g., SEQ ID NO: 9, SEQ ID NO: 10, SEQ ID NO: 11, SEQ ID NO: 55; SEQ ID NO: 56; SEQ ID NO: 57; SEQ ID NO: 58; SEQ ID NO: 59; SEQ ID NO: 14; SEQ ID NO: 60; SEQ ID NO: 61; SEQ ID NO: 62; or SEQ ID NO: 63.

In yet other embodiments, the X2 comprises an amino acid sequence having a length of at least about 36 amino acids, at least 42 amino acids, at least 144 amino acids, at least 288 amino acids, at least 576 amino acids, or at least 864 amino acids, e.g., AE42, AE72, AE864, AE576, AE288, AE144, AG864, AG576, AG288, or AG144, e.g., SEQ ID NO: 9; SEQ ID NO: 10; SEQ ID NO: 15; SEQ ID NO: 16; SEQ ID NO: 8; SEQ ID NO: 11; SEQ ID NO: 17; SEQ ID NO: 18, SEQ ID NO: 19, or SEQ ID NO: 14. In a particular embodiment, the X2 is AE288 or AG288, e.g., SEQ ID NO: 8 or 19.

In certain embodiments, the chimeric protein comprising the X or X1 and/or X2 has an extended half-life compared to a chimeric protein without the X or X1 and/or X2. In other embodiments, the L1 and/or L2 is a cleavable linker. In still other embodiments, the L4 and/or L5 is a cleavable linker.

II.A. Von Willebrand Factor (VWF) Proteins

VWF (also known as F8VWF) is a large multimeric glycoprotein present in blood plasma and produced constitutively in endothelium (in the Weibel-Palade bodies), megakaryocytes (α-granules of platelets), and subendothelian connective tissue. The basic VWF monomer is a 2813 amino acid protein. Every monomer contains a number of specific domains with a specific function, the D'/D3 domain (which binds to Factor VIII), the A1 domain (which binds to platelet GPIb-receptor, heparin, and/or possibly collagen), the A3 domain (which binds to collagen), the C1 domain (in which the RGD domain binds to platelet integrin αIIbβ3 when this is activated), and the "cysteine knot" domain at the C-terminal end of the protein (which VWF shares with platelet-derived growth factor (PDGF), transforming growth factor-β (TGFβ) and β-human chorionic gonadotropin (βHCG)).

In one embodiment, the VWF protein is a VWF fragment. The term "a VWF fragment" as used herein includes, but is not limited to, functional VWF fragments comprising a D' domain and a D3 domain, which are capable of inhibiting binding of endogenous VWF to FVIII. In one embodiment, the VWF fragment binds to the FVIII protein. In another embodiment, the VWF fragment blocks the VWF binding site on the FVIII protein, thereby inhibiting interaction of the FVIII protein with endogenous VWF. The VWF fragments include derivatives, variants, mutants, or analogues that retain these activities of VWF.

The 2813 monomer amino acid sequence for human VWF is reported as Accession Number_NP_000543.2_in Genbank. The nucleotide sequence encoding the human VWF is reported as Accession Number__NM_000552.3_in Genbank. A nucleotide sequence of human VWF is designated as SEQ ID NO: 20. SEQ ID NO: 21 is the amino acid sequence of full-length VWF. Each domain of VWF is listed in Table 1.

TABLE 1

| VWF domains | | Amino acid Sequence | |
|---|---|---|---|
| VWF Signal Peptide (Amino acids 1 to 22 of SEQ ID NO: 21) | 1 | MIPAFAGVL LALALILPGT LC | 22 |
| VWF D1D2 region (Amino acids 23 to 763 of SEQ ID NO: 21) | 23 | AEGTRGRS STARCSLFGS DFVNTFDGSM | |
| | 51 | YSFAGYCSYL LAGGCQKRSF SIIGDFQNGK RVSLSVYLGE FFDIHLFVNG | |
| | 101 | TVTQGDQRVS MPYASKGLYL ETEAGYYKLS GEAYGFVARI DGSGNFQVLL | |
| | 151 | SDRYFNKTCG LCGNFNIFAE DDFMTQEGTL TSDPYDFANS WALSSGEQWC | |
| | 201 | ERASPPSSSC NISSGEMQKG LWEQCQLLKS TSVFARCHPL VDPEPFVALC | |
| | 251 | EKTLCECAGG LECACPALLE YARTCAQEGM VLYGWTDHSA CSPVCPAGME | |
| | 301 | YRQCVSPCAR TCQSLHINEM CQERCVDGCS CPEGQLLDEG LCVESTECPC | |
| | 351 | VHSGKRYPPG TSLSRDCNTC ICRNSQWICS NEECPGECLV TGQSHFKSFD | |
| | 401 | NRYFTFSGIC QYLLARDCQD HSFSIVIETV QCADDRDAVC TRSVTVRLPG | |
| | 451 | LHNSLVKLKH GAGVAMDGQD IQLPLLKGDL RIQHTVTASV RLSYGEDLQM | |
| | 501 | DWDGRGRLLV KLSPVYAGKT CGLCGNYNGN QGDDFLTPSG LAEPRVEDFG | |
| | 551 | NAWKLHGDCQ DLQKQHSDPC ALNPRMTRFS EEACAVLTSP TFEACHRAVS | |

TABLE 1-continued

| VWF domains | | Amino acid Sequence | |
|---|---|---|---|
| | 601 | **PLPYLRNCRY DVCSCSDGRE CLCGALASYA AACAGRGVRV AWREPGRCEL** | |
| | 651 | **NCPKGQVYLQ CGTPCNLTCR SLSYPDEECN EACLEGCFCP PGLYMDERGD** | |
| | 701 | **CVPKAQCPCY YDGEIFQPED IFSDHHTMCY CEDGFMHCTM SGVPGSLLPD** | |
| | 751 | **AVLSSPLSHR SKR** | 763 |
| VWF D' Domain | 764 | SLSCRPP MVKLVCPADN LRAEGLECTK TCQNYDLECM | |
| | 801 | SMGCVSGCLC PPGMVRHENR CVALERCPCF HQGKEYAPGE TVKIGCNTCV | |
| | 851 | CRDRKWNCTD HVCDAT | 866 |
| VWF D3 Domain | 867 | CSTI GMAHYLTFDG LKYLFPGECQ YVLVQDYCGS | |
| | 901 | NPGTFRILVG NKGCSHPSVK CKKRVTILVE GGEIELFDGE VNVKRPMKDE | |
| | 951 | THFEVVESGR YIILLLGKAL SVVWDRHLSI SVVLKQTYQE KVCGLCGNFD | |
| | 1001 | GIQNNDLTSS NLQVEEDPVD FGNSWKVSSQ CADTRKVPLD SSPATCHNNI | |
| | 1051 | MKQTMVDSSC RILTSDVFQD CNKLVDPEPY LDVCIYDTCS CESIGDCACF | |
| | 1101 | CDTIAAYAHV CAQHGKVVTW RTATLCPQSC EERNLRENGY ESEWRYNSCA | |
| | 1151 | PACQVTCQHP EPLACPVQCV EGCHAHCPPG KILDELLQTC VDPEDCPVCE | |
| | 1201 | VAGRREFASGK KVTLNPSDPE HCQICHCDVV NLTCEACQEP | |
| | 1240 | | |
| VWF A1 Domain | 1241 | GGLVVPPTDA | |
| | 1251 | PVSPTTLYVE DISEPPLHDF YCSRLLDLVF LLDGSSRLSE AEFEVLKAFV | |
| | 1301 | VDMMERLRIS QKWVRVAVVE YHDGSHAYIG LKDRKRPSEL RRIASQVKYA | |
| | 1351 | GSQVASTSEV LKYTLFQIFS KIDRPEASRI ALLLMASQEP QRMSRNFVRY | |
| | 1401 | VQGLKKKKVI VIPVGIGPHA NLKQIRLIEK QAPENKAFVL SSVDELEQQR | |
| | 1451 | DEIVSYLCDL APEAPPPTLP PDMAQVTVG | 1479 |
| | 1480 | P GLLGVSTLGP KRNSMVLDVA | |
| | 1501 | FVLEGSDKIG EADFNRSKEF MEEVIQRMDV GQDSIHVTVL QYSYMVTVEY | |
| | 1551 | PFSEAQSKGD ILQRVREIRY QGGNRTNTGL ALRYLSDHSF LVSQGDREQA | 1600 |
| | 1601 | PNLVYMVTGN PASDEIKRLP GDIQVVPIGV GPNANVQELE RIGWPNAPIL | |
| | 1651 | IQDFETLPRE APDLVLQRCC SGEGLQIPTL SPAPDCSQPL DVILLLDGSS | |
| | 1701 | SFPASYFDEM KSFAKAFISK ANIGPRLTQV SVLQYGSITT IDVPWNVVPE | |
| | 1751 | KAHLLSLVDV MQREGGPSQI GDALGFAVRY LTSEMHGARP GASKAVVILV | |
| | 1801 | TDVSVDSVDA AADAARSNRV TVFPIGIGDR YDAAQLRILA GPAGDSNVVK | |
| | 1851 | LQRIEDLPTM VTLGNSFLHK LCSGFVRICM DEDGNEKRPG DVWTLPDQCH | |
| | 1901 | TVTCQPDGQT LLKSHRVNCD RGLRPSCPNS QSPVKVEETC GCRWTCPCVC | |
| | 1951 | TGSSTRHIVT FDGQNFKLTG SCSYVLFQNK EQDLEVILHN GACSPGARQG | |
| | 2001 | CMKSIEVKHS ALSVEXHSDM EVTVNGRLVS VPYVGGNMEV NVYGAIMHEV | |

TABLE 1-continued

| VWF domains | Amino acid Sequence |
|---|---|
| | 2051 RFNHLGHIFT FTPQNNEFQL QLSPKTFASK TYGLCGICDE NGANDFMLRD |
| | 2101 GTVTTDWKTL VQEWTVQRPG QTCQPILEEQ CLVPDSSHCQ VLLLPLFAEC |
| | 2151 HKVLAPATFY AICQQDSCHQ EQVCEVIASY AHLCRTNGVC VDWRTPDFCA |
| | 2201 MSCPPSLVYN HCEHGCPRHC DGNVSSCGDH PSEGCFCPPD KVMLEGSCVP |
| | 2251 EEACTQCIGE DGVQHQFLEA WVPDHQPCQI CTCLSGRKVN CTTQPCPTAK |
| | 2301 APTCGLCEVA RLRQNADQCC PEYECVCDPV SCDLPPVPHC ERGLQPTLTN |
| | 2351 PGECRPNFTC ACRKEECKRV SPPSCPPHRL PTLRKTQCCD EYECACNCVN |
| | 2401 STVSCPLGYL ASTATNDCGC TTTTCLPDKV CVHRSTIYPV GQFWEEGCDV |
| | 2451 CTCTDMEDAV MGLRVAQCSQ KPCEDSCRSG FTYVLHEGEC CGRCLPSACE |
| | 2501 VVTGSPRGDS QSSWKSVGSQ WASPENPCLI NECVRVKEEV FIQQRNVSCP |
| | 2551 QLEVPVCPSG FQLSCKTSAC CPSCRCERME ACMLNGTVIG PGKTVMIDVC |
| | 2601 TTCRCMVQVG VISGFKLECR KTTCNPCPLG YKEENNTGEC CGRCLPTACT |
| | 2651 IQLRGGQIMT LKRDETLQDG CDTHFCKVNE RGEYFWEKRV TGCPPFDEHK |
| | 2701 CLAEGGKIMK IPGTCCDTCE EPECNDITAR LQYVKVGSCK SEVEVDIHYC |
| | 2751 QGKCASKAMY SIDINDVQDQ CSCCSPTRTE PMQVALHCTN GSVVYHEVLN |
| | 2801 AMECKCSPRK CSK |
| | Nucleotide Sequence (SEQ ID NO: 20) |
| Full-length VWF | 1 ATGATTCCTG CCAGATTTGC CGGGGTGCTG CTTGCTCTGG CCCTCATTTT |
| | 51 GCCAGGGACC CTTTGTGCAG AAGGAACTCG CGGCAGGTCA TCCACGGCCC |
| | 101 GATGCAGCCT TTTCGGAAGT GACTTCGTCA ACACCTTTGA TGGGAGCATG |
| | 151 TACAGCTTTG CGGGATACTG CAGTTACCTC CTGGCAGGGG GCTGCCAGAA |
| | 201 ACGCTCCTTC TCGATTATTG GGACTTCCA GAATGGCAAG AGAGTGAGCC |
| | 251 TCTCCGTGTA TCTTGGGGAA TTTTTTGACA TCCATTTGTT TGTCAATGGT |
| | 301 ACCGTGACAC AGGGGGACCA AAGAGTCTCC ATGCCCTATG CCTCCAAAGG |
| | 351 GCTGTATCTA GAAACTGAGG CTGGGTACTA CAAGCTGTCC GGTGAGGCCT |
| | 401 ATGGCTTTGT GGCCAGGATC GATGGCAGCG GCAACTTTCA AGTCCTGCTG |
| | 451 TCAGACAGAT ACTTCAACAA GACCTGCGGG CTGTGTGGCA ACTTTAACAT |
| | 501 CTTTGCTGAA GATGACTTTA TGACCCAAGA AGGGACCTTG ACCTCGGACC |
| | 551 CTTATGACTT TGCCAACTCA TGGGCTCTGA GCAGTGGAGA ACAGTGGTGT |
| | 601 GAACGGGCAT CTCCTCCCAG CAGCTCATGC AACATCTCCT CTGGGGAAAT |
| | 651 GCAGAAGGGC CTGTGGGAGC AGTGCCAGCT TCTGAAGAGC ACCTCGGTGT |
| | 701 TTGCCCGCTG CCACCCTCTG GTGGACCCCG AGCCTTTTGT GGCCCTGTGT |
| | 751 GAGAAGACTT TGTGTGAGTG TGCTGGGGGG CTGGAGTGCG CCTGCCCTGC |
| | 801 CCTCCTGGAG TACGCCCGGA CCTGTGCCCA GGAGGGAATG GTGCTGTACG |
| | 851 GCTGGACCGA CCACAGCGCG TGCAGCCCAG TGTGCCCTGC TGGTATGGAG |
| | 901 TATAGGCAGT GTGTGTCCCC TTGCGCCAGG ACCTGCCAGA GCCTGCACAT |
| | 951 CAATGAAATG TGTCAGGAGC GATGCGTGGA TGGCTGCAGC TGCCCTGAGG |
| | 1001 GACAGCTCCT GGATGAAGGC CTCTGCGTGG AGAGCACCGA GTGTCCCTGC |
| | 1051 GTGCATTCCG GAAAGCGCTA CCCTCCCGGC ACCTCCCTCT CTCGAGACTG |

TABLE 1-continued

| VWF domains | Amino acid Sequence |
|---|---|
| | 1101 CAACACCTGC ATTTGCCGAA ACAGCCAGTG GATCTGCAGC AATGAAGAAT |
| | 1151 GTCCAGGGGA GTGCCTTGTC ACTGGTCAAT CCCACTTCAA GAGCTTTGAC |
| | 1201 AACAGATACT TCACCTTCAG TGGGATCTGC CAGTACCTGC TGGCCCGGGA |
| | 1251 TTGCCAGGAC CACTCCTTCT CCATTGTCAT TGAGACTGTC CAGTGTGCTG |
| | 1301 ATGACCGCGA CGCTGTGTGC ACCCGCTCCG TCACCGTCCG GCTGCCTGGC |
| | 1351 CTGCACAACA GCCTTGTGAA ACTGAAGCAT GGGGCAGGAG TTGCCATGGA |
| | 1401 TGGCCAGGAC ATCCAGCTCC CCCTCCTGAA AGGTGACCTC CGCATCCAGC |
| | 1451 ATACAGTGAC GGCCTCCGTG CGCCTCAGCT ACGGGGAGGA CCTGCAGATG |
| | 1501 GACTGGGATG GCCGCGGGAG GCTGCTGGTG AAGCTGTCCC CCGTCTATGC |
| | 1551 CGGGAAGACC TGCGGCCTGT GTGGGAATTA CAATGGCAAC CAGGGCGACG |
| | 1601 ACTTCCTTAC CCCCTCTGGG CTGGCRGAGC CCCGGGTGGA GGACTTCGGG |
| | 1651 AACGCCTGGA AGCTGCACGG GGACTGCCAG GACCTGCAGA AGCAGCACAG |
| | 1701 CGATCCCTGC GCCCTCAACC CGCGCATGAC CAGGTTCTCC GAGGAGGCGT |
| | 1751 GCGCGGTCCT GACGTCCCCC ACATTCGAGG CCTGCCATCG TGCCGTCAGC |
| | 1801 CCGCTGCCCT ACCTGCGGAA CTGCCGCTAC GACGTGTGCT CCTGCTCGGA |
| | 1851 CGGCCGCGAG TGCCTGTGCG GCGCCCTGGC CAGCTATGCC GCGGCCTGCG |
| | 1901 CGGGGAGAGG CGTGCGCGTC GCGTGGCGCG AGCCAGGCCG CTGTGAGCTG |
| | 1951 AACTGCCCGA AAGGCCAGGT GTACCTGCAG TGCGGGACCC CCTGCAACCT |
| | 2001 GACCTGCCGC TCTCTCTCTT ACCCGGATGA GGAATGCAAT GAGGCCTGCC |
| | 2051 TGGAGGGCTG CTTCTGCCCC CCAGGGCTCT ACATGGATGA GAGGGGGGAC |
| | 2101 TGCGTGCCCA AGGCCCAGTG CCCCTGTTAC TATGACGGTG AGATCTTCCA |
| | 2151 GCCAGAAGAC ATCTTCTCAG ACCATCACAC CATGTGCTAC TGTGAGGATG |
| | 2201 GCTTCATGCA CTGTACCATG AGTGGAGTCC CCGGAAGCTT GCTGCCTGAC |
| | 2251 GCTGTCCTCA GCAGTCCCCT GTCTCATCGC AGCAAAAGGA GCCTATCCTG |
| | 2301 TCGGCCCCCC ATGGTCAAGC TGGTGTGTCC CGCTGACAAC CTGCGGGCTG |
| | 2351 AAGGGCTCGA GTGTACCAAA ACGTGCCAGA ACTATGACCT GGAGTGCATG |
| | 2401 AGCATGGGCT GTGTCTCTGG CTGCCTCTGC CCCCCGGGCA TGGTCCGGCA |
| | 2451 TGAGAACAGA TGTGTGGCCC TGGAAAGGTG TCCCTGCTTC CATCAGGGCA |
| | 2501 AGGAGTATGC CCCTGGAGAA ACAGTGAAGA TTGGCTGCAA CACTTGTGTC |
| | 2551 TGTCGGGACC GGAAGTGGAA CTGCACAGAC CATGTGTGTG ATGCCACGTG |
| | 2601 CTCCACGATC GGCATGGCCC ACTACCTCAC CTTCGACGGG CTCAAATACC |
| | 2651 TGTTCCCCGG GGAGTGCCAG TACGTTCTGG TGCAGGATTA CTGCGGCAGT |
| | 2701 AACCCTGGGA CCTTTCGGAT CCTAGTGGGG AATAAGGGAT GCAGCCACCC |
| | 2751 CTCAGTGAAA TGCAAGAAAC GGGTCACCAT CCTGGTGGAG GGAGGAGAGA |
| | 2801 TTGAGCTGTT TGACGGGGAG GTGAATGTGA AGAGGCCCAT GAAGGATGAG |
| | 2851 ACTCACTTTG AGGTGGTGGA GTCTGGCCGG TACATCATTC TGCTGCTGGG |
| | 2901 CAAAGCCCTC TCCGTGGTCT GGGACCGCCA CCTGAGCATC TCCGTGGTCC |
| | 2951 TGAAGCAGAC ATACCAGGAG AAAGTGTGTG GCCTGTGTGG GAATTTTGAT |
| | 3001 GGCATCCAGA ACAATGACCT CACCAGCAGC AACCTCCAAG TGGAGGAAGA |

TABLE 1-continued

| VWF domains | Amino acid Sequence |
|---|---|
| | 3051 CCCTGTGGAC TTTGGGAACT CCTGGAAAGT GAGCTCGCAG TGTGCTGACA |
| | 3101 CCAGAAAAGT GCCTCTGGAC TCATCCCCTG CCACCTGCCA TAACAACATC |
| | 3151 ATGAAGCAGA CGATGGTGGA TTCCTCCTGT AGAATCCTTA CCAGTGACGT |
| | 3201 CTTCCAGGAC TGCAACAAGC TGGTGGACCC CGAGCCATAT CTGGATGTCT |
| | 3251 GCATTTACGA CACCTGCTCC TGTGAGTCCA TTGGGGACTG CGCCTGCTTC |
| | 3301 TGCGACACCA TTGCTGCCTA TGCCCACGTG TGTGCCCAGC ATGGCAAGGT |
| | 3351 GGTGACCTGG AGGACGGCCA CATTGTGCCC CCAGAGCTGC GAGGAGAGGA |
| | 3401 ATCTCCGGGA GAACGGGTAT GAGTGTGAGT GGCGCTATAA CAGCTGTGCA |
| | 3451 CCTGCCTGTC AAGTCACGTG TCAGCACCCT GAGCCACTGG CCTGCCCTGT |
| | 3501 GCAGTGTGTG GAGGGCTGCC ATGCCCACTG CCCTCCAGGG AAAATCCTGG |
| | 3551 ATGAGCTTTT GCAGACCTGC GTTGACCCTG AAGACTGTCC AGTGTGTGAG |
| | 3601 GTGGCTGGCC GGCGTTTTGC CTCAGGAAAG AAAGTCACCT TGAATCCCAG |
| | 3651 TGACCCTGAG CACTGCCAGA TTTGCCACTG TGATGTTGTC AACCTCACCT |
| | 3701 GTGAAGCCTG CCAGGAGCCG GGAGGCCTGG TGGTGCCTCC CACAGATGCC |
| | 3751 CCGGTGAGCC CCACCACTCT GTATGTGGAG GACATCTCGG AACCGCCGTT |
| | 3801 GCACGATTTC TACTGCAGCA GGCTACTGGA CCTGGTCTTC CTGCTGGATG |
| | 3851 GCTCCTCCAG GCTGTCCGAG GCTGAGTTTG AAGTGCTGAA GGCCTTTGTG |
| | 3901 GTGGACATGA TGGAGCGGCT GCGCATCTCC CAGAAGTGGG TCCGCGTGGC |
| | 3951 CGTGGTGGAG TACCACGACG GCTCCCACGC CTACATCGGG CTCAAGGACC |
| | 4001 GGAAGCGACC GTCAGAGCTG CGGCGCATTG CCAGCCAGGT GAAGTATGCG |
| | 4051 GGCAGCCAGG TGGCCTCCAC CAGCGAGGTC TTGAAATACA CACTGTTCCA |
| | 4101 AATCTTCAGC AAGATCGACC GCCCTGAAGC CTCCCGCATC GCCCTGCTCC |
| | 4151 TGATGGCCAG CCAGGAGCCC CAACGGATGT CCCGGAACTT TGTCCGCTAC |
| | 4201 GTCCAGGGCC TGAAGAAGAA GAAGGTCATT GTGATCCCGG TGGGCATTGG |
| | 4151 GCCCCATGCC AACCTCAAGC AGATCCGCCT CATCGAGAAG CAGGCCCCTG |
| | 4301 AGAACAAGGC CTTCGTGCTG AGCAGTGTGG ATGAGCTGGA GCAGCAAAGG |
| | 4351 GACGAGATCG TTAGCTACCT CTGTGACCTT GCCCCTGAAG CCCCTCCTCC |
| | 4401 TACTCTGCCC CCCGACATGG CACAAGTCAC TGTGGGCCCG GGGCTCTTGG |
| | 4451 GGGTTTCGAC CCTGGGGCCC AAGAGGAACT CCATGGTTCT GGATGTGGCG |
| | 4501 TTCGTCCTGG AAGGATCGGA CAAAATTGGT GAAGCCGACT TCAACAGGAG |
| | 4551 CAAGGAGTTC ATGGAGGAGG TGATTCAGCG GATGGATGTG GGCCAGGACA |
| | 4601 GCATCCACGT CACGGTGCTG CAGTACTCCT ACATGGTGAC CGTGGAGTAC |
| | 4651 CCCTTCAGCG AGGCACAGTC CAAAGGGGAC ATCCTGCAGC GGGTGCGAGA |
| | 4701 GATCCGCTAC CAGGGCGGCA ACAGGACCAA CACTGGGCTG GCCCTGCGGT |
| | 4751 ACCTCTCTGA CCACAGCTTC TTGGTCAGCC AGGGTGACCG GGAGCAGGCG |
| | 4801 CCCAACCTGG TCTACATGGT CACCGGAAAT CCTGCCTCTG ATGAGATCAA |
| | 4851 GAGGCTGCCT GGAGACATCC AGGTGGTGCC CATTGGAGTG GGCCCTAATG |
| | 4901 CCAACGTGCA GGAGCTGGAG AGGATTGGCT GGCCCAATGC CCCTATCCTC |
| | 4951 ATCCAGGACT TTGAGACGCT CCCCCGAGAG GCTCCTGACC TGGTGCTGCA |

TABLE 1-continued

| VWF domains | Amino acid Sequence |
|---|---|
| | 5001 GAGGTGCTGC TCCGGAGAGG GGCTGCAGAT CCCCACCCTC TCCCCTGCAC<br>5051 CTGACTGCAG CCAGCCCCTG GACGTGATCC TTCTCCTGGA TGGCTCCTCC<br>5101 AGTTTCCCAG CTTCTTATTT TGATGAAATG AAGAGTTTCG CCAAGGCTTT<br>5151 CATTTCAAAA GCCAATATAG GGCCTCGTCT CACTCAGGTG TCAGTGCTGC<br>5201 AGTATGGAAG CATCACCACC ATTGACGTGC CATGGAACGT GGTCCCGGAG<br>5251 AAAGCCCATT TGCTGAGCCT TGTGGACGTC ATGCAGCGGG AGGGAGGCCC<br>5301 CAGCCAAATC GGGGATGCCT TGGGCTTTGC TGTGCGATAC TTGACTTCAG<br>5351 AAATGCATGG TGCCAGGCCG GGAGCCTCAA AGGCGGTGGT CATCCTGGTC<br>5401 ACGGACGTCT CTGTGGATTC AGTGGATGCA GCAGCTGATG CCGCCAGGTC<br>5451 CAACAGAGTG ACAGTGTTCC CTATTGGAAT TGGAGATCGC TACGATGCAG<br>5501 CCCAGCTACG GATCTTGGCA GGCCCAGCAG GCGACTCCAA CGTGGTGAAG<br>5551 CTCCAGCGAA TCGAAGACCT CCCTACCATG GTCACCTTGG GCAATTCCTT<br>5601 CCTCCACAAA CTGTGCTCTG GATTTGTTAG GATTTGCATG GATGAGGATG<br>5651 GGAATGAGAA GAGGCCCGGG GACGTCTGGA CCTTGCCAGA CCAGTGCCAC<br>5701 ACCGTGACTT GCCAGCCAGA TGGCCAGACC TTGCTGAAGA GTCATCGGGT<br>5751 CAACTGTGAC CGGGGGCTGA GGCCTTCGTG CCCTAACAGC CAGTCCCCTG<br>5801 TTAAAGTGGA AGAGACCTGT GGCTGCCGCT GGACCTGCCC CTGYGTGTGC<br>5851 ACAGGCAGCT CCACTCGGCA CATCGTGACC TTTGATGGGC AGAATTTCAA<br>5901 GCTGACTGGC AGCTGTTCTT ATGTCCTATT TCAAAACAAG GAGCAGGACC<br>5951 TGGAGGTGAT TCTCCATAAT GGTGCCTGCA GCCCTGGAGC AAGGCAGGGC<br>6001 TGCATGAAAT CCATCGAGGT GAAGCACAGT GCCCTCTCCG TCGAGSTGCA<br>6051 CAGTGACATG GAGGTGACGG TGAATGGGAG ACTGGTCTCT GTTCCTTACG<br>6101 TGGGTGGGAA CATGGAAGTC AACGTTTATG GTGCCATCAT GCATGAGGTC<br>6151 AGATTCAATC ACCTTGGTCA CATCTTCACA TTCACTCCAC AAAACAATGA<br>6201 GTTCCAACTG CAGCTCAGCC CCAAGACTTT TGCTTCAAAG ACGTATGGTC<br>6251 TGTGTGGGAT CTGTGATGAG AACGGAGCCA ATGACTTCAT GCTGAGGGAT<br>6501 GGCACAGTCA CCACAGACTG GAAAACACTT GTTCAGGAAT GGACTGTGCA<br>6351 GCGGCCAGGG CAGACGTGCC AGCCCATCCT GGAGGAGCAG TGTCTTGTCC<br>6401 CCGACAGCTC CCACTGCCAG GTCCTCCTCT TACCACTGTT TGCTGAATGC<br>6451 CACAAGGTCC TGGCTCCAGC CACATTCTAT GCCATCTGCC AGCAGGACAG<br>6501 TTGCCACCAG GAGCAAGTGT GTGAGGTGAT CGCCTCTTAT GCCCACCTCT<br>6551 GTCGGACCAA CGGGGTCTGC GTTGACTGGA GGACACCTGA TTTCTGTGCT<br>6601 ATGTCATGCC CACCATCTCT GGTCTACAAC CACTGTGAGC ATGGCTGTCC<br>6651 CCGGCACTGT GATGGCAACG TGAGCTCCTG TGGGGACCAT CCCTCCGAAG<br>6701 GCTGTTTCTG CCCTCCAGAT AAAGTCATGT TGGAAGGCAG CTGTGTCCCT<br>6751 GAAGAGGCCT GCACTCAGTG CATTGGTGAG GATGGAGTCC AGCACCAGTT<br>6801 CCTGGAAGCC TGGGTCCCGG ACCACCAGCC CTGTCAGATC TGCACATGCC<br>6851 TCAGCGGGCG GAAGGTCAAC TGCACAACGC AGCCCTGCCC CACGGCCAAA<br>6901 GCTCCCACGT GTGGCCTGTG TGAAGTAGCC CGCCTCCGCC AGAATGCAGA |

TABLE 1-continued

| VWF domains | Amino acid Sequence |
|---|---|
| | 6951 CCAGTGCTGC CCCGAGTATG AGTGTGTGTG TGACCCAGTG AGCTGTGACC |
| | 7001 TGCCCCCAGT GCCTCACTGT GAACGTGGCC TCCAGCCCAC ACTGACCAAC |
| | 7051 CCTGGCGAGT GCAGACCCAA CTTCACCTGC GCCTGCAGGA AGGAGGAGTG |
| | 7101 CAAAAGAGTG TCCCCACCCT CCTGCCCCCC GCACCGTTTG CCCACCCTTC |
| | 7151 GGAAGACCCA GTGCTGTGAT GAGTATGAGT GTGCCTGCAA CTGTGTCAAC |
| | 7201 TCCACAGTGA GCTGTCCCCT TGGGTACTTG GCCTCAACCG CCACCAATGA |
| | 7251 CTGTGGCTGT ACCACAACCA CCTGCCTTCC CGACAAGGTG TGTGTCCACC |
| | 7301 GAAGCACCAT CTACCCTGTG GGCCAGTTCT GGGAGGAGGG CTGCGATGTG |
| | 7351 TGCACCTGCA CCGACATGGA GGATGCCGTG ATGGGCCTCC GCGTGGCCCA |
| | 7401 GTGCTCCCAG AAGCCCTGTG AGGACAGCTG TCGGTCGGGC TTCACTTACG |
| | 7451 TTCTGCATGA AGGCGAGTGC TGTGGAAGGT GCCTGCCATC TGCCTGTGAG |
| | 7501 GTGGTGACTG GCTCACCGCG GGGGGACTCC CAGTCTTCCT GGAAGAGTGT |
| | 7551 CGGCTCCCAG TGGGCCTCCC CGGAGAACCC CTGCCTCATC AATGAGTGTG |
| | 7601 TCCGAGTGAA GGAGGAGGTC TTTATACAAC AAAGGAACGT CTCCTGCCCC |
| | 7651 CAGCTGGAGG TCCCTGTCTG CCCCTCGGGC TTTCAGCTGA GCTGTAAGAC |
| | 7701 CTCAGCGTGC TGCCCAAGCT GTCGCTGTGA GCGCATGGAG GCCTGCATGC |
| | 7751 TCAATGGCAC TGTCATTGGG CCCGGGAAGA CTGTGATGAT CGATGTGTGC |
| | 7801 ACGACCTGCC GCTGCATGGT GCAGGTGGGG GTCATCTCTG GATTCAAGCT |
| | 7851 GGAGTGCAGG AAGACCACCT GCAACCCCTG CCCCCTGGGT TACAAGGAAG |
| | 7901 AAAATAACAC AGGTGAATGT TGTGGGAGAT GTTTGCCTAC GGCTTGCACC |
| | 7951 ATTCAGCTAA GAGGAGGACA GATCATGACA CTGAAGCGTG ATGAGACGCT |
| | 8001 CCAGGATGGC TGTGATACTC ACTTCTGCAA GGTCAATGAG AGAGGAGAGT |
| | 8051 ACTTCTGGGA GAAGAGGGTC ACAGGCTGCC CACCCTTTGA TGAACACAAG |
| | 8101 TGTCTTGCTG AGGGAGGTAA AATTATGAAA ATTCCAGGCA CCTGCTGTGA |
| | 8151 CACATGTGAG GAGCCTGAGT GCAACGACAT CACTGCCAGG CTGCAGTATG |
| | 8201 TCAAGGTGGG AAGCTGTAAG TCTGAAGTAG AGGTGGATAT CCACTACTGC |
| | 8251 CAGGGCAAAT GTGCCAGCAA AGCCATGTAC TCCATTGACA TCAACGATGT |
| | 8301 GCAGGACCAG TGCTCCTGCT GCTCTCCGAC ACGGACGGAG CCCATGCAGG |
| | 8351 TGGCCCTGCA CTGCACCAAT GGCTCTGTTG TGTACCATGA GGTTCTCAAT |
| | 8401 GCCATGGAGT GCAAATGCTC CCCCAGGAAG TGCAGCAAGT GA |

The VWF protein as used herein can be a VWF fragment comprising a D' domain and a D3 domain of VWF, wherein the VWF fragment binds to Factor VIII (FVIII) and inhibits binding of endogenous VWF (full-length VWF) to FVIII. The VWF fragment comprising the D' domain and the D3 domain can further comprise a VWF domain selected from the group consisting of an A1 domain, an A2 domain, an A3 domain, a D1 domain, a D2 domain, a D4 domain, a B1 domain, a B2 domain, a B3 domain, a C1 domain, a C2 domain, a CK domain, one or more fragments thereof, and any combinations thereof. In one embodiment, a VWF fragment comprises, consists essentially of, or consists of: (1) the D' and D3 domains of VWF or fragments thereof; (2) the D1, D', and D3 domains of VWF or fragments thereof; (3) the D2, D', and D3 domains of VWF or fragments thereof; (4) the D1, D2, D', and D3 domains of VWF or fragments thereof; or (5) the D1, D2, D', D3, and A1 domains of VWF or fragments thereof. The VWF fragment described herein does not contain a site binding to a VWF clearance receptor. In another embodiment, the VWF fragment described herein is not amino acids 764 to 1274 of SEQ ID NO: 21. The VWF fragment of the present invention can comprise any other sequences linked to or fused to the VWF fragment. For example, a VWF fragment described herein can further comprise a signal peptide.

In one embodiment, the VWF fragment comprising a D' domain and a D3 domain binds to or is associated with a FVIII protein. By binding to or associating with a FVIII protein, a VWF fragment of the invention protects FVIII from protease cleavage and FVIII activation, stabilizes the heavy chain and light chain of FVIII, and prevents clearance of FVIII by scavenger receptors. In another embodiment, the VWF fragment binds to or associates with a FVIII protein and blocks or prevents binding of the FVIII protein to phospholipid and activated Protein C. By preventing or inhibiting binding of the FVIII protein with endogenous, full-length VWF, the VWF fragment of the invention reduces the clearance of FVIII by VWF clearance receptors and thus extends half-life of the chimeric protein. The half-life extension of a chimeric protein is thus due to the binding of or associating with the VWF fragment lacking a VWF clearance receptor binding site to the FVIII protein and shielding or protecting of the FVIII protein by the VWF fragment from endogenous VWF which contains the VWF clearance receptor binding site. The FVIII protein bound to or protected by the VWF fragment can also allow recycling of a FVIII protein. By eliminating the VWF clearance pathway receptor binding sites contained in the full length VWF molecule, the FVIII/VWF heterodimers of the invention are shielded from the VWF clearance pathway, further extending FVIII half-life.

In one embodiment, a VWF protein useful for the present invention comprises a D' domain and a D3 domain of VWF, wherein the D' domain is at least 60%, 70%, 80%, 85%, 90%, 95%, 96%, 97%, 98%, 99%, or 100% identical to amino acids 764 to 866 of SEQ ID NO: 21, wherein the VWF protein prevents or inhibits binding of endogenous VWF to FVIII. In another embodiment, a VWF protein comprises the D' domain and the D3 domain of VWF, wherein the D3 domain is at least 60%, 70%, 80%, 85%, 90%, 95%, 96%, 97%, 98%, 99%, or 100% identical to amino acids 867 to 1240 of SEQ ID NO: 21, wherein the VWF protein prevents or inhibits binding of endogenous VWF to FVIII. In some embodiments, a VWF protein described herein comprises, consists essentially of, or consists of the D' domain and D3 domain of VWF, which are at least 60%, 70%, 80%, 85%, 90%, 95%, 96%, 97%, 98%, 99%, or 100% identical to amino acids 764 to 1240 of SEQ ID NO: 21, wherein the VWF protein prevents or inhibits binding of endogenous VWF to FVIII. In other embodiments, a VWF protein comprises, consists essentially of, or consists of the D1, D2, D', and D3 domains at least 60%, 70%, 80%, 85%, 90%, 95%, 96%, 97%, 98%, 99%, or 100% identical to amino acids 23 to 1240 of SEQ ID NO: 21, wherein the VWF protein prevents or inhibits binding of endogenous VWF to FVIII. In still other embodiments, the VWF protein further comprises a signal peptide operably linked thereto.

In some embodiments, a VWF protein useful for the invention consists essentially of or consists of (1) the D'D3 domain, the D1D'D3 domain, D2D'D3 domain, or D1D2D'D3 domain and (2) an additional VWF sequence up to about 10 amino acids (e.g., any sequences from amino acids 764 to 1240 of SEQ ID NO: 21 to amino acids 764 to 1250 of SEQ ID NO: 21), up to about 15 amino acids (e.g., any sequences from amino acids 764 to 1240 of SEQ ID NO: 21 to amino acids 764 to 1255 of SEQ ID NO: 21), up to about 20 amino acids (e.g., any sequences from amino acids 764 to 1240 of SEQ ID NO: 21 to amino acids 764 to 1260 of SEQ ID NO: 21), up to about 25 amino acids (e.g., any sequences from amino acids 764 to 1240 of SEQ ID NO: 21 to amino acids 764 to 1265 of SEQ ID NO: 21), or up to about 30 amino acids (e.g., any sequences from amino acids 764 to 1240 of SEQ ID NO: 21 to amino acids 764 to 1260 of SEQ ID NO: 21). In a particular embodiment, the VWF protein comprising or consisting essentially of the D' domain and the D3 domain is neither amino acids 764 to 1274 of SEQ ID NO: 21 nor the full-length mature VWF. In some embodiments, the D1D2 domain is expressed in trans with the D'D3 domain. In some embodiments, the D1D2 domain is expressed in cis with the D'D3 domain.

In other embodiments, the VWF protein comprising the D'D3 domains linked to the D1D2 domains further comprises an intracellular cleavage site, e.g., (a cleavage site by PACE (furin) or PC5), allowing cleavage of the D1D2 domains from the D'D3 domains upon expression. Non-limiting examples of the intracellular cleavage site are disclosed elsewhere herein.

In yet other embodiments, a VWF protein comprises a D' domain and a D3 domain, but does not comprise an amino acid sequence selected from the group consisting of (1) amino acids 1241 to 2813 corresponding to SEQ ID NO: 21, (2) amino acids 1270 to amino acids 2813 corresponding to SEQ ID NO: 21, (3) amino acids 1271 to amino acids 2813 corresponding to SEQ ID NO: 21, (4) amino acids 1272 to amino acids 2813 corresponding to SEQ ID NO: 21, (5) amino acids 1273 to amino acids 2813 corresponding to SEQ ID NO: 21, (6) amino acids 1274 to amino acids 2813 corresponding to SEQ ID NO: 21, and any combinations thereof.

In still other embodiments, a VWF protein of the present invention comprises, consists essentially of, or consists of an amino acid sequence corresponding to the D' domain, D3 domain, and A1 domain, wherein the amino acid sequence is at least 60%, 70%, 75%, 80%, 85%, 90%, 95%, 96%, 97%, 98%, 99%, or 100% identical to amino acid 764 to 1479 of SEQ ID NO: 21, wherein the VWF protein prevents binding of endogenous VWF to FVIII. In a particular embodiment, the VWF protein is not amino acids 764 to 1274 of SEQ ID NO: 21.

In some embodiments, a VWF protein of the invention comprises a D' domain and a D3 domain, but does not comprise at least one VWF domain selected from the group consisting of (1) an A1 domain, (2) an A2 domain, (3) an A3 domain, (4) a D4 domain, (5) a B1 domain, (6) a B2 domain, (7) a B3 domain, (8) a C1 domain, (9) a C2 domain, (10) a CK domain, (11) a CK domain and C2 domain, (12) a CK domain, a C2 domain, and a C1 domain, (13) a CK domain, a C2 domain, a C1 domain, a B3 domain, (14) a CK domain, a C2 domain, a C1 domain, a B3 domain, a B2 domain, (15) a CK domain, a C2 domain, a C1 domain, a B3 domain, a B2 domain, and a B1 domain, (16) a CK domain, a C2 domain, a C1 domain, a B3 domain, a B2 domain, a B1 domain, and a D4 domain, (17) a CK domain, a C2 domain, a C1 domain, a B3 domain, a B2 domain, a B1 domain, a D4 domain, and an A3 domain, (18) a CK domain, a C2 domain, a C1 domain, a B3 domain, a B2 domain, a B1 domain, a D4 domain, an A3 domain, and an A2 domain, (19) a CK domain, a C2 domain, a C1 domain, a B3 domain, a B2 domain, a B1 domain, a D4 domain, an A3 domain, an A2 domain, and an A1 domain, and (20) any combinations thereof.

In yet other embodiments, the VWF protein comprises the D'D3 domains and one or more domains or modules. Examples of such domains or modules include, but are not limited to, the domains and modules disclosed in Zhour et al., Blood published online Apr. 6, 2012: DOI 10.1182/blood-2012-01-405134, which is incorporated herein by reference in its entirety. For example, the VWF protein can comprise the D'D3 domain and one or more domains or modules selected from the group consisting of A1 domain, A2 domain, A3 domain, D4N module, VWD4 module, C8-4 module, TIL-4 module, C1 module, C2 module, C3 module, C4 module, C5 module, C5 module, C6 module, and any combinations thereof.

In still other embodiments, the VWF protein is linked to a heterologous moiety, wherein the heterologous moiety is linked to the N-terminus or the C-terminus of the VWF protein or inserted immediately downstream of one or more amino acids (e.g., one or more XTEN insertion sites) in the VWF protein. For example, the insertion sites for the heterologous moiety in the VWF protein can be in the D' domain, the D3 domain, or both. The heterologous moiety can be a half-life extender.

In certain embodiments, a VWF protein useful for the invention forms a multimer, e.g., dimer, trimer, tetramer, pentamer, hexamer, heptamer, or the higher order multimers. In other embodiments, the VWF protein is a monomer having only one VWF protein. In some embodiments, the VWF protein of the present invention can have one or more amino acid substitutions, deletions, additions, or modifications. In one embodiment, the VWF protein can include amino acid substitutions, deletions, additions, or modifications such that the VWF protein is not capable of forming a disulfide bond or forming a dimer or a multimer. In another embodiment, the amino acid substitution is within the D' domain and the D3 domain. In a particular embodiment, a VWF protein useful for the invention contains at least one amino acid substitution at a residue corresponding to residue 1099, residue 1142, or both residues 1099 and 1142 corresponding to SEQ ID NO: 21. The at least one amino acid substitution can be any amino acids that are not occurring naturally in the wild type VWF. For example, the amino acid substitution can be any amino acids other than cysteine, e.g., Isoleucine, Alanine, Leucine, Asparagine, Lysine, Aspartic acid, Methionine, Phenylalanine, Glutamic acid, Threonine, Glutamine, Tryptophan, Glycine, Valine, Proline, Serine, Tyrosine, Arginine, or Histidine. In another example, the amino acid substitution has one or more amino acids that prevent or inhibit the VWF proteins from forming multimers.

In certain embodiments, the VWF protein useful herein can be further modified to improve its interaction with FVIII, e.g., to improve binding affinity to FVIII. As a non-limiting example, the VWF protein comprises a serine residue at the residue corresponding to amino acid 764 of SEQ ID NO: 21 and a lysine residue at the residue corresponding to amino acid 773 of SEQ ID NO: 21. Residues 764 and/or 773 can contribute to the binding affinity of the VWF proteins to FVIII. In other embodiments, The VWF proteins useful for the invention can have other modifications, e.g., the protein can be pegylated, glycosylated, hesylated, or polysialylated.

II.B. XTEN Sequences

As used herein "XTEN sequence" refers to extended length polypeptides with non-naturally occurring, substantially non-repetitive sequences that are composed mainly of small hydrophilic amino acids, with the sequence having a low degree or no secondary or tertiary structure under physiologic conditions. As a chimeric protein partner, XTENs can serve as a carrier, conferring certain desirable pharmacokinetic, physicochemical and pharmaceutical properties when linked to a VWF protein or a FVIII sequence of the invention to create a chimeric protein. Such desirable properties include but are not limited to enhanced pharmacokinetic parameters and solubility characteristics. As used herein, "XTEN" specifically excludes antibodies or antibody fragments such as single-chain antibodies or Fc fragments of a light chain or a heavy chain.

The present invention provides that a shorter XTEN sequence provides an improved half-life extending property compared to a longer XTEN sequence when the XTEN sequence is fused to a VWF protein and/or the second Ig constant region or a portion thereof. Therefore, the XTEN sequence fused to a VWF protein and/or the second Ig constant region or a portion thereof contains less than 288 amino acids in length, i.e., is shorter than 288 amino acids. In one embodiment, the XTEN sequence fused to a VWF protein and/or the second Ig constant region or a portion thereof consists of an amino acid sequence having a length of between 12 amino acids and 287 amino acids. In another embodiment, the XTEN sequence fused to a VWF protein and/or the second Ig constant region or a portion thereof comprise at least about 36 amino acids, at least about 42 amino acids, at least about 72 amino acids, or at least about 144 amino acids, but less than 288 amino acids. In other embodiments, the XTEN sequence fused to a VWF protein and/or the second Ig constant region or a portion thereof is selected from AE36, AG36, AE42, AG42, AE72, AG72, AE144, or AG144. In one embodiment, the XTEN sequence fused to a VWF protein and/or the second Ig constant region or a portion thereof is an amino acid sequence at least 80%, 85%, 90%, 95%, 96%, 97%, 98%, 99%, or 100% identical to SEQ ID NO: 9, SEQ ID NO: 10, SEQ ID NO: 11, or SEQ ID NO: 14, wherein the chimeric protein exhibits an improved half-life compared to a chimeric protein without the XTEN sequence.

The chimeric protein of the invention can further comprise an additional (second, third, or more) XTEN sequences. The additional XTEN sequence can further be fused to the FVIII protein or the first Ig constant region or a portion thereof. The additional XTEN sequences can be any length. For example, the additional XTEN sequence fused to the FVIII protein or the first Ig constant region or a portion thereof is a peptide or a polypeptide having greater than about 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, or 2000 amino acid residues. In certain embodiments, the additional XTEN sequence is a peptide or a polypeptide having greater than about 20 to about 3000 amino acid residues, greater than about 30 to about 2500 residues, greater than about 40 to about 2000 residues, greater than about 50 to about 1500 residues, greater than about 60 to about 1000 residues, greater than about 70 to about 900 residues, greater than about 80 to about 800 residues, greater than about 90 to about 700 residues, greater than about 100 to about 600 residues, greater than about 110 to about 500 residues, or greater than about 120 to about 400 residues.

The XTEN sequences (i.e., the XTEN sequence fused to the VWF protein and/or the second Ig constant region or a portion thereof or the XTEN sequence fused to the FVIII protein and/or the first Ig constant region or a portion thereof or inserted at one or more insertion sites within the FVIII protein) can comprise one or more sequence motif of 9 to 14 amino acid residues or an amino acid sequence at least 80%, 90%, 91%, 92%, 93%, 94%, 95%, 96%, 97%, 98%, or 99% identical to the sequence motif, wherein the motif comprises, consists essentially of, or consists of 4 to 6 types of amino acids selected from the group consisting of glycine (G), alanine (A), serine (S), threonine (T), glutamate (E) and proline (P). See US 2010-0239554 A1.

In some embodiments, the XTEN sequence comprises non-overlapping sequence motifs in which at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% or about 100% of the sequence consists of multiple units of non-overlapping sequences selected from a single motif family selected from Table 2A, resulting in a family sequence. As used herein, "family" means that the XTEN has motifs selected only from a single motif category from Table 2A; i.e., AD, AE, AF, AG, AM, AQ, BC, or BD XTEN, and that any other amino acids in the XTEN not from a family motif are selected to achieve a needed property, such as to permit incorporation of a restriction site by the encoding nucleotides, incorporation of a cleavage sequence, or to achieve a better linkage to FVIII or VWF. In some embodiments of XTEN families, an XTEN sequence comprises multiple units of non-overlapping sequence motifs of the AD motif family, or of the AE motif family, or of the AF motif family, or of the AG motif family, or of the AM motif family, or of the AQ motif family, or of the BC family, or of the BD family, with the resulting XTEN exhibiting the range of homology described above. In other embodiments, the XTEN comprises multiple units of motif sequences from two or more of the motif families of Table 2A. These sequences can be selected to achieve desired physical/chemical characteristics, including such properties as net charge, hydrophilicity, lack of secondary structure, or lack of repetitiveness that are conferred by the amino acid composition of the motifs, described more fully below. In the embodiments hereinabove described in this paragraph, the motifs incorporated into the XTEN can be selected and assembled using the methods described herein to achieve an XTEN of about 36 to about 3000 amino acid residues.

TABLE 2A

XTEN Sequence Motifs of 12 Amino Acids and Motif Families

| Motif Family* | MOTIF SEQUENCE |
|---|---|
| AD | GESPGGSSGSES (SEQ ID NO: 24) |
| AD | GSEGSSGPGESS (SEQ ID NO: 25) |
| AD | GSSESGSSEGGP (SEQ ID NO: 26) |
| AD | GSGGEPSESGSS (SEQ ID NO: 27) |
| AE, AM | GSPAGSPTSTEE (SEQ ID NO: 28) |
| AE, AM, AQ | GSEPATSGSETP (SEQ ID NO: 29) |
| AE, AM, AQ | GTSESATPESGP (SEQ ID NO: 30) |
| AE, AM, AQ | GTSTEPSEGSAP (SEQ ID NO: 31) |
| AF, AM | GSTSESPSGTAP (SEQ ID NO: 32) |
| AF, AM | GTSTPESGSASP (SEQ ID NO: 33) |
| AF, AM | GTSPSGESSTAP (SEQ ID NO: 34) |
| AF, AM | GSTSSTAESPGP (SEQ ID NO: 35) |
| AG, AM | GTPGSGTASSSP (SEQ ID NO: 36) |
| AG, AM | GSSTPSGATGSP (SEQ ID NO: 37) |
| AG, AM | GSSPSASTGTGP (SEQ ID NO: 38) |
| AG, AM | GASPGTSSTGSP (SEQ ID NO: 39) |
| AQ | GEPAGSPTSTSE (SEQ ID NO: 40) |
| AQ | GTGEPSSTPASE (SEQ ID NO: 41) |

TABLE 2A-continued

XTEN Sequence Motifs of 12 Amino Acids and Motif Families

| Motif Family* | MOTIF SEQUENCE |
|---|---|
| AQ | GSGPSTESAPTE (SEQ ID NO: 42) |
| AQ | GSETPSGPSETA (SEQ ID NO: 43) |
| AQ | GPSETSTSEPGA (SEQ ID NO: 44) |
| AQ | GSPSEPTEGTSA (SEQ ID NO: 45) |
| BC | GSGASEPTSTEP (SEQ ID NO: 46) |
| BC | GSEPATSGTEPS (SEQ ID NO: 47) |
| BC | GTSEPSTSEPGA (SEQ ID NO: 48) |
| BC | GTSTEPSEPGSA (SEQ ID NO: 49) |
| BD | GSTAGSETSTEA (SEQ ID NO: 50) |
| BD | GSETATSGSETA (SEQ ID NO: 51) |
| BD | GTSESATSESGA (SEQ ID NO: 52) |
| BD | GTSTEASEGSAS (SEQ ID NO: 53) |

Denotes individual motif sequences that, when used together in various permutations,results in a "family sequence"

In some embodiments, the XTEN sequence used in the invention is at least 60%, 70%, 80%, 85%, 90%, 91%, 92%, 93%, 94%, 95%, 96%, 97%, 98%, 99%, or 100% identical to a sequence selected from the group consisting of AE42, AG42, AE48, AM48, AE72, AG72, AE108, AG108, AE144, AF144, AG144, AE180, AG180, AE216, AG216, AE252, AG252, AE288, AG288, AE324, AG324, AE360, AG360, AE396, AG396, AE432, AG432, AE468, AG468, AE504, AG504, AF504, AE540, AG540, AF540, AD576, AE576, AF576, AG576, AE612, AG612, AE624, AE648, AG648, AG684, AE720, AG720, AE756, AG756, AE792, AG792, AE828, AG828, AD836, AE864, AF864, AG864, AM875, AE912, AM923, AM1318, BC864, BD864, AE948, AE1044, AE1140, AE1236, AE1332, AE1428, AE1524, AE1620, AE1716, AE1812, AE1908, AE2004A, AG948, AG1044, AG1140, AG1236, AG1332, AG1428, AG1524, AG1620, AG1716, AG1812, AG1908, and AG2004. See US 2010-0239554 A1.

In one embodiment, the XTEN sequence is at least 60%, 70%, 80%, 90%, 95%, 96%, 97%, 98%, 99% or 100% identical to an amino acid sequence selected from the group consisting of AE42 (SEQ ID NO: 9), AE72 (SEQ ID NO: 10), AE144_2A (SEQ ID NO: 55), AE144_3B (SEQ ID NO: 56), AE144_4A (SEQ ID NO: 57), AE144_5A (SEQ ID NO: 58), AE144_6B (SEQ ID NO: 59), AG144_A (SEQ ID NO: 60), AG144_B (SEQ ID NO: 61), AG144_C (SEQ ID NO: 62), AG144_F (SEQ ID NO: 63), AE864 (SEQ ID NO: 15), AE576 (SEQ ID NO: 16), AE288 (SEQ ID NO: 8), AE288_2 (SEQ ID NO: 54), AE144 (SEQ ID NO: 11), AG864 (SEQ ID NO: 17), AG576 (SEQ ID NO: 18), AG288 (SEQ ID NO: 19), AG144 (SEQ ID NO: 14), and any combinations thereof. In another embodiment, the XTEN sequence is selected from the group consisting of AE42 (SEQ ID NO: 9), AE72 (SEQ ID NO: 10), AE144_2A (SEQ ID NO: 55), AE144_3B (SEQ ID NO: 56), AE144_4A (SEQ ID NO: 57), AE144_5A (SEQ ID NO: 58), AE144_6B (SEQ ID NO: 59), AG144_A (SEQ ID NO: 60), AG144_B (SEQ ID NO: 61), AG144_C (SEQ ID NO: 62), AG144_F (SEQ ID NO: 63), AE864 (SEQ ID NO: 15), AE576 (SEQ ID NO: 16), AE288 (SEQ ID NO: 8), AE288_2 (SEQ ID NO: 54), AE144 (SEQ ID NO: 11), AG864 (SEQ ID NO: 17), AG576 (SEQ ID NO: 18), AG288 (SEQ ID NO: 19), AG144 (SEQ ID NO: 14), and any combinations thereof. In a specific embodiment, the XTEN sequence is AE288. The amino acid sequences for certain XTEN sequences of the invention are shown in Table 2B.

TABLE 2B

| XTEN Sequences | |
|---|---|
| XTEN | Amino Acid Sequence |
| AE42<br>SEQ ID NO: 9 | GAPGSPAGSPTSTEEGTSESATPESGPGSEPATSGSETPASS |
| AE72<br>SEQ ID NO: 10 | GAP TSESATPESG PGSEPATSGS ETPGTSESAT PESGPGSEPA<br>TSGSETPGTS ESATPESGPG TSTEPSEGSA PGASS |
| AE144<br>SEQ ID NO: 11 | GSEPATSGSETPGTSESATPESGPGSEPATSGSETPGSPAGSPTSTEEGTSTEPSEG<br>SAPGSEPATSGSETPGSEPATSGSETPGSEPATSGSETPGTSTEPSEGSAPGTSESA<br>PESGPGSEPATSGSETPGTSTEPSEGSAP |
| AE144_2A<br>(SEQ ID NO:<br>55) | TSTEPSEGSAPGSPAGSPTSTEEGTSTEPSEGSAPGTSTEPSEGSAPGTSESATPESGPGTS<br>TEPSEGSAPGTSESATPESGPGSEPATSGSETPGTSTEPSEGSAPGTSTEPSEGSAPGTSES<br>ATPESGPGTSESATPESGPG |
| AE144_3B<br>(SEQ ID NO:<br>56) | SPAGSPTSTEEGTSESATPESGPGSEPATSGSETPGTSESATPESGPGTSTEPSEGSAPGTS<br>TEPSEGSAPGTSTEPSEGSAPGTSTEPSEGSAPGTSTEPSEGSAPGTSTEPSEGSAPGSPAG<br>SPTSTEEGTSTEPSEGSAPG |
| AE144_4A<br>(SEQ ID NO:<br>57) | TSESATPESGPGSEPATSGSETPGTSESATPESGPGSEPATSGSETPGTSESATPESGPGTS<br>TEPSEGSAPGTSESATPESGPGSPAGSPTSTEEGSPAGSPTSTEEGSPAGSPTSTEEGTSES<br>ATPESGPGTSTEPSEGSAPG |
| AE144_5A<br>(SEQ ID NO:<br>58) | TSESATPESGPGSEPATSGSETPGTSESATPESGPGSEPATSGSETPGTSESATPESGPGTS<br>TEPSEGSAPGSPAGSPTSTEEGTSESATPESGPGSEPATSGSETPGTSESATPESGPGSPAG<br>SPTSTEEGSPAGSPTSTEEG |
| AE144_6B<br>(SEQ ID NO:<br>59) | TSTEPSEGSAPGTSESATPESGPGTSESATPESGPGTSESATPESGPGSEPATSGSETPGSE<br>PATSGSETPGSPAGSPTSTEEGTSTEPSEGSAPGTSTEPSEGSAPGSEPATSGSETPGTSES<br>ATPESGPGTSTEPSEGSAPG |
| AG144<br>SEQ ID NO: 14 | GTPGSGTASSSPGSSTPSGATGSPGSSPSASTGTGPGSSPSASTGTGPGASPGTSST<br>GSPGASPGTSSTGSPGSSTPSGATGSPGSSPSASTGTGPGASPGTSSTGSPGSSPSA<br>STGTGPGTPGSGTASSSPGSSTPSGATGSP |
| AG144_A<br>(SEQ ID NO:<br>60) | GASPGTSSTGSPGSSPSASTGTGPGSSPSASTGTGPGTPGSGTASSSPGSSTPSGATGSPGS<br>SPSASTGTGPGASPGTSSTGSPGTPGSGTASSSPGSSTPSGATGSPGTPGSGTASSSPGASP<br>GTSSTGSPGASPGTSSTGSP |
| AG144_B<br>(SEQ ID NO:<br>61) | GTPGSGTASSSPGSSTPSGATGSPGASPGTSSTGSPGTPGSGTASSSPGSSTPSGATGSPGS<br>SPSASTGTGPGSSPSASTGTGPGSSTPSGATGSPGSSTPSGATGSPGASPGTSSTGSPGASP<br>GTSSTGSPGASPGTSSTGSP |
| AG144_C<br>(SEQ ID NO:<br>62) | GTPGSGTASSSPGASPGTSSTGSPGASPGTSSTGSPGASPGTSSTGSPGSSPSASTGTGPGT<br>PGSGTASSSPGASPGTSSTGSPGASPGTSSTGSPGASPGTSSTGSPGSSTPSGATGSPGSST<br>PSGATGSPGASPGTSSTGSP |
| AG144_F<br>(SEQ ID NO:<br>63) | GSSPSASTGTGPGSSPSASTGTGPGASPGTSSTGSPGASPGTSSTGSPGSSTPSGATGSPGS<br>SPSASTGTGPGASPGTSSTGSPGSSPSASTGTGPGTPGSGTASSSPGSSTPSGATGSPGSST<br>PSGATGSPGASPGTSSTGSP |
| AE288<br>SEQ ID NO: 8 | GTSESATPESGPGSEPATSGSETPGTSESATPESGPGSEPATSGSETPGTSESATPESG<br>PGTSTEPSEGSAPGSPAGSPTSTEEGTSESATPESGPGSEPATSGSETPGTSESATPES<br>GPGSPAGSPTSTEEGSPAGSPTSTEEGTSTEPSEGSAPGTSESATPESGPGTSESATPE<br>SGPGTSESATPESGPGSEPATSGSETPGSEPATSGSETPGSPAGSPTSTEEGTSTEPSE<br>GSAPGTSTEPSEGSAPGSEPATSGSETPGTSESATPESGPGTSTEPSEGSAP |
| AE288_2<br>(SEQ ID NO:<br>54) | GSPAGSPTSTEEGTSESATPESGPGSEPATSGSETPGTSESATPESGPGTSTEPSEGSAPGT<br>STEPSEGSAPGTSTEPSEGSAPGTSTEPSEGSAPGTSTEPSEGSAPGTSTEPSEGSAPGSPA<br>GSPTSTEEGTSTEPSEGSAPGTSESATPESGPGSEPATSGSETPGTSESATPESGPGSEPAT<br>SGSETPGTSESATPESGPGTSTEPSEGSAPGTSESATPESGPGSPAGSPTSTEEGSPAGSPT<br>STEEGSPAGSPTSTEEGTSESATPESGPGTSTEPSEGSAP |
| AG288<br>SEQ ID NO: 19 | PGASPGTSSTGSPGASPGTSSTGSPGTPGSGTASSSPGSSTPSGATGSPGTPGSGTASS<br>SPGSSTPSGATGSPGTPGSGTASSSPGSSTPSGATGSPGSSTPSGATGSPGSSPSASTG<br>TGPGSSPSASTGTGPGASPGTSSTGSPGTPGSGTASSSPGSSTPSGATGSPGSSPSAST<br>GTGPGSSPSASTGTGPGASPGTSSTGSPGASPGTSSTGSPGSSTPSGATGSPGSSPSAS<br>TGTGPGASPGTSSTGSPGSSPSASTGTGPGTPGSGTASSSPGSSTPSGATGS |
| AE576<br>SEQ ID NO: 16 | GSPAGSPTSTEEGTSESATPESGPGTSTEPSEGSAPGSPAGSPTSTEEGTSTEPSEGSA<br>PGTSTEPSEGSAPGTSESATPESGPGSEPATSGSETPGSEPATSGSETPGSPAGSPTST<br>EEGTSESATPESGPGTSTEPSEGSAPGTSTEPSEGSAPGSPAGSPTSTEEGTSTEPSEG |

TABLE 2B-continued

| XTEN Sequences | |
|---|---|
| XTEN | Amino Acid Sequence |
| | SAPGTSTEPSEGSAPGTSESATPESGPGTSTEPSEGSAPGTSESATPESGPGSEPATSG<br>SETPGTSTEPSEGSAPGTSTEPSEGSAPGTSESATPESGPGTSESATPESGPGSPAGSP<br>TSTEEGTSESATPESGPGSEPATSGSETPGTSESATPESGPGTSTEPSEGSAPGTSTEP<br>SEGSAPGTSTEPSEGSAPGTSTEPSEGSAPGTSTEPSEGSAPGTSTEPSEGSAPGSPAG<br>SPTSTEEGTSTEPSEGSAPGTSESATPESGPGSEPATSGSETPGTSESATPESGPGSEP<br>ATSGSETPGTSESATPESGPGTSTEPSEGSAPGTSESATPESGPGSPAGSPTSTEEGSP<br>AGSPTSTEEGSPAGSPTSTEEGTSESATPESGPGTSTEPSEGSAP |
| AG576<br>SEQ ID NO: 18 | PGTPGSGTASSSPGSSTPSGATGSPGSSPSASTGTGPGSSPSASTGTGPGSSTPSGATG<br>SPGSSTPSGATGSPGASPGTSSTGSPGASPGTSSTGSPGASPGTSSTGSPGTPGSGTAS<br>SSPGASPGTSSTGSPGASPGTSSTGSPGASPGTSSTGSPGSSPSASTGTGPGTPGSGTA<br>SSSPGASPGTSSTGSPGASPGTSSTGSPGASPGTSSTGSPGSSTPSGATGSPGSSTPSG<br>ATGSPGASPGTSSTGSPGTPGSGTASSSPGSSTPSGATGSPGSSTPSGATGSPGSSTPS<br>GATGSPGSSPSASTGTGPGASPGTSSTGSPGASPGTSSTGSPGTPGSGTASSSPGASPG<br>TSSTGSPGASPGTSSTGSPGASPGTSSTGSPGASPGTSSTGSPGTPGSGTASSSPGSST<br>PSGATGSPGTPGSGTASSSPGSSTPSGATGSPGTPGSGTASSSPGSSTPSGATGSPGSS<br>TPSGATGSPGSSPSASTGTGPGSSPSASTGTGPGASPGTSSTGSPGTPGSGTASSSPGS<br>STPSGATGSPGSSPSASTGTGPGSSPSASTGTGPGASPGTSSTGS |
| AE864<br>SEQ ID NO: 15 | GSPAGSPTSTEEGTSESATPESGPGTSTEPSEGSAPGSPAGSPTSTEEGTSTEPSEGSA<br>PGTSTEPSEGSAPGTSESATPESGPGSEPATSGSETPGSEPATSGSETPGSPAGSPTST<br>EEGTSESATPESGPGTSTEPSEGSAPGTSTEPSEGSAPGSPAGSPTSTEEGTSTEPSEG<br>SAPGTSTEPSEGSAPGTSESATPESGPGTSTEPSEGSAPGTSESATPESGPGSEPATSG<br>SETPGTSTEPSEGSAPGTSTEPSEGSAPGTSESATPESGPGTSESATPESGPGSPAGSP<br>TSTEEGTSESATPESGPGSEPATSGSETPGTSESATPESGPGTSTEPSEGSAPGTSTEP<br>SEGSAPGTSTEPSEGSAPGTSTEPSEGSAPGTSTEPSEGSAPGTSTEPSEGSAPGSPAG<br>SPTSTEEGTSTEPSEGSAPGTSESATPESGPGSEPATSGSETPGTSESATPESGPGSEP<br>ATSGSETPGTSESATPESGPGTSTEPSEGSAPGTSESATPESGPGSPAGSPTSTEEGSP<br>AGSPTSTEEGSPAGSPTSTEEGTSESATPESGPGTSTEPSEGSAPGTSESATPESGPGS<br>EPATSGSETPGTSESATPESGPGSEPATSGSETPGTSESATPESGPGTSTEPSEGSAPG<br>SPAGSPTSTEEGTSESATPESGPGSEPATSGSETPGTSESATPESGPGSPAGSPTSTEE<br>GSPAGSPTSTEEGTSTEPSEGSAPGTSESATPESGPGTSESATPESGPGTSESATPESG<br>PGSEPATSGSETPGSEPATSGSETPGSPAGSPTSTEEGTSTEPSEGSAPGTSTEPSEGS<br>APGSEPATSGSETPGTSESATPESGPGTSTEPSEGSAP |
| AG864<br>SEQ ID NO: 17 | GASPGTSSTGSPGSSPSASTGTGPGSSPSASTGTGPGTPGSGTASSSPGSSTPSGATGS<br>PGSSPSASTGTGPGASPGTSSTGSPGTPGSGTASSSPGSSTPSGATGSPGTPGSGTASS<br>SPGASPGTSSTGSPGASPGTSSTGSPGTPGSGTASSSPGSSTPSGATGSPGASPGTSST<br>GSPGTPGSGTASSSPGSSTPSGATGSPGSSPSASTGTGPGSSPSASTGTGPGSSTPSGA<br>TGSPGSSTPSGATGSPGASPGTSSTGSPGASPGTSSTGSPGASPGTSSTGSPGTPGSGT<br>ASSSPGASPGTSSTGSPGASPGTSSTGSPGASPGTSSTGSPGSSPSASTGTGPGTPGSG<br>TASSSPGASPGTSSTGSPGASPGTSSTGSPGASPGTSSTGSPGSSTPSGATGSPGSSTP<br>SGATGSPGASPGTSSTGSPGTPGSGTASSSPGSSTPSGATGSPGSSTPSGATGSPGSST<br>PSGATGSPGSSPSASTGTGPGASPGTSSTGSPGASPGTSSTGSPGTPGSGTASSSPGAS<br>PGTSSTGSPGASPGTSSTGSPGASPGTSSTGSPGASPGTSSTGSPGTPGSGTASSSPGS<br>STPSGATGSPGTPGSGTASSSPGSSTPSGATGSPGTPGSGTASSSPGSSTPSGATGSPG<br>SSTPSGATGSPGSSPSASTGTGPGSSPSASTGTGPGASPGTSSTGSPGTPGSGTASSSP<br>GSSTPSGATGSPGSSPSASTGTGPGSSPSASTGTGPGASPGTSSTGSPGASPGTSSTGS<br>PGSSTPSGATGSPGSSPSASTGTGPGASPGTSSTGSPGSSPSASTGTGPGTPGSGTASS<br>SPGSSTPSGATGSPGSSTPSGATGSPGASPGTSSTGSP |

In those embodiments wherein the XTEN component(s) have less than 100% of its amino acids consisting of 4, 5, or 6 types of amino acid selected from glycine (G), alanine (A), serine (S), threonine (T), glutamate (E) and proline (P), or less than 100% of the sequence consisting of the sequence motifs from Table 3 or the XTEN sequences of Tables 4, and 13-17, the other amino acid residues of the XTEN are selected from any of the other 14 natural L-amino acids, but are preferentially selected from hydrophilic amino acids such that the XTEN sequence contains at least about 90%, 91%, 92%, 93%, 94%, 95%, 96%, 97%, 98%, or at least about 99% hydrophilic amino acids. The XTEN amino acids that are not glycine (G), alanine (A), serine (S), threonine (T), glutamate (E) and proline (P) are either interspersed throughout the XTEN sequence, are located within or between the sequence motifs, or are concentrated in one or more short stretches of the XTEN sequence, e.g., to create a linker between the XTEN and the FVIII or VWF components. In such cases where the XTEN component comprises amino acids other than glycine (G), alanine (A), serine (S), threonine (T), glutamate (E) and proline (P), it is preferred that less than about 2% or less than about 1% of the amino acids be hydrophobic residues such that the resulting sequences generally lack secondary structure, e.g., not having more than 2% alpha helices or 2% beta-sheets, as determined by the methods disclosed herein. Hydrophobic residues that are less favored in construction of XTEN include tryptophan, phenylalanine, tyrosine, leucine, isoleucine, valine, and methionine. Additionally, one can design the XTEN sequences to contain less than 5% or less than 4% or less than 3% or less than 2% or less than 1% or none of the following amino acids: cysteine (to avoid disulfide formation and oxidation), methionine (to avoid oxidation), asparagine and glutamine (to avoid desamidation). Thus, in some embodiments, the XTEN component comprising other amino acids in addition to glycine (G), alanine (A), serine (S), threonine (T), glutamate (E) and proline (P) have a sequence with less than 5% of the residues contributing to alpha-helices and beta-sheets as measured by the Chou-Fasman algorithm and have at least 90%, or at least about 95% or more random coil formation as measured by the GOR algorithm.

In further embodiments, the XTEN sequence used in the invention affects the physical or chemical property, e.g., pharmacokinetics, of the chimeric protein of the present invention. The XTEN sequence used in the present invention can exhibit one or more of the following advantageous properties: conformational flexibility, enhanced aqueous solubility, high degree of protease resistance, low immunogenicity, low binding to mammalian receptors, or increased hydrodynamic (or Stokes) radii. In a specific embodiment, the XTEN sequence linked to a FVIII protein in this invention increases pharmacokinetic properties such as longer terminal half-life or increased area under the curve (AUC), so that the chimeric protein described herein stays in vivo for an increased period of time compared to wild type FVIII. In further embodiments, the XTEN sequence used in this invention increases pharmacokinetic properties such as longer terminal half-life or increased area under the curve (AUC), so that FVIII protein stays in vivo for an increased period of time compared to wild type FVIII.

One embodiment of the present invention is a FVIII/VWF fusion protein comprising a FVIII portion fused to an Fc region and a VWF portion fused to an Fc region, wherein an XTEN sequence (e.g., AE288) is inserted within the FVIII portion, and wherein an XTEN sequence having less than 288 amino acids (e.g., AE144) is inserted between the VWF portion and the Fc portion. As described in the examples, insertion of an XTEN having less than 288 amino acids between the VWF portion and the Fc portion has a greater effect on the pharmacokinetics of the chimeric protein than the insertion of an XTEN having 288 amino acids between the VWF portion and the Fc portion. For example, insertion of an XTEN sequence having less than 288 amino acids between the VWF portion and the Fc portion in FVIII/VWF fusion protein can increase the terminal half-life of the chimeric protein compared to an XTEN having 288 amino acids. In some embodiments, the terminal half-life is increased by at least about 5%, at least about 10%, at least about 15%, at least about 20%, at least about 25%, or at least about 30%, relative to the insertion of an XTEN sequence having 288 amino acids. In one particular embodiment, the terminal half-life is increased by at least about 35% relative to the insertion of an XTEN having 288 amino acids. Insertion of an XTEN sequence having less than 288 amino acids can also increase the AUC value of the chimeric protein. In some embodiments, AUC is increased by at least about 50%, at least about 100%, or at least about 200% relative to the insertion of an XTEN having 288 amino acids. In one particular embodiment, AUC is increased by about two-fold. Insertion of an XTEN sequence having less than 288 amino acids can also reduce the clearance of the chimeric protein. For example, clearance can be decreased by at least about 5%, at least about 10%, at least about 15%, at least about 20%, at least about 25%, or at least about 30%, relative to the insertion of an XTEN sequence having 288 amino acids. Insertion of an XTEN sequence having less than 288 amino acids can increase mean residence time (MRT) and/or decrease the apparent volume of distribution at steady state (Vss) relative to the insertion of an XTEN having 288 amino acids.

A variety of methods and assays can be employed to determine the physical/chemical properties of proteins comprising the XTEN sequence. Such methods include, but are not limited to analytical centrifugation, EPR, HPLC-ion exchange, HPLC-size exclusion, HPLC-reverse phase, light scattering, capillary electrophoresis, circular dichroism, differential scanning calorimetry, fluorescence, HPLC-ion exchange, HPLC-size exclusion, IR, NMR, Raman spectroscopy, refractometry, and UV/Visible spectroscopy. Additional methods are disclosed in Amau et al., *Prot Expr and Purif* 48, 1-13 (2006).

Additional examples of XTEN sequences that can be used according to the present invention and are disclosed in US Patent Publication Nos. 2010/0239554 A1, 2010/0323956 A1, 2011/0046060 A1, 2011/0046061 A1, 2011/0077199 A1, or 2011/0172146 A1, or International Patent Publication Nos. WO 2010091122 A1, WO 2010144502 A2, WO 2010144508 A1, WO 2011028228 A1, WO 2011028229 A1, WO 2011028344 A2, or WO 20130122617 A1.

II.C. Factor VIII (FVIII) Protein

"A FVIII protein" as used herein means a functional FVIII polypeptide in its normal role in coagulation, unless otherwise specified. The term a FVIII protein includes a functional fragment, variant, analog, or derivative thereof that retains the function of full-length wild-type Factor VIII in the coagulation pathway. "A FVIII protein" is used interchangeably with FVIII polypeptide (or protein) or FVIII. Examples of the FVIII functions include, but not limited to, an ability to activate coagulation, an ability to act as a cofactor for factor IX, or an ability to form a tenase complex with factor IX in the presence of $Ca^{2+}$ and phospholipids, which then converts Factor X to the activated form Xa. The FVIII protein can be the human, porcine, canine, rat, or murine FVIII protein. In addition, comparisons between FVIII from humans and other species have identified conserved residues that are likely to be required for function (Cameron et al., *Thromb. Haemost.* 79:317-22 (1998); U.S. Pat. No. 6,251,632).

A number of tests are available to assess the function of the coagulation system: activated partial thromboplastin time (aPTT) test, chromogenic assay, ROTEM assay, prothrombin time (PT) test (also used to determine INR), fibrinogen testing (often by the Clauss method), platelet count, platelet function testing (often by PFA-100), TCT, bleeding time, mixing test (whether an abnormality corrects if the patient's plasma is mixed with normal plasma), coagulation factor assays, antiphospholipid antibodies, D-dimer, genetic tests (e.g., factor V Leiden, prothrombin mutation G20210A), dilute Russell's viper venom time (dRVVT), miscellaneous platelet function tests, thromboelastography (TEG or Sonoclot), thromboelastometry (TEM®, e.g., ROTEM©), or euglobulin lysis time (ELT).

The aPTT test is a performance indicator measuring the efficacy of both the "intrinsic" (also referred to the contact activation pathway) and the common coagulation pathways. This test is commonly used to measure clotting activity of commercially available recombinant clotting factors, e.g., FVIII or FIX. It is used in conjunction with prothrombin time (PT), which measures the extrinsic pathway.

ROTEM analysis provides information on the whole kinetics of haemostasis: clotting time, clot formation, clot stability and lysis. The different parameters in thromboelastometry are dependent on the activity of the plasmatic coagulation system, platelet function, fibrinolysis, or many factors which influence these interactions. This assay can provide a complete view of secondary haemostasis.

The FVIII polypeptide and polynucleotide sequences are known, as are many functional fragments, mutants and modified versions. Examples of human FVIII sequences (full-length) are shown below.

TABLE 3

Amino Acid Sequence of Full-length Factor VIII (Full-length FVIII (FVIII signal peptide underlined; FVIII heavy chain is double underlined; B domain is italicized; and FVIII light chain is in plain text)

Signal Peptide: (SEQ ID NO: 64)
MQIELSTCFFLCLLRFCFS

Mature Factor VIII (SEQ ID NO: 65)*
ATRRYYLGAVELSWDYMQSDLGELPVDARFPPRVPKSFPFNTSVVYKKTLFVEFTDHLFNIAKPRPPWMGLL
GPTIQAEVYDTVVITLKNMASHPVSLHAVGVSYWKASEGAEYDDQTSQREKEDDKVFPGGSHTYVWQVLKEN
GPMASDPLCLTYSYLSHVDLVKDLNSGLIGALLVCREGSLAKEKTQTLHKFILLFAVFDEGKSWHSETKNSL
MQDRDAASARAWPKMHTVNGYVNRSLPGLIGCHRKSVYWHVIGMGTTPEVHSIFLEGHTFLVRNHRQASLEI
SPITFLTAQTLLMDLGQFLLFCHISSHQHDGMEAYVKVDSCPEEPQLRMKNNEEAEDYDDDLTDSEMDVVRF
DDDNSPSFIQIRSVAKKHPKTWVHYIAAEEEDWDYAPLVLAPDDRSYKSQYLNNGPQRIGRKYKKVRFMAYT
DETFKTREAIQHESGILGPLLYGEVGDTLLIIFKNQASRPYNTYPHGTTDVRPLYSRRLPKGVKHLKDFPIL
PGEIFKYKWTVTVEDGPTKSDPRCLTRYYSSFVNMERDLASGLIGPLLICYKESVDQRGNQIMSDKRNVILF
SVFDENRSWYLTENIQRFLPNPAGVQLEDPEFQASNIMHSINGYVFDSLQLSVCLHEVAYWYILSIGAQTDF
LSVFFSGYTFKHKMVYEDTLTLFPFSGETVFMSMENPGLWILGCHNSDFRNRGMTALLKVSSCDKNTGDYYE
DSYEDISAYLLSKNNAIEPR*SFSQNSRHPSTRQKQFNATTIPENDIEKTDPWFAHRTPMPKIQNVSSSDLLM*
*LLRQSPTPHGLSLSDLQEAKYETFSDDPSPGAIDSNNSLSEMTHFRPQLHHSGDMVFTPESGLQLRLNEKLG*
*TTAATELKKLDFKVSSTSNNLISTIPSDNLAAGTDNTSSLGPPSMPVHYDSQLDTTLFGKKSSPLTESGGPL*
*SLSEENNDSKLLESGLMNSQESSWGKNVSSTESGRLFKGKRAHGPALLTKDNALFKVSISLLKTNKTSNNSA*
*TNRKTHIDGPSLLIENSPSVWQNILESDTEFKKVTPLIHDRMLMDKNATALRLNHMSNKTTSSKNMEMVQQK*
*KEGPIPPDAQNPDMSFFKMLFLPESARWIQRTHGKNSLNSGQGPSPKQLVSLGPEKSVEGQNFLSEKNKVVV*
*GKGEFTKDVGLKEMVFPSSRNLFLTNLDNLHENNTHNQEKKIQEEIEKKETLIQENVVLPQIHTVTGTKNFM*
*KNLFLLSTRQNVEGSYDGAYAPVLQDFRSLNDSTNRTKKHTAHFSKKGEEENLEGLGNQTKQIVEKYACTTR*
*ISPNTSQQNFVTQRSKRALKQFRLPLEETELEKRIIVDDTSTQWSKNMKHLTPSTLTQIDYNEKEKGAITQS*
*PLSDCLTRSHSIPQANRSPLPIAKVSSFPSIRPIYLTRVLFQDNSSHLPAASYRKKDSGVQESSHFLQGAKK*
*NNLSLAILTLEMTGDQREVGSLGTSATNSVTYKKVENTVLPKPDLPKTSGKVELLPKVHIYQKDLFPTETSN*
*GSPGHLDLVEGSLLQGTEGAIKWNEANRPGKVPFLRVATESSAKTPSKLLDPLAWDNHYGTQIPKEEWKSQE*
*KSPEKTAFKKKDTILSLNACESNHAIAAINEGQNKPEIEVTWAKQGRTERLCSQNPPVLKRHQR*EITRTTLQ
SDQEEIDYDDTISVEMKKEDFDIYDEDENQSPRSFQKKTRHYFIAAVERLWDYGMSSSPHVLRNRAQSGSVP
QFKKVVFQEFTDGSFTQPLYRGELNEHLGLLGPYIRAEVEDNIMVTFRNQASRPYSFYSSLISYEEDQRQGA
EPRKNFVKPNETKTYFWKVQHHMAPTKDEFDCKAWAYFSDVDLEKDVHSGLIGPLLVCHTNTLNPAHGRQVT
VQEFALFFTIFDETKSWYFTENMERNCRAPCNIQMEDPTFKENYRFHAINGYIMDTLPGLVMAQDQRIRWYL
LSMGSNENIHSIHFSGHVFTVRKKEEYKMALYNLYPGVFETVEMLPSKAGIWRVECLIGEHLHAGMSTLFLV
YSNKCQTPLGMASGHIRDFQITASGQYGQWAPKLARLHYSGSINAWSTKEPFSWIKVDLLAPMIIHGIKTQG
ARQKFSSLYISQFIIMYSLDGKKWQTYRGNSTGTLMVFFGNVDSSGIKHNIFNPPIIARYIRLHPTHYSIRS
TLRMELMGCDLNSCSMPLGMESKAISDAQITASSYFTNMFATWSPSKARLHLQGRSNAWRPQVNNPKEWLQV
DFQKTMKVTGVTTQGVKSLLTSMYVKEFLISSSQDGHQWTLFFQNGKVKVFQGNQDSFTPVVNSLDPPLLTR
YLRIHPQSWVHQIALRMEVLGCEAQDLY

TABLE 4

Nucleotide Sequence Encoding Full-Length FVIII (SEQ ID NO: 66)*

| | | | | | | |
|---|---|---|---|---|---|---|
| 661 | | | | ATG | CAAATAGAGC | TCTCCACCTG |
| 721 | CTTCTTTCTG | TGCCTTTTGC | GATTCTGCTT | TAGTGCCACC | AGAAGATACT | ACCTGGGTGC |
| 781 | AGTGGAACTG | TCATGGGACT | ATATGCAAAG | TGATCTCGGT | GAGCTGCCTG | TGGACGCAAG |
| 841 | ATTTCCTCCT | AGAGTGCCAA | AATCTTTTCC | ATTCAACACC | TCAGTCGTGT | ACAAAAAGAC |
| 901 | TCTGTTTGTA | GAATTCACGG | ATCACCTTTT | CAACATCGCT | AAGCCAAGGC | CACCCTGGAT |
| 961 | GGGTCTGCTA | GGTCCTACCA | TCCAGGCTGA | GGTTTATGAT | ACAGTGGTCA | TTACACTTAA |
| 1021 | GAACATGGCT | TCCCATCCTG | TCAGTCTTCA | TGCTGTTGGT | GTATCCTACT | GGAAAGCTTC |
| 1081 | TGAGGGAGCT | GAATATGATG | ATCAGACCAG | TCAAAGGGAG | AAAGAAGATG | ATAAAGTCTT |
| 1141 | CCCTGGTGGA | AGCCATACAT | ATGTCTGGCA | GGTCCTGAAA | GAGAATGGTC | CAATGGCCTC |
| 1201 | TGACCCACTG | TGCCTTACCT | ACTCATATCT | TTCTCATGTG | GACCTGGTAA | AAGACTTGAA |
| 1261 | TTCAGGCCTC | ATTGGAGCCC | TACTAGTATG | TAGAGAAGGG | AGTCTGGCCA | AGGAAAAGAC |
| 1321 | ACAGACCTTG | CACAAATTTA | TACTACTTTT | TGCTGTATTT | GATGAAGGGA | AAAGTTGGCA |
| 1381 | CTCAGAAACA | AAGAACTCCT | TGATGCAGGA | TAGGGATGCT | GCATCTGCTC | GGGCCTGGCC |
| 1441 | TAAAATGCAC | ACAGTCAATG | GTTATGTAAA | CAGGTCTCTG | CCAGGTCTGA | TTGGATGCCA |
| 1501 | CAGGAAATCA | GTCTATTGGC | ATGTGATTGG | AATGGGCACC | ACTCCTGAAG | TGCACTCAAT |

TABLE 4-continued

| Nucleotide Sequence Encoding Full-Length FVIII (SEQ ID NO: 66)* | | | | | | |
|---|---|---|---|---|---|---|
| 1561 | ATTCCTCGAA | GGTCACACAT | TTCTTGTGAG | GAACCATCGC | CAGGCGTCCT | TGGAAATCTC |
| 1621 | GCCAATAACT | TTCCTTACTG | CTCAAACACT | CTTGATGGAC | CTTGGACAGT | TTCTACTGTT |
| 1681 | TTGTCATATC | TCTTCCCACC | AACATGATGG | CATGGAAGCT | TATGTCAAAG | TAGACAGCTG |
| 1741 | TCCAGAGGAA | CCCCAACTAC | GAATGAAAAA | TAATGAAGAA | GCGGAAGACT | ATGATGATGA |
| 1801 | TCTTACTGAT | TCTGAAATGG | ATGTGGTCAG | GTTTGATGAT | GACAACTCTC | CTTCCTTTAT |
| 1861 | CCAAATTCGC | TCAGTTGCCA | AGAAGCATCC | TAAAACTTGG | GTACATTACA | TTGCTGCTGA |
| 1921 | AGAGGAGGAC | TGGGACTATG | CTCCCTTAGT | CCTCGCCCCC | GATGACAGAA | GTTATAAAAG |
| 1981 | TCAATATTTG | AACAATGGCC | CTCAGCGGAT | TGGTAGGAAG | TACAAAAAAG | TCCGATTTAT |
| 2041 | GGCATACACA | GATGAAACCT | TTAAGACTCG | TGAAGCTATT | CAGCATGAAT | CAGGAATCTT |
| 2101 | GGGACCTTTA | CTTTATGGGG | AAGTTGGAGA | CACACTGTTG | ATTATATTTA | AGAATCAAGC |
| 2161 | AAGCAGACCA | TATAACATCT | ACCCTCACGG | AATCACTGAT | GTCCGTCCTT | TGTATTCAAG |
| 2221 | GAGATTACCA | AAAGGTGTAA | AACATTTGAA | GGATTTTCCA | ATTCTGCCAG | GAGAAATATT |
| 2281 | CAAATATAAA | TGGACAGTGA | CTGTAGAAGA | TGGGCCAACT | AAATCAGATC | CTCGGTGCCT |
| 2341 | GACCCGCTAT | TACTCTAGTT | TCGTTAATAT | GGAGAGAGAT | CTAGCTTCAG | GACTCATTGG |
| 2401 | CCCTCTCCTC | ATCTGCTACA | AAGAATCTGT | AGATCAAAGA | GGAAACCAGA | TAATGTCAGA |
| 2461 | CAAGAGGAAT | GTCATCCTGT | TTTCTGTATT | TGATGAGAAC | CGAAGCTGGT | ACCTCACAGA |
| 2521 | GAATATACAA | CGCTTTCTCC | CCAATCCAGC | TGGAGTGCAG | CTTGAGGATC | CAGAGTTCCA |
| 2581 | AGCCTCCAAC | ATCATGCACA | GCATCAATGG | CTATGTTTTT | GATAGTTTGC | AGTTGTCAGT |
| 2641 | TTGTTTGCAT | GAGGTGGCAT | ACTGGTACAT | TCTAAGCATT | GGAGCACAGA | CTGACTTCCT |
| 2701 | TTCTGTCTTC | TTCTCTGGAT | ATACCTTCAA | ACACAAAATG | GTCTATGAAG | ACACACTCAC |
| 2761 | CCTATTCCCA | TTCTCAGGAG | AAACTGTCTT | CATGTCGATG | GAAAACCCAG | GTCTATGGAT |
| 2821 | TCTGGGGTGC | CACAACTCAG | ACTTTCGGAA | CAGAGGCATG | ACCGCCTTAC | TGAAGGTTTC |
| 2881 | TAGTTGTGAC | AAGAACACTG | GTGATTATTA | CGAGGACAGT | TATGAAGATA | TTTCAGCATA |
| 2941 | CTTGCTGAGT | AAAAACAATG | CCATTGAACC | AAGAAGCTTC | TCCCAGAATT | CAAGACACCC |
| 3001 | TAGCACTAGG | CAAAAGCAAT | TTAATGCCAC | CACAATTCCA | GAAAATGACA | TAGAGAAGAC |
| 3061 | TGACCCTTGG | TTTGCACACA | GAACACCTAT | GCCTAAAATA | CAAAATGTCT | CCTCTAGTGA |
| 3121 | TTTGTTGATG | CTCTTGCGAC | AGAGTCCTAC | TCCACATGGG | CTATCCTTAT | CTGATCTCCA |
| 3181 | AGAAGCCAAA | TATGAGACTT | TTTCTGATGA | TCCATCACCT | GGAGCAATAG | ACAGTAATAA |
| 3241 | CAGCCTGTCT | GAAATGACAC | ACTTCAGGCC | ACAGCTCCAT | CACAGTGGGG | ACATGGTATT |
| 3301 | TACCCCTGAG | TCAGGCCTCC | AATTAAGATT | AAATGAGAAA | CTGGGGACAA | CTGCAGCAAC |
| 3361 | AGAGTTGAAG | AAACTTGATT | TCAAAGTTTC | TAGTACATCA | AATAATCTGA | TTTCAACAAT |
| 3421 | TCCATCAGAC | AATTTGGCAG | CAGGTACTGA | TAATACAAGT | TCCTTAGGAC | CCCCAAGTAT |
| 3481 | GCCAGTTCAT | TATGATAGTC | AATTAGATAC | CACTCTATTT | GGCAAAAAGT | CATCTCCCCT |
| 3541 | TACTGAGTCT | GGTGGACCTC | TGAGCTTGAG | TGAAGAAAAT | AATGATTCAA | AGTTGTTAGA |
| 3601 | ATCAGGTTTA | ATGAATAGCC | AAGAAAGTTC | ATGGGGAAAA | AATGTATCGT | CAACAGAGAG |
| 3661 | TGGTAGGTTA | TTTAAAGGGA | AAAGAGCTCA | TGGACCTGCT | TTGTTGACTA | AAGATAATGC |
| 3721 | CTTATTCAAA | GTTAGCATCT | CTTTGTTAAA | GACAAACAAA | ACTTCCAATA | ATTCAGCAAC |
| 3781 | TAATAGAAAG | ACTCACATTG | ATGGCCCATC | ATTATTAATT | GAGAATAGTC | CATCAGTCTG |
| 3841 | GCAAAATATA | TTAGAAAGTG | ACACTGAGTT | TAAAAAAGTG | ACACCTTTGA | TTCATGACAG |

TABLE 4-continued

| Nucleotide Sequence Encoding Full-Length FVIII (SEQ ID NO: 66)* | |
|---|---|
| 3901 | AATGCTTATG GACAAAAATG CTACAGCTTT GAGGCTAAAT CATATGTCAA ATAAAACTAC |
| 3961 | TTCATCAAAA AACATGGAAA TGGTCCAACA GAAAAAAGAG GGCCCCATTC CACCAGATGC |
| 4021 | ACAAAATCCA GATATGTCGT TCTTTAAGAT GCTATTCTTG CCAGAATCAG CAAGGTGGAT |
| 4081 | ACAAAGGACT CATGGAAAGA ACTCTCTGAA CTCTGGGCAA GGCCCCAGTC CAAAGCAATT |
| 4141 | AGTATCCTTA GGACCAGAAA AATCTGTGGA AGGTCAGAAT TTCTTGTCTG AGAAAAACAA |
| 4201 | AGTGGTAGTA GGAAAGGGTG AATTTACAAA GGACGTAGGA CTCAAAGAGA TGGTTTTTCC |
| 4261 | AAGCAGCAGA AACCTATTTC TTACTAACTT GGATAATTTA CATGAAAATA ATACACACAA |
| 4321 | TCAAGAAAAA AAAATTCAGG AAGAAATAGA AAAGAAGGAA ACATTAATCC AAGAGAATGT |
| 4381 | AGTTTTGCCT CAGATACATA CAGTGACTGG CACTAAGAAT TTCATGAAGA ACCTTTTCTT |
| 4441 | ACTGAGCACT AGGCAAAATG TAGAAGGTTC ATATGACGGG GCATATGCTC CAGTACTTCA |
| 4501 | AGATTTTAGG TCATTAAATG ATTCAACAAA TAGAACAAAG AAACACACAG CTCATTTCTC |
| 4561 | AAAAAAAGGG GAGGAAGAAA ACTTGGAAGG CTTGGGAAAT CAAACCAAGC AAATTGTAGA |
| 4621 | GAAATATGCA TGCACCACAA GGATATCTCC TAATACAAGC CAGCAGAATT TTGTCACGCA |
| 4681 | ACGTAGTAAG AGAGCTTTGA AACAATTCAG ACTCCCACTA GAAGAAACAG AACTTGAAAA |
| 4741 | AAGGATAATT GTGGATGACA CCTCAACCCA GTGGTCCAAA AACATGAAAC ATTTGACCCC |
| 4801 | GAGCACCCTC ACACAGATAG ACTACAATGA GAAGGAGAAA GGGGCCATTA CTCAGTCTCC |
| 4861 | CTTATCAGAT TGCCTTACGA GGAGTCATAG CATCCCTCAA GCAAATAGAT CTCCATTACC |
| 4921 | CATTGCAAAG GTATCATCAT TTCCATCTAT TAGACCTATA TATCTGACCA GGGTCCTATT |
| 4981 | CCAAGACAAC TCTTCTCATC TTCCAGCAGC ATCTTATAGA AAGAAAGATT CTGGGGTCCA |
| 5041 | AGAAAGCAGT CATTTCTTAC AAGGAGCCAA AAAAAATAAC CTTTCTTTAG CCATTCTAAC |
| 5101 | CTTGGAGATG ACTGGTGATC AAAGAGAGGT TGGCTCCCTG GGGACAAGTG CCACAAATTC |
| 5161 | AGTCACATAC AAGAAAGTTG AGAACACTGT TCTCCCGAAA CCAGACTTGC CCAAAACATC |
| 5221 | TGGCAAAGTT GAATTGCTTC CAAAAGTTCA CATTTATCAG AAGGACCTAT TCCCTACGGA |
| 5281 | AACTAGCAAT GGGTCTCCTG GCCATCTGGA TCTCGTGGAA GGGAGCCTTC TTCAGGGAAC |
| 5341 | AGAGGGAGCG ATTAAGTGGA ATGAAGCAAA CAGACCTGGA AAAGTTCCCT TTCTGAGAGT |
| 5401 | AGCAACAGAA AGCTCTGCAA AGACTCCCTC CAAGCTATTG GATCCTCTTG CTTGGGATAA |
| 5461 | CCACTATGGT ACTCAGATAC CAAAAGAAGA GTGGAAATCC CAAGAGAAGT CACCAGAAAA |
| 5521 | AACAGCTTTT AAGAAAAAGG ATACCATTTT GTCCCTGAAC GCTTGTGAAA GCAATCATGC |
| 5581 | AATAGCAGCA ATAAATGAGG GACAAAATAA GCCCGAAATA GAAGTCACCT GGGCAAAGCA |
| 5641 | AGGTAGGACT GAAAGGCTGT GCTCTCAAAA CCCACCAGTC TTGAAACGCC ATCAACGGGA |
| 5701 | AATAACTCGT ACTACTCTTC AGTCAGATCA AGAGGAAATT GACTATGATG ATACCATATC |
| 5761 | AGTTGAAATG AAGAAGGAAG ATTTTGACAT TTATGATGAG GATGAAAATC AGAGCCCCCG |
| 5821 | CAGCTTTCAA AAGAAAACAC GACACTATTT TATTGCTGCA GTGGAGAGGC TCTGGGATTA |
| 5881 | TGGGATGAGT AGCTCCCCAC ATGTTCTAAG AAACAGGGCT CAGAGTGGCA GTGTCCCTCA |
| 5941 | GTTCAAGAAA GTTGTTTTCC AGGAATTTAC TGATGGCTCC TTTACTCAGC CCTTATACCG |
| 6001 | TGGAGAACTA AATGAACATT TGGGACTCCT GGGGCCATAT ATAAGAGCAG AAGTTGAAGA |
| 6061 | TAATATCATG GTAACTTTCA GAAATCAGGC CTCTCGTCCC TATTCCTTCT ATTCTAGCCT |
| 6121 | TATTTCTTAT GAGGAAGATC AGAGGCAAGG AGCAGAACCT AGAAAAAACT TTGTCAAGCC |
| 6181 | TAATGAAACC AAAACTTACT TTTGGAAAGT GCAACATCAT ATGGCACCCA CTAAAGATGA |

TABLE 4-continued

| Nucleotide Sequence Encoding Full-Length FVIII (SEQ ID NO: 66)* | |
|---|---|
| 6241 | GTTTGACTGC AAAGCCTGGG CTTATTTCTC TGATGTTGAC CTGGAAAAAG ATGTGCACTC |
| 6301 | AGGCCTGATT GGACCCCTTC TGGTCTGCCA CACTAACACA CTGAACCCTG CTCATGGGAG |
| 6361 | ACAAGTGACA GTACAGGAAT TTGCTCTGTT TTTCACCATC TTTGATGAGA CCAAAAGCTG |
| 6421 | GTACTTCACT GAAAATATGG AAAGAAACTG CAGGGCTCCC TGCAATATCC AGATGGAAGA |
| 6481 | TCCCACTTTT AAAGAGAATT ATCGCTTCCA TGCAATCAAT GGCTACATAA TGGATACACT |
| 6541 | ACCTGGCTTA GTAATGGCTC AGGATCAAAG GATTCGATGG TATCTGCTCA GCATGGGCAG |
| 6601 | CAATGAAAAC ATCCATTCTA TTCATTTCAG TGGACATGTG TTCACTGTAC GAAAAAAAGA |
| 6661 | GGAGTATAAA ATGGCACTGT ACAATCTCTA TCCAGGTGTT TTTGAGACAG TGGAAATGTT |
| 6721 | ACCATCCAAA GCTGGAATTT GGCGGGTGGA ATGCCTTATT GGCGAGCATC TACATGCTGG |
| 6781 | GATGAGCACA CTTTTTCTGG TGTACAGCAA TAAGTGTCAG ACTCCCCTGG GAATGGCTTC |
| 6841 | TGGACACATT AGAGATTTTC AGATTACAGC TTCAGGACAA TATGGACAGT GGGCCCCAAA |
| 6901 | GCTGGCCAGA CTTCATTATT CCGGATCAAT CAATGCCTGG AGCACCAAGG AGCCCTTTTC |
| 6961 | TTGGATCAAG GTGGATCTGT TGGCACCAAT GATTATTCAC GGCATCAAGA CCCAGGGTGC |
| 7021 | CCGTCAGAAG TTCTCCAGCC TCTACATCTC TCAGTTTATC ATCATGTATA GTCTTGATGG |
| 7081 | GAAGAAGTGG CAGACTTATC GAGGAAATTC CACTGGAACC TTAATGGTCT TCTTTGGCAA |
| 7141 | TGTGGATTCA TCTGGGATAA AACACAATAT TTTTAACCCT CCAATTATTG CTCGATACAT |
| 7201 | CCGTTTGCAC CCAACTCATT ATAGCATTCG CAGCACTCTT CGCATGGAGT TGATGGGCTG |
| 7261 | TGATTTAAAT AGTTGCAGCA TGCCATTGGG AATGGAGAGT AAAGCAATAT CAGATGCACA |
| 7321 | GATTACTGCT TCATCCTACT TTACCAATAT GTTTGCCACC TGGTCTCCTT CAAAAGCTCG |
| 7381 | ACTTCACCTC CAAGGGAGGA GTAATGCCTG GAGACCTCAG GTGAATAATC CAAAAGAGTG |
| 7441 | GCTGCAAGTG GACTTCCAGA AGACAATGAA AGTCACAGGA GTAACTACTC AGGGAGTAAA |
| 7501 | ATCTCTGCTT ACCAGCATGT ATGTGAAGGA GTTCCTCATC TCCAGCAGTC AAGATGGCCA |
| 7561 | TCAGTGGACT CTCTTTTTTC AGAATGGCAA AGTAAAGGTT TTTCAGGGAA ATCAAGACTC |
| 7621 | CTTCACACCT GTGGTGAACT CTCTAGACCC ACCGTTACTG ACTCGCTACC TTCGAATTCA |
| 7681 | CCCCCAGAGT TGGGTGCACC AGATTGCCCT GAGGATGGAG GTTCTGGGCT GCGAGGCACA |
| 7741 | GGACCTCTAC |

*The underlined nucleic acids encode a signal peptide.

FVIII polypeptides include full-length FVIII, full-length FVIII minus Met at the N-terminus, mature FVIII (minus the signal sequence), mature FVIII with an additional Met at the N-terminus, and/or FVIII with a full or partial deletion of the B domain. In certain embodiments, FVIII variants include B domain deletions, whether partial or full deletions.

The sequence of native mature human FVIII is presented as SEQ ID NO: 65. A native FVIII protein has the following formula: A1-a1-A2-a2-B-a3-A3-C1-C2, where A1, A2, and A3 are the structurally-related "A domains," B is the "B domain," C1 and C2 are the structurally-related "C domains," and a1, a2 and a3 are acidic spacer regions. Referring to the primary amino acid sequence position in SEQ ID NO:65, the A1 domain of human FVIII extends from Ala1 to about Arg336, the a1 spacer region extends from about Met337 to about Val374, the A2 domain extends from about Ala375 to about Tyr719, the a2 spacer region extends from about Glu720 to about Arg740, the B domain extends from about Ser741 to about Arg 1648, the a3 spacer region extends from about Glu1649 to about Arg1689, the A3 domain extends from about Ser1690 to about Leu2025, the C1 domain extends from about Gly2026 to about Asn2072, and the C2 domain extends from about Ser2073 to Tyr2332. Other than specific proteolytic cleavage sites, designation of the locations of the boundaries between the domains and regions of FVIII can vary in different literature references. The boundaries noted herein are therefore designated as approximate by use of the term "about."

The human FVIII gene was isolated and expressed in mammalian cells (Toole, J. J., et al., *Nature* 312:342-347 (1984); Gitschier, J., et al., *Nature* 312:326-330 (1984); Wood, W. I., et al., *Nature* 312:330-337 (1984); Vehar, G. A., et al., *Nature* 312:337-342 (1984); WO 87/04187; WO 88/08035; WO 88/03558; and U.S. Pat. No. 4,757,006). The FVIII amino acid sequence was deduced from cDNA as shown in U.S. Pat. No. 4,965,199. In addition, partially or fully B-domain deleted FVIII is shown in U.S. Pat. Nos. 4,994,371 and 4,868,112. In some embodiments, the human FVIII B-domain is replaced with the human Factor V B-domain as shown in U.S. Pat. No. 5,004,803. The cDNA sequence encoding human Factor VIII and amino acid sequence are shown in SEQ ID NOs: 1 and 2, respectively, of US Application Publ. No. 2005/0100990.

The porcine FVIII sequence is published in Toole, J. J., et al., *Proc. Natl. Acad. Sci. USA* 83:5939-5942 (1986). Further, the complete porcine cDNA sequence obtained from PCR amplification of FVIII sequences from a pig spleen cDNA library has been reported in Healey, J. F., et al., *Blood* 88:4209-4214 (1996). Hybrid human/porcine FVIII having substitutions of all domains, all subunits, and specific amino acid sequences were disclosed in U.S. Pat. No. 5,364,771 by Lollar and Runge, and in WO 93/20093. More recently, the nucleotide and corresponding amino acid sequences of the A1 and A2 domains of porcine FVIII and a chimeric FVIII with porcine A1 and/or A2 domains substituted for the corresponding human domains were reported in WO 94/11503. U.S. Pat. No. 5,859,204, Lollar, J. S., also discloses the porcine cDNA and deduced amino acid sequences. U.S. Pat. No. 6,458,563 discloses a B-domain-deleted porcine FVIII.

U.S. Pat. No. 5,859,204 to Lollar, J. S. reports functional mutants of FVIII having reduced antigenicity and reduced immunoreactivity. U.S. Pat. No. 6,376,463 to Lollar, J. S. also reports mutants of FVIII having reduced immunoreactivity. US Appl. Publ. No. 2005/0100990 to Saenko et al. reports functional mutations in the A2 domain of FVIII.

In one embodiment, the FVIII (or FVIII portion of a chimeric protein) may be at least 50%, 60%, 70%, 80%, 90%, 95%, 96%, 97%, 98%, 99%, or 100% identical to a FVIII amino acid sequence of amino acids 1 to 1438 of SEQ ID NO: 67 or amino acids 1 to 2332 of SEQ ID NO: 65 (without a signal sequence) or a FVIII amino acid sequence of amino acids 1 to 19 of SEQ ID NO: 64 and 1 to 1438 of SEQ ID NO: 67 or amino acids 1 to 19 of SEQ ID NO: 64 and amino acids 1 to 2332 of SEQ ID NO: 65 (with a signal sequence), wherein the FVIII has a clotting activity, e.g., activates Factor IX as a cofactor to convert Factor X to activated Factor X. The FVIII (or FVIII portion of a chimeric protein) may be identical to a FVIII amino acid sequence of amino acids 1 to 1438 of SEQ ID NO: 67 or amino acids 1 to 2332 of SEQ ID NO: 65 (without a signal sequence). The FVIII may further comprise a signal sequence.

The "B-domain" of FVIII, as used herein, is the same as the B-domain known in the art that is defined by internal amino acid sequence identity and sites of proteolytic cleavage, e.g., residues Ser741-Arg1648 of full-length human FVIII. The other human FVIII domains are defined by the following amino acid residues: A1, residues Ala1-Arg372; A2, residues Ser373-Arg740; A3, residues Ser1690-Asn2019; C1, residues Lys2020-Asn2172; C2, residues Ser2173-Tyr2332. The A3-C1-C2 sequence includes residues Ser1690-Tyr2332. The remaining sequence, residues Glu1649-Arg1689, is usually referred to as the a3 acidic region. The locations of the boundaries for all of the domains, including the B-domains, for porcine, mouse and canine FVIII are also known in the art. In one embodiment, the B domain of FVIII is deleted ("B-domain-deleted factor VIII" or "BDD FVIII"). An example of a BDD FVIII is REFACTO® (recombinant BDD FVIII), which has the same sequence as the Factor VIII portion of the sequence in Table 5. (BDD FVIII heavy chain is double underlined; B domain is italicized; and BDD FVIII light chain is in plain text). A nucleotide sequence encoding Table 6 (SEQ ID NO: 68) is shown in Table 6.

TABLE 5

| Amino Acid Sequence of B-domain Deleted Factor VIII (BDD FVIII) |
|---|
| BDD FVIII (SEQ ID NO: 67)<br>ATRRYYLGAVELSWDYMQSDLGELPVDARFPPRVPKSFPFNTSVVYKKTLFVEFTDHLFNIAKPRPPWMGLL<br>GPTIQAEVYDTVVITLKNMASHPVSLHAVGVSYWKASEGAEYDDQTSQREKEDDKVFPGGSHTYVWQVLKEN<br>GPMASDPLCLTYSYLSHVDLVKDLNSGLIGALLVCREGSLAKEKTQTLHKFILLFAVFDEGKSWHSETKNSL<br>MQDRDAASARAWPKMHTVNGYVNRSLPGLIGCHRKSVYWHVIGMGTTPEVHSIFLEGHTFLVRNHRQASLEI<br>SPITFLTAQTLLMDLGQFLLFCHISSHQHDGMEAYVKVDSCPEEPQLRMKNNEEAEDYDDDLTDSEMDVVRF<br>DDDNSPSFIQIRSVAKKHPKTWVHYIAAEEEDWDYAPLVLAPDDRSYKSQYLNNGPQRIGRKYKKVRFMAYT<br>DETFKTREAIQHESGILGPLLYGEVGDTLLIIFKNQASRPYNIYPHGITDVRPLYSRRLPKGVKHLKDFPIL<br>PGEIFKYKWTVTVEDGPTKSDPRCLTRYYSSFVNMERDLASGLIGPLLICYKESVDQRGNQIMSDKRNVILF<br>SVFDENRSWYLTENIQRFLPNPAGVQLEDPEFQASNIMHSINGYVFDSLQLSVCLHEVAYWYILSIGAQTDF<br>LSVFFSGYTFKHKMVYEDTLTLFPFSGETVFMSMENPGLWILGCHNSDFRNRGMTALLKVSSCDKNTGDYYE<br>DSYEDISAYLLSKNNAIEPR*SFSQNPPVLKRHQR*EITRTTLQSDQEEIDYDDTISVEMKKEDFDIYDEDENQ<br>SPRSFQKKTRHYFIAAVERLWDYGMSSSPHVLRNRAQSGSVPQFKKVVFQEFTDGSFTQPLYRGELNEHLGL<br>LGPYIRAEVEDNIMVTFRNQASRPYSFYSSLISYEEDQRQGAEPRKNFVKPNETKTYFWKVQHHMAPTKDEF<br>DCKAWAYFSDVDLEKDVHSGLIGPLLVCHTNTLNPAHGRQVTVQEFALFFTIFDETKSWYFTENMERNCRAP<br>CNIQMEDPTFKENYRFHAINGYIMDTLPGLVMAQDQRIRWYLLSMGSNENIHSIHFSGHVFTVRKKEEYKMA<br>LYNLYPGVFETVEMLPSKAGIWRVECLIGEHLHAGMSTLFLVYSNKCQTPLGMASGHIRDFQITASGQYGQW<br>APKLARLHYSGSINAWSTKEPFSWIKVDLLAPMIIHGIKTQGARQKFSSLYISQFIIMYSLDGKKWQTYRGN<br>STGTLMVFFGNVDSSGIKHNIFNPPIIARYIRLHPTHYSIRSTLRMELMGCDLNSCSMPLGMESKAISDAQI<br>TASSYFTNMFATWSPSKARLHLQGRSNAWRPQVNNPKEWLQVDFQKTMKVTGVTTQGVKSLLTSMYVKEFLI<br>SSSQDGHQWTLFFQNGKVKVFQGNQDSFTPVVNSLDPPLLTRYLRIHPQSWVHQIALRMEVLGCEAQDLY |

TABLE 6

| Nucleotide Sequence Encoding BDD FVIII (SEQ ID NO: 68)* | |
|---|---|
| 661 | A TGCAAATAGA GCTCTCCACC TGCTTCTTTC |
| 721 | TGTGCCTTTT GCGATTCTGC TTTAGTGCCA CCAGAAGATA CTACCTGGGT GCAGTGGAAC |
| 781 | TGTCATGGGA CTATATGCAA AGTGATCTCG GTGAGCTGCC TGTGGACGCA AGATTTCCTC |
| 841 | CTAGAGTGCC AAAATCTTTT CCATTCAACA CCTCAGTCGT GTACAAAAAG ACTCTGTTTG |

TABLE 6-continued

| Nucleotide Sequence Encoding BDD FVIII (SEQ ID NO: 68)* | |
|---|---|
| 901 | TAGAATTCAC GGATCACCTT TTCAACATCG CTAAGCCAAG GCCACCCTGG ATGGGTCTGC |
| 961 | TAGGTCCTAC CATCCAGGCT GAGGTTTATG ATACAGTGGT CATTACACTT AAGAACATGG |
| 1021 | CTTCCCATCC TGTCAGTCTT CATGCTGTTG GTGTATCCTA CTGGAAAGCT TCTGAGGGAG |
| 1081 | CTGAATATGA TGATCAGACC AGTCAAAGGG AGAAAGAAGA TGATAAAGTC TTCCCTGGTG |
| 1141 | GAAGCCATAC ATATGTCTGG CAGGTCCTGA AAGAGAATGG TCCAATGGCC TCTGACCCAC |
| 1201 | TGTGCCTTAC CTACTCATAT CTTTCTCATG TGGACCTGGT AAAAGACTTG AATTCAGGCC |
| 1261 | TCATTGGAGC CCTACTAGTA TGTAGAGAAG GGAGTCTGGC CAAGGAAAAG ACACAGACCT |
| 1321 | TGCACAAATT TATACTACTT TTTGCTGTAT TTGATGAAGG GAAAAGTTGG CACTCAGAAA |
| 1381 | CAAAGAACTC CTTGATGCAG GATAGGGATG CTGCATCTGC TCGGGCCTGG CCTAAAATGC |
| 1441 | ACACAGTCAA TGGTTATGTA AACAGGTCTC TGCCAGGTCT GATTGGATGC CACAGGAAAT |
| 1501 | CAGTCTATTG GCATGTGATT GGAATGGGCA CCACTCCTGA AGTGCACTCA ATATTCCTCG |
| 1561 | AAGGTCACAC ATTTCTTGTG AGGAACCATC GCCAGGCGTC CTTGGAAATC TCGCCAATAA |
| 1621 | CTTTCCTTAC TGCTCAAACA CTCTTGATGG ACCTTGGACA GTTTCTACTG TTTTGTCATA |
| 1681 | TCTCTTCCCA CCAACATGAT GGCATGGAAG CTTATGTCAA AGTAGACAGC TGTCCAGAGG |
| 1741 | AACCCCAACT ACGAATGAAA AATAATGAAG AAGCGGAAGA CTATGATGAT GATCTTACTG |
| 1801 | ATTCTGAAAT GGATGTGGTC AGGTTTGATG ATGACAACTC TCCTTCCTTT ATCCAAATTC |
| 1861 | GCTCAGTTGC CAAGAAGCAT CCTAAAACTT GGGTACATTA CATTGCTGCT GAAGAGGAGG |
| 1921 | ACTGGGACTA TGCTCCCTTA GTCCTCGCCC CCGATGACAG AAGTTATAAA AGTCAATATT |
| 1981 | TGAACAATGG CCCTCAGCGG ATTGGTAGGA AGTACAAAAA AGTCCGATTT ATGGCATACA |
| 2041 | CAGATGAAAC CTTTAAGACT CGTGAAGCTA TTCAGCATGA ATCAGGAATC TTGGGACCTT |
| 2101 | TACTTTATGG GGAAGTTGGA GACACACTGT TGATTATATT TAAGAATCAA GCAAGCAGAC |
| 2161 | CATATAACAT CTACCCTCAC GGAATCACTG ATGTCCGTCC TTTGTATTCA AGGAGATTAC |
| 2221 | CAAAAGGTGT AAAACATTTG AAGGATTTTC CAATTCTGCC AGGAGAAATA TTCAAATATA |
| 2281 | AATGGACAGT GACTGTAGAA GATGGGCCAA CTAAATCAGA TCCTCGGTGC CTGACCCGCT |
| 2341 | ATTACTCTAG TTTCGTTAAT ATGGAGAGAG ATCTAGCTTC AGGACTCATT GGCCCTCTCC |
| 2401 | TCATCTGCTA CAAAGAATCT GTAGATCAAA GAGGAAACCA GATAATGTCA GACAAGAGGA |
| 2461 | ATGTCATCCT GTTTTCTGTA TTTGATGAGA ACCGAAGCTG GTACCTCACA GAGAATATAC |
| 2521 | AACGCTTTCT CCCCAATCCA GCTGGAGTGC AGCTTGAGGA TCCAGAGTTC CAAGCCTCCA |
| 2581 | ACATCATGCA CAGCATCAAT GGCTATGTTT TTGATAGTTT GCAGTTGTCA GTTTGTTTGC |
| 2641 | ATGAGGTGGC ATACTGGTAC ATTCTAAGCA TTGGAGCACA GACTGACTTC CTTTCTGTCT |
| 2701 | TCTTCTCTGG ATATACCTTC AAACACAAAA TGGTCTATGA AGACACACTC ACCCTATTCC |
| 2761 | CATTCTCAGG AGAAACTGTC TTCATGTCGA TGGAAAACCC AGGTCTATGG ATTCTGGGGT |
| 2821 | GCCACAACTC AGACTTTCGG AACAGAGGCA TGACCGCCTT ACTGAAGGTT TCTAGTTGTG |
| 2881 | ACAAGAACAC TGGTGATTAT TACGAGGACA GTTATGAAGA TATTTCAGCA TACTTGCTGA |
| 2941 | GTAAAAACAA TGCCATTGAA CCAAGAAGCT TCTCTCAAAA CCCACCAGTC TTGAAACGCC |
| 3001 | ATCAACGGGA AATAACTCGT ACTACTCTTC AGTCAGATCA AGAGGAAATT GACTATGATG |
| 3061 | ATACCATATC AGTTGAAATG AAGAAGGAAG ATTTTGACAT TTATGATGAG GATGAAAATC |
| 3121 | AGAGCCCCCG CAGCTTTCAA AAGAAAACAC GACACTATTT TATTGCTGCA GTGGAGAGGC |
| 3181 | TCTGGGATTA TGGGATGAGT AGCTCCCCAC ATGTTCTAAG AAACAGGGCT CAGAGTGGCA |

TABLE 6-continued

| Nucleotide Sequence Encoding BDD FVIII (SEQ ID NO: 68)* | |
|---|---|
| 3241 | GTGTCCCTCA GTTCAAGAAA GTTGTTTTCC AGGAATTTAC TGATGGCTCC TTTACTCAGC |
| 3301 | CCTTATACCG TGGAGAACTA AATGAACATT TGGGACTCCT GGGGCCATAT ATAAGAGCAG |
| 3361 | AAGTTGAAGA TAATATCATG GTAACTTTCA GAAATCAGGC CTCTCGTCCC TATTCCTTCT |
| 3421 | ATTCTAGCCT TATTTCTTAT GAGGAAGATC AGAGGCAAGG AGCAGAACCT AGAAAAAACT |
| 3481 | TTGTCAAGCC TAATGAAACC AAAACTTACT TTTGGAAAGT GCAACATCAT ATGGCACCCA |
| 3541 | CTAAAGATGA GTTTGACTGC AAAGCCTGGG CTTATTTCTC TGATGTTGAC CTGGAAAAAG |
| 3601 | ATGTGCACTC AGGCCTGATT GGACCCCTTC TGGTCTGCCA CACTAACACA CTGAACCCTG |
| 3661 | CTCATGGGAG ACAAGTGACA GTACAGGAAT TTGCTCTGTT TTTCACCATC TTTGATGAGA |
| 3721 | CCAAAAGCTG GTACTTCACT GAAAATATGG AAAGAAACTG CAGGGCTCCC TGCAATATCC |
| 3781 | AGATGGAAGA TCCCACTTTT AAAGAGAATT ATCGCTTCCA TGCAATCAAT GGCTACATAA |
| 3841 | TGGATACACT ACCTGGCTTA GTAATGGCTC AGGATCAAAG GATTCGATGG TATCTGCTCA |
| 3901 | GCATGGGCAG CAATGAAAAC ATCCATTCTA TTCATTTCAG TGGACATGTG TTCACTGTAC |
| 3961 | GAAAAAAAGA GGAGTATAAA ATGGCACTGT ACAATCTCTA TCCAGGTGTT TTTGAGACAG |
| 4021 | TGGAAATGTT ACCATCCAAA GCTGGAATTT GGCGGGTGGA ATGCCTTATT GGCGAGCATC |
| 4081 | TACATGCTGG GATGAGCACA CTTTTTCTGG TGTACAGCAA TAAGTGTCAG ACTCCCCTGG |
| 4141 | GAATGGCTTC TGGACACATT AGAGATTTTC AGATTACAGC TTCAGGACAA TATGGACAGT |
| 4201 | GGGCCCCAAA GCTGGCCAGA CTTCATTATT CCGGATCAAT CAATGCCTGG AGCACCAAGG |
| 4261 | AGCCCTTTTC TTGGATCAAG GTGGATCTGT TGGCACCAAT GATTATTCAC GGCATCAAGA |
| 4321 | CCCAGGGTGC CCGTCAGAAG TTCTCCAGCC TCTACATCTC TCAGTTTATC ATCATGTATA |
| 4381 | GTCTTGATGG GAAGAAGTGG CAGACTTATC GAGGAAATTC CACTGGAACC TTAATGGTCT |
| 4441 | TCTTTGGCAA TGTGGATTCA TCTGGGATAA AACACAATAT TTTTAACCCT CCAATTATTG |
| 4501 | CTCGATACAT CCGTTTGCAC CCAACTCATT ATAGCATTCG CAGCACTCTT CGCATGGAGT |
| 4561 | TGATGGGCTG TGATTTAAAT AGTTGCAGCA TGCCATTGGG AATGGAGAGT AAAGCAATAT |
| 4621 | CAGATGCACA GATTACTGCT TCATCCTACT TTACCAATAT GTTTGCCACC TGGTCTCCTT |
| 4681 | CAAAAGCTCG ACTTCACCTC CAAGGGAGGA GTAATGCCTG GAGACCTCAG GTGAATAATC |
| 4741 | CAAAAGAGTG GCTGCAAGTG GACTTCCAGA AGACAATGAA AGTCACAGGA GTAACTACTC |
| 4801 | AGGGAGTAAA ATCTCTGCTT ACCAGCATGT ATGTGAAGGA GTTCCTCATC TCCAGCAGTC |
| 4861 | AAGATGGCCA TCAGTGGACT CTCTTTTTTC AGAATGGCAA AGTAAAGGTT TTTCAGGGAA |
| 4921 | ATCAAGACTC CTTCACACCT GTGGTGAACT CTCTAGACCC ACCGTTACTG ACTCGCTACC |
| 4981 | TTCGAATTCA CCCCCAGAGT TGGGTGCACC AGATTGCCCT GAGGATGGAG GTTCTGGGCT |
| 5041 | GCGAGGCACA GGACCTCTAC |

*The underlined nucleic acids encode a signal peptide.

A "B-domain-deleted FVIII" may have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563. In some embodiments, a B-domain-deleted FVIII sequence of the present invention comprises any one of the deletions disclosed at col. 4, line 4 to col. 5, line 28 and Examples 1-5 of U.S. Pat. No. 6,316,226 (also in U.S. Pat. No. 6,346,513). In another embodiment, a B-domain deleted Factor VIII is the S743/Q1638 B-domain deleted Factor VIII (SQ BDD FVIII) (e.g., Factor VIII having a deletion from amino acid 744 to amino acid 1637, e.g., Factor VIII having amino acids 1-743 and amino acids 1638-2332 of SEQ ID NO: 65, i.e., SEQ ID NO: 67). In some embodiments, a B-domain-deleted FVIII of the present invention has a deletion disclosed at col. 2, lines 26-51 and examples 5-8 of U.S. Pat. No. 5,789,203 (also U.S. Pat. Nos. 6,060,447, 5,595,886, and 6,228,620). In some embodiments, a B-domain-deleted Factor VIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No.

5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, a B-domain-deleted FVIII has a deletion of most of the B domain, but still contains amino-terminal sequences of the B domain that are essential for in vivo proteolytic processing of the primary translation product into two polypeptide chain, as disclosed in WO 91/09122. In some embodiments, a B-domain-deleted FVIII is constructed with a deletion of amino acids 747-1638, i.e., virtually a complete deletion of the B domain. Hoeben R. C., et al. *J. Biol. Chem.* 265 (13): 7318-7323 (1990). A B-domain-deleted Factor VIII may also contain a deletion of amino acids 771-1666 or amino acids 868-1562 of FVIII. Meulien P., et al. *Protein Eng.* 2(4): 301-6 (1988). Additional B domain deletions that are part of the invention include: deletion of amino acids 982 through 1562 or 760 through 1639 (Toole et al., *Proc. Natl. Acad. Sci. U.S.A.* (1986) 83, 5939-5942)), 797 through 1562 (Eaton, et al. *Biochemistry* (1986) 25:8343-8347)), 741 through 1646 (Kaufman (PCT published application No. WO 87/04187)), 747-1560 (Sarver, et al., DNA (1987) 6:553-564)), 741 through 1648 (Pasek (PCT application No. 88/00831)), or 816 through 1598 or 741 through 1648 (Lagner (Behring Inst. Mitt. (1988) No 82:16-25, EP 295597)). In other embodiments, BDD FVIII includes a FVIII polypeptide containing fragments of the B-domain that retain one or more N-linked glycosylation sites, e.g., residues 757, 784, 828, 900, 963, or optionally 943, which correspond to the amino acid sequence of the full-length FVIII sequence. Examples of the B-domain fragments include 226 amino acids or 163 amino acids of the B-domain as disclosed in Miao, H. Z., et al., *Blood* 103(a): 3412-3419 (2004), Kasuda, A, et al., *J. Thromb. Haemost.* 6: 1352-1359 (2008), and Pipe, S. W., et al., *J. Thromb. Haemost.* 9: 2235-2242 (2011) (i.e., the first 226 amino acids or 163 amino acids of the B domain are retained). In still other embodiments, BDD FVIII further comprises a point mutation at residue 309 (from Phe to Ser) to improve expression of the BDD FVIII protein. See Miao, H. Z., et al., Blood 103(a): 3412-3419 (2004). In still other embodiments, the BDD FVIII includes a FVIII polypeptide containing a portion of the B-domain, but not containing one or more furin cleavage sites (e.g., Arg1313 and Arg 1648). See Pipe, S. W., et al., *J. Thromb. Haemost.* 9: 2235-2242 (2011). Each of the foregoing deletions may be made in any FVIII sequence.

In some embodiments, the FVIII has a partial B-domain. In some embodiments, the FVIII protein with a partial B-domain is FVIII198. FVIII198 is a partial B-domain containing single chain FVIIIFc molecule-226N6. Number 226 represents the N-terminus 226 amino acid of the FVIII B-domain, and N6 represents six N-glycosylation sites in the B-domain.

In one embodiment, FVIII is cleaved right after Arginine at amino acid 1648 (in full-length Factor VIII or SEQ ID NO: 65), amino acid 754 (in the 5743/Q1638 B-domain deleted Factor VIII or SEQ ID NO: 67), or the corresponding Arginine residue (in other variants), thereby resulting in a heavy chain and a light chain. In another embodiment, FVIII comprises a heavy chain and a light chain, which are linked or associated by a metal ion-mediated non-covalent bond.

In other embodiments, FVIII is a single chain FVIII that has not been cleaved right after Arginine at amino acid 1648 (in full-length FVIII or SEQ ID NO: 65), amino acid 754 (in the 5743/Q1638 B-domain-deleted FVIII or SEQ ID NO: 67), or the corresponding Arginine residue (in other variants). A single chain FVIII may comprise one or more amino acid substitutions. In one embodiment, the amino acid substitution is at a residue corresponding to residue 1648, residue 1645, or both of full-length mature Factor VIII polypeptide (SEQ ID NO: 65) or residue 754, residue 751, or both of SQ BDD Factor VIII (SEQ ID NO: 67). The amino acid substitution can be any amino acids other than Arginine, e.g., isoleucine, leucine, lysine, methionine, phenylalanine, threonine, tryptophan, valine, alanine, asparagine, aspartic acid, cysteine, glutamic acid, glutamine, glycine, proline, selenocysteine, serine, tyrosine, histidine, ornithine, pyrrolysine, or taurine.

FVIII can further be cleaved by thrombin and then activated as FVIIIa, serving as a cofactor for activated Factor IX (FIXa). And the activated FIX together with activated FVIII forms a Xase complex and converts Factor X to activated Factor X (FXa). For activation, FVIII is cleaved by thrombin after three Arginine residues, at amino acids 372, 740, and 1689 (corresponding to amino acids 372, 740, and 795 in the B-domain deleted FVIII sequence), the cleavage generating FVIIIa having the 50 kDa A1, 43 kDa A2, and 73 kDa A3-C1-C2 chains. In one embodiment, the FVIII protein useful for the present invention is non-active FVIII. In another embodiment, the FVIII protein is an activated FVIII.

The protein having FVIII polypeptide linked to or associated with the VWF protein can comprise a sequence at least 50%, 60%, 70%, 80%, 90%, 95%, 96%, 97%, 98%, 99%, or 100% identical to SEQ ID NO: 65 or 67, wherein the sequence has the FVIII clotting activity, e.g., activating Factor IX as a cofactor to convert Factor X to activated Factor X (FXa).

"Hybrid" or "chimeric" polypeptides and proteins, as used herein, includes a combination of a first polypeptide chain, e.g., the VWF protein fused to an XTEN sequence having less than 288 amino acids and a first Ig constant region or a portion thereof, with a second polypeptide chain, e.g., a FVIII protein fused to a second Ig constant region or a portion thereof, thereby forming a heterodimer. In one embodiment, the first polypeptide and the second polypeptide in a hybrid are associated with each other via protein-protein interactions, such as charge-charge or hydrophobic interactions. In another embodiment, a first polypeptide comprises a VWF protein-XTEN-Fc fusion protein, and a second polypeptide comprises FVIII-Fc fusion protein, making the hybrid a heterodimer, wherein the XTEN contains less than 288 amino acids. In other embodiments, the first polypeptide comprises a VWF protein-XTEN-Fc fusion protein, and the second polypeptide comprises FVIII(X)-Fc fusion protein, making the hybrid a heterodimer, wherein the XTEN contains less than 288 amino acids. The first polypeptide and the second polypeptide can be associated through a covalent bond, e.g., a disulfide bond, between the first Fc region and the second Fc region. The first polypeptide and the second polypeptide can further be associated with each other by binding between the VWF fragment and the FVIII protein.

A FVIII protein useful in the present invention can include FVIII having one or more additional XTEN sequences, which do not affect the FVIII coagulation activity. Such XTEN sequences can be fused to the C-terminus or N-terminus of the FVIII protein or inserted between one or more of the two amino acid residues in the FVIII protein while the insertions do not affect the FVIII coagulation activity or FVIII function. In one embodiment, the insertions improve pharmacokinetic properties of the FVIII protein (e.g., half-life). In another embodiment, the insertions can be multiple insertions, e.g., more than two, three, four, five, six, seven, eight, nine, or ten insertions. Examples of the insertion sites include, but are not limited to, the sites listed in Tables 7, 8, 9, 10, 11, 12, 13, 14, 15 or any combinations thereof.

The FVIII protein linked to one or more XTEN sequences can be represented as FVIII(X2) or $FVIII_{(a \rightarrow b)}$-X-$FVIII_{(c \rightarrow d)}$, wherein $FVIII_{(a \rightarrow b)}$; comprises, consists essentially of, or consists of a first portion of a FVIII protein from amino acid residue "a" to amino acid residue "b": X2 comprises, consists essentially of, or consists of one or more XTEN sequences, $FVIII_{(c \rightarrow d)}$ comprises, consists essentially of, or consists of a second portion of a FVIII protein from amino acid residue "c" to amino acid residue "d";

- a is the N-terminal amino acid residue of the first portion of the FVIII protein,
- b is the C-terminal amino acid residue of the first portion of the FVIII protein but is also the N-terminal amino acid residue of the two amino acids of an insertion site in which the XTEN sequence is inserted,
- c is the N-terminal amino acid residue of the second portion of the FVIII protein but is also the C-terminal amino acid residue of the two amino acids of an insertion site in which the XTEN sequence is inserted, and
- d is the C-terminal amino acid residue of the FVIII protein, and
- wherein the first portion of the FVIII protein and the second portion of the FVIII protein are not identical to each other and are of sufficient length together such that the FVIII protein has a FVIII coagulation activity.

In one embodiment, the first portion of the FVIII protein and the second portion of the FVIII protein are fragments of SEQ ID NO: 65 [full length mature FVIII sequence] or SEQ ID NO: 67 [B-domain deleted FVIII], e.g., N-terminal portion and C-terminal portion, respectively. In certain embodiments, the first portion of the FVIII protein comprises the A1 domain and the A2 domain of the FVIII protein. The second portion of the FVIII protein comprises the A3 domain, the C1 domain, and optionally the C2 domain. In yet other embodiments, the first portion of the FVIII protein comprises the A1 domain and A2 domain, and the second portion of the FVIII protein comprises a portion of the B domain, the A3 domain, the C1 domain, and optionally the C2 domain. In still other embodiments, the first portion of the FVIII protein comprises the A1 domain, A2 domain, and a portion of the B domain of the FVIII protein, and the second portion of the FVIII protein comprises the A3 domain, the C1 domain, and optionally the C2 domain. In still other embodiments, the first portion of the FVIII protein comprises the A1 domain, A2 domain, and a first portion of the B domain of the FVIII protein. The second portion of the FVIII protein comprises a second portion of the B domain, the A3 domain, the C1 domain, and optionally the C2 domain. In some embodiments, the two amino acids ("b" and "c") can be any one or more of the amino acid residues insertion sites shown in Tables 7, 8, 9, 10, 11, 12, 13, 14, and 15. For example, "b" can be the amino acid residue immediately upstream of the site in which one or more XTEN sequences are inserted or linked, and "c" can be the amino acid residue immediately downstream of the site in which the one or more XTEN sequences are inserted or linked. In some embodiments, "a" is the first mature amino acid sequence of a FVIII protein, and "d" is the last amino acid sequence of a FVIII protein. For example, $FVIII_{(a \rightarrow b)}$ can be an amino acid sequence at least 70%, 80%, 90%, 95%, 96%, 97%, 98%, 99%, or 100% identical to amino acids 1 to 745 of SEQ ID NO: 67 [B domain deleted FVIII amino acid sequence] or SEQ ID NO: 65 [full length FVIII] and $FVIII_{(c \rightarrow d)}$ can be amino acids 746 to 1438 of SEQ ID NO: 67 or amino acids 1641 to 2332 of SEQ ID NO: 65, respectively.

In some aspects, the insertion site in the FVIII protein is located in one or more domains of the FVIII protein, which is the N-terminus, the A1 domain, the A2 domain, the A3 domain, the B domain, the C1 domain, the C2 domain, the C-terminus, or two or more combinations thereof or between two domains of the FVIII protein, which are the A1 domain and a1 acidic region, and the a1 acidic region and A2 domain, the A2 domain and a2 acidic region, the a2 acidic region and B domain, the B domain and A3 domain, and the A3 domain and C1 domain, the C1 domain and C2 domain, or any combinations thereof. For example, the insertion sites in which the XTEN sequence can be inserted are selected from the group consisting of the N-terminus and A1 domain, the N-terminus and A2 domain, the N-terminus and A3 domain, the N-terminus and B domain, the N-terminus and C1 domain, the N-terminus and C2 domain, the N-terminus and the C-terminus, the A1 and A2 domains, the A1 and A3 domains, the A1 and B domains, the A1 and C1 domains, the A1 and C2 domains, the A1 domain and the C-terminus, the A2 and A3 domains, the A2 and B domains, the A2 and C1 domains, the A2 and C2 domains, the A2 domain and the C-terminus, the A3 and B domains, the A3 and C1 domains, the A3 and C2 domains, the A3 domain and the C-terminus, the B and C1 domains, the B and C2 domains, the B domain and the C-terminus, the C1 and C2 domains, the C1 and the C-terminus, the C2 domain, and the C-terminus, and two or more combinations thereof. Non-limiting examples of the insertion sites are listed in Tables 7, 8, 9, 10, 11, 12, 13, 14, and 15.

The FVIII protein, in which the XTEN sequence is inserted immediately downstream of one or more amino acids (e.g., one or more XTEN insertion sites) in the FVIII protein or linked at the C-terminus or the N-terminus, retains the FVIII activity after linkage to or insertion by the XTEN sequence. The XTEN sequence can be inserted in the FVIII protein once or more than once, twice, three times, four times, five times, or six times such that the insertions do not affect the FVIII activity (i.e., the FVIII protein still retains the coagulation property).

The FVIII protein useful in the present invention can be linked to one or more XTEN polypeptides at the N-terminus or C-terminus of the FVIII protein by an optional linker or inserted immediately downstream of one or more amino acids (e.g., one or more XTEN insertion sites) in the FVIII protein by one or more optional linkers. In one embodiment, the two amino acid residues in which the XTEN sequence is inserted or the amino acid residue to which the XTEN sequence is linked correspond to the two or one amino acid residues of SEQ ID NO: 65 [full length mature FVIII] selected from the group consisting of the residues in Table 7, Table 8, Table 9, and Table 10 and any combinations thereof.

In other embodiments, at least one XTEN sequence is inserted in any one or more XTEN insertion sites disclosed herein or any combinations thereof. In one aspect, at least one XTEN sequence is inserted in one or more XTEN insertion sites disclosed in one or more amino acids disclosed in Table 7.

TABLE 7

Exemplary XTEN Insertion Sites

| No. | XTEN Insertion Point* | Insertion Residue | FVIII BDD Downstream Sequence | FVIII Domain |
|---|---|---|---|---|
| 1 | 0 | (N-terminus) | ATR | A1 |
| 2 | 3 | R | RYY | A1 |
| 3 | 17 | M | QSD | A1 |
| 4 | 18 | Q | SDL | A1 |
| 5 | 22 | G | ELP | A1 |
| 6 | 24 | L | PVD | A1 |
| 7 | 26 | V | DAR | A1 |
| 8 | 28 | A | RFP | A1 |
| 9 | 32 | P | RVP | A1 |
| 10 | 38 | F | PFN | A1 |
| 11 | 40 | F | NTS | A1 |
| 12 | 41 | N | TSV | A1 |
| 13 | 60 | N | IAK | A1 |
| 14 | 61 | I | AKP | A1 |
| 15 | 65 | R | PPW | A1 |
| 16 | 81 | Y | DTV | A1 |
| 17 | 111 | G | AEY | A1 |
| 18 | 116 | D | QTS | A1 |
| 19 | 119 | S | QRE | A1 |
| 20 | 120 | Q | REK | A1 |
| 21 | 128 | V | FPG | A1 |
| 22 | 129 | F | PGG | A1 |
| 23 | 130 | P | GGS | A1 |
| 24 | 182 | G | SLA | A1 |
| 25 | 185 | A | KEK | A1 |
| 26 | 188 | K | TQT | A1 |
| 27 | 205 | G | KSW | A1 |
| 28 | 210 | S | ETK | A1 |
| 29 | 211 | E | TKN | A1 |
| 30 | 216 | L | MQD | A1 |
| 31 | 220 | R | DAA | A1 |
| 32 | 222 | A | ASA | A1 |
| 33 | 223 | A | SAR | A1 |
| 34 | 224 | S | ARA | A1 |
| 35 | 230 | K | MHT | A1 |
| 36 | 243 | P | GLI | A1 |
| 37 | 244 | G | LIG | A1 |
| 38 | 250 | R | KSV | A1 |
| 39 | 318 | D | GME | A1 |
| 40 | 333 | P | QLR | A1 |
| 42 | 334 | Q | LRM | A1 |
| 43 | 336 | R | MKN | a1 |
| 44 | 339 | N | NEE | a1 |
| 45 | 345 | D | YDD | a1 |
| 46 | 357 | V | VRF | a1 |
| 47 | 367 | S | FIQ | a1 |
| 48 | 370 | S | RPY | a1 |
| 49 | 375 | A | KKH | A2 |
| 50 | 376 | K | KHP | A2 |
| 51 | 378 | H | PKT | A2 |
| 52 | 399 | V | LAP | A2 |
| 53 | 403 | D | DRS | A2 |
| 54 | 405 | R | SYK | A2 |
| 55 | 409 | S | QYL | A2 |
| 56 | 416 | P | QRI | A2 |
| 57 | 434 | E | TFK | A2 |
| 58 | 438 | T | REA | A2 |
| 59 | 441 | A | IQH | A2 |
| 60 | 442 | I | QHE | A2 |
| 61 | 463 | I | IFK | A2 |
| 62 | 487 | Y | SRR | A2 |
| 63 | 490 | R | LPK | A2 |
| 64 | 492 | P | KGV | A2 |
| 65 | 493 | K | GVK | A2 |
| 66 | 494 | G | VKH | A2 |
| 67 | 500 | D | FPI | A2 |
| 68 | 506 | G | EIF | A2 |
| 69 | 518 | E | DGP | A2 |
| 70 | 556 | K | ESV | A2 |
| 71 | 565 | Q | IMS | A2 |
| 72 | 566 | I | MSD | A2 |
| 73 | 598 | P | AGV | A2 |
| 74 | 599 | A | GVQ | A2 |
| 75 | 603 | L | EDP | A2 |
| 76 | 616 | S | ING | A2 |
| 77 | 686 | G | LWI | A2 |
| 78 | 713 | K | NTG | A2 |
| 79 | 719 | Y | EDS | A2 |
| 80 | 730 | L | LSK | A2 |
| 81 | 733 | K | NNA | A2 |
| 82 | 745 | N | PPV** | B |
| 83 | 1640 | P | PVL | B |
| 84 | 1652 | R | TTL | B |
| 85 | 1656 | Q | SDQ | A3 |
| 86 | 1685 | N | QSP | A3 |
| 87 | 1711 | M | SSS | A3 |
| 88 | 1713 | S | SPH | A3 |
| 89 | 1720 | N | RAQ | A3 |
| 90 | 1724 | S | GSV | A3 |
| 91 | 1725 | G | SVP | A3 |
| 92 | 1726 | S | VPQ | A3 |
| 93 | 1741 | G | SFT | A3 |
| 94 | 1744 | T | QPL | A3 |
| 95 | 1749 | R | GEL | A3 |
| 96 | 1773 | V | TFR | A3 |
| 97 | 1792 | Y | EED | A3 |
| 98 | 1793 | E | EDQ | A3 |
| 99 | 1796 | Q | RQG | A3 |
| 100 | 1798 | Q | GAE | A3 |
| 101 | 1799 | G | AEP | A3 |
| 102 | 1802 | P | RKN | A3 |
| 103 | 1803 | R | KNF | A3 |
| 104 | 1807 | V | KPN | A3 |
| 105 | 1808 | K | PNE | A3 |
| 106 | 1827 | K | DEF | A3 |
| 107 | 1844 | E | KDV | A3 |
| 108 | 1861 | N | TLN | A3 |
| 109 | 1863 | L | NPA | A3 |
| 110 | 1896 | E | RNC | A3 |
| 111 | 1900 | R | APC | A3 |
| 112 | 1904 | N | IQM | A3 |
| 113 | 1905 | I | QME | A3 |
| 114 | 1910 | P | TFK | A3 |
| 115 | 1920 | A | ING | A3 |
| 116 | 1937 | D | QRI | A3 |
| 117 | 1981 | G | VFE | A3 |
| 118 | 2019 | N | KCQ | A3 |
| 119 | 2020 | K | CQT | C1 |
| 120 | 2044 | G | QWA | C1 |
| 121 | 2068 | F | SWI | C1 |
| 122 | 2073 | V | DLL | C1 |
| 123 | 2090 | R | QKF | C1 |
| 124 | 2092 | K | FSS | C1 |
| 125 | 2093 | F | SSL | C1 |
| 126 | 2111 | K | WQT | C1 |
| 127 | 2115 | Y | RGN | C1 |
| 128 | 2120 | T | GTL | C1 |
| 129 | 2125 | V | FFG | C1 |
| 130 | 2171 | L | NSC | C1 |
| 131 | 2173 | S | CSM | C2 |
| 132 | 2188 | A | QIT | C2 |
| 133 | 2223 | V | NNP | C2 |
| 134 | 2224 | N | NPK | C2 |
| 135 | 2227 | K | EWL | C2 |
| 136 | 2268 | G | HQW | C2 |
| 137 | 2277 | N | GKV | C2 |
| 138 | 2278 | G | KVK | C2 |
| 139 | 2290 | F | TPV | C2 |
| 140 | 2332 | Y | C terminus of FVIII | CT |

*Indicates an insertion point for XTEN based on the amino acid number of mature full-length human FVIII, wherein the insertion could be either on the N- or C-terminal side of the indicated amino acid.

In some embodiments, one or more XTEN sequences are inserted within about six amino acids up or down from amino acids 32, 220, 224, 336, 339, 399, 416, 603, 1656, 1711, 1725, 1905, or 1910, corresponding to SEQ ID NO: 65 or any combinations thereof.

TABLE 8

| Exemplary XTEN Insertion Ranges | | | | | |
|---|---|---|---|---|---|
| No. | XTEN Insertion Point | Insertion Residue | FVIII BDD Downstream Sequence | FVIII Domain | Distance from insertion residue* |
| 9 | 32 | P | RVP | A1 | −3, +6 |
| 31 | 220 | R | DAA | A1 | — |
| 34 | 224 | S | ARA | A1 | +5 |
| 43 | 336 | R | MKN | a1 | −1, +6 |
| 44 | 339 | N | NEE | a1 | −4, +5 |
| 52 | 399 | V | LAP | A2 | −6, +3 |
| 56 | 416 | P | QRI | A2 | +6 |
| 75 | 603 | L | EDP | A2 | _6, +6 |
| 85 | 1656 | Q | SDQ | B | −3, +6 |
| 87 | 1711 | M | SSS | A3 | −6, +1 |
| 91 | 1725 | G | SVP | A3 | +6 |
| 113 | 1905 | I | QME | A3 | +6 |
| 114 | 1910 | P | TFK | A3 | −5, +6 |

*Distance from insertion residue refers to the relative number of amino acids away from the N-terminus (negative numbers) or C-terminus (positive numbers) of the designated insertion residue (residue "0") where an insertion may be made. The designation "−x" refers to an insertion site which is x amino acids away on the N-terminal side of the designated insertion residue. Similarly, the designation "+x" refers to an insertion site which is x amino acids away on the C-terminal side of the designated insertion residue. For example, "−1, +2" indicates that the insertion is made at the N-terminus or C-terminus of amino acid residues denoted −1, 0, +1 or +2.

In other embodiments, one or more XTEN sequences are inserted immediately down stream of one or more amino acids corresponding to the full-length mature human FVIII selected from the group consisting of one or more insertion sites in Table 9.

TABLE 9

| Exemplary XTEN Insertion Sites or Ranges | | | |
|---|---|---|---|
| No. | XTEN Insertion Point Range* | First Insertion Residue | FVIII Domain |
| 3 | 18-32 | Q | A1 |
| 8 | 40 | F | A1 |
| 18 | 211-224 | E | A1 |
| 27 | 336-403 | R | A1, A2 |
| 43 | 599 | A | A2 |
| 47 | 745-1640 | N | B |
| 50 | 1656-1728 | Q | B, a3, A3 |
| 57 | 1796-1804 | R | A3 |
| 65 | 1900-1912 | R | A3 |
| 81 | 2171-2332 | L | C1, C2 |

*indicates range of insertion sites numbered relative to the amino acid number of mature human FVIII In yet other embodiments, one or more XTENs are inserted in the B domain of FVIII. In one example, an XTEN is inserted between amino acids 740 and 1640 corresponding to SEQ ID NO: 65, wherein the FVIII sequence between amino acids 740 and 1640 is optionally not present. In another example, an XTEN is inserted between amino acids 741 and 1690 corresponding to SEQ ID NO: 65, wherein the FVIII sequence between amino acids 740 and 1690 is optionally not present. In other examples, an XTEN is inserted between amino acids 741 and 1648 corresponding to SEQ ID NO: 65, wherein the FVIII sequence between amino acids 741 and 1648 is optionally not present. In yet other examples, an XTEN is inserted between amino acids 743 and 1638 corresponding to SEQ ID NO: 65, wherein the FVIII sequence between amino acids 743 and 1638 is optionally not present. In still other examples, an XTEN is inserted between amino acids 745 and 1656 corresponding to SEQ ID NO: 65, wherein the FVIII sequence between amino acids 745 and 1656 is optionally not present. In some examples, an XTEN is inserted between amino acids 745 and 1657 corresponding to SEQ ID NO: 65, wherein the FVIII sequence between amino acids 745 and 1657 is optionally not present. In certain examples, an XTEN is inserted between amino acids 745 and 1667 corresponding to SEQ ID NO: 65, wherein the FVIII sequence between amino acids 745 and 1667 is optionally not present. In still other examples, an XTEN is inserted between amino acids 745 and 1686 corresponding to SEQ ID NO: 65, wherein the FVIII sequence between amino acids 745 and 1686 is optionally not present. In some other examples, an XTEN is inserted between amino acids 747 and 1642 corresponding to SEQ ID NO: 65, wherein the FVIII sequence between amino acids 747 and 1642 is optionally not present. In still other examples, an XTEN is inserted between amino acids 751 and 1667 corresponding to SEQ ID NO: 65, wherein the FVIII sequence between amino acids 751 and 1667 is optionally not present.

In some embodiments, one or more XTENs are inserted in one or more amino acids immediately downstream of an amino acid of an insertion site selected from the group consisting of the amino acid residues in Table 10.

TABLE 10

| FVIII XTEN insertion sites and construct designations | | | | | |
|---|---|---|---|---|---|
| Construct Number | Domain | Upstream Residue No.* | Downstream Residue No.* | Upstream Sequence | Downstream Sequence |
| F8X-1 | A1 | 3 | 4 | ATR | RYY |
| F8X-2 | A1 | 18 | 19 | YMQ | SDL |
| F8X-3 | A1 | 22 | 23 | DLG | ELP |
| F8X-4 | A1 | 26 | 27 | LPV | DAR |
| F8X-5 | A1 | 40 | 41 | FPF | NTS |
| F8X-6 | A1 | 60 | 61 | LFN | IAK |
| F8X-7 | A1 | 116 | 117 | YDD | QTS |
| F8X-8 | A1 | 130 | 131 | VFP | GGS |
| F8X-9 | A1 | 188 | 189 | KEK | TQT |
| F8X-10 | A1 | 216 | 217 | NSL | MQD |
| F8X-11 | A1 | 230 | 231 | WPK | MHT |
| F8X-12 | A1 | 333 | 334 | EEP | QLR |
| F8X-13 | A2 | 375 | 376 | SVA | KKH |
| F8X-14 | A2 | 403 | 404 | APD | DRS |
| F8X-15 | A2 | 442 | 443 | EAI | QHE |
| F8X-16 | A2 | 490 | 491 | RRL | PKG |
| F8X-17 | A2 | 518 | 519 | TVE | DGP |
| F8X-18 | A2 | 599 | 600 | NPA | GVQ |
| F8X-19 | A2 | 713 | 714 | CDK | NTG |
| F8X-20 | BD | 745 | 746 | SQN | PPV |
| F8X-21 | BD | 745 | 746 | SQN | PPV |
| F8X-22 | BD** | 745 | 746 | SQN | PPV |
| F8X-23 | A3 | 1720 | 1721 | APT | KDE |
| F8X-24 | A3 | 1796 | 1797 | EDQ | RQG |
| F8X-25 | A3 | 1802 | 1803 | AEP | RKN |
| F8X-26 | A3 | 1827 | 1828 | PTK | DEF |
| F8X-27 | A3 | 1861 | 1862 | HTN | TLN |
| F8X-28 | A3 | 1896 | 1897 | NME | RNC |
| F8X-29 | A3 | 1900 | 1901 | NCR | APC |
| F8X-30 | A3 | 1904 | 1905 | PCN | IQM |
| F8X-31 | A3 | 1937 | 1938 | AQD | QRI |
| F8X-32 | C1 | 2019 | 2020 | YSN | KCQ |
| F8X-33 | C1 | 2068 | 2069 | EPF | SWI |
| F8X-34 | C1 | 2111 | 2112 | GKK | WQT |
| F8X-35 | C1 | 2120 | 2121 | NST | GTL |
| F8X-36 | C2 | 2171 | 2172 | CDL | NSC |
| F8X-37 | C2 | 2188 | 2189 | SDA | QIT |
| F8X-38 | C2 | 2227 | 2228 | NPK | EWL |
| F8X-39 | C2 | 2277 | 2278 | FQN | GKV |
| F8X-40 | CT | 2332 | NA | DLY | NA |
| F8X-41 | CT | 2332 | NA | DLY | NA |
| F8X-42 | A1 | 3 | 4 | ATR | ATR |
| pSD0001 | A2 | 403 | 404 | | |
| pSD0002 | A2 | 599 | 600 | | |
| pSD0021 | N-term | 0 | 1 | | |
| pSD0022 | A1 | 32 | 33 | | |
| pSD0023 | A1 | 65 | 66 | | |
| pSD0024 | A1 | 81 | 82 | | |

TABLE 10-continued

FVIII XTEN insertion sites and construct designations

| Construct Number | Domain | Upstream Residue No.* | Downstream Residue No.* | Upstream Sequence | Downstream Sequence |
|---|---|---|---|---|---|
| pSD0025 | A1 | 119 | 120 | | |
| pSD0026 | A1 | 211 | 212 | | |
| pSD0027 | A1 | 220 | 221 | | |
| pSD0028 | A1 | 224 | 225 | | |
| pSD0029 | A1 | 336 | 337 | | |
| pSD0030 | A1 | 339 | 340 | | |
| pSD0031 | A2 | 378 | 379 | | |
| pSD0032 | A2 | 399 | 400 | | |
| pSD0033 | A2 | 409 | 410 | | |
| pSD0034 | A2 | 416 | 417 | | |
| pSD0035 | A2 | 487 | 488 | | |
| pSD0036 | A2 | 494 | 495 | | |
| pSD0037 | A2 | 500 | 501 | | |
| pSD0038 | A2 | 603 | 604 | | |
| pSD0039 | A3 | 1656 | 1657 | | |
| pSD0040 | A3 | 1711 | 1712 | | |
| pSD0041 | A3 | 1725 | 1726 | | |
| pSD0042 | A3 | 1749 | 1750 | | |
| pSD0043 | A3 | 1905 | 1906 | | |
| pSD0044 | A3 | 1910 | 1911 | | |
| pDS0062 | A3 | 1900 | 1901 | | |

*Indicates the amino acid number of the mature FVIII protein

In one embodiment, the one or more XTEN insertion sites are located within one or more surface-exposed, flexible loop structure of the FVIII protein (e.g., a permissive loop). For example, at least one XTEN sequence can be inserted in each FVIII "A" domain comprising at least two "permissive loops" into which at least one XTEN polypeptide can be inserted without eliminating procoagulant activity of the recombinant protein, or the ability of the recombinant proteins to be expressed in vivo or in vitro in a host cell. The permissive loops are regions that allow insertion of at least one XTEN sequence with, among other attributes, high surface or solvent exposure and high conformational flexibility. The A1 domain comprises a permissive loop-1 (A1-1) region and a permissive loop-2 (A1-2) region, the A2 domain comprises a permissive loop-1 (A2-1) region and a permissive loop-2 (A2-2) region, the A3 domain comprises a permissive loop-1 (A3-1) region and a permissive loop-2 (A3-2) region.

In one aspect, a first permissive loop in the FVIII A1 domain (A1-1) is located between beta strand 1 and beta strand 2, and a second permissive loop in the FVIII A2 domain (A1-2) is located between beta strand 11 and beta strand 12. A first permissive loop in the FVIII A2 domain (A2-1) is located between beta strand 22 and beta strand 23, and a second permissive loop in the FVIII A2 domain (A2-2) is located between beta strand 32 and beta strand 33. A first permissive loop in the FVIII A3 domain (A3-1) is located between beta strand 38 and beta strand 39, and a second permissive loop in the FVIII A3 (A3-2) is located between beta strand 45 and beta strand 46. In certain aspects, the surface-exposed, flexible loop structure comprising A1-1 corresponds to a region in native mature human FVIII from about amino acid 15 to about amino acid 45 of SEQ ID NO: 65, e.g., from about amino acid 18 to about amino acid 41 of SEQ ID NO: 65. In other aspects, the surface-exposed, flexible loop structure comprising A1-2 corresponds to a region in native mature human FVIII from about amino acid 201 to about amino acid 232 of SEQ ID NO: 65, e.g., from about amino acid 218 to about amino acid 229 of SEQ ID NO: 65. In yet other aspects, the surface-exposed, flexible loop structure comprising A2-1 corresponds to a region in native mature human FVIII from about amino acid 395 to about amino acid 421 of SEQ ID NO: 65, e.g. from about amino acid 397 to about amino acid 418 of SEQ ID NO: 65. In still other embodiments, the surface-exposed, flexible loop structure comprising A2-2 corresponds to a region in native mature human FVIII from about amino acid 577 to about amino acid 635 of SEQ ID NO: 65, e.g., from about amino acid 595 to about amino acid 607 of SEQ ID NO: 65. In certain aspects the surface-exposed, flexible loop structure comprising A3-1 corresponds to a region in native mature human FVIII from about amino acid 1705 to about amino acid 1732 of SEQ ID NO: 65, e.g., from about amino acid 1711 to about amino acid 1725 of SEQ ID NO: 65. In yet other aspects, the surface-exposed, flexible loop structure comprising A3-2 corresponds to a region in native mature human FVIII from about amino acid 1884 to about amino acid 1917 of SEQ ID NO: 65, e.g., from about amino acid 1899 to about amino acid 1911 of SEQ ID NO: 65.

In another embodiment, the one or more amino acids in which at least one XTEN sequence is inserted is located within a3 domain, e.g., amino acids 1649 to 1689, corresponding to full-length mature FVIII polypeptide. In a particular embodiment, an XTEN sequence is inserted between amino acids 1656 and 1657 of SEQ ID NO: 65 (full-length mature FVIII). In a specific embodiment, a FVIII protein comprising an XTEN sequence inserted immediately downstream of amino acid 1656 corresponding to SEQ ID NO: 65 further comprises a deletion from amino acid 745 to amino acid 1656 corresponding to SEQ ID NO: 65.

In some embodiments, the one or more insertion sites for one or more XTEN insertions are immediately downstream of one or more amino acids corresponding to mature full-length FVIII, selected from the group consisting of:

| | | |
|---|---|---|
| (1) amino acid 3, | (2) amino acid 18, | (3) amino acid 22, |
| (4) amino acid 26, | (5) amino acid 32, | (6) amino acid 40, |
| (7) amino acid 60, | (8) amino acid 65, | (9) amino acid 81, |
| (10) amino acid 116, | (11) amino acid 119, | (12) amino acid 130, |
| (13) amino acid 188, | (14) amino acid 211, | (15) amino acid 216, |
| (16) amino acid 220, | (17) amino acid 224, | (18) amino acid 230, |
| (19) amino acid 333, | (20) amino acid 336, | (21) amino acid 339, |
| (22) amino acid 375, | (23) amino acid 399, | (24) amino acid 403, |
| (25) amino acid 409, | (26) amino acid 416, | (26) amino acid 442, |
| (28) amino acid 487, | (29) amino acid 490, | (30) amino acid 494, |
| (31) amino acid 500, | (32) amino acid 518, | (33) amino acid 599, |
| (34) amino acid 603, | (35) amino acid 713, | (36) amino acid 745, |
| (37) amino acid 1656, | (38) amino acid 1711, | (39) amino acid 1720, |
| (40) amino acid 1725, | (41) amino acid 1749, | (42) amino acid 1796, |
| (43) amino acid 1802, | (44) amino acid 1827, | (45) amino acid 1861, |
| (46) amino acid 1896, | (47) amino acid 1900, | (48) amino acid 1904, |
| (49) amino acid 1905, | (50) amino acid 1910, | (51) amino acid 1937, |
| (52) amino acid 2019, | (53) amino acid 2068, | (54) amino acid 2111, |
| (55) amino acid 2120, | (56) amino acid 2171, | (57) amino acid 2188, |
| (58) amino acid 2227, | (59) amino acid 2277, and | |
| (60) two or more combinations thereof. | | |

In one embodiment, a FVIII protein useful for the invention comprises two XTEN sequences, a first XTEN sequence inserted into a first XTEN insertion site and a second XTEN inserted into a second XTEN insertion site. Non-limiting examples of the first XTEN insertion site and the second XTEN insertion site are listed in Table 11.

TABLE 11

| Exemplary Insertion Sites for Two XTENs | | | |
|---|---|---|---|
| Insertion 1 | | Insertion 2 | |
| Insertion Site | Domain | Insertion Site | Domain |
| 745 | B | 2332 | CT |
| 26 | A1 | 403 | A2 |
| 40 | A1 | 403 | A2 |
| 18 | A1 | 403 | A2 |
| 26 | A1 | 599 | A2 |
| 40 | A1 | 599 | A2 |
| 18 | A1 | 599 | A2 |
| 1720 | A3 | 1900 | A3 |
| 1725 | A3 | 1900 | A3 |
| 1711 | A3 | 1905 | A3 |
| 1720 | A3 | 1905 | A3 |
| 1725 | A3 | 1905 | A3 |
| 1656 | A3 | 26 | A1 |
| 1656 | A3 | 18 | A1 |
| 1656 | A3 | 40 | A1 |
| 1656 | A3 | 399 | A2 |
| 1656 | A3 | 403 | A2 |
| 1656 | A3 | 1725 | A3 |
| 1656 | A3 | 1720 | A3 |
| 1900 | A3 | 18 | A1 |
| 1900 | A3 | 26 | A1 |
| 1900 | A3 | 40 | A1 |
| 1905 | A3 | 18 | A1 |
| 1905 | A3 | 40 | A1 |
| 1905 | A3 | 26 | A1 |
| 1910 | A3 | 26 | A1 |
| 18 | A1 | 399 | A2 |
| 26 | A1 | 399 | A2 |
| 40 | A1 | 399 | A2 |
| 18 | A1 | 403 | A2 |
| 1656 | A3 | 1900 | A3 |
| 1656 | A3 | 1905 | A3 |
| 1711 | A3 | 40 | A1 |
| 1711 | A3 | 26 | A1 |
| 1720 | A3 | 26 | A1 |
| 1720 | A3 | 40 | A1 |
| 1720 | A3 | 18 | A1 |
| 1725 | A3 | 26 | A1 |
| 1725 | A3 | 40 | A1 |
| 1725 | A3 | 18 | A1 |
| 1720 | A3 | 403 | A2 |
| 1720 | A3 | 399 | A2 |
| 1711 | A3 | 403 | A2 |
| 1720 | A3 | 403 | A2 |
| 1725 | A3 | 403 | A2 |
| 1725 | A3 | 399 | A2 |
| 1711 | A3 | 403 | A2 |
| 1900 | A3 | 399 | A2 |
| 1900 | A3 | 403 | A2 |
| 1905 | A3 | 403 | A2 |
| 1905 | A3 | 399 | A2 |
| 1910 | A3 | 403 | A2 |

The two XTENs inserted or linked to the FVIII protein can be identical or different. In some embodiments, a FVIII protein useful for the invention comprises two XTEN sequences inserted in the FVIII protein, a first XTEN sequence inserted immediately downstream of amino acid 745 corresponding to SEQ ID NO: 65, and a second XTEN sequence inserted immediately downstream of amino acid 2332 corresponding to SEQ ID NO: 65 (the C-terminus). In other embodiments, the first XTEN sequence is inserted immediately downstream of amino acid 18, 26, 40, 1656, or 1720 corresponding to SEQ ID NO: 65, and a second XTEN sequence inserted immediately downstream of amino acid 403 corresponding to SEQ ID NO: 65. In yet other embodiments, the first XTEN sequence is inserted immediately downstream of amino acid 18, 26, or 40 corresponding to SEQ ID NO: 65, and a second XTEN sequence inserted immediately downstream of amino acid 599 corresponding to SEQ ID NO: 65. In still other embodiments, the first XTEN sequence is inserted immediately downstream of amino acid 1656 corresponding to SEQ ID NO: 65, and a second XTEN sequence inserted immediately downstream of amino acid 18, 26, 40, 399, 403, 1725, 1720, 1900, 1905, or 2332 corresponding to SEQ ID NO: 65. In certain embodiments, the first XTEN sequence is inserted immediately downstream of amino acid 1900 corresponding to SEQ ID NO: 65, and a second XTEN sequence inserted immediately downstream of amino acid 18, 26, or 40 corresponding to SEQ ID NO: 65. In some embodiments, the first XTEN sequence is inserted immediately downstream of amino acid 18, 26, or 40 corresponding to SEQ ID NO: 65, and a second XTEN sequence inserted immediately downstream of amino acid 399 corresponding to SEQ ID NO: 65. In other embodiments, the first XTEN sequence is inserted immediately downstream of amino acid 1720 corresponding to SEQ ID NO: 65, and a second XTEN sequence inserted immediately downstream of amino acid 18, 26, or 40 corresponding to SEQ ID NO: 65. In still other embodiments, the first XTEN sequence is inserted immediately downstream of amino acid 1720 corresponding to SEQ ID NO: 65, and a second XTEN sequence inserted immediately downstream of amino acid 18 corresponding to SEQ ID NO: 65. In a particular embodiment, the FVIII protein comprising two XTEN sequences, a first XTEN sequence inserted immediately downstream of amino acid 745 corresponding to SEQ ID NO: 65 and a second XTEN sequence inserted immediately downstream of amino acid 2332 corresponding to SEQ ID NO: 65, wherein the FVIII protein further has a deletion from amino acid 745 corresponding to SEQ ID NO: 65 to amino acid 1685 corresponding to SEQ ID NO: 65, a mutation or substitution at amino acid 1680 corresponding to SEQ ID NO: 65, e.g., Y1680F, a mutation or substitution at amino acid 1648 corresponding to SEQ ID NO: 65, e.g., R1648A, or at least two mutations or substitutions at amino acid 1648 corresponding to SEQ ID NO: 65, e.g., R1648A, and amino acid 1680 corresponding to SEQ ID NO: 65, e.g., Y1680F. In a specific embodiment, the FVIII protein comprises two XTEN sequences, a first XTEN inserted immediately downstream of amino acid 1656 corresponding to SEQ ID NO: 65 and a second XTEN sequence inserted immediately downstream of amino acid 2332 of SEQ ID NO: 65, wherein the FVIII protein further has a deletion from amino acid 745 to amino acid 1656 corresponding to SEQ ID NO: 65.

In certain embodiments, a FVIII protein comprises three XTEN sequences, a first XTEN sequence inserted into a first XTEN insertion site, a second XTEN sequence inserted into a second XTEN sequence, and a third XTEN sequence inserted into a third XTEN insertion site. The first, second, or third XTEN sequences can be identical or different. The first, second, and third insertion sites can be selected from the group of any one of the insertion sites disclosed herein. In some embodiments, the FVIII protein comprising three XTEN sequences can further comprise a mutation or substitution, e.g., amino acid 1648 corresponding to SEQ ID NO: 65, e.g., R1648A. For example, non-limiting examples of the first, second, and third XTEN insertion sites are listed in Table 12.

TABLE 12

| Exemplary Insertion Sites for Three XTENs | | | | | |
|---|---|---|---|---|---|
| Insertion 1 | | Insertion 2 | | Insertion 3 | |
| Insertion Site | Domain | Insertion Site | Domain | Insertion Site | Domain |
| 26 | A1 | 403 | A2 | 1656 | A3 |
| 26 | A1 | 403 | A2 | 1720 | A3 |
| 26 | A1 | 403 | A2 | 1900 | A3 |
| 26 | A1 | 1656 | A3 | 1720 | A3 |
| 26 | A1 | 1656 | A3 | 1900 | A3 |
| 26 | A1 | 1720 | A3 | 1900 | A3 |
| 403 | A2 | 1656 | A3 | 1720 | A3 |
| 403 | A2 | 1656 | A3 | 1900 | A3 |
| 403 | A2 | 1720 | A3 | 1900 | A3 |
| 1656 | A3 | 1720 | A3 | 1900 | A3 |
| 745 | B | 1900 | | 2332 | |
| 18 | A1 | 745 | B | 2332 | CT |
| 26 | A1 | 745 | B | 2332 | CT |
| 40 | A1 | 745 | B | 2332 | CT |
| 18 | A1 | 745 | B | 2332 | CT |
| 40 | A1 | 745 | B | 2332 | CT |
| 403 | A2 | 745 | B | 2332 | CT |
| 399 | A2 | 745 | B | 2332 | CT |
| 1725 | A3 | 745 | B | 2332 | CT |
| 1720 | A3 | 745 | B | 2332 | CT |
| 1711 | A3 | 745 | B | 2332 | CT |
| 1900 | A3 | 745 | B | 2332 | CT |
| 1905 | A3 | 745 | B | 2332 | CT |
| 1910 | A3 | 745 | B | 2332 | CT |

In some embodiments, a FVIII protein comprises three XTEN sequences, a first XTEN sequence inserted immediately downstream of amino acid 26 corresponding to SEQ ID NO: 65, a second XTEN sequence inserted downstream of amino acid 403 corresponding to SEQ ID NO: 65, and a third XTEN sequence inserted downstream of amino acid 1656, 1720, or 1900 corresponding to SEQ ID NO: 65. In other embodiments, the first XTEN sequence is inserted immediately downstream of amino acid 26 corresponding to SEQ ID NO: 65, a second XTEN sequence is inserted downstream of amino acid 1656 corresponding to SEQ ID NO: 65, and a third XTEN sequence is inserted downstream of amino acid 1720 or 1900 corresponding to SEQ ID NO: 65. In yet other embodiments, the first XTEN sequence is inserted immediately downstream of amino acid 26 corresponding to SEQ ID NO: 65, a second XTEN sequence is inserted downstream of amino acid 1720 corresponding to SEQ ID NO: 65, and a third XTEN sequence is inserted downstream of amino acid 1900 corresponding to SEQ ID NO: 65. In still other embodiments, the first XTEN sequence is inserted immediately downstream of amino acid 403 corresponding to SEQ ID NO: 65, a second XTEN sequence is inserted downstream of amino acid 1656 corresponding to SEQ ID NO: 65, and a third XTEN sequence is inserted downstream of amino acid 1720 or 1900 corresponding to SEQ ID NO: 65. In other embodiments, the first XTEN sequence is inserted immediately downstream of amino acid 403 or 1656 corresponding to SEQ ID NO: 65, a second XTEN sequence is inserted downstream of amino acid 1720 corresponding to SEQ ID NO: 65, and a third XTEN sequence is inserted downstream of amino acid 1900 corresponding to SEQ ID NO: 65. In other embodiments, the first XTEN sequence is inserted immediately downstream of amino acid 18, 26, 40, 399, 403, 1711, 1720, 1725, 1900, 1905, or 1910 corresponding to SEQ ID NO: 65, a second XTEN sequence is inserted downstream of amino acid 745 corresponding to SEQ ID NO: 65, and a third XTEN sequence is inserted downstream of amino acid 2332 corresponding to SEQ ID NO: 65.

In other embodiments, a FVIII protein in the invention comprises four XTEN sequences, a first XTEN sequence inserted into a first insertion site, a second XTEN sequence inserted into a second insertion site, a third XTEN sequence inserted into a third insertion site, and a fourth XTEN sequence inserted into a fourth insertion site. The first, second, third, and fourth XTEN sequences can be identical, different, or combinations thereof. In some embodiments, the FVIII protein comprising four XTEN sequences can further comprise a mutation or substitution, e.g., amino acid 1648 corresponding to SEQ ID NO: 65, e.g., R1648A. Non-limiting examples of the first, second, third, and fourth XTEN insertion sites are listed in Table 13.

TABLE 13

| Exemplary Insertion Sites for Four XTENs | | | | | | | |
|---|---|---|---|---|---|---|---|
| Insertion 1 | | Insertion 2 | | Insertion 3 | | Insertion 4 | |
| Insertion Site | Domain | Insertion Site | Domain | Insertion Site | Domain | Insertion Site | Domain |
| 26 | A1 | 403 | A2 | 1656 | a3 | 1720 | A3 |
| 26 | A1 | 403 | A2 | 1656 | a3 | 1900 | A3 |
| 26 | A1 | 403 | A2 | 1720 | A3 | 1900 | A3 |
| 26 | A1 | 1656 | a3 | 1720 | A3 | 1900 | A3 |
| 403 | A2 | 1656 | a3 | 1720 | A3 | 1900 | A3 |
| 0040 | A1 | 0403 | A2 | 745 | B | 2332 | CT |
| 0040 | A1 | 0403 | A2 | 745 | B | 2332 | CT |
| 0018 | A1 | 0409 | A2 | 745 | B | 2332 | CT |
| 0040 | A1 | 0409 | A2 | 745 | B | 2332 | CT |
| 0040 | A1 | 0409 | A2 | 745 | B | 2332 | CT |
| 0018 | A1 | 0409 | A2 | 745 | B | 2332 | CT |
| 0040 | A1 | 1720 | A3 | 745 | B | 2332 | CT |
| 0026 | A1 | 1720 | A3 | 745 | B | 2332 | CT |
| 0018 | A1 | 1720 | A3 | 745 | B | 2332 | CT |
| 0018 | A1 | 1720 | A3 | 745 | B | 2332 | CT |
| 0018 | A1 | 1720 | A3 | 745 | B | 2332 | CT |
| 0026 | A1 | 1720 | A3 | 745 | B | 2332 | CT |
| 0018 | A1 | 1720 | A3 | 745 | B | 2332 | CT |
| 0018 | A1 | 1900 | A3 | 745 | B | 2332 | CT |
| 0018 | A1 | 1900 | A3 | 745 | B | 2332 | CT |
| 0026 | A1 | 1900 | A3 | 745 | B | 2332 | CT |
| 0040 | A1 | 1900 | A3 | 745 | B | 2332 | CT |
| 0040 | A1 | 1905 | A3 | 745 | B | 2332 | CT |
| 0018 | A1 | 1905 | A3 | 745 | B | 2332 | CT |
| 0040 | A1 | 1905 | A3 | 745 | B | 2332 | CT |
| 0026 | A1 | 1905 | A3 | 745 | B | 2332 | CT |
| 0018 | A1 | 1905 | A3 | 745 | B | 2332 | CT |
| 0018 | A1 | 1905 | A3 | 745 | B | 2332 | CT |
| 0018 | A1 | 1910 | A3 | 745 | B | 2332 | CT |
| 0018 | A1 | 1910 | A3 | 745 | B | 2332 | CT |
| 0040 | A1 | 1910 | A3 | 745 | B | 2332 | CT |
| 0026 | A1 | 1910 | A3 | 745 | B | 2332 | CT |
| 0018 | A1 | 1910 | A3 | 745 | B | 2332 | CT |
| 0026 | A1 | 1910 | A3 | 745 | B | 2332 | CT |
| 0040 | A1 | 1910 | A3 | 745 | B | 2332 | CT |
| 0018 | A1 | 1910 | A3 | 745 | B | 2332 | CT |
| 0409 | A2 | 1720 | A3 | 745 | B | 2332 | CT |
| 0403 | A2 | 1720 | A3 | 745 | B | 2332 | CT |
| 0409 | A2 | 1720 | A3 | 745 | B | 2332 | CT |
| 0403 | A2 | 1720 | A3 | 745 | B | 2332 | CT |
| 0403 | A2 | 1720 | A3 | 745 | B | 2332 | CT |
| 0403 | A2 | 1900 | A3 | 745 | B | 2332 | CT |
| 0403 | A2 | 1900 | A3 | 745 | B | 2332 | CT |
| 0409 | A2 | 1900 | A3 | 745 | B | 2332 | CT |
| 0403 | A2 | 1900 | A3 | 745 | B | 2332 | CT |
| 0403 | A2 | 1900 | A3 | 745 | B | 2332 | CT |
| 0409 | A2 | 1900 | A3 | 745 | B | 2332 | CT |
| 0409 | A2 | 1905 | A3 | 745 | B | 2332 | CT |
| 0403 | A2 | 1905 | A3 | 745 | B | 2332 | CT |
| 0403 | A2 | 1905 | A3 | 745 | B | 2332 | CT |
| 0403 | A2 | 1905 | A3 | 745 | B | 2332 | CT |
| 0409 | A2 | 1905 | A3 | 745 | B | 2332 | CT |
| 0403 | A2 | 1905 | A3 | 745 | B | 2332 | CT |
| 0409 | A2 | 1910 | A3 | 745 | B | 2332 | CT |
| 0403 | A2 | 1910 | A3 | 745 | B | 2332 | CT |

TABLE 13-continued

| Exemplary Insertion Sites for Four XTENs | | | | | | | |
|---|---|---|---|---|---|---|---|
| Insertion 1 | | Insertion 2 | | Insertion 3 | | Insertion 4 | |
| Insertion Site | Domain | Insertion Site | Domain | Insertion Site | Domain | Insertion Site | Domain |
| 0403 | A2 | 1910 | A3 | 745 | B | 2332 | CT |
| 0403 | A2 | 1910 | A3 | 745 | B | 2332 | CT |
| 0403 | A2 | 1910 | A3 | 745 | B | 2332 | CT |
| 1720 | A3 | 1900 | A3 | 745 | B | 2332 | CT |
| 1720 | A3 | 1905 | A3 | 745 | B | 2332 | CT |
| 1720 | A3 | 1910 | A3 | 745 | B | 2332 | CT |
| 1720 | A3 | 1910 | A3 | 745 | B | 2332 | CT |
| 0403 | A2 | 1656 | a3 | 1720 | A3 | 2332 | CT |
| 0403 | A2 | 1656 | a3 | 1900 | A3 | 2332 | CT |
| 0403 | A2 | 1720 | A3 | 1900 | A3 | 2332 | CT |
| 1656 | a3 | 1720 | A3 | 1900 | A3 | 2332 | CT |
| 0018 | A1 | 0403 | A2 | 1656 | a3 | 2332 | CT |
| 0018 | A1 | 0403 | A2 | 1720 | A3 | 2332 | CT |
| 0018 | A1 | 0403 | A2 | 1900 | A3 | 2332 | CT |
| 0018 | A1 | 1656 | a3 | 1720 | A3 | 2332 | CT |
| 0018 | A1 | 1656 | a3 | 1900 | A3 | 2332 | CT |
| 0018 | A1 | 1720 | A3 | 1900 | A3 | 2332 | CT |
| 0018 | A1 | 0403 | A2 | 0745 | B | 2332 | CT |
| 0018 | A1 | 0745 | B | 1720 | A3 | 2332 | CT |
| 0018 | A1 | 0745 | B | 1900 | A3 | 2332 | CT |
| 0403 | A2 | 0745 | B | 1720 | A3 | 2332 | CT |
| 0403 | A2 | 0745 | B | 1900 | A3 | 2332 | CT |
| 0745 | B | 1720 | A3 | 1900 | A3 | 2332 | CT |
| 0188 | A1 | 1900 | A3 | 0745 | B | 2332 | CT |
| 0599 | | 1900 | A3 | 0745 | B | 2332 | CT |
| 2068 | | 1900 | A3 | 0745 | B | 2332 | CT |
| 2171 | | 1900 | A3 | 0745 | B | 2332 | CT |
| 2227 | | 1900 | A3 | 0745 | B | 2332 | CT |
| 2277 | | 1900 | A3 | 0745 | B | 2332 | CT |

In some embodiments, a FVIII protein comprises five XTEN sequences, a first XTEN sequence inserted into a first insertion site, a second XTEN sequence inserted into a second insertion site, a third XTEN sequence inserted into a third XTEN insertion site, a fourth XTEN sequence inserted into a fourth XTEN insertion site, and a fifth XTEN sequence inserted into a fifth XTEN insertion site. The first, second, third, fourth, of fifth XTEN sequences can be identical, different, or combinations thereof. Non-limiting examples of the first, second, third, fourth, and fifth insertion sites are listed in Table 14.

TABLE 14

| Exemplary Insertion Sites for Five XTENs | | | | |
|---|---|---|---|---|
| XTEN Insertion 1 | XTEN insertion 2 | XTEN Insertion 3 | XTEN Insertion 4 | XTEN Insertion 5 |
| 0403 | 1656 | 1720 | 1900 | 2332 |
| 0018 | 0403 | 1656 | 1720 | 2332 |
| 0018 | 0403 | 1656 | 1900 | 2332 |
| 0018 | 0403 | 1720 | 1900 | 2332 |
| 0018 | 1656 | 1720 | 1900 | 2332 |
| 0018 | 0403 | 0745 | 1720 | 2332 |
| 0018 | 0403 | 0745 | 1900 | 2332 |
| 0018 | 0745 | 1720 | 1900 | 2332 |
| 0403 | 0745 | 1720 | 1900 | 2332 |

In certain embodiments, a FVIII protein comprises six XTEN sequences, a first XTEN sequence inserted into a first XTEN insertion site, a second XTEN sequence inserted into a second XTEN insertion site, a third XTEN sequence inserted into a third XTEN insertion site, a fourth XTEN sequence inserted into a fourth XTEN insertion site, a fifth XTEN sequence inserted into a fifth XTEN insertion site, and a sixth XTEN sequence inserted into a sixth XTEN insertion site. The first, second, third, fourth, fifth, or sixth XTEN sequences can be identical, different, or combinations thereof. Examples of the six XTEN insertion sites include, but are not limited to the insertion sites listed in Table 15.

TABLE 15

| Exemplary XTEN Insertion Sites for Six XTENs | | | | | |
|---|---|---|---|---|---|
| XTEN Insertion 1 | XTEN insertion 2 | XTEN Insertion 3 | XTEN Insertion 4 | XTEN Insertion 5 | XTEN Insertion 5 |
| 0018 | 0403 | 1656 | 1720 | 1900 | 2332 |
| 0018 | 0403 | 0745 | 1720 | 1900 | 2332 |

In a particular example, a first XTEN is inserted between amino acids 26 and 27 corresponding to SEQ ID NO: 65, and a second XTEN is inserted between amino acids 1720 and 1721 corresponding to SEQ ID NO: 65 (full-length mature FVIII). In another example, a first XTEN is inserted between amino acids 403 and 404 corresponding to SEQ ID NO: 65, and a second XTEN is inserted between amino acids 1720 and 1721 corresponding to SEQ ID NO: 65. In some examples, a first XTEN is inserted between amino acids 1656 and 1657 corresponding to SEQ ID NO: 65, and a second XTEN is inserted between amino acids 1720 and 1721 corresponding to SEQ ID NO: 65. In other examples, a first XTEN is inserted between amino acids 26 and 27 corresponding to SEQ ID NO: 65, a second XTEN is inserted between amino acids 1656 and 1657 corresponding to SEQ ID NO: 65, and a third XTEN is inserted between amino acids 1720 and 1721 corresponding to SEQ ID NO: 65. In yet other embodiments, a first XTEN is inserted between amino acids 403 and 404 corresponding to SEQ ID NO: 65, a second XTEN is inserted between amino acids 1656 and 1657 corresponding to SEQ ID NO: 65, and a third XTEN is inserted between amino acids 1720 and 1721 corresponding to SEQ ID NO: 65. In still other embodiments, a first XTEN is inserted between amino acids 403 and 404 corresponding to SEQ ID NO: 65, a second XTEN is inserted between amino acids 1656 and 1657 corresponding to SEQ ID NO: 65, and a third XTEN is inserted between amino acids 1720 and 1721 corresponding to SEQ ID NO: 65. In certain embodiments, a first XTEN is inserted between amino acids 26 and 27 corresponding to SEQ ID NO: 65, a second XTEN is inserted between amino acids 1720 and 1721 corresponding to SEQ ID NO: 65, and a third XTEN is inserted between amino acids 1900 and 1901 corresponding to SEQ ID NO: 65. In some embodiments, a first XTEN is inserted between amino acids 26 and 27 corresponding to SEQ ID NO: 65, a second XTEN is inserted between amino acids 1656 and 1657 corresponding to SEQ ID NO: 65, a third XTEN is inserted between amino acids 1720 and 1721 corresponding to SEQ ID NO: 65, and a fourth XTEN is inserted between 1900 and 1901 corresponding to SEQ ID NO: 65.

In a particular embodiment, an XTEN sequence is inserted between amino acids 745 and 746 of a full-length Factor VIII or the corresponding insertion site of the B-domain deleted Factor VIII.

In some embodiments, a chimeric protein of the invention comprises two polypeptide sequences, a first polypeptide sequence comprising an amino acid sequence at least about 80%, 90%, 95%, or 100% identical to a sequence selected from FVIII-161 (SEQ ID NO: 69), FVIII-169 (SEQ ID NO: 70), FVIII-170 (SEQ ID NO: 71), FVIII-173 (SEQ ID NO: 72); FVIII-195 (SEQ ID NO: 73); FVIII-196 (SEQ ID NO: 74), FVIII199 (SEQ ID NO: 75), FVIII-201 (SEQ ID NO:

76); FVIII-203 (SEQ ID NO: 77), FVIII-204 (SEQ ID NO: 78), FVIII-205 (SEQ ID NO: 79), FVIII-266 (SEQ ID NO: 80), FVIII-267 (SEQ ID NO: 81), FVIII-268 (SEQ ID NO: 82), FVIII-269 (SEQ ID NO: 83), FVIII-271 (SEQ ID NO: 84) or FVIII-272 (SEQ ID NO: 85) and a second polypeptide sequence comprising an amino acid sequence at least about 80%, 90%, 95%, or 100% identical to a sequence selected from VWF031 (SEQ ID NO: 86), VWF034 (SEQ ID NO: 87), or VWF-036.

II.D. Ig Constant Region or a Portion Thereof

The chimeric protein of the invention also includes two Ig constant region or a portion thereof, a first Ig constant region or a portion thereof fused to a FVIII protein by an optional linker and a second Ig constant region or a portion thereof fused to a VWF protein through the XTEN sequence having less than 288 amino acids. The Ig constant region or a portion thereof can improve pharmacokinetic or pharmacodynamic properties of the chimeric protein in combination with the XTEN sequence and the VWF protein. In certain embodiments, the Ig constant region or a portion thereof extends a half-life of a molecule fused to the Ig constant region or a portion thereof.

An Ig constant region is comprised of domains denoted CH (constant heavy) domains (CH1, CH2, etc.). Depending on the isotype, (i.e. IgG, IgM, IgA, IgD, or IgE), the constant region can be comprised of three or four CH domains. Some isotypes (e.g. IgG) constant regions also contain a hinge region. See Janeway et al. 2001, *Immunobiology*, Garland Publishing, N.Y., N.Y.

An Ig constant region or a portion thereof for producing the chimeric protein of the present invention may be obtained from a number of different sources. In some embodiments, an Ig constant region or a portion thereof is derived from a human Ig. It is understood, however, that the Ig constant region or a portion thereof may be derived from an Ig of another mammalian species, including for example, a rodent (e.g. a mouse, rat, rabbit, guinea pig) or non-human primate (e.g. chimpanzee, macaque) species. Moreover, the Ig constant region or a portion thereof may be derived from any Ig class, including IgM, IgG, IgD, IgA, and IgE, and any Ig isotype, including IgG1, IgG2, IgG3, and IgG4. In one embodiment, the human isotype IgG1 is used.

A variety of the Ig constant region gene sequences (e.g., human constant region gene sequences) are available in the form of publicly accessible deposits. Constant region domains sequence can be selected having a particular effector function (or lacking a particular effector function) or with a particular modification to reduce immunogenicity. Many sequences of antibodies and antibody-encoding genes have been published and suitable Ig constant region sequences (e.g., hinge, CH2, and/or CH3 sequences, or portions thereof) can be derived from these sequences using art recognized techniques. The genetic material obtained using any of the foregoing methods may then be altered or synthesized to obtain polypeptides of the present invention. It will further be appreciated that the scope of this invention encompasses alleles, variants and mutations of constant region DNA sequences.

The sequences of the Ig constant region or a portion thereof can be cloned, e.g., using the polymerase chain reaction and primers which are selected to amplify the domain of interest. To clone a sequence of the Ig constant region or a portion thereof from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, CA (1990); Ho et al. 1989. Gene 77:51; Horton et al. 1993. Methods Enzymol. 217:270). PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250). The cloning of antibody sequences is further described in Newman et al., U.S. Pat. No. 5,658,570, filed Jan. 25, 1995, which is incorporated by reference herein.

An Ig constant region used herein can include all domains and the hinge region or portions thereof. In one embodiment, the Ig constant region or a portion thereof comprises CH2 domain, CH3 domain, and a hinge region, i.e., an Fc region or an FcRn binding partner.

As used herein, the term "Fc region" is defined as the portion of a polypeptide which corresponds to the Fc region of native Ig, i.e., as formed by the dimeric association of the respective Fc domains of its two heavy chains. A native Fc region forms a homodimer with another Fc region. In contrast, the term "genetically-fused Fc region" or "single-chain Fc region" (scFc region), as used herein, refers to a synthetic dimeric Fc region comprised of Fc domains genetically linked within a single polypeptide chain (i.e., encoded in a single contiguous genetic sequence).

In one embodiment, the "Fc region" refers to the portion of a single Ig heavy chain beginning in the hinge region just upstream of the papain cleavage site (i.e. residue 216 in IgG, taking the first residue of heavy chain constant region to be 114) and ending at the C-terminus of the antibody. Accordingly, a complete Fc domain comprises at least a hinge domain, a CH2 domain, and a CH3 domain.

The Fc region of an Ig constant region, depending on the Ig isotype can include the CH2, CH3, and CH4 domains, as well as the hinge region. Chimeric proteins comprising an Fc region of an Ig bestow several desirable properties on a chimeric protein including increased stability, increased serum half-life (see Capon et al., 1989, *Nature* 337:525) as well as binding to Fc receptors such as the neonatal Fc receptor (FcRn) (U.S. Pat. Nos. 6,086,875, 6,485,726, 6,030,613; WO 03/077834; US2003-0235536A1), which are incorporated herein by reference in their entireties.

An Ig constant region or a portion thereof can be an FcRn binding partner. FcRn is active in adult epithelial tissues and expressed in the lumen of the intestines, pulmonary airways, nasal surfaces, vaginal surfaces, colon and rectal surfaces (U.S. Pat. No. 6,485,726). An FcRn binding partner is a portion of an Ig that binds to FcRn.

The FcRn receptor has been isolated from several mammalian species including humans. The sequences of the human FcRn, monkey FcRn, rat FcRn, and mouse FcRn are known (Story et al. 1994, J. Exp. Med. 180:2377). The FcRn receptor binds IgG (but not other Ig classes such as IgA, IgM, IgD, and IgE) at relatively low pH, actively transports the IgG transcellularly in a luminal to serosal direction, and then releases the IgG at relatively higher pH found in the interstitial fluids. It is expressed in adult epithelial tissue (U.S. Pat. Nos. 6,485,726, 6,030,613, 6,086,875; WO 03/077834; US2003-0235536A1) including lung and intestinal epithelium (Israel et al. 1997, Immunology 92:69) renal proximal tubular epithelium (Kobayashi et al. 2002, Am. J. Physiol. Renal Physiol. 282:F358) as well as nasal epithelium, vaginal surfaces, and biliary tree surfaces.

FcRn binding partners useful in the present invention encompass molecules that can be specifically bound by the FcRn receptor including whole IgG, the Fc fragment of IgG, and other fragments that include the complete binding region of the FcRn receptor. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The FcRn binding partners include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of Igs or Ig fragments, or regions, are all based on Kabat et al. 1991, Sequences of Proteins of Immunological Interest, U.S. Department of Public Health, Bethesda, Md.

Fc regions or FcRn binding partners bound to FcRn can be effectively shuttled across epithelial barriers by FcRn, thus providing a non-invasive means to systemically administer a desired therapeutic molecule. Additionally, fusion proteins comprising an Fc region or an FcRn binding partner are endocytosed by cells expressing the FcRn. But instead of being marked for degradation, these fusion proteins are recycled out into circulation again, thus increasing the in vivo half-life of these proteins. In certain embodiments, the portions of Ig constant regions are an Fc region or an FcRn binding partner that typically associates, via disulfide bonds and other non-specific interactions, with another Fc region or another FcRn binding partner to form dimers and higher order multimers.

Two FcRn receptors can bind a single Fc molecule. Crystallographic data suggest that each FcRn molecule binds a single polypeptide of the Fc homodimer. In one embodiment, linking the FcRn binding partner, e.g., an Fc fragment of an IgG, to a biologically active molecule provides a means of delivering the biologically active molecule orally, buccally, sublingually, rectally, vaginally, as an aerosol administered nasally or via a pulmonary route, or via an ocular route. In another embodiment, the chimeric protein can be administered invasively, e.g., subcutaneously, intravenously.

An FcRn binding partner region is a molecule or a portion thereof that can be specifically bound by the FcRn receptor with consequent active transport by the FcRn receptor of the Fc region. Specifically bound refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant KA is higher than $10^6$ $M^{-1}$, or higher than $10^8$ $M^{-1}$. If necessary, non-specific binding can be reduced without substantially affecting specific binding by varying the binding conditions. The appropriate binding conditions such as concentration of the molecules, ionic strength of the solution, temperature, time allowed for binding, concentration of a blocking agent (e.g. serum albumin, milk casein), etc., may be optimized by a skilled artisan using routine techniques.

In certain embodiments, a chimeric protein of the invention comprises one or more truncated Fc regions that are nonetheless sufficient to confer Fc receptor (FcR) binding properties to the Fc region. For example, the portion of an Fc region that binds to FcRn (i.e., the FcRn binding portion) comprises from about amino acids 282-438 of IgG1, EU numbering (with the primary contact sites being amino acids 248, 250-257, 272, 285, 288, 290-291, 308-311, and 314 of the CH2 domain and amino acid residues 385-387, 428, and 433-436 of the CH3 domain. Thus, an Fc region of the invention may comprise or consist of an FcRn binding portion. FcRn binding portions may be derived from heavy chains of any isotype, including IgG1, IgG2, IgG3 and IgG4. In one embodiment, an FcRn binding portion from an antibody of the human isotype IgG1 is used. In another embodiment, an FcRn binding portion from an antibody of the human isotype IgG4 is used.

In another embodiment, the "Fc region" includes an amino acid sequence of an Fc domain or derived from an Fc domain. In certain embodiments, an Fc region comprises at least one of: a hinge (e.g., upper, middle, and/or lower hinge region) domain (about amino acids 216-230 of an antibody Fc region according to EU numbering), a CH2 domain (about amino acids 231-340 of an antibody Fc region according to EU numbering), a CH3 domain (about amino acids 341-438 of an antibody Fc region according to EU numbering), a CH4 domain, or a variant, portion, or fragment thereof. In other embodiments, an Fc region comprises a complete Fc domain (i.e., a hinge domain, a CH2 domain, and a CH3 domain). In some embodiments, an Fc region comprises, consists essentially of, or consists of a hinge domain (or a portion thereof) fused to a CH3 domain (or a portion thereof), a hinge domain (or a portion thereof) fused to a CH2 domain (or a portion thereof), a CH2 domain (or a portion thereof) fused to a CH3 domain (or a portion thereof), a CH2 domain (or a portion thereof) fused to both a hinge domain (or a portion thereof) and a CH3 domain (or a portion thereof). In still other embodiments, an Fc region lacks at least a portion of a CH2 domain (e.g., all or part of a CH2 domain). In a particular embodiment, an Fc region comprises or consists of amino acids corresponding to EU numbers 221 to 447.

The Fc regions denoted as F, F1, or F2 herein may be obtained from a number of different sources. In one embodiment, an Fc region of the polypeptide is derived from a human Ig. It is understood, however, that an Fc region may be derived from an Ig of another mammalian species, including for example, a rodent (e.g. a mouse, rat, rabbit, or guinea pig) or non-human primate (e.g. chimpanzee, macaque) species. Moreover, the polypeptide of the Fc domains or portions thereof may be derived from any Ig class, including IgM, IgG, IgD, IgA and IgE, and any Ig isotype, including IgG1, IgG2, IgG3 and IgG4. In another embodiment, the human isotype IgG1 is used.

In certain embodiments, the Fc variant confers a change in at least one effector function imparted by an Fc region comprising said wild-type Fc domain (e.g., an improvement or reduction in the ability of the Fc region to bind to Fc receptors (e.g. FcγRI, FcγRII, or FcγRIII) or complement proteins (e.g. C1q), or to trigger antibody-dependent cytotoxicity (ADCC), phagocytosis, or complement-dependent cytotoxicity (CDCC)). In other embodiments, the Fc variant provides an engineered cysteine residue.

The Fc regions of the invention may employ art-recognized Fc variants which are known to impart a change (e.g., an enhancement or reduction) in effector function and/or FcR or FcRn binding. Specifically, a binding molecule of the invention may include, for example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US20070248603, US20070286859, US20080057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; 7,404,956, and 7,317,091, each of which is incorporated by reference herein. In one embodiment, the specific change (e.g., the specific substitution of one or more amino acids disclosed in the art) may be made at one or more of the disclosed amino acid positions. In another embodiment, a different change at one or more of the disclosed amino acid positions (e.g., the different substitution of one or more amino acid position disclosed in the art) may be made.

The Fc region or FcRn binding partner of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example, the following single amino acid residues in human IgG1 Fc (Fc γ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wild type proline substituted by alanine at position number 238. As an example, a specific embodiment incorporates the N297A mutation, removing a highly conserved N-glycosylation site. In addition to alanine other amino acids may be substituted for the wild type amino acids at the positions specified above. Mutations may be introduced singly into Fc giving rise to more than one hundred Fc regions distinct from the native Fc. Additionally, combinations of two, three, or more of these individual mutations may be introduced together, giving rise to hundreds more Fc regions. Moreover, one of the Fc region of a construct of the invention may be mutated and the other Fc region of the construct not mutated at all, or they both may be mutated but with different mutations.

Certain of the above mutations may confer new functionality upon the Fc region or FcRn binding partner. For example, one embodiment incorporates N297A, removing a highly conserved N-glycosylation site. The effect of this mutation is to reduce immunogenicity, thereby enhancing circulating half-life of the Fc region, and to render the Fc region incapable of binding to FcγRI, FcγRIIA, FcγRIIB, and FcγRIIIA, without compromising affinity for FcRn (Routledge et al. 1995, Transplantation 60:847; Friend et al. 1999, Transplantation 68:1632; Shields et al. 1995, *J. Biol. Chem.* 276:6591). As a further example of new functionality arising from mutations described above affinity for FcRn may be increased beyond that of wild type in some instances. This increased affinity may reflect an increased "on" rate, a decreased "off" rate or both an increased "on" rate and a decreased "off" rate. Examples of mutations believed to impart an increased affinity for FcRn include, but not limited to, T256A, T307A, E380A, and N434A (Shields et al. 2001, J. Biol. Chem. 276:6591).

Additionally, at least three human Fc gamma receptors appear to recognize a binding site on IgG within the lower hinge region, generally amino acids 234-237. Therefore, another example of new functionality and potential decreased immunogenicity may arise from mutations of this region, as for example by replacing amino acids 233-236 of human IgG1 "ELLG" to the corresponding sequence from IgG2 "PVA" (with one amino acid deletion). It has been shown that FcγRI, FcγRII, and FcγRIII, which mediate various effector functions will not bind to IgG1 when such mutations have been introduced. Ward and Ghetie 1995, Therapeutic Immunology 2:77 and Armour et al. 1999, Eur. J. Immunol. 29:2613.

In one embodiment, the Ig constant region or a portion thereof, e.g., an Fc region, is a polypeptide including the sequence PKNSSMISNTP (SEQ ID NO: 89 or SEQ ID NO: 3 of U.S. Pat. No. 5,739,277) and optionally further including a sequence selected from HQSLGTQ (SEQ ID NO: 90), HQNLSDGK (SEQ ID NO: 91), HQNISDGK (SEQ ID NO: 92), or VISSHLGQ (SEQ ID NO: 93) (or SEQ ID NOs: 11, 1, 2, and 31, respectively of U.S. Pat. No. 5,739,277).

In another embodiment, the immunoglobulin constant region or a portion thereof comprises an amino acid sequence in the hinge region or a portion thereof that forms one or more disulfide bonds with another immunoglobulin constant region or a portion thereof. The disulfide bond by the immunoglobulin constant region or a portion thereof places the first polypeptide comprising FVIII and the second polypeptide comprising the VWF fragment together so that endogenous VWF does not replace the VWF fragment and does not bind to the FVIII. Therefore, the disulfide bond between the first immunoglobulin constant region or a portion thereof and a second immunoglobulin constant region or a portion thereof prevents interaction between endogenous VWF and the FVIII protein. This inhibition of interaction between the VWF and the FVIII protein allows the half-life of the chimeric protein to go beyond the two fold limit. The hinge region or a portion thereof can further be linked to one or more domains of CH1, CH2, CH3, a fragment thereof, and any combinations thereof. In a particular embodiment, the immunoglobulin constant region or a portion thereof is a hinge region and CH2.

In certain embodiments, the Ig constant region or a portion thereof is hemi-glycosylated. For example, the chimeric protein comprising two Fc regions or FcRn binding partners may contain a first, glycosylated, Fc region (e.g., a glycosylated CH2 region) or FcRn binding partner and a second, aglycosylated, Fc region (e.g., an aglycosylated CH2 region) or FcRn binding partner. In one embodiment, a linker may be interposed between the glycosylated and aglycosylated Fc regions. In another embodiment, the Fc region or FcRn binding partner is fully glycosylated, i.e., all of the Fc regions are glycosylated. In other embodiments, the Fc region may be aglycosylated, i.e., none of the Fc moieties are glycosylated.

In certain embodiments, a chimeric protein of the invention comprises an amino acid substitution to an Ig constant region or a portion thereof (e.g., Fc variants), which alters the antigen-independent effector functions of the Ig constant region, in particular the circulating half-life of the protein.

Such proteins exhibit either increased or decreased binding to FcRn when compared to proteins lacking these substitutions and, therefore, have an increased or decreased half-life in serum, respectively. Fc variants with improved affinity for FcRn are anticipated to have longer serum half-lives, and such molecules have useful applications in methods of treating mammals where long half-life of the administered polypeptide is desired, e.g., to treat a chronic disease or disorder (see, e.g., U.S. Pat. Nos. 7,348,004, 7,404,956, and 7,862,820). In contrast, Fc variants with decreased FcRn binding affinity are expected to have shorter half-lives, and such molecules are also useful, for example, for administration to a mammal where a shortened circulation time may be advantageous, e.g. for in vivo diagnostic imaging or in situations where the starting polypeptide has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, and/or liver is desired. In one exemplary embodiment, the chimeric protein of the invention exhibit reduced transport across the epithelium of kidney glomeruli from the vasculature. In another embodiment, the chimeric protein of the invention exhibit reduced transport across the blood brain barrier (BBB) from the brain, into the vascular space. In one embodiment, a protein with altered FcRn binding comprises at least one Fc region or FcRn binding partner (e.g, one or two Fc regions or FcRn binding partners) having one or more amino acid substitutions within the "FcRn binding loop" of an Ig constant region. The FcRn binding loop is comprised of amino acid residues 280-299 (according to EU numbering) of a wild-type, full-length, Fc region. In other embodiments, an Ig constant region or a portion thereof in a chimeric protein of the invention having altered FcRn binding affinity comprises at least one Fc region or FcRn binding partner having one or more amino acid substitutions within the 15 Å FcRn "contact zone." As used herein, the term 15 Å FcRn "contact zone" includes residues at the following positions of a wild-type, full-length Fc moiety: 243-261, 275-280, 282-293, 302-319, 336-348, 367, 369, 372-389, 391, 393, 408, 424, 425-440 (EU numbering). In other embodiments, a Ig constant region or a portion thereof of the invention having altered FcRn binding affinity comprises at least one Fc region or FcRn binding partner having one or more amino acid substitutions at an amino acid position corresponding to any one of the following EU positions: 256, 277-281, 283-288, 303-309, 313, 338, 342, 376, 381, 384, 385, 387, 434 (e.g., N434A or N434K), and 438. Exemplary amino acid substitutions which altered FcRn binding activity are disclosed in International PCT Publication No. WO05/047327 which is incorporated by reference herein.

An Fc region or FcRn binding partner used in the invention may also comprise an art recognized amino acid substitution which alters the glycosylation of the chimeric protein. For example, the Fc region or FcRn binding partner of the chimeric protein linked to a VWF fragment or a FVIII protein may comprise an Fc region having a mutation leading to reduced glycosylation (e.g., N- or O-linked glycosylation) or may comprise an altered glycoform of the wild-type Fc moiety (e.g., a low fucose or fucose-free glycan).

In one embodiment, an unprocessed chimeric protein of the invention may comprise a genetically fused Fc region (i.e., scFc region) having two or more of its constituent Ig constant region or a portion thereof independently selected from the Ig constant region or a portion thereof described herein. In one embodiment, the Fc regions of a dimeric Fc region are the same. In another embodiment, at least two of the Fc regions are different. For example, the Fc regions or FcRn binding partners of the proteins of the invention comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In yet other embodiments, the Fc regions or FcRn binding partners of the protein of the invention may differ in sequence at one or more amino acid positions. For example, at least two of the Fc regions or FcRn binding partners may differ at about 5 amino acid positions (e.g., 1, 2, 3, 4, or 5 amino acid positions), about 10 positions, about 15 positions, about 20 positions, about 30 positions, about 40 positions, or about 50 positions).

II.E. Linkers

The chimeric protein of the present invention further comprises one or more linkers. One type of the linkers is a cleavable linker, which can be cleaved by various proteases when administered to a subject in vivo, e.g., at a site of coagulation. In one embodiment, the cleavable linker allows cleavage of moiety, e.g., a VWF protein, from the XTEN sequence, thus from the chimeric protein at the site of the coagulation cascade, thereby allowing activated FVIII (FVIIIa) to have its FVIIIa activity. Another type of the linkers is a processable linker, which contains an intracellular cleavage site and thus can be cleaved by an intracellular processing enzyme in a host cell, allowing convenient expression of a polypeptide and formation of a chimeric protein.

One or more linkers can be present between any two proteins in the chimeric protein. In one embodiment, a chimeric protein comprises a first polypeptide which comprises (i) a FVIII protein and (ii) a first Ig constant region or a portion thereof and a second polypeptide which comprises (iii) a VWF protein, (iv) a linker (e.g., a cleavable linker), (v) an XTEN sequence, and (vi) a second Ig constant region or a portion thereof. In another embodiment, a chimeric protein comprises a first polypeptide which comprises (i) a FVIII protein and (ii) a first Ig constant region or a portion thereof and a second polypeptide which comprises (iii) a VWF protein, (iv) an XTEN sequence, (v) a linker (e.g., a cleavable linker), and (vi) a second Ig constant region or a portion thereof. In other embodiments, a chimeric protein comprises a first polypeptide which comprises (i) a FVIII protein and (ii) a first Ig constant region or a portion thereof and a second polypeptide which comprises (iii) a VWF protein, (iv) a first linker (e.g., a cleavable linker), (v) an XTEN sequence, (vi) a second linker (e.g., a cleavable linker), and (vii) a second Ig constant region or a portion thereof. In some embodiments, the first polypeptide further comprises a linker, e.g., a cleavable linker between the FVIII protein and the first Ig constant region.

In certain embodiments, a chimeric protein comprises a single chain comprising (i) a FVIII protein, (ii) a first Ig constant region or a portion thereof, (iii) a linker (e.g., a processable linker), (iv) a VWF protein, (v) an XTEN sequence, and (vi) a second Ig constant region or a portion thereof. In other embodiments, a chimeric protein comprises a single chain comprising (i) a FVIII protein, (ii) a first Ig constant region or a portion thereof, (iii) a first linker (e.g., a processable linker), (iv) a VWF protein, (v) a second linker (e.g., a cleavable linker), (vi) an XTEN sequence, and (vii) a second Ig constant region or a portion thereof. The processable linker can be processed after the chimeric protein is expressed in the host cell; thus the chimeric protein produced in the host cell can be in the final form comprising two or three polypeptide chains.

The linker useful in the present invention can comprise any organic molecule. In one embodiment, the linker comprises a polymer, e.g., polyethylene glycol (PEG) or hydroxyethyl starch (HES). In another embodiment, the linker comprises an amino acids sequence. The linker can comprise at least about 10, 20, 30, 40, 50, 60, 70, 80, 90, 100, 150, 200, 300, 400,500, 600, 700, 800, 900, 1000, 1100, 1200, 1300, 1400, 1500, 1600, 1700, 1800, 1900, or 2000 amino acids. The linker can comprise 1-5 amino acids, 1-10 amino acids, 1-20 amino acids, 10-50 amino acids, 50-100 amino acids, 100-200 amino acids, 200-300 amino acids, 300-400 amino acids, 400-500 amino acids, 500-600 amino acids, 600-700 amino acids, 700-800 amino acids, 800-900 amino acids, or 900-1000 amino acids. In one embodiment, the linker comprises an XTEN sequence. Additional examples of XTEN can be used according to the present invention and are disclosed in US Patent Publication Nos. 2010/0239554 A1, 2010/0323956 A1, 2011/0046060 A1, 2011/0046061 A1, 2011/0077199 A1, or 2011/0172146 A1, or International Patent Publication Nos. WO 2010091122 A1, WO 2010144502 A2, WO 2010144508 A1, WO 2011028228 A1, WO 2011028229 A1, or WO 2011028344 A2. In another embodiment, the linker is a PAS sequence.

In one embodiment, the linker is a polymer, e.g., polyethylene glycol (PEG) or hydroxyethyl starch (HES). In another embodiment, the linker is an amino acid sequence. The linker can comprise at least about 10, 20, 30, 40, 50, 60, 70, 80, 90, 100, 150, 200, 300, 400, 500, 600, 700, 800, 900, 1000, 1100, 1200, 1300, 1400, 1500, 1600, 1700, 1800, 1900, or 2000 amino acids. The linker can comprise 1-5 amino acids, 1-10 amino acids, 1-20 amino acids, 10-50 amino acids, 50-100 amino acids, 100-200 amino acids, 200-300 amino acids, 300-400 amino acids, 400-500 amino acids, 500-600 amino acids, 600-700 amino acids, 700-800 amino acids, 800-900 amino acids, or 900-1000 amino acids.

Examples of linkers are well known in the art. In one embodiment, the linker comprises the sequence $G_n$. The linker can comprise the sequence $(GA)_n$. The linker can comprise the sequence $(GGS)_n$. In other embodiments, the linker comprises $(GGGS)_n$ (SEQ ID NO: 101). In still other embodiments, the linker comprises the sequence $(GGS)_n$ $(GGGGS)_n$ (SEQ ID NO: 95). In these instances, n may be an integer from 1-100. In other instances, n may be an integer from 1-20, i.e., 1, 2, 3, 4, 5, 6, 7, 8, 9, 10, 11, 12, 13, 14, 15, 16, 17, 18, 19, or 20. Examples of linkers include, but are not limited to, GGG, SGGSGGS (SEQ ID NO: 96), GGSGGSGGSGGSGGG (SEQ ID NO: 97), GGSGGSGGGGSGGGGS (SEQ ID NO: 98), GGSGGSGGSGGSGGSGGS (SEQ ID NO: 99), or GGGGSGGGGSGGGGS (SEQ ID NO: 100). The linker does not eliminate or diminish the VWF protein activity or the clotting activity of Factor VIII. Optionally, the linker enhances the VWF protein activity or the clotting activity of Factor VIII protein, e.g., by further diminishing the effects of steric hindrance and making the VWF protein or Factor VIII portion more accessible to its target binding site.

In one embodiment, the linker useful for the chimeric protein is 15-25 amino acids long. In another embodiment, the linker useful for the chimeric protein is 15-20 amino acids long. In some embodiments, the linker for the chimeric protein is 10-25 amino acids long. In other embodiments, the linker for the chimeric protein is 15 amino acids long. In still other embodiments, the linker for the chimeric protein is $(GGGGS)_n$ (SEQ ID NO: 94) where G represents glycine, S represents serine and n is an integer from 1-20.

II.F. Cleavage Sites

A cleavable linkers can incorporate a moiety capable of being cleaved either chemically (e.g., hydrolysis of an ester bond), enzymatically (i.e., incorporation of a protease cleavage sequence), or photolytically (e.g., a chromophore such as 3-amino-3-(2-nitrophenyl) proprionic acid (ANP)) in order to release one molecule from another.

In one embodiment, a cleavable linker comprises one or more cleavage sites at the N-terminus or C-terminus or both. In another embodiment, the cleavable linker consists essentially of or consists of one or more cleavable sites. In other embodiments, the cleavable linker comprises heterologous amino acid linker sequences described herein or polymers and one or more cleavable sites.

In certain embodiments, a cleavable linker comprises one or more cleavage sites that can be cleaved in a host cell (i.e., intracellular processing sites). Non limiting examples of the cleavage site include RRRR (SEQ ID NO: 102), RKRRKR (SEQ ID NO: 103), and RRRRS (SEQ ID NO: 104).

In some embodiments, a cleavable linker comprises an a1 region from FVIII, an a2 region from FVIII, an a3 region from FVIII, a thrombin cleavable site which comprises X-V-P-R (SEQ ID NO: 105) and a PAR1 exosite interaction motif, wherein X is an aliphatic amino acid, or any combinations thereof. comprises the a2 region which comprises an amino acid sequence at least about 80%, about 85%, about 90%, about 95%, or 100% identical to Glu720 to Arg740 corresponding to full-length FVIII, wherein the a2 region is capable of being cleaved by thrombin. In a particular embodiment, a cleavable linker useful for the invention comprises an a2 region which comprises ISDKNTGDYYEDSYEDISAYLLSKNNAIEPRSFS (SEQ ID NO: 106). In other embodiments, a cleavable linker for the invention comprises the a1 region which comprises an amino acid sequence at least about 80%, about 85%, about 90%, about 95%, or 100% identical to Met337 to Arg372 corresponding to full-length FVIII, wherein the a1 region is capable of being cleaved by thrombin. In a particular embodiment, the a1 region comprises ISMKNNEEAE-DYDDDLTDSEMDVVRFDDDNSPSFIQIRSV (SEQ ID NO: 107). In some embodiments, a cleavable linker of the invention comprises the a3 region which comprises an amino acid sequence at least about 80%, about 85%, about 90%, about 95%, or 100% identical to Glu1649 to Arg1689 corresponding to full-length FVIII, wherein the a3 region is capable of being cleaved by thrombin. In a specific embodiment, a cleavable linker for the invention comprises an a3 region comprises ISEITRTTLQSDQEEIDYDDTIS-VEMKKEDFDIYDEDENQSPRSFQ (SEQ ID NO: 108).

In other embodiments, a cleavable linker comprises the thrombin cleavage site which comprises X-V-P-R (SEQ ID NO: 105) and the PAR1 exosite interaction motif and wherein the PAR1 exosite interaction motif comprises S-F-L-L-R-N(SEQ ID NO: 109). The PAR1 exosite interaction motif can further comprise an amino acid sequence selected from P, P-N, P-N-D, P-N-D-K (SEQ ID NO: 110), P-N-D-K-Y (SEQ ID NO: 111), P-N-D-K-Y-E (SEQ ID NO: 112), P-N-D-K-Y-E-P (SEQ ID NO: 113), P-N-D-K-Y-E-P-F (SEQ ID NO: 114), P-N-D-K-Y-E-P-F-W (SEQ ID NO: 115), P-N-D-K-Y-E-P-F-W-E (SEQ ID NO: 116), P-N-D-K-Y-E-P-F-W-E-D (SEQ ID NO: 117), P-N-D-K-Y-E-P-F-W-E-D-E (SEQ ID NO: 118), P-N-D-K-Y-E-P-F-W-E-D-E-E (SEQ ID NO: 119), P-N-D-K-Y-E-P-F-W-E-D-E-E-S (SEQ ID NO: 120), or any combination thereof. In some embodiments, the aliphatic amino acid is selected from Glycine, Alanine, Valine, Leucine, or Isoleucine.

In other embodiments, a cleavable linker comprises one or more cleavage sites that are cleaved by a protease after a chimeric protein comprising the cleavable linker is administered to a subject. In one embodiment, the cleavage site is cleaved by a protease selected from the group consisting of factor XIa, factor XIIa, kallikrein, factor VIIa, factor IXa, factor Xa, factor IIa (thrombin), Elastase-2, MMP-12, MMP-13, MMP-17, and MMP-20. In another embodiment, the cleavage site is selected from the group consisting of a FXIa cleavage site (e.g., KLTR↓AET (SEQ ID NO: 121)), a FXIa cleavage site (e.g, DFTR↓VVG (SEQ ID NO: 122)), a FXIIa cleavage site (e.g., TMTRJIVGG (SEQ ID NO: 123)), a Kallikrein cleavage site (e.g., SPFR↓STGG (SEQ ID NO: 124)), a FVIIa cleavage site (e.g., LQVR↓IVGG (SEQ ID NO: 125)), a FIXa cleavage site (e.g., PLGR↓IVGG (SEQ ID NO: 126)), a FXa cleavage site (e.g., IEGR↓TVGG (SEQ ID NO: 127)), a FIIa (thrombin) cleavage site (e.g, LTPR↓SLLV (SEQ ID NO: 128)), a Elastase-2 cleavage site (e.g., LGPV↓SGVP (SEQ ID NO: 129)), a Granzyme-B cleavage (e.g., VAGD↓SLEE (SEQ ID NO: 130)), a MMP-12 cleavage site (e.g., GPAG↓LGGA (SEQ ID NO: 131)), a MMP-13 cleavage site (e.g., GPAG↓LRGA (SEQ ID NO: 132)), a MMP-17 cleavage site (e.g., APLG↓LRLR (SEQ ID NO: 133)), a MMP-20 cleavage site (e.g., PALP↓LVAQ (SEQ ID NO: 134)), a TEV cleavage site (e.g., ENLYFQ↓G (SEQ ID NO: 135)), a Enterokinase cleavage site (e.g., DDDK↓IVGG (SEQ ID NO: 136)), a Protease 3C (PRESCISSION™) cleavage site (e.g., LEVLFQ↓GP (SEQ ID NO: 137)), and a Sortase A cleavage site (e.g., LPKT↓GSES) (SEQ ID NO: 138). In certain embodiments, the FXIa cleavage sites include, but are not limited to, e.g., TQSFNDFTR (SEQ ID NO: 1) and SVSQTSKLTR (SEQ ID NO: 3). Non-limiting exemplary thrombin cleavage sites include, e.g., DFLAEGGGVR (SEQ ID NO: 4), TTKIKPR (SEQ ID NO: 5), LVPRG (SEQ ID NO: 6), DKNTGDYYEDSYEDISAYLLSKN-NAIEPRSFS (SEQ ID NO: 88), or IEPRSFS (SEQ ID NO: 194), and a sequence comprising, consisting essentially of, or consisting of ALRPR (SEQ ID NO: 7) (e.g., ALR-PRVVGGA (SEQ ID NO: 145)).

In a specific embodiment, the cleavage site is TLDPRSFLLRNPNDKYEPFWEDEEK (SEQ ID NO: 146). In another embodiment, the cleavage site comprises DKNTGDYYEDSYEDISAYLLSKNNAIEPRSFS (SEQ ID NO: 88) or a fragment thereof. In one particular embodiment, the cleavage site comprises IEPRSFS (SEQ ID NO: 194). In another embodiment, the cleavage site comprises EPRSFS (SEQ ID NO: 195), wherein the cleavage site is not the full-length a2 region of FVIII. In still another embodiment, the cleavage site comprises IEPR (SEQ ID NO: 200). In another embodiment, the cleavage site comprises IEPR (SEQ ID NO: 200), wherein the cleavage site is not the full-length a2 region of FVIII or does not comprise the full-length a2 region of FVIII. In other embodiments, the cleavage site comprises DKNTGDYYEDSYEDISAYLL-SKNNAIEPRSFS (SEQ ID NO: 88), KNTGDYYEDSYE-DISAYLLSKNNAIEPRSFS (SEQ ID NO: 139), NTGDYYEDSYEDISAYLLSKNNAIEPRSFS (SEQ ID NO: 140), TGDYYEDSYEDISAYLLSKNNAIEPRSFS (SEQ ID NO: 141), GDYYEDSYEDISAYLLSKN-NAIEPRSFS (SEQ ID NO: 142), DYYEDSYEDISAYLL-SKNNAIEPRSFS (SEQ ID NO: 143), YYEDSYEDISAY-LLSKNNAIEPRSFS (SEQ ID NO: 144), YEDSYEDISAYLLSKNNAIEPRSFS (SEQ ID NO: 176), EDSYEDISAYLLSKNNAIEPRSFS (SEQ ID NO: 177), DSYEDISAYLLSKNNAIEPRSFS (SEQ ID NO: 178), SYEDISAYLLSKNNAIEPRSFS (SEQ ID NO: 179), YEDISAYLLSKNNAIEPRSFS (SEQ ID NO: 180), EDIS-AYLLSKNNAIEPRSFS (SEQ ID NO: 181), DISAYLL-SKNNAIEPRSFS (SEQ ID NO: 182), ISAYLLSKN-NAIEPRSFS (SEQ ID NO: 183), SAYLLSKNN AIEPRSFS (SEQ ID NO: 184), AYLLSK AIEPRSFS (SEQ ID NO: 185), YLLSKNNAIEPRSFS (SEQ ID NO: 186), LLSKN-NAIEPRSFS (SEQ ID NO: 187), LSKNNAIEPRSFS (SEQ ID NO: 188), SKNNAIEPRSFS (SEQ ID NO: 189), KNNAIEPRSFS (SEQ ID NO: 190), NNAIEPRSFS (SEQ ID NO: 191), NAIEPRSFS (SEQ ID NO: 192), AIEPRSFS (SEQ ID NO: 193), or IEPRSFS (SEQ ID NO: 194). In other embodiments, the cleavage site comprises DKNTGDYYEDSYEDISAYLLSKNNAIEPRSFS (SEQ ID NO: 88), KNTGDYYEDSYEDISAYLLSKN-NAIEPRSFS (SEQ ID NO: 139), NTGDYYEDSYEDIS-AYLLSKNNAIEPRSFS (SEQ ID NO: 140), TGDYYED-SYEDISAYLLSKNNAIEPRSFS (SEQ ID NO: 141), GDYYEDSYEDISAYLLSKNNAIEPRSFS (SEQ ID NO: 142), DYYEDSYEDISAYLLSKNNAIEPRSFS (SEQ ID NO: 143), YYEDSYEDISAYLLSKNNAIEPRSFS (SEQ ID NO: 144), YEDSYEDISAYLLSKNNAIEPRSFS (SEQ ID NO: 176), EDSYEDISAYLLSKNNAIEPRSFS (SEQ ID NO: 177), DSYEDISAYLLSKNNAIEPRSFS (SEQ ID NO: 178), SYEDISAYLLSKNNAIEPRSFS (SEQ ID NO: 179), YEDISAYLLSKNNAIEPRSFS (SEQ ID NO: 180), EDIS-AYLLSKNNAIEPRSFS (SEQ ID NO: 181), DISAYLL-SKNNAIEPRSFS (SEQ ID NO: 182), ISAYLLSKN-NAIEPRSFS (SEQ ID NO: 183), SAYLLSKNNAIEPRSFS (SEQ ID NO: 184), AYLLSKNNAIEPRSFS (SEQ ID NO: 185), YLLSKNNAIEPRSFS (SEQ ID NO: 186), LLSKN-NAIEPRSFS (SEQ ID NO: 187), LSKNNAIEPRSFS (SEQ ID NO: 188), SKNNAIEPRSFS (SEQ ID NO: 189), KNNAIEPRSFS (SEQ ID NO: 190), NNAIEPRSFS (SEQ ID NO: 191), NAIEPRSFS (SEQ ID NO: 192), AIEPRSFS (SEQ ID NO: 193), or IEPRSFS (SEQ ID NO: 194), wherein the cleavage site is not the full-length FVIII a2 region. In certain embodiments the cleavable linker is cleavable in a thrombin cleavage assay as provided herein or as known in the art.

III. Polynucleotides, Vectors, and Host Cells

Also provided in the invention is a polynucleotide encoding a chimeric protein of the invention. In one embodiment, the first polypeptide chain and the second polypeptide chain can be encoded by a single polynucleotide chain. In another embodiment, the first polypeptide chain and the second polypeptide chain are encoded by two different polynucleotides, i.e., a first nucleotide sequence and a second nucleotide sequence. In another embodiment, the first nucleotide sequence and the second nucleotide sequence are on two different polynucleotides (e.g., different vectors).

The invention includes a polynucleotide encoding a single polypeptide chain (e.g., FVIII(X2)-F1-L3-F2-L2-X1-L1-V), wherein FVIII(X2) comprises a FVIII protein in which an XTEN sequence is inserted at one or more insertion sites, F1 comprises a first Ig constant region or a portion thereof, e.g., a first Fc region, L1 comprises a first linker, V comprises a VWF protein, X1 comprises an XTEN sequence having less than 288 amino acids in length, L2 comprises a second linker, L3 comprises a third linker, and F2 comprises a second Ig constant region or a portion thereof, e.g., a second Fc region. The invention also includes two polynucleotides, a first polynucleotide sequence encoding a first polypeptide which comprises a FVIII protein fused to a first Ig constant region or a portion thereof and a second polynucleotide sequence encoding a second polypeptide which comprises a VWF protein, an XTEN sequence having less than 288 amino acids in length, and a second Ig constant region or a portion thereof. In some embodiments, a chimeric protein comprising two polypeptide chains or three polypeptide chains can be encoded by a single polynucleotide chain, and then processed into two or three (or more) polypeptide chains. In yet other embodiments, a chimeric protein comprising these polypeptide chains can be encoded by two or three polynucleotide chains.

In other embodiments, the set of the polynucleotides further comprises an additional nucleotide chain (e.g., a second nucleotide chain when the chimeric polypeptide is encoded by a single polynucleotide chain or a third nucleotide chain when the chimeric protein is encoded by two polynucleotide chains) which encodes a protein convertase. The protein convertase can be selected from the group consisting of proprotein convertase subtilisin/kexin type 5 (PCSK5 or PC5), proprotein convertase subtilisin/kexin type 7 (PCSK7 or PC5), a yeast Kex 2, proprotein convertase subtilisin/kexin type 3 (PACE or PCSK3), and two or more combinations thereof. In some embodiments, the protein convertase is PACE, PC5, or PC7. In a specific embodiment, the protein convertase is PC5 or PC7. See International Application no. PCT/US2011/043568.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

Expression vectors of the invention will include polynucleotides encoding the chimeric protein described herein. In one embodiment, one or more of the coding sequences for the first polypeptide comprising a FVIII protein and a first Ig constant region, the second polypeptide comprising a VWF protein, an XTEN sequence having less than 288 amino acids, and a second Ig constant region or a portion thereof, or both are operably linked to an expression control sequence. As used herein, two nucleic acid sequences are operably linked when they are covalently linked in such a way as to permit each component nucleic acid sequence to retain its functionality. A coding sequence and a gene expression control sequence are said to be operably linked when they are covalently linked in such a way as to place the expression or transcription and/or translation of the coding sequence under the influence or control of the gene expression control sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding nucleic acid sequence if the gene expression sequence were capable of effecting transcription of that coding nucleic acid sequence such that the resulting transcript is translated into the desired protein or polypeptide.

A gene expression control sequence as used herein is any regulatory nucleotide sequence, such as a promoter sequence or promoter-enhancer combination, which facilitates the efficient transcription and translation of the coding nucleic acid to which it is operably linked. The gene expression control sequence may, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression control sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined coding nucleic acid. The gene expression sequences optionally include enhancer sequences or upstream activator sequences as desired.

Viral vectors include, but are not limited to, nucleic acid sequences from the following viruses: retrovirus, such as Moloney murine leukemia virus, Harvey murine sarcoma virus, murine mammary tumor virus, and Rous sarcoma virus; adenovirus, adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors well-known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

In one embodiment, the virus is an adeno-associated virus, a double-stranded DNA virus. The adeno-associated virus can be engineered to be replication-deficient and is capable of infecting a wide range of cell types and species. It further has advantages such as heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, CA). Other plasmids are well-known to those of ordinary skill in the art. Additionally, plasmids may be custom designed using standard molecular biology techniques to remove and/or add specific fragments of DNA.

In one insect expression system that may be used to produce the proteins of the invention, *Autographa californica* nuclear polyhidrosis virus (AcNPV) is used as a vector to express the foreign genes. The virus grows in *Spodoptera frugiperda* cells. A coding sequence may be cloned into non-essential regions (for example, the polyhedron gene) of the virus and placed under control of an ACNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed. (see, e.g., Smith et al. (1983) *J Virol* 46:584; U.S. Pat. No. 4,215,051). Further examples of this expression system may be found in Ausubel et al., eds. (1989) Current Protocols in Molecular Biology, Vol. 2, Greene Publish. Assoc. & Wiley Interscience.

Another system which can be used to express the proteins of the invention is the glutamine synthetase gene expression system, also referred to as the "GS expression system" (Lonza Biologics PLC, Berkshire UK). This expression system is described in detail in U.S. Pat. No. 5,981,216.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. See, e.g., Logan & Shenk (1984) *Proc Natl Acad Sci USA* 81:3655). Alternatively, the vaccinia 7.5 K promoter may be used. See, e.g., Mackett et al. (1982) *Proc Natl Acad Sci USA* 79:7415; Mackett et al. (1984) *J Virol* 49:857; Panicali et al. (1982) *Proc Natl Acad Sci USA* 79:4927.

To increase efficiency of production, the polynucleotides can be designed to encode multiple units of the protein of the invention separated by enzymatic cleavage sites. The resulting polypeptide can be cleaved (e.g., by treatment with the appropriate enzyme) in order to recover the polypeptide units. This can increase the yield of polypeptides driven by a single promoter. When used in appropriate viral expression systems, the translation of each polypeptide encoded by the mRNA is directed internally in the transcript; e.g., by an internal ribosome entry site, IRES. Thus, the polycistronic construct directs the transcription of a single, large polycistronic mRNA which, in turn, directs the translation of multiple, individual polypeptides. This approach eliminates the production and enzymatic processing of polyproteins and may significantly increase the yield of polypeptides driven by a single promoter.

Vectors used in transformation will usually contain a selectable marker used to identify transformants. In bacterial systems, this can include an antibiotic resistance gene such as ampicillin or kanamycin. Selectable markers for use in cultured mammalian cells include genes that confer resistance to drugs, such as neomycin, hygromycin, and methotrexate. The selectable marker may be an amplifiable selectable marker. One amplifiable selectable marker is the dihydrofolate reductase (DHFR) gene. Simonsen C C et al. (1983) *Proc Natl Acad Sci USA* 80:2495-9. Selectable markers are reviewed by Thilly (1986) Mammalian Cell Technology, Butterworth Publishers, Stoneham, Mass., and the choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, U.S. Pat. No. 4,713,339).

The expression vectors can encode for tags that permit easy purification of the recombinantly produced protein. Examples include, but are not limited to, vector pUR278 (Ruther et al. (1983) *EMBO J* 2:1791), in which coding sequences for the protein to be expressed may be ligated into the vector in frame with the lac z coding region so that a tagged fusion protein is produced; pGEX vectors may be used to express proteins of the invention with a glutathione S-transferase (GST) tag. These proteins are usually soluble and can easily be purified from cells by adsorption to glutathione-agarose beads followed by elution in the presence of free glutathione. The vectors include cleavage sites (thrombin or Factor Xa protease or PRESCISSION PROTEASE™ (Pharmacia, Peapack, N.J.)) for easy removal of the tag after purification.

The expression vector or vectors are then transfected or co-transfected into a suitable target cell, which will express the polypeptides. Transfection techniques known in the art include, but are not limited to, calcium phosphate precipitation (Wigler et al. (1978) *Cell* 14:725), electroporation (Neumann et al. (1982) *EMBO J* 1:841), and liposome-based reagents. A variety of host-expression vector systems may be utilized to express the proteins described herein including both prokaryotic and eukaryotic cells. These include, but are not limited to, microorganisms such as bacteria (e.g., *E. coli*) transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems, including mammalian cells (e.g., HEK 293, CHO, Cos, HeLa, HKB11, and BHK cells).

In one embodiment, the host cell is a eukaryotic cell. As used herein, a eukaryotic cell refers to any animal or plant cell having a definitive nucleus. Eukaryotic cells of animals include cells of vertebrates, e.g., mammals, and cells of invertebrates, e.g., insects. Eukaryotic cells of plants specifically can include, without limitation, yeast cells. A eukaryotic cell is distinct from a prokaryotic cell, e.g., bacteria.

In certain embodiments, the eukaryotic cell is a mammalian cell. A mammalian cell is any cell derived from a mammal. Mammalian cells specifically include, but are not limited to, mammalian cell lines. In one embodiment, the mammalian cell is a human cell. In another embodiment, the mammalian cell is a HEK 293 cell, which is a human embryonic kidney cell line. HEK 293 cells are available as CRL-1533 from American Type Culture Collection, Manassas, VA, and as 293-H cells, Catalog No. 11631-017 or 293-F cells, Catalog No. 11625-019 from Invitrogen (Carlsbad, Calif.). In some embodiments, the mammalian cell is a PER.C6® cell, which is a human cell line derived from retina. PER.C6® cells are available from Crucell (Leiden, The Netherlands). In other embodiments, the mammalian cell is a Chinese hamster ovary (CHO) cell. CHO cells are available from American Type Culture Collection, Manassas, VA (e.g., CHO-K1; CCL-61). In still other embodiments, the mammalian cell is a baby hamster kidney (BHK) cell. BHK cells are available from American Type Culture Collection, Manassas, Va. (e.g., CRL-1632). In some embodiments, the mammalian cell is a HKB11 cell, which is a hybrid cell line of a HEK293 cell and a human B cell line. Mei et al., *Mol. Biotechnol.* 34(2): 165-78 (2006).

In one embodiment, a plasmid including a FVIII(X2)-Fc fusion coding sequence, a VWF protein-L1-X1-L2-Fc coding sequence, or both and a selectable marker, e.g., zeocin resistance, are transfected into HEK 293 cells, for production of a chimeric protein.

In another embodiment, a plasmid including a FVIII-Fc fusion coding sequence, a VWF protein-L1-X-L2-Fc coding sequence, or both and a selectable marker, e.g., zeocin resistance, are transfected into HEK 293 cells, for production of a chimeric protein.

In some embodiments, a first plasmid including a FVIII (X2)-Fc fusion coding sequence and a first selectable marker, e.g., a zeocin resistance gene, and a second plasmid including a VWF protein-L1-X1-L2-Fc coding sequence and a second selectable marker, e.g., a neomycin resistance gene, and a third plasmid including a protein convertase coding sequence and a third selectable marker, e.g., a hygromycin resistance gene, are cotransfected into HEK 293 cells, for production of the chimeric protein. The first and second plasmids can be introduced in equal amounts (i.e., 1:1 molar ratio), or they can be introduced in unequal amounts.

In still other embodiments, a first plasmid including a FVIII-Fc fusion coding sequence and a first selectable marker, e.g., a zeocin resistance gene, and a second plasmid including a VWF protein-L1-X-L2-Fc coding sequence and a second selectable marker, e.g., a neomycin resistance gene, and a third plasmid including a protein convertase coding sequence and a third selectable marker, e.g., a hygromycin resistance gene, are cotransfected into HEK 293 cells, for production of the chimeric protein. The first and second plasmids can be introduced in equal amounts (i.e., 1:1 molar ratio), or they can be introduced in unequal amounts.

In yet other embodiments, a first plasmid including a FVIII(X2)-Fc fusion coding sequence and a first selectable marker, e.g., a zeocin resistance gene, and a second plasmid including a VWF protein-L1-X1-L2-Fc fusion coding sequence and a second selectable marker, e.g., a neomycin resistance gene, and a third plasmid including a protein convertase coding sequence and a third selectable marker, e.g., a hygromycin resistance gene, are cotransfected into HEK 293 cells, for production of the chimeric protein. The first and second plasmids can be introduced in equal amounts (i.e., 1:1 molar ratio), or they can be introduced in unequal amounts.

In certain embodiments, a first plasmid, including a chimeric protein encoding FVIII (with or without XTEN)-F1-L3-F2-L2-X-L1-V coding sequence and a first selectable marker, e.g., a zeocin resistance gene, and a second plasmid including a protein convertase coding sequence and a second selectable marker, e.g., a hygromycin resistance gene, are cotransfected into HEK 293 cells, for production of the chimeric protein. The promoters for the FVIII(X)-F1 coding sequence and the V-L2-X-L1-F2 coding sequence can be different or they can be the same.

In still other embodiments, transfected cells are stably transfected. These cells can be selected and maintained as a stable cell line, using conventional techniques known to those of skill in the art.

Host cells containing DNA constructs of the protein are grown in an appropriate growth medium. As used herein, the term "appropriate growth medium" means a medium containing nutrients required for the growth of cells. Nutrients required for cell growth may include a carbon source, a nitrogen source, essential amino acids, vitamins, minerals, and growth factors. Optionally, the media can contain one or more selection factors. Optionally the media can contain bovine calf serum or fetal calf serum (FCS). In one embodiment, the media contains substantially no IgG. The growth medium will generally select for cells containing the DNA construct by, for example, drug selection or deficiency in an essential nutrient which is complemented by the selectable marker on the DNA construct or co-transfected with the DNA construct. Cultured mammalian cells are generally grown in commercially available serum-containing or serum-free media (e.g., MEM, DMEM, DMEM/F12). In one embodiment, the medium is CD293 (Invitrogen, Carlsbad, CA). In another embodiment, the medium is CD17 (Invitrogen, Carlsbad, CA). Selection of a medium appropriate for the particular cell line used is within the level of those ordinary skilled in the art.

In order to co-express the two polypeptide chains of the chimeric protein, the host cells are cultured under conditions that allow expression of both chains. As used herein, culturing refers to maintaining living cells in vitro for at least a definite time. Maintaining can, but need not include, an increase in population of living cells. For example, cells maintained in culture can be static in population, but still viable and capable of producing a desired product, e.g., a recombinant protein or recombinant fusion protein. Suitable conditions for culturing eukaryotic cells are well known in the art and include appropriate selection of culture media, media supplements, temperature, pH, oxygen saturation, and the like. For commercial purposes, culturing can include the use of any of various types of scale-up systems including shaker flasks, roller bottles, hollow fiber bioreactors, stirred-tank bioreactors, airlift bioreactors, Wave bioreactors, and others.

The cell culture conditions are also selected to allow association of the VWF fragment with the FVIII protein. Conditions that allow expression of the VWF fragment and/or the FVIII protein may include the presence of a source of vitamin K. For example, in one embodiment, stably transfected HEK 293 cells are cultured in CD293 media (Invitrogen, Carlsbad, CA) or OptiCHO media (Invitrogen, Carlsbad, CA) supplemented with 4 mM glutamine.

In one aspect, the present invention is directed to a method of expressing, making, or producing the chimeric protein of the invention comprising a) transfecting a host cell comprising a polynucleotide encoding the chimeric protein and b) culturing the host cell in a culture medium under a condition suitable for expressing the chimeric protein, wherein the chimeric protein is expressed.

In further embodiments, the protein product containing the FVIII protein linked to a first Ig constant region or a portion thereof and/or the VWF protein fused to a second Ig constant region or a portion thereof by an XTEN sequence is secreted into the media. Media is separated from the cells, concentrated, filtered, and then passed over two or three affinity columns, e.g., a protein A column and one or two anion exchange columns.

In certain aspects, the present invention relates to the chimeric protein produced by the methods described herein.

In vitro production allows scale-up to give large amounts of the desired altered polypeptides of the invention. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, hydrophobic interaction chromatography (HIC, chromatography over DEAE-cellulose or affinity chromatography.

IV. Pharmaceutical Composition

Compositions containing the chimeric protein of the present invention may contain a suitable pharmaceutically acceptable carrier. For example, they may contain excipients and/or auxiliaries that facilitate processing of the active compounds into preparations designed for delivery to the site of action.

The pharmaceutical composition can be formulated for parenteral administration (i.e. intravenous, subcutaneous, or intramuscular) by bolus injection. Formulations for injection can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, e.g., pyrogen free water.

Suitable formulations for parenteral administration also include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances, which increase the viscosity of the suspension, including, for example, sodium carboxymethyl cellulose, sorbitol and dextran. Optionally, the suspension may also contain stabilizers. Liposomes also can be used to encapsulate the molecules of the invention for delivery into cells or interstitial spaces. Exemplary pharmaceutically acceptable carriers are physiologically compatible solvents, dispersion media, coatings, antibacterial and antifungal agents, isotonic and absorption delaying agents, water, saline, phosphate buffered saline, dextrose, glycerol, ethanol and the like. In some embodiments, the composition comprises isotonic agents, for example, sugars, polyalcohols such as mannitol, sorbitol, or sodium chloride. In other embodiments, the compositions comprise pharmaceutically acceptable substances such as wetting agents or minor amounts of auxiliary substances such as wetting or emulsifying agents, preservatives or buffers, which enhance the shelf life or effectiveness of the active ingredients.

Compositions of the invention may be in a variety of forms, including, for example, liquid (e.g., injectable and infusible solutions), dispersions, suspensions, semi-solid and solid dosage forms. The preferred form depends on the mode of administration and therapeutic application.

The composition can be formulated as a solution, micro emulsion, dispersion, liposome, or other ordered structure suitable to high drug concentration. Sterile injectable solutions can be prepared by incorporating the active ingredient in the required amount in an appropriate solvent with one or a combination of ingredients enumerated above, as required, followed by filtered sterilization. Generally, dispersions are prepared by incorporating the active ingredient into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The active ingredient can be formulated with a controlled-release formulation or device. Examples of such formulations and devices include implants, transdermal patches, and microencapsulated delivery systems. Biodegradable, biocompatible polymers can be used, for example, ethylene vinyl acetate, polyanhydrides, polyglycolic acid, collagen, polyorthoesters, and polylactic acid. Methods for the preparation of such formulations and devices are known in the art. See e.g., Sustained and Controlled Release Drug Delivery Systems, J. R. Robinson, ed., Marcel Dekker, Inc., New York, 1978.

Injectable depot formulations can be made by forming microencapsulated matrices of the drug in biodegradable polymers such as polylactide-polyglycolide. Depending on the ratio of drug to polymer, and the nature of the polymer employed, the rate of drug release can be controlled. Other exemplary biodegradable polymers are polyorthoesters and polyanhydrides. Depot injectable formulations also can be prepared by entrapping the drug in liposomes or microemulsions.

Supplementary active compounds can be incorporated into the compositions. In one embodiment, the chimeric protein of the invention is formulated with another clotting factor, or a variant, fragment, analogue, or derivative thereof. For example, the clotting factor includes, but is not limited to, factor V, factor VII, factor VIII, factor IX, factor X, factor XI, factor XII, factor XIII, prothrombin, fibrinogen, von Willebrand factor or recombinant soluble tissue factor (rsTF) or activated forms of any of the preceding. The clotting factor of hemostatic agent can also include anti-fibrinolytic drugs, e.g., epsilon-amino-caproic acid, tranexamic acid.

Dosage regimens may be adjusted to provide the optimum desired response. For example, a single bolus may be administered, several divided doses may be administered over time, or the dose may be proportionally reduced or increased as indicated by the exigencies of the therapeutic situation. It is advantageous to formulate parenteral compositions in dosage unit form for ease of administration and uniformity of dosage. See, e.g., Remington's Pharmaceutical Sciences (Mack Pub. Co., Easton, Pa. 1980).

In addition to the active compound, the liquid dosage form may contain inert ingredients such as water, ethyl alcohol, ethyl carbonate, ethyl acetate, benzyl alcohol, benzyl benzoate, propylene glycol, 1,3-butylene glycol, dimethylformamide, oils, glycerol, tetrahydrofurfuryl alcohol, polyethylene glycols, and fatty acid esters of sorbitan.

Non-limiting examples of suitable pharmaceutical carriers are also described in Remington's Pharmaceutical Sciences by E. W. Martin. Some examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain pH buffering reagents, and wetting or emulsifying agents.

For oral administration, the pharmaceutical composition can take the form of tablets or capsules prepared by conventional means. The composition can also be prepared as a liquid for example a syrup or a suspension. The liquid can include suspending agents (e.g., sorbitol syrup, cellulose derivatives or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring and sweetening agents. Alternatively, the composition can be presented as a dry product for constitution with water or another suitable vehicle.

For buccal administration, the composition may take the form of tablets or lozenges according to conventional protocols.

For administration by inhalation, the compounds for use according to the present invention are conveniently delivered in the form of a nebulized aerosol with or without excipients or in the form of an aerosol spray from a pressurized pack or nebulizer, with optionally a propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The pharmaceutical composition can also be formulated for rectal administration as a suppository or retention enema, e.g., containing conventional suppository bases such as cocoa butter or other glycerides.

In one embodiment, a pharmaceutical composition comprises a chimeric protein, the polynucleotide encoding the chimeric protein, the vector comprising the polynucleotide, or the host cell comprising the vector, and a pharmaceutically acceptable carrier. The FVIII protein in a chimeric protein has extended half-life compared to wild type FVIII protein or the corresponding FVIII protein without the VWF fragment. In one embodiment, wherein the half-life of the chimeric protein is extended at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than wild type FVIII. In another embodiment, the half-life of Factor VIII is at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours.

In some embodiments, the composition is administered by a route selected from the group consisting of topical administration, intraocular administration, parenteral administration, intrathecal administration, subdural administration and oral administration. The parenteral administration can be intravenous or subcutaneous administration.

In other embodiments, the composition is used to treat a bleeding disease or condition in a subject in need thereof. The bleeding disease or condition is selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath and any combinations thereof. In still other embodiments, the subject is scheduled to undergo a surgery. In yet other embodiments, the treatment is prophylactic or on-demand.

V. Gene Therapy

A chimeric protein thereof of the invention can be produced in vivo in a mammal, e.g., a human patient, using a gene therapy approach to treatment of a bleeding disease or disorder selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath would be therapeutically beneficial. In one embodiment, the bleeding disease or disorder is hemophilia. In another embodiment, the bleeding disease or disorder is hemophilia A. This involves administration of a suitable chimeric protein-encoding nucleic acid operably linked to suitable expression control sequences. In certain embodiment, these sequences are incorporated into a viral vector. Suitable viral vectors for such gene therapy include adenoviral vectors, lentiviral vectors, baculoviral vectors, Epstein Barr viral vectors, papovaviral vectors, vaccinia viral vectors, herpes simplex viral vectors, and adeno associated virus (AAV) vectors. The viral vector can be a replication-defective viral vector. In other embodiments, an adenoviral vector has a deletion in its E1 gene or E3 gene. When an adenoviral vector is used, the mammal may not be exposed to a nucleic acid encoding a selectable marker gene. In other embodiments, the sequences are incorporated into a non-viral vector known to those skilled in the art.

VI. Methods of Using Chimeric Protein

The present invention is directed to a method of using a chimeric protein described herein to prevent or inhibit endogenous VWF binding to a FVIII protein. The present invention is also directed to a method of using a chimeric protein having a FVIII protein linked to XTEN and an Ig constant region or a portion thereof.

One aspect of the present invention is directed to preventing or inhibiting FVIII interaction with endogenous VWF by blocking or shielding the VWF binding site on the FVIII from endogenous VWF and at the same time extending half-life of the chimeric protein using an XTEN sequence in combination with an Ig constant region or a portion thereof, which can also be a half-life extender. In one embodiment, the invention is directed to a method of constructing a FVIII protein having half-life longer than wild-type FVIII. The chimeric protein useful in the method includes any one or more chimeric protein described herein.

Another aspect of the invention includes a method of administering to a subject in need thereof a chimeric protein comprising a FVIII protein having half-life longer than wild-type FVIII, wherein the method comprises administering the chimeric protein described herein to the subject.

In one embodiment, the invention is directed to a method of using an XTEN sequence and an Ig constant region or a portion thereof to improve a half-life of a chimeric protein comprising FVIII protein and a VWF protein, which prevents or inhibits endogenous VWF interaction with a FVIII protein. A FVIII protein linked to an XTEN sequence (e.g., FVIII(X)) and then bound to or associated with a VWF protein fused to an XTEN and an Ig constant region or a portion thereof is shielded or protected from the clearance pathway of VWF and thus has reduced clearance compared to the FVIII protein not bound to the VWF protein. The shielded FVIII protein thus has maximum extension of a half-life compared to a FVIII protein not bound to or associated with the XTEN sequence and the VWF protein. In certain embodiments, the FVIII protein associated with or protected by a VWF protein and linked to an XTEN sequence is not cleared by a VWF clearance receptor. In other embodiments, the FVIII protein associated with or protected by a VWF protein and linked to an XTEN sequence is cleared from the system slower than the FVIII protein that is not associated with or protected by the VWF protein and linked to the XTEN sequence.

In one aspect, the chimeric protein comprising the FVIII protein linked to an XTEN sequence or the FVIII protein bound to or associated with a VWF protein linked to XTEN has reduced clearance from circulation as the VWF protein does not contain a VWF clearance receptor binding site. The VWF protein prevents or inhibits clearance of FVIII bound to or associated with the VWF protein from the system through the VWF clearance pathway. The VWF proteins useful for the present invention can also provide at least one or more VWF-like FVIII protection properties that are provided by endogenous VWF. In certain embodiments, the VWF protein or the XTEN sequence can also mask one or more FVIII clearance receptor binding site, thereby preventing clearance of FVIII by its own clearance pathway.

In some embodiments, the prevention or inhibition of a FVIII protein binding to endogenous VWF by the VWF protein or the XTEN sequence can be in vitro or in vivo.

Also provided is a method of increasing the half-life of a chimeric protein comprising administering the chimeric protein described herein to a subject in need thereof. The half-life of non-activated FVIII bound to or associated with full-length VWF is about 12 to 14 hours in plasma. In VWD type 3, wherein there is almost no VWF in circulation, the half-life of FVIII is only about six hours, leading to symptoms of mild to moderate hemophilia A in such patients due to decreased concentrations of FVIII. The half-life of the chimeric protein linked to or associated with the VWF fragment or the XTEN sequence of the present invention can increase at least about 1.5 times, 1.6 times, 1.7 times, 1.8 times, 1.9 times, 2.0 times, 2.1 times, 2.2 times, 2.3 times, 2.4 times, 2.6 times, 2.7. times, 2.8 times, 2.9 times, 3.0 times, 3.1 times, 3.2 times, 3.3 times, 3.4 times, 3.5 times, 3.6 times, 3.7 times, 3.8 times, 3.9 times, or 4.0 times higher than the half-life of the non-activated FVIII bound to or associated with full-length VWF.

In one embodiment, a chimeric protein comprising a first polypeptide comprising a FVIII protein and a first Ig constant region or a portion thereof and a second polypeptide comprising a VWF protein, an XTEN having less than 288 amino acids, and an Ig constant region or a portion thereof exhibits a half-life at least about 2 times, 2.5 times, 3.0 times, 3.5 times, 4.0 times, 4.5 times, 5.0 times, 5.5 times, 6.0 times, 7 times, 8 times, 9 times, or 10 times higher than a corresponding chimeric protein comprising the same first polypeptide and the second polypeptide without the XTEN sequence or wild type FVIII. In another embodiment, a chimeric protein comprising a first polypeptide comprising a FVIII protein and a first Ig constant region or a portion thereof and a second polypeptide comprising a VWF protein, an XTEN having less than 288 amino acids, and an Ig constant region or a portion thereof exhibits a half-life about 2 to about 5 times, about 3 to about 10 times, about 5 to about 15 times, about 10 to about 20 times, about 15 to about 25 times, about 20 to about 30 times, about 25 to about 35 times, about 30 to about 40 times, about 35 to about 45 times higher than a corresponding chimeric protein comprising the same first polypeptide and the second polypeptide without the XTEN sequence or wild type FVIII. In a specific embodiment, the half-life of a chimeric protein of the invention increases at least about 30, 31, 32, 33, 34, 35, 36, 37, 38, 39, or 40 times higher than the half-life of the wild type FVIII in a FVIII and VWF double knockout mouse.

In certain embodiments, a chimeric protein exhibits a half-life of about 40 hours in mice.

In some embodiments, the half-life of a chimeric protein is longer than the half-life of a FVIII associated with endogenous VWF. In other embodiments, the half-life of the chimeric protein is at least about 1.5 times, 2 times, 2.5 times, 3.5 times, 3.6 times, 3.7 times, 3.8 times, 3.9 times, 4.0 times, 4.5 times, or 5.0 times the half-life of wild type FVIII or a FVIII protein associated with endogenous VWF.

In some embodiments, as a result of the invention the half-life of the chimeric protein is extended compared to a FVIII protein without the VWF protein or wild-type FVIII. The half-life of the chimeric protein of the invention is at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the half-life of a chimeric protein without the VWF protein or wild-type FVIII. In one embodiment, the half-life of FVIII is about 1.5-fold to about 20-fold, about 1.5 fold to about 15 fold, or about 1.5 fold to about 10 fold longer than the half-life of wild-type FVIII. In another embodiment, the half-life of the FVIII is extended about 2-fold to about 10-fold, about 2-fold to about 9-fold, about 2-fold to about 8-fold, about 2-fold to about 7-fold, about 2-fold to about 6-fold, about 2-fold to about 5-fold, about 2-fold to about 4-fold, about 2-fold to about 3-fold, about 2.5-fold to about 10-fold, about 2.5-fold to about 9-fold, about 2.5-fold to about 8-fold, about 2.5-fold to about 7-fold, about 2.5-fold to about 6-fold, about 2.5-fold to about 5-fold, about 2.5-fold to about 4-fold, about 2.5-fold to about 3-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 3-fold to about 4-fold, about 4-fold to about 6 fold, about 5-fold to about 7-fold, or about 6-fold to about 8 fold as compared to wild-type FVIII or a FVIII protein without the VWF protein. In other embodiments, the half-life of the chimeric protein of the invention is at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 40 hours, at least about 48 hours, at least about 60 hours, at least about 72 hours, at least about 84 hours, at least about 96 hours, or at least about 108 hours. In still other embodiments, the half-life of the chimeric protein of the invention is about 15 hours to about two weeks, about 16 hours to about one week, about 17 hours to about one week, about 18 hours to about one week, about 19 hours to about one week, about 20 hours to about one week, about 21 hours to about one week, about 22 hours to about one week, about 23 hours to about one week, about 24 hours to about one week, about 36 hours to about one week, about 48 hours to about one week, about 60 hours to about one week, about 24 hours to about six days, about 24 hours to about five days, about 24 hours to about four days, about 24 hours to about three days, or about 24 hours to about two days.

In some embodiments, the average half-life of the chimeric protein of the invention per subject is about 15 hours, about 16 hours, about 17 hours, about 18 hours, about 19 hours, about 20 hours, about 21 hours, about 22 hours, about 23 hours, about 24 hours (1 day), about 25 hours, about 26 hours, about 27 hours, about 28 hours, about 29 hours, about 30 hours, about 31 hours, about 32 hours, about 33 hours, about 34 hours, about 35 hours, about 36 hours, about 40 hours, about 44 hours, about 48 hours (2 days), about 54 hours, about 60 hours, about 72 hours (3 days), about 84 hours, about 96 hours (4 days), about 108 hours, about 120 hours (5 days), about six days, about seven days (one week), about eight days, about nine days, about 10 days, about 11 days, about 12 days, about 13 days, or about 14 days.

In addition, the invention provides a method of treating or preventing a bleeding disease or disorder comprising administering an effective amount of a chimeric protein. In one embodiment, the bleeding disease or disorder is selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath. In a specific embodiment, the bleeding disease or disorder is hemophilia A.

The chimeric protein comprising an XTEN sequence and an Ig constant region or a portion thereof in combination with a VWF protein described herein, that prevents or inhibits interaction of the FVIII protein with endogenous VWF prepared by the invention, has many uses as will be recognized by one skilled in the art, including, but not limited to methods of treating a subject having a hemostatic disorder and methods of treating a subject in need of a general hemostatic agent. In one embodiment, the invention relates to a method of treating a subject having a hemostatic disorder comprising administering a therapeutically effective amount of the chimeric protein.

The FVIII protein portion in the chimeric protein treats or prevents a hemostatic disorder by serving as a cofactor to Factor IX on a negatively charged phospholipid surface, thereby forming a Xase complex. The binding of activated coagulation factors to a phospholipid surface localizes this process to sites of vascular damage. On a phospholipid surface, Factor VIIIa increases the maximum velocity of Factor X activation by Factor IXa, by approximately 200,000-fold, leading to the large second burst of thrombin generation.

The chimeric protein of the invention can be used to treat any hemostatic disorder. The hemostatic disorders that may be treated by administration of the chimeric protein of the invention include, but are not limited to, hemophilia A, as well as deficiencies or structural abnormalities relating to Factor VIII. In one embodiment, the hemostatic disorder is hemophilia A.

The chimeric protein of the invention can be used prophylactically to treat a subject with a hemostatic disorder. The chimeric protein of the invention can be used to treat an acute bleeding episode in a subject with a hemostatic disorder. In another embodiment, the hemostatic disorder can be the result of a defective clotting factor, e.g., von Willebrand's factor. In one embodiment, the hemostatic disorder is an inherited disorder. In another embodiment, the hemostatic disorder is an acquired disorder. The acquired disorder can result from an underlying secondary disease or condition. The unrelated condition can be, as an example, but not as a limitation, cancer, an auto-immune disease, or pregnancy. The acquired disorder can result from old age or from medication to treat an underlying secondary disorder (e.g. cancer chemotherapy).

The invention also relates to methods of treating a subject that does not have a congenital hemostatic disorder, but has a secondary disease or condition resulting in acquisition of a hemostatic disorder, e.g., due to development of an anti-FVIII antibody or a surgery. The invention thus relates to a method of treating a subject in need of a general hemostatic agent comprising administering a therapeutically effective amount of the chimeric protein prepared by the present methods.

The present invention is also related to methods of reducing immunogenicity of FVIII or inducing less immunogenicity against FVIII comprising administering an effective amount of the chimeric proteins described herein, or the polynucleotides encoding the same.

In one embodiment, the subject in need of a general hemostatic agent is undergoing, or is about to undergo, surgery. The chimeric protein of the invention can be administered prior to, during, or after surgery as a prophylactic regimen. The chimeric protein of the invention can be administered prior to, during, or after surgery to control an acute bleeding episode.

The chimeric protein of the invention can be used to treat a subject having an acute bleeding episode who does not have a hemostatic disorder. The acute bleeding episode can result from severe trauma, e.g., surgery, an automobile accident, wound, laceration gun shot, or any other traumatic event resulting in uncontrolled bleeding. Non limiting examples of bleeding episodes include a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath, and any combinations thereof.

In prophylactic applications, one or more compositions containing the chimeric protein of the invention or a cocktail thereof are administered to a patient not already in the disease state to enhance the patient's resistance or reduce symptoms associated with a disease or disorder. Such an amount is defined to be a "prophylactic effective dose." In therapeutic applications, a relatively high dosage (e.g., from about 1 to 400 mg/kg of polypeptide per dose, with dosages of from 5 to 25 mg being more commonly used for radioimmuno conjugates and higher doses for cytotoxin-drug modified polypeptides) at relatively short intervals is sometimes required until progression of the disease is reduced or terminated, and until the patient shows partial or complete amelioration of symptoms of disease. Thereafter, the patient can be administered a prophylactic regime.

In some embodiments, a chimeric protein or a composition of the invention is used for on-demand treatment, which includes treatment for a bleeding episode, hemarthrosis, muscle bleed, oral bleed, hemorrhage, hemorrhage into muscles, oral hemorrhage, trauma, trauma capitis (head trauma), gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. The subject may be in need of surgical prophylaxis, peri-operative management, or treatment for surgery. Such surgeries include, e.g., minor surgery, major surgery, tooth extraction, tonsillectomy, inguinal herniotomy, synovectomy, total knee replacement, craniotomy, osteosynthesis, trauma surgery, intracranial surgery, intra-abdominal surgery, intrathoracic surgery, or joint replacement surgery.

In one embodiment, the chimeric protein of the present invention is administered intravenously, subcutaneously, intramuscularly, or via any mucosal surface, e.g., orally, sublingually, buccally, nasally, rectally, vaginally or via pulmonary route. The chimeric protein comprising a VWF fragment and a FVIII protein of the present invention can be implanted within or linked to a biopolymer solid support that allows for the slow release of the chimeric protein to the site of bleeding or implanted into bandage/dressing. The dose of the chimeric protein will vary depending on the subject and upon the particular route of administration used. Dosages can range from 0.1 to 100,000 μg/kg body weight. In one embodiment, the dosing range is 0.1-1,000 μg/kg. In another embodiment, the dosing range is 0.1-500 μg/kg. The protein can be administered continuously or at specific timed intervals. In vitro assays may be employed to determine optimal dose ranges and/or schedules for administration. In vitro assays that measure clotting factor activity are known in the art, e.g., STA-CLOT VIIa-rTF clotting assay or ROTEM clotting assay. Additionally, effective doses may be extrapolated from dose-response curves obtained from animal models, e.g., a hemophiliac dog (Mount et al. 2002, *Blood* 99(8):2670).

Having now described the present invention in detail, the same will be more clearly understood by reference to the following examples, which are included herewith for purposes of illustration only and are not intended to be limiting of the invention. All patents, publications, and articles referred to herein are expressly and specifically incorporated herein by reference.

EXAMPLES

Throughout the examples, the following materials and methods were used unless otherwise stated.

Materials and Methods

In general, the practice of the present invention employs, unless otherwise indicated, conventional techniques of chemistry, biophysics, molecular biology, recombinant DNA technology, immunology (especially, e.g., antibody technology), and standard techniques in electrophoresis. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., CS.H.L. Press, Pub. (1999); and Current Protocols in Molecular Biology, eds. Ausubel et al., John Wiley & *Sons* (1992).

Example 1: FVIII-XTEN-Fc/D'D3-XTEN-Fc Heterodimers

The present invention is directed to generate a chimeric FVIII molecule which is coupled to D'D3 domain of von Willebrand Factor (VWF) protein via Fc domain of IgG. Attached D'D3 domain prevents the interaction of FVIII with endogenous VWF multimers. This molecule serves as a platform to incorporate other half-life extension technologies in order to improve the pharmacokinetics of the chimeric protein. XTEN sequences were incorporated into the FVIII B-domain and in between D'D3 and Fc region to increase the half-life of FVIII/VWF heterodimer.

Thrombin cleavage site in between D'D3 and Fc allows the release of D'D3 domain upon the activation of FVIII molecule by thrombin.

Example 2: Plasmid Construction of FVIII-XTEN-Fc/D'D3-Fc Heterodimers

Cloning of VWF050-IHH Triple Mutation in VWF031

IHH triple mutation in Fc prevents interaction with FcRn, thus there is no recycling of Fc containing molecule by FcRn pathway. The 3 mutations in Fc are 1253A, H310A, H435A.

VWF050 was generated by swapping the Fc region of VWF031 plasmid with Fc fragment containing IHH triple mutation between the RsRII and Not 1 restriction sites.

Cloning of VWF057-Cloning VWF-Fc with 144 AE XTEN+35aa thrombin cleavable linker.

```
Oligos
ESC 155-Oligo for 144 AE XTEN in VWF034-rev
CCCCGCCACCGGATCCCCCGCCACCGGATCCCCCGCCACCGGATCCCCC
GCCACCGGAACCTCCACCGCCGCTCGAGGCACCTTCTTCAGTGCTGGTG
GGCGAGCCCGCTGGTGACCCTTCCTC

ESC 156-Oligo for 144 AE XTEN-GS linker in
VWF034-rev
GGGGAAGAGGAAGACTGACGGTCCGCCCAGGAGTTCTGGAGCTGGGCAC
GGTGGGCATGTGTGAGTTTTGTCGCCTCCGCTGCCCCGGGGGACCAGGG
ATCCCCCGCCACCGGATCCCCCGCCACCGGATCCCCCGCCACCGGATCC
CCCGCC

ESC 157-Oligo for 144 AE XTEN in VW-F031-Fwd
GTGAAGCCTGCCAGGAGCCGATATCGGGCGCGCCAACATCAGAGAGCGC
CACCCCTGAAAGTGGTCCCGGGAGCGAGCCAGC
```

PCR was done twice to obtain the 144 AE-XTEN+35 aa GS linker with thrombin cleavage site.

First PCR reaction was done using 144-AE XTEN coding DNA as template and ESC 157/ESC155 primer pair. About 550 bp long PCR product obtained from this reaction was used as template for second PCR reaction and was amplified using ESC 157/156 primer pair. This reaction gave ~700 bp long product. This 700 bp PCR product and VWF034 plasmid was then digested with EcoRV-HF and RsRII. Plasmid backbone from digested.

VWF034 was then used to ligate 700 bp PCR product.

Cloning of VWF058-IHH Triple Mutation in VWF034

IHH triple mutation in Fc prevents interaction with FcRn, thus there is no recycling of Fc containing molecule by FcRn pathway. The 3 mutations in Fc are 1253A, H310A, H435A.

VWF058 was generated by swapping the Fc region of VWF034 plasmid with Fc fragment containing IHH triple mutation between the RsRII and Not 1 restriction sites.

Cloning of FVIII-263-FVIII 205 with IHH Triple Mutation

IHH triple mutation in Fc prevents interaction with FcRn, thus there is no recycling of Fc containing molecule by FcRn pathway. The 3 mutations in Fc are 1253A, H310A, H435A.

FVIII-263 was generated by swapping the Fc region of FVIII 205 plasmid with Fc fragment containing IHH triple mutation between the RsRII and Not 1 restriction sites.

Cloning of FVIII-282-FVIII-Fc with 144 AE XTEN in B-Domain

```
ESC 158-Oligo for 144 AE XTEN in B-domain-fwd
AAGAAGCTTCTCTCAAAACGGCGCGCCAACATCAGAGAGCGCCACCCCTG
AAAGTGGTCCCGGGAGCGAGCCAGCCACATCTGGGTCGGAAACGCCAGGC

ESC 159-Oligo for 144 AE XTEN in B-domain-rev
GGTATCATCATAATCGATTTCCTCTTGATCTGACTGAAGAGTAGTACGAG
TTATTTCAGCTTGATGGCGTTTCAAGACTGGTGGGCTCGAGGCACCTTCT
TCAGTGCTGGTGGGCGAGCCCGCTGGTGACCCTTCCTCAGTGGACGTAGG
```

First PCR reaction was done using 144-AE XTEN coding DNA as template and ESC 158/ESC159 primer pair. About 550 bp long PCR product obtained from this reaction and FVIII 169 plasmid was then digested with AscI and ClaI. Plasmid backbone from digested FVIII 169 was then used to ligate 550 bp PCR product in order to obtain FVIII 282.

Cloning of FVIII-283-FVIII 169 with IHH Triple Mutation

IHH triple mutation in Fc prevents interaction with FcRn, thus there is no recycling of Fc containing molecule by FcRn pathway. The 3 mutations in Fc are I253A, H310A, H435A.

FVIII-283 was generated by swapping the Fc region of FVIII 169 plasmid with Fc fragment containing IHH triple mutation between the RsRII and Not 1 restriction sites.

Example 3: Production of FVIII-XTEN-Fc/D'D3-XTEN-Fc in HEK293 Cells

FIG. 2. Schematic diagram showing the expression of FVIII-XTEN-Fc/D'D3-XTEN-Fc construct. Three plasmids co-transfection was done in HEK293 cells using Polyethylenimine (PEI). First plasmid derives the expression of FVIII-XTEN-Fc, second plasmid expresses D1D2D'D3-XTEN-Fc and the third plasmid expression PACE/furin, which is required to enzymatically remove propeptide, i.e., D1D2 domain from D1D2D'D3-XTEN-Fc. Products of this three plasmid expression system includes of FVIII-XTEN-Fc/D'D3-XTEN-Fc heterodimer, D'D3-XTEN-Fc homodimer and traces of FVIII-XTEN-Fc hemizygous looking species.

Example 4: Purification of FVIII-XTEN-Fc/D'D3-XTEN-Fc Heterodimers

To purify the FVIII-XTEN-Fc/D'D3-XTEN-Fc heterodimers, a tangential flow filtration (TFF) step was used to first concentrate the conditioned media by 10 fold. Products in the filtrate were then further purified using affinity chromatography follow by a desalting column. Purity of the molecule was acceptable by HPLC-SEC and was further confirmed by western blotting. The specific activity of the molecule was comparable to B-domain deleted FVIII, as measured by FVIII activity assay (example 5) and OD280 measurement.

Example 5: Specific Activity of FVIII-XTEN-Fc/D'D3-XTEN-Fc Heterodimers

The activity of FVIII-XTEN-Fc/D'D3-XTEN-Fc heterodimers was measure by FVIII chromogenic assay and activated Partial Thromboplastin Time (aPTT) assay. The specific chromogenic activity and specific aPTT activity of SQ BDD-FVIII, rFVIII169/VWF034 and rFVIII169/VWF057 were listed in Table 16. Compared to SQ BDD-FVIII, we have observed comparable specific chromogenic activities and 60% reduction on the specific aPTT activity for rFVIII169/VWF034 and rFVIII169/VWF057.

TABLE 16

Specific activity of heterodimer variants

| FVIII | SQ BDD-FVIII | rFVIII169/ VWF034 | rFVIII160/ VWF057 |
|---|---|---|---|
| Specific Chromogenic Activity (IU/pmol) | 0.9-2.0 | 1.1-1.2 | 0.8-1.6 |
| Specific aPTT Activity (IU/pmol) | 0.75-1.7 | 0.4 | 0.3-0.6 |

FVIII Chromogenic Assay

The FVIII activity was measured using the COATEST SP FVIII kit from DiaPharma (produce #: K824086) and all incubations were performed on a 37° C. plate heater with shaking.

The WHO 8th International Standard for Blood Coagulation Factor VIII:C, Concentrate, coded 07/350 was used as assay standard, the range of the standard was from 100 mIU/mL to 0.78 mIU/mL. A pooled normal human plasma assay control and testing samples (diluted with 1× Coatest buffer) were added into Immulon 2HB 96-well plates in duplicate (25 μL/well). Freshly prepared IXa/FX/Phospholipid mix (50 μL), 25 μL of 25 mM $CaCl_2$, and 50 μL of FXa substrate were added sequentially into each well with 5 minutes incubation between each addition. After incubating with the substrate, 25 μL of 20% Acetic Acid was added to terminate the color reaction, and the absorbance of OD405 was measured with a SpectraMAX plus (Molecular Devices) instrument. Data were analyzed with SoftMax Pro software (version 5.2). The Lowest Level of Quantification (LLOQ) is 7.8 mIU/mL.

FVIII aPTT Assay

The FVIII aPTT assay was performed on the Sysmex CA-1500 coagulation analyzer as follows: First, 50 uL of manually diluted samples, standards and Controls in aPTT buffer (50 mM Tris, 100 mM NaCl, 1% HSA, pH 7.4) were added by the instrument into the reaction cuvette, followed by adding 50 uL of FVIII-deficient plasma (George King Bio-Medical, product #: 0800). Following incubation at 37° C. for 1 minute, 50 uL of aPTT reagent (Actin® FSL activated cephaloplastin reagent—Dade Behring, reference #B4219-2) was added to the reaction mixture, and incubated at 37° C. for 4 minutes. Subsequently, 50 ul of 20 mM $CaCl_2$ (Dade Behring, reference #ORFO37) was added, and the reaction cuvette was immediately transferred to one of four spectrophotometer channel positions to measure the amount of refracted light in the mixture, which was converted to the onset of clotting by the instrument's software algorithm. Reported clotting time was the length of time from the addition of $CaCl_2$ until the onset of clot formation. Assay standard was generated by diluting the WHO 8th International FVIII Standard into aPTT buffer in a range from 100 mIU/ml to 0.78 mIU/ml. The standard curve was plotted as the clotting time (in seconds) as Y-axis versus the log (base 10) of the FVIII activity (mIU/mL) as X-axis in MS Excel, and the activity of the individual samples was calculated using the formula for the linear regression line of this standard curve. Based on the assay performance, the lower limit of quantization (LLOQ) was 7.8 mIU/mL.

Example 6: Additive Effect of XTEN Insertions on the Half-Life Extension of Heterodimer XTEN insertions were incorporated into the heterodimers for half-life extension. Insertion of a single 288 amino acid (aa) AE-XTEN at FVIII B-domain resulted in a 16.7 hrs half-life of the heterodimer in HemA mice, as demonstrated by rFVIII169/VWF031 in FIG. 3. To further improve the half-life of the heterodimer, a second XTEN insertion at 144 aa or 288 aa length was incorporated into FVIII169/VWF031 either in the FVIII A1 domain or immediate down stream of D'D3 fragment respectively, the heterodimer variants were named as FVIII205/VWF031 and FVIII169/VWF034.

The half-life of rFVIII169/VWF031, rFVIII205/VWF031 and rFVIII169/VWF034 were evaluated in FVIII deficient (HemA) mice by a single intravenous administration of test molecules at 200 IU/kg dose. Plasma samples were collected at designate time points as indicated in FIG. 3, the FVIII activity of the samples were determined by FVIII chromogenic assay, the PK parameters were calculated using WinNonlin-Phoenix program and listed in Table 17.

As shown in FIG. 3 and Table 17, the addition of the second XTEN insertion either at A1 domain of FVIII or down stream of D'D3 further improves the half-life of heterodimer to 29.45 or 31.10 respectively. Furthermore, more than 2-fold improvements on clearance and AUC were also observed from both XTEN insertions.

TABLE 17

PK parameter of heterodimers in HemA mice

| FVIII | XTEN Insertions Insertion 1 | Insertion 2 | $T_{1/2}$ (hr) | MRT (hr) | Cl (mL/hr/kg) | Vss (mL/kg) | AUC_D (kg*hr/mL) |
|---|---|---|---|---|---|---|---|
| rFVIII169/VWF031 | B*-AE288 | | 16.65 | 18.44 | 3.57 | 85.72 | 0.28 |
| rFVIII205/VWF031 | B*-AE288 | A1-AE144 | 29.45 | 36.02 | 1.76 | 63.56 | 0.57 |
| rFVIII169/VWF034 | B*-AE288 | D'D3-AE288 | 31.10 | 34.57 | 1.73 | 59.77 | 0.58 |

Example 7: 144 Aa AE-XTEN Confers Better Half-Life Benefit then 288 Aa AE-XTEN when Inserted in Between D'D3 and Fc Domains Another heterodimer-FVIII169/VWF057 was constructed in the effort of identifying the optimal length of XTEN insertion within the D'D3-XTEN-Fc chain, in which the length of XTEN insertion was reduced to 144aa from 288aa. As shown in FIG. 4, compared to rFVIII169/VWF034, the half-life of rFVIII169/VWF057 was increased from 31 hrs to 42 hrs. Improved clearance and AUC were also observed for rFVIII169/VWF057, data was listed in Table 18. Thus, 144aa AE-XTEN insertion is more optimal than AE-288aa XTEN when inserted between D'D3 and Fc domain of the FVIII-XTEN-Fc/D'D3-XTEN-Fc heterodimers.

TABLE 18

PK parameters of rFVIII169/VWF034 and rFVIII169/VWF057 in HemA mice

| FVIII | $T_{1/2}$ (hr) | MRT (hr) | Cl (mL/hr/kg) | Vss (mL/kg) | AUC_D (kg*hr/mL) |
|---|---|---|---|---|---|
| rFVIII169/VWF034 | 31.10 | 34.57 | 1.73 | 59.77 | 0.58 |
| rFVIII169/VWF057 | 42.23 | 53.24 | 0.97 | 51.44 | 1.03 |

Example 8: Fc Domain Extents the Half-Life of Heterodimer

Fc domains extent its fusion protein's half-life through FcRn mediated recycling pathway. To confirm the necessity of the Fc domain on the half-life extension of the heterodimer, the wild-type Fc domains were replaced by a triple mutant (I253A/H310A/H435A; IHH) in rFVIII205/VWF031 to form rFVIII263/VWF050, and complete elimination of FcRn binding was confirmed by Surface Plasmon Resonance (Biacore) assay for rFVIII263/VWF050. The half-life of FVIII263/VWF050 was evaluated in HemA mice in comparison with rFVIII205/VWF031. Increased clearance rate, as well as reduced half-life and AUC were observed for rFVIII263/VWF050 as shown in FIG. 5 and Table 19. This result demonstrated that in addition to ensure the covalent binding of FVIII and D'D3, the Fc domains is also necessary for the half-life improvement of the heterodimer.

TABLE 19

PK parameters of rFVIII205/VWF031 and rFV111263/VWF040 in HemA mice

| FVIII | Mutation in Fc domain | $T_{1/2}$ (hr) | MRT (hr) | Cl (mL/hr/kg) | Vss (mL/kg) | AUC_D (kg*hr/mL) |
|---|---|---|---|---|---|---|
| rFVIII205/VWF031 | None | 29.45 | 36.02 | 1.76 | 63.56 | 0.57 |
| rFVIII263/VWF050 | IHH | 22.96 | 26.15 | 2.36 | 61.69 | 0.42 |

Example 9: Acute Efficacy of FVIII-XTEN-Fc/D'D3-XTEN-Fc Heterodimers in HemA Mouse Tail Clip Bleeding Model The acute efficacy of lead heterodimer candidates were evaluated using HemA mouse tail clip bleeding model.

8-12 weeks old male HemA mice were randomized into 4 treatment groups, and treated with a single intravenous administration of SQ BDD-FVIII, rFVIII169/VWF034, rFVIII169/VWF057 or vehicle solution respectively. In order to mimic the episodic treatment of FVIII (to reconstitute 50-100% of normal FVIII plasma level), the selected FVIII treatment dose is 75 IU/kg as measured by FVIII aPTT activity. At this dose level, all testing FVIII variants will reconstitute ~70% of normal murine plasma FVIII activity 5 min post dosing.

Blood Loss Volume from Each Individual Animal in the Study was Plotted in FIGS. 6A-6B. Significant reduction on blood loss volume was observed for all FVIII treatment groups compared to vehicle treated animals. Within the three FVIII treatment groups, no statistical significant different were found on blood loss reduction, suggesting the heterodimer molecules could potentially as efficacious as SQ BDD-FVIII for on demand treatment.

Blood loss volume from each individual animal in the study was plotted in FIGS. 6A-6B. Significant reduction on blood loss volume was observed for all FVIII treatment groups compared to vehicle treated animals. Within the three FVIII treatment groups, no statistical significant different were found on blood loss reduction, suggesting the heterodimer molecules could potentially as efficacious as SQ BDD-FVIII for on demand treatment.

In addition, HemA mice were treated with a lower dose (37.5 IU/kg) of rBDD-FVIII or rFVIII169/VWF034, and the results are shown in FIG. 6B. Same as the 75 IU/kg dose, rFVIII169/VWF034 provided similar protection as BDD-FVIII to HemA mice post tail clip injury, indicating the molecule was still efficacious to treat severe bleeding episodes at ~35% of normal murine circulating FVIII level in HemA mice.

The Tail Clip procedure was carried out as follows. Briefly, mice were anesthetized with a 50 mg/kg Ketamine/0.5 mg/kg Dexmedetomidine cocktail prior to tail injury and placed on a 37° C. heating pad to help maintain the body temperature. The tails of the mice were then be immersed in 37° C. saline for 10 minutes to dilate the lateral vein. After vein dilation, FVIII variants or vehicle solution were injected via the tail vein and the distal 5 mm of the tail was then cut off using a straight edged #11 scalpel 5 min post dosing. The shed blood was collected into 13 ml of 37° C. saline for 30 minutes and blood loss volume was determined by the weight change of the blood collection tube: blood loss volume=(collection tube end weight−beginning weight+0.10) ml. Statistical analysis were conducted using t test (Mann Whitney test) and one way ANOVA (KRUSKAL-Wallis test, posttest: Dunns multiple comparison test).

Example 10: Prophylactic Efficacy of FVIII-XTEN-Fc/D'D3-XTEN-Fc Heterodimer in HemA Mouse Tail Vein Transection Bleeding Model The prophylactic efficacy of FVIII169/VWF057 was tested in HemA mouse tail vein transection (TVT) model. The TVT model induces bleeding by introducing injury to the lateral vein of the mouse tail, which mimics the spontaneous bleeding episodes in patients with hemophilia bleeding disorder.

8-10 weeks old male HemA mice were randomized into four treatment groups, and treated with either FVIII169/VWF057 at 72 hr prior of the tail vein injury, or SQ BDD-FVIII at 24 hr or 48 hr before the injury. Vehicle treated animal were used as negative control. Events of re-bleeding or euthanasia due to the excessive blood loss within 24 hrs post injury were plotted in FIGS. 7A-7B.

As shown in FIGS. 7A-7B, unlike mice treated with SQ BDD-FVIII at 48 hr prior to TVT, of whom only limited protection was observed post injury, mice that received rFVIII169/VWF057 at 72 hr prior the tail injury had similar protection on re-bleeding and survival compared to the mice that received SQ BDD-FVIII treatment 24 hr before TVT, indicating rFVIII169/VWF057 can provide at least 3-fold or more (e.g., 4-fold) longer-protection to HemA mice in TVT model. Therefor rFVIII169/VWF057 might significantly reduce the treatment frequency of the current FVIII prophylaxis.

Similarly, HemA mice were treated with FVIII-XTEN-Fc/D'D3-XTEN-Fc heterodimers: rFVIII169/VWF034 and rFVIII169/VWF057. at 24 or 96 hours prior to the tail vein injury. The rebleeding and survival data of the treatments were compared with the data by the rBDD-FVIII at 24 or 48 hour prior to the injury and vehicle. While the rebleeding in mice treated with rBDD-FVIII at 24 hours prior to the tail vein injury was similar to the mice treated with vehicle, the rebleeding data of mice treated with the heterodimers at 24 hr before the injury are significantly better than the vehicle treatment group. Furthermore, the rebleeding data of mice treated with the heterodimers at 96 hr before the injury were comparable to mice received rBDD-FVIII at 24 hr before the injury. As for the survival rate at 24 hr post the TVT injury, in contrast of the less than 50% survival rate of mice treated with rBDD-FVIII, more than 90% of the mice survived the TVT injury with FVIII-XTEN-Fc/D'D3-XTEN-Fc heterodimers treatment when FVIII molecules were administered at 24 hr before the injury. In addition, the survival in mice treated with the FVIII-XTEN-Fc/D'D3-XTEN-Fc heterodimers at 96 hours prior to the tail vein injury were better (in the case of rFVIII169/VWF034) or comparable (in the case of rFVIII169/VWF057) when compared with the mice that received rBDD-FVIII treatment at 24 hours prior to the injury. Both rebleeding and survival data had indicated a 4-fold efficacy prolongation of FVIII-XTEN-Fc/D'D3-XTEN-Fc heterodimer treatment vs. rBDD-FVIII treatment.

HemA Mouse Tail Vein Transection Model

The tail vein transection procedure was conducted as follows. Mice were anesthetized with a cocktail containing 50 mg/kg of Ketamine, 0.125 mg/kg of Dexmedetomidine, and 0.1 mg/kg of Buprenex. At an adequate anesthetic depth, the lateral tail vein of the mice was transected with straight edged number 11 surgical blade at an area where the diameter of the tail is approximately 2.7 mm. The shedding blood was washed away with warm saline to ensure clear observation of the wound. The treated mice were then single housed in a clean cage with white paper bedding for the next 24 hours. Tail re-bleed and the mouse's physical activity were observed and recorded hourly up to 12 hour post tail injury. Moribund mice were euthanized immediately, and a final observation was performed at 24 hour post tail injury. To mimic the bleeding situation in hemophilia patients and to ensure the animal's completely recovery from anesthesia, 1 mg/kg of Atipamezole solution was given to reverse Dexmedetomidine effect at the beginning of the Tail Vein Transection. An additional dose of 0.1 mg/kg Buprenex was administered at the end of the 12 hour observation period for overnight pain management. The survival curve of Time to Re-bleed and Time to Euthanasia was generated for data analysis, and Log-rank (Mantel-COX) test was used for statistic evaluation.

Example 11: Preparation of FVIII169/VWF059 and Other Constructs pSYN FVIII 310 Cloning:

A synthetic DNA fragment flanked with BamH1 site at the N-terminus and Cla 1 site at the C-terminus was commercially made. This synthetic DNA was used to replace the BamH1 to Cla1 region in pSYN FVIII 169 construct (SEQ ID NO: 155). Both synthetic DNA and pSYN FVIII 169 DNA were double digested with BamH1 and Cla1, digested synthetic DNA was inserted into digested pSYN FVIII 169 to create pSYN FVIII 310 (SEQ ID NO: 168; Table 20).

Cloning pSYN FVIII 312:

A synthetic DNA fragment flanked with BamH1 site at the N-terminus and Afe 1 site at the C-terminus was commercially made. This synthetic DNA was used to replace the BamH1 to Afe1 region in pSYN FVIII 169 construct (SEQ ID NO: 155). Both synthetic DNA and pSYN FVIII 169 DNA were double digested with BamH1 and Afe1, digested synthetic DNA was inserted into digested pSYN FVIII 169 to create pSYN FVIII 312 (SEQ ID NO: 169; Table 20). pSYN FVIII 312A (SEQ ID NO: 2; Table 20) was created from pSYN FVIII312 to remove AscI site which codes for amino acid residues GAP at the junction of FVIII and XTEN.

TABLE 20

Synthetic FVIII constructs.

| Construct | Protein Sequence |
|---|---|
| pSYN FVIII 169 | PRSFSQNGAPGTSESATPESGPGSEPATSGSETPGTSESATPESGPGSEPATSGS<br>ETPGTSESATPESGPGTSTEPSEGSAPGSPAGSPTSTEEGTSESATPESGPGSEP<br>ATSGSETPGTSESATPESGPGSPAGSPTSTEEGSPAGSPTSTEEGTSTEPSEGSA<br>PGTSESATPESGPGTSESATPESGPGTSESATPESGPGSEPATSGSETPGSEPAT<br>SGSETPGSPAGSPTSTEEGTSTEPSEGSAPGTSTEPSEGSAPGSEPATSGSETPG<br>TSESATPESGPGTSTEPSEGSAPASSPPVLKRHQAEITR (SEQ ID NO: 167)<br>(Underlined = XTEN residues; not underlined = FVIII residues) |
| pSYN FVIII 310 | PRSFGAPGTSESATPESGPGSEPATSGSETPGTSESATPESGPGSEPATSGSETP<br>GTSESATPESGPGTSTEPSEGSAPGSPAGSPTSTEEGTSESATPESGPGSEPATS<br>GSETPGTSESATPESGPGSPAGSPTSTEEGSPAGSPTSTEEGTSTEPSEGSAPGT<br>SESATPESGPGTSESATPESGPGTSESATPESGPGSEPATSGSETPGSEPATSGS<br>ETPGSPAGSPTSTEEGTSTEPSEGSAPGTSTEPSEGSAPGSEPATSGSETPGTSE<br>SATPESGPGTSTEPSEGSAPASSEITR (SEQ ID NO: 168)<br>(Underlined = XTEN residues; not underlined = FVIII residues) |
| pSYN FVIII 312 | PRSFSQNGAPGTSESATPESGPGSEPATSGSETPGTSESATPESGPGSEPATSGS<br>ETPGTSESATPESGPGTSTEPSEGSAPGSPAGSPTSTEEGTSESATPESGPGSEP<br>ATSGSETPGTSESATPESGPGSPAGSPTSTEEGSPAGSPTSTEEGTSTEPSEGSA<br>PGTSESATPESGPGTSESATPESGPGTSESATPESGPGSEPATSGSETPGSEPAT<br>SGSETPGSPAGSPTSTEEGTSTEPSEGSAPGTSTEPSEGSAPGSEPATSGSETPG<br>TSESATPESGPGTSTEPSEGSAPASSEITR (SEQ ID NO: 169)<br>(Underlined = XTEN residues; not underlined = FVIII residues) |
| pSYN FVIII 312A | PRSFSQNGTSESATPESGPGSEPATSGSETPGTSESATPESGPGSEPATSGSETP<br>GTSESATPESGPGTSTEPSEGSAPGSPAGSPTSTEEGTSESATPESGPGSEPATS |

TABLE 20-continued

| Synthetic FVIII constructs. | |
|---|---|
| Construct | Protein Sequence |
| | GSETPGTSESATPESGPGSPAGSPTSTEEGSPAGSPTSTEEGTSTEPSEGSAPGT SESATPESGPGTSESATPESGPGTSESATPESGPGSEPATSGSETPGSEPATSGS ETPGSPAGSPTSTEEGTSTEPSEGSAPGTSTEPSEGSAPGSEPATSGSETPGTSE SATPESGPGTSTEPSEGSAPASSEITR (SEQ ID NO: 2) |

(similar sequence as pSYN FEUD 1 2 just residues corresponding to AscI site i.e GAP are removed)
(Underlined = XTEN residues; not underlined = EVIII residues)

Cloning pSYN VWFG59 and VWFG73:

Various synthetic DNA fragments coding for different linker regions between D'D3-XTEN and Fc were made. These synthetic DNA fragments were flanked with Asc1 site at N-terminus and Not 1 site at the C-terminus. These synthetic DNAs were used to replace the Asc1 to Not1 region in pSYN VWF57 construct (SEQ ID NO: 152). The pSYN VWF059 construct (Table 21) comprises a linker region (SEQ ID NO: 13), which includes the entire FVIII acidic region 2 (a2). This site is reported to be cleaved by thrombin, and upon FVIII activation D'D3XTEN is released. The pSYN VWFS73 construct (Table 21) contains only the thrombin cleavage site of FVIII acidic region 2 (a2) (i.e., IEPRSFS) (SEQ ID NO: 23). Both synthetic DNA and pSYN VWF057 DNA were double digested with Asc1 and Not1. Digested synthetic DNA was inserted into digested pSYN VWF057 to create pSYN VWF059 and pSYN VWF073. The pSYN VWF59A construct (Table 21) was generated from pSYN VWF59 by removing the EcoRV restriction site. FVIII169/VWF057 and FVIII169/VWF059 heterodimer proteins were generated by co-expression of FVIII169 and VWF057 or VWF059 in HEK293 cells.

TABLE 21

| Synthetic VWF constructs-Cleavable Linker Regions. | |
|---|---|
| Construct | Protein Sequence |
| pSYN VWF057 | TSTEEGASS*GGGGSGGGGSGGGGSGGGGSGGGGSGGGGSGGGGS**LVPR**GSGG* DKTH (SEQ ID NO: 12)<br>Italics and underlined sequence shows GS linker and LVPR thrombin cleavage site (also bold). |
| pSYN VWF059 | TSTEEGASIS*DKNTGDYYEDSYEDISAYLLSKNNA**IEPRSFS***DKTH (SEQ ID NO: 13)<br>Italics and underlined sequence shows 32 aa from FVIII acidic region 2 (a2). Bold sequence shows thrombin cleavage site used in pSYN VWF059A. |
| pSYN VWF059A | TSTEEGASS*DKNTGDYYEDSYEDISAYLLSKNNAIEPRSFS*DKTH (SEQ ID NO: 22)<br>Italics and underlined sequence shows 32 aa from FVIII acidic region 2 (a2). This sequence is similar sequence to VWF059, except that residues corresponding to the EcoRV site (i.e., IS) are removed. |
| pSYN VWF073 | TSTEEGASS*GGGGSGGGGSGGGGSGGGGSGGGGSGGGGS**IEPRSFS**GSGG*DKT H (SEQ ID NO: 23)<br>Italics and underlined sequence shows GS linker with truncated thrombin cleavage site from FVIII acidic region 2 (bold 7 amino acids-IEPRSFS). |

Example 12: Thrombin Digestion of FVIII Heterodimer to Analyze the Release of D'D3 from Fc Two FVIII heterodimer proteins were tested in thrombin digestion experiments and their rate of cleavage by thrombin was examined. The two heterodimer constructs used in this experiment were FVIII169/VWF057 heterodimer and FVIII169/VWF059 heterodimer along with FVIIIFc. The FVIII169/VWF057 and FVIII169/VWF059 heterodimers are described above. Three digestion reactions were carried out: i) FVIIIFc ii) FVIII169/VWF057 (FIG. 11), and iii) FVIII 169/VWF059 (FIG. 12). Test samples were treated with human α-thrombin at a molar ratio if FVIII:thrombin of approximately 22:1. Each reaction was incubated in a 37° C. water bath. At each indicated time point (t=5, 15, 30, 45, 60 minutes), a 22.5 μL sample was withdrawn, stopped with 22.5 μL non-reducing 2×SDS loading dye, and heated for 3 minutes. The digested protein was then run on an SDS-PAGE gel. Western blotting was performed using anti-FVIII heavy chain (GMA012) and anti-VWF-D3 (Ab96340) antibodies using a LICOR system.

As shown in FIGS. 11A-11C, exposure of FVIII169/VWF057 to thrombin resulted in a gradual decrease in the detected level of D'D3-XTEN-Fc, correlating with an increase in the level of D'D3-144 XTEN, the cleaved product. Un-cleaved FVIII169/VWF057 remained after 15 minutes. Conversely, FIGS. 12A-12C shows that FVIII 169/VWF059 is cleaved more rapidly by thrombin, as evidenced by little to no detectable un-cleaved FVIII 169/VWF059 after 5 minutes. Accordingly, FVIII 169/VWF059 showed better release of D'D3 from Fc upon thrombin activation as compared or FVIII169/VWF057.

Parallel experiments were done to investigate thrombin cleavage using mass spectroscopy (MS). By MS, FVIII 169/VWF059 again showed better release of D'D3 from Fc as compared to VWF057.

Example 13: In Vivo Evaluation of FVIII169/VWF059 in HemA Mice

To further evaluate the pharmacokinetic profile and in vivo potency of FVIII169/VWF059, HemA mice were treated with FVIII169/VWF059 through intravenous administration at 150 IU/kg dose. Plasma samples were collected via vena cava blood collection at 5 minutes, 24, 48, 72, 96 and 120 hours post injection. FVIII activity in plasma samples were measured by FVIII chromogenic assay and PK parameters were calculated using Phoenix program. A similar PK profile of FVIII169/VWF059 was observed in comparison with FVIII169/VWF057, as shown in Table 22, indicating that the a2 thrombin cleavage linker has no negative effect on the PK profile of the heterodimer.

TABLE 22

PK profile of FVIII169/VWF057 and FVIII169/VWF059 in HemA mice

| Heterodimer | $T_{1/2}$ (hr) | AUC/D (hr*kg*mIU/mL/mIU) | Cl (mL/hr/kg) | MRT (hr) | Vss (mL/kg) |
|---|---|---|---|---|---|
| FVIII169/VWF057 | 38.53 | 0.80 | 1.26 | 44.92 | 56.38 |

TABLE 22-continued

PK profile of FVIII169/VWF057 and FVIII169/VWF059 in HemA mice

| Heterodimer | $T_{1/2}$ (hr) | AUC/D (hr*kg*mIU/mL/mIU) | Cl (mL/hr/kg) | MRT (hr) | Vss (mL/kg) |
|---|---|---|---|---|---|
| FVIII169/VWF059 | 40.51 | 0.74 | 1.35 | 49.22 | 66.26 |

The acute efficacy of FVIII169/VWF059 was evaluated in a HemA mouse tail clip model (described in Example 9) in comparison with wild type BDD-FVIII. HemA mice were treated with 75 IU/kg of either FVIII169/VWF059 or BDD-FVIII, and blood loss volume of each experimental mouse was plotted in FIG. 13. Compared to BDD-FVIII, FVIII169/VWF059 provided the same degree of protection to HemA mice (p=0.9883), indicating that FVIII169/VWF059 is fully functional in vivo.

Plasmid Construction of FVIII-XTEN-Fc/D'D3-Fc Heterodimers

```
VWF031 nucleotide Sequence (SEQ ID NO: 147)
   1  ATGAT TCCTG CCAGA TTTGC CGGGG TGCTG CTTGC TCTGG CCCTC ATTTT
  51  GCCAG GGACC CTTTG TGCAG AAGGA ACTCG CGGCA GGTCA TCCAC GGCCC
 101  GATGC AGCCT TTTCG GAAGT GACTT CGTCA ACACC TTTGA TGGGA GCATG
 151  TACAG CTTTG CGGGA TACTG CAGTT ACCTC CTGGC AGGGG GCTGC CAGAA
 201  ACGCT CCTTC TCGAT TATTG GGGAC TTCCA GAATG GCAAG AGAGT GAGCC
 251  TCTCC GTGTA TCTTG GGGAA TTTTT TGACA TCCAT TTGTT TGTCA ATGGT
 301  ACCGT GACAC AGGGG GACCA AAGAG TCTCC ATGCC CTATG CCTCC AAAGG
 351  GCTGT ATCTA GAAAC TGAGG CTGGG TACTA CAAGC TGTCC GGTGA GGCCT
 401  ATGGC TTTGT GGCCA GGATC GATGG CAGCG GCAAC TTTCA AGTCC TGCTG
 451  TCAGA CAGAT ACTTC AACAA GACCT GCGGG CTGTG TGGCA ACTTT AACAT
 501  CTTTG CTGAA GATGA CTTTA TGACC CAAGA AGGGA CCTTG ACCTC GGACC
 551  CTTAT GACTT TGCCA ACTCA TGGGC TCTGA GCAGT GGAGA ACAGT GGTGT
 601  GAACG GGCAT CTCCT CCCAG CAGCT CATGC AACAT CTCCT CTGGG GAAAT
 651  GCAGA AGGGC CTGTG GGAGC AGTGC CAGCT TCTGA AGAGC ACCTC GGTGT
 701  TTGCC CGCTG CCACC CTCTG GTGGA CCCCG AGCCT TTTGT GGCCC TGTGT
 751  GAGAA GACTT TGTGT GAGTG TGCTG GGGGG CTGGA GTGCG CCTGC CCTGC
 801  CCTCC TGGAG TACGC CCGGA CCTGT GCCCA GGAGG GAATG GTGCT GTACG
 851  GCTGG ACCGA CCACA GCGCG TGCAG CCCAG TGTGC CCTGC TGGTA TGGAG
 901  TATAG GCAGT GTGTG TCCCC TTGCG CCAGG ACCTG CCAGA GCCTG CACAT
 951  CAATG AAATG TGTCA GGAGC GATGC GTGGA TGGCT GCAGC TGCCC TGAGG
1001  GACAG CTCCT GGATG AAGGC CTCTG CGTGG AGAGC ACCGA GTGTC CCTGC
1051  GTGCA TTCCG GAAAG CGCTA CCCTC CCGGC ACCTC CCTCT CTCGA GACTG
1101  CAACA CCTGC ATTTG CCGAA ACAGC CAGTG GATCT GCAGC AATGA AGAAT
1151  GTCCA GGGGA GTGCC TTGTC ACTGG TCAAT CCCAC TTCAA GAGCT TTGAC
1201  AACAG ATACT TCACC TTCAG TGGGA TCTGC CAGTA CCTGC TGGCC CGGGA
```

-continued

1251 TTGCC AGGAC CACTC CTTCT CCATT GTCAT TGAGA CTGTC CAGTG TGCTG

1301 ATGAC CGCGA CGCTG TGTGC ACCCG CTCCG TCACC GTCCG GCTGC CTGGC

1351 CTGCA CAACA GCCTT GTGAA ACTGA AGCAT GGGGC AGGAG TTGCC ATGGA

1401 TGGCC AGGAC ATCCA GCTCC CCCTC CTGAA AGGTG ACCTC CGCAT CCAGC

1451 ATACA GTGAC GGCCT CCGTG CGCCT CAGCT ACGGG GAGGA CCTGC AGATG

1501 GACTG GGATG GCCGC GGGAG GCTGC TGGTG AAGCT GTCCC CCGTC TATGC

1551 CGGGA AGACC TGCGG CCTGT GTGGG AATTA CAATG GCAAC CAGGG CGACG

1601 ACTTC CTTAC CCCCT CTGGG CTGGC GGAGC CCCGG GTGGA GGACT TCGGG

1651 AACGC CTGGA AGCTG CACGG GGACT GCCAG GACCT GCAGA AGCAG CACAG

1701 CGATC CCTGC GCCCT CAACC CGCGC ATGAC CAGGT TCTCC GAGGA GGCGT

1751 GCGCG GTCCT GACGT CCCCC ACATT CGAGG CCTGC CATCG TGCCG TCAGC

1801 CCGCT GCCCT ACCTG CGGAA CTGCC GCTAC GACGT GTGCT CCTGC TCGGA

1851 CGGCC GCGAG TGCCT GTGCG GCGCC CTGGC CAGCT ATGCC GCGGC CTGCG

1901 CGGGG AGAGG CGTGC GCGTC GCGTG GCGCG AGCCA GGCCG CTGTG AGCTG

1951 AACTG CCCGA AAGGC CAGGT GTACC TGCAG TGCGG GACCC CCTGC AACCT

2001 GACCT GCCGC TCTCT CTCTT ACCCG GATGA GGAAT GCAAT GAGGC CTGCC

2051 TGGAG GGCTG CTTCT GCCCC CCAGG GCTCT ACATG GATGA GAGGG GGGAC

2101 TGCGT GCCCA AGGCC CAGTG CCCCT GTTAC TATGA CGGTG AGATC TTCCA

2151 GCCAG AAGAC ATCTT CTCAG ACCAT CACAC CATGT GCTAC TGTGA GGATG

2201 GCTTC ATGCA CTGTA CCATG AGTGG AGTCC CCGGA AGCTT GCTGC CTGAC

2251 GCTGT CCTCA GCAGT CCCCT GTCTC ATCGC AGCAA AAGGA GCCTA TCCTG

2301 TCGGC CCCCC ATGGT CAAGC TGGTG TGTCC CGCTG ACAAC CTGCG GGCTG

2351 AAGGG CTCGA GTGTA CCAAA ACGTG CCAGA ACTAT GACCT GGAGT GCATG

2401 AGCAT GGGCT GTGTC TCTGG CTGCC TCTGC CCCCC GGGCA TGGTC CGGCA

2451 TGAGA ACAGA TGTGT GGCCC TGGAA AGGTG TCCCT GCTTC CATCA GGGCA

2501 AGGAG TATGC CCCTG GAGAA ACAGT GAAGA TTGGC TGCAA CACTT GTGTC

2551 TGTCG GGACC GGAAG TGGAA CTGCA CAGAC CATGT GTGTG ATGCC ACGTG

2601 CTCCA CGATC GGCAT GGCCC ACTAC CTCAC CTTCG ACGGG CTCAA ATACC

2651 TGTTC CCCGG GGAGT GCCAG TACGT TCTGG TGCAG GATTA CTGCG GCAGT

2701 AACCC TGGGA CCTTT CGGAT CCTAG TGGGG AATAA GGGAT GCAGC CACCC

2751 CTCAG TGAAA TGCAA GAAAC GGGTC ACCAT CCTGG TGGAG GGAGG AGAGA

2801 TTGAG CTGTT TGACG GGGAG GTGAA TGTGA AGAGG CCCAT GAAGG ATGAG

2851 ACTCA CTTTG AGGTG GTGGA GTCTG GCCGG TACAT CATTC TGCTG CTGGG

2901 CAAAG CCCTC TCCGT GGTCT GGGAC CGCCA CCTGA GCATC TCCGT GGTCC

2951 TGAAG CAGAC ATACC AGGAG AAAGT GTGTG GCCTG TGTGG GAATT TTGAT

3001 GGCAT CCAGA ACAAT GACCT CACCA GCAGC AACCT CCAAG TGGAG GAAGA

3051 CCCTG TGGAC TTTGG GAACT CCTGG AAAGT GAGCT CGCAG TGTGC TGACA

3101 CCAGA AAAGT GCCTC TGGAC TCATC CCCTG CCACC TGCCA TAACA ACATC

3151 ATGAA GCAGA CGATG GTGGA TTCCT CCTGT AGAAT CCTTA CCAGT GACGT

3201 CTTCC AGGAC TGCAA CAAGC TGGTG GACCC CGAGC CATAT CTGGA TGTCT

-continued

3251 GCATT TACGA CACCT GCTCC TGTGA GTCCA TTGGG GACTG CGCCG CATTC

3301 TGCGA CACCA TTGCT GCCTA TGCCC ACGTG TGTGC CCAGC ATGGC AAGGT

3351 GGTGA CCTGG AGGAC GGCCA CATTG TGCCC CCAGA GCTGC GAGGA GAGGA

3401 ATCTC CGGGA GAACG GGTAT GAGGC TGAGT GGCGC TATAA CAGCT GTGCA

3451 CCTGC CTGTC AAGTC ACGTG TCAGC ACCCT GAGCC ACTGG CCTGC CCTGT

3501 GCAGT GTGTG GAGGG CTGCC ATGCC CACTG CCCTC CAGGG AAAAT CCTGG

3551 ATGAG CTTTT GCAGA CCTGC GTTGA CCCTG AAGAC TGTCC AGTGT GTGAG

3601 GTGGC TGGCC GGCGT TTTGC CTCAG GAAAG AAAGT CACCT TGAAT CCCAG

3651 TGACC CTGAG CACTG CCAGA TTTGC CACTG TGATG TTGTC AACCT CACCT

3701 GTGAA GCCTG CCAGG AGCCG ATATC TGGCG GTGGA GGTTC CGGTG GCGGG

3751 GGATC CGGCG GTGGA GGTTC CGGCG GTGGA GGTTC CGGTG GCGGG GGATC

3801 CGGTG GCGGG GGATC CCTGG TCCCC CGGGG CAGCG GCGGT GGAGG TTCCG

3851 GTGGC GGGGG ATCCG ACAAA ACTCA CACAT GCCCA CCGTG CCCAG CTCCA

3901 GAACT CCTGG GCGGA CCGTC AGTCT TCCTC TTCCC CCCAA AACCC AAGGA

3951 CACCC TCATG ATCTC CCGGA CCCCT GAGGT CACAT GCGTG GTGGT GGACG

4001 TGAGC CACGA AGACC CTGAG GTCAA GTTCA ACTGG TACGT GGACG GCGTG

4051 GAGGT GCATA ATGCC AAGAC AAAGC CGCGG GAGGA GCAGT ACAAC AGCAC

4101 GTACC GTGTG GTCAG CGTCC TCACC GTCCT GCACC AGGAC TGGCT GAATG

4151 GCAAG GAGTA CAAGT GCAAG GTCTC CAACA AAGCC CTCCC AGCCC CCATC

4201 GAGAA AACCA TCTCC AAAGC CAAAG GGCAG CCCCG AGAAC CACAG GTGTA

4251 CACCC TGCCC CCATC CCGCG ATGAG CTGAC CAAGA ACCAG GTCAG CCTGA

4301 CCTGC CTGGT CAAAG GCTTC TATCC CAGCG ACATC GCCGT GGAGT GGGAG

4351 AGCAA TGGGC AGCCG GAGAA CAACT ACAAG ACCAC GCCTC CCGTG TTGGA

4401 CTCCG ACGGC TCCTT CTTCC TCTAC AGCAA GCTCA CCGTG GACAA GAGCA

4451 GGTGG CAGCA GGGGA ACGTC TTCTC ATGCT CCGTG ATGCA TGAGG CTCTG

4501 CACAA CCACT ACACG CAGAA GAGCC TCTCC CTGTC TCCGG GTAAA TGA

VWF031 protein Sequence (SEQ ID NO: 86)

1 MIPARFAGVL LALALILPGT LCAEGTRGRS STARCSLFGS DFVNTFDGSM

51 YSFAGYCSYL LAGGCQKRSF SIIGDFQNGK RVSLSVYLGE FFDIHLFVNG

101 TVTQGDQRVS MPYASKGLYL ETEAGYYKLS GEAYGFVARI DGSGNFQVLL

151 SDRYFNKTCG LCGNFNIFAE DDFMTQEGTL TSDPYDFANS WALSSGEQWC

201 ERASPPSSSC NISSGEMQKG LWEQCQLLKS TSVFARCHPL VDPEPFVALC

251 EKTLCECAGG LECACPALLE YARTCAQEGM VLYGWTDHSA CSPVCPAGME

301 YRQCVSPCAR TCQSLHINEM CQERCVDGCS CPEGQLLDEG LCVESTECPC

351 VHSGKRYPPG TSLSRDCNTC ICRNSQWICS NEECPGECLV TGQSHFKSFD

401 NRYFTFSGIC QYLLARDCQD HSFSIVIETV QCADDRDAVC TRSVTVRLPG

451 LHNSLVKLKH GAGVAMDGQD IQLPLLKGDL RIQHTVTASV RLSYGEDLQM

501 DWDGRGRLLV KLSPVYAGKT CGLCGNYNGN QGDDFLTPSG LAEPRVEDFG

551 NAWKLHGDCQ DLQKQHSDPC ALNPRMTRFS EEACAVLTSP TFEACHRAVS

601 PLPYLRNCRY DVCSCSDGRE CLCGALASYA AACAGRGVRV AWREPGRCEL

-continued

651 NCPKGQVYLQ CGTPCNLTCR SLSYPDEECN EACLEGCFCP PGLYMDERGD

701 CVPKAQCPCY YDGEIFQPED IFSDHHTMCY CEDGFMHCTM SGVPGSLLPD

751 AVLSSPLSHR SKRSLSCRPP MVKLVCPADN LRAEGLECTK TCQNYDLECM

801 SMGCVSGCLC PPGMVRHENR CVALERCPCF HQGKEYAPGE TVKIGCNTCV

851 CRDRKWNCTD HVCDATCSTI GMAHYLTFDG LKYLFPGECQ YVLVQDYCGS

901 NPGTFRILVG NKGCSHPSVK CKKRVTILVE GGEIELFDGE VNVKRPMKDE

951 THFEVVESGR YIILLLGKAL SVVWDRHLSI SVVLKQTYQE KVCGLCGNFD

1001 GIQNNDLTSS NLQVEEDPVD FGNSWKVSSQ CADTRKVPLD SSPATCHNNI

1051 MKQTMVDSSC RILTSDVFQD CNKLVDPEPY LDVCIYDTCS CESIGDCAAF

1101 CDTIAAYAHV CAQHGKVVTW RTATLCPQSC EERNLRENGY EAEWRYNSCA

1151 PACQVTCQHP EPLACPVQCV EGCHAHCPPG KILDELLQTC VDPEDCPVCE

1201 VAGRRFASGK KVTLNPSDPE HCQICHCDVV NLTCEACQEP ISGGGGSGGG

1251 GSGGGGSGGG GSGGGGSGGG GSLVPRGSGG GGSGGGGSDK THTCPPCPAP

1301 ELLGGPSVFL FPPKPKDTLM ISRTPEVTCV VVDVSHEDPE VKFNWYVDGV

1351 EVHNAKTKPR EEQYNSTYRV VSVLTVLHQD WLNGKEYKCK VSNKALPAPI

1401 EKTISKAKGQ PREPQVYTLP PSRDELTKNQ VSLTCLVKGF YPSDIAVEWE

1451 SNGQPENNYK TTPPVLDSDG SFFLYSKLTV DKSRWQQGNV FSCSVMHEAL

1501 HNHYTQKSLS LSPGK*

VWF034 nucleotide Sequence (SEQ ID NO: 148)

1 ATGAT TCCTG CCAGA TTTGC CGGGG TGCTG CTTGC TCTGG CCCTC ATTTT

51 GCCAG GGACC CTTTG TGCAG AAGGA ACTCG CGGCA GGTCA TCCAC GGCCC

101 GATGC AGCCT TTTCG GAAGT GACTT CGTCA ACACC TTTGA TGGGA GCATG

151 TACAG CTTTG CGGGA TACTG CAGTT ACCTC CTGGC AGGGG GCTGC CAGAA

201 ACGCT CCTTC TCGAT TATTG GGGAC TTCCA GAATG GCAAG AGAGT GAGCC

251 TCTCC GTGTA TCTTG GGGAA TTTTT TGACA TCCAT TTGTT TGTCA ATGGT

301 ACCGT GACAC AGGGG GACCA AAGAG TCTCC ATGCC CTATG CCTCC AAAGG

351 GCTGT ATCTA GAAAC TGAGG CTGGG TACTA CAAGC TGTCC GGTGA GGCCT

401 ATGGC TTTGT GGCCA GGATC GATGG CAGCG GCAAC TTTCA AGTCC TGCTG

451 TCAGA CAGAT ACTTC AACAA GACCT GCGGG CTGTG TGGCA ACTTT AACAT

501 CTTTG CTGAA GATGA CTTTA TGACC CAAGA AGGGA CCTTG ACCTC GGACC

551 CTTAT GACTT TGCCA ACTCA TGGGC TCTGA GCAGT GGAGA ACAGT GGTGT

601 GAACG GGCAT CTCCT CCCAG CAGCT CATGC AACAT CTCCT CTGGG GAAAT

651 GCAGA AGGGC CTGTG GGAGC AGTGC CAGCT TCTGA AGAGC ACCTC GGTGT

701 TTGCC CGCTG CCACC CTCTG GTGGA CCCCG AGCCT TTTGT GGCCC TGTGT

751 GAGAA GACTT TGTGT GAGTG TGCTG GGGGG CTGGA GTGCG CCTGC CCTGC

801 CCTCC TGGAG TACGC CCGGA CCTGT GCCCA GGAGG GAATG GTGCT GTACG

851 GCTGG ACCGA CCACA GCGCG TGCAG CCCAG TGTGC CCTGC TGGTA TGGAG

901 TATAG GCAGT GTGTG TCCCC TTGCG CCAGG ACCTG CCAGA GCCTG CACAT

951 CAATG AAATG TGTCA GGAGC GATGC GTGGA TGGCT GCAGC TGCCC TGAGG

1001 GACAG CTCCT GGATG AAGGC CTCTG CGTGG AGAGC ACCGA GTGTC CCTGC

-continued

1051 GTGCA TTCCG GAAAG CGCTA CCCTC CCGGC ACCTC CCTCT CTCGA GACTG

1101 CAACA CCTGC ATTTG CCGAA ACAGC CAGTG GATCT GCAGC AATGA AGAAT

1151 GTCCA GGGGA GTGCC TTGTC ACTGG TCAAT CCCAC TTCAA GAGCT TTGAC

1201 AACAG ATACT TCACC TTCAG TGGGA TCTGC CAGTA CCTGC TGGCC CGGGA

1251 TTGCC AGGAC CACTC CTTCT CCATT GTCAT TGAGA CTGTC CAGTG TGCTG

1301 ATGAC CGCGA CGCTG TGTGC ACCCG CTCCG TCACC GTCCG GCTGC CTGGC

1351 CTGCA CAACA GCCTT GTGAA ACTGA AGCAT GGGGC AGGAG TTGCC ATGGA

1401 TGGCC AGGAC ATCCA GCTCC CCCTC CTGAA AGGTG ACCTC CGCAT CCAGC

1451 ATACA GTGAC GGCCT CCGTG CGCCT CAGCT ACGGG GAGGA CCTGC AGATG

1501 GACTG GGATG GCCGC GGGAG GCTGC TGGTG AAGCT GTCCC CCGTC TATGC

1551 CGGGA AGACC TGCGG CCTGT GTGGG AATTA CAATG GCAAC CAGGG CGACG

1601 ACTTC CTTAC CCCCT CTGGG CTGGC GGAGC CCCGG GTGGA GGACT TCGGG

1651 AACGC CTGGA AGCTG CACGG GGACT GCCAG GACCT GCAGA AGCAG CACAG

1701 CGATC CCTGC GCCCT CAACC CGCGC ATGAC CAGGT TCTCC GAGGA GGCGT

1751 GCGCG GTCCT GACGT CCCCC ACATT CGAGG CCTGC CATCG TGCCG TCAGC

1801 CCGCT GCCCT ACCTG CGGAA CTGCC GCTAC GACGT GTGCT CCTGC TCGGA

1851 CGGCC GCGAG TGCCT GTGCG GCGCC CTGGC CAGCT ATGCC GCGGC CTGCG

1901 CGGGG AGAGG CGTGC GCGTC GCGTG GCGCG AGCCA GGCCG CTGTG AGCTG

1951 AACTG CCCGA AAGGC CAGGT GTACC TGCAG TGCGG GACCC CCTGC AACCT

2001 GACCT GCCGC TCTCT CTCTT ACCCG GATGA GGAAT GCAAT GAGGC CTGCC

2051 TGGAG GGCTG CTTCT GCCCC CCAGG GCTCT ACATG GATGA GAGGG GGGAC

2101 TGCGT GCCCA AGGCC CAGTG CCCCT GTTAC TATGA CGGTG AGATC TTCCA

2151 GCCAG AAGAC ATCTT CTCAG ACCAT CACAC CATGT GCTAC TGTGA GGATG

2201 GCTTC ATGCA CTGTA CCATG AGTGG AGTCC CCGGA AGCTT GCTGC CTGAC

2251 GCTGT CCTCA GCAGT CCCCT GTCTC ATCGC AGCAA AAGGA GCCTA TCCTG

2301 TCGGC CCCCC ATGGT CAAGC TGGTG TGTCC CGCTG ACAAC CTGCG GGCTG

2351 AAGGG CTCGA GTGTA CCAAA ACGTG CCAGA ACTAT GACCT GGAGT GCATG

2401 AGCAT GGGCT GTGTC TCTGG CTGCC TCTGC CCCCC GGGCA TGGTC CGGCA

2451 TGAGA ACAGA TGTGT GGCCC TGGAA AGGTG TCCCT GCTTC CATCA GGGCA

2501 AGGAG TATGC CCCTG GAGAA ACAGT GAAGA TTGGC TGCAA CACTT GTGTC

2551 TGTCG GGACC GGAAG TGGAA CTGCA CAGAC CATGT GTGTG ATGCC ACGTG

2601 CTCCA CGATC GGCAT GGCCC ACTAC CTCAC CTTCG ACGGG CTCAA ATACC

2651 TGTTC CCCGG GGAGT GCCAG TACGT TCTGG TGCAG GATTA CTGCG GCAGT

2701 AACCC TGGGA CCTTT CGGAT CCTAG TGGGG AATAA GGGAT GCAGC CACCC

2751 CTCAG TGAAA TGCAA GAAAC GGGTC ACCAT CCTGG TGGAG GGAGG AGAGA

2801 TTGAG CTGTT TGACG GGGAG GTGAA TGTGA AGAGG CCCAT GAAGG ATGAG

2851 ACTCA CTTTG AGGTG GTGGA GTCTG GCCGG TACAT CATTC TGCTG CTGGG

2901 CAAAG CCCTC TCCGT GGTCT GGGAC CGCCA CCTGA GCATC TCCGT GGTCC

2951 TGAAG CAGAC ATACC AGGAG AAAGT GTGTG GCCTG TGTGG GAATT TTGAT

-continued

| | |
|---|---|
| 3001 | GGCAT CCAGA ACAAT GACCT CACCA GCAGC AACCT CCAAG TGGAG GAAGA |
| 3051 | CCCTG TGGAC TTTGG GAACT CCTGG AAAGT GAGCT CGCAG TGTGC TGACA |
| 3101 | CCAGA AAAGT GCCTC TGGAC TCATC CCCTG CCACC TGCCA TAACA ACATC |
| 3151 | ATGAA GCAGA CGATG GTGGA TTCCT CCTGT AGAAT CCTTA CCAGT GACGT |
| 3201 | CTTCC AGGAC TGCAA CAAGC TGGTG GACCC CGAGC CATAT CTGGA TGTCT |
| 3251 | GCATT TACGA CACCT GCTCC TGTGA GTCCA TTGGG GACTG CGCCG CATTC |
| 3301 | TGCGA CACCA TTGCT GCCTA TGCCC ACGTG TGTGC CCAGC ATGGC AAGGT |
| 3351 | GGTGA CCTGG AGGAC GGCCA CATTG TGCCC CCAGA GCTGC GAGGA GAGGA |
| 3401 | ATCTC CGGGA GAACG GGTAT GAGGC TGAGT GGCGC TATAA CAGCT GTGCA |
| 3451 | CCTGC CTGTC AAGTC ACGTG TCAGC ACCCT GAGCC ACTGG CCTGC CCTGT |
| 3501 | GCAGT GTGTG GAGGG CTGCC ATGCC CACTG CCCTC CAGGG AAAAT CCTGG |
| 3551 | ATGAG CTTTT GCAGA CCTGC GTTGA CCCTG AAGAC TGTCC AGTGT GTGAG |
| 3601 | GTGGC TGGCC GGCGT TTTGC CTCAG GAAAG AAAGT CACCT TGAAT CCCAG |
| 3651 | TGACC CTGAG CACTG CCAGA TTTGC CACTG TGATG TTGTC AACCT CACCT |
| 3701 | GTGAA GCCTG CCAGG AGCCG ATATC GGGTA CCTCA GAGTC TGCTA CCCCC |
| 3901 | GGACC AGGAA CATCT ACAGA GCCCT CTGAA GGCTC CGCTC CAGGG TCCCC |
| 3951 | AGCCG GCAGT CCCAC TAGCA CCGAG GAGGG AACCT CTGAA AGCGC CACAC |
| 4001 | CCGAA TCAGG GCCAG GGTCT GAGCC TGCTA CCAGC GGCAG CGAGA CACCA |
| 4051 | GGCAC CTCTG AGTCC GCCAC ACCAG AGTCC GGACC CGGAT CTCCC GCTGG |
| 4101 | GAGCC CCACC TCCAC TGAGG AGGGA TCTCC TGCTG GCTCT CCAAC ATCTA |
| 4151 | CTGAG GAAGG TACCT CAACC GAGCC ATCCG AGGGA TCAGC TCCCG GCACC |
| 4201 | TCAGA GTCGG CAACC CCGGA GTCTG GACCC GGAAC TTCCG AAAGT GCCAC |
| 4251 | ACCAG AGTCC GGTCC CGGGA CTTCA GAATC AGCAA CACCC GAGTC CGGCC |
| 4301 | CTGGG TCTGA ACCCG CCACA AGTGG TAGTG AGACA CCAGG ATCAG AACCT |
| 4351 | GCTAC CTCAG GGTCA GAGAC ACCCG GATCT CCGGC AGGCT CACCA ACCTC |
| 4401 | CACTG AGGAG GGCAC CAGCA CAGAA CCAAG CGAGG GCTCC GCACC CGGAA |
| 4451 | CAAGC ACTGA ACCCA GTGAG GGTTC AGCAC CCGGC TCTGA GCCGG CCACA |
| 4501 | AGTGG CAGTG AGACA CCCGG CACTT CAGAG AGTGC CACCC CCGAG AGTGG |
| 4551 | CCCAG GCACT AGTAC CGAGC CCTCT GAAGG CAGTG CGCCA GATTC TGGCG |
| 4601 | GTGGA GGTTC CGGTG GCGGG GGATC CGGTG GCGGG GGATC CGGTG GCGGG |
| 4651 | GGATC CGGTG GCGGG GGATC CCTGG TCCCC CGGGG CAGCG GAGGC GACAA |
| 4701 | AACTC ACACA TGCCC ACCGT GCCCA GCTCC AGAAC TCCTG GGCGG ACCGT |
| 4751 | CAGTC TTCCT CTTCC CCCCA AAACC CAAGG ACACC CTCAT GATCT CCCGG |
| 4801 | ACCCC TGAGG TCACA TGCGT GGTGG TGGAC GTGAG CCACG AAGAC CCTGA |
| 4851 | GGTCA AGTTC AACTG GTACG TGGAC GGCGT GGAGG TGCAT AATGC CAAGA |
| 4901 | CAAAG CCGCG GGAGG AGCAG TACAA CAGCA CGTAC CGTGT GGTCA GCGTC |
| 4951 | CTCAC CGTCC TGCAC CAGGA CTGGC TGAAT GGCAA GGAGT ACAAG TGCAA |
| 5001 | GGTCT CCAAC AAAGC CCTCC CAGCC CCCAT CGAGA AAACC ATCTC CAAAG |
| 5051 | CCAAA GGGCA GCCCC GAGAA CCACA GGTGT ACACC CTGCC CCCAT CCCGG |
| 5101 | GATGA GCTGA CCAAG AACCA GGTCA GCCTG ACCTG CCTGG TCAAA GGCTT |

-continued

```
5151  CTATC CCAGC GACAT CGCCG TGGAG TGGGA GAGCA ATGGG CAGCC GGAGA

5201  ACAAC TACAA GACCA CGCCT CCCGT GTTGG ACTCC GACGG CTCCT TCTTC

5251  CTCTA CAGCA AGCTC ACCGT GGACA AGAGC AGGTG GCAGC AGGGG AACGT

5301  CTTCT CATGC TCCGT GATGC ATGAG GCTCT GCACA ACCAC TACAC GCAGA

5351  AGAGC CTCTC CCTGT CTCCG GGTAA ATGA
```

VWF034 Protein Sequence (SEQ ID NO: 87)

```
   1  MIPARFAGVL LALALILPGT LCAEGTRGRS STARCSLFGS DFVNTFDGSM

  51  YSFAGYCSYL LAGGCQKRSF SIIGDFQNGK RVSLSVYLGE FFDIHLFVNG

 101  TVTQGDQRVS MPYASKGLYL ETEAGYYKLS GEAYGFVARI DGSGNFQVLL

 151  SDRYFNKTCG LCGNFNIFAE DDFMTQEGTL TSDPYDFANS WALSSGEQWC

 201  ERASPPSSSC NISSGEMQKG LWEQCQLLKS TSVFARCHPL VDPEPFVALC

 251  EKTLCECAGG LECACPALLE YARTCAQEGM VLYGWTDHSA CSPVCPAGME

 301  YRQCVSPCAR TCQSLHINEM CQERCVDGCS CPEGQLLDEG LCVESTECPC

 351  VHSGKRYPPG TSLSRDCNTC ICRNSQWICS NEECPGECLV TGQSHFKSFD

 401  NRYFTFSGIC QYLLARDCQD HSFSIVIETV QCADDRDAVC TRSVTVRLPG

 451  LHNSLVKLKH GAGVAMDGQD IQLPLLKGDL RIQHTVTASV RLSYGEDLQM

 501  DWDGRGRLLV KLSPVYAGKT CGLCGNYNGN QGDDFLTPSG LAEPRVEDFG

 551  NAWKLHGDCQ DLQKQHSDPC ALNPRMTRFS EEACAVLTSP TFEACHRAVS

 601  PLPYLRNCRY DVCSCSDGRE CLCGALASYA AACAGRGVRV AWREPGRCEL

 651  NCPKGQVYLQ CGTPCNLTCR SLSYPDEECN EACLEGCFCP PGLYMDERGD

 701  CVPKAQCPCY YDGEIFQPED IFSDHHTMCY CEDGFMHCTM SGVPGSLLPD

 751  AVLSSPLSHR SKRSLSCRPP MVKLVCPADN LRAEGLECTK TCQNYDLECM

 801  SMGCVSGCLC PPGMVRHENR CVALERCPCF HQGKEYAPGE TVKIGCNTCV

 851  CRDRKWNCTD HVCDATCSTI GMAHYLTFDG LKYLFPGECQ YVLVQDYCGS

 901  NPGTFRILVG NKGCSHPSVK CKKRVTILVE GGEIELFDGE VNVKRPMKDE

 951  THFEVVESGR YIILLLGKAL SVVWDRHLSI SVVLKQTYQE KVCGLCGNFD

1001  GIQNNDLTSS NLQVEEDPVD FGNSWKVSSQ CADTRKVPLD SSPATCHNNI

1051  MKQTMVDSSC RILTSDVFQD CNKLVDPEPY LDVCIYDTCS CESIGDCAAF

1101  CDTIAAYAHV CAQHGKVVTW RTATLCPQSC EERNLRENGY EAEWRYNSCA

1151  PACQVTCQHP EPLACPVQCV EGCHAHCPPG KILDELLQTC VDPEDCPVCE

1201  VAGRRFASGK KVTLNPSDPE HCQICHCDVV NLTCEACQEP ISGTSESATP

1251  ESGPGSEPAT SGSETPGTSE SATPESGPGS EPATSGSETP GTSESATPES

1301  GPGTSTEPSE GSAPGSPAGS PTSTEEGTSE SATPESGPGS EPATSGSETP

1351  GTSESATPES GPGSPAGSPT STEEGSPAGS PTSTEEGTST EPSEGSAPGT

1401  SESATPESGP GTSESATPES GPGTSESATP ESGPGSEPAT SGSETPGSEP

1451  ATSGSETPGS PAGSPTSTEE GTSTEPSEGS APGTSTEPSE GSAPGSEPAT

1501  SGSETPGTSE SATPESGPGT STEPSEGSAP DIGGGGGSGG GGSLVPRGSG

1551  GDKTHTCPPC PAPELLGGPS VFLFPPKPKD TLMISRTPEV TCVVVDVSHE

1601  DPEVKFNWYV DGVEVHNAKT KPREEQYNST YRVVSVLTVL HQDWLNGKEY

1651  KCKVSNKALP APIEKTISKA KGQPREPQVY TLPPSRDELT KNQVSLTCLV
```

-continued

1701 KGFYPSDIAV EWESNGQPEN NYKTTPPVLD SDGSFFLYSK LTVDKSRWQQ

1751 GNVFSCSVMH EALHNHYTQK SLSLSPGK*

VWF050 nucleotide sequence (IHH triple mutant) (SEQ ID NO: 149)

```
   1 ATGAT TCCTG CCAGA TTTGC CGGGG TGCTG CTTGC TCTGG CCCTC ATTTT
  51 GCCAG GGACC CTTTG TGCAG AAGGA ACTCG CGGCA GGTCA TCCAC GGCCC
 101 GATGC AGCCT TTTCG GAAGT GACTT CGTCA ACACC TTTGA TGGGA GCATG
 151 TACAG CTTTG CGGGA TACTG CAGTT ACCTC CTGGC AGGGG GCTGC CAGAA
 201 ACGCT CCTTC TCGAT TATTG GGGAC TTCCA GAATG GCAAG AGAGT GAGCC
 251 TCTCC GTGTA TCTTG GGGAA TTTTT TGACA TCCAT TTGTT TGTCA ATGGT
 301 ACCGT GACAC AGGGG GACCA AAGAG TCTCC ATGCC CTATG CCTCC AAAGG
 351 GCTGT ATCTA GAAAC TGAGG CTGGG TACTA CAAGC TGTCC GGTGA GGCCT
 401 ATGGC TTTGT GGCCA GGATC GATGG CAGCG GCAAC TTTCA AGTCC TGCTG
 451 TCAGA CAGAT ACTTC AACAA GACCT GCGGG CTGTG TGGCA ACTTT AACAT
 501 CTTTG CTGAA GATGA CTTTA TGACC CAAGA AGGGA CCTTG ACCTC GGACC
 551 CTTAT GACTT TGCCA ACTCA TGGGC TCTGA GCAGT GGAGA ACAGT GGTGT
 601 GAACG GGCAT CTCCT CCCAG CAGCT CATGC AACAT CTCCT CTGGG GAAAT
 651 GCAGA AGGGC CTGTG GGAGC AGTGC CAGCT TCTGA AGAGC ACCTC GGTGT
 701 TTGCC CGCTG CCACC CTCTG GTGGA CCCCG AGCCT TTTGT GGCCC TGTGT
 751 GAGAA GACTT TGTGT GAGTG TGCTG GGGGG CTGGA GTGCG CCTGC CCTGC
 801 CCTCC TGGAG TACGC CCGGA CCTGT GCCCA GGAGG GAATG GTGCT GTACG
 851 GCTGG ACCGA CCACA GCGCG TGCAG CCCAG TGTGC CCTGC TGGTA TGGAG
 901 TATAG GCAGT GTGTG TCCCC TTGCG CCAGG ACCTG CCAGA GCCTG CACAT
 951 CAATG AAATG TGTCA GGAGC GATGC GTGGA TGGCT GCAGC TGCCC TGAGG
1001 GACAG CTCCT GGATG AAGGC CTCTG CGTGG AGAGC ACCGA GTGTC CCTGC
1051 GTGCA TTCCG GAAAG CGCTA CCCTC CCGGC ACCTC CCTCT CTCGA GACTG
1101 CAACA CCTGC ATTTG CCGAA ACAGC CAGTG GATCT GCAGC AATGA AGAAT
1151 GTCCA GGGGA GTGCC TTGTC ACTGG TCAAT CCCAC TTCAA GAGCT TTGAC
1201 AACAG ATACT TCACC TTCAG TGGGA TCTGC CAGTA CCTGC TGGCC CGGGA
1251 TTGCC AGGAC CACTC CTTCT CCATT GTCAT TGAGA CTGTC CAGTG TGCTG
1301 ATGAC CGCGA CGCTG TGTGC ACCCG CTCCG TCACC GTCCG GCTGC CTGGC
1351 CTGCA CAACA GCCTT GTGAA ACTGA AGCAT GGGGC AGGAG TTGCC ATGGA
1401 TGGCC AGGAC ATCCA GCTCC CCCTC CTGAA AGGTG ACCTC CGCAT CCAGC
1451 ATACA GTGAC GGCCT CCGTG CGCCT CAGCT ACGGG GAGGA CCTGC AGATG
1501 GACTG GGATG GCCGC GGGAG GCTGC TGGTG AAGCT GTCCC CCGTC TATGC
1551 CGGGA AGACC TGCGG CCTGT GTGGG AATTA CAATG GCAAC CAGGG CGACG
1601 ACTTC CTTAC CCCCT CTGGG CTGGC GGAGC CCCGG GTGGA GGACT TCGGG
1651 AACGC CTGGA AGCTG CACGG GGACT GCCAG GACCT GCAGA AGCAG CACAG
1701 CGATC CCTGC GCCCT CAACC CGCGC ATGAC CAGGT TCTCC GAGGA GGCGT
1751 GCGCG GTCCT GACGT CCCCC ACATT CGAGG CCTGC CATCG TGCCG TCAGC
1801 CCGCT GCCCT ACCTG CGGAA CTGCC GCTAC GACGT GTGCT CCTGC TCGGA
```

-continued

```
1851   CGGCC GCGAG TGCCT GTGCG GCGCC CTGGC CAGCT ATGCC GCGGC CTGCG
1901   CGGGG AGAGG CGTGC GCGTC GCGTG GCGCG AGCCA GGCCG CTGTG AGCTG
1951   AACTG CCCGA AAGGC CAGGT GTACC TGCAG TGCGG GACCC CCTGC AACCT
2001   GACCT GCCGC TCTCT CTCTT ACCCG GATGA GGAAT GCAAT GAGGC CTGCC
2051   TGGAG GGCTG CTTCT GCCCC CCAGG GCTCT ACATG GATGA GAGGG GGGAC
2101   TGCGT GCCCA AGGCC CAGTG CCCCT GTTAC TATGA CGGTG AGATC TTCCA
2151   GCCAG AAGAC ATCTT CTCAG ACCAT CACAC CATGT GCTAC TGTGA GGATG
2201   GCTTC ATGCA CTGTA CCATG AGTGG AGTCC CCGGA AGCTT GCTGC CTGAC
2251   GCTGT CCTCA GCAGT CCCCT GTCTC ATCGC AGCAA AAGGA GCCTA TCCTG
2301   TCGGC CCCCC ATGGT CAAGC TGGTG TGTCC CGCTG ACAAC CTGCG GGCTG
2351   AAGGG CTCGA GTGTA CCAAA ACGTG CCAGA ACTAT GACCT GGAGT GCATG
2401   AGCAT GGGCT GTGTC TCTGG CTGCC TCTGC CCCCC GGGCA TGGTC CGGCA
2451   TGAGA ACAGA TGTGT GGCCC TGGAA AGGTG TCCCT GCTTC CATCA GGGCA
2501   AGGAG TATGC CCCTG GAGAA ACAGT GAAGA TTGGC TGCAA CACTT GTGTC
2551   TGTCG GGACC GGAAG TGGAA CTGCA CAGAC CATGT GTGTG ATGCC ACGTG
2601   CTCCA CGATC GGCAT GGCCC ACTAC CTCAC CTTCG ACGGG CTCAA ATACC
2651   TGTTC CCCGG GGAGT GCCAG TACGT TCTGG TGCAG GATTA CTGCG GCAGT
2701   AACCC TGGGA CCTTT CGGAT CCTAG TGGGG AATAA GGGAT GCAGC CACCC
2751   CTCAG TGAAA TGCAA GAAAC GGGTC ACCAT CCTGG TGGAG GGAGG AGAGA
2801   TTGAG CTGTT TGACG GGGAG GTGAA TGTGA AGAGG CCCAT GAAGG ATGAG
2851   ACTCA CTTTG AGGTG GTGGA GTCTG GCCGG TACAT CATTC TGCTG CTGGG
2901   CAAAG CCCTC TCCGT GGTCT GGGAC CGCCA CCTGA GCATC TCCGT GGTCC
2951   TGAAG CAGAC ATACC AGGAG AAAGT GTGTG GCCTG TGTGG GAATT TTGAT
3001   GGCAT CCAGA ACAAT GACCT CACCA GCAGC AACCT CCAAG TGGAG GAAGA
3051   CCCTG TGGAC TTTGG GAACT CCTGG AAAGT GAGCT CGCAG TGTGC TGACA
3101   CCAGA AAAGT GCCTC TGGAC TCATC CCCTG CCACC TGCCA TAACA ACATC
3151   ATGAA GCAGA CGATG GTGGA TTCCT CCTGT AGAAT CCTTA CCAGT GACGT
3201   CTTCC AGGAC TGCAA CAAGC TGGTG GACCC CGAGC CATAT CTGGA TGTCT
3251   GCATT TACGA CACCT GCTCC TGTGA GTCCA TTGGG GACTG CGCCG CATTC
3301   TGCGA CACCA TTGCT GCCTA TGCCC ACGTG TGTGC CCAGC ATGGC AAGGT
3351   GGTGA CCTGG AGGAC GGCCA CATTG TGCCC CCAGA GCTGC GAGGA GAGGA
3401   ATCTC CGGGA GAACG GGTAT GAGGC TGAGT GGCGC TATAA CAGCT GTGCA
3451   CCTGC CTGTC AAGTC ACGTG TCAGC ACCCT GAGCC ACTGG CCTGC CCTGT
3501   GCAGT GTGTG GAGGG CTGCC ATGCC CACTG CCCTC CAGGG AAAAT CCTGG
3551   ATGAG CTTTT GCAGA CCTGC GTTGA CCCTG AAGAC TGTCC AGTGT GTGAG
3601   GTGGC TGGCC GGCGT TTTGC CTCAG GAAAG AAAGT CACCT TGAAT CCCAG
3651   TGACC CTGAG CACTG CCAGA TTTGC CACTG TGATG TTGTC AACCT CACCT
3701   GTGAA GCCTG CCAGG AGCCG ATATC TGGCG GTGGA GGTTC CGGTG GCGGG
3751   GGATC CGGCG GTGGA GGTTC CGGCG GTGGA GGTTC CGGTG GCGGG GGATC
```

```
3801  CGGTG GCGGG GGATC CCTGG TCCCC CGGGG CAGCG GCGGT GGAGG TTCCG
3851  GTGGC GGGGG ATCCG ACAAA ACTCA CACAT GCCCA CCGTG CCCAG CTCCA
3901  GAACT CCTGG GCGGA CCGTC AGTCT TCCTC TTCCC CCCAA AACCC AAGGA
3951  CACCC TCATG GCCTC CCGGA CCCCT GAGGT CACAT GCGTG GTGGT GGACG
4001  TGAGC CACGA AGACC CTGAG GTCAA GTTCA ACTGG TACGT GGACG GCGTG
4051  GAGGT GCATA ATGCC AAGAC AAAGC CGCGG GAGGA GCAGT ACAAC AGCAC
4101  GTACC GTGTG GTCAG CGTCC TCACC GTCCT GGCCC AGGAC TGGCT GAATG
4151  GCAAG GAGTA CAAGT GCAAG GTCTC CAACA AAGCC CTCCC AGCCC CCATC
4201  GAGAA AACCA TCTCC AAAGC CAAAG GGCAG CCCCG AGAAC CACAG GTGTA
4251  CACCC TGCCC CCATC CCGCG ATGAG CTGAC CAAGA ACCAG GTCAG CCTGA
4301  CCTGC CTGGT CAAAG GCTTC TATCC CAGCG ACATC GCCGT GGAGT GGGAG
4351  AGCAA TGGGC AGCCG GAGAA CAACT ACAAG ACCAC GCCTC CCGTG TTGGA
4401  CTCCG ACGGC TCCTT CTTCC TCTAC AGCAA GCTCA CCGTG GACAA GAGCA
4451  GGTGG CAGCA GGGGA ACGTC TTCTC ATGCT CCGTG ATGCA TGAGG CTCTG
4501  CACAA CGCCT ACACG CAGAA GAGCC TCTCC CTGTC TCCGG GTAAA TGA
```

VWF050 protein sequence (IHH triple mutant) (SEQ ID NO: 150)

```
   1  MIPARFAGVL LALALILPGT LCAEGTRGRS STARCSLFGS DFVNTFDGSM
  51  YSFAGYCSYL LAGGCQKRSF SIIGDFQNGK RVSLSVYLGE FFDIHLFVNG
 101  TVTQGDQRVS MPYASKGLYL ETEAGYYKLS GEAYGFVARI DGSGNFQVLL
 151  SDRYFNKTCG LCGNFNIFAE DDFMTQEGTL TSDPYDFANS WALSSGEQWC
 201  ERASPPSSSC NISSGEMQKG LWEQCQLLKS TSVFARCHPL VDPEPFVALC
 251  EKTLCECAGG LECACPALLE YARTCAQEGM VLYGWTDHSA CSPVCPAGME
 301  YRQCVSPCAR TCQSLHINEM CQERCVDGCS CPEGQLLDEG LCVESTECPC
 351  VHSGKRYPPG TSLSRDCNTC ICRNSQWICS NEECPGECLV TGQSHFKSFD
 401  NRYFTFSGIC QYLLARDCQD HSFSIVIETV QCADDRDAVC TRSVTVRLPG
 451  LHNSLVKLKH GAGVAMDGQD IQLPLLKGDL RIQHTVTASV RLSYGEDLQM
 501  DWDGRGRLLV KLSPVYAGKT CGLCGNYNGN QGDDFLTPSG LAEPRVEDFG
 551  NAWKLHGDCQ DLQKQHSDPC ALNPRMTRFS EEACAVLTSP TFEACHRAVS
 601  PLPYLRNCRY DVCSCSDGRE CLCGALASYA AACAGRGVRV AWREPGRCEL
 651  NCPKGQVYLQ CGTPCNLTCR SLSYPDEECN EACLEGCFCP PGLYMDERGD
 701  CVPKAQCPCY YDGEIFQPED IFSDHHTMCY CEDGFMHCTM SGVPGSLLPD
 751  AVLSSPLSHR SKRSLSCRPP MVKLVCPADN LRAEGLECTK TCQNYDLECM
 801  SMGCVSGCLC PPGMVRHENR CVALERCPCF HQGKEYAPGE TVKIGCNTCV
 851  CRDRKWNCTD HVCDATCSTI GMAHYLTFDG LKYLFPGECQ YVLVQDYCGS
 901  NPGTFRILVG NKGCSHPSVK CKKRVTILVE GGEIELFDGE VNVKRPMKDE
 951  THFEVVESGR YIILLLGKAL SVVWDRHLSI SVVLKQTYQE KVCGLCGNFD
1001  GIQNNDLTSS NLQVEEDPVD FGNSWKVSSQ CADTRKVPLD SSPATCHNNI
1051  MKQTMVDSSC RILTSDVFQD CNKLVDPEPY LDVCIYDTCS CESIGDCAAF
1101  CDTIAAYAHV CAQHGKVVTW RTATLCPQSC EERNLRENGY EAEWRYNSCA
1151  PACQVTCQHP EPLACPVQCV EGCHAHCPPG KILDELLQTC VDPEDCPVCE
```

-continued

1201 VAGRRFASGK KVTLNPSDPE HCQICHCDVV NLTCEACQEP ISGGGGSGGG

1251 GSGGGGSGGG GSGGGGSGGG GSLVPRGSGG GGSGGGGSDK THTCPPCPAP

1301 ELLGGPSVFL FPPKPKDTLM ASRTPEVTCV VVDVSHEDPE VKFNWYVDGV

1351 EVHNAKTKPR EEQYNSTYRV VSVLTVLAQD WLNGKEYKCK VSNKALPAPI

1401 EKTISKAKGQ PREPQVYTLP PSRDELTKNQ VSLTCLVKGF YPSDIAVEWE

1451 SNGQPENNYK TTPPVLDSDG SFFLYSKLTV DKSRWQQGNV FSCSVMHEAL

1501 HNAYTQKSLS LSPGK*

VWF057 nucleotide sequence (SEQ ID NO: 151)

1 ATGAT TCCTG CCAGA TTTGC CGGGG TGCTG CTTGC TCTGG CCCTC ATTTT

51 GCCAG GGACC CTTTG TGCAG AAGGA ACTCG CGGCA GGTCA TCCAC GGCCC

101 GATGC AGCCT TTTCG GAAGT GACTT CGTCA ACACC TTTGA TGGGA GCATG

151 TACAG CTTTG CGGGA TACTG CAGTT ACCTC CTGGC AGGGG GCTGC CAGAA

201 ACGCT CCTTC TCGAT TATTG GGGAC TTCCA GAATG GCAAG AGAGT GAGCC

251 TCTCC GTGTA TCTTG GGGAA TTTTT TGACA TCCAT TTGTT TGTCA ATGGT

301 ACCGT GACAC AGGGG GACCA AAGAG TCTCC ATGCC CTATG CCTCC AAAGG

351 GCTGT ATCTA GAAAC TGAGG CTGGG TACTA CAAGC TGTCC GGTGA GGCCT

401 ATGGC TTTGT GGCCA GGATC GATGG CAGCG GCAAC TTTCA AGTCC TGCTG

451 TCAGA CAGAT ACTTC AACAA GACCT GCGGG CTGTG TGGCA ACTTT AACAT

501 CTTTG CTGAA GATGA CTTTA TGACC CAAGA AGGGA CCTTG ACCTC GGACC

551 CTTAT GACTT TGCCA ACTCA TGGGC TCTGA GCAGT GGAGA ACAGT GGTGT

601 GAACG GGCAT CTCCT CCCAG CAGCT CATGC AACAT CTCCT CTGGG GAAAT

651 GCAGA AGGGC CTGTG GGAGC AGTGC CAGCT TCTGA AGAGC ACCTC GGTGT

701 TTGCC CGCTG CCACC CTCTG GTGGA CCCCG AGCCT TTTGT GGCCC TGTGT

751 GAGAA GACTT TGTGT GAGTG TGCTG GGGGG CTGGA GTGCG CCTGC CCTGC

801 CCTCC TGGAG TACGC CCGGA CCTGT GCCCA GGAGG GAATG GTGCT GTACG

851 GCTGG ACCGA CCACA GCGCG TGCAG CCCAG TGTGC CCTGC TGGTA TGGAG

901 TATAG GCAGT GTGTG TCCCC TTGCG CCAGG ACCTG CCAGA GCCTG CACAT

951 CAATG AAATG TGTCA GGAGC GATGC GTGGA TGGCT GCAGC TGCCC TGAGG

1001 GACAG CTCCT GGATG AAGGC CTCTG CGTGG AGAGC ACCGA GTGTC CCTGC

1051 GTGCA TTCCG GAAAG CGCTA CCCTC CCGGC ACCTC CCTCT CTCGA GACTG

1101 CAACA CCTGC ATTTG CCGAA ACAGC CAGTG GATCT GCAGC AATGA AGAAT

1151 GTCCA GGGGA GTGCC TTGTC ACTGG TCAAT CCCAC TTCAA GAGCT TTGAC

1201 AACAG ATACT TCACC TTCAG TGGGA TCTGC CAGTA CCTGC TGGCC CGGGA

1251 TTGCC AGGAC CACTC CTTCT CCATT GTCAT TGAGA CTGTC CAGTG TGCTG

1301 ATGAC CGCGA CGCTG TGTGC ACCCG CTCCG TCACC GTCCG GCTGC CTGGC

1351 CTGCA CAACA GCCTT GTGAA ACTGA AGCAT GGGGC AGGAG TTGCC ATGGA

1401 TGGCC AGGAC ATCCA GCTCC CCCTC CTGAA AGGTG ACCTC CGCAT CCAGC

1451 ATACA GTGAC GGCCT CCGTG CGCCT CAGCT ACGGG GAGGA CCTGC AGATG

1501 GACTG GGATG GCCGC GGGAG GCTGC TGGTG AAGCT GTCCC CCGTC TATGC

1551 CGGGA AGACC TGCGG CCTGT GTGGG AATTA CAATG GCAAC CAGGG CGACG

-continued

1601 ACTTC CTTAC CCCCT CTGGG CTGGC GGAGC CCCGG GTGGA GGACT TCGGG

1651 AACGC CTGGA AGCTG CACGG GGACT GCCAG GACCT GCAGA AGCAG CACAG

1701 CGATC CCTGC GCCCT CAACC CGCGC ATGAC CAGGT TCTCC GAGGA GGCGT

1751 GCGCG GTCCT GACGT CCCCC ACATT CGAGG CCTGC CATCG TGCCG TCAGC

1801 CCGCT GCCCT ACCTG CGGAA CTGCC GCTAC GACGT GTGCT CCTGC TCGGA

1851 CGGCC GCGAG TGCCT GTGCG GCGCC CTGGC CAGCT ATGCC GCGGC CTGCG

1901 CGGGG AGAGG CGTGC GCGTC GCGTG GCGCG AGCCA GGCCG CTGTG AGCTG

1951 AACTG CCCGA AAGGC CAGGT GTACC TGCAG TGCGG GACCC CCTGC AACCT

2001 GACCT GCCGC TCTCT CTCTT ACCCG GATGA GGAAT GCAAT GAGGC CTGCC

2051 TGGAG GGCTG CTTCT GCCCC CCAGG GCTCT ACATG GATGA GAGGG GGGAC

2101 TGCGT GCCCA AGGCC CAGTG CCCCT GTTAC TATGA CGGTG AGATC TTCCA

2151 GCCAG AAGAC ATCTT CTCAG ACCAT CACAC CATGT GCTAC TGTGA GGATG

2201 GCTTC ATGCA CTGTA CCATG AGTGG AGTCC CCGGA AGCTT GCTGC CTGAC

2251 GCTGT CCTCA GCAGT CCCCT GTCTC ATCGC AGCAA AAGGA GCCTA TCCTG

2301 TCGGC CCCCC ATGGT CAAGC TGGTG TGTCC CGCTG ACAAC CTGCG GGCTG

2351 AAGGG CTCGA GTGTA CCAAA ACGTG CCAGA ACTAT GACCT GGAGT GCATG

2401 AGCAT GGGCT GTGTC TCTGG CTGCC TCTGC CCCCC GGGCA TGGTC CGGCA

2451 TGAGA ACAGA TGTGT GGCCC TGGAA AGGTG TCCCT GCTTC CATCA GGGCA

2501 AGGAG TATGC CCCTG GAGAA ACAGT GAAGA TTGGC TGCAA CACTT GTGTC

2551 TGTCG GGACC GGAAG TGGAA CTGCA CAGAC CATGT GTGTG ATGCC ACGTG

2601 CTCCA CGATC GGCAT GGCCC ACTAC CTCAC CTTCG ACGGG CTCAA ATACC

2651 TGTTC CCCGG GGAGT GCCAG TACGT TCTGG TGCAG GATTA CTGCG GCAGT

2701 AACCC TGGGA CCTTT CGGAT CCTAG TGGGG AATAA GGGAT GCAGC CACCC

2751 CTCAG TGAAA TGCAA GAAAC GGGTC ACCAT CCTGG TGGAG GGAGG AGAGA

2801 TTGAG CTGTT TGACG GGGAG GTGAA TGTGA AGAGG CCCAT GAAGG ATGAG

2851 ACTCA CTTTG AGGTG GTGGA GTCTG GCCGG TACAT CATTC TGCTG CTGGG

2901 CAAAG CCCTC TCCGT GGTCT GGGAC CGCCA CCTGA GCATC TCCGT GGTCC

2951 TGAAG CAGAC ATACC AGGAG AAAGT GTGTG GCCTG TGTGG GAATT TTGAT

3001 GGCAT CCAGA ACAAT GACCT CACCA GCAGC AACCT CCAAG TGGAG GAAGA

3051 CCCTG TGGAC TTTGG GAACT CCTGG AAAGT GAGCT CGCAG TGTGC TGACA

3101 CCAGA AAAGT GCCTC TGGAC TCATC CCCTG CCACC TGCCA TAACA ACATC

3151 ATGAA GCAGA CGATG GTGGA TTCCT CCTGT AGAAT CCTTA CCAGT GACGT

3201 CTTCC AGGAC TGCAA CAAGC TGGTG GACCC CGAGC CATAT CTGGA TGTCT

3251 GCATT TACGA CACCT GCTCC TGTGA GTCCA TTGGG GACTG CGCCG CATTC

3301 TGCGA CACCA TTGCT GCCTA TGCCC ACGTG TGTGC CCAGC ATGGC AAGGT

3351 GGTGA CCTGG AGGAC GGCCA CATTG TGCCC CCAGA GCTGC GAGGA GAGGA

3401 ATCTC CGGGA GAACG GGTAT GAGGC TGAGT GGCGC TATAA CAGCT GTGCA

3451 CCTGC CTGTC AAGTC ACGTG TCAGC ACCCT GAGCC ACTGG CCTGC CCTGT

3501 GCAGT GTGTG GAGGG CTGCC ATGCC CACTG CCCTC CAGGG AAAAT CCTGG

3551 ATGAG CTTTT GCAGA CCTGC GTTGA CCCTG AAGAC TGTCC AGTGT GTGAG

-continued

```
3601  GTGGC TGGCC GGCGT TTTGC CTCAG GAAAG AAAGT CACCT TGAAT CCCAG
3651  TGACC CTGAG CACTG CCAGA TTTGC CACTG TGATG TTGTC AACCT CACCT
3701  GTGAA GCCTG CCAGG AGCCG ATATC GGGCG CGCCA ACATC AGAGA GCGCC
3751  ACCCC TGAAA GTGGT CCCGG GAGCG AGCCA GCCAC ATCTG GGTCG GAAAC
3801  GCCAG GCACA AGTGA GTCTG CAACT CCCGA GTCCG GACCT GGCTC CGAGC
3851  CTGCC ACTAG CGGCT CCGAG ACTCC GGGAA CTTCC GAGAG CGCTA CACCA
3901  GAAAG CGGAC CCGGA ACCAG TACCG AACCT AGCGA GGGCT CTGCT CCGGG
3951  CAGCC CAGCC GGCTC TCCTA CATCC ACGGA GGAGG GCACT TCCGA ATCCG
4001  CCACC CCGGA GTCAG GGCCA GGATC TGAAC CCGCT ACCTC AGGCA GTGAG
4051  ACGCC AGGAA CGAGC GAGTC CGCTA CACCG GAGAG TGGGC CAGGG AGCCC
4101  TGCTG GATCT CCTAC GTCCA CTGAG GAAGG GTCAC CAGCG GGCTC GCCCA
4151  CCAGC ACTGA AGAAG GTGCC TCGAG CGGCG GTGGA GGTTC CGGTG GCGGG
4201  GGATC CGGTG GCGGG GGATC CGGTG GCGGG GGATC CGGTG GCGGG GGATC
4251  CCTGG TCCCC CGGGG CAGCG GAGGC GACAA AACTC ACACA TGCCC ACCGT
4301  GCCCA GCTCC AGAAC TCCTG GGCGG ACCGT CAGTC TTCCT CTTCC CCCCA
4351  AAACC CAAGG ACACC CTCAT GATCT CCCGG ACCCC TGAGG TCACA TGCGT
4401  GGTGG TGGAC GTGAG CCACG AAGAC CCTGA GGTCA AGTTC AACTG GTACG
4451  TGGAC GGCGT GGAGG TGCAT AATGC CAAGA CAAAG CCGCG GGAGG AGCAG
4501  TACAA CAGCA CGTAC CGTGT GGTCA GCGTC CTCAC CGTCC TGCAC CAGGA
4551  CTGGC TGAAT GGCAA GGAGT ACAAG TGCAA GGTCT CCAAC AAAGC CCTCC
4601  CAGCC CCCAT CGAGA AAACC ATCTC CAAAG CCAAA GGGCA GCCCC GAGAA
4651  CCACA GGTGT ACACC CTGCC CCCAT CCCGG GATGA GCTGA CCAAG AACCA
4701  GGTCA GCCTG ACCTG CCTGG TCAAA GGCTT CTATC CCAGC GACAT CGCCG
4751  TGGAG TGGGA GAGCA ATGGG CAGCC GGAGA ACAAC TACAA GACCA CGCCT
4801  CCCGT GTTGG ACTCC GACGG CTCCT TCTTC CTCTA CAGCA AGCTC ACCGT
4851  GGACA AGAGC AGGTG GCAGC AGGGG AACGT CTTCT CATGC TCCGT GATGC
4901  ATGAG GCTCT GCACA ACCAC TACAC GCAGA AGAGC CTCTC CCTGT CTCCG
4951  GGTAA ATGA
```

VWF057 protein sequence (SEQ ID NO: 152)

```
  1  MIPARFAGVL LALALILPGT LCAEGTRGRS STARCSLFGS DFVNTFDGSM
 51  YSFAGYCSYL LAGGCQKRSF SIIGDFQNGK RVSLSVYLGE FFDIHLFVNG
101  TVTQGDQRVS MPYASKGLYL ETEAGYYKLS GEAYGFVARI DGSGNFQVLL
151  SDRYFNKTCG LCGNFNIFAE DDFMTQEGTL TSDPYDFANS WALSSGEQWC
201  ERASPPSSSC NISSGEMQKG LWEQCQLLKS TSVFARCHPL VDPEPFVALC
251  EKTLCECAGG LECACPALLE YARTCAQEGM VLYGWTDHSA CSPVCPAGME
301  YRQCVSPCAR TCQSLHINEM CQERCVDGCS CPEGQLLDEG LCVESTECPC
351  VHSGKRYPPG TSLSRDCNTC ICRNSQWICS NEECPGECLV TGQSHFKSFD
401  NRYFTFSGIC QYLLARDCQD HSFSIVIETV QCADDRDAVC TRSVTVRLPG
451  LHNSLVKLKH GAGVAMDGQD IQLPLLKGDL RIQHTVTASV RLSYGEDLQM
501  DWDGRGRLLV KLSPVYAGKT CGLCGNYNGN QGDDFLTPSG LAEPRVEDFG
```

-continued

```
 551  NAWKLHGDCQ DLQKQHSDPC ALNPRMTRFS EEACAVLTSP TFEACHRAVS
 601  PLPYLRNCRY DVCSCSDGRE CLCGALASYA AACAGRGVRV AWREPGRCEL
 651  NCPKGQVYLQ CGTPCNLTCR SLSYPDEECN EACLEGCFCP PGLYMDERGD
 701  CVPKAQCPCY YDGEIFQPED IFSDHHTMCY CEDGFMHCTM SGVPGSLLPD
 751  AVLSSPLSHR SKRSLSCRPP MVKLVCPADN LRAEGLECTK TCQNYDLECM
 801  SMGCVSGCLC PPGMVRHENR CVALERCPCF HQGKEYAPGE TVKIGCNTCV
 851  CRDRKWNCTD HVCDATCSTI GMAHYLTFDG LKYLFPGECQ YVLVQDYCGS
 901  NPGTFRILVG NKGCSHPSVK CKKRVTILVE GGEIELFDGE VNVKRPMKDE
 951  THFEVVESGR YIILLLGKAL SVVWDRHLSI SVVLKQTYQE KVCGLCGNFD
1001  GIQNNDLTSS NLQVEEDPVD FGNSWKVSSQ CADTRKVPLD SSPATCHNNI
1051  MKQTMVDSSC RILTSDVFQD CNKLVDPEPY LDVCIYDTCS CESIGDCAAF
1101  CDTIAAYAHV CAQHGKVVTW RTATLCPQSC EERNLRENGY EAEWRYNSCA
1151  PACQVTCQHP EPLACPVQCV EGCHAHCPPG KILDELLQTC VDPEDCPVCE
1201  VAGRRFASGK KVTLNPSDPE HCQICHCDVV NLTCEACQEP ISGAPTSESA
1251  TPESGPGSEP ATSGSETPGT SESATPESGP GSEPATSGSE TPGTSESATP
1301  ESGPGTSTEP SEGSAPGSPA GSPTSTEEGT SESATPESGP GSEPATSGSE
1351  TPGTSESATP ESGPGSPAGS PTSTEEGSPA GSPTSTEEGA SSGGGGSGGG
1401  GSGGGGSGGG GSGGGGSLVP RGSGGDKTHT CPPCPAPELL GGPSVFLFPP
1451  KPKDTLMISR TPEVTCVVVD VSHEDPEVKF NWYVDGVEVH NAKTKPREEQ
1501  YNSTYRVVSV LTVLHQDWLN GKEYKCKVSN KALPAPIEKT ISKAKGQPRE
1551  PQVYTLPPSR DELTKNQVSL TCLVKGFYPS DIAVEWESNG QPENNYKTTP
1601  PVLDSDGSFF LYSKLTVDKS RWQQGNVFSC SVMHEALHNH YTQKSLSLSP
1651  GK*
```

VWF058 nucleotide sequence (VWF034 with IHH mutation) (SEQ ID NO: 153)

```
   1  ATGAT TCCTG CCAGA TTTGC CGGGG TGCTG CTTGC TCTGG CCCTC ATTTT
  51  GCCAG GGACC CTTTG TGCAG AAGGA ACTCG CGGCA GGTCA TCCAC GGCCC
 101  GATGC AGCCT TTTCG GAAGT GACTT CGTCA ACACC TTTGA TGGGA GCATG
 151  TACAG CTTTG CGGGA TACTG CAGTT ACCTC CTGGC AGGGG GCTGC CAGAA
 201  ACGCT CCTTC TCGAT TATTG GGGAC TTCCA GAATG GCAAG AGAGT GAGCC
 251  TCTCC GTGTA TCTTG GGGAA TTTTT TGACA TCCAT TTGTT TGTCA ATGGT
 301  ACCGT GACAC AGGGG GACCA AAGAG TCTCC ATGCC CTATG CCTCC AAAGG
 351  GCTGT ATCTA GAAAC TGAGG CTGGG TACTA CAAGC TGTCC GGTGA GGCCT
 401  ATGGC TTTGT GGCCA GGATC GATGG CAGCG GCAAC TTTCA AGTCC TGCTG
 451  TCAGA CAGAT ACTTC AACAA GACCT GCGGG CTGTG TGGCA ACTTT AACAT
 501  CTTTG CTGAA GATGA CTTTA TGACC CAAGA AGGGA CCTTG ACCTC GGACC
 551  CTTAT GACTT TGCCA ACTCA TGGGC TCTGA GCAGT GGAGA ACAGT GGTGT
 601  GAACG GGCAT CTCCT CCCAG CAGCT CATGC AACAT CTCCT CTGGG GAAAT
 651  GCAGA AGGGC CTGTG GGAGC AGTGC CAGCT TCTGA AGAGC ACCTC GGTGT
 701  TTGCC CGCTG CCACC CTCTG GTGGA CCCCG AGCCT TTTGT GGCCC TGTGT
 751  GAGAA GACTT TGTGT GAGTG TGCTG GGGGG CTGGA GTGCG CCTGC CCTGC
```

-continued

801 CCTCC TGGAG TACGC CCGGA CCTGT GCCCA GGAGG GAATG GTGCT GTACG
851 GCTGG ACCGA CCACA GCGCG TGCAG CCCAG TGTGC CCTGC TGGTA TGGAG
901 TATAG GCAGT GTGTG TCCCC TTGCG CCAGG ACCTG CCAGA GCCTG CACAT
951 CAATG AAATG TGTCA GGAGC GATGC GTGGA TGGCT GCAGC TGCCC TGAGG
1001 GACAG CTCCT GGATG AAGGC CTCTG CGTGG AGAGC ACCGA GTGTC CCTGC
1051 GTGCA TTCCG GAAAG CGCTA CCCTC CCGGC ACCTC CCTCT CTCGA GACTG
1101 CAACA CCTGC ATTTG CCGAA ACAGC CAGTG GATCT GCAGC AATGA AGAAT
1151 GTCCA GGGGA GTGCC TTGTC ACTGG TCAAT CCCAC TTCAA GAGCT TTGAC
1201 AACAG ATACT TCACC TTCAG TGGGA TCTGC CAGTA CCTGC TGGCC CGGGA
1251 TTGCC AGGAC CACTC CTTCT CCATT GTCAT TGAGA CTGTC CAGTG TGCTG
1301 ATGAC CGCGA CGCTG TGTGC ACCCG CTCCG TCACC GTCCG GCTGC CTGGC
1351 CTGCA CAACA GCCTT GTGAA ACTGA AGCAT GGGGC AGGAG TTGCC ATGGA
1401 TGGCC AGGAC ATCCA GCTCC CCCTC CTGAA AGGTG ACCTC CGCAT CCAGC
1451 ATACA GTGAC GGCCT CCGTG CGCCT CAGCT ACGGG GAGGA CCTGC AGATG
1501 GACTG GGATG GCCGC GGGAG GCTGC TGGTG AAGCT GTCCC CCGTC TATGC
1551 CGGGA AGACC TGCGG CCTGT GTGGG AATTA CAATG GCAAC CAGGG CGACG
1601 ACTTC CTTAC CCCCT CTGGG CTGGC GGAGC CCCGG GTGGA GGACT TCGGG
1651 AACGC CTGGA AGCTG CACGG GGACT GCCAG GACCT GCAGA AGCAG CACAG
1701 CGATC CCTGC GCCCT CAACC CGCGC ATGAC CAGGT TCTCC GAGGA GGCGT
1751 GCGCG GTCCT GACGT CCCCC ACATT CGAGG CCTGC CATCG TGCCG TCAGC
1801 CCGCT GCCCT ACCTG CGGAA CTGCC GCTAC GACGT GTGCT CCTGC TCGGA
1851 CGGCC GCGAG TGCCT GTGCG GCGCC CTGGC CAGCT ATGCC GCGGC CTGCG
1901 CGGGG AGAGG CGTGC GCGTC GCGTG GCGCG AGCCA GGCCG CTGTG AGCTG
1951 AACTG CCCGA AAGGC CAGGT GTACC TGCAG TGCGG GACCC CCTGC AACCT
2001 GACCT GCCGC TCTCT CTCTT ACCCG GATGA GGAAT GCAAT GAGGC CTGCC
2051 TGGAG GGCTG CTTCT GCCCC CCAGG GCTCT ACATG GATGA GAGGG GGGAC
2101 TGCGT GCCCA AGGCC CAGTG CCCCT GTTAC TATGA CGGTG AGATC TTCCA
2151 GCCAG AAGAC ATCTT CTCAG ACCAT CACAC CATGT GCTAC TGTGA GGATG
2201 GCTTC ATGCA CTGTA CCATG AGTGG AGTCC CCGGA AGCTT GCTGC CTGAC
2251 GCTGT CCTCA GCAGT CCCCT GTCTC ATCGC AGCAA AAGGA GCCTA TCCTG
2301 TCGGC CCCCC ATGGT CAAGC TGGTG TGTCC CGCTG ACAAC CTGCG GGCTG
2351 AAGGG CTCGA GTGTA CCAAA ACGTG CCAGA ACTAT GACCT GGAGT GCATG
2401 AGCAT GGGCT GTGTC TCTGG CTGCC TCTGC CCCCC GGGCA TGGTC CGGCA
2451 TGAGA ACAGA TGTGT GGCCC TGGAA AGGTG TCCCT GCTTC CATCA GGGCA
2501 AGGAG TATGC CCCTG GAGAA ACAGT GAAGA TTGGC TGCAA CACTT GTGTC
2551 TGTCG GGACC GGAAG TGGAA CTGCA CAGAC CATGT GTGTG ATGCC ACGTG
2601 CTCCA CGATC GGCAT GGCCC ACTAC CTCAC CTTCG ACGGG CTCAA ATACC
2651 TGTTC CCCGG GGAGT GCCAG TACGT TCTGG TGCAG GATTA CTGCG GCAGT
2701 AACCC TGGGA CCTTT CGGAT CCTAG TGGGG AATAA GGGAT GCAGC CACCC

-continued

```
2751 CTCAG TGAAA TGCAA GAAAC GGGTC ACCAT CCTGG TGGAG GGAGG AGAGA
2801 TTGAG CTGTT TGACG GGGAG GTGAA TGTGA AGAGG CCCAT GAAGG ATGAG
2851 ACTCA CTTTG AGGTG GTGGA GTCTG GCCGG TACAT CATTC TGCTG CTGGG
2901 CAAAG CCCTC TCCGT GGTCT GGGAC CGCCA CCTGA GCATC TCCGT GGTCC
2951 TGAAG CAGAC ATACC AGGAG AAAGT GTGTG GCCTG TGTGG GAATT TTGAT
3001 GGCAT CCAGA ACAAT GACCT CACCA GCAGC AACCT CCAAG TGGAG GAAGA
3051 CCCTG TGGAC TTTGG GAACT CCTGG AAAGT GAGCT CGCAG TGTGC TGACA
3101 CCAGA AAAGT GCCTC TGGAC TCATC CCCTG CCACC TGCCA TAACA ACATC
3151 ATGAA GCAGA CGATG GTGGA TTCCT CCTGT AGAAT CCTTA CCAGT GACGT
3301 TGCGA CACCA TTGCT GCCTA TGCCC ACGTG TGTGC CCAGC ATGGC AAGGT
3351 GGTGA CCTGG AGGAC GGCCA CATTG TGCCC CCAGA GCTGC GAGGA GAGGA
3401 ATCTC CGGGA GAACG GGTAT GAGGC TGAGT GGCGC TATAA CAGCT GTGCA
3451 CCTGC CTGTC AAGTC ACGTG TCAGC ACCCT GAGCC ACTGG CCTGC CCTGT
3501 GCAGT GTGTG GAGGG CTGCC ATGCC CACTG CCCTC CAGGG AAAAT CCTGG
3551 ATGAG CTTTT GCAGA CCTGC GTTGA CCCTG AAGAC TGTCC AGTGT GTGAG
3601 GTGGC TGGCC GGCGT TTTGC CTCAG GAAAG AAAGT CACCT TGAAT CCCAG
3651 TGACC CTGAG CACTG CCAGA TTTGC CACTG TGATG TTGTC AACCT CACCT
3701 GTGAA GCCTG CCAGG AGCCG ATATC GGGTA CCTCA GAGTC TGCTA CCCCC
3751 GAGTC AGGGC CAGGA TCAGA GCCAG CCACC TCCGG GTCTG AGACA CCCGG
3801 GACTT CCGAG AGTGC CACCC CTGAG TCCGG ACCCG GGTCC GAGCC CGCCA
3851 CTTCC GGCTC CGAAA CTCCC GGCAC AAGCG AGAGC GCTAC CCCAG AGTCA
3901 GGACC AGGAA CATCT ACAGA GCCCT CTGAA GGCTC CGCTC CAGGG TCCCC
3951 AGCCG GCAGT CCCAC TAGCA CCGAG GAGGG AACCT CTGAA AGCGC CACAC
4001 CCGAA TCAGG GCCAG GGTCT GAGCC TGCTA CCAGC GGCAG CGAGA CACCA
4051 GGCAC CTCTG AGTCC GCCAC ACCAG AGTCC GGACC CGGAT CTCCC GCTGG
4101 GAGCC CCACC TCCAC TGAGG AGGGA TCTCC TGCTG GCTCT CCAAC ATCTA
4151 CTGAG GAAGG TACCT CAACC GAGCC ATCCG AGGGA TCAGC TCCCG GCACC
4201 TCAGA GTCGG CAACC CCGGA GTCTG GACCC GGAAC TTCCG AAAGT GCCAC
4251 ACCAG AGTCC GGTCC CGGGA CTTCA GAATC AGCAA CACCC GAGTC CGGCC
4301 CTGGG TCTGA ACCCG CCACA AGTGG TAGTG AGACA CCAGG ATCAG AACCT
4351 GCTAC CTCAG GGTCA GAGAC ACCCG GATCT CCGGC AGGCT CACCA ACCTC
4401 CACTG AGGAG GGCAC CAGCA CAGAA CCAAG CGAGG GCTCC GCACC CGGAA
4451 CAAGC ACTGA ACCCA GTGAG GGTTC AGCAC CCGGC TCTGA GCCGG CCACA
4501 AGTGG CAGTG AGACA CCCGG CACTT CAGAG AGTGC CACCC CCGAG AGTGG
4551 CCCAG GCACT AGTAC CGAGC CCTCT GAAGG CAGTG CGCCA GATTC TGGCG
4601 GTGGA GGTTC CGGTG GCGGG GGATC CGGTG GCGGG GGATC CGGTG GCGGG
4651 GGATC CGGTG GCGGG GGATC CCTGG TCCCC CGGGG CAGCG GAGGC GACAA
4701 AACTC ACACA TGCCC ACCGT GCCCA GCTCC AGAAC TCCTG GGCGG ACCGT
4751 CAGTC TTCCT CTTCC CCCCA AAACC CAAGG ACACC CTCAT GGCCT CCCGG
4801 ACCCC TGAGG TCACA TGCGT GGTGG TGGAC GTGAG CCACG AAGAC CCTGA
```

-continued

4851 GGTCA AGTTC AACTG GTACG TGGAC GGCGT GGAGG TGCAT AATGC CAAGA

4901 CAAAG CCGCG GGAGG AGCAG TACAA CAGCA CGTAC CGTGT GGTCA GCGTC

4951 CTCAC CGTCC TGGCC CAGGA CTGGC TGAAT GGCAA GGAGT ACAAG TGCAA

5001 GGTCT CCAAC AAAGC CCTCC CAGCC CCCAT CGAGA AAACC ATCTC CAAAG

5051 CCAAA GGGCA GCCCC GAGAA CCACA GGTGT ACACC CTGCC CCCAT CCCGC

5101 GATGA GCTGA CCAAG AACCA GGTCA GCCTG ACCTG CCTGG TCAAA GGCTT

5151 CTATC CCAGC GACAT CGCCG TGGAG TGGGA GAGCA ATGGG CAGCC GGAGA

5201 ACAAC TACAA GACCA CGCCT CCCGT GTTGG ACTCC GACGG CTCCT TCTTC

5251 CTCTA CAGCA AGCTC ACCGT GGACA AGAGC AGGTG GCAGC AGGGG AACGT

5301 CTTCT CATGC TCCGT GATGC ATGAG GCTCT GCACA ACGCC TACAC GCAGA

5351 AGAGC CTCTC CCTGT CTCCG GGTAA ATGA

VWF058 protein sequence (VWF034 with IHH mutation) (SEQ ID NO: 154)

1 MIPARFAGVL LALALILPGT LCAEGTRGRS STARCSLFGS DFVNTFDGSM

51 YSFAGYCSYL LAGGCQKRSF SIIGDFQNGK RVSLSVYLGE FFDIHLFVNG

101 TVTQGDQRVS MPYASKGLYL ETEAGYYKLS GEAYGFVARI DGSGNFQVLL

151 SDRYFNKTCG LCGNFNIFAE DDFMTQEGTL TSDPYDFANS WALSSGEQWC

201 ERASPPSSSC NISSGEMQKG LWEQCQLLKS TSVFARCHPL VDPEPFVALC

251 EKTLCECAGG LECACPALLE YARTCAQEGM VLYGWTDHSA CSPVCPAGME

301 YRQCVSPCAR TCQSLHINEM CQERCVDGCS CPEGQLLDEG LCVESTECPC

351 VHSGKRYPPG TSLSRDCNTC ICRNSQWICS NEECPGECLV TGQSHFKSFD

401 NRYFTFSGIC QYLLARDCQD HSFSIVIETV QCADDRDAVC TRSVTVRLPG

451 LHNSLVKLKH GAGVAMDGQD IQLPLLKGDL RIQHTVTASV RLSYGEDLQM

501 DWDGRGRLLV KLSPVYAGKT CGLCGNYNGN QGDDFLTPSG LAEPRVEDFG

551 NAWKLHGDCQ DLQKQHSDPC ALNPRMTRFS EEACAVLTSP TFEACHRAVS

601 PLPYLRNCRY DVCSCSDGRE CLCGALASYA AACAGRGVRV AWREPGRCEL

651 NCPKGQVYLQ CGTPCNLTCR SLSYPDEECN EACLEGCFCP PGLYMDERGD

701 CVPKAQCPCY YDGEIFQPED IFSDHHTMCY CEDGFMHCTM SGVPGSLLPD

751 AVLSSPLSHR SKRSLSCRPP MVKLVCPADN LRAEGLECTK TCQNYDLECM

801 SMGCVSGCLC PPGMVRHENR CVALERCPCF HQGKEYAPGE TVKIGCNTCV

851 CRDRKWNCTD HVCDATCSTI GMAHYLTFDG LKYLFPGECQ YVLVQDYCGS

901 NPGTFRILVG NKGCSHPSVK CKKRVTILVE GGEIELFDGE VNVKRPMKDE

951 THFEVVESGR YIILLLGKAL SVVWDRHLSI SVVLKQTYQE KVCGLCGNFD

1001 GIQNNDLTSS NLQVEEDPVD FGNSWKVSSQ CADTRKVPLD SSPATCHNNI

1051 MKQTMVDSSC RILTSDVFQD CNKLVDPEPY LDVCIYDTCS CESIGDCAAF

1101 CDTIAAYAHV CAQHGKVVTW RTATLCPQSC EERNLRENGY EAEWRYNSCA

1151 PACQVTCQHP EPLACPVQCV EGCHAHCPPG KILDELLQTC VDPEDCPVCE

1201 VAGRRFASGK KVTLNPSDPE HCQICHCDVV NLTCEACQEP ISGTSESATP

1251 ESGPGSEPAT SGSETPGTSE aATPESGPGS EPATSGSETP GTSESATPES

1301 GPGTSTEPSE GSAPGSPAGS PTSTEEGTSE SATPESGPGS EPATSGSETP

1351 GTSESATPES GPGSPAGSPT STEEGSPAGS PTSTEEGTST EPSEGSAPGT

-continued

1401 SESATPESGP GTSESATPES GPGTSESATP ESGPGSEPAT SGSETPGSEP

1451 ATSGSETPGS PAGSPTSTEE GTSTEPSEGS APGTSTEPSE GSAPGSEPAT

1501 SGSETPGTSE aATPESGPGT STEPSEGSAP DSGGGGSGGG GSGGGGSGGG

1551 GSGGGGSLVP RGSGGDKTHT CPPCPAPELL GGPSVFLFPP KPKDTLMASR

1601 TPEVTCVVVD VSHEDPEVKF NWYVDGVEVH NAKTKPREEQ YNSTYRVVSV

1651 LTVLAQDWLN GKEYKCKVSN KALPAPIEKT ISKAKGQPRE PQVYTLPPSR

1701 DELTKNQVSL TCLVKGFYPS DIAVEWESNG QPENNYKTTP PVLDSDGSFF

1751 LYSKLTVDKS RWQQGNVFSC SVMHEALHNA YTQKSLSLSP GK*

FVIII 169 nucleotide sequence (SEQ ID NO: 155)

1 ATGCA AATAG AGCTC TCCAC CTGCT TCTTT CTGTG CCTTT TGCGA TTCTG

51 CTTTA GTGCC ACCAG AAGAT ACTAC CTGGG TGCAG TGGAA CTGTC ATGGG

101 ACTAT ATGCA AAGTG ATCTC GGTGA GCTGC CTGTG GACGC AAGAT TTCCT

151 CCTAG AGTGC CAAAA TCTTT TCCAT TCAAC ACCTC AGTCG TGTAC AAAAA

201 GACTC TGTTT GTAGA ATTCA CGGAT CACCT TTTCA ACATC GCTAA GCCAA

251 GGCCA CCCTG GATGG GTCTG CTAGG TCCTA CCATC CAGGC TGAGG TTTAT

301 GATAC AGTGG TCATT ACACT TAAGA ACATG GCTTC CCATC CTGTC AGTCT

351 TCATG CTGTT GGTGT ATCCT ACTGG AAAGC TTCTG AGGGA GCTGA ATATG

401 ATGAT CAGAC CAGTC AAAGG GAGAA AGAAG ATGAT AAAGT CTTCC CTGGT

451 GGAAG CCATA CATAT GTCTG GCAGG TCCTG AAAGA GAATG GTCCA ATGGC

501 CTCTG ACCCA CTGTG CCTTA CCTAC TCATA TCTTT CTCAT GTGGA CCTGG

551 TAAAA GACTT GAATT CAGGC CTCAT TGGAG CCCTA CTAGT ATGTA GAGAA

601 GGGAG TCTGG CCAAG GAAAA GACAC AGACC TTGCA CAAAT TTATA CTACT

651 TTTTG CTGTA TTTGA TGAAG GGAAA AGTTG GCACT CAGAA ACAAA GAACT

701 CCTTG ATGCA GGATA GGGAT GCTGC ATCTG CTCGG GCCTG GCCTA AAATG

751 CACAC AGTCA ATGGT TATGT AAACA GGTCT CTGCC AGGTC TGATT GGATG

801 CCACA GGAAA TCAGT CTATT GGCAT GTGAT TGGAA TGGGC ACCAC TCCTG

851 AAGTG CACTC AATAT TCCTC GAAGG TCACA CATTT CTTGT GAGGA ACCAT

901 CGCCA GGCTA GCTTG GAAAT CTCGC CAATA ACTTT CCTTA CTGCT CAAAC

951 ACTCT TGATG GACCT TGGAC AGTTT CTACT GTTTT GTCAT ATCTC TTCCC

1001 ACCAA CATGA TGGCA TGGAA GCTTA TGTCA AAGTA GACAG CTGTC CAGAG

1051 GAACC CCAAC TACGA ATGAA AAATA ATGAA GAAGC GGAAG ACTAT GATGA

1101 TGATC TTACT GATTC TGAAA TGGAT GTGGT CAGGT TTGAT GATGA CAACT

1151 CTCCT TCCTT TATCC AAATT CGCTC AGTTG CCAAG AAGCA TCCTA AAACT

1201 TGGGT ACATT ACATT GCTGC TGAAG AGGAG GACTG GGACT ATGCT CCCTT

1251 AGTCC TCGCC CCCGA TGACA GAAGT TATAA AAGTC AATAT TTGAA CAATG

1301 GCCCT CAGCG GATTG GTAGG AAGTA CAAAA AAGTC CGATT TATGG CATAC

1351 ACAGA TGAAA CCTTT AAGAC TCGTG AAGCT ATTCA GCATG AATCA GGAAT

1401 CTTGG GACCT TTACT TTATG GGGAA GTTGG AGACA CACTG TTGAT TATAT

1451 TTAAG AATCA AGCAA GCAGA CCATA TAACA TCTAC CCTCA CGGAA TCACT

1501 GATGT CCGTC CTTTG TATTC AAGGA GATTA CCAAA AGGTG TAAAA CATTT

-continued

```
1551  GAAGG ATTTT CCAAT TCTGC CAGGA GAAAT ATTCA AATAT AAATG GACAG
1601  TGACT GTAGA AGATG GGCCA ACTAA ATCAG ATCCT CGGTG CCTGA CCCGC
1651  TATTA CTCTA GTTTC GTTAA TATGG AGAGA GATCT AGCTT CAGGA CTCAT
1701  TGGCC CTCTC CTCAT CTGCT ACAAA GAATC TGTAG ATCAA AGAGG AAACC
1751  AGATA ATGTC AGACA AGAGG AATGT CATCC TGTTT TCTGT ATTTG ATGAG
1801  AACCG AAGCT GGTAC CTCAC AGAGA ATATA CAACG CTTTC TCCCC AATCC
1851  AGCTG GAGTG CAGCT TGAGG ATCCA GAGTT CCAAG CCTCC AACAT CATGC
1901  ACAGC ATCAA TGGCT ATGTT TTTGA TAGTT TGCAG TTGTC AGTTT GTTTG
1951  CATGA GGTGG CATAC TGGTA CATTC TAAGC ATTGG AGCAC AGACT GACTT
2001  CCTTT CTGTC TTCTT CTCTG GATAT ACCTT CAAAC ACAAA ATGGT CTATG
2051  AAGAC ACACT CACCC TATTC CCATT CTCAG GAGAA ACTGT CTTCA TGTCG
2101  ATGGA AAACC CAGGT CTATG GATTC TGGGG TGCCA CAACT CAGAC TTTCG
2151  GAACA GAGGC ATGAC CGCCT TACTG AAGGT TTCTA GTTGT GACAA GAACA
2201  CTGGT GATTA TTACG AGGAC AGTTA TGAAG ATATT TCAGC ATACT TGCTG
2251  AGTAA AAACA ATGCC ATTGA ACCAA GAAGC TTCTC TCAAA ACGGC GCGCC
2301  AGGTA CCTCA GAGTC TGCTA CCCCC GAGTC AGGGC CAGGA TCAGA GCCAG
2351  CCACC TCCGG GTCTG AGACA CCCGG GACTT CCGAG AGTGC CACCC CTGAG
2401  TCCGG ACCCG GGTCC GAGCC CGCCA CTTCC GGCTC CGAAA CTCCC GGCAC
2451  AAGCG AGAGC GCTAC CCCAG AGTCA GGACC AGGAA CATCT ACAGA GCCCT
2501  CTGAA GGCTC CGCTC CAGGG TCCCC AGCCG GCAGT CCCAC TAGCA CCGAG
2551  GAGGG AACCT CTGAA AGCGC CACAC CCGAA TCAGG GCCAG GGTCT GAGCC
2601  TGCTA CCAGC GGCAG CGAGA CACCA GGCAC CTCTG AGTCC GCCAC ACCAG
2651  AGTCC GGACC CGGAT CTCCC GCTGG GAGCC CCACC TCCAC TGAGG AGGGA
2701  TCTCC TGCTG GCTCT CCAAC ATCTA CTGAG GAAGG TACCT CAACC GAGCC
2751  ATCCG AGGGA TCAGC TCCCG GCACC TCAGA GTCGG CAACC CCGGA GTCTG
2801  GACCC GGAAC TTCCG AAAGT GCCAC ACCAG AGTCC GGTCC CGGGA CTTCA
2851  GAATC AGCAA CACCC GAGTC CGGCC CTGGG TCTGA ACCCG CCACA AGTGG
2901  TAGTG AGACA CCAGG ATCAG AACCT GCTAC CTCAG GGTCA GAGAC ACCCG
2951  GATCT CCGGC AGGCT CACCA ACCTC CACTG AGGAG GGCAC CAGCA CAGAA
3001  CCAAG CGAGG GCTCC GCACC CGGAA CAAGC ACTGA ACCCA GTGAG GGTTC
3051  AGCAC CCGGC TCTGA GCCGG CCACA AGTGG CAGTG AGACA CCCGG CACTT
3101  CAGAG AGTGC CACCC CCGAG AGTGG CCCAG GCACT AGTAC CGAGC CCTCT
3151  GAAGG CAGTG CGCCA GCCTC GAGCC CACCA GTCTT GAAAC GCCAT CAAGC
3201  TGAAA TAACT CGTAC TACTC TTCAG TCAGA TCAAG AGGAA ATCGA TTATG
3251  ATGAT ACCAT ATCAG TTGAA ATGAA GAAGG AAGAT TTTGA CATTT ATGAT
3301  GAGGA TGAAA ATCAG AGCCC CCGCA GCTTT CAAAA GAAAA CACGA CACTA
3351  TTTTA TTGCT GCAGT GGAGA GGCTC TGGGA TTATG GGATG AGTAG CTCCC
3401  CACAT GTTCT AAGAA ACAGG GCTCA GAGTG GCAGT GTCCC TCAGT TCAAG
3451  AAAGT TGTTT TCCAG GAATT TACTG ATGGC TCCTT TACTC AGCCC TTATA
```

-continued

3501 CCGTG GAGAA CTAAA TGAAC ATTTG GGACT CCTGG GGCCA TATAT AAGAG

3551 CAGAA GTTGA AGATA ATATC ATGGT AACTT TCAGA AATCA GGCCT CTCGT

3601 CCCTA TTCCT TCTAT TCTAG CCTTA TTTCT TATGA GGAAG ATCAG AGGCA

3651 AGGAG CAGAA CCTAG AAAAA ACTTT GTCAA GCCTA ATGAA ACCAA AACTT

3701 ACTTT TGGAA AGTGC AACAT CATAT GGCAC CCACT AAAGA TGAGT TTGAC

3751 TGCAA AGCCT GGGCT TATTT CTCTG ATGTT GACCT GGAAA AAGAT GTGCA

3801 CTCAG GCCTG ATTGG ACCCC TTCTG GTCTG CCACA CTAAC ACACT GAACC

3851 CTGCT CATGG GAGAC AAGTG ACAGT ACAGG AATTT GCTCT GTTTT TCACC

3901 ATCTT TGATG AGACC AAAAG CTGGT ACTTC ACTGA AAATA TGGAA AGAAA

3951 CTGCA GGGCT CCCTG CAATA TCCAG ATGGA AGATC CCACT TTTAA AGAGA

4001 ATTAT CGCTT CCATG CAATC AATGG CTACA TAATG GATAC ACTAC CTGGC

4051 TTAGT AATGG CTCAG GATCA AAGGA TTCGA TGGTA TCTGC TCAGC ATGGG

4101 CAGCA ATGAA AACAT CCATT CTATT CATTT CAGTG GACAT GTGTT CACTG

4151 TACGA AAAAA AGAGG AGTAT AAAAT GGCAC TGTAC AATCT CTATC CAGGT

4201 GTTTT TGAGA CAGTG GAAAT GTTAC CATCC AAAGC TGGAA TTTGG CGGGT

4251 GGAAT GCCTT ATTGG CGAGC ATCTA CATGC TGGGA TGAGC ACACT TTTTC

4301 TGGTG TACAG CAATA AGTGT CAGAC TCCCC TGGGA ATGGC TTCTG GACAC

4351 ATTAG AGATT TTCAG ATTAC AGCTT CAGGA CAATA TGGAC AGTGG GCCCC

4401 AAAGC TGGCC AGACT TCATT ATTCC GGATC AATCA ATGCC TGGAG CACCA

4451 AGGAG CCCTT TTCTT GGATC AAGGT GGATC TGTTG GCACC AATGA TTATT

4501 CACGG CATCA AGACC CAGGG TGCCC GTCAG AAGTT CTCCA GCCTC TACAT

4551 CTCTC AGTTT ATCAT CATGT ATAGT CTTGA TGGGA AGAAG TGGCA GACTT

4601 ATCGA GGAAA TTCCA CTGGA ACCTT AATGG TCTTC TTTGG CAATG TGGAT

4651 TCATC TGGGA TAAAA CACAA TATTT TTAAC CCTCC AATTA TTGCT CGATA

4701 CATCC GTTTG CACCC AACTC ATTAT AGCAT TCGCA GCACT CTTCG CATGG

4751 AGTTG ATGGG CTGTG ATTTA AATAG TTGCA GCATG CCATT GGGAA TGGAG

4801 AGTAA AGCAA TATCA GATGC ACAGA TTACT GCTTC ATCCT ACTTT ACCAA

4851 TATGT TTGCC ACCTG GTCTC CTTCA AAAGC TCGAC TTCAC CTCCA AGGGA

4901 GGAGT AATGC CTGGA GACCT CAGGT GAATA ATCCA AAAGA GTGGC TGCAA

4951 GTGGA CTTCC AGAAG ACAAT GAAAG TCACA GGAGT AACTA CTCAG GGAGT

5001 AAAAT CTCTG CTTAC CAGCA TGTAT GTGAA GGAGT TCCTC ATCTC CAGCA

5051 GTCAA GATGG CCATC AGTGG ACTCT CTTTT TTCAG AATGG CAAAG TAAAG

5101 GTTTT TCAGG GAAAT CAAGA CTCCT TCACA CCTGT GGTGA ACTCT CTAGA

5151 CCCAC CGTTA CTGAC TCGCT ACCTT CGAAT TCACC CCCAG AGTTG GGTGC

5201 ACCAG ATTGC CCTGA GGATG GAGGT TCTGG GCTGC GAGGC ACAGG ACCTC

5251 TACGA CAAAA CTCAC ACATG CCCAC CGTGC CCAGC TCCAG AACTC CTGGG

5301 CGGAC CGTCA GTCTT CCTCT TCCCC CCAAA ACCCA AGGAC ACCCT CATGA

5351 TCTCC CGGAC CCCTG AGGTC ACATG CGTGG TGGTG GACGT GAGCC ACGAA

5401 GACCC TGAGG TCAAG TTCAA CTGGT ACGTG GACGG CGTGG AGGTG CATAA

5451 TGCCA AGACA AAGCC GCGGG AGGAG CAGTA CAACA GCACG TACCG TGTGG

-continued

5501 TCAGC GTCCT CACCG TCCTG CACCA GGACT GGCTG AATGG CAAGG AGTAC

5551 AAGTG CAAGG TCTCC AACAA AGCCC TCCCA GCCCC CATCG AGAAA ACCAT

5601 CTCCA AAGCC AAAGG GCAGC CCCGA GAACC ACAGG TGTAC ACCCT GCCCC

5651 CATCC CGGGA TGAGC TGACC AAGAA CCAGG TCAGC CTGAC CTGCC TGGTC

5701 AAAGG CTTCT ATCCC AGCGA CATCG CCGTG GAGTG GGAGA GCAAT GGGCA

5751 GCCGG AGAAC AACTA CAAGA CCACG CCTCC CGTGT TGGAC TCCGA CGGCT

5801 CCTTC TTCCT CTACA GCAAG CTCAC CGTGG ACAAG AGCAG GTGGC AGCAG

5851 GGGAA CGTCT TCTCA TGCTC CGTGA TGCAT GAGGC TCTGC ACAAC CACTA

5901 CACGC AGAAG AGCCT CTCCC TGTCT CCGGG TAAAT GA

FVIII 169 protein sequence(SEQ ID NO: 70)

1 MQIELSTCFF LCLLRFCFSA TRRYYLGAVE LSWDYMQSDL GELPVDARFP

51 PRVPKSFPFN TSVVYKKTLF VEFTDHLFNI AKPRPPWMGL LGPTIQAEVY

101 DTVVITLKNM ASHPVSLHAV GVSYWKASEG AEYDDQTSQR EKEDDKVFPG

151 GSHTYVWQVL KENGPMASDP LCLTYSYLSH VDLVKDLNSG LIGALLVCRE

201 GSLAKEKTQT LHKFILLFAV FDEGKSWHSE TKNSLMQDRD AASARAWPKM

251 HTVNGYVNRS LPGLIGCHRK SVYWHVIGMG TTPEVHSIFL EGHTFLVRNH

301 RQASLEISPI TFLTAQTLLM DLGQFLLFCH ISSHQHDGME AYVKVDSCPE

351 EPQLRMKNNE EAEDYDDDLT DSEMDVVRFD DDNSPSFIQI RSVAKKHPKT

401 WVHYIAAEEE DWDYAPLVLA PDDRSYKSQY LNNGPQRIGR KYKKVRFMAY

451 TDETFKTREA IQHESGILGP LLYGEVGDTL LIIFKNQASR PYNIYPHGIT

501 DVRPLYSRRL PKGVKHLKDF PILPGEIFKY KWTVTVEDGP TKSDPRCLTR

551 YYSSFVNMER DLASGLIGPL LICYKESVDQ RGNQIMSDKR NVILFSVFDE

601 NRSWYLTENI QRFLPNPAGV QLEDPEFQAS NIMHSINGYV FDSLQLSVCL

651 HEVAYWYILS IGAQTDFLSV FFSGYTFKHK MVYEDTLTLF PFSGETVFMS

701 MENPGLWILG CHNSDFRNRG MTALLKVSSC DKNTGDYYED SYEDISAYLL

751 SKNNAIEPRS FSQNGAPGTS ESATPESGPG SEPATSGSET PGTSESATPE

801 SGPGSEPATS GSETPGTSES ATPESGPGTS TEPSEGSAPG SPAGSPTSTE

851 EGTSESATPE SGPGSEPATS GSETPGTSES ATPESGPGSP AGSPTSTEEG

901 SPAGSPTSTE EGTSTEPSEG aAPGTSESAT PESGPGTSES ATPESGPGTS

951 ESATPESGPG SEPATSGSET PGSEPATSGS ETPGSPAGSP TSTEEGTSTE

1001 PSEGSAPGTS TEPSEGSAPG SEPATSGSET PGTSESATPE SGPGTSTEPS

1051 EGSAPASSPP VLKRHQAEIT RTTLQSDQEE IDYDDTISVE MKKEDFDIYD

1101 EDENQSPRSF QKKTRHYFIA AVERLWDYGM SSSPHVLRNR AQSGSVPQFK

1151 KVVFQEFTDG SFTQPLYRGE LNEHLGLLGP YIRAEVEDNI MVTFRNQASR

1201 PYSFYSSLIS YEEDQRQGAE PRKNFVKPNE TKTYFWKVQH HMAPTKDEFD

1251 CKAWAYFSDV DLEKDVHSGL IGPLLVCHTN TLNPAHGRQV TVQEFALFFT

1301 IFDETKSWYF TENMERNCRA PCNIQMEDPT FKENYRFHAI NGYIMDTLPG

1351 LVMAQDQRIR WYLLSMGSNE NIHSIHFSGH VFTVRKKEEY KMALYNLYPG

1401 VFETVEMLPS KAGIWRVECL IGEHLHAGMS TLFLVYSNKC QTPLGMASGH

1451 IRDFQITASG QYGQWAPKLA RLHYSGSINA WSTKEPFSWI KVDLLAPMII

-continued

1501 HGIKTQGARQ KFSSLYISQF IIMYSLDGKK WQTYRGNSTG TLMVFFGNVD

1551 SSGIKHNIFN PPIIARYIRL HPTHYSIRST LRMELMGCDL NSCSMPLGME

1601 SKAISDAQIT ASSYFTNMFA TWSPSKARLH LQGRSNAWRP QVNNPKEWLQ

1651 VDFQKTMKVT GVTTQGVKSL LTSMYVKEFL ISSSQDGHQW TLFFQNGKVK

1701 VFQGNQDSFT PVVNSLDPPL LTRYLRIHPQ SWVHQIALRM EVLGCEAQDL

1751 YDKTHTCPPC PAPELLGGPS VFLFPPKPKD TLMISRTPEV TCVVVDVSHE

1801 DPEVKFNWYV DGVEVHNAKT KPREEQYNST YRVVSVLTVL HQDWLNGKEY

1851 KCKVSNKALP APIEKTISKA KGQPREPQVY TLPPSRDELT KNQVSLTCLV

1901 KGFYPSDIAV EWESNGQPEN NYKTTPPVLD SDGSFFLYSK LTVDKSRWQQ

1951 GNVFSCSVMH EALHNHYTQK SLSLSPGK*

FVIII 263 nucleotide sequence (IHH triple mutant) (SEQ ID NO: 156)

1 ATGCA AATAG AGCTC TCCAC CTGCT TCTTT CTGTG CCTTT TGCGA TTCTG

51 CTTTA GTGCC ACCAG AAGAT ACTAC CTGGG TGCAG TGGAA CTGTC ATGGG

101 ACTAT ATGCA AGGCG CGCCA ACATC AGAGA GCGCC ACCCC TGAAA GTGGT

151 CCCGG GAGCG AGCCA GCCAC ATCTG GGTCG GAAAC GCCAG GCACA AGTGA

201 GTCTG CAACT CCCGA GTCCG GACCT GGCTC CGAGC CTGCC ACTAG CGGCT

251 CCGAG ACTCC GGGAA CTTCC GAGAG CGCTA CACCA GAAAG CGGAC CCGGA

301 ACCAG TACCG AACCT AGCGA GGGCT CTGCT CCGGG CAGCC CAGCC GGCTC

351 TCCTA CATCC ACGGA GGAGG GCACT TCCGA ATCCG CCACC CCGGA GTCAG

401 GGCCA GGATC TGAAC CCGCT ACCTC AGGCA GTGAG ACGCC AGGAA CGAGC

451 GAGTC CGCTA CACCG GAGAG TGGGC CAGGG AGCCC TGCTG GATCT CCTAC

501 GTCCA CTGAG GAAGG GTCAC CAGCG GGCTC GCCCA CCAGC ACTGA AGAAG

551 GTGCC TCGAG CAGTG ATCTC GGTGA GCTGC CTGTG GACGC AAGAT TTCCT

601 CCTAG AGTGC CAAAA TCTTT TCCAT TCAAC ACCTC AGTCG TGTAC AAAAA

651 GACTC TGTTT GTAGA ATTCA CGGAT CACCT TTTCA ACATC GCTAA GCCAA

701 GGCCA CCCTG GATGG GTCTG CTAGG TCCTA CCATC CAGGC TGAGG TTTAT

751 GATAC AGTGG TCATT ACACT TAAGA ACATG GCTTC CCATC CTGTC AGTCT

801 TCATG CTGTT GGTGT ATCCT ACTGG AAAGC TTCTG AGGGA GCTGA ATATG

851 ATGAT CAGAC CAGTC AAAGG GAGAA AGAAG ATGAT AAAGT CTTCC CTGGT

901 GGAAG CCATA CATAT GTCTG GCAGG TCCTG AAAGA GAATG GTCCA ATGGC

951 CTCTG ACCCA CTGTG CCTTA CCTAC TCATA TCTTT CTCAT GTGGA CCTGG

1001 TAAAA GACTT GAATT CAGGC CTCAT TGGAG CCCTA CTAGT ATGTA GAGAA

1051 GGGAG TCTGG CCAAG GAAAA GACAC AGACC TTGCA CAAAT TTATA CTACT

1101 TTTTG CTGTA TTTGA TGAAG GGAAA AGTTG GCACT CAGAA ACAAA GAACT

1151 CCTTG ATGCA GGATA GGGAT GCTGC ATCTG CTCGG GCCTG GCCTA AAATG

1201 CACAC AGTCA ATGGT TATGT AAACA GGTCT CTGCC AGGTC TGATT GGATG

1251 CCACA GGAAA TCAGT CTATT GGCAT GTGAT TGGAA TGGGC ACCAC TCCTG

1301 AAGTG CACTC AATAT TCCTC GAAGG TCACA CATTT CTTGT GAGGA ACCAT

1351 CGCCA GGCTA GCTTG GAAAT CTCGC CAATA ACTTT CCTTA CTGCT CAAAC

1401 ACTCT TGATG GACCT TGGAC AGTTT CTACT GTTTT GTCAT ATCTC TTCCC

-continued

```
1451  ACCAA CATGA TGGCA TGGAA GCTTA TGTCA AAGTA GACAG CTGTC CAGAG
1501  GAACC CCAAC TACGA ATGAA AAATA ATGAA GAAGC GGAAG ACTAT GATGA
1551  TGATC TTACT GATTC TGAAA TGGAT GTGGT CAGGT TTGAT GATGA CAACT
1601  CTCCT TCCTT TATCC AAATT CGCTC AGTTG CCAAG AAGCA TCCTA AAACT
1651  TGGGT ACATT ACATT GCTGC TGAAG AGGAG GACTG GGACT ATGCT CCCTT
1701  AGTCC TCGCC CCCGA TGACA GAAGT TATAA AAGTC AATAT TTGAA CAATG
1751  GCCCT CAGCG GATTG GTAGG AAGTA CAAAA AAGTC CGATT TATGG CATAC
1801  ACAGA TGAAA CCTTT AAGAC TCGTG AAGCT ATTCA GCATG AATCA GGAAT
1851  CTTGG GACCT TTACT TTATG GGGAA GTTGG AGACA CACTG TTGAT TATAT
1901  TTAAG AATCA AGCAA GCAGA CCATA TAACA TCTAC CCTCA CGGAA TCACT
1951  GATGT CCGTC CTTTG TATTC AAGGA GATTA CCAAA AGGTG TAAAA CATTT
2001  GAAGG ATTTT CCAAT TCTGC CAGGA GAAAT ATTCA AATAT AAATG GACAG
2051  TGACT GTAGA AGATG GGCCA ACTAA ATCAG ATCCT CGGTG CCTGA CCCGC
2101  TATTA CTCTA GTTTC GTTAA TATGG AGAGA GATCT AGCTT CAGGA CTCAT
2151  TGGCC CTCTC CTCAT CTGCT ACAAA GAATC TGTAG ATCAA AGAGG AAACC
2201  AGATA ATGTC AGACA AGAGG AATGT CATCC TGTTT TCTGT ATTTG ATGAG
2251  AACCG AAGCT GGTAC CTCAC AGAGA ATATA CAACG CTTTC TCCCC AATCC
2301  AGCTG GAGTG CAGCT TGAGG ATCCA GAGTT CCAAG CCTCC AACAT CATGC
2351  ACAGC ATCAA TGGCT ATGTT TTTGA TAGTT TGCAG TTGTC AGTTT GTTTG
2401  CATGA GGTGG CATAC TGGTA CATTC TAAGC ATTGG AGCAC AGACT GACTT
2451  CCTTT CTGTC TTCTT CTCTG GATAT ACCTT CAAAC ACAAA ATGGT CTATG
2501  AAGAC ACACT CACCC TATTC CCATT CTCAG GAGAA ACTGT CTTCA TGTCG
2551  ATGGA AAACC CAGGT CTATG GATTC TGGGG TGCCA CAACT CAGAC TTTCG
2601  GAACA GAGGC ATGAC CGCCT TACTG AAGGT TTCTA GTTGT GACAA GAACA
2651  CTGGT GATTA TTACG AGGAC AGTTA TGAAG ATATT TCAGC ATACT TGCTG
2701  AGTAA AAACA ATGCC ATTGA ACCAA GAAGC TTCTC TCAAA ACGGC GCGCC
2751  AGGTA CCTCA GAGTC TGCTA CCCCC GAGTC AGGGC CAGGA TCAGA GCCAG
2801  CCACC TCCGG GTCTG AGACA CCCGG GACTT CCGAG AGTGC CACCC CTGAG
2851  TCCGG ACCCG GGTCC GAGCC CGCCA CTTCC GGCTC CGAAA CTCCC GGCAC
2901  AAGCG AGAGC GCTAC CCCAG AGTCA GGACC AGGAA CATCT ACAGA GCCCT
2951  CTGAA GGCTC CGCTC CAGGG TCCCC AGCCG GCAGT CCCAC TAGCA CCGAG
3001  GAGGG AACCT CTGAA AGCGC CACAC CCGAA TCAGG GCCAG GGTCT GAGCC
3051  TGCTA CCAGC GGCAG CGAGA CACCA GGCAC CTCTG AGTCC GCCAC ACCAG
3101  AGTCC GGACC CGGAT CTCCC GCTGG GAGCC CCACC TCCAC TGAGG AGGGA
3151  TCTCC TGCTG GCTCT CCAAC ATCTA CTGAG GAAGG TACCT CAACC GAGCC
3201  ATCCG AGGGA TCAGC TCCCG GCACC TCAGA GTCGG CAACC CCGGA GTCTG
3251  GACCC GGAAC TTCCG AAAGT GCCAC ACCAG AGTCC GGTCC CGGGA CTTCA
3301  GAATC AGCAA CACCC GAGTC CGGCC CTGGG TCTGA ACCCG CCACA AGTGG
3351  TAGTG AGACA CCAGG ATCAG AACCT GCTAC CTCAG GGTCA GAGAC ACCCG
```

-continued

3401 GATCT CCGGC AGGCT CACCA ACCTC CACTG AGGAG GGCAC CAGCA CAGAA

3451 CCAAG CGAGG GCTCC GCACC CGGAA CAAGC ACTGA ACCCA GTGAG GGTTC

3501 AGCAC CCGGC TCTGA GCCGG CCACA AGTGG CAGTG AGACA CCCGG CACTT

3551 CAGAG AGTGC CACCC CCGAG AGTGG CCCAG GCACT AGTAC CGAGC CCTCT

3601 GAAGG CAGTG CGCCA GCCTC GAGCC CACCA GTCTT GAAAC GCCAT CAAGC

3651 TGAAA TAACT CGTAC TACTC TTCAG TCAGA TCAAG AGGAA ATCGA TTATG

3701 ATGAT ACCAT ATCAG TTGAA ATGAA GAAGG AAGAT TTTGA CATTT ATGAT

3751 GAGGA TGAAA ATCAG AGCCC CCGCA GCTTT CAAAA GAAAA CACGA CACTA

3801 TTTTA TTGCT GCAGT GGAGA GGCTC TGGGA TTATG GGATG AGTAG CTCCC

3851 CACAT GTTCT AAGAA ACAGG GCTCA GAGTG GCAGT GTCCC TCAGT TCAAG

3901 AAAGT TGTTT TCCAG GAATT TACTG ATGGC TCCTT TACTC AGCCC TTATA

3951 CCGTG GAGAA CTAAA TGAAC ATTTG GGACT CCTGG GGCCA TATAT AAGAG

4001 CAGAA GTTGA AGATA ATATC ATGGT AACTT TCAGA AATCA GGCCT CTCGT

4051 CCCTA TTCCT TCTAT TCTAG CCTTA TTTCT TATGA GGAAG ATCAG AGGCA

4101 AGGAG CAGAA CCTAG AAAAA ACTTT GTCAA GCCTA ATGAA ACCAA AACTT

4151 ACTTT TGGAA AGTGC AACAT CATAT GGCAC CCACT AAAGA TGAGT TTGAC

4201 TGCAA AGCCT GGGCT TATTT CTCTG ATGTT GACCT GGAAA AAGAT GTGCA

4251 CTCAG GCCTG ATTGG ACCCC TTCTG GTCTG CCACA CTAAC ACACT GAACC

4301 CTGCT CATGG GAGAC AAGTG ACAGT ACAGG AATTT GCTCT GTTTT TCACC

4351 ATCTT TGATG AGACC AAAAG CTGGT ACTTC ACTGA AAATA TGGAA AGAAA

4401 CTGCA GGGCT CCCTG CAATA TCCAG ATGGA AGATC CCACT TTTAA AGAGA

4451 ATTAT CGCTT CCATG CAATC AATGG CTACA TAATG GATAC ACTAC CTGGC

4501 TTAGT AATGG CTCAG GATCA AAGGA TTCGA TGGTA TCTGC TCAGC ATGGG

4551 CAGCA ATGAA AACAT CCATT CTATT CATTT CAGTG GACAT GTGTT CACTG

4601 TACGA AAAAA AGAGG AGTAT AAAAT GGCAC TGTAC AATCT CTATC CAGGT

4651 GTTTT TGAGA CAGTG GAAAT GTTAC CATCC AAAGC TGGAA TTTGG CGGGT

4701 GGAAT GCCTT ATTGG CGAGC ATCTA CATGC TGGGA TGAGC ACACT TTTTC

4751 TGGTG TACAG CAATA AGTGT CAGAC TCCCC TGGGA ATGGC TTCTG GACAC

4801 ATTAG AGATT TTCAG ATTAC AGCTT CAGGA CAATA TGGAC AGTGG GCCCC

4851 AAAGC TGGCC AGACT TCATT ATTCC GGATC AATCA ATGCC TGGAG CACCA

4901 AGGAG CCCTT TTCTT GGATC AAGGT GGATC TGTTG GCACC AATGA TTATT

4951 CACGG CATCA AGACC CAGGG TGCCC GTCAG AAGTT CTCCA GCCTC TACAT

5001 CTCTC AGTTT ATCAT CATGT ATAGT CTTGA TGGGA AGAAG TGGCA GACTT

5051 ATCGA GGAAA TTCCA CTGGA ACCTT AATGG TCTTC TTTGG CAATG TGGAT

5101 TCATC TGGGA TAAAA CACAA TATTT TTAAC CCTCC AATTA TTGCT CGATA

5151 CATCC GTTTG CACCC AACTC ATTAT AGCAT TCGCA GCACT CTTCG CATGG

5201 AGTTG ATGGG CTGTG ATTTA AATAG TTGCA GCATG CCATT GGGAA TGGAG

5251 AGTAA AGCAA TATCA GATGC ACAGA TTACT GCTTC ATCCT ACTTT ACCAA

5301 TATGT TTGCC ACCTG GTCTC CTTCA AAAGC TCGAC TTCAC CTCCA AGGGA

5351 GGAGT AATGC CTGGA GACCT CAGGT GAATA ATCCA AAAGA GTGGC TGCAA

-continued

```
5401   GTGGA CTTCC AGAAG ACAAT GAAAG TCACA GGAGT AACTA CTCAG GGAGT
5451   AAAAT CTCTG CTTAC CAGCA TGTAT GTGAA GGAGT TCCTC ATCTC CAGCA
5501   GTCAA GATGG CCATC AGTGG ACTCT CTTTT TTCAG AATGG CAAAG TAAAG
5551   GTTTT TCAGG GAAAT CAAGA CTCCT TCACA CCTGT GGTGA ACTCT CTAGA
5601   CCCAC CGTTA CTGAC TCGCT ACCTT CGAAT TCACC CCCAG AGTTG GGTGC
5651   ACCAG ATTGC CCTGA GGATG GAGGT TCTGG GCTGC GAGGC ACAGG ACCTC
5701   TACGA CAAAA CTCAC ACATG CCCAC CGTGC CCAGC TCCAG AACTC CTGGG
5751   CGGAC CGTCA GTCTT CCTCT TCCCC CCAAA ACCCA AGGAC ACCCT CATGG
5801   CCTCC CGGAC CCCTG AGGTC ACATG CGTGG TGGTG GACGT GAGCC ACGAA
5851   GACCC TGAGG TCAAG TTCAA CTGGT ACGTG GACGG CGTGG AGGTG CATAA
5901   TGCCA AGACA AAGCC GCGGG AGGAG CAGTA CAACA GCACG TACCG TGTGG
5951   TCAGC GTCCT CACCG TCCTG GCCCA GGACT GGCTG AATGG CAAGG AGTAC
6001   AAGTG CAAGG TCTCC AACAA AGCCC TCCCA GCCCC CATCG AGAAA ACCAT
6051   CTCCA AAGCC AAAGG GCAGC CCCGA GAACC ACAGG TGTAC ACCCT GCCCC
6101   CATCC CGCGA TGAGC TGACC AAGAA CCAGG TCAGC CTGAC CTGCC TGGTC
6151   AAAGG CTTCT ATCCC AGCGA CATCG CCGTG GAGTG GGAGA GCAAT GGGCA
6201   GCCGG AGAAC AACTA CAAGA CCACG CCTCC CGTGT TGGAC TCCGA CGGCT
6251   CCTTC TTCCT CTACA GCAAG CTCAC CGTGG ACAAG AGCAG GTGGC AGCAG
6301   GGGAA CGTCT TCTCA TGCTC CGTGA TGCAT GAGGC TCTGC ACAAC GCCTA
6351   CACGC AGAAG AGCCT CTCCC TGTCT CCGGG TAAAT GA
```

FVIII 263 protein sequence (IHH triple mutant) (SEQ ID NO: 157)

```
   1   MQIELSTCFF LCLLRFCFSA TRRYYLGAVE LSWDYMQGAP TSESATPESG
  51   PGSEPATSGS ETPGTSESAT PESGPGSEPA TSGSETPGTS ESATPESGPG
 101   TSTEPSEGSA PGSPAGSPTS TEEGTSESAT PESGPGSEPA TSGSETPGTS
 151   ESATPESGPG SPAGSPTSTE EGSPAGSPTS TEEGASSSDL GELPVDARFP
 201   PRVPKSFPFN TSVVYKKTLF VEFTDHLFNI AKPRPPWMGL LGPTIQAEVY
 251   DTVVITLKNM ASHPVSLHAV GVSYWKASEG AEYDDQTSQR EKEDDKVFPG
 301   GSHTYVWQVL KENGPMASDP LCLTYSYLSH VDLVKDLNSG LIGALLVCRE
 351   GSLAKEKTQT LHKFILLFAV FDEGKSWHSE TKNSLMQDRD AASARAWPKM
 401   HTVNGYVNRS LPGLIGCHRK SVYWHVIGMG TTPEVHSIFL EGHTFLVRNH
 451   RQASLEISPI TFLTAQTLLM DLGQFLLFCH ISSHQHDGME AYVKVDSCPE
 501   EPQLRMKNNE EAEDYDDDLT DSEMDVVRFD DDNSPSFIQI RSVAKKHPKT
 551   WVHYIAAEEE DWDYAPLVLA PDDRSYKSQY LNNGPQRIGR KYKKVRFMAY
 601   TDETFKTREA IQHESGILGP LLYGEVGDTL LIIFKNQASR PYNIYPHGIT
 651   DVRPLYSRRL PKGVKHLKDF PILPGEIFKY KWTVTVEDGP TKSDPRCLTR
 701   YYSSFVNMER DLASGLIGPL LICYKESVDQ RGNQIMSDKR NVILFSVFDE
 751   NRSWYLTENI QRFLPNPAGV QLEDPEFQAS NIMHSINGYV FDSLQLSVCL
 801   HEVAYWYILS IGAQTDFLSV FFSGYTFKHK MVYEDTLTLF PFSGETVFMS
 851   MENPGLWILG CHNSDFRNRG MTALLKVSSC DKNTGDYYED SYEDISAYLL
 901   SKNNAIEPRS FSQNGAPGTS ESATPESGPG SEPATSGSET PGTSESATPE
```

-continued

```
 951   SGPGSEPATS GSETPGTSES ATPESGPGTS TEPSEGSAPG SPAGSPTSTE
1001   EGTSESATPE SGPGSEPATS GSETPGTSES ATPESGPGSP AGSPTSTEEG
1051   SPAGSPTSTE EGTSTEPSEG aAPGTSESAT PESGPGTSES ATPESGPGTS
1101   ESATPESGPG SEPATSGSET PGSEPATSGS ETPGSPAGSP TSTEEGTSTE
1151   PSEGSAPGTS TEPSEGSAPG SEPATSGSET PGTSESATPE SGPGTSTEPS
1201   EGSAPASSPP VLKRHQAEIT RTTLQSDQEE IDYDDTISVE MKKEDFDIYD
1251   EDENQSPRSF QKKTRHYFIA AVERLWDYGM SSSPHVLRNR AQSGSVPQFK
1301   KVVFQEFTDG SFTQPLYRGE LNEHLGLLGP YIRAEVEDNI MVTFRNQASR
1351   PYSFYSSLIS YEEDQRQGAE PRKNFVKPNE TKTYFWKVQH HMAPTKDEFD
1401   CKAWAYFSDV DLEKDVHSGL IGPLLVCHTN TLNPAHGRQV TVQEFALFFT
1451   IFDETKSWYF TENMERNCRA PCNIQMEDPT FKENYRFHAI NGYIMDTLPG
1501   LVMAQDQRIR WYLLSMGSNE NIHSIHFSGH VFTVRKKEEY KMALYNLYPG
1551   VFETVEMLPS KAGIWRVECL IGEHLHAGMS TLFLVYSNKC QTPLGMASGH
1601   IRDFQITASG QYGQWAPKLA RLHYSGSINA WSTKEPFSWI KVDLLAPMII
1651   HGIKTQGARQ KFSSLYISQF IIMYSLDGKK WQTYRGNSTG TLMVFFGNVD
1701   SSGIKHNIFN PPIIARYIRL HPTHYSIRST LRMELMGCDL NSCSMPLGME
1751   SKAISDAQIT ASSYFTNMFA TWSPSKARLH LQGRSNAWRP QVNNPKEWLQ
1801   VDFQKTMKVT GVTTQGVKSL LTSMYVKEFL ISSSQDGHQW TLFFQNGKVK
1851   VFQGNQDSFT PVVNSLDPPL LTRYLRIHPQ SWVHQIALRM EVLGCEAQDL
1901   YDKTHTCPPC PAPELLGGPS VFLFPPKPKD TLMASRTPEV TCVVVDVSHE
1951   DPEVKFNWYV DGVEVHNAKT KPREEQYNST YRVVSVLTVL AQDWLNGKEY
2001   KCKVSNKALP APIEKTISKA KGQPREPQVY TLPPSRDELT KNQVSLTCLV
2051   KGFYPSDIAV EWESNGQPEN NYKTTPPVLD SDGSFFLYSK LTVDKSRWQQ
2101   GNVFSCSVMH EALHNAYTQK SLSLSPGK*
```

FVIII 282 nucleotide sequence(SEQ ID NO: 158)

```
  1   ATGCA AATAG AGCTC TCCAC CTGCT TCTTT CTGTG CCTTT TGCGA TTCTG
 51   CTTTA GTGCC ACCAG AAGAT ACTAC CTGGG TGCAG TGGAA CTGTC ATGGG
101   ACTAT ATGCA AAGTG ATCTC GGTGA GCTGC CTGTG GACGC AAGAT TTCCT
151   CCTAG AGTGC CAAAA TCTTT TCCAT TCAAC ACCTC AGTCG TGTAC AAAAA
201   GACTC TGTTT GTAGA ATTCA CGGAT CACCT TTTCA ACATC GCTAA GCCAA
251   GGCCA CCCTG GATGG GTCTG CTAGG TCCTA CCATC CAGGC TGAGG TTTAT
301   GATAC AGTGG TCATT ACACT TAAGA ACATG GCTTC CCATC CTGTC AGTCT
351   TCATG CTGTT GGTGT ATCCT ACTGG AAAGC TTCTG AGGGA GCTGA ATATG
401   ATGAT CAGAC CAGTC AAAGG GAGAA AGAAG ATGAT AAAGT CTTCC CTGGT
451   GGAAG CCATA CATAT GTCTG GCAGG TCCTG AAAGA GAATG GTCCA ATGGC
501   CTCTG ACCCA CTGTG CCTTA CCTAC TCATA TCTTT CTCAT GTGGA CCTGG
551   TAAAA GACTT GAATT CAGGC CTCAT TGGAG CCCTA CTAGT ATGTA GAGAA
601   GGGAG TCTGG CCAAG GAAAA GACAC AGACC TTGCA CAAAT TTATA CTACT
651   TTTTG CTGTA TTTGA TGAAG GGAAA AGTTG GCACT CAGAA ACAAA GAACT
701   CCTTG ATGCA GGATA GGGAT GCTGC ATCTG CTCGG GCCTG GCCTA AAATG
```

-continued

751 CACAC AGTCA ATGGT TATGT AAACA GGTCT CTGCC AGGTC TGATT GGATG

801 CCACA GGAAA TCAGT CTATT GGCAT GTGAT TGGAA TGGGC ACCAC TCCTG

851 AAGTG CACTC AATAT TCCTC GAAGG TCACA CATTT CTTGT GAGGA ACCAT

901 CGCCA GGCTA GCTTG GAAAT CTCGC CAATA ACTTT CCTTA CTGCT CAAAC

951 ACTCT TGATG GACCT TGGAC AGTTT CTACT GTTTT GTCAT ATCTC TTCCC

1001 ACCAA CATGA TGGCA TGGAA GCTTA TGTCA AAGTA GACAG CTGTC CAGAG

1051 GAACC CCAAC TACGA ATGAA AAATA ATGAA GAAGC GGAAG ACTAT GATGA

1101 TGATC TTACT GATTC TGAAA TGGAT GTGGT CAGGT TTGAT GATGA CAACT

1151 CTCCT TCCTT TATCC AAATT CGCTC AGTTG CCAAG AAGCA TCCTA AAACT

1201 TGGGT ACATT ACATT GCTGC TGAAG AGGAG GACTG GGACT ATGCT CCCTT

1251 AGTCC TCGCC CCCGA TGACA GAAGT TATAA AAGTC AATAT TTGAA CAATG

1301 GCCCT CAGCG GATTG GTAGG AAGTA CAAAA AAGTC CGATT TATGG CATAC

1351 ACAGA TGAAA CCTTT AAGAC TCGTG AAGCT ATTCA GCATG AATCA GGAAT

1401 CTTGG GACCT TTACT TTATG GGGAA GTTGG AGACA CACTG TTGAT TATAT

1451 TTAAG AATCA AGCAA GCAGA CCATA TAACA TCTAC CCTCA CGGAA TCACT

1501 GATGT CCGTC CTTTG TATTC AAGGA GATTA CCAAA AGGTG TAAAA CATTT

1551 GAAGG ATTTT CCAAT TCTGC CAGGA GAAAT ATTCA AATAT AAATG GACAG

1601 TGACT GTAGA AGATG GGCCA ACTAA ATCAG ATCCT CGGTG CCTGA CCCGC

1651 TATTA CTCTA GTTTC GTTAA TATGG AGAGA GATCT AGCTT CAGGA CTCAT

1701 TGGCC CTCTC CTCAT CTGCT ACAAA GAATC TGTAG ATCAA AGAGG AAACC

1751 AGATA ATGTC AGACA AGAGG AATGT CATCC TGTTT TCTGT ATTTG ATGAG

1801 AACCG AAGCT GGTAC CTCAC AGAGA ATATA CAACG CTTTC TCCCC AATCC

1851 AGCTG GAGTG CAGCT TGAGG ATCCA GAGTT CCAAG CCTCC AACAT CATGC

1901 ACAGC ATCAA TGGCT ATGTT TTTGA TAGTT TGCAG TTGTC AGTTT GTTTG

1951 CATGA GGTGG CATAC TGGTA CATTC TAAGC ATTGG AGCAC AGACT GACTT

2001 CCTTT CTGTC TTCTT CTCTG GATAT ACCTT CAAAC ACAAA ATGGT CTATG

2051 AAGAC ACACT CACCC TATTC CCATT CTCAG GAGAA ACTGT CTTCA TGTCG

2101 ATGGA AAACC CAGGT CTATG GATTC TGGGG TGCCA CAACT CAGAC TTTCG

2151 GAACA GAGGC ATGAC CGCCT TACTG AAGGT TTCTA GTTGT GACAA GAACA

2201 CTGGT GATTA TTACG AGGAC AGTTA TGAAG ATATT TCAGC ATACT TGCTG

2251 AGTAA AAACA ATGCC ATTGA ACCAA GAAGC TTCTC TCAAA ACGGC GCGCC

2301 AACAT CAGAG AGCGC CACCC CTGAA AGTGG TCCCG GGAGC GAGCC AGCCA

2351 CATCT GGGTC GGAAA CGCCA GGCAC AAGTG AGTCT GCAAC TCCCG AGTCC

2401 GGACC TGGCT CCGAG CCTGC CACTA GCGGC TCCGA GACTC CGGGA ACTTC

2451 CGAGA GCGCT ACACC AGAAA GCGGA CCCGG AACCA GTACC GAACC TAGCG

2501 AGGGC TCTGC TCCGG GCAGC CCAGC CGGCT CTCCT ACATC CACGG AGGAG

2551 GGCAC TTCCG AATCC GCCAC CCCGG AGTCA GGGCC AGGAT CTGAA CCCGC

2601 TACCT CAGGC AGTGA GACGC CAGGA ACGAG CGAGT CCGCT ACACC GGAGA

2651 GTGGG CCAGG GAGCC CTGCT GGATC TCCTA CGTCC ACTGA GGAAG GGTCA

-continued

```
2701  CCAGC GGGCT CGCCC ACCAG CACTG AAGAA GGTGC CTCGA GCCCA CCAGT
2751  CTTGA AACGC CATCA AGCTG AAATA ACTCG TACTA CTCTT CAGTC AGATC
2801  AAGAG GAAAT CGATT ATGAT GATAC CATAT CAGTT GAAAT GAAGA AGGAA
2851  GATTT TGACA TTTAT GATGA GGATG AAAAT CAGAG CCCCC GCAGC TTTCA
2901  AAAGA AAACA CGACA CTATT TTATT GCTGC AGTGG AGAGG CTCTG GGATT
2951  ATGGG ATGAG TAGCT CCCCA CATGT TCTAA GAAAC AGGGC TCAGA GTGGC
3001  AGTGT CCCTC AGTTC AAGAA AGTTG TTTTC CAGGA ATTTA CTGAT GGCTC
3051  CTTTA CTCAG CCCTT ATACC GTGGA GAACT AAATG AACAT TTGGG ACTCC
3101  TGGGG CCATA TATAA GAGCA GAAGT TGAAG ATAAT ATCAT GGTAA CTTTC
3151  AGAAA TCAGG CCTCT CGTCC CTATT CCTTC TATTC TAGCC TTATT TCTTA
3201  TGAGG AAGAT CAGAG GCAAG GAGCA GAACC TAGAA AAAAC TTTGT CAAGC
3251  CTAAT GAAAC CAAAA CTTAC TTTTG GAAAG TGCAA CATCA TATGG CACCC
3301  ACTAA AGATG AGTTT GACTG CAAAG CCTGG GCTTA TTTCT CTGAT GTTGA
3351  CCTGG AAAAA GATGT GCACT CAGGC CTGAT TGGAC CCCTT CTGGT CTGCC
3401  ACACT AACAC ACTGA ACCCT GCTCA TGGGA GACAA GTGAC AGTAC AGGAA
3451  TTTGC TCTGT TTTTC ACCAT CTTTG ATGAG ACCAA AAGCT GGTAC TTCAC
3501  TGAAA ATATG GAAAG AAACT GCAGG GCTCC CTGCA ATATC CAGAT GGAAG
3551  ATCCC ACTTT TAAAG AGAAT TATCG CTTCC ATGCA ATCAA TGGCT ACATA
3601  ATGGA TACAC TACCT GGCTT AGTAA TGGCT CAGGA TCAAA GGATT CGATG
3651  GTATC TGCTC AGCAT GGGCA GCAAT GAAAA CATCC ATTCT ATTCA TTTCA
3701  GTGGA CATGT GTTCA CTGTA CGAAA AAAAG AGGAG TATAA AATGG CACTG
3751  TACAA TCTCT ATCCA GGTGT TTTTG AGACA GTGGA AATGT TACCA TCCAA
3801  AGCTG GAATT TGGCG GGTGG AATGC CTTAT TGGCG AGCAT CTACA TGCTG
3851  GGATG AGCAC ACTTT TTCTG GTGTA CAGCA ATAAG TGTCA GACTC CCCTG
3901  GGAAT GGCTT CTGGA CACAT TAGAG ATTTT CAGAT TACAG CTTCA GGACA
3951  ATATG GACAG TGGGC CCCAA AGCTG GCCAG ACTTC ATTAT TCCGG ATCAA
4001  TCAAT GCCTG GAGCA CCAAG GAGCC CTTTT CTTGG ATCAA GGTGG ATCTG
4051  TTGGC ACCAA TGATT ATTCA CGGCA TCAAG ACCCA GGGTG CCCGT CAGAA
4101  GTTCT CCAGC CTCTA CATCT CTCAG TTTAT CATCA TGTAT AGTCT TGATG
4151  GGAAG AAGTG GCAGA CTTAT CGAGG AAATT CCACT GGAAC CTTAA TGGTC
4201  TTCTT TGGCA ATGTG GATTC ATCTG GGATA AAACA CAATA TTTTT AACCC
4251  TCCAA TTATT GCTCG ATACA TCCGT TTGCA CCCAA CTCAT TATAG CATTC
4301  GCAGC ACTCT TCGCA TGGAG TTGAT GGGCT GTGAT TTAAA TAGTT GCAGC
4351  ATGCC ATTGG GAATG GAGAG TAAAG CAATA TCAGA TGCAC AGATT ACTGC
4401  TTCAT CCTAC TTTAC CAATA TGTTT GCCAC CTGGT CTCCT TCAAA AGCTC
4451  GACTT CACCT CCAAG GGAGG AGTAA TGCCT GGAGA CCTCA GGTGA ATAAT
4501  CCAAA AGAGT GGCTG CAAGT GGACT TCCAG AAGAC AATGA AAGTC ACAGG
4551  AGTAA CTACT CAGGG AGTAA AATCT CTGCT TACCA GCATG TATGT GAAGG
4601  AGTTC CTCAT CTCCA GCAGT CAAGA TGGCC ATCAG TGGAC TCTCT TTTTT
4651  CAGAA TGGCA AAGTA AAGGT TTTTC AGGGA AATCA AGACT CCTTC ACACC
```

-continued

4701 TGTGG TGAAC TCTCT AGACC CACCG TTACT GACTC GCTAC CTTCG AATTC

4751 ACCCC CAGAG TTGGG TGCAC CAGAT TGCCC TGAGG ATGGA GGTTC TGGGC

4801 TGCGA GGCAC AGGAC CTCTA CGACA AAACT CACAC ATGCC CACCG TGCCC

4851 AGCTC CAGAA CTCCT GGGCG GACCG TCAGT CTTCC TCTTC CCCCC AAAAC

4901 CCAAG GACAC CCTCA TGATC TCCCG GACCC CTGAG GTCAC ATGCG TGGTG

4951 GTGGA CGTGA GCCAC GAAGA CCCTG AGGTC AAGTT CAACT GGTAC GTGGA

5001 CGGCG TGGAG GTGCA TAATG CCAAG ACAAA GCCGC GGGAG GAGCA GTACA

5051 ACAGC ACGTA CCGTG TGGTC AGCGT CCTCA CCGTC CTGCA CCAGG ACTGG

5101 CTGAA TGGCA AGGAG TACAA GTGCA AGGTC TCCAA CAAAG CCCTC CCAGC

5151 CCCCA TCGAG AAAAC CATCT CCAAA GCCAA AGGGC AGCCC CGAGA ACCAC

5201 AGGTG TACAC CCTGC CCCCA TCCCG GGATG AGCTG ACCAA GAACC AGGTC

5251 AGCCT GACCT GCCTG GTCAA AGGCT TCTAT CCCAG CGACA TCGCC GTGGA

5301 GTGGG AGAGC AATGG GCAGC CGGAG AACAA CTACA AGACC ACGCC TCCCG

5351 TGTTG GACTC CGACG GCTCC TTCTT CCTCT ACAGC AAGCT CACCG TGGAC

5401 AAGAG CAGGT GGCAG CAGGG GAACG TCTTC TCATG CTCCG TGATG CATGA

5451 GGCTC TGCAC AACCA CTACA CGCAG AAGAG CCTCT CCCTG TCTCC GGGTA

5501 AATGA

FVIII 282 protein sequence (SEQ ID NO: 159)

1 MQIELSTCFF LCLLRFCFSA TRRYYLGAVE LSWDYMQSDL GELPVDARFP

51 PRVPKSFPFN TSVVYKKTLF VEFTDHLFNI AKPRPPWMGL LGPTIQAEVY

101 DTVVITLKNM ASHPVSLHAV GVSYWKASEG AEYDDQTSQR EKEDDKVFPG

151 GSHTYVWQVL KENGPMASDP LCLTYSYLSH VDLVKDLNSG LIGALLVCRE

201 GSLAKEKTQT LHKFILLFAV FDEGKSWHSE TKNSLMQDRD AASARAWPKM

251 HTVNGYVNRS LPGLIGCHRK SVYWHVIGMG TTPEVHSIFL EGHTFLVRNH

301 RQASLEISPI TFLTAQTLLM DLGQFLLFCH ISSHQHDGME AYVKVDSCPE

351 EPQLRMKNNE EAEDYDDDLT DSEMDVVRFD DDNSPSFIQI RSVAKKHPKT

401 WVHYIAAEEE DWDYAPLVLA PDDRSYKSQY LNNGPQRIGR KYKKVRFMAY

451 TDETFKTREA IQHESGILGP LLYGEVGDTL LIIFKNQASR PYNIYPHGIT

501 DVRPLYSRRL PKGVKHLKDF PILPGEIFKY KWTVTVEDGP TKSDPRCLTR

551 YYSSFVNMER DLASGLIGPL LICYKESVDQ RGNQIMSDKR NVILFSVFDE

601 NRSWYLTENI QRFLPNPAGV QLEDPEFQAS NIMHSINGYV FDSLQLSVCL

651 HEVAYWYILS IGAQTDFLSV FFSGYTFKHK MVYEDTLTLF PFSGETVFMS

701 MENPGLWILG CHNSDFRNRG MTALLKVSSC DKNTGDYYED SYEDISAYLL

751 SKNNAIEPRS FSQNGAPTSE SATPESGPGS EPATSGSETP GTSESATPES

801 GPGSEPATSG SETPGTSESA TPESGPGTST EPSEGSAPGS PAGSPTSTEE

851 GTSESATPES GPGSEPATSG SETPGTSESA TPESGPGSPA GSPTSTEEGS

901 PAGSPTSTEE GASSPPVLKR HQAEITRTTL QSDQEEIDYD DTISVEMKKE

951 DFDIYDEDEN QSPRSFQKKT RHYFIAAVER LWDYGMSSSP HVLRNRAQSG

1001 SVPQFKKVVF QEFTDGSFTQ PLYRGELNEH LGLLGPYIRA EVEDNIMVTF

1051 RNQASRPYSF YSSLISYEED QRQGAEPRKN FVKPNETKTY FWKVQHHMAP

-continued

1101 TKDEFDCKAW AYFSDVDLEK DVHSGLIGPL LVCHTNTLNP AHGRQVTVQE

1151 FALFFTIFDE TKSWYFTENM ERNCRAPCNI QMEDPTFKEN YRFHAINGYI

1201 MDTLPGLVMA QDQRIRWYLL SMGSNENIHS IHFSGHVFTV RKKEEYKMAL

1251 YNLYPGVFET VEMLPSKAGI WRVECLIGEH LHAGMSTLFL VYSNKCQTPL

1301 GMASGHIRDF QITASGQYGQ WAPKLARLHY SGSINAWSTK EPFSWIKVDL

1351 LAPMIIHGIK TQGARQKFSS LYISQFIIMY SLDGKKWQTY RGNSTGTLMV

1401 FFGNVDSSGI KHNIFNPPII ARYIRLHPTH YSIRSTLRME LMGCDLNSCS

1451 MPLGMESKAI SDAQITASSY FTNMFATWSP SKARLHLQGR SNAWRPQVNN

1501 PKEWLQVDFQ KTMKVTGVTT QGVKSLLTSM YVKEFLISSS QDGHQWTLFF

1551 QNGKVKVFQG NQDSFTPVVN SLDPPLLTRY LRIHPQSWVH QIALRMEVLG

1601 CEAQDLYDKT HTCPPCPAPE LLGGPSVFLF PPKPKDTLMI SRTPEVTCVV

1651 VDVSHEDPEV KFNWYVDGVE VHNAKTKPRE EQYNSTYRVV SVLTVLHQDW

1701 LNGKEYKCKV SNKALPAPIE KTISKAKGQP REPQVYTLPP SRDELTKNQV

1751 SLTCLVKGFY PSDIAVEWES NGQPENNYKT TPPVLDSDGS FFLYSKLTVD

1801 KSRWQQGNVF SCSVMHEALH NHYTQKSLSL SPGK*

FVIII 283 nucleotide sequence (FVIII 169 with IHH triple mutation)
(SEQ ID NO: 160)

1 ATGCA AATAG AGCTC TCCAC CTGCT TCTTT CTGTG CCTTT TGCGA TTCTG

51 CTTTA GTGCC ACCAG AAGAT ACTAC CTGGG TGCAG TGGAA CTGTC ATGGG

101 ACTAT ATGCA AAGTG ATCTC GGTGA GCTGC CTGTG GACGC AAGAT TTCCT

151 CCTAG AGTGC CAAAA TCTTT TCCAT TCAAC ACCTC AGTCG TGTAC AAAAA

201 GACTC TGTTT GTAGA ATTCA CGGAT CACCT TTTCA ACATC GCTAA GCCAA

251 GGCCA CCCTG GATGG GTCTG CTAGG TCCTA CCATC CAGGC TGAGG TTTAT

301 GATAC AGTGG TCATT ACACT TAAGA ACATG GCTTC CCATC CTGTC AGTCT

351 TCATG CTGTT GGTGT ATCCT ACTGG AAAGC TTCTG AGGGA GCTGA ATATG

401 ATGAT CAGAC CAGTC AAAGG GAGAA AGAAG ATGAT AAAGT CTTCC CTGGT

451 GGAAG CCATA CATAT GTCTG GCAGG TCCTG AAAGA GAATG GTCCA ATGGC

501 CTCTG ACCCA CTGTG CCTTA CCTAC TCATA TCTTT CTCAT GTGGA CCTGG

551 TAAAA GACTT GAATT CAGGC CTCAT TGGAG CCCTA CTAGT ATGTA GAGAA

601 GGGAG TCTGG CCAAG GAAAA GACAC AGACC TTGCA CAAAT TTATA CTACT

651 TTTTG CTGTA TTTGA TGAAG GGAAA AGTTG GCACT CAGAA ACAAA GAACT

701 CCTTG ATGCA GGATA GGGAT GCTGC ATCTG CTCGG GCCTG GCCTA AAATG

751 CACAC AGTCA ATGGT TATGT AAACA GGTCT CTGCC AGGTC TGATT GGATG

801 CCACA GGAAA TCAGT CTATT GGCAT GTGAT TGGAA TGGGC ACCAC TCCTG

851 AAGTG CACTC AATAT TCCTC GAAGG TCACA CATTT CTTGT GAGGA ACCAT

901 CGCCA GGCTA GCTTG GAAAT CTCGC CAATA ACTTT CCTTA CTGCT CAAAC

951 ACTCT TGATG GACCT TGGAC AGTTT CTACT GTTTT GTCAT ATCTC TTCCC

1001 ACCAA CATGA TGGCA TGGAA GCTTA TGTCA AAGTA GACAG CTGTC CAGAG

1051 GAACC CCAAC TACGA ATGAA AAATA ATGAA GAAGC GGAAG ACTAT GATGA

1101 TGATC TTACT GATTC TGAAA TGGAT GTGGT CAGGT TTGAT GATGA CAACT

-continued

1151 CTCCT TCCTT TATCC AAATT CGCTC AGTTG CCAAG AAGCA TCCTA AAACT

1201 TGGGT ACATT ACATT GCTGC TGAAG AGGAG GACTG GGACT ATGCT CCCTT

1251 AGTCC TCGCC CCCGA TGACA GAAGT TATAA AAGTC AATAT TTGAA CAATG

1301 GCCCT CAGCG GATTG GTAGG AAGTA CAAAA AAGTC CGATT TATGG CATAC

1351 ACAGA TGAAA CCTTT AAGAC TCGTG AAGCT ATTCA GCATG AATCA GGAAT

1401 CTTGG GACCT TTACT TTATG GGGAA GTTGG AGACA CACTG TTGAT TATAT

1451 TTAAG AATCA AGCAA GCAGA CCATA TAACA TCTAC CCTCA CGGAA TCACT

1501 GATGT CCGTC CTTTG TATTC AAGGA GATTA CCAAA AGGTG TAAAA CATTT

1551 GAAGG ATTTT CCAAT TCTGC CAGGA GAAAT ATTCA AATAT AAATG GACAG

1601 TGACT GTAGA AGATG GGCCA ACTAA ATCAG ATCCT CGGTG CCTGA CCCGC

1651 TATTA CTCTA GTTTC GTTAA TATGG AGAGA GATCT AGCTT CAGGA CTCAT

1701 TGGCC CTCTC CTCAT CTGCT ACAAA GAATC TGTAG ATCAA AGAGG AAACC

1751 AGATA ATGTC AGACA AGAGG AATGT CATCC TGTTT TCTGT ATTTG ATGAG

1801 AACCG AAGCT GGTAC CTCAC AGAGA ATATA CAACG CTTTC TCCCC AATCC

1851 AGCTG GAGTG CAGCT TGAGG ATCCA GAGTT CCAAG CCTCC AACAT CATGC

1901 ACAGC ATCAA TGGCT ATGTT TTTGA TAGTT TGCAG TTGTC AGTTT GTTTG

1951 CATGA GGTGG CATAC TGGTA CATTC TAAGC ATTGG AGCAC AGACT GACTT

2001 CCTTT CTGTC TTCTT CTCTG GATAT ACCTT CAAAC ACAAA ATGGT CTATG

2051 AAGAC ACACT CACCC TATTC CCATT CTCAG GAGAA ACTGT CTTCA TGTCG

2101 ATGGA AAACC CAGGT CTATG GATTC TGGGG TGCCA CAACT CAGAC TTTCG

2151 GAACA GAGGC ATGAC CGCCT TACTG AAGGT TTCTA GTTGT GACAA GAACA

2201 CTGGT GATTA TTACG AGGAC AGTTA TGAAG ATATT TCAGC ATACT TGCTG

2251 AGTAA AAACA ATGCC ATTGA ACCAA GAAGC TTCTC TCAAA ACGGC GCGCC

2301 AGGTA CCTCA GAGTC TGCTA CCCCC GAGTC AGGGC CAGGA TCAGA GCCAG

2351 CCACC TCCGG GTCTG AGACA CCCGG GACTT CCGAG AGTGC CACCC CTGAG

2401 TCCGG ACCCG GGTCC GAGCC CGCCA CTTCC GGCTC CGAAA CTCCC GGCAC

2451 AAGCG AGAGC GCTAC CCCAG AGTCA GGACC AGGAA CATCT ACAGA GCCCT

2501 CTGAA GGCTC CGCTC CAGGG TCCCC AGCCG GCAGT CCCAC TAGCA CCGAG

2551 GAGGG AACCT CTGAA AGCGC CACAC CCGAA TCAGG GCCAG GGTCT GAGCC

2601 TGCTA CCAGC GGCAG CGAGA CACCA GGCAC CTCTG AGTCC GCCAC ACCAG

2651 AGTCC GGACC CGGAT CTCCC GCTGG GAGCC CCACC TCCAC TGAGG AGGGA

2701 TCTCC TGCTG GCTCT CCAAC ATCTA CTGAG GAAGG TACCT CAACC GAGCC

2751 ATCCG AGGGA TCAGC TCCCG GCACC TCAGA GTCGG CAACC CCGGA GTCTG

2801 GACCC GGAAC TTCCG AAAGT GCCAC ACCAG AGTCC GGTCC CGGGA CTTCA

2851 GAATC AGCAA CACCC GAGTC CGGCC CTGGG TCTGA ACCCG CCACA AGTGG

2901 TAGTG AGACA CCAGG ATCAG AACCT GCTAC CTCAG GGTCA GAGAC ACCCG

2951 GATCT CCGGC AGGCT CACCA ACCTC CACTG AGGAG GGCAC CAGCA CAGAA

3001 CCAAG CGAGG GCTCC GCACC CGGAA CAAGC ACTGA ACCCA GTGAG GGTTC

3051 AGCAC CCGGC TCTGA GCCGG CCACA AGTGG CAGTG AGACA CCCGG CACTT

3101 CAGAG AGTGC CACCC CCGAG AGTGG CCCAG GCACT AGTAC CGAGC CCTCT

-continued

3151 GAAGG CAGTG CGCCA GCCTC GAGCC CACCA GTCTT GAAAC GCCAT CAAGC

3201 TGAAA TAACT CGTAC TACTC TTCAG TCAGA TCAAG AGGAA ATCGA TTATG

3251 ATGAT ACCAT ATCAG TTGAA ATGAA GAAGG AAGAT TTTGA CATTT ATGAT

3301 GAGGA TGAAA ATCAG AGCCC CCGCA GCTTT CAAAA GAAAA CACGA CACTA

3351 TTTTA TTGCT GCAGT GGAGA GGCTC TGGGA TTATG GGATG AGTAG CTCCC

3401 CACAT GTTCT AAGAA ACAGG GCTCA GAGTG GCAGT GTCCC TCAGT TCAAG

3451 AAAGT TGTTT TCCAG GAATT TACTG ATGGC TCCTT TACTC AGCCC TTATA

3501 CCGTG GAGAA CTAAA TGAAC ATTTG GGACT CCTGG GGCCA TATAT AAGAG

3551 CAGAA GTTGA AGATA ATATC ATGGT AACTT TCAGA AATCA GGCCT CTCGT

3601 CCCTA TTCCT TCTAT TCTAG CCTTA TTTCT TATGA GGAAG ATCAG AGGCA

3651 AGGAG CAGAA CCTAG AAAAA ACTTT GTCAA GCCTA ATGAA ACCAA AACTT

3701 ACTTT TGGAA AGTGC AACAT CATAT GGCAC CCACT AAAGA TGAGT TTGAC

3751 TGCAA AGCCT GGGCT TATTT CTCTG ATGTT GACCT GGAAA AAGAT GTGCA

3801 CTCAG GCCTG ATTGG ACCCC TTCTG GTCTG CCACA CTAAC ACACT GAACC

3851 CTGCT CATGG GAGAC AAGTG ACAGT ACAGG AATTT GCTCT GTTTT TCACC

3901 ATCTT TGATG AGACC AAAAG CTGGT ACTTC ACTGA AAATA TGGAA AGAAA

3951 CTGCA GGGCT CCCTG CAATA TCCAG ATGGA AGATC CCACT TTTAA AGAGA

4001 ATTAT CGCTT CCATG CAATC AATGG CTACA TAATG GATAC ACTAC CTGGC

4051 TTAGT AATGG CTCAG GATCA AAGGA TTCGA TGGTA TCTGC TCAGC ATGGG

4101 CAGCA ATGAA AACAT CCATT CTATT CATTT CAGTG GACAT GTGTT CACTG

4151 TACGA AAAAA AGAGG AGTAT AAAAT GGCAC TGTAC AATCT CTATC CAGGT

4201 GTTTT TGAGA CAGTG GAAAT GTTAC CATCC AAAGC TGGAA TTTGG CGGGT

4251 GGAAT GCCTT ATTGG CGAGC ATCTA CATGC TGGGA TGAGC ACACT TTTTC

4301 TGGTG TACAG CAATA AGTGT CAGAC TCCCC TGGGA ATGGC TTCTG GACAC

4351 ATTAG AGATT TTCAG ATTAC AGCTT CAGGA CAATA TGGAC AGTGG GCCCC

4401 AAAGC TGGCC AGACT TCATT ATTCC GGATC AATCA ATGCC TGGAG CACCA

4451 AGGAG CCCTT TTCTT GGATC AAGGT GGATC TGTTG GCACC AATGA TTATT

4501 CACGG CATCA AGACC CAGGG TGCCC GTCAG AAGTT CTCCA GCCTC TACAT

4551 CTCTC AGTTT ATCAT CATGT ATAGT CTTGA TGGGA AGAAG TGGCA GACTT

4601 ATCGA GGAAA TTCCA CTGGA ACCTT AATGG TCTTC TTTGG CAATG TGGAT

4651 TCATC TGGGA TAAAA CACAA TATTT TTAAC CCTCC AATTA TTGCT CGATA

4701 CATCC GTTTG CACCC AACTC ATTAT AGCAT TCGCA GCACT CTTCG CATGG

4751 AGTTG ATGGG CTGTG ATTTA AATAG TTGCA GCATG CCATT GGGAA TGGAG

4801 AGTAA AGCAA TATCA GATGC ACAGA TTACT GCTTC ATCCT ACTTT ACCAA

4851 TATGT TTGCC ACCTG GTCTC CTTCA AAAGC TCGAC TTCAC CTCCA AGGGA

4901 GGAGT AATGC CTGGA GACCT CAGGT GAATA ATCCA AAAGA GTGGC TGCAA

4951 GTGGA CTTCC AGAAG ACAAT GAAAG TCACA GGAGT AACTA CTCAG GGAGT

5001 AAAAT CTCTG CTTAC CAGCA TGTAT GTGAA GGAGT TCCTC ATCTC CAGCA

5051 GTCAA GATGG CCATC AGTGG ACTCT CTTTT TTCAG AATGG CAAAG TAAAG

-continued

```
5101  GTTTT TCAGG GAAAT CAAGA CTCCT TCACA CCTGT GGTGA ACTCT CTAGA

5151  CCCAC CGTTA CTGAC TCGCT ACCTT CGAAT TCACC CCCAG AGTTG GGTGC

5201  ACCAG ATTGC CCTGA GGATG GAGGT TCTGG GCTGC GAGGC ACAGG ACCTC

5251  TACGA CAAAA CTCAC ACATG CCCAC CGTGC CCAGC TCCAG AACTC CTGGG

5301  CGGAC CGTCA GTCTT CCTCT TCCCC CCAAA ACCCA AGGAC ACCCT CATGG

5351  CCTCC CGGAC CCCTG AGGTC ACATG CGTGG TGGTG GACGT GAGCC ACGAA

5401  GACCC TGAGG TCAAG TTCAA CTGGT ACGTG GACGG CGTGG AGGTG CATAA

5451  TGCCA AGACA AAGCC GCGGG AGGAG CAGTA CAACA GCACG TACCG TGTGG

5501  TCAGC GTCCT CACCG TCCTG GCCCA GGACT GGCTG AATGG CAAGG AGTAC

5551  AAGTG CAAGG TCTCC AACAA AGCCC TCCCA GCCCC CATCG AGAAA ACCAT

5601  CTCCA AAGCC AAAGG GCAGC CCCGA GAACC ACAGG TGTAC ACCCT GCCCC

5651  CATCC CGGGA TGAGC TGACC AAGAA CCAGG TCAGC CTGAC CTGCC TGGTC

5701  AAAGG CTTCT ATCCC AGCGA CATCG CCGTG GAGTG GGAGA GCAAT GGGCA

5751  GCCGG AGAAC AACTA CAAGA CCACG CCTCC CGTGT TGGAC TCCGA CGGCT

5801  CCTTC TTCCT CTACA GCAAG CTCAC CGTGG ACAAG AGCAG GTGGC AGCAG

5851  GGGAA CGTCT TCTCA TGCTC CGTGA TGCAT GAGGC TCTGC ACAAC GCCTA

5901  CACGC AGAAG AGCCT CTCCC TGTCT CCGGG TAAAT GA
```

FVIII 283 protein sequence (FVIII 169 with IHH triple mutation) (SEQ ID NO: 161)

```
   1  MQIELSTCFF LCLLRFCFSA TRRYYLGAVE LSWDYMQSDL GELPVDARFP

  51  PRVPKSFPFN TSVVYKKTLF VEFTDHLFNI AKPRPPWMGL LGPTIQAEVY

 101  DTVVITLKNM ASHPVSLHAV GVSYWKASEG AEYDDQTSQR EKEDDKVFPG

 151  GSHTYVWQVL KENGPMASDP LCLTYSYLSH VDLVKDLNSG LIGALLVCRE

 201  GSLAKEKTQT LHKFILLFAV FDEGKSWHSE TKNSLMQDRD AASARAWPKM

 251  HTVNGYVNRS LPGLIGCHRK SVYWHVIGMG TTPEVHSIFL EGHTFLVRNH

 301  RQASLEISPI TFLTAQTLLM DLGQFLLFCH ISSHQHDGME AYVKVDSCPE

 351  EPQLRMKNNE EAEDYDDDLT DSEMDVVRFD DDNSPSFIQI RSVAKKHPKT

 401  WVHYIAAEEE DWDYAPLVLA PDDRSYKSQY LNNGPQRIGR KYKKVRFMAY

 451  TDETFKTREA IQHESGILGP LLYGEVGDTL LIIFKNQASR PYNIYPHGIT

 501  DVRPLYSRRL PKGVKHLKDF PILPGEIFKY KWTVTVEDGP TKSDPRCLTR

 551  YYSSFVNMER DLASGLIGPL LICYKESVDQ RGNQIMSDKR NVILFSVFDE

 601  NRSWYLTENI QRFLPNPAGV QLEDPEFQAS NIMHSINGYV FDSLQLSVCL

 651  HEVAYWYILS IGAQTDFLSV FFSGYTFKHK MVYEDTLTLF PFSGETVFMS

 701  MENPGLWILG CHNSDFRNRG MTALLKVSSC DKNTGDYYED SYEDISAYLL

 751  SKNNAIEPRS FSQNGAPGTS ESATPESGPG SEPATSGSET PGTSESATPE

 801  SGPGSEPATS GSETPGTSES ATPESGPGTS TEPSEGSAPG SPAGSPTSTE

 851  EGTSESATPE SGPGSEPATS GSETPGTSES ATPESGPGSP AGSPTSTEEG

 901  SPAGSPTSTE EGTSTEPSEG SAPGTSESAT PESGPGTSES ATPESGPGTS

 951  ESATPESGPG SEPATSGSET PGSEPATSGS ETPGSPAGSP TSTEEGTSTE

1001  PSEGSAPGTS TEPSEGSAPG SEPATSGSET PGTSESATPE SGPGTSTEPS

1051  EGSAPASSPP VLKRHQAEIT RTTLQSDQEE IDYDDTISVE MKKEDFDIYD
```

-continued

```
1101   EDENQSPRSF QKKTRHYFIA AVERLWDYGM SSSPHVLRNR AQSGSVPQFK

1151   KVVFQEFTDG SFTQPLYRGE LNEHLGLLGP YIRAEVEDNI MVTFRNQASR

1201   PYSFYSSLIS YEEDQRQGAE PRKNFVKPNE TKTYFWKVQH HMAPTKDEFD

1251   CKAWAYFSDV DLEKDVHSGL IGPLLVCHTN TLNPAHGRQV TVQEFALFFT

1301   IFDETKSWYF TENMERNCRA PCNIQMEDPT FKENYRFHAI NGYIMDTLPG

1351   LVMAQDQRIR WYLLSMGSNE NIHSIHFSGH VFTVRKKEEY KMALYNLYPG

1401   VFETVEMLPS KAGIWRVECL IGEHLHAGMS TLFLVYSNKC QTPLGMASGH

1451   IRDFQITASG QYGQWAPKLA RLHYSGSINA WSTKEPFSWI KVDLLAPMII

1501   HGIKTQGARQ KFSSLYISQF IIMYSLDGKK WQTYRGNSTG TLMVFFGNVD

1551   SSGIKHNIFN PPIIARYIRL HPTHYSIRST LRMELMGCDL NSCSMPLGME

1601   SKAISDAQIT ASSYFTNMFA TWSPSKARLH LQGRSNAWRP QVNNPKEWLQ

1651   VDFQKTMKVT GVTTQGVKSL LTSMYVKEFL ISSSQDGHQW TLFFQNGKVK

1701   VFQGNQDSFT PVVNSLDPPL LTRYLRIHPQ SWVHQIALRM EVLGCEAQDL

1751   YDKTHTCPPC PAPELLGGPS VFLFPPKPKD TLMASRTPEV TCVVVDVSHE

1801   DPEVKFNWYV DGVEVHNAKT KPREEQYNST YRVVSVLTVL AQDWLNGKEY

1851   KCKVSNKALP APIEKTISKA KGQPREPQVY TLPPSRDELT KNQVSLTCLV

1901   KGFYPSDIAV EWESNGQPEN NYKTTPPVLD SDGSFFLYSK LTVDKSRWQQ

1951   GNVFSCSVMH EALHNAYTQK SLSLSPGK*
```

pSYNFVIII 010 nucleotide sequence-(Dual chain FVIIIFc) (SEQ ID NO: 162)

```
   1   ATGCAAATAG AGCTCTCCAC CTGCTTCTTT CTGTGCCTTT TGCGATTCTG

  51   CTTTAGTGCC ACCAGAAGAT ACTACCTGGG TGCAGTGGAA CTGTCATGGG

 101   ACTATATGCA AAGTGATCTC GGTGAGCTGC CTGTGGACGC AAGATTTCCT

 151   CCTAGAGTGC CAAAATCTTT TCCATTCAAC ACCTCAGTCG TGTACAAAAA

 201   GACTCTGTTT GTAGAATTCA CGGATCACCT TTTCAACATC GCTAAGCCAA

 251   GGCCACCCTG GATGGGTCTG CTAGGTCCTA CCATCCAGGC TGAGGTTTAT

 301   GATACAGTGG TCATTACACT TAAGAACATG GCTTCCCATC CTGTCAGTCT

 351   TCATGCTGTT GGTGTATCCT ACTGGAAAGC TTCTGAGGGA GCTGAATATG

 401   ATGATCAGAC CAGTCAAAGG GAGAAAGAAG ATGATAAAGT CTTCCCTGGT

 451   GGAAGCCATA CATATGTCTG GCAGGTCCTG AAAGAGAATG GTCCAATGGC

 501   CTCTGACCCA CTGTGCCTTA CCTACTCATA TCTTTCTCAT GTGGACCTGG

 551   TAAAAGACTT GAATTCAGGC CTCATTGGAG CCCTACTAGT ATGTAGAGAA

 601   GGGAGTCTGG CCAAGGAAAA GACACAGACC TTGCACAAAT TTATACTACT

 651   TTTTGCTGTA TTTGATGAAG GGAAAAGTTG GCACTCAGAA ACAAAGAACT

 701   CCTTGATGCA GGATAGGGAT GCTGCATCTG CTCGGGCCTG GCCTAAAATG

 751   CACACAGTCA ATGGTTATGT AAACAGGTCT CTGCCAGGTC TGATTGGATG

 801   CCACAGGAAA TCAGTCTATT GGCATGTGAT TGGAATGGGC ACCACTCCTG

 851   AAGTGCACTC AATATTCCTC GAAGGTCACA CATTTCTTGT GAGGAACCAT

 901   CGCCAGGCGT CCTTGGAAAT CTCGCCAATA ACTTTCCTTA CTGCTCAAAC

 951   ACTCTTGATG GACCTTGGAC AGTTTCTACT GTTTTGTCAT ATCTCTTCCC

1001   ACCAACATGA TGGCATGGAA GCTTATGTCA AAGTAGACAG CTGTCCAGAG
```

-continued

```
1051  GAACCCCAAC TACGAATGAA AAATAATGAA GAAGCGGAAG ACTATGATGA
1101  TGATCTTACT GATTCTGAAA TGGATGTGGT CAGGTTTGAT GATGACAACT
1151  CTCCTTCCTT TATCCAAATT CGCTCAGTTG CCAAGAAGCA TCCTAAAACT
1201  TGGGTACATT ACATTGCTGC TGAAGAGGAG GACTGGGACT ATGCTCCCTT
1251  AGTCCTCGCC CCCGATGACA GAAGTTATAA AAGTCAATAT TTGAACAATG
1301  GCCCTCAGCG GATTGGTAGG AAGTACAAAA AAGTCCGATT TATGGCATAC
1351  ACAGATGAAA CCTTTAAGAC TCGTGAAGCT ATTCAGCATG AATCAGGAAT
1401  CTTGGGACCT TTACTTTATG GGGAAGTTGG AGACACACTG TTGATTATAT
1451  TTAAGAATCA AGCAAGCAGA CCATATAACA TCTACCCTCA CGGAATCACT
1501  GATGTCCGTC CTTTGTATTC AAGGAGATTA CCAAAAGGTG TAAAACATTT
1551  GAAGGATTTT CCAATTCTGC CAGGAGAAAT ATTCAAATAT AAATGGACAG
1601  TGACTGTAGA AGATGGGCCA ACTAAATCAG ATCCTCGGTG CCTGACCCGC
1651  TATTACTCTA GTTTCGTTAA TATGGAGAGA GATCTAGCTT CAGGACTCAT
1701  TGGCCCTCTC CTCATCTGCT ACAAAGAATC TGTAGATCAA AGAGGAAACC
1751  AGATAATGTC AGACAAGAGG AATGTCATCC TGTTTTCTGT ATTTGATGAG
1801  AACCGAAGCT GGTACCTCAC AGAGAATATA CAACGCTTTC TCCCCAATCC
1851  AGCTGGAGTG CAGCTTGAGG ATCCAGAGTT CCAAGCCTCC AACATCATGC
1901  ACAGCATCAA TGGCTATGTT TTTGATAGTT TGCAGTTGTC AGTTTGTTTG
1951  CATGAGGTGG CATACTGGTA CATTCTAAGC ATTGGAGCAC AGACTGACTT
2001  CCTTTCTGTC TTCTTCTCTG GATATACCTT CAAACACAAA ATGGTCTATG
2051  AAGACACACT CACCCTATTC CCATTCTCAG GAGAAACTGT CTTCATGTCG
2101  ATGGAAAACC CAGGTCTATG GATTCTGGGG TGCCACAACT CAGACTTTCG
2151  GAACAGAGGC ATGACCGCCT TACTGAAGGT TTCTAGTTGT GACAAGAACA
2201  CTGGTGATTA TTACGAGGAC AGTTATGAAG ATATTTCAGC ATACTTGCTG
2251  AGTAAAAACA ATGCCATTGA ACCAAGAAGC TTCTCTCAAA ACCCACCAGT
2301  CTTGAAACGC CATCAACGGG AAATAACTCG TACTACTCTT CAGTCAGATC
2351  AAGAGGAAAT TGACTATGAT GATACCATAT CAGTTGAAAT GAAGAAGGAA
2401  GATTTTGACA TTTATGATGA GGATGAAAAT CAGAGCCCCC GCAGCTTTCA
2451  AAAGAAAACA CGACACTATT TTATTGCTGC AGTGGAGAGG CTCTGGGATT
2501  ATGGGATGAG TAGCTCCCCA CATGTTCTAA GAAACAGGGC TCAGAGTGGC
2551  AGTGTCCCTC AGTTCAAGAA AGTTGTTTTC CAGGAATTTA CTGATGGCTC
2601  CTTTACTCAG CCCTTATACC GTGGAGAACT AAATGAACAT TTGGGACTCC
2651  TGGGGCCATA TATAAGAGCA GAAGTTGAAG ATAATATCAT GGTAACTTTC
2701  AGAAATCAGG CCTCTCGTCC CTATTCCTTC TATTCTAGCC TTATTTCTTA
2751  TGAGGAAGAT CAGAGGCAAG GAGCAGAACC TAGAAAAAAC TTTGTCAAGC
2801  CTAATGAAAC CAAAACTTAC TTTTGGAAAG TGCAACATCA TATGGCACCC
2851  ACTAAAGATG AGTTTGACTG CAAAGCCTGG GCTTATTTCT CTGATGTTGA
2901  CCTGGAAAAA GATGTGCACT CAGGCCTGAT TGGACCCCTT CTGGTCTGCC
2951  ACACTAACAC ACTGAACCCT GCTCATGGGA GACAAGTGAC AGTACAGGAA
```

-continued

3001 TTTGCTCTGT TTTTCACCAT CTTTGATGAG ACCAAAAGCT GGTACTTCAC

3051 TGAAAATATG GAAAGAAACT GCAGGGCTCC CTGCAATATC CAGATGGAAG

3101 ATCCCACTTT TAAAGAGAAT TATCGCTTCC ATGCAATCAA TGGCTACATA

3151 ATGGATACAC TACCTGGCTT AGTAATGGCT CAGGATCAAA GGATTCGATG

3201 GTATCTGCTC AGCATGGGCA GCAATGAAAA CATCCATTCT ATTCATTTCA

3251 GTGGACATGT GTTCACTGTA CGAAAAAAAG AGGAGTATAA AATGGCACTG

3301 TACAATCTCT ATCCAGGTGT TTTTGAGACA GTGGAAATGT TACCATCCAA

3351 AGCTGGAATT TGGCGGGTGG AATGCCTTAT TGGCGAGCAT CTACATGCTG

3401 GGATGAGCAC ACTTTTTCTG GTGTACAGCA ATAAGTGTCA GACTCCCCTG

3451 GGAATGGCTT CTGGACACAT TAGAGATTTT CAGATTACAG CTTCAGGACA

3501 ATATGGACAG TGGGCCCCAA AGCTGGCCAG ACTTCATTAT TCCGGATCAA

3551 TCAATGCCTG GAGCACCAAG GAGCCCTTTT CTTGGATCAA GGTGGATCTG

3601 TTGGCACCAA TGATTATTCA CGGCATCAAG ACCCAGGGTG CCCGTCAGAA

3651 GTTCTCCAGC CTCTACATCT CTCAGTTTAT CATCATGTAT AGTCTTGATG

3701 GGAAGAAGTG GCAGACTTAT CGAGGAAATT CCACTGGAAC CTTAATGGTC

3751 TTCTTTGGCA ATGTGGATTC ATCTGGGATA AAACACAATA TTTTTAACCC

3801 TCCAATTATT GCTCGATACA TCCGTTTGCA CCCAACTCAT TATAGCATTC

3851 GCAGCACTCT TCGCATGGAG TTGATGGGCT GTGATTTAAA TAGTTGCAGC

3901 ATGCCATTGG GAATGGAGAG TAAAGCAATA TCAGATGCAC AGATTACTGC

3951 TTCATCCTAC TTTACCAATA TGTTTGCCAC CTGGTCTCCT TCAAAAGCTC

4001 GACTTCACCT CCAAGGGAGG AGTAATGCCT GGAGACCTCA GGTGAATAAT

4051 CCAAAAGAGT GGCTGCAAGT GGACTTCCAG AAGACAATGA AAGTCACAGG

4101 AGTAACTACT CAGGGAGTAA AATCTCTGCT TACCAGCATG TATGTGAAGG

4151 AGTTCCTCAT CTCCAGCAGT CAAGATGGCC ATCAGTGGAC TCTCTTTTTT

4201 CAGAATGGCA AAGTAAAGGT TTTTCAGGGA AATCAAGACT CCTTCACACC

4251 TGTGGTGAAC TCTCTAGACC CACCGTTACT GACTCGCTAC CTTCGAATTC

4301 ACCCCCAGAG TTGGGTGCAC CAGATTGCCC TGAGGATGGA GGTTCTGGGC

4351 TGCGAGGCAC AGGACCTCTA CGACAAAACT CACACATGCC CACCGTGCCC

4401 AGCTCCAGAA CTCCTGGGCG GACCGTCAGT CTTCCTCTTC CCCCCAAAAC

4451 CCAAGGACAC CCTCATGATC TCCCGGACCC CTGAGGTCAC ATGCGTGGTG

4501 GTGGACGTGA GCCACGAAGA CCCTGAGGTC AAGTTCAACT GGTACGTGGA

4551 CGGCGTGGAG GTGCATAATG CCAAGACAAA GCCGCGGGAG GAGCAGTACA

4601 ACAGCACGTA CCGTGTGGTC AGCGTCCTCA CCGTCCTGCA CCAGGACTGG

4651 CTGAATGGCA AGGAGTACAA GTGCAAGGTC TCCAACAAAG CCCTCCCAGC

4701 CCCCATCGAG AAAACCATCT CCAAAGCCAA AGGGCAGCCC CGAGAACCAC

4751 AGGTGTACAC CCTGCCCCCA TCCCGGGATG AGCTGACCAA GAACCAGGTC

4801 AGCCTGACCT GCCTGGTCAA AGGCTTCTAT CCCAGCGACA TCGCCGTGGA

4851 GTGGGAGAGC AATGGGCAGC CGGAGAACAA CTACAAGACC ACGCCTCCCG

4901 TGTTGGACTC CGACGGCTCC TTCTTCCTCT ACAGCAAGCT CACCGTGGAC

4951 AAGAGCAGGT GGCAGCAGGG GAACGTCTTC TCATGCTCCG TGATGCATGA

-continued

5001 GGCTCTGCAC AACCACTACA CGCAGAAGAG CCTCTCCCTG TCTCCGGGTA

5051 AATGA pSYNFVIII 010 protein sequence-(Dual chain FVIIIFc) (SEQ ID NO: 163)

1 MQIELSTCFF LCLLRFCFSA TRRYYLGAVE LSWDYMQSDL GELPVDARFP

51 PRVPKSFPFN TSVVYKKTLF VEFTDHLFNI AKPRPPWMGL LGPTIQAEVY

101 DTVVITLKNM ASHPVSLHAV GVSYWKASEG AEYDDQTSQR EKEDDKVFPG

151 GSHTYVWQVL KENGPMASDP LCLTYSYLSH VDLVKDLNSG LIGALLVCRE

201 GSLAKEKTQT LHKFILLFAV FDEGKSWHSE TKNSLMQDRD AASARAWPKM

251 HTVNGYVNRS LPGLIGCHRK SVYWHVIGMG TTPEVHSIFL EGHTFLVRNH

301 RQASLEISPI TFLTAQTLLM DLGQFLLFCH ISSHQHDGME AYVKVDSCPE

351 EPQLRMKNNE EAEDYDDDLT DSEMDVVRFD DDNSPSFIQI RSVAKKHPKT

401 WVHYIAAEEE DWDYAPLVLA PDDRSYKSQY LNNGPQRIGR KYKKVRFMAY

451 TDETFKTREA IQHESGILGP LLYGEVGDTL LIIFKNQASR PYNIYPHGIT

501 DVRPLYSRRL PKGVKHLKDF PILPGEIFKY KWTVTVEDGP TKSDPRCLTR

551 YYSSFVNMER DLASGLIGPL LICYKESVDQ RGNQIMSDKR NVILFSVFDE

601 NRSWYLTENI QRFLPNPAGV QLEDPEFQAS NIMHSINGYV FDSLQLSVCL

651 HEVAYWYILS IGAQTDFLSV FFSGYTFKHK MVYEDTLTLF PFSGETVFMS

701 MENPGLWILG CHNSDFRNRG MTALLKVSSC DKNTGDYYED SYEDISAYLL

751 SKNNAIEPRS FSQNPPVLKR HQREITRTTL QSDQEEIDYD DTISVEMKKE

801 DFDIYDEDEN QSPRSFQKKT RHYFIAAVER LWDYGMSSSP HVLRNRAQSG

851 SVPQFKKVVF QEFTDGSFTQ PLYRGELNEH LGLLGPYIRA EVEDNIMVTF

901 RNQASRPYSF YSSLISYEED QRQGAEPRKN FVKPNETKTY FWKVQHHMAP

951 TKDEFDCKAW AYFSDVDLEK DVHSGLIGPL LVCHTNTLNP AHGRQVTVQE

1001 FALFFTIFDE TKSWYFTENM ERNCRAPCNI QMEDPTFKEN YRFHAINGYI

1051 MDTLPGLVMA QDQRIRWYLL SMGSNENIHS IHFSGHVFTV RKKEEYKMAL

1101 YNLYPGVFET VEMLPSKAGI WRVECLIGEH LHAGMSTLFL VYSNKCQTPL

1151 GMASGHIRDF QITASGQYGQ WAPKLARLHY SGSINAWSTK EPFSWIKVDL

1201 LAPMIIHGIK TQGARQKFSS LYISQFIIMY SLDGKKWQTY RGNSTGTLMV

1251 FFGNVDSSGI KHNIFNPPII ARYIRLHPTH YSIRSTLRME LMGCDLNSCS

1301 MPLGMESKAI SDAQITASSY FTNMFATWSP SKARLHLQGR SNAWRPQVNN

1351 PKEWLQVDFQ KTMKVTGVTT QGVKSLLTSM YVKEFLISSS QDGHQWTLFF

1401 QNGKVKVFQG NQDSFTPVVN SLDPPLLTRY LRIHPQSWVH QIALRMEVLG

1451 CEAQDLYDKT HTCPPCPAPE LLGGPSVFLF PPKPKDTLMI SRTPEVTCVV

1501 VDVSHEDPEV KFNWYVDGVE VHNAKTKPRE EQYNSTYRVV SVLTVLHQDW

1551 LNGKEYKCKV SNKALPAPIE KTISKAKGQP REPQVYTLPP SRDELTKNQV

1601 SLTCLVKGFY PSDIAVEWES NGQPENNYKT TPPVLDSDGS FFLYSKLTVD

1651 KSRWQQGNVF SCSVMHEALH NHYTQKSLSL SPGK*

FVIII 195 protein sequence (dual chain FVIIIFc with two 144 AE XTENs at amino acid 1656 and 1900) (SEQ ID NO: 73)

1 MQIELSTCFF LCLLRFCFSA TRRYYLGAVE LSWDYMQSDL GELPVDARFP

51 PRVPKSFPFN TSVVYKKTLF VEFTDHLFNI AKPRPPWMGL LGPTIQAEVY

-continued

```
 101  DTVVITLKNM ASHPVSLHAV GVSYWKASEG AEYDDQTSQR EKEDDKVFPG
 151  GSHTYVWQVL KENGPMASDP LCLTYSYLSH VDLVKDLNSG LIGALLVCRE
 201  GSLAKEKTQT LHKFILLFAV FDEGKSWHSE TKNSLMQDRD AASARAWPKM
 251  HTVNGYVNRS LPGLIGCHRK SVYWHVIGMG TTPEVHSIFL EGHTFLVRNH
 301  RQASLEISPI TFLTAQTLLM DLGQFLLFCH ISSHQHDGME AYVKVDSCPE
 351  EPQLRMKNNE EAEDYDDDLT DSEMDVVRFD DDNSPSFIQI RSVAKKHPKT
 401  WVHYIAAEEE DWDYAPLVLA PDDRSYKSQY LNNGPQRIGR KYKKVRFMAY
 451  TDETFKTREA IQHESGILGP LLYGEVGDTL LIIFKNQASR PYNIYPHGIT
 501  DVRPLYSRRL PKGVKHLKDF PILPGEIFKY KWTVTVEDGP TKSDPRCLTR
 551  YYSSFVNMER DLASGLIGPL LICYKESVDQ RGNQIMSDKR NVILFSVFDE
 601  NRSWYLTENI QRFLPNPAGV QLEDPEFQAS NIMHSINGYV FDSLQLSVCL
 651  HEVAYWYILS IGAQTDFLSV FFSGYTFKHK MVYEDTLTLF PFSGETVFMS
 701  MENPGLWILG CHNSDFRNRG MTALLKVSSC DKNTGDYYED SYEDISAYLL
 751  SKNNAIEPRS FSQNPPVLKR HQREITRTTL QGAPGTPGSG TASSSPGASP
 801  GTSSTGSPGA SPGTSSTGSP GASPGTSSTG SPGSSPSAST GTGPGTPGSG
 851  TASSSPGASP GTSSTGSPGA SPGTSSTGSP GASPGTSSTG SPGSSTPSGA
 901  TGSPGSSTPS GATGSPGASP GTSSTGSPAS SSDQEEIDYD DTISVEMKKE
 951  DFDIYDEDEN QSPRSFQKKT RHYFIAAVER LWDYGMSSSP HVLRNRAQSG
1001  SVPQFKKVVF QEFTDGSFTQ PLYRGELNEH LGLLGPYIRA EVEDNIMVTF
1051  RNQASRPYSF YSSLISYEED QRQGAEPRKN FVKPNETKTY FWKVQHHMAP
1101  TKDEFDCKAW AYFSDVDLEK DVHSGLIGPL LVCHTNTLNP AHGRQVTVQE
1151  FALFFTIFDE TKSWYFTENM ERNCRGAPTS ESATPESGPG SEPATSGSET
1201  PGTSESATPE SGPGSEPATS GSETPGTSES ATPESGPGTS TEPSEGSAPG
1251  TSESATPESG PGSPAGSPTS TEEGSPAGSP TSTEEGSPAG SPTSTEEGTS
1301  ESATPESGPG TSTEPSEGSA PGASSAPCNI QMEDPTFKEN YRFHAINGYI
1351  MDTLPGLVMA QDQRIRWYLL SMGSNENIHS IHFSGHVFTV RKKEEYKMAL
1401  YNLYPGVFET VEMLPSKAGI WRVECLIGEH LHAGMSTLFL VYSNKCQTPL
1451  GMASGHIRDF QITASGQYGQ WAPKLARLHY SGSINAWSTK EPFSWIKVDL
1501  LAPMIIHGIK TQGARQKFSS LYISQFIIMY SLDGKKWQTY RGNSTGTLMV
1551  FFGNVDSSGI KHNIFNPPII ARYIRLHPTH YSIRSTLRME LMGCDLNSCS
1601  MPLGMESKAI SDAQITASSY FTNMFATWSP SKARLHLQGR SNAWRPQVNN
1651  PKEWLQVDFQ KTMKVTGVTT QGVKSLLTSM YVKEFLISSS QDGHQWTLFF
1701  QNGKVKVFQG NQDSFTPVVN SLDPPLLTRY LRIHPQSWVH QIALRMEVLG
1751  CEAQDLYDKT HTCPPCPAPE LLGGPSVFLF PPKPKDTLMI SRTPEVTCVV
1801  VDVSHEDPEV KFNWYVDGVE VHNAKTKPRE EQYNSTYRVV SVLTVLHQDW
1851  LNGKEYKCKV SNKALPAPIE KTISKAKGQP REPQVYTLPP SRDELTKNQV
1901  SLTCLVKGFY PSDIAVEWES NGQPENNYKT TPPVLDSDGS FFLYSKLTVD
1951  KSRWQQGNVF SCSVMHEALH NHYTQKSLSL SPGK*
```

pSYN-FVIII-173 mature Protein sequencing (SEQ ID NO: 72):

```
   1  ATRRYYLGAV ELSWDYMQSD LGELPVDARF PPRVPKSFPF NTSVVYKKTL
```

-continued

51 FVEFTDHLFN IAKPRPPWMG LLGPTIQAEV YDTVVITLKN MASHPVSLHA

101 VGVSYWKASE GAEYDDQTSQ REKEDDKVFP GGSHTYVWQV LKENGPMASD

151 PLCLTYSYLS HVDLVKDLNS GLIGALLVCR EGSLAKEKTQ TLHKFILLFA

201 VFDEGKSWHS ETKNSLMQDR DAASARAWPK MHTVNGYVNR SLPGLIGCHR

251 KSVYWHVIGM GTTPEVHSIF LEGHTFLVRN HRQASLEISP ITFLTAQTLL

301 MDLGQFLLFC HISSHQHDGM EAYVKVDSCP EEPQLRMKNN EEAEDYDDDL

351 TDSEMDVVRF DDDNSPSFIQ IRSVAKKHPK TWVHYIAAEE EDWDYAPLVL

401 APDDRSYKSQ YLNNGPQRIG RKYKKVRFMA YTDETFKTRE AIQHESGILG

451 PLLYGEVGDT LLIIFKNQAS RPYNIYPHGI TDVRPLYSRR LPKGVKHLKD

501 FPILPGEIFK YKWTVTVEDG PTKSDPRCLT RYYSSFVNME RDLASGLIGP

551 LLICYKESVD QRGNQIMSDK RNVILFSVFD ENRSWYLTEN IQRFLPNPAG

601 VQLEDPEFQA SNIMHSINGY VFDSLQLSVC LHEVAYWYIL SIGAQTDFLS

651 VFFSGYTFKH KMVYEDTLTL FPFSGETVFM SMENPGLWIL GCHNSDFRNR

701 GMTALLKVSS CDKNTGDYYE DSYEDISAYL LSKNNAIEPR SFSQNGAPGT

751 SESATPESGP GSEPATSGSE TPGTSESATP ESGPGSEPAT SGSETPGTSE

801 SATPESGPGT STEPSEGSAP GSPAGSPTST EEGTSESATP ESGPGSEPAT

851 SGSETPGTSE SATPESGPGS PAGSPTSTEE GSPAGSPTST EEGTSTEPSE

901 GSAPGTSESA TPESGPGTSE SATPESGPGT SESATPESGP GSEPATSGSE

951 TPGSEPATSG SETPGSPAGS PTSTEEGTST EPSEGSAPGT STEPSEGSAP

1001 GSEPATSGSE TPGTSESATP ESGPGTSTEP SEGSAPASSP PVLKRHQREI

1051 TRTTLQSDQE EIDYDDTISV EMKKEDFDIY DEDENQSPRS FQKKTRHYFI

1101 AAVERLWDYG MSSSPHVLRN RAQSGSVPQF KKVVFQEFTD GSFTQPLYRG

1151 ELNEHLGLLG PYIRAEVEDN IMVTFRNQAS RPYSFYSSLI SYEEDQRQGA

1201 EPRKNFVKPN ETKTYFWKVQ HHMAPTKDEF DCKAWAYFSD VDLEKDVHSG

1251 LIGPLLVCHT NTLNPAHGRQ VTVQEFALFF TIFDETKSWY FTENMERNCR

1301 APCNIQMEDP TFKENYRFHA INGYIMDTLP GLVMAQDQRI RWYLLSMGSN

1351 ENIHSIHFSG HVFTVRKKEE YKMALYNLYP GVFETVEMLP SKAGIWRVEC

1401 LIGEHLHAGM STLFLVYSNK CQTPLGMASG HIRDFQITAS GQYGQWAPKL

1451 ARLHYSGSIN AWSTKEPFSW IKVDLLAPMI IHGIKTQGAR QKFSSLYISQ

1501 FIIMYSLDGK KWQTYRGNST GTLMVFFGNV DSSGIKHNIF NPPIIARYIR

1551 LHPTHYSIRS TLRMELMGCD LNSCSMPLGM ESKAISDAQI TASSYFTNMF

1601 ATWSPSKARL HLQGRSNAWR PQVNNPKEWL QVDFQKTMKV TGVTTQGVKS

1651 LLTSMYVKEF LISSSQDGHQ WTLFFQNGKV KVFQGNQDSF TPVVNSLDPP

1701 LLTRYLRIHP QSWVHQIALR MEVLGCEAQD LYDKTHTCPP CPAPELLGGP

1751 SVFLFPPKPK DTLMISRTPE VTCVVVDVSH EDPEVKFNWY VDGVEVHNAK

1801 TKPREEQYNS TYRVVSVLTV LHQDWLNGKE YKCKVSNKAL PAPIEKTISK

1851 AKGQPREPQV YTLPPSRDEL TKNQVSLTCL VKGFYPSDIA VEWESNGQPE

1901 NNYKTTPPVL DSDGSFFLYS KLTVDKSRWQ QGNVFSCSVM HEALHNHYTQ

1951 KSLSLSPGK

-continued

FVIII 196 protein sequence (dual chain FVIIIFc with three 144 AE XTENs at amino acid 26, 1656 and 1900) (SEQ ID NO: 74)

```
   1 MQIELSTCFF LCLLRFCFSA TRRYYLGAVE LSWDYMQSDL GELPVGAPGS
  51 SPSASTGTGP GSSPSASTGT GPGASPGTSS TGSPGASPGT SSTGSPGSST
 101 PSGATGSPGS SPSASTGTGP GASPGTSSTG SPGSSPSAST GTGPGTPGSG
 151 TASSSPGSST PSGATGSPGS STPSGATGSP GASPGTSSTG SPASSDARFP
 201 PRVPKSFPFN TSVVYKKTLF VEFTDHLFNI AKPRPPWMGL LGPTIQAEVY
 251 DTVVITLKNM ASHPVSLHAV GVSYWKASEG AEYDDQTSQR EKEDDKVFPG
 301 GSHTYVWQVL KENGPMASDP LCLTYSYLSH VDLVKDLNSG LIGALLVCRE
 351 GSLAKEKTQT LHKFILLFAV FDEGKSWHSE TKNSLMQDRD AASARAWPKM
 401 HTVNGYVNRS LPGLIGCHRK SVYWHVIGMG TTPEVHSIFL EGHTFLVRNH
 451 RQASLEISPI TFLTAQTLLM DLGQFLLFCH ISSHQHDGME AYVKVDSCPE
 501 EPQLRMKNNE EAEDYDDDLT DSEMDVVRFD DDNSPSFIQI RSVAKKHPKT
 551 WVHYIAAEEE DWDYAPLVLA PDDRSYKSQY LNNGPQRIGR KYKKVRFMAY
 601 TDETFKTREA IQHESGILGP LLYGEVGDTL LIIFKNQASR PYNIYPHGIT
 651 DVRPLYSRRL PKGVKHLKDF PILPGEIFKY KWTVTVEDGP TKSDPRCLTR
 701 YYSSFVNMER DLASGLIGPL LICYKESVDQ RGNQIMSDKR NVILFSVFDE
 751 NRSWYLTENI QRFLPNPAGV QLEDPEFQAS NIMHSINGYV FDSLQLSVCL
 801 HEVAYWYILS IGAQTDFLSV FFSGYTFKHK MVYEDTLTLF PFSGETVFMS
 851 MENPGLWILG CHNSDFRNRG MTALLKVSSC DKNTGDYYED SYEDISAYLL
 901 SKNNAIEPRS FSQNPPVLKR HQREITRTTL QGAPGTPGSG TASSSPGASP
 951 GTSSTGSPGA SPGTSSTGSP GASPGTSSTG SPGSSPSAST GTGPGTPGSG
1001 TASSSPGASP GTSSTGSPGA SPGTSSTGSP GASPGTSSTG SPGSSTPSGA
1051 TGSPGSSTPS GATGSPGASP GTSSTGSPAS SSDQEEIDYD DTISVEMKKE
1101 DFDIYDEDEN QSPRSFQKKT RHYFIAAVER LWDYGMSSSP HVLRNRAQSG
1151 SVPQFKKVVF QEFTDGSFTQ PLYRGELNEH LGLLGPYIRA EVEDNIMVTF
1201 RNQASRPYSF YSSLISYEED QRQGAEPRKN FVKPNETKTY FWKVQHHMAP
1251 TKDEFDCKAW AYFSDVDLEK DVHSGLIGPL LVCHTNTLNP AHGRQVTVQE
1301 FALFFTIFDE TKSWYFTENM ERNCRGAPTS ESATPESGPG SEPATSGSET
1351 PGTSESATPE SGPGSEPATS GSETPGTSES ATPESGPGTS TEPSEGSAPG
1401 TSESATPESG PGSPAGSPTS TEEGSPAGSP TSTEEGSPAG SPTSTEEGTS
1451 ESATPESGPG TSTEPSEGSA PGASSAPCNI QMEDPTFKEN YRFHAINGYI
1501 MDTLPGLVMA QDQRIRWYLL SMGSNENIHS IHFSGHVFTV RKKEEYKMAL
1551 YNLYPGVFET VEMLPSKAGI WRVECLIGEH LHAGMSTLFL VYSNKCQTPL
1601 GMASGHIRDF QITASGQYGQ WAPKLARLHY SGSINAWSTK EPFSWIKVDL
1651 LAPMIIHGIK TQGARQKFSS LYISQFIIMY SLDGKKWQTY RGNSTGTLMV
1701 FFGNVDSSGI KHNIFNPPII ARYIRLHPTH YSIRSTLRME LMGCDLNSCS
1751 MPLGMESKAI SDAQITASSY FTNMFATWSP SKARLHLQGR SNAWRPQVNN
1801 PKEWLQVDFQ KTMKVTGVTT QGVKSLLTSM YVKEFLISSS QDGHQWTLFF
1851 QNGKVKVFQG NQDSFTPVVN SLDPPLLTRY LRIHPQSWVH QIALRMEVLG
1901 CEAQDLYDKT HTCPPCPAPE LLGGPSVFLF PPKPKDTLMI SRTPEVTCVV
```

-continued

```
1951  VDVSHEDPEV KFNWYVDGVE VHNAKTKPRE EQYNSTYRVV SVLTVLHQDW

2001  LNGKEYKCKV SNKALPAPIE KTISKAKGQP REPQVYTLPP SRDELTKNQV

2051  SLTCLVKGFY PSDIAVEWES NGQPENNYKT TPPVLDSDGS FFLYSKLTVD

2101  KSRWQQGNVF SCSVMHEALH NHYTQKSLSL SPGK*
```

FVIII 199 protein sequence (single chain FVIIIFc with three 144 AE XTENs at amino acid 1656 and 1900) (SEQ ID NO: 75)

```
   1  MQIELSTCFF LCLLRFCFSA TRRYYLGAVE LSWDYMQSDL GELPVDARFP

  51  PRVPKSFPFN TSVVYKKTLF VEFTDHLFNI AKPRPPWMGL LGPTIQAEVY

 101  DTVVITLKNM ASHPVSLHAV GVSYWKASEG AEYDDQTSQR EKEDDKVFPG

 151  GSHTYVWQVL KENGPMASDP LCLTYSYLSH VDLVKDLNSG LIGALLVCRE

 201  GSLAKEKTQT LHKFILLFAV FDEGKSWHSE TKNSLMQDRD AASARAWPKM

 251  HTVNGYVNRS LPGLIGCHRK SVYWHVIGMG TTPEVHSIFL EGHTFLVRNH

 301  RQASLEISPI TFLTAQTLLM DLGQFLLFCH ISSHQHDGME AYVKVDSCPE

 351  EPQLRMKNNE EAEDYDDDLT DSEMDVVRFD DDNSPSFIQI RSVAKKHPKT

 401  WVHYIAAEEE DWDYAPLVLA PDDRSYKSQY LNNGPQRIGR KYKKVRFMAY

 451  TDETFKTREA IQHESGILGP LLYGEVGDTL LIIFKNQASR PYNIYPHGIT

 501  DVRPLYSRRL PKGVKHLKDF PILPGEIFKY KWTVTVEDGP TKSDPRCLTR

 551  YYSSFVNMER DLASGLIGPL LICYKESVDQ RGNQIMSDKR NVILFSVFDE

 601  NRSWYLTENI QRFLPNPAGV QLEDPEFQAS NIMHSINGYV FDSLQLSVCL

 651  HEVAYWYILS IGAQTDFLSV FFSGYTFKHK MVYEDTLTLF PFSGETVFMS

 701  MENPGLWILG CHNSDFRNRG MTALLKVSSC DKNTGDYYED SYEDISAYLL

 751  SKNNAIEPRS FSQNPPVLKR HQAEITRTTL QGAPGTPGSG TASSSPGASP

 801  GTSSTGSPGA SPGTSSTGSP GASPGTSSTG SPGSSPSAST GTGPGTPGSG

 851  TASSSPGASP GTSSTGSPGA SPGTSSTGSP GASPGTSSTG SPGSSTPSGA

 901  TGSPGSSTPS GATGSPGASP GTSSTGSPAS SSDQEEIDYD DTISVEMKKE

 951  DFDIYDEDEN QSPRSFQKKT RHYFIAAVER LWDYGMSSSP HVLRNRAQSG

1001  SVPQFKKVVF QEFTDGSFTQ PLYRGELNEH LGLLGPYIRA EVEDNIMVTF

1051  RNQASRPYSF YSSLISYEED QRQGAEPRKN FVKPNETKTY FWKVQHHMAP

1101  TKDEFDCKAW AYFSDVDLEK DVHSGLIGPL LVCHTNTLNP AHGRQVTVQE

1151  FALFFTIFDE TKSWYFTENM ERNCRGAPTS ESATPESGPG SEPATSGSET

1201  PGTSESATPE SGPGSEPATS GSETPGTSES ATPESGPGTS TEPSEGSAPG

1251  TSESATPESG PGSPAGSPTS TEEGSPAGSP TSTEEGSPAG SPTSTEEGTS

1301  ESATPESGPG TSTEPSEGSA PGASSAPCNI QMEDPTFKEN YRFHAINGYI

1351  MDTLPGLVMA QDQRIRWYLL SMGSNENIHS IHFSGHVFTV RKKEEYKMAL

1401  YNLYPGVFET VEMLPSKAGI WRVECLIGEH LHAGMSTLFL VYSNKCQTPL

1451  GMASGHIRDF QITASGQYGQ WAPKLARLHY SGSINAWSTK EPFSWIKVDL

1501  LAPMIIHGIK TQGARQKFSS LYISQFIIMY SLDGKKWQTY RGNSTGTLMV

1551  FFGNVDSSGI KHNIFNPPII ARYIRLHPTH YSIRSTLRME LMGCDLNSCS

1601  MPLGMESKAI SDAQITASSY FTNMFATWSP SKARLHLQGR SNAWRPQVNN

1651  PKEWLQVDFQ KTMKVTGVTT QGVKSLLTSM YVKEFLISSS QDGHQWTLFF
```

-continued

1701 QNGKVKVFQG NQDSFTPVVN SLDPPLLTRY LRIHPQSWVH QIALRMEVLG

1751 CEAQDLYDKT HTCPPCPAPE LLGGPSVFLF PPKPKDTLMI SRTPEVTCVV

1801 VDVSHEDPEV KFNWYVDGVE VHNAKTKPRE EQYNSTYRVV SVLTVLHQDW

1851 LNGKEYKCKV SNKALPAPIE KTISKAKGQP REPQVYTLPP SRDELTKNQV

1901 SLTCLVKGFY PSDIAVEWES NGQPENNYKT TPPVLDSDGS FFLYSKLTVD

1951 KSRWQQGNVF SCSVMHEALH NHYTQKSLSL SPGK*

FVIII 201 protein sequence (single chain FVIIIFc with three 144 AE XTENs at amino acid 26, 1656 & 1900) (SEQ ID NO: 76)

1 MQIELSTCFF LCLLRFCFSA TRRYYLGAVE LSWDYMQSDL GELPVGAPGS

51 SPSASTGTGP GSSPSASTGT GPGASPGTSS TGSPGASPGT SSTGSPGSST

101 PSGATGSPGS SPSASTGTGP GASPGTSSTG SPGSSPSAST GTGPGTPGSG

151 TASSSPGSST PSGATGSPGS STPSGATGSP GASPGTSSTG SPASSDARFP

201 PRVPKSFPFN TSVVYKKTLF VEFTDHLFNI AKPRPPWMGL LGPTIQAEVY

251 DTVVITLKNM ASHPVSLHAV GVSYWKASEG AEYDDQTSQR EKEDDKVFPG

301 GSHTYVWQVL KENGPMASDP LCLTYSYLSH VDLVKDLNSG LIGALLVCRE

351 GSLAKEKTQT LHKFILLFAV FDEGKSWHSE TKNSLMQDRD AASARAWPKM

401 HTVNGYVNRS LPGLIGCHRK SVYWHVIGMG TTPEVHSIFL EGHTFLVRNH

451 RQASLEISPI TFLTAQTLLM DLGQFLLFCH ISSHQHDGME AYVKVDSCPE

501 EPQLRMKNNE EAEDYDDDLT DSEMDVVRFD DDNSPSFIQI RSVAKKHPKT

551 WVHYIAAEEE DWDYAPLVLA PDDRSYKSQY LNNGPQRIGR KYKKVRFMAY

601 TDETFKTREA IQHESGILGP LLYGEVGDTL LIIFKNQASR PYNIYPHGIT

651 DVRPLYSRRL PKGVKHLKDF PILPGEIFKY KWTVTVEDGP TKSDPRCLTR

701 YYSSFVNMER DLASGLIGPL LICYKESVDQ RGNQIMSDKR NVILFSVFDE

751 NRSWYLTENI QRFLPNPAGV QLEDPEFQAS NIMHSINGYV FDSLQLSVCL

801 HEVAYWYILS IGAQTDFLSV FFSGYTFKHK MVYEDTLTLF PFSGETVFMS

851 MENPGLWILG CHNSDFRNRG MTALLKVSSC DKNTGDYYED SYEDISAYLL

901 SKNNAIEPRS FSQNPPVLKR HQAEITRTTL QGAPGTPGSG TASSSPGASP

951 GTSSTGSPGA SPGTSSTGSP GASPGTSSTG SPGSSPSAST GTGPGTPGSG

1001 TASSSPGASP GTSSTGSPGA SPGTSSTGSP GASPGTSSTG SPGSSTPSGA

1051 TGSPGSSTPS GATGSPGASP GTSSTGSPAS SSDQEEIDYD DTISVEMKKE

1101 DFDIYDEDEN QSPRSFQKKT RHYFIAAVER LWDYGMSSSP HVLRNRAQSG

1151 SVPQFKKVVF QEFTDGSFTQ PLYRGELNEH LGLLGPYIRA EVEDNIMVTF

1201 RNQASRPYSF YSSLISYEED QRQGAEPRKN FVKPNETKTY FWKVQHHMAP

1251 TKDEFDCKAW AYFSDVDLEK DVHSGLIGPL LVCHTNTLNP AHGRQVTVQE

1301 FALFFTIFDE TKSWYFTENM ERNCRGAPTS ESATPESGPG SEPATSGSET

1351 PGTSESATPE SGPGSEPATS GSETPGTSES ATPESGPGTS TEPSEGSAPG

1401 TSESATPESG PGSPAGSPTS TEEGSPAGSP TSTEEGSPAG SPTSTEEGTS

1451 ESATPESGPG TSTEPSEGSA PGASSAPCNI QMEDPTFKEN YRFHAINGYI

1501 MDTLPGLVMA QDQRIRWYLL SMGSNENIHS IHFSGHVFTV RKKEEYKMAL

1551 YNLYPGVFET VEMLPSKAGI WRVECLIGEH LHAGMSTLFL VYSNKCQTPL

1601 GMASGHIRDF QITASGQYGQ WAPKLARLHY SGSINAWSTK EPFSWIKVDL

-continued

```
1651  LAPMIIHGIK TQGARQKFSS LYISQFIIMY SLDGKKWQTY RGNSTGTLMV

1701  FFGNVDSSGI KHNIFNPPII ARYIRLHPTH YSIRSTLRME LMGCDLNSCS

1751  MPLGMESKAI SDAQITASSY FTNMFATWSP SKARLHLQGR SNAWRPQVNN

1801  PKEWLQVDFQ KTMKVTGVTT QGVKSLLTSM YVKEFLISSS QDGHQWTLFF

1851  QNGKVKVFQG NQDSFTPVVN SLDPPLLTRY LRIHPQSWVH QIALRMEVLG

1901  CEAQDLYDKT HTCPPCPAPE LLGGPSVFLF PPKPKDTLMI SRTPEVTCVV

1951  VDVSHEDPEV KFNWYVDGVE VHNAKTKPRE EQYNSTYRVV SVLTVLHQDW

2001  LNGKEYKCKV SNKALPAPIE KTISKAKGQP REPQVYTLPP SRDELTKNQV

2051  SLTCLVKGFY PSDIAVEWES NGQPENNYKT TPPVLDSDGS FFLYSKLTVD

2101  KSRWQQGNVF SCSVMHEALH NHYTQKSLSL SPGK*
```

FVIII 203 protein sequence (single chain FVIIIFc with two AE XTENs; one 288AE XTEN in B-domain and one 144 AE XTEN at amino acid 1900) (SEQ ID NO: 77)

```
   1  MQIELSTCFF LCLLRFCFSA TRRYYLGAVE LSWDYMQSDL GELPVDARFP

  51  PRVPKSFPFN TSVVYKKTLF VEFTDHLFNI AKPRPPWMGL LGPTIQAEVY

 101  DTVVITLKNM ASHPVSLHAV GVSYWKASEG AEYDDQTSQR EKEDDKVFPG

 151  GSHTYVWQVL KENGPMASDP LCLTYSYLSH VDLVKDLNSG LIGALLVCRE

 201  GSLAKEKTQT LHKFILLFAV FDEGKSWHSE TKNSLMQDRD AASARAWPKM

 251  HTVNGYVNRS LPGLIGCHRK SVYWHVIGMG TTPEVHSIFL EGHTFLVRNH

 301  RQASLEISPI TFLTAQTLLM DLGQFLLFCH ISSHQHDGME AYVKVDSCPE

 351  EPQLRMKNNE EAEDYDDDLT DSEMDVVRFD DDNSPSFIQI RSVAKKHPKT

 401  WVHYIAAEEE DWDYAPLVLA PDDRSYKSQY LNNGPQRIGR KYKKVRFMAY

 451  TDETFKTREA IQHESGILGP LLYGEVGDTL LIIFKNQASR PYNIYPHGIT

 501  DVRPLYSRRL PKGVKHLKDF PILPGEIFKY KWTVTVEDGP TKSDPRCLTR

 551  YYSSFVNMER DLASGLIGPL LICYKESVDQ RGNQIMSDKR NVILFSVFDE

 601  NRSWYLTENI QRFLPNPAGV QLEDPEFQAS NIMHSINGYV FDSLQLSVCL

 651  HEVAYWYILS IGAQTDFLSV FFSGYTFKHK MVYEDTLTLF PFSGETVFMS

 701  MENPGLWILG CHNSDFRNRG MTALLKVSSC DKNTGDYYED SYEDISAYLL

 751  SKNNAIEPRS FSQNGAPGTS ESATPESGPG SEPATSGSET PGTSESATPE

 801  SGPGSEPATS GSETPGTSES ATPESGPGTS TEPSEGSAPG SPAGSPTSTE

 851  EGTSESATPE SGPGSEPATS GSETPGTSES ATPESGPGSP AGSPTSTEEG

 901  SPAGSPTSTE EGTSTEPSEG SAPGTSESAT PESGPGTSES ATPESGPGTS

 951  ESATPESGPG SEPATSGSET PGSEPATSGS ETPGSPAGSP TSTEEGTSTE

1001  PSEGSAPGTS TEPSEGSAPG SEPATSGSET PGTSESATPE SGPGTSTEPS

1051  EGSAPASSPP VLKRHQAEIT RTTLQSDQEE IDYDDTISVE MKKEDFDIYD

1101  EDENQSPRSF QKKTRHYFIA AVERLWDYGM SSSPHVLRNR AQSGSVPQFK

1151  KVVFQEFTDG SFTQPLYRGE LNEHLGLLGP YIRAEVEDNI MVTFRNQASR

1201  PYSFYSSLIS YEEDQRQGAE PRKNFVKPNE TKTYFWKVQH HMAPTKDEFD

1251  CKAWAYFSDV DLEKDVHSGL IGPLLVCHTN TLNPAHGRQV TVQEFALFFT

1301  IFDETKSWYF TENMERNCRG APTSESATPE SGPGSEPATS GSETPGTSES

1351  ATPESGPGSE PATSGSETPG TSESATPESG PGTSTEPSEG SAPGTSESAT
```

-continued

1401 PESGPGSPAG SPTSTEEGSP AGSPTSTEEG SPAGSPTSTE EGTSESATPE

1451 SGPGTSTEPS EGSAPGASSA PCNIQMEDPT FKENYRFHAI NGYIMDTLPG

1501 LVMAQDQRIR WYLLSMGSNE NIHSIHFSGH VFTVRKKEEY KMALYNLYPG

1551 VFETVEMLPS KAGIWRVECL IGEHLHAGMS TLFLVYSNKC QTPLGMASGH

1601 IRDFQITASG QYGQWAPKLA RLHYSGSINA WSTKEPFSWI KVDLLAPMII

1651 HGIKTQGARQ KFSSLYISQF IIMYSLDGKK WQTYRGNSTG TLMVFFGNVD

1701 SSGIKHNIFN PPIIARYIRL HPTHYSIRST LPMELMGCDL NSCSMPLGME

1751 SKAISDAQIT ASSYFTNMFA TWSPSKARLH LQGRSNAWRP QVNNPKEWLQ

1801 VDFQKTMKVT GVTTQGVKSL LTSMYVKEFL ISSSQDGHQW TLFFQNGKVK

1851 VFQGNQDSFT PVVNSLDPPL LTRYLRIHPQ SWVHQIALRM EVLGCEAQDL

1901 YDKTHTCPPC PAPELLGGPS VFLFPPKPKD TLMISRTPEV TCVVVDVSHE

1951 DPEVKFNWYV DGVEVHNAKT KPREEQYNST YRVVSVLTVL HQDWLNGKEY

2001 KCKVSNKALP APIEKTISKA KGQPREPQVY TLPPSRDELT KNQVSLTCLV

2051 KGFYPSDIAV EWESNGQPEN NYKTTPPVLD SDGSFFLYSK LTVDKSRWQQ

2101 GNVFSCSVMH EALHNHYTQK SLSLSPGK*

FVIII 204 protein sequence (single chain FVIIIFc with two AE XTENs; one 288AE XTEN in B-domain and one 144 AE XTEN at amino acid 403) (SEQ ID NO: 78)

1 MQIELSTCFF LCLLRFCFSA TRRYYLGAVE LSWDYMQSDL GELPVDARFP

51 PRVPKSFPFN TSVVYKKTLF VEFTDHLFNI AKPRPPWMGL LGPTIQAEVY

101 DTVVITLKNM ASHPVSLHAV GVSYWKASEG AEYDDQTSQR EKEDDKVFPG

151 GSHTYVWQVL KENGPMASDP LCLTYSYLSH VDLVKDLNSG LIGALLVCRE

201 GSLAKEKTQT LHKFILLFAV FDEGKSWHSE TKNSLMQDRD AASARAWPKM

251 HTVNGYVNRS LPGLIGCHRK SVYWHVIGMG TTPEVHSIFL EGHTFLVRNH

301 RQASLEISPI TFLTAQTLLM DLGQFLLFCH ISSHQHDGME AYVKVDSCPE

351 EPQLRMKNNE EAEDYDDDLT DSEMDVVRFD DDNSPSFIQI RSVAKKHPKT

401 WVHYIAAEEE DWDYAPLVLA PDGAPTSTEP SEGSAPGSPA GSPTSTEEGT

451 STEPSEGSAP GTSTEPSEGS APGTSESATP ESGPGTSTEP SEGSAPGTSE

501 SATPESGPGS EPATSGSETP GTSTEPSEGS APGTSTEPSE GSAPGTSESA

551 TPESGPGTSE SATPESGPGA SSDRSYKSQY LNNGPQRIGR KYKKVRFMAY

601 TDETFKTREA IQHESGILGP LLYGEVGDTL LIIFKNQASR PYNIYPHGIT

651 DVRPLYSRRL PKGVKHLKDF PILPGEIFKY KWTVTVEDGP TKSDPRCLTR

701 YYSSFVNMER DLASGLIGPL LICYKESVDQ RGNQIMSDKR NVILFSVFDE

751 NRSWYLTENI QRFLPNPAGV QLEDPEFQAS NIMHSINGYV FDSLQLSVCL

801 HEVAYWYILS IGAQTDFLSV FFSGYTFKHK MVYEDTLTLF PFSGETVFMS

851 MENPGLWILG CHNSDFRNRG MTALLKVSSC DKNTGDYYED SYEDISAYLL

901 SKNNAIEPRS FSQNGAPGTS ESATPESGPG SEPATSGSET PGTSESATPE

951 SGPGSEPATS GSETPGTSES ATPESGPGTS TEPSEGSAPG SPAGSPTSTE

1001 EGTSESATPE SGPGSEPATS GSETPGTSES ATPESGPGSP AGSPTSTEEG

1051 SPAGSPTSTE EGTSTEPSEG SAPGTSESAT PESGPGTSES ATPESGPGTS

1101 ESATPESGPG SEPATSGSET PGSEPATSGS ETPGSPAGSP TSTEEGTSTE

-continued

1151 PSEGSAPGTS TEPSEGSAPG SEPATSGSET PGTSESATPE SGPGTSTEPS

1201 EGSAPASSPP VLKRHQAEIT RTTLQSDQEE IDYDDTISVE MKKEDFDIYD

1251 EDENQSPRSF QKKTRHYFIA AVERLWDYGM SSSPHVLRNR AQSGSVPQFK

1301 KVVFQEFTDG SFTQPLYRGE LNEHLGLLGP YIRAEVEDNI MVTFRNQASR

1351 PYSFYSSLIS YEEDQRQGAE PRKNFVKPNE TKTYFWKVQH HMAPTKDEFD

1401 CKAWAYFSDV DLEKDVHSGL IGPLLVCHTN TLNPAHGRQV TVQEFALFFT

1451 IFDETKSWYF TENMERNCRA PCNIQMEDPT FKENYRFHAI NGYIMDTLPG

1501 LVMAQDQRIR WYLLSMGSNE NIHSIHFSGH VFTVRKKEEY KMALYNLYPG

1551 VFETVEMLPS KAGIWRVECL IGEHLHAGMS TLFLVYSNKC QTPLGMASGH

1601 IRDFQITASG QYGQWAPKLA RLHYSGSINA WSTKEPFSWI KVDLLAPMII

1651 HGIKTQGARQ KFSSLYISQF IIMYSLDGKK WQTYRGNSTG TLMVFFGNVD

1701 SSGIKHNIFN PPIIARYIRL HPTHYSIRST LPMELMGCDL NSCSMPLGME

1751 SKAISDAQIT ASSYFTNMFA TWSPSKARLH LQGRSNAWRP QVNNPKEWLQ

1801 VDFQKTMKVT GVTTQGVKSL LTSMYVKEFL ISSSQDGHQW TLFFQNGKVK

1851 VFQGNQDSFT PVVNSLDPPL LTRYLRIHPQ SWVHQIALRM EVLGCEAQDL

1901 YDKTHTCPPC PAPELLGGPS VFLFPPKPKD TLMISRTPEV TCVVVDVSHE

1951 DPEVKFNWYV DGVEVHNAKT KPREEQYNST YRVVSVLTVL HQDWLNGKEY

2001 KCKVSNKALP APIEKTISKA KGQPREPQVY TLPPSRDELT KNQVSLTCLV

2051 KGFYPSDIAV EWESNGQPEN NYKTTPPVLD SDGSFFLYSK LTVDKSRWQQ

2101 GNVFSCSVMH EALHNHYTQK SLSLSPGK*

FVIII 205 protein sequence (single chain FVIIIFc with two AE XTENs; one 288AE XTEN in B-domain and one 144 AE XTEN at amino acid 18) (SEQ ID NO: 79)

1 MQIELSTCFF LCLLRFCFSA TRRYYLGAVE LSWDYMQGAP TSESATPESG

51 PGSEPATSGS ETPGTSESAT PESGPGSEPA TSGSETPGTS ESATPESGPG

101 TSTEPSEGSA PGSPAGSPTS TEEGTSESAT PESGPGSEPA TSGSETPGTS

151 ESATPESGPG SPAGSPTSTE EGSPAGSPTS TEEGASSSDL GELPVDARFP

201 PRVPKSFPFN TSVVYKKTLF VEFTDHLFNI AKPRPPWMGL LGPTIQAEVY

251 DTVVITLKNM ASHPVSLHAV GVSYWKASEG AEYDDQTSQR EKEDDKVFPG

301 GSHTYVWQVL KENGPMASDP LCLTYSYLSH VDLVKDLNSG LIGALLVCRE

351 GSLAKEKTQT LHKFILLFAV FDEGKSWHSE TKNSLMQDRD AASARAWPKM

401 HTVNGYVNRS LPGLIGCHRK SVYWHVIGMG TTPEVHSIFL EGHTFLVRNH

451 RQASLEISPI TFLTAQTLLM DLGQFLLFCH ISSHQHDGME AYVKVDSCPE

501 EPQLRMKNNE EAEDYDDDLT DSEMDVVRFD DDNSPSFIQI RSVAKKHPKT

551 WVHYIAAEEE DWDYAPLVLA PDDRSYKSQY LNNGPQRIGR KYKKVRFMAY

601 TDETFKTREA IQHESGILGP LLYGEVGDTL LIIFKNQASR PYNIYPHGIT

651 DVRPLYSRRL PKGVKHLKDF PILPGEIFKY KWTVTVEDGP TKSDPRCLTR

701 YYSSFVNMER DLASGLIGPL LICYKESVDQ RGNQIMSDKR NVILFSVFDE

751 NRSWYLTENI QRFLPNPAGV QLEDPEFQAS NIMHSINGYV FDSLQLSVCL

801 HEVAYWYILS IGAQTDFLSV FFSGYTFKHK MVYEDTLTLF PFSGETVFMS

851 MENPGLWILG CHNSDFRNRG MTALLKVSSC DKNTGDYYED SYEDISAYLL

901 SKNNAIEPRS FSQNGAPGTS ESATPESGPG SEPATSGSET PGTSESATPE

951 SGPGSEPATS GSETPGTSES ATPESGPGTS TEPSEGSAPG SPAGSPTSTE

1001 EGTSESATPE SGPGSEPATS GSETPGTSES ATPESGPGSP AGSPTSTEEG

1051 SPAGSPTSTE EGTSTEPSEG SAPGTSESAT PESGPGTSES ATPESGPGTS

1101 ESATPESGPG SEPATSGSET PGSEPATSGS ETPGSPAGSP TSTEEGTSTE

1151 PSEGSAPGTS TEPSEGSAPG SEPATSGSET PGTSESATPE SGPGTSTEPS

1201 EGSAPASSPP VLKRHQAEIT RTTLQSDQEE IDYDDTISVE MKKEDFDIYD

1251 EDENQSPRSF QKKTRHYFIA AVERLWDYGM SSSPHVLRNR AQSGSVPQFK

1301 KVVFQEFTDG SFTQPLYRGE LNEHLGLLGP YIRAEVEDNI MVTFRNQASR

1351 PYSFYSSLIS YEEDQRQGAE PRKNFVKPNE TKTYFWKVQH HMAPTKDEFD

1401 CKAWAYFSDV DLEKDVHSGL IGPLLVCHTN TLNPAHGRQV TVQEFALFFT

1451 IFDETKSWYF TENMERNCRA PCNIQMEDPT FKENYRFHAI NGYIMDTLPG

1501 LVMAQDQRIR WYLLSMGSNE NIHSIHFSGH VFTVRKKEEY KMALYNLYPG

1551 VFETVEMLPS KAGIWRVECL IGEHLHAGMS TLFLVYSNKC QTPLGMASGH

1601 IRDFQITASG QYGQWAPKLA RLHYSGSINA WSTKEPFSWI KVDLLAPMII

1651 HGIKTQGARQ KFSSLYISQF IIMYSLDGKK WQTYRGNSTG TLMVFFGNVD

1701 SSGIKHNIFN PPIIARYIRL HPTHYSIRST LPMELMGCDL NSCSMPLGME

1751 SKAISDAQIT ASSYFTNMFA TWSPSKARLH LQGRSNAWRP QVNNPKEWLQ

1801 VDFQKTMKVT GVTTQGVKSL LTSMYVKEFL ISSSQDGHQW TLFFQNGKVK

1851 VFQGNQDSFT PVVNSLDPPL LTRYLRIHPQ SWVHQIALRM EVLGCEAQDL

1901 YDKTHTCPPC PAPELLGGPS VFLFPPKPKD TLMISRTPEV TCVVVDVSHE

1951 DPEVKFNWYV DGVEVHNAKT KPREEQYNST YRVVSVLTVL HQDWLNGKEY

2001 KCKVSNKALP APIEKTISKA KGQPREPQVY TLPPSRDELT KNQVSLTCLV

2051 KGFYPSDIAV EWESNGQPEN NYKTTPPVLD SDGSFFLYSK LTVDKSRWQQ

2101 GNVFSCSVMH EALHNHYTQK SLSLSPGK* pSYN FVIII 266 protein sequence (FVIII Fc with 42 AE-XTEN at amino acid 18 and 288 AE XTEN in B-domain) SEQ ID NO: 80)

1 MQIELSTCFF LCLLRFCFSA TRRYYLGAVE LSWDYMQGAP GSPAGSPTST

51 EEGTSESATP ESGPGSEPAT SGSETPASSS DLGELPVDAR FPPRVPKSFP

101 FNTSVVYKKT LFVEFTDHLF NIAKPRPPWM GLLGPTIQAE VYDTVVITLK

151 NMASHPVSLH AVGVSYWKAS EGAEYDDQTS QREKEDDKVF PGGSHTYVWQ

201 VLKENGPMAS DPLCLTYSYL SHVDLVKDLN SGLIGALLVC REGSLAKEKT

251 QTLHKFILLF AVFDEGKSWH SETKNSLMQD RDAASARAWP KMHTVNGYVN

301 RSLPGLIGCH RKSVYWHVIG MGTTPEVHSI FLEGHTFLVR NHRQASLEIS

351 PITFLTAQTL LMDLGQFLLF CHISSHQHDG MEAYVKVDSC PEEPQLRMKN

401 NEEAEDYDDD LTDSEMDVVR FDDDNSPSFI QIRSVAKKHP KTWVHYIAAE

451 EEDWDYAPLV LAPDDRSYKS QYLNNGPQRI GRKYKKVRFM AYTDETFKTR

501 EAIQHESGIL GPLLYGEVGD TLLIIFKNQA SRPYNIYPHG ITDVRPLYSR

551 RLPKGVKHLK DFPILPGEIF KYKWTVTVED GPTKSDPRCL TRYYSSFVNM

601 ERDLASGLIG PLLICYKESV DQRGNQIMSD KRNVILFSVF DENRSWYLTE

-continued

651 NIQRFLPNPA GVQLEDPEFQ ASNIMHSING YVFDSLQLSV CLHEVAYWYI

701 LSIGAQTDFL SVFFSGYTFK HKMVYEDTLT LFPFSGETVF MSMENPGLWI

751 LGCHNSDFRN RGMTALLKVS SCDKNTGDYY EDSYEDISAY LLSKNNAIEP

801 RSFSQNGAPG TSESATPESG PGSEPATSGS ETPGTSESAT PESGPGSEPA

851 TSGSETPGTS ESATPESGPG TSTEPSEGSA PGSPAGSPTS TEEGTSESAT

901 PESGPGSEPA TSGSETPGTS ESATPESGPG SPAGSPTSTE EGSPAGSPTS

951 TEEGTSTEPS EGSAPGTSES ATPESGPGTS ESATPESGPG TSESATPESG

1001 PGSEPATSGS ETPGSEPATS GSETPGSPAG SPTSTEEGTS TEPSEGSAPG

1051 TSTEPSEGSA PGSEPATSGS ETPGTSESAT PESGPGTSTE PSEGSAPASS

1101 PPVLKRHQAE ITRTTLQSDQ EEIDYDDTIS VEMKKEDFDI YDEDENQSPR

1151 SFQKKTRHYF IAAVERLWDY GMSSSPHVLR NRAQSGSVPQ FKKVVFQEFT

1201 DGSFTQPLYR GELNEHLGLL GPYIRAEVED NIMVTFRNQA SRPYSFYSSL

1251 ISYEEDQRQG AEPRKNFVKP NETKTYFWKV QHHMAPTKDE FDCKAWAYFS

1301 DVDLEKDVHS GLIGPLLVCH TNTLNPAHGR QVTVQEFALF FTIFDETKSW

1351 YFTENMERNC RAPCNIQMED PTFKENYRFH AINGYIMDTL PGLVMAQDQR

1401 IRWYLLSMGS NENIHSIHFS GHVFTVRKKE EYKMALYNLY PGVFETVEML

1451 PSKAGIWRVE CLIGEHLHAG MSTLFLVYSN KCQTPLGMAS GHIRDFQITA

1501 SGQYGQWAPK LARLHYSGSI NAWSTKEPFS WIKVDLLAPM IIHGIKTQGA

1551 RQKFSSLYIS QFIIMYSLDG KKWQTYRGNS TGTLMVFFGN VDSSGIKHNI

1601 FNPPIIARYI RLHPTHYSIR STLRMELMGC DLNSCSMPLG MESKAISDAQ

1651 ITASSYFTNM FATWSPSKAR LHLQGRSNAW RPQVNNPKEW LQVDFQKTMK

1701 VTGVTTQGVK SLLTSMYVKE FLISSSQDGH QWTLFFQNGK VKVFQGNQDS

1751 FTPVVNSLDP PLLTRYLRIH PQSWVHQIAL RMEVLGCEAQ DLYDKTHTCP

1801 PCPAPELLGG PSVFLFPPKP KDTLMISRTP EVTCVVVDVS HEDPEVKFNW

1851 YVDGVEVHNA KTKPREEQYN STYRVVSVLT VLHQDWLNGK EYKCKVSNKA

1901 LPAPIEKTIS KAKGQPREPQ VYTLPPSRDE LTKNQVSLTC LVKGFYPSDI

1951 AVEWESNGQP ENNYKTTPPV LDSDGSFFLY SKLTVDKSRW QQGNVFSCSV

2001 MHEALHNHYT QKSLSLSPGK * pSYN FVIII 267 protein sequence (FVIII Fc with 72 AE-XTEN at amino acid 18 and 288 AE XTEN in B-domain) SEQ ID NO: 81)

1 MQIELSTCFF LCLLRFCFSA TRRYYLGAVE LSWDYMQGAP TSESATPESG

51 PGSEPATSGS ETPGTSESAT PESGPGSEPA TSGSETPGTS ESATPESGPG

101 TSTEPSEGSA PGASSSDLGE LPVDARFPPR VPKSFPFNTS VVYKKTLFVE

151 FTDHLFNIAK PRPPWMGLLG PTIQAEVYDT VVITLKNMAS HPVSLHAVGV

201 SYWKASEGAE YDDQTSQREK EDDKVFPGGS HTYVWQVLKE NGPMASDPLC

251 LTYSYLSHVD LVKDLNSGLI GALLVCREGS LAKEKTQTLH KFILLFAVFD

301 EGKSWHSETK NSLMQDRDAA SARAWPKMHT VNGYVNRSLP GLIGCHRKSV

351 YWHVIGMGTT PEVHSIFLEG HTFLVRNHRQ ASLEISPITF LTAQTLLMDL

401 GQFLLFCHIS SHQHDGMEAY VKVDSCPEEP QLRMKNNEEA EDYDDDLTDS

451 EMDVVRFDDD NSPSFIQIRS VAKKHPKTWV HYIAAEEEDW DYAPLVLAPD

501 DRSYKSQYLN NGPQRIGRKY KKVRFMAYTD ETFKTREAIQ HESGILGPLL

-continued

```
 551   YGEVGDTLLI IFKNQASRPY NIYPHGITDV RPLYSRRLPK GVKHLKDFPI

 601   LPGEIFKYKW TVTVEDGPTK SDPRCLTRYY SSFVNMERDL ASGLIGPLLI

 651   CYKESVDQRG NQIMSDKRNV ILFSVFDENR SWYLTENIQR FLPNPAGVQL

 701   EDPEFQASNI MHSINGYVFD SLQLSVCLHE VAYWYILSIG AQTDFLSVFF

 751   SGYTFKHKMV YEDTLTLFPF SGETVFMSME NPGLWILGCH NSDFRNRGMT

 801   ALLKVSSCDK NTGDYYEDSY EDISAYLLSK NNAIEPRSFS QNGAPGTSES

 851   ATPESGPGSE PATSGSETPG TSESATPESG PGSEPATSGS ETPGTSESAT

 901   PESGPGTSTE PSEGSAPGSP AGSPTSTEEG TSESATPESG PGSEPATSGS

 951   ETPGTSESAT PESGPGSPAG SPTSTEEGSP AGSPTSTEEG TSTEPSEGSA

1001   PGTSESATPE SGPGTSESAT PESGPGTSES ATPESGPGSE PATSGSETPG

1051   SEPATSGSET PGSPAGSPTS TEEGTSTEPS EGSAPGTSTE PSEGSAPGSE

1101   PATSGSETPG TSESATPESG PGTSTEPSEG SAPASSPPVL KRHQAEITRT

1151   TLQSDQEEID YDDTISVEMK KEDFDIYDED ENQSPRSFQK KTRHYFIAAV

1201   ERLWDYGMSS SPHVLRNRAQ SGSVPQFKKV VFQEFTDGSF TQPLYRGELN

1251   EHLGLLGPYI RAEVEDNIMV TFRNQASRPY SFYSSLISYE EDQRQGAEPR

1301   KNFVKPNETK TYFWKVQHHM APTKDEFDCK AWAYFSDVDL EKDVHSGLIG

1351   PLLVCHTNTL NPAHGRQVTV QEFALFFTIF DETKSWYFTE NMERNCRAPC

1401   NIQMEDPTFK ENYRFHAING YIMDTLPGLV MAQDQRIRWY LLSMGSNENI

1451   HSIHFSGHVF TVRKKEEYKM ALYNLYPGVF ETVEMLPSKA GIWRVECLIG

1501   EHLHAGMSTL FLVYSNKCQT PLGMASGHIR DFQITASGQY GQWAPKLARL

1551   HYSGSINAWS TKEPFSWIKV DLLAPMIIHG IKTQGARQKF SSLYISQFII

1601   MYSLDGKKWQ TYRGNSTGTL MVFFGNVDSS GIKHNIFNPP IIARYIRLHP

1651   THYSIRSTLR MELMGCDLNS CSMPLGMESK AISDAQITAS SYFTNMFATW

1701   SPSKARLHLQ GRSNAWRPQV NNPKEWLQVD FQKTMKVTGV TTQGVKSLLT

1751   SMYVKEFLIS SSQDGHQWTL FFQNGKVKVF QGNQDSFTPV VNSLDPPLLT

1801   RYLRIHPQSW VHQIALRMEV LGCEAQDLYD KTHTCPPCPA PELLGGPSVF

1851   LFPPKPKDTL MISRTPEVTC VVVDVSHEDP EVKFNWYVDG VEVHNAKTKP

1901   REEQYNSTYR VVSVLTVLHQ DWLNGKEYKC KVSNKALPAP IEKTISKAKG

1951   QPREPQVYTL PPSRDELTKN QVSLTCLVKG FYPSDIAVEW ESNGQPENNY

2001   KTTPPVLDSD GSFFLYSKLT VDKSRWQQGN VFSCSVMHEA LHNHYTQKSL

2051   SLSPGK*
```

pSYN FVIII 268 protein sequence (FVIII Fc with 144 AE-XTEN at amino acid 18) SEQ ID NO: 82)

```
   1   MQIELSTCFF LCLLRFCFSA TRRYYLGAVE LSWDYMQGAP TSESATPESG

  51   PGSEPATSGS ETPGTSESAT PESGPGSEPA TSGSETPGTS ESATPESGPG

 101   TSTEPSEGSA PGSPAGSPTS TEEGTSESAT PESGPGSEPA TSGSETPGTS

 151   ESATPESGPG SPAGSPTSTE EGSPAGSPTS TEEGASSSDL GELPVDARFP

 201   PRVPKSFPFN TSVVYKKTLF VEFTDHLFNI AKPRPPWMGL LGPTIQAEVY

 251   DTVVITLKNM ASHPVSLHAV GVSYWKASEG AEYDDQTSQR EKEDDKVFPG

 301   GSHTYVWQVL KENGPMASDP LCLTYSYLSH VDLVKDLNSG LIGALLVCRE
```

-continued

```
 351 GSLAKEKTQT LHKFILLFAV FDEGKSWHSE TKNSLMQDRD AASARAWPKM

 401 HTVNGYVNRS LPGLIGCHRK SVYWHVIGMG TTPEVHSIFL EGHTFLVRNH

 451 RQASLEISPI TFLTAQTLLM DLGQFLLFCH ISSHQHDGME AYVKVDSCPE

 501 EPQLRMKNNE EAEDYDDDLT DSEMDVVRFD DDNSPSFIQI RSVAKKHPKT

 551 WVHYIAAEEE DWDYAPLVLA PDDRSYKSQY LNNGPQRIGR KYKKVRFMAY

 601 TDETFKTREA IQHESGILGP LLYGEVGDTL LIIFKNQASR PYNIYPHGIT

 651 DVRPLYSRRL PKGVKHLKDF PILPGEIFKY KWTVTVEDGP TKSDPRCLTR

 701 YYSSFVNMER DLASGLIGPL LICYKESVDQ RGNQIMSDKR NVILFSVFDE

 751 NRSWYLTENI QRFLPNPAGV QLEDPEFQAS NIMHSINGYV FDSLQLSVCL

 801 HEVAYWYILS IGAQTDFLSV FFSGYTFKHK MVYEDTLTLF PFSGETVFMS

 851 MENPGLWILG CHNSDFRNRG MTALLKVSSC DKNTGDYYED SYEDISAYLL

 901 SKNNAIEPRS FSQNPPVLKR HQAEITRTTL QSDQEEIDYD DTISVEMKKE

 951 DFDIYDEDEN QSPRSFQKKT RHYFIAAVER LWDYGMSSSP HVLRNRAQSG

1001 SVPQFKKVVF QEFTDGSFTQ PLYRGELNEH LGLLGPYIRA EVEDNIMVTF

1051 RNQASRPYSF YSSLISYEED QRQGAEPRKN FVKPNETKTY FWKVQHHMAP

1101 TKDEFDCKAW AYFSDVDLEK DVHSGLIGPL LVCHTNTLNP AHGRQVTVQE

1151 FALFFTIFDE TKSWYFTENM ERNCRAPCNI QMEDPTFKEN YRFHAINGYI

1201 MDTLPGLVMA QDQRIRWYLL SMGSNENIHS IHFSGHVFTV RKKEEYKMAL

1251 YNLYPGVFET VEMLPSKAGI WRVECLIGEH LHAGMSTLFL VYSNKCQTPL

1301 GMASGHIRDF QITASGQYGQ WAPKLARLHY SGSINAWSTK EPFSWIKVDL

1351 LAPMIIHGIK TQGARQKFSS LYISQFIIMY SLDGKKWQTY RGNSTGTLMV

1401 FFGNVDSSGI KHNIFNPPII ARYIRLHPTH YSIRSTLRME LMGCDLNSCS

1451 MPLGMESKAI SDAQITASSY FTNMFATWSP SKARLHLQGR SNAWRPQVNN

1501 PKEWLQVDFQ KTMKVTGVTT QGVKSLLTSM YVKEFLISSS QDGHQWTLFF

1551 QNGKVKVFQG NQDSFTPVVN SLDPPLLTRY LRIHPQSWVH QIALRMEVLG

1601 CEAQDLYDKT HTCPPCPAPE LLGGPSVFLF PPKPKDTLMI SRTPEVTCVV

1651 VDVSHEDPEV KFNWYVDGVE VHNAKTKPRE EQYNSTYRVV SVLTVLHQDW

1701 LNGKEYKCKV SNKALPAPIE KTISKAKGQP REPQVYTLPP SRDELTKNQV

1751 SLTCLVKGFY PSDIAVEWES NGQPENNYKT TPPVLDSDGS FFLYSKLTVD

1801 KSRWQQGNVF SCSVMHEALH NHYTQKSLSL SPGK*
```

pSYN FVIII 269 protein sequence (FVIII Fc with 72 AE-XTEN at amino acid 18) SEQ ID NO: 83)

```
   1 MQIELSTCFF LCLLRFCFSA TRRYYLGAVE LSWDYMQGAP TSESATPESG

  51 PGSEPATSGS ETPGTSESAT PESGPGSEPA TSGSETPGTS ESATPESGPG

 101 TSTEPSEGSA PGASSSDLGE LPVDARFPPR VPKSFPFNTS VVYKKTLFVE

 151 FTDHLFNIAK PRPPWMGLLG PTIQAEVYDT VVITLKNMAS HPVSLHAVGV

 201 SYWKASEGAE YDDQTSQREK EDDKVFPGGS HTYVWQVLKE NGPMASDPLC

 251 LTYSYLSHVD LVKDLNSGLI GALLVCREGS LAKEKTQTLH KFILLFAVFD

 301 EGKSWHSETK NSLMQDRDAA SARAWPKMHT VNGYVNRSLP GLIGCHRKSV

 351 YWHVIGMGTT PEVHSIFLEG HTFLVRNHRQ ASLEISPITF LTAQTLLMDL

 401 GQFLLFCHIS SHQHDGMEAY VKVDSCPEEP QLRMKNNEEA EDYDDDLTDS
```

-continued

```
 451   EMDVVRFDDD NSPSFIQIRS VAKKHPKTWV HYIAAEEEDW DYAPLVLAPD

 501   DRSYKSQYLN NGPQRIGRKY KKVRFMAYTD ETFKTREAIQ HESGILGPLL

 551   YGEVGDTLLI IFKNQASRPY NIYPHGITDV RPLYSRRLPK GVKHLKDFPI

 601   LPGEIFKYKW TVTVEDGPTK SDPRCLTRYY SSFVNMERDL ASGLIGPLLI

 651   CYKESVDQRG NQIMSDKRNV ILFSVFDENR SWYLTENIQR FLPNPAGVQL

 701   EDPEFQASNI MHSINGYVFD SLQLSVCLHE VAYWYILSIG AQTDFLSVFF

 751   SGYTFKHKMV YEDTLTLFPF SGETVFMSME NPGLWILGCH NSDFRNRGMT

 801   ALLKVSSCDK NTGDYYEDSY EDISAYLLSK NNAIEPRSFS QNPPVLKRHQ

 851   AEITRTTLQS DQEEIDYDDT ISVEMKKEDF DIYDEDENQS PRSFQKKTRH

 901   YFIAAVERLW DYGMSSSPHV LRNRAQSGSV PQFKKVVFQE FTDGSFTQPL

 951   YRGELNEHLG LLGPYIRAEV EDNIMVTFRN QASRPYSFYS SLISYEEDQR

1001   QGAEPRKNFV KPNETKTYFW KVQHHMAPTK DEFDCKAWAY FSDVDLEKDV

1051   HSGLIGPLLV CHTNTLNPAH GRQVTVQEFA LFFTIFDETK SWYFTENMER

1101   NCRAPCNIQM EDPTFKENYR FHAINGYIMD TLPGLVMAQD QRIRWYLLSM

1151   GSNENIHSIH FSGHVFTVRK KEEYKMALYN LYPGVFETVE MLPSKAGIWR

1201   VECLIGEHLH AGMSTLFLVY SNKCQTPLGM ASGHIRDFQI TASGQYGQWA

1251   PKLARLHYSG SINAWSTKEP FSWIKVDLLA PMIIHGIKTQ GARQKFSSLY

1301   ISQFIIMYSL DGKKWQTYRG NSTGTLMVFF GNVDSSGIKH NIFNPPIIAR

1351   YIRLHPTHYS IRSTLRMELM GCDLNSCSMP LGMESKAISD AQITASSYFT

1401   NMFATWSPSK ARLHLQGRSN AWRPQVNNPK EWLQVDFQKT MKVTGVTTQG

1451   VKSLLTSMYV KEFLISSSQD GHQWTLFFQN GKVKVFQGNQ DSFTPVVNSL

1501   DPPLLTRYLR IHPQSWVHQI ALRMEVLGCE AQDLYDKTHT CPPCPAPELL

1551   GGPSVFLFPP KPKDTLMISR TPEVTCVVVD VSHEDPEVKF NWYVDGVEVH

1601   NAKTKPREEQ YNSTYRVVSV LTVLHQDWLN GKEYKCKVSN KALPAPIEKT

1651   ISKAKGQPRE PQVYTLPPSR DELTKNQVSL TCLVKGFYPS DIAVEWESNG

1701   QPENNYKTTP PVLDSDGSFF LYSKLTVDKS RWQQGNVFSC SVMHEALHNH

1751   YTQKSLSLSP GK*
```

pSYNFVIII 271 protein sequence (FVIII Fc with 42 AE-XTEN at amino acid 18) SEQ ID NO: 84)

```
   1   MQIELSTCFF LCLLRFCFSA TRRYYLGAVE LSWDYMQGAP GSPAGSPTST

  51   EEGTSESATP ESGPGSEPAT SGSETPASSS DLGELPVDAR FPPRVPKSFP

 101   FNTSVVYKKT LFVEFTDHLF NIAKPRPPWM GLLGPTIQAE VYDTVVITLK

 151   NMASHPVSLH AVGVSYWKAS EGAEYDDQTS QREKEDDKVF PGGSHTYVWQ

 201   VLKENGPMAS DPLCLTYSYL SHVDLVKDLN SGLIGALLVC REGSLAKEKT

 251   QTLHKFILLF AVFDEGKSWH SETKNSLMQD RDAASARAWP KMHTVNGYVN

 301   RSLPGLIGCH RKSVYWHVIG MGTTPEVHSI FLEGHTFLVR NHRQASLEIS

 351   PITFLTAQTL LMDLGQFLLF CHISSHQHDG MEAYVKVDSC PEEPQLRMKN

 401   NEEAEDYDDD LTDSEMDVVR FDDDNSPSFI QIRSVAKKHP KTWVHYIAAE

 451   EEDWDYAPLV LAPDDRSYKS QYLNNGPQRI GRKYKKVRFM AYTDETFKTR

 501   EAIQHESGIL GPLLYGEVGD TLLIIFKNQA SRPYNIYPHG ITDVRPLYSR
```

-continued

551 RLPKGVKHLK DFPILPGEIF KYKWTVTVED GPTKSDPRCL TRYYSSFVNM

601 ERDLASGLIG PLLICYKESV DQRGNQIMSD KRNVILFSVF DENRSWYLTE

651 NIQRFLPNPA GVQLEDPEFQ ASNIMHSING YVFDSLQLSV CLHEVAYWYI

701 LSIGAQTDFL SVFFSGYTFK HKMVYEDTLT LFPFSGETVF MSMENPGLWI

751 LGCHNSDFRN RGMTALLKVS SCDKNTGDYY EDSYEDISAY LLSKNNAIEP

801 RSFSQNPPVL KRHQAEITRT TLQSDQEEID YDDTISVEMK KEDFDIYDED

851 ENQSPRSFQK KTRHYFIAAV ERLWDYGMSS SPHVLRNRAQ SGSVPQFKKV

901 VFQEFTDGSF TQPLYRGELN EHLGLLGPYI RAEVEDNIMV TFRNQASRPY

951 SFYSSLISYE EDQRQGAEPR KNFVKPNETK TYFWKVQHHM APTKDEFDCK

1001 AWAYFSDVDL EKDVHSGLIG PLLVCHTNTL NPAHGRQVTV QEFALFFTIF

1051 DETKSWYFTE NMERNCRAPC NIQMEDPTFK ENYRFHAING YIMDTLPGLV

1101 MAQDQRIRWY LLSMGSNENI HSIHFSGHVF TVRKKEEYKM ALYNLYPGVF

1151 ETVEMLPSKA GIWRVECLIG EHLHAGMSTL FLVYSNKCQT PLGMASGHIR

1201 DFQITASGQY GQWAPKLARL HYSGSINAWS TKEPFSWIKV DLLAPMIIHG

1251 IKTQGARQKF SSLYISQFII MYSLDGKKWQ TYRGNSTGTL MVFFGNVDSS

1301 GIKHNIFNPP IIARYIRLHP THYSIRSTLR MELMGCDLNS CSMPLGMESK

1351 AISDAQITAS SYFTNMFATW SPSKARLHLQ GRSNAWRPQV NNPKEWLQVD

1401 FQKTMKVTGV TTQGVKSLLT SMYVKEFLIS SSQDGHQWTL FFQNGKVKVF

1451 QGNQDSFTPV VNSLDPPLLT RYLRIHPQSW VHQIALRMEV LGCEAQDLYD

1501 KTHTCPPCPA PELLGGPSVF LFPPKPKDTL MISRTPEVTC VVVDVSHEDP

1551 EVKFNWYVDG VEVHNAKTKP REEQYNSTYR VVSVLTVLHQ DWLNGKEYKC

1601 KVSNKALPAP IEKTISKAKG QPREPQVYTL PPSRDELTKN QVSLTCLVKG

1651 FYPSDIAVEW ESNGQPENNY KTTPPVLDSD GSFFLYSKLT VDKSRWQQGN

1701 VFSCSVMHEA LHNHYTQKSL SLSPGK* pSYN FVIII protein sequence 272 (FVIII with 144 AE XTEN at amino acid 18 and 244 AE XTEN in B-domain-no Fc) SEQ ID NO: 85)

1 MQIELSTCFF LCLLRFCFSA TRRYYLGAVE LSWDYMQGAP TSESATPESG

51 PGSEPATSGS ETPGTSESAT PESGPGSEPA TSGSETPGTS ESATPESGPG

101 TSTEPSEGSA PGSPAGSPTS TEEGTSESAT PESGPGSEPA TSGSETPGTS

151 ESATPESGPG SPAGSPTSTE EGSPAGSPTS TEEGASSSDL GELPVDARFP

201 PRVPKSFPFN TSVVYKKTLF VEFTDHLFNI AKPRPPWMGL LGPTIQAEVY

251 DTVVITLKNM ASHPVSLHAV GVSYWKASEG AEYDDQTSQR EKEDDKVFPG

301 GSHTYVWQVL KENGPMASDP LCLTYSYLSH VDLVKDLNSG LIGALLVCRE

351 GSLAKEKTQT LHKFILLFAV FDEGKSWHSE TKNSLMQDRD AASARAWPKM

401 HTVNGYVNRS LPGLIGCHRK SVYWHVIGMG TTPEVHSIFL EGHTFLVRNH

451 RQASLEISPI TFLTAQTLLM DLGQFLLFCH ISSHQHDGME AYVKVDSCPE

501 EPQLRMKNNE EAEDYDDDLT DSEMDVVRFD DDNSPSFIQI RSVAKKHPKT

551 WVHYIAAEEE DWDYAPLVLA PDDRSYKSQY LNNGPQRIGR KYKKVRFMAY

601 TDETFKTREA IQHESGILGP LLYGEVGDTL LIIFKNQASR PYNIYPHGIT

651 DVRPLYSRRL PKGVKHLKDF PILPGEIFKY KWTVTVEDGP TKSDPRCLTR

701 YYSSFVNMER DLASGLIGPL LICYKESVDQ RGNQIMSDKR NVILFSVFDE

-continued

```
 751   NRSWYLTENI QRFLPNPAGV QLEDPEFQAS NIMHSINGYV FDSLQLSVCL
 801   HEVAYWYILS IGAQTDFLSV FFSGYTFKHK MVYEDTLTLF PFSGETVFMS
 851   MENPGLWILG CHNSDFRNRG MTALLKVSSC DKNTGDYYED SYEDISAYLL
 901   SKNNAIEPRS FSQNGAPGTS ESATPESGPG SEPATSGSET PGTSESATPE
 951   SGPGSEPATS GSETPGTSES ATPESGPGTS TEPSEGSAPG SPAGSPTSTE
1001   EGTSESATPE SGPGSEPATS GSETPGTSES ATPESGPGSP AGSPTSTEEG
1051   SPAGSPTSTE EGTSTEPSEG SAPGTSESAT PESGPGTSES ATPESGPGTS
1101   ESATPESGPG SEPATSGSET PGSEPATSGS ETPGSPAGSP TSTEEGTSTE
1151   PSEGSAPGTS TEPSEGSAPG SEPATSGSET PGTSESATPE SGPGTSTEPS
1201   EGSAPASSPP VLKRHQAEIT RTTLQSDQEE IDYDDTISVE MKKEDFDIYD
1251   EDENQSPRSF QKKTRHYFIA AVERLWDYGM SSSPHVLRNR AQSGSVPQFK
1301   KVVFQEFTDG SFTQPLYRGE LNEHLGLLGP YIRAEVEDNI MVTFRNQASR
1351   PYSFYSSLIS YEEDQRQGAE PRKNFVKPNE TKTYFWKVQH HMAPTKDEFD
1401   CKAWAYFSDV DLEKDVHSGL IGPLLVCHTN TLNPAHGRQV TVQEFALFFT
1451   IFDETKSWYF TENMERNCRA PCNIQMEDPT FKENYRFHAI NGYIMDTLPG
1501   LVMAQDQRIR WYLLSMGSNE NIHSIHFSGH VFTVRKKEEY KMALYNLYPG
1551   VFETVEMLPS KAGIWRVECL IGEHLHAGMS TLFLVYSNKC QTPLGMASGH
1601   IRDFQITASG QYGQWAPKLA RLHYSGSINA WSTKEPFSWI KVDLLAPMII
1651   HGIKTQGARQ KFSSLYISQF IIMYSLDGKK WQTYRGNSTG TLMVFFGNVD
1701   SSGIKHNIFN PPIIARYIRL HPTHYSIRST LPMELMGCDL NSCSMPLGME
1751   SKAISDAQIT ASSYFTNMFA TWSPSKARLH LQGRSNAWRP QVNNPKEWLQ
1801   VDFQKTMKVT GVTTQGVKSL LTSMYVKEFL ISSSQDGHQW TLFFQNGKVK
1851   VFQGNQDSFT PVVNSLDPPL LTRYLRIHPQ SWVHQIALRM EVLGCEAQDL
1901   Y*
```

pSYN-FVIII-161 protein sequence (SEQ ID NO: 69) (FVIII sequence amino acid position 1-1457; underlined region represents Fc region; curvy underline represents cleavable linker in between first Fc and VWF fragment; double underlined region represents VWF fragment; bold region represents cleavable linker in between VWF fragment and Fc).

```
  1 MQIELSTCFF LCLLRFCFSA TRRYYLGAVE LSWDYMQSDL GELPVDARFP
 51 PRVPKSFPFN TSVVYKKTLF VEFTDHLFNI AKPRPPWMGL LGPTIQAEVY
101 DTVVITLKNM ASHPVSLHAV GVSYWKASEG AEYDDQTSQR EKEDDKVFPG
151 GSHTYVWQVL KENGPMASDP LCLTYSYLSH VDLVKDLNSG LIGALLVCRE
201 GSLAKEKTQT LHKFILLFAV FDEGKSWHSE TKNSLMQDRD AASARAWPKM
251 HTVNGYVNRS LPGLIGCHRK SVYWHVIGMG TTPEVHSIFL EGHTFLVRNH
301 RQASLEISPI TFLTAQTLLM DLGQFLLFCH ISSHQHDGME AYVKVDSCPE
351 EPQLRMKNNE EAEDYDDDLT DSEMDVVRFD DDNSPSFIQI RSVAKKHPKT
401 WVHYIAAEEE DWDYAPLVLA PDDRSYKSQY LNNGPQRIGR KYKKVRFMAY
```

-continued

451 TDETFKTREA IQHESGILGP LLYGEVGDTL LIIFKNQASR PYNIYPHGIT

501 DVRPLYSRRL PKGVKHLKDF PILPGEIFKY KWTVTVEDGP TKSDPRCLTR

551 YYSSFVNMER DLASGLIGPL LICYKESVDQ RGNQIMSDKR NVILFSVFDE

601 NRSWYLTENI QRFLPNPAGV QLEDPEFQAS NIMHSINGYV FDSLQLSVCL

651 HEVAYWYILS IGAQTDFLSV FFSGYTFKHK MVYEDTLTLF PFSGETVFMS

701 MENPGLWILG CHNSDFRNRG MTALLKVSSC DKNTGDYYED SYEDISAYLL

751 SKNNAIEPRS FSQNPPVLKR HQREITRTTL QSDQEEIDYD DTISVEMKKE

801 DFDIYDEDEN QSPRSFQKKT RHYFIAAVER LWDYGMSSSP HVLRNRAQSG

851 SVPQFKKVVF QEFTDGSFTQ PLYRGELNEH LGLLGPYIRA EVEDNIMVTF

901 RNQASRPYSF YSSLISYEED QRQGAEPRKN FVKPNETKTY FWKVQHHMAP

951 TKDEFDCKAW AYFSDVDLEK DVHSGLIGPL LVCHTNTLNP AHGRQVTVQE

1001 FALFFTIFDE TKSWYFTENM ERNCRAPCNI QMEDPTFKEN YRFHAINGYI

1051 MDTLPGLVMA QDQRIRWYLL SMGSNENIHS IHFSGHVFTV RKKEEYKMAL

1101 YNLYPGVFET VEMLPSKAGI WRVECLIGEH LHAGMSTLFL VYSNKCQTPL

1151 GMASGHIRDF QITASGQYGQ WAPKLARLHY SGSINAWSTK EPFSWIKVDL

1201 LAPMIIHGIK TQGARQKFSS LYISQFIIMY SLDGKKWQTY RGNSTGTLMV

1251 FFGNVDSSGI KHNIFNPPII ARYIRLHPTH YSIRSTLRME LMGCDLNSCS

1301 MPLGMESKAI SDAQITASSY FTNMFATWSP SKARLHLQGR SNAWRPQVNN

1351 PKEWLQVDFQ KTMKVTGVTT QGVKSLLTSM YVKEFLISSS QDGHQWTLFF

1401 QNGKVKVFQG NQDSFTPVVN SLDPPLLTRY LRIHPQSWVH QIALRMEVLG

1451 CEAQDLYDKT HTCPPCPAPE LLGGPSVFLF PPKPKDTLMI SRTPEVTCVV

1501 VDVSHEDPEV KFNWYVDGVE VHNAKTKPRE EQYNSTYRVV SVLTVLHQDW

1551 LNGKEYKCKV SNKALPAPIE KTISKAKGQP REPQVYTLPP SRDELTKNQV

1601 SLTCLVKGFY PSDIAVEWES NGQPENNYKT TPPVLDSDGS FFLYSKLTVD

1651 KSRWQQGNVF SCSVMHEALH NHYTQKSLSL SPGKRRRRSG GGGSGGGGSG

1701 GGGSGGGGSG GGGSGGGGSR KRRKRSLSCR PPMVKLVCPA DNLRAEGLEC

1751 TKTCQNYDLE CMSMGCVSGC LCPPGMVRHE NRCVALERCP CFHQGKEYAP

1801 GETVKIGCNT CVCRDRKWNC TDHVCDATCS TIGMAHYLTF DGLKYLFPGE

1851 CQYVLVQDYC GSNPGTFRIL VGNKGCSHPS VKCKKRVTIL VEGGEIELFD

1901 GEVNVKRPMK DETHFEVVES GRYIILLLGK ALSVVWDRHL SISVVLKQTY

1951 QEKVCGLCGN FDGIQNNDLT SSNLQVEEDP VDFGNSWKVS SQCADTRKVP

2001 LDSSPATCHN NIMKQTMVDS SCRILTSDVF QDCNKLVDPE PYLDVCIYDT

2051 CSCESIGDCA AFCDTIAAYA HVCAQHGKVV TWRTATLCPQ SCEERNLREN

2101 GYEAEWRYNS CAPACQVTCQ HPEPLACPVQ CVEGCHAHCP PGKILDELLQ

2151 TCVDPEDCPV CEVAGRRFAS GKKVTLNPSD PEHCQICHCD VVNLTCEACQ

2201 EPISGTSESA TPESGPGSEP ATSGSETPGT SESATPESGP GSEPATSGSE

2251 TPGTSESATP ESGPGTSTEP SEGSAPGSPA GSPTSTEEGT SESATPESGP

2301 GSEPATSGSE TPGTSESATP ESGPGSPAGS PTSTEEGSPA GSPTSTEEGT

2351 STEPSEGSAP GTSESATPES GPGTSESATP ESGPGTSESA TPESGPGSEP

2401 ATSGSETPGS EPATSGSETP GSPAGSPTST EEGTSTEPSE GSAPGTSTEP

2451 SEGSAPGSEP ATSGSETPGT SESATPESGP GTSTEPSEGS APDSGGGGSG

-continued

2501 GGGSGGGGSG GGGSGGGGSL VPRGSGGDKT HTCPPCPAPE LLGGPSVFLF

2551 PPKPKDTLMI SRTPEVTCVV VDVSHEDPEV KFNWYVDGVE VHNAKTKPRE

2601 EQYNSTYRVV SVLTVLHQDW LNGKEYKCKV SNKALPAPIE KTISKAKGQP

2651 REPQVYTLPP SRDELTKNQV SLTCLVKGFY PSDIAVEWES NGQPENNYKT

2701 TPPVLDSDGS FFLYSKLTVD KSRWQQGNVF SCSVMHEALH NHYTQKSLSL

2751 SPGK pSYN-FVIII-170 protein sequence (SEQ ID NO: 71)

1 SLSCRPPMVK LVCPADNLRA EGLECTKTCQ NYDLECMSMG CVSGCLCPPG

51 MVRHENRCVA LERCPCFHQG KEYAPGETVK IGCNTCVCRD RKWNCTDHVC

101 DATCSTIGMA HYLTFDGLKY LFPGECQYVL VQDYCGSNPG TFRILVGNKG

151 CSHPSVKCKK RVTILVEGGE IELFDGEVNV KRPMKDETHF EVVESGRYII

201 LLLGKALSVV WDRHLSISVV LKQTYQEKVC GLCGNFDGIQ NNDLTSSNLQ

251 VEEDPVDFGN SWKVSSQCAD TRKVPLDSSP ATCHNNIMKQ TMVDSSCRIL

301 TSDVFQDCNK LVDPEPYLDV CIYDTCSCES IGDCAAFCDT IAAYAHVCAQ

351 HGKVVTWRTA TLCPQSCEER NLRENGYEAE WRYNSCAPAC QVTCQHPEPL

401 ACPVQCVEGC HAHCPPGKIL DELLQTCVDP EDCPVCEVAG RRFASGKKVT

451 LNPSDPEHCQ ICHCDVVNLT CEACQEPISG TSESATPESG PGSEPATSGS

501 ETPGTSESAT PESGPGSEPA TSGSETPGTS ESATPESGPG TSTEPSEGSA

551 PGSPAGSPTS TEEGTSESAT PESGPGSEPA TSGSETPGTS ESATPESGPG

601 SPAGSPTSTE EGSPAGSPTS TEEGTSTEPS EGSAPGTSES ATPESGPGTS

651 ESATPESGPG TSESATPESG PGSEPATSGS ETPGSEPATS GSETPGSPAG

701 SPTSTEEGTS TEPSEGSAPG TSTEPSEGSA PGSEPATSGS ETPGTSESAT

751 PESGPGTSTE PSEGSAPDSG GGGSGGGGSG GGGSGGGGSG GGGSLVPRGS

801 GGASATRRYY LGAVELSWDY MQSDLGELPV DARFPPRVPK SFPFNTSVVY

851 KKTLFVEFTD HLFNIAKPRP PWMGLLGPTI QAEVYDTVVI TLKNMASHPV

901 SLHAVGVSYW KASEGAEYDD QTSQREKEDD KVFPGGSHTY VWQVLKENGP

951 MASDPLCLTY SYLSHVDLVK DLNSGLIGAL LVCREGSLAK EKTQTLHKFI

1001 LLFAVFDEGK SWHSETKNSL MQDRDAASAR AWPKMHTVNG YVNRSLPGLI

1051 GCHRKSVYWH VIGMGTTPEV HSIFLEGHTF LVRNHRQASL EISPITFLTA

1101 QTLLMDLGQF LLFCHISSHQ HDGMEAYVKV DSCPEEPQLR MKNNEEAEDY

1151 DDDLTDSEMD VVRFDDDNSP SFIQIRSVAK KHPKTWVHYI AAEEEDWDYA

1201 PLVLAPDDRS YKSQYLNNGP QRIGRKYKKV RFMAYTDETF KTREAIQHES

1251 GILGPLLYGE VGDTLLIIFK NQASRPYNIY PHGITDVRPL YSRRLPKGVK

1301 HLKDFPILPG EIFKYKWTVT VEDGPTKSDP RCLTRYYSSF VNMERDLASG

1351 LIGPLLICYK ESVDQRGNQI MSDKRNVILF SVFDENRSWY LTENIQRFLP

1401 NPAGVQLEDP EFQASNIMHS INGYVFDSLQ LSVCLHEVAY WYILSIGAQT

1451 DFLSVFFSGY TFKHKMVYED TLTLFPFSGE TVFMSMENPG LWILGCHNSD

1501 FRNRGMTALL KVSSCDKNTG DYYEDSYEDI SAYLLSKNNA IEPRSFSQNP

1551 PVLKRHQREI TRTTLQSDQE EIDYDDTISV EMKKEDFDIY DEDENQSPRS

1601 FQKKTRHYFI AAVERLWDYG MSSSPHVLRN RAQSGSVPQF KKVVFQEFTD

-continued

1651 GSFTQPLYRG ELNEHLGLLG PYIRAEVEDN IMVTFRNQAS RPYSFYSSLI

1701 SYEEDQRQGA EPRKNFVKPN ETKTYFWKVQ HHMAPTKDEF DCKAWAYFSD

1751 VDLEKDVHSG LIGPLLVCHT NTLNPAHGRQ VTVQEFALFF TIFDETKSWY

1801 FTENMERNCR APCNIQMEDP TFKENYRFHA INGYIMDTLP GLVMAQDQRI

1851 RWYLLSMGSN ENIHSIHFSG HVFTVRKKEE YKMALYNLYP GVFETVEMLP

1901 SKAGIWRVEC LIGEHLHAGM STLFLVYSNK CQTPLGMASG HIRDFQITAS

1951 GQYGQWAPKL ARLHYSGSIN AWSTKEPFSW IKVDLLAPMI IHGIKTQGAR

2001 QKFSSLYISQ FIIMYSLDGK KWQTYRGNST GTLMVFFGNV DSSGIKHNIF

2051 NPPIIARYIR LHPTHYSIRS TLRMELMGCD LNSCSMPLGM ESKAISDAQI

2101 TASSYFTNMF ATWSPSKARL HLQGRSNAWR PQVNNPKEWL QVDFQKTMKV

2151 TGVTTQGVKS LLTSMYVKEF LISSSQDGHQ WTLFFQNGKV KVFQGNQDSF

2201 TPVVNSLDPP LLTRYLRIHP QSWVHQIALR MEVLGCEAQD LY pSYN-FVIII-310 nucleotide sequence (encoding FVIII with complete B-domain deletion except 2 amino acid residues and 288 AE-XTEN inserted after aa 742)

(SEQ ID NO: 170)

1 ATGCAAATAG AGCTCTCCAC CTGCTTCTTT CTGTGCCTTT TGCGATTCTG

51 CTTTAGTGCC ACCAGAAGAT ACTACCTGGG TGCAGTGGAA CTGTCATGGG

101 ACTATATGCA AAGTGATCTC GGTGAGCTGC CTGTGGACGC AAGATTTCCT

151 CCTAGAGTGC CAAAATCTTT TCCATTCAAC ACCTCAGTCG TGTACAAAAA

201 GACTCTGTTT GTAGAATTCA CGGATCACCT TTTCAACATC GCTAAGCCAA

251 GGCCACCCTG GATGGGTCTG CTAGGTCCTA CCATCCAGGC TGAGGTTTAT

301 GATACAGTGG TCATTACACT TAAGAACATG GCTTCCCATC CTGTCAGTCT

351 TCATGCTGTT GGTGTATCCT ACTGGAAAGC TTCTGAGGGA GCTGAATATG

401 ATGATCAGAC CAGTCAAAGG GAGAAAGAAG ATGATAAAGT CTTCCCTGGT

451 GGAAGCCATA CATATGTCTG GCAGGTCCTG AAAGAGAATG GTCCAATGGC

501 CTCTGACCCA CTGTGCCTTA CCTACTCATA TCTTTCTCAT GTGGACCTGG

551 TAAAAGACTT GAATTCAGGC CTCATTGGAG CCCTACTAGT ATGTAGAGAA

601 GGGAGTCTGG CCAAGGAAAA GACACAGACC TTGCACAAAT TTATACTACT

651 TTTTGCTGTA TTTGATGAAG GGAAAAGTTG GCACTCAGAA ACAAAGAACT

701 CCTTGATGCA GGATAGGGAT GCTGCATCTG CTCGGGCCTG GCCTAAAATG

751 CACACAGTCA ATGGTTATGT AAACAGGTCT CTGCCAGGTC TGATTGGATG

801 CCACAGGAAA TCAGTCTATT GGCATGTGAT TGGAATGGGC ACCACTCCTG

851 AAGTGCACTC AATATTCCTC GAAGGTCACA CATTTCTTGT GAGGAACCAT

901 CGCCAGGCGT CCTTGGAAAT CTCGCCAATA ACTTTCCTTA CTGCTCAAAC

951 ACTCTTGATG GACCTTGGAC AGTTTCTACT GTTTTGTCAT ATCTCTTCCC

1001 ACCAACATGA TGGCATGGAA GCTTATGTCA AAGTAGACAG CTGTCCAGAG

1051 GAACCCCAAC TACGAATGAA AATAATGAA GAAGCGGAAG ACTATGATGA

1101 TGATCTTACT GATTCTGAAA TGGATGTGGT CAGGTTTGAT GATGACAACT

1151 CTCCTTCCTT TATCCAAATT CGCTCAGTTG CCAAGAAGCA TCCTAAAACT

1201 TGGGTACATT ACATTGCTGC TGAAGAGGAG GACTGGGACT ATGCTCCCTT

1251 AGTCCTCGCC CCCGATGACA GAAGTTATAA AAGTCAATAT TTGAACAATG

1301 GCCCTCAGCG GATTGGTAGG AAGTACAAAA AAGTCCGATT TATGGCATAC

-continued

1351 ACAGATGAAA CCTTTAAGAC TCGTGAAGCT ATTCAGCATG AATCAGGAAT

1401 CTTGGGACCT TTACTTTATG GGGAAGTTGG AGACACACTG TTGATTATAT

1451 TTAAGAATCA AGCAAGCAGA CCATATAACA TCTACCCTCA CGGAATCACT

1501 GATGTCCGTC CTTTGTATTC AAGGAGATTA CCAAAAGGTG TAAAACATTT

1551 GAAGGATTTT CCAATTCTGC CAGGAGAAAT ATTCAAATAT AAATGGACAG

1601 TGACTGTAGA AGATGGGCCA ACTAAATCAG ATCCTCGGTG CCTGACCCGC

1651 TATTACTCTA GTTTCGTTAA TATGGAGAGA GATCTAGCTT CAGGACTCAT

1701 TGGCCCTCTC CTCATCTGCT ACAAAGAATC TGTAGATCAA AGAGGAAACC

1751 AGATAATGTC AGACAAGAGG AATGTCATCC TGTTTTCTGT ATTTGATGAG

1801 AACCGAAGCT GGTACCTCAC AGAGAATATA CAACGCTTTC TCCCCAATCC

1851 AGCTGGAGTG CAGCTTGAGG ATCCAGAGTT CCAAGCCTCC AACATCATGC

1901 ACAGCATCAA TGGCTATGTT TTTGATAGTT TGCAGTTGTC AGTTTGTTTG

1951 CATGAGGTGG CATACTGGTA CATTCTAAGC ATTGGAGCAC AGACTGACTT

2001 CCTTTCTGTC TTCTTCTCTG GATATACCTT CAAACACAAA ATGGTCTATG

2051 AAGACACACT CACCCTATTC CCATTCTCAG GAGAAACTGT CTTCATGTCG

2101 ATGGAAAACC CAGGTCTATG GATTCTGGGG TGCCACAACT CAGACTTTCG

2151 GAACAGAGGC ATGACCGCCT TACTGAAGGT TTCTAGTTGT GACAAGAACA

2201 CTGGTGATTA TTACGAGGAC AGTTATGAAG ATATTTCAGC ATACTTGCTG

2251 AGTAAAAACA ATGCCATTGA ACCAAGAAGC TTCGGTACCT CAGAGTCTGC

2301 TACCCCCGAG TCAGGGCCAG GATCAGAGCC AGCCACCTCC GGGTCTGAGA

2351 CACCCGGGAC TTCCGAGAGT GCCACCCCTG AGTCCGGACC CGGGTCCGAG

2401 CCCGCCACTT CCGGCTCCGA AACTCCCGGC ACAAGCGAGA GCGCTACCCC

2451 AGAGTCAGGA CCAGGAACAT CTACAGAGCC CTCTGAAGGC TCCGCTCCAG

2501 GGTCCCCAGC CGGCAGTCCC ACTAGCACCG AGGAGGGAAC CTCTGAAAGC

2551 GCCACACCCG AATCAGGGCC AGGGTCTGAG CCTGCTACCA GCGGCAGCGA

2601 GACACCAGGC ACCTCTGAGT CCGCCACACC AGAGTCCGGA CCCGGATCTC

2651 CCGCTGGGAG CCCCACCTCC ACTGAGGAGG GATCTCCTGC TGGCTCTCCA

2701 ACATCTACTG AGGAAGGTAC CTCAACCGAG CCATCCGAGG GATCAGCTCC

2751 CGGCACCTCA GAGTCGGCAA CCCCGGAGTC TGGACCCGGA ACTTCCGAAA

2801 GTGCCACACC AGAGTCCGGT CCCGGGACTT CAGAATCAGC AACACCCGAG

2851 TCCGGCCCTG GGTCTGAACC CGCCACAAGT GGTAGTGAGA CACCAGGATC

2901 AGAACCTGCT ACCTCAGGGT CAGAGACACC CGGATCTCCG GCAGGCTCAC

2951 CAACCTCCAC TGAGGAGGGC ACCAGCACAG AACCAAGCGA GGGCTCCGCA

3001 CCCGGAACAA GCACTGAACC CAGTGAGGGT TCAGCACCCG GCTCTGAGCC

3051 GGCCACAAGT GGCAGTGAGA CACCCGGCAC TTCAGAGAGT GCCACCCCCG

3101 AGAGTGGCCC AGGCACTAGT ACCGAGCCCT CTGAAGGCAG TGCGCCAGCC

3151 TCGAGCGAAA TAACTCGTAC TACTCTTCAG TCAGATCAAG AGGAAATCGA

3201 TTATGATGAT ACCATATCAG TTGAAATGAA GAAGGAAGAT TTTGACATTT

3251 ATGATGAGGA TGAAAATCAG AGCCCCCGCA GCTTTCAAAA GAAAACACGA

3301 CACTATTTTA TTGCTGCAGT GGAGAGGCTC TGGGATTATG GGATGAGTAG

-continued

3351 CTCCCCACAT GTTCTAAGAA ACAGGGCTCA GAGTGGCAGT GTCCCTCAGT

3401 TCAAGAAAGT TGTTTTCCAG GAATTTACTG ATGGCTCCTT TACTCAGCCC

3451 TTATACCGTG GAGAACTAAA TGAACATTTG GGACTCCTGG GGCCATATAT

3501 AAGAGCAGAA GTTGAAGATA ATATCATGGT AACTTTCAGA AATCAGGCCT

3551 CTCGTCCCTA TTCCTTCTAT TCTAGCCTTA TTTCTTATGA GGAAGATCAG

3601 AGGCAAGGAG CAGAACCTAG AAAAAACTTT GTCAAGCCTA ATGAAACCAA

3651 AACTTACTTT TGGAAAGTGC AACATCATAT GGCACCCACT AAAGATGAGT

3701 TTGACTGCAA AGCCTGGGCT TATTTCTCTG ATGTTGACCT GGAAAAAGAT

3751 GTGCACTCAG GCCTGATTGG ACCCCTTCTG GTCTGCCACA CTAACACACT

3801 GAACCCTGCT CATGGGAGAC AAGTGACAGT ACAGGAATTT GCTCTGTTTT

3851 TCACCATCTT TGATGAGACC AAAAGCTGGT ACTTCACTGA AAATATGGAA

3901 AGAAACTGCA GGGCTCCCTG CAATATCCAG ATGGAAGATC CCACTTTTAA

3951 AGAGAATTAT CGCTTCCATG CAATCAATGG CTACATAATG GATACACTAC

4001 CTGGCTTAGT AATGGCTCAG GATCAAAGGA TTCGATGGTA TCTGCTCAGC

4051 ATGGGCAGCA ATGAAAACAT CCATTCTATT CATTTCAGTG GACATGTGTT

4101 CACTGTACGA AAAAAAGAGG AGTATAAAAT GGCACTGTAC AATCTCTATC

4151 CAGGTGTTTT TGAGACAGTG GAAATGTTAC CATCCAAAGC TGGAATTTGG

4201 CGGGTGGAAT GCCTTATTGG CGAGCATCTA CATGCTGGGA TGAGCACACT

4251 TTTTCTGGTG TACAGCAATA AGTGTCAGAC TCCCCTGGGA ATGGCTTCTG

4301 GACACATTAG AGATTTTCAG ATTACAGCTT CAGGACAATA TGGACAGTGG

4351 GCCCCAAAGC TGGCCAGACT TCATTATTCC GGATCAATCA ATGCCTGGAG

4401 CACCAAGGAG CCCTTTTCTT GGATCAAGGT GGATCTGTTG GCACCAATGA

4451 TTATTCACGG CATCAAGACC CAGGGTGCCC GTCAGAAGTT CTCCAGCCTC

4501 TACATCTCTC AGTTTATCAT CATGTATAGT CTTGATGGGA AGAAGTGGCA

4551 GACTTATCGA GGAAATTCCA CTGGAACCTT AATGGTCTTC TTTGGCAATG

4601 TGGATTCATC TGGGATAAAA CACAATATTT TTAACCCTCC AATTATTGCT

4651 CGATACATCC GTTTGCACCC AACTCATTAT AGCATTCGCA GCACTCTTCG

4701 CATGGAGTTG ATGGGCTGTG ATTTAAATAG TTGCAGCATG CCATTGGGAA

4751 TGGAGAGTAA AGCAATATCA GATGCACAGA TTACTGCTTC ATCCTACTTT

4801 ACCAATATGT TTGCCACCTG GTCTCCTTCA AAAGCTCGAC TTCACCTCCA

4851 AGGGAGGAGT AATGCCTGGA GACCTCAGGT GAATAATCCA AAAGAGTGGC

4901 TGCAAGTGGA CTTCCAGAAG ACAATGAAAG TCACAGGAGT AACTACTCAG

4951 GGAGTAAAAT CTCTGCTTAC CAGCATGTAT GTGAAGGAGT TCCTCATCTC

5001 CAGCAGTCAA GATGGCCATC AGTGGACTCT CTTTTTTCAG AATGGCAAAG

5051 TAAAGGTTTT TCAGGGAAAT CAAGACTCCT TCACACCTGT GGTGAACTCT

5101 CTAGACCCAC CGTTACTGAC TCGCTACCTT CGAATTCACC CCCAGAGTTG

5151 GGTGCACCAG ATTGCCCTGA GGATGGAGGT TCTGGGCTGC GAGGCACAGG

5201 ACCTCTACGA CAAAACTCAC ACATGCCCAC CGTGCCCAGC TCCAGAACTC

5251 CTGGGCGGAC CGTCAGTCTT CCTCTTCCCC CCAAAACCCA AGGACACCCT

5301 CATGATCTCC CGGACCCCTG AGGTCACATG CGTGGTGGTG GACGTGAGCC

5351 ACGAAGACCC TGAGGTCAAG TTCAACTGGT ACGTGGACGG CGTGGAGGTG

-continued

5401 CATAATGCCA AGACAAAGCC GCGGGAGGAG CAGTACAACA GCACGTACCG

5451 TGTGGTCAGC GTCCTCACCG TCCTGCACCA GGACTGGCTG AATGGCAAGG

5501 AGTACAAGTG CAAGGTCTCC AACAAAGCCC TCCCAGCCCC CATCGAGAAA

5551 ACCATCTCCA AAGCCAAAGG GCAGCCCCGA GAACCACAGG TGTACACCCT

5601 GCCCCCATCC CGGGATGAGC TGACCAAGAA CCAGGTCAGC CTGACCTGCC

5651 TGGTCAAAGG CTTCTATCCC AGCGACATCG CCGTGGAGTG GGAGAGCAAT

5701 GGGCAGCCGG AGAACAACTA CAAGACCACG CCTCCCGTGT TGGACTCCGA

5751 CGGCTCCTTC TTCCTCTACA GCAAGCTCAC CGTGGACAAG AGCAGGTGGC

5801 AGCAGGGGAA CGTCTTCTCA TGCTCCGTGA TGCATGAGGC TCTGCACAAC

5851 CACTACACGC AGAAGAGCCT CTCCCTGTCT CCGGGTAAAT GA pSYN FVIII 310 protein sequence (FVIII with complete B-domain deletion except 2 amino acid residues and 288 AE-XTEN inserted after aa 742)

(SEQ ID NO: 171)

1 ATRRYYLGAV ELSWDYMQSD LGELPVDARF PPRVPKSFPF NTSVVYKKTL

51 FVEFTDHLFN IAKPRPPWMG LLGPTIQAEV YDTVVITLKN MASHPVSLHA

101 VGVSYWKASE GAEYDDQTSQ REKEDDKVFP GGSHTYVWQV LKENGPMASD

151 PLCLTYSYLS HVDLVKDLNS GLIGALLVCR EGSLAKEKTQ TLHKFILLFA

201 VFDEGKSWHS ETKNSLMQDR DAASARAWPK MHTVNGYVNR SLPGLIGCHR

251 KSVYWHVIGM GTTPEVHSIF LEGHTFLVRN HRQASLEISP ITFLTAQTLL

301 MDLGQFLLFC HISSHQHDGM EAYVKVDSCP EEPQLRMKNN EEAEDYDDDL

351 TDSEMDVVRF DDDNSPSFIQ IRSVAKKHPK TWVHYIAAEE EDWDYAPLVL

401 APDDRSYKSQ YLNNGPQRIG RKYKKVRFMA YTDETFKTRE AIQHESGILG

451 PLLYGEVGDT LLIIFKNQAS RPYNIYPHGI TDVRPLYSRR LPKGVKHLKD

501 FPILPGEIFK YKWTVTVEDG PTKSDPRCLT RYYSSFVNME RDLASGLIGP

551 LLICYKESVD QRGNQIMSDK RNVILFSVFD ENRSWYLTEN IQRFLPNPAG

601 VQLEDPEFQA SNIMHSINGY VFDSLQLSVC LHEVAYWYIL SIGAQTDFLS

651 VFFSGYTFKH KMVYEDTLTL FPFSGETVFM SMENPGLWIL GCHNSDFRNR

701 GMTALLKVSS CDKNTGDYYE DSYEDISAYL LSKNNAIEPR SFGTSESATP

751 ESGPGSEPAT SGSETPGTSE SATPESGPGS EPATSGSETP GTSESATPES

801 GPGTSTEPSE GSAPGSPAGS PTSTEEGTSE SATPESGPGS EPATSGSETP

851 GTSESATPES GPGSPAGSPT STEEGSPAGS PTSTEEGTST EPSEGSAPGT

901 SESATPESGP GTSESATPES GPGTSESATP ESGPGSEPAT SGSETPGSEP

951 ATSGSETPGS PAGSPTSTEE GTSTEPSEGS APGTSTEPSE GSAPGSEPAT

1001 SGSETPGTSE SATPESGPGT STEPSEGSAP ASSEITRTTL QSDQEEIDYD

1051 DTISVEMKKE DFDIYDEDEN QSPRSFQKKT RHYFIAAVER LWDYGMSSSP

1101 HVLRNRAQSG SVPQFKKVVF QEFTDGSFTQ PLYRGELNEH LGLLGPYIRA

1151 EVEDNIMVTF RNQASRPYSF YSSLISYEED QRQGAEPRKN FVKPNETKTY

1201 FWKVQHHMAP TKDEFDCKAW AYFSDVDLEK DVHSGLIGPL LVCHTNTLNP

1251 AHGRQVTVQE FALFFTIFDE TKSWYFTENM ERNCRAPCNI QMEDPTFKEN

1301 YRFHAINGYI MDTLPGLVMA QDQRIRWYLL SMGSNENIHS IHFSGHVFTV

1351 RKKEEYKMAL YNLYPGVFET VEMLPSKAGI WRVECLIGEH LHAGMSTLFL

-continued

1401 VYSNKCQTPL GMASGHIRDF QITASGQYGQ WAPKLARLHY SGSINAWSTK

1451 EPFSWIKVDL LAPMIIHGIK TQGARQKFSS LYISQFIIMY SLDGKKWQTY

1501 RGNSTGTLMV FFGNVDSSGI KHNIFNPPII ARYIRLHPTH YSIRSTLRME

1551 LMGCDLNSCS MPLGMESKAI SDAQITASSY FTNMFATWSP SKARLHLQGR

1601 SNAWRPQVNN PKEWLQVDFQ KTMKVTGVTT QGVKSLLTSM YVKEFLISSS

1651 QDGHQWTLFF QNGKVKVFQG NQDSFTPVVN SLDPPLLTRY LRIHPQSWVH

1701 QIALRMEVLG CEAQDLYDKT HTCPPCPAPE LLGGPSVFLF PPKPKDTLMI

1751 SRTPEVTCVV VDVSHEDPEV KFNWYVDGVE VHNAKTKPRE EQYNSTYRVV

1801 SVLTVLHQDW LNGKEYKCKV SNKALPAPIE KTISKAKGQP REPQVYTLPP

1851 SRDELTKNQV SLTCLVKGFY PSDIAVEWES NGQPENNYKT TPPVLDSDGS

1901 FFLYSKLTVD KSRWQQGNVF SCSVMHEALH NHYTQKSLSL SPGK* pSYN FVIII 312 nucleotide sequence (encoding FVIII with complete B-domain deletion except 5 amino acid residues and 288 AE-XTEN inserted after aa 745-B5 version)

(SEQ ID NO: 172)

1 ATGCAAATAG AGCTCTCCAC CTGCTTCTTT CTGTGCCTTT TGCGATTCTG

51 CTTTAGTGCC ACCAGAAGAT ACTACCTGGG TGCAGTGGAA CTGTCATGGG

101 ACTATATGCA AAGTGATCTC GGTGAGCTGC CTGTGGACGC AAGATTTCCT

151 CCTAGAGTGC CAAAATCTTT TCCATTCAAC ACCTCAGTCG TGTACAAAAA

201 GACTCTGTTT GTAGAATTCA CGGATCACCT TTTCAACATC GCTAAGCCAA

251 GGCCACCCTG GATGGGTCTG CTAGGTCCTA CCATCCAGGC TGAGGTTTAT

301 GATACAGTGG TCATTACACT TAAGAACATG GCTTCCCATC CTGTCAGTCT

351 TCATGCTGTT GGTGTATCCT ACTGGAAAGC TTCTGAGGGA GCTGAATATG

401 ATGATCAGAC CAGTCAAAGG GAGAAAGAAG ATGATAAAGT CTTCCCTGGT

451 GGAAGCCATA CATATGTCTG GCAGGTCCTG AAAGAGAATG GTCCAATGGC

501 CTCTGACCCA CTGTGCCTTA CCTACTCATA TCTTTCTCAT GTGGACCTGG

551 TAAAAGACTT GAATTCAGGC CTCATTGGAG CCCTACTAGT ATGTAGAGAA

601 GGGAGTCTGG CCAAGGAAAA GACACAGACC TTGCACAAAT TTATACTACT

651 TTTTGCTGTA TTTGATGAAG GGAAAAGTTG GCACTCAGAA ACAAAGAACT

701 CCTTGATGCA GGATAGGGAT GCTGCATCTG CTCGGGCCTG GCCTAAAATG

751 CACACAGTCA ATGGTTATGT AAACAGGTCT CTGCCAGGTC TGATTGGATG

801 CCACAGGAAA TCAGTCTATT GGCATGTGAT TGGAATGGGC ACCACTCCTG

851 AAGTGCACTC AATATTCCTC GAAGGTCACA CATTTCTTGT GAGGAACCAT

901 CGCCAGGCGT CCTTGGAAAT CTCGCCAATA ACTTTCCTTA CTGCTCAAAC

951 ACTCTTGATG GACCTTGGAC AGTTTCTACT GTTTTGTCAT ATCTCTTCCC

1001 ACCAACATGA TGGCATGGAA GCTTATGTCA AAGTAGACAG CTGTCCAGAG

1051 GAACCCCAAC TACGAATGAA AAATAATGAA GAAGCGGAAG ACTATGATGA

1101 TGATCTTACT GATTCTGAAA TGGATGTGGT CAGGTTTGAT GATGACAACT

1151 CTCCTTCCTT TATCCAAATT CGCTCAGTTG CCAAGAAGCA TCCTAAAACT

1201 TGGGTACATT ACATTGCTGC TGAAGAGGAG GACTGGGACT ATGCTCCCTT

1251 AGTCCTCGCC CCCGATGACA GAAGTTATAA AAGTCAATAT TTGAACAATG

1301 GCCCTCAGCG GATTGGTAGG AAGTACAAAA AAGTCCGATT TATGGCATAC

1351 ACAGATGAAA CCTTTAAGAC TCGTGAAGCT ATTCAGCATG AATCAGGAAT

-continued

1401 CTTGGGACCT TTACTTTATG GGGAAGTTGG AGACACACTG TTGATTATAT
1451 TTAAGAATCA AGCAAGCAGA CCATATAACA TCTACCCTCA CGGAATCACT
1501 GATGTCCGTC CTTTGTATTC AAGGAGATTA CCAAAAGGTG TAAAACATTT
1551 GAAGGATTTT CCAATTCTGC CAGGAGAAAT ATTCAAATAT AAATGGACAG
1601 TGACTGTAGA AGATGGGCCA ACTAAATCAG ATCCTCGGTG CCTGACCCGC
1651 TATTACTCTA GTTTCGTTAA TATGGAGAGA GATCTAGCTT CAGGACTCAT
1701 TGGCCCTCTC CTCATCTGCT ACAAAGAATC TGTAGATCAA AGAGGAAACC
1751 AGATAATGTC AGACAAGAGG AATGTCATCC TGTTTTCTGT ATTTGATGAG
1801 AACCGAAGCT GGTACCTCAC AGAGAATATA CAACGCTTTC TCCCCAATCC
1851 AGCTGGAGTG CAGCTTGAGG ATCCAGAGTT CCAAGCCTCC AACATCATGC
1901 ACAGCATCAA TGGCTATGTT TTTGATAGTT TGCAGTTGTC AGTTTGTTTG
1951 CATGAGGTGG CATACTGGTA CATTCTAAGC ATTGGAGCAC AGACTGACTT
2001 CCTTTCTGTC TTCTTCTCTG GATATACCTT CAAACACAAA ATGGTCTATG
2051 AAGACACACT CACCCTATTC CCATTCTCAG GAGAAACTGT CTTCATGTCG
2101 ATGGAAAACC CAGGTCTATG GATTCTGGGG TGCCACAACT CAGACTTTCG
2151 GAACAGAGGC ATGACCGCCT TACTGAAGGT TTCTAGTTGT GACAAGAACA
2201 CTGGTGATTA TTACGAGGAC AGTTATGAAG ATATTTCAGC ATACTTGCTG
2251 AGTAAAAACA ATGCCATTGA ACCAAGAAGC TTCTCTCAAA ACGGTACCTC
2301 AGAGTCTGCT ACCCCCGAGT CAGGGCCAGG ATCAGAGCCA GCCACCTCCG
2351 GGTCTGAGAC ACCCGGGACT TCCGAGAGTG CCACCCCTGA GTCCGGACCC
2401 GGGTCCGAGC CCGCCACTTC CGGCTCCGAA ACTCCCGGCA CAAGCGAGAG
2451 CGCTACCCCA GAGTCAGGAC CAGGAACATC TACAGAGCCC TCTGAAGGCT
2501 CCGCTCCAGG GTCCCCAGCC GGCAGTCCCA CTAGCACCGA GGAGGGAACC
2551 TCTGAAAGCG CCACACCCGA ATCAGGGCCA GGGTCTGAGC CTGCTACCAG
2601 CGGCAGCGAG ACACCAGGCA CCTCTGAGTC CGCCACACCA GAGTCCGGAC
2651 CCGGATCTCC CGCTGGGAGC CCCACCTCCA CTGAGGAGGG ATCTCCTGCT
2701 GGCTCTCCAA CATCTACTGA GGAAGGTACC TCAACCGAGC CATCCGAGGG
2751 ATCAGCTCCC GGCACCTCAG AGTCGGCAAC CCCGGAGTCT GGACCCGGAA
2801 CTTCCGAAAG TGCCACACCA GAGTCCGGTC CCGGGACTTC AGAATCAGCA
2851 ACACCCGAGT CCGGCCCTGG GTCTGAACCC GCCACAAGTG GTAGTGAGAC
2901 ACCAGGATCA GAACCTGCTA CCTCAGGGTC AGAGACACCC GGATCTCCGG
2951 CAGGCTCACC AACCTCCACT GAGGAGGGCA CCAGCACAGA ACCAAGCGAG
3001 GGCTCCGCAC CCGGAACAAG CACTGAACCC AGTGAGGGTT CAGCACCCGG
3051 CTCTGAGCCG GCCACAAGTG GCAGTGAGAC ACCCGGCACT TCAGAGAGTG
3101 CCACCCCCGA GAGTGGCCCA GGCACTAGTA CCGAGCCCTC TGAAGGCAGT
3151 GCGCCAGCCT CGAGCGAAAT AACTCGTACT ACTCTTCAGT CAGATCAAGA
3201 GGAAATCGAT TATGATGATA CCATATCAGT TGAAATGAAG AAGGAAGATT
3251 TTGACATTTA TGATGAGGAT GAAAATCAGA GCCCCCGCAG CTTTCAAAAG
3301 AAAACACGAC ACTATTTTAT TGCTGCAGTG GAGAGGCTCT GGGATTATGG
3351 GATGAGTAGC TCCCCACATG TTCTAAGAAA CAGGGCTCAG AGTGGCAGTG

-continued

```
3401 TCCCTCAGTT CAAGAAAGTT GTTTTCCAGG AATTTACTGA TGGCTCCTTT
3451 ACTCAGCCCT TATACCGTGG AGAACTAAAT GAACATTTGG GACTCCTGGG
3501 GCCATATATA AGAGCAGAAG TTGAAGATAA TATCATGGTA ACTTTCAGAA
3551 ATCAGGCCTC TCGTCCCTAT TCCTTCTATT CTAGCCTTAT TTCTTATGAG
3601 GAAGATCAGA GGCAAGGAGC AGAACCTAGA AAAAACTTTG TCAAGCCTAA
3651 TGAAACCAAA ACTTACTTTT GGAAAGTGCA ACATCATATG GCACCCACTA
3701 AAGATGAGTT TGACTGCAAA GCCTGGGCTT ATTTCTCTGA TGTTGACCTG
3751 GAAAAAGATG TGCACTCAGG CCTGATTGGA CCCCTTCTGG TCTGCCACAC
3801 TAACACACTG AACCCTGCTC ATGGGAGACA AGTGACAGTA CAGGAATTTG
3851 CTCTGTTTTT CACCATCTTT GATGAGACCA AAAGCTGGTA CTTCACTGAA
3901 AATATGGAAA GAAACTGCAG GGCTCCCTGC AATATCCAGA TGGAAGATCC
3951 CACTTTTAAA GAGAATTATC GCTTCCATGC AATCAATGGC TACATAATGG
4001 ATACACTACC TGGCTTAGTA ATGGCTCAGG ATCAAAGGAT TCGATGGTAT
4051 CTGCTCAGCA TGGGCAGCAA TGAAAACATC CATTCTATTC ATTTCAGTGG
4101 ACATGTGTTC ACTGTACGAA AAAAAGAGGA GTATAAAATG GCACTGTACA
4151 ATCTCTATCC AGGTGTTTTT GAGACAGTGG AAATGTTACC ATCCAAAGCT
4201 GGAATTTGGC GGGTGGAATG CCTTATTGGC GAGCATCTAC ATGCTGGGAT
4251 GAGCACACTT TTTCTGGTGT ACAGCAATAA GTGTCAGACT CCCCTGGGAA
4301 TGGCTTCTGG ACACATTAGA GATTTTCAGA TTACAGCTTC AGGACAATAT
4351 GGACAGTGGG CCCCAAAGCT GGCCAGACTT CATTATTCCG GATCAATCAA
4401 TGCCTGGAGC ACCAAGGAGC CCTTTTCTTG GATCAAGGTG GATCTGTTGG
4451 CACCAATGAT TATTCACGGC ATCAAGACCC AGGGTGCCCG TCAGAAGTTC
4501 TCCAGCCTCT ACATCTCTCA GTTTATCATC ATGTATAGTC TTGATGGGAA
4551 GAAGTGGCAG ACTTATCGAG GAAATTCCAC TGGAACCTTA ATGGTCTTCT
4601 TTGGCAATGT GGATTCATCT GGGATAAAAC ACAATATTTT TAACCCTCCA
4651 ATTATTGCTC GATACATCCG TTTGCACCCA ACTCATTATA GCATTCGCAG
4701 CACTCTTCGC ATGGAGTTGA TGGGCTGTGA TTTAAATAGT TGCAGCATGC
4751 CATTGGGAAT GGAGAGTAAA GCAATATCAG ATGCACAGAT TACTGCTTCA
4801 TCCTACTTTA CCAATATGTT TGCCACCTGG TCTCCTTCAA AAGCTCGACT
4851 TCACCTCCAA GGGAGGAGTA ATGCCTGGAG ACCTCAGGTG AATAATCCAA
4901 AAGAGTGGCT GCAAGTGGAC TTCCAGAAGA CAATGAAAGT CACAGGAGTA
4951 ACTACTCAGG GAGTAAAATC TCTGCTTACC AGCATGTATG TGAAGGAGTT
5001 CCTCATCTCC AGCAGTCAAG ATGGCCATCA GTGGACTCTC TTTTTTCAGA
5051 ATGGCAAAGT AAAGGTTTTT CAGGGAAATC AAGACTCCTT CACACCTGTG
5101 GTGAACTCTC TAGACCCACC GTTACTGACT CGCTACCTTC GAATTCACCC
5151 CCAGAGTTGG GTGCACCAGA TTGCCCTGAG GATGGAGGTT CTGGGCTGCG
5201 AGGCACAGGA CCTCTACGAC AAAACTCACA CATGCCCACC GTGCCCAGCT
5251 CCAGAACTCC TGGGCGGACC GTCAGTCTTC CTCTTCCCCC CAAAACCCAA
5301 GGACACCCTC ATGATCTCCC GGACCCCTGA GGTCACATGC GTGGTGGTGG
5351 ACGTGAGCCA CGAAGACCCT GAGGTCAAGT TCAACTGGTA CGTGGACGGC
5401 GTGGAGGTGC ATAATGCCAA GACAAAGCCG CGGGAGGAGC AGTACAACAG
```

-continued

5451 CACGTACCGT GTGGTCAGCG TCCTCACCGT CCTGCACCAG GACTGGCTGA

5501 ATGGCAAGGA GTACAAGTGC AAGGTCTCCA ACAAAGCCCT CCCAGCCCCC

5551 ATCGAGAAAA CCATCTCCAA AGCCAAAGGG CAGCCCCGAG AACCACAGGT

5601 GTACACCCTG CCCCCATCCC GGGATGAGCT GACCAAGAAC CAGGTCAGCC

5651 TGACCTGCCT GGTCAAAGGC TTCTATCCCA GCGACATCGC CGTGGAGTGG

5701 GAGAGCAATG GGCAGCCGGA GAACAACTAC AAGACCACGC CTCCCGTGTT

5751 GGACTCCGAC GGCTCCTTCT TCCTCTACAG CAAGCTCACC GTGGACAAGA

5801 GCAGGTGGCA GCAGGGGAAC GTCTTCTCAT GCTCCGTGAT GCATGAGGCT

5851 CTGCACAACC ACTACACGCA GAAGAGCCTC TCCCTGTCTC CGGGTAAATG pSYN FVIII 312 protein sequence (FVIII with complete
B-domain deletion except 5 amino acid residues and 288
AE-XTEN inserted after aa 745-B5 version)
(SEQ ID NO: 173)

1 ATRRYYLGAV ELSWDYMQSD LGELPVDARF PPRVPKSFPF NTSVVYKKTL

51 FVEFTDHLFN IAKPRPPWMG LLGPTIQAEV YDTVVITLKN MASHPVSLHA

101 VGVSYWKASE GAEYDDQTSQ REKEDDKVFP GGSHTYVWQV LKENGPMASD

151 PLCLTYSYLS HVDLVKDLNS GLIGALLVCR EGSLAKEKTQ TLHKFILLFA

201 VFDEGKSWHS ETKNSLMQDR DAASARAWPK MHTVNGYVNR SLPGLIGCHR

251 KSVYWHVIGM GTTPEVHSIF LEGHTFLVRN HRQASLEISP ITFLTAQTLL

301 MDLGQFLLFC HISSHQHDGM EAYVKVDSCP EEPQLRMKNN EEAEDYDDDL

351 TDSEMDVVRF DDDNSPSFIQ IRSVAKKHPK TWVHYIAAEE EDWDYAPLVL

401 APDDRSYKSQ YLNNGPQRIG RKYKKVRFMA YTDETFKTRE AIQHESGILG

451 PLLYGEVGDT LLIIFKNQAS RPYNIYPHGI TDVRPLYSRR LPKGVKHLKD

501 FPILPGEIFK YKWTVTVEDG PTKSDPRCLT RYYSSFVNME RDLASGLIGP

551 LLICYKESVD QRGNQIMSDK RNVILFSVFD ENRSWYLTEN IQRFLPNPAG

601 VQLEDPEFQA SNIMHSINGY VFDSLQLSVC LHEVAYWYIL SIGAQTDFLS

651 VFFSGYTFKH KMVYEDTLTL FPFSGETVFM SMENPGLWIL GCHNSDFRNR

701 GMTALLKVSS CDKNTGDYYE DSYEDISAYL LSKNNAIEPR SFSQNGTSES

751 ATPESGPGSE PATSGSETPG TSESATPESG PGSEPATSGS ETPGTSESAT

801 PESGPGTSTE PSEGSAPGSP AGSPTSTEEG TSESATPESG PGSEPATSGS

851 ETPGTSESAT PESGPGSPAG SPTSTEEGSP AGSPTSTEEG TSTEPSEGSA

901 PGTSESATPE SGPGTSESAT PESGPGTSES ATPESGPGSE PATSGSETPG

951 SEPATSGSET PGSPAGSPTS TEEGTSTEPS EGSAPGTSTE PSEGSAPGSE

1001 PATSGSETPG TSESATPESG PGTSTEPSEG SAPASSEITR TTLQSDQEEI

1051 DYDDTISVEM KKEDFDIYDE DENQSPRSFQ KKTRHYFIAA VERLWDYGMS

1101 SSPHVLRNRA QSGSVPQFKK VVFQEFTDGS FTQPLYRGEL NEHLGLLGPY

1151 IRAEVEDNIM VTFRNQASRP YSFYSSLISY EEDQRQGAEP RKNFVKPNET

1201 KTYFWKVQHH MAPTKDEFDC KAWAYFSDVD LEKDVHSGLI GPLLVCHTNT

1251 LNPAHGRQVT VQEFALFFTI FDETKSWYFT ENMERNCRAP CNIQMEDPTF

1301 KENYRFHAIN GYIMDTLPGL VMAQDQRIRW YLLSMGSNEN IHSIHFSGHV

1351 FTVRKKEEYK MALYNLYPGV FETVEMLPSK AGIWRVECLI GEHLHAGMST

1401 LFLVYSNKCQ TPLGMASGHI RDFQITASGQ YGQWAPKLAR LHYSGSINAW

-continued

1451 STKEPFSWIK VDLLAPMIIH GIKTQGARQK FSSLYISQFI IMYSLDGKKW

1501 QTYRGNSTGT LMVFFGNVDS SGIKHNIFNP PIIARYIRLH PTHYSIRSTL

1551 RMELMGCDLN SCSMPLGMES KAISDAQITA SSYFTNMFAT WSPSKARLHL

1601 QGRSNAWRPQ VNNPKEWLQV DFQKTMKVTG VTTQGVKSLL TSMYVKEFLI

1651 SSSQDGHQWT LFFQNGKVKV FQGNQDSFTP VVNSLDPPLL TRYLRIHPQS

1701 WVHQIALRME VLGCEAQDLY DKTHTCPPCP APELLGGPSV FLFPPKPKDT

1751 LMISRTPEVT CVVVDVSHED PEVKFNWYVD GVEVHNAKTK PREEQYNSTY

1801 RVVSVLTVLH QDWLNGKEYK CKVSNKALPA PIEKTISKAK GQPREPQVYT

1851 LPPSRDELTK NQVSLTCLVK GFYPSDIAVE WESNGQPENN YKTTPPVLDS

1901 DGSFFLYSKL TVDKSRWQQG NVFSCSVMHE ALHNHYTQKS LSLSPGK* pSYN VWF059 nucleotide sequence (encoding VWF D'D3-Fc
with acidic region 2 (a2) thrombin site in the linker)
(SEQ ID NO: 196)

1 ATGATTCCTG CCAGATTTGC CGGGGTGCTG CTTGCTCTGG CCCTCATTTT

51 GCCAGGGACC CTTTGTGCAG AAGGAACTCG CGGCAGGTCA TCCACGGCCC

101 GATGCAGCCT TTTCGGAAGT GACTTCGTCA ACACCTTTGA TGGGAGCATG

151 TACAGCTTTG CGGGATACTG CAGTTACCTC CTGGCAGGGG GCTGCCAGAA

201 ACGCTCCTTC TCGATTATTG GGACTTCCA GAATGGCAAG AGAGTGAGCC

251 TCTCCGTGTA TCTTGGGGAA TTTTTTGACA TCCATTTGTT TGTCAATGGT

301 ACCGTGACAC AGGGGGACCA AAGAGTCTCC ATGCCCTATG CCTCCAAAGG

351 GCTGTATCTA GAAACTGAGG CTGGGTACTA CAAGCTGTCC GGTGAGGCCT

401 ATGGCTTTGT GGCCAGGATC GATGGCAGCG GCAACTTTCA AGTCCTGCTG

451 TCAGACAGAT ACTTCAACAA GACCTGCGGG CTGTGTGGCA ACTTTAACAT

501 CTTTGCTGAA GATGACTTTA TGACCCAAGA AGGGACCTTG ACCTCGGACC

551 CTTATGACTT TGCCAACTCA TGGGCTCTGA GCAGTGGAGA ACAGTGGTGT

601 GAACGGGCAT CTCCTCCCAG CAGCTCATGC AACATCTCCT CTGGGGAAAT

651 GCAGAAGGGC CTGTGGGAGC AGTGCCAGCT TCTGAAGAGC ACCTCGGTGT

701 TTGCCCGCTG CCACCCTCTG GTGGACCCCG AGCCTTTTGT GGCCCTGTGT

751 GAGAAGACTT TGTGTGAGTG TGCTGGGGGG CTGGAGTGCG CCTGCCCTGC

801 CCTCCTGGAG TACGCCCGGA CCTGTGCCCA GGAGGGAATG GTGCTGTACG

851 GCTGGACCGA CCACAGCGCG TGCAGCCCAG TGTGCCCTGC TGGTATGGAG

901 TATAGGCAGT GTGTGTCCCC TTGCGCCAGG ACCTGCCAGA GCCTGCACAT

951 CAATGAAATG TGTCAGGAGC GATGCGTGGA TGGCTGCAGC TGCCCTGAGG

1001 GACAGCTCCT GGATGAAGGC CTCTGCGTGG AGAGCACCGA GTGTCCCTGC

1051 GTGCATTCCG GAAAGCGCTA CCCTCCCGGC ACCTCCCTCT CTCGAGACTG

1101 CAACACCTGC ATTTGCCGAA ACAGCCAGTG GATCTGCAGC AATGAAGAAT

1151 GTCCAGGGGA GTGCCTTGTC ACTGGTCAAT CCCACTTCAA GAGCTTTGAC

1201 AACAGATACT TCACCTTCAG TGGGATCTGC CAGTACCTGC TGGCCCGGGA

1251 TTGCCAGGAC CACTCCTTCT CCATTGTCAT TGAGACTGTC CAGTGTGCTG

1301 ATGACCGCGA CGCTGTGTGC ACCCGCTCCG TCACCGTCCG GCTGCCTGGC

1351 CTGCACAACA GCCTTGTGAA ACTGAAGCAT GGGGCAGGAG TTGCCATGGA

1401 TGGCCAGGAC ATCCAGCTCC CCCTCCTGAA AGGTGACCTC CGCATCCAGC

-continued

1451 ATACAGTGAC GGCCTCCGTG CGCCTCAGCT ACGGGGAGGA CCTGCAGATG

1501 GACTGGGATG GCCGCGGGAG GCTGCTGGTG AAGCTGTCCC CCGTCTATGC

1551 CGGGAAGACC TGCGGCCTGT GTGGGAATTA CAATGGCAAC CAGGGCGACG

1601 ACTTCCTTAC CCCCTCTGGG CTGGCGGAGC CCCGGGTGGA GGACTTCGGG

1651 AACGCCTGGA AGCTGCACGG GGACTGCCAG GACCTGCAGA AGCAGCACAG

1701 CGATCCCTGC GCCCTCAACC CGCGCATGAC CAGGTTCTCC GAGGAGGCGT

1751 GCGCGGTCCT GACGTCCCCC ACATTCGAGG CCTGCCATCG TGCCGTCAGC

1801 CCGCTGCCCT ACCTGCGGAA CTGCCGCTAC GACGTGTGCT CCTGCTCGGA

1851 CGGCCGCGAG TGCCTGTGCG GCGCCCTGGC CAGCTATGCC GCGGCCTGCG

1901 CGGGGAGAGG CGTGCGCGTC GCGTGGCGCG AGCCAGGCCG CTGTGAGCTG

1951 AACTGCCCGA AAGGCCAGGT GTACCTGCAG TGCGGGACCC CCTGCAACCT

2001 GACCTGCCGC TCTCTCTCTT ACCCGGATGA GGAATGCAAT GAGGCCTGCC

2051 TGGAGGGCTG CTTCTGCCCC CCAGGGCTCT ACATGGATGA GAGGGGGGAC

2101 TGCGTGCCCA AGGCCCAGTG CCCCTGTTAC TATGACGGTG AGATCTTCCA

2151 GCCAGAAGAC ATCTTCTCAG ACCATCACAC CATGTGCTAC TGTGAGGATG

2201 GCTTCATGCA CTGTACCATG AGTGGAGTCC CCGGAAGCTT GCTGCCTGAC

2251 GCTGTCCTCA GCAGTCCCCT GTCTCATCGC AGCAAAAGGA GCCTATCCTG

2301 TCGGCCCCCC ATGGTCAAGC TGGTGTGTCC CGCTGACAAC CTGCGGGCTG

2351 AAGGGCTCGA GTGTACCAAA ACGTGCCAGA ACTATGACCT GGAGTGCATG

2401 AGCATGGGCT GTGTCTCTGG CTGCCTCTGC CCCCCGGGCA TGGTCCGGCA

2451 TGAGAACAGA TGTGTGGCCC TGGAAAGGTG TCCCTGCTTC CATCAGGGCA

2501 AGGAGTATGC CCCTGGAGAA ACAGTGAAGA TTGGCTGCAA CACTTGTGTC

2551 TGTCGGGACC GGAAGTGGAA CTGCACAGAC CATGTGTGTG ATGCCACGTG

2601 CTCCACGATC GGCATGGCCC ACTACCTCAC CTTCGACGGG CTCAAATACC

2651 TGTTCCCCGG GGAGTGCCAG TACGTTCTGG TGCAGGATTA CTGCGGCAGT

2701 AACCCTGGGA CCTTTCGGAT CCTAGTGGGG AATAAGGGAT GCAGCCACCC

2751 CTCAGTGAAA TGCAAGAAAC GGGTCACCAT CCTGGTGGAG GGAGGAGAGA

2801 TTGAGCTGTT TGACGGGGAG GTGAATGTGA AGAGGCCCAT GAAGGATGAG

2851 ACTCACTTTG AGGTGGTGGA GTCTGGCCGG TACATCATTC TGCTGCTGGG

2901 CAAAGCCCTC TCCGTGGTCT GGGACCGCCA CCTGAGCATC TCCGTGGTCC

2951 TGAAGCAGAC ATACCAGGAG AAAGTGTGTG GCCTGTGTGG GAATTTTGAT

3001 GGCATCCAGA ACAATGACCT CACCAGCAGC AACCTCCAAG TGGAGGAAGA

3051 CCCTGTGGAC TTTGGGAACT CCTGGAAAGT GAGCTCGCAG TGTGCTGACA

3101 CCAGAAAAGT GCCTCTGGAC TCATCCCCTG CCACCTGCCA TAACAACATC

3151 ATGAAGCAGA CGATGGTGGA TTCCTCCTGT AGAATCCTTA CCAGTGACGT

3201 CTTCCAGGAC TGCAACAAGC TGGTGGACCC CGAGCCATAT CTGGATGTCT

3251 GCATTTACGA CACCTGCTCC TGTGAGTCCA TTGGGGACTG CGCCGCATTC

3301 TGCGACACCA TTGCTGCCTA TGCCCACGTG TGTGCCCAGC ATGGCAAGGT

3351 GGTGACCTGG AGGACGGCCA CATTGTGCCC CCAGAGCTGC GAGGAGAGGA

3401 ATCTCCGGGA GAACGGGTAT GAGGCTGAGT GGCGCTATAA CAGCTGTGCA

3451 CCTGCCTGTC AAGTCACGTG TCAGCACCCT GAGCCACTGG CCTGCCCTGT

-continued

3501 GCAGTGTGTG GAGGGCTGCC ATGCCCACTG CCCTCCAGGG AAAATCCTGG

3551 ATGAGCTTTT GCAGACCTGC GTTGACCCTG AAGACTGTCC AGTGTGTGAG

3601 GTGGCTGGCC GGCGTTTTGC CTCAGGAAAG AAAGTCACCT TGAATCCCAG

3651 TGACCCTGAG CACTGCCAGA TTTGCCACTG TGATGTTGTC AACCTCACCT

3701 GTGAAGCCTG CCAGGAGCCG ATATCGGGCG CGCCAACATC AGAGAGCGCC

3751 ACCCCTGAAA GTGGTCCCGG GAGCGAGCCA GCCACATCTG GGTCGGAAAC

3801 GCCAGGCACA AGTGAGTCTG CAACTCCCGA GTCCGGACCT GGCTCCGAGC

3851 CTGCCACTAG CGGCTCCGAG ACTCCGGGAA CTTCCGAGAG CGCTACACCA

3901 GAAAGCGGAC CCGGAACCAG TACCGAACCT AGCGAGGGCT CTGCTCCGGG

3951 CAGCCCAGCC GGCTCTCCTA CATCCACGGA GGAGGGCACT TCCGAATCCG

4001 CCACCCCGGA GTCAGGGCCA GGATCTGAAC CCGCTACCTC AGGCAGTGAG

4051 ACGCCAGGAA CGAGCGAGTC CGCTACACCG GAGAGTGGGC CAGGGAGCCC

4101 TGCTGGATCT CCTACGTCCA CTGAGGAAGG GTCACCAGCG GGCTCGCCCA

4151 CCAGCACTGA AGAAGGTGCC TCGATATCTG ACAAGAACAC TGGTGATTAT

4201 TACGAGGACA GTTATGAAGA TATTTCAGCA TACTTGCTGA GTAAAAACAA

4251 TGCCATTGAA CCAAGAAGCT TCTCTGACAA AACTCACACA TGCCCACCGT

4301 GCCCAGCTCC AGAACTCCTG GGCGGACCGT CAGTCTTCCT CTTCCCCCCA

4351 AAACCCAAGG ACACCCTCAT GATCTCCCGG ACCCCTGAGG TCACATGCGT

4401 GGTGGTGGAC GTGAGCCACG AAGACCCTGA GGTCAAGTTC AACTGGTACG

4451 TGGACGGCGT GGAGGTGCAT AATGCCAAGA CAAAGCCGCG GGAGGAGCAG

4501 TACAACAGCA CGTACCGTGT GGTCAGCGTC CTCACCGTCC TGCACCAGGA

4551 CTGGCTGAAT GGCAAGGAGT ACAAGTGCAA GGTCTCCAAC AAAGCCCTCC

4601 CAGCCCCCAT CGAGAAAACC ATCTCCAAAG CCAAAGGGCA GCCCCGAGAA

4651 CCACAGGTGT ACACCCTGCC CCCATCCCGG GATGAGCTGA CCAAGAACCA

4701 GGTCAGCCTG ACCTGCCTGG TCAAAGGCTT CTATCCCAGC GACATCGCCG

4751 TGGAGTGGGA GAGCAATGGG CAGCCGGAGA ACAACTACAA GACCACGCCT

4801 CCCGTGTTGG ACTCCGACGG CTCCTTCTTC CTCTACAGCA AGCTCACCGT

4851 GGACAAGAGC AGGTGGCAGC AGGGGAACGT CTTCTCATGC TCCGTGATGC

4901 ATGAGGCTCT GCACAACCAC TACACGCAGA AGAGCCTCTC CCTGTCTCCG

4951 GGTAAATGA pSYN VWF059 protein sequence (VWF D'D3-Fc with a2 region of FVIII thrombin site in the linker)-bold underlined area shows a2 region (SEQ ID NO: 197)

1 MIPARFAGVL LALALILPGT LCAEGTRGRS STARCSLFGS DFVNTFDGSM

51 YSFAGYCSYL LAGGCQKRSF SIIGDFQNGK RVSLSVYLGE FFDIHLFVNG

101 TVTQGDQRVS MPYASKGLYL ETEAGYYKLS GEAYGFVARI DGSGNFQVLL

151 SDRYFNKTCG LCGNFNIFAE DDFMTQEGTL TSDPYDFANS WALSSGEQWC

201 ERASPPSSSC NISSGEMQKG LWEQCQLLKS TSVFARCHPL VDPEPFVALC

251 EKTLCECAGG LECACPALLE YARTCAQEGM VLYGWTDHSA CSPVCPAGME

301 YRQCVSPCAR TCQSLHINEM CQERCVDGCS CPEGQLLDEG LCVESTECPC

351 VHSGKRYPPG TSLSRDCNTC ICRNSQWICS NEECPGECLV TGQSHFKSFD

-continued

401 NRYFTFSGIC QYLLARDCQD HSFSIVIETV QCADDRDAVC TRSVTVRLPG

451 LHNSLVKLKH GAGVAMDGQD IQLPLLKGDL RIQHTVTASV RLSYGEDLQM

501 DWDGRGRLLV KLSPVYAGKT CGLCGNYNGN QGDDFLTPSG LAEPRVEDFG

551 NAWKLHGDCQ DLQKQHSDPC ALNPRMTRFS EEACAVLTSP TFEACHRAVS

601 PLPYLRNCRY DVCSCSDGRE CLCGALASYA AACAGRGVRV AWREPGRCEL

651 NCPKGQVYLQ CGTPCNLTCR SLSYPDEECN EACLEGCFCP PGLYMDERGD

701 CVPKAQCPCY YDGEIFQPED IFSDHHTMCY CEDGFMHCTM SGVPGSLLPD

751 AVLSSPLSHR SKRSLSCRPP MVKLVCPADN LRAEGLECTK TCQNYDLECM

801 SMGCVSGCLC PPGMVRHENR CVALERCPCF HQGKEYAPGE TVKIGCNTCV

851 CRDRKWNCTD HVCDATCSTI GMAHYLTFDG LKYLFPGECQ YVLVQDYCGS

901 NPGTFRILVG NKGCSHPSVK CKKRVTILVE GGEIELFDGE VNVKRPMKDE

951 THFEVVESGR YIILLLGKAL SVVWDRHLSI SVVLKQTYQE KVCGLCGNFD

1001 GIQNNDLTSS NLQVEEDPVD FGNSWKVSSQ CADTRKVPLD SSPATCHNNI

1051 MKQTMVDSSC RILTSDVFQD CNKLVDPEPY LDVCIYDTCS CESIGDCAAF

1101 CDTIAAYAHV CAQHGKVVTW RTATLCPQSC EERNLRENGY EAEWRYNSCA

1151 PACQVTCQHP EPLACPVQCV EGCHAHCPPG KILDELLQTC VDPEDCPVCE

1201 VAGRRFASGK KVTLNPSDPE HCQICHCDVV NLTCEACQEP ISGAPTSESA

1251 TPESGPGSEP ATSGSETPGT SESATPESGP GSEPATSGSE TPGTSESATP

1301 ESGPGTSTEP SEGSAPGSPA GSPTSTEEGT SESATPESGP GSEPATSGSE

1351 TPGTSESATP ESGPGSPAGS PTSTEEGSPA GSPTSTEEGA SISDKNTGDY

1401 YEDSYEDISA YLLSKNNAIE PRSFSDKTHT CPPCPAPELL GGPSVFLFPP

1451 KPKDTLMISR TPEVTCVVVD VSHEDPEVKF NWYVDGVEVH NAKTKPREEQ

1501 YNSTYRVVSV LTVLHQDWLN GKEYKCKVSN KALPAPIEKT ISKAKGQPRE

1551 PQVYTLPPSR DELTKNQVSL TCLVKGFYPS DIAVEWESNG QPENNYKTTP

1601 PVLDSDGSFF LYSKLTVDKS RWQQGNVFSC SVMHEALHNH YTQKSLSLSP

1651 GK* pSYN VWF062 nucleotide sequence (encoding VWF D'D3-Fc with no thrombin site in the linker)

(SEQ ID NO: 198)

1 ATGATTCCTG CCAGATTTGC CGGGGTGCTG CTTGCTCTGG CCCTCATTTT

51 GCCAGGGACC CTTTGTGCAG AAGGAACTCG CGGCAGGTCA TCCACGGCCC

101 GATGCAGCCT TTTCGGAAGT GACTTCGTCA ACACCTTTGA TGGGAGCATG

151 TACAGCTTTG CGGGATACTG CAGTTACCTC CTGGCAGGGG GCTGCCAGAA

201 ACGCTCCTTC TCGATTATTG GGGACTTCCA GAATGGCAAG AGAGTGAGCC

251 TCTCCGTGTA TCTTGGGGAA TTTTTTGACA TCCATTTGTT TGTCAATGGT

301 ACCGTGACAC AGGGGGACCA AAGAGTCTCC ATGCCCTATG CCTCCAAAGG

351 GCTGTATCTA GAAACTGAGG CTGGGTACTA CAAGCTGTCC GGTGAGGCCT

401 ATGGCTTTGT GGCCAGGATC GATGGCAGCG GCAACTTTCA AGTCCTGCTG

451 TCAGACAGAT ACTTCAACAA GACCTGCGGG CTGTGTGGCA ACTTTAACAT

501 CTTTGCTGAA GATGACTTTA TGACCCAAGA AGGGACCTTG ACCTCGGACC

551 CTTATGACTT TGCCAACTCA TGGGCTCTGA GCAGTGGAGA ACAGTGGTGT

601 GAACGGGCAT CTCCTCCCAG CAGCTCATGC AACATCTCCT CTGGGGAAAT

-continued

```
651 GCAGAAGGGC CTGTGGGAGC AGTGCCAGCT TCTGAAGAGC ACCTCGGTGT
701 TTGCCCGCTG CCACCCTCTG GTGGACCCCG AGCCTTTTGT GGCCCTGTGT
751 GAGAAGACTT TGTGTGAGTG TGCTGGGGGG CTGGAGTGCG CCTGCCCTGC
801 CCTCCTGGAG TACGCCCGGA CCTGTGCCCA GGAGGGAATG GTGCTGTACG
851 GCTGGACCGA CCACAGCGCG TGCAGCCCAG TGTGCCCTGC TGGTATGGAG
901 TATAGGCAGT GTGTGTCCCC TTGCGCCAGG ACCTGCCAGA GCCTGCACAT
951 CAATGAAATG TGTCAGGAGC GATGCGTGGA TGGCTGCAGC TGCCCTGAGG
1001 GACAGCTCCT GGATGAAGGC CTCTGCGTGG AGAGCACCGA GTGTCCCTGC
1051 GTGCATTCCG GAAAGCGCTA CCCTCCCGGC ACCTCCCTCT CTCGAGACTG
1101 CAACACCTGC ATTTGCCGAA ACAGCCAGTG GATCTGCAGC AATGAAGAAT
1151 GTCCAGGGGA GTGCCTTGTC ACTGGTCAAT CCCACTTCAA GAGCTTTGAC
1201 AACAGATACT TCACCTTCAG TGGGATCTGC CAGTACCTGC TGGCCCGGGA
1251 TTGCCAGGAC CACTCCTTCT CCATTGTCAT TGAGACTGTC CAGTGTGCTG
1301 ATGACCGCGA CGCTGTGTGC ACCCGCTCCG TCACCGTCCG GCTGCCTGGC
1351 CTGCACAACA GCCTTGTGAA ACTGAAGCAT GGGGCAGGAG TTGCCATGGA
1401 TGGCCAGGAC ATCCAGCTCC CCCTCCTGAA AGGTGACCTC CGCATCCAGC
1451 ATACAGTGAC GGCCTCCGTG CGCCTCAGCT ACGGGGAGGA CCTGCAGATG
1501 GACTGGGATG GCCGCGGGAG GCTGCTGGTG AAGCTGTCCC CCGTCTATGC
1551 CGGGAAGACC TGCGGCCTGT GTGGGAATTA CAATGGCAAC CAGGGCGACG
1601 ACTTCCTTAC CCCCTCTGGG CTGGCGGAGC CCCGGGTGGA GGACTTCGGG
1651 AACGCCTGGA AGCTGCACGG GGACTGCCAG GACCTGCAGA AGCAGCACAG
1701 CGATCCCTGC GCCCTCAACC CGCGCATGAC CAGGTTCTCC GAGGAGGCGT
1751 GCGCGGTCCT GACGTCCCCC ACATTCGAGG CCTGCCATCG TGCCGTCAGC
1801 CCGCTGCCCT ACCTGCGGAA CTGCCGCTAC GACGTGTGCT CCTGCTCGGA
1851 CGGCCGCGAG TGCCTGTGCG GCGCCCTGGC CAGCTATGCC GCGGCCTGCG
1901 CGGGGAGAGG CGTGCGCGTC GCGTGGCGCG AGCCAGGCCG CTGTGAGCTG
1951 AACTGCCCGA AAGGCCAGGT GTACCTGCAG TGCGGGACCC CCTGCAACCT
2001 GACCTGCCGC TCTCTCTCTT ACCCGGATGA GGAATGCAAT GAGGCCTGCC
2051 TGGAGGGCTG CTTCTGCCCC CCAGGGCTCT ACATGGATGA GAGGGGGGAC
2101 TGCGTGCCCA AGGCCCAGTG CCCCTGTTAC TATGACGGTG AGATCTTCCA
2151 GCCAGAAGAC ATCTTCTCAG ACCATCACAC CATGTGCTAC TGTGAGGATG
2201 GCTTCATGCA CTGTACCATG AGTGGAGTCC CCGGAAGCTT GCTGCCTGAC
2251 GCTGTCCTCA GCAGTCCCCT GTCTCATCGC AGCAAAAGGA GCCTATCCTG
2301 TCGGCCCCCC ATGGTCAAGC TGGTGTGTCC CGCTGACAAC CTGCGGGCTG
2351 AAGGGCTCGA GTGTACCAAA ACGTGCCAGA ACTATGACCT GGAGTGCATG
2401 AGCATGGGCT GTGTCTCTGG CTGCCTCTGC CCCCCGGGCA TGGTCCGGCA
2451 TGAGAACAGA TGTGTGGCCC TGGAAAGGTG TCCCTGCTTC CATCAGGGCA
2501 AGGAGTATGC CCCTGGAGAA ACAGTGAAGA TTGGCTGCAA CACTTGTGTC
2551 TGTCGGGACC GGAAGTGGAA CTGCACAGAC CATGTGTGTG ATGCCACGTG
2601 CTCCACGATC GGCATGGCCC ACTACCTCAC CTTCGACGGG CTCAAATACC
2651 TGTTCCCCGG GGAGTGCCAG TACGTTCTGG TGCAGGATTA CTGCGGCAGT
```

-continued

2701 AACCCTGGGA CCTTTCGGAT CCTAGTGGGG AATAAGGGAT GCAGCCACCC

2751 CTCAGTGAAA TGCAAGAAAC GGGTCACCAT CCTGGTGGAG GGAGGAGAGA

2801 TTGAGCTGTT TGACGGGGAG GTGAATGTGA AGAGGCCCAT GAAGGATGAG

2851 ACTCACTTTG AGGTGGTGGA GTCTGGCCGG TACATCATTC TGCTGCTGGG

2901 CAAAGCCCTC TCCGTGGTCT GGGACCGCCA CCTGAGCATC TCCGTGGTCC

2951 TGAAGCAGAC ATACCAGGAG AAAGTGTGTG GCCTGTGTGG GAATTTTGAT

3001 GGCATCCAGA ACAATGACCT CACCAGCAGC AACCTCCAAG TGGAGGAAGA

3051 CCCTGTGGAC TTTGGGAACT CCTGGAAAGT GAGCTCGCAG TGTGCTGACA

3101 CCAGAAAAGT GCCTCTGGAC TCATCCCCTG CCACCTGCCA TAACAACATC

3151 ATGAAGCAGA CGATGGTGGA TTCCTCCTGT AGAATCCTTA CCAGTGACGT

3201 CTTCCAGGAC TGCAACAAGC TGGTGGACCC CGAGCCATAT CTGGATGTCT

3251 GCATTTACGA CACCTGCTCC TGTGAGTCCA TTGGGGACTG CGCCGCATTC

3301 TGCGACACCA TTGCTGCCTA TGCCCACGTG TGTGCCCAGC ATGGCAAGGT

3351 GGTGACCTGG AGGACGGCCA CATTGTGCCC CCAGAGCTGC GAGGAGAGGA

3401 ATCTCCGGGA GAACGGGTAT GAGGCTGAGT GGCGCTATAA CAGCTGTGCA

3451 CCTGCCTGTC AAGTCACGTG TCAGCACCCT GAGCCACTGG CCTGCCCTGT

3501 GCAGTGTGTG GAGGGCTGCC ATGCCCACTG CCCTCCAGGG AAAATCCTGG

3551 ATGAGCTTTT GCAGACCTGC GTTGACCCTG AAGACTGTCC AGTGTGTGAG

3601 GTGGCTGGCC GGCGTTTTGC CTCAGGAAAG AAAGTCACCT TGAATCCCAG

3651 TGACCCTGAG CACTGCCAGA TTTGCCACTG TGATGTTGTC AACCTCACCT

3701 GTGAAGCCTG CCAGGAGCCG ATATCGGGCG CGCCAACATC AGAGAGCGCC

3751 ACCCCTGAAA GTGGTCCCGG GAGCGAGCCA GCCACATCTG GGTCGGAAAC

3801 GCCAGGCACA AGTGAGTCTG CAACTCCCGA GTCCGGACCT GGCTCCGAGC

3851 CTGCCACTAG CGGCTCCGAG ACTCCGGGAA CTTCCGAGAG CGCTACACCA

3901 GAAAGCGGAC CCGGAACCAG TACCGAACCT AGCGAGGGCT CTGCTCCGGG

3951 CAGCCCAGCC GGCTCTCCTA CATCCACGGA GGAGGGCACT TCCGAATCCG

4001 CCACCCCGGA GTCAGGGCCA GGATCTGAAC CCGCTACCTC AGGCAGTGAG

4051 ACGCCAGGAA CGAGCGAGTC CGCTACACCG GAGAGTGGGC CAGGGAGCCC

4101 TGCTGGATCT CCTACGTCCA CTGAGGAAGG GTCACCAGCG GGCTCGCCCA

4151 CCAGCACTGA AGAAGGTGCC TCGAGCGACA AAACTCACAC ATGCCCACCG

4201 TGCCCAGCTC CAGAACTCCT GGGCGGACCG TCAGTCTTCC TCTTCCCCCC

4251 AAAACCCAAG GACACCCTCA TGATCTCCCG GACCCCTGAG GTCACATGCG

4301 TGGTGGTGGA CGTGAGCCAC GAAGACCCTG AGGTCAAGTT CAACTGGTAC

4351 GTGGACGGCG TGGAGGTGCA TAATGCCAAG ACAAAGCCGC GGGAGGAGCA

4401 GTACAACAGC ACGTACCGTG TGGTCAGCGT CCTCACCGTC CTGCACCAGG

4451 ACTGGCTGAA TGGCAAGGAG TACAAGTGCA AGGTCTCCAA CAAAGCCCTC

4501 CCAGCCCCCA TCGAGAAAAC CATCTCCAAA GCCAAAGGGC AGCCCCGAGA

4551 ACCACAGGTG TACACCCTGC CCCCATCCCG GGATGAGCTG ACCAAGAACC

4601 AGGTCAGCCT GACCTGCCTG GTCAAAGGCT TCTATCCCAG CGACATCGCC

4651 GTGGAGTGGG AGAGCAATGG GCAGCCGGAG AACAACTACA AGACCACGCC

-continued

```
4701 TCCCGTGTTG GACTCCGACG GCTCCTTCTT CCTCTACAGC AAGCTCACCG

4751 TGGACAAGAG CAGGTGGCAG CAGGGGAACG TCTTCTCATG CTCCGTGATG

4801 CATGAGGCTC TGCACAACCA CTACACGCAG AAGAGCCTCT CCCTGTCTCC

4851 GGGTAAATGA
```

pSYN VWF062 protein sequence (VWF D′D3-Fc with no thrombin site in the linker)

(SEQ ID NO: 199

```
   1 MIPARFAGVL LALALILPGT LCAEGTRGRS STARCSLFGS DFVNTFDGSM

  51 YSFAGYCSYL LAGGCQKRSF SIIGDFQNGK RVSLSVYLGE FFDIHLFVNG

 101 TVTQGDQRVS MPYASKGLYL ETEAGYYKLS GEAYGFVARI DGSGNFQVLL

 151 SDRYFNKTCG LCGNFNIFAE DDFMTQEGTL TSDPYDFANS WALSSGEQWC

 201 ERASPPSSSC NISSGEMQKG LWEQCQLLKS TSVFARCHPL VDPEPFVALC

 251 EKTLCECAGG LECACPALLE YARTCAQEGM VLYGWTDHSA CSPVCPAGME

 301 YRQCVSPCAR TCQSLHINEM CQERCVDGCS CPEGQLLDEG LCVESTECPC

 351 VHSGKRYPPG TSLSRDCNTC ICRNSQWICS NEECPGECLV TGQSHFKSFD

 401 NRYFTFSGIC QYLLARDCQD HSFSIVIETV QCADDRDAVC TRSVTVRLPG

 451 LHNSLVKLKH GAGVAMDGQD IQLPLLKGDL RIQHTVTASV RLSYGEDLQM

 501 DWDGRGRLLV KLSPVYAGKT CGLCGNYNGN QGDDFLTPSG LAEPRVEDFG

 551 NAWKLHGDCQ DLQKQHSDPC ALNPRMTRFS EEACAVLTSP TFEACHRAVS

 601 PLPYLRNCRY DVCSCSDGRE CLCGALASYA AACAGRGVRV AWREPGRCEL

 651 NCPKGQVYLQ CGTPCNLTCR SLSYPDEECN EACLEGCFCP PGLYMDERGD

 701 CVPKAQCPCY YDGEIFQPED IFSDHHTMCY CEDGFMHCTM SGVPGSLLPD

 751 AVLSSPLSHR SKRSLSCRPP MVKLVCPADN LRAEGLECTK TCQNYDLECM

 801 SMGCVSGCLC PPGMVRHENR CVALERCPCF HQGKEYAPGE TVKIGCNTCV

 851 CRDRKWNCTD HVCDATCSTI GMAHYLTFDG LKYLFPGECQ YVLVQDYCGS

 901 NPGTFRILVG NKGCSHPSVK CKKRVTILVE GGEIELFDGE VNVKRPMKDE

 951 THFEVVESGR YIILLLGKAL SVVWDRHLSI SVVLKQTYQE KVCGLCGNFD

1001 GIQNNDLTSS NLQVEEDPVD FGNSWKVSSQ CADTRKVPLD SSPATCHNNI

1051 MKQTMVDSSC RILTSDVFQD CNKLVDPEPY LDVCIYDTCS CESIGDCAAF

1101 CDTIAAYAHV CAQHGKVVTW RTATLCPQSC EERNLRENGY EAEWRYNSCA

1151 PACQVTCQHP EPLACPVQCV EGCHAHCPPG KILDELLQTC VDPEDCPVCE

1201 VAGRRFASGK KVTLNPSDPE HCQICHCDVV NLTCEACQEP ISGAPTSESA

1251 TPESGPGSEP ATSGSETPGT SESATPESGP GSEPATSGSE TPGTSESATP

1301 ESGPGTSTEP SEGSAPGSPA GSPTSTEEGT SESATPESGP GSEPATSGSE

1351 TPGTSESATP ESGPGSPAGS PTSTEEGSPA GSPTSTEEGA SSDKTHTCPP

1401 CPAPELLGGP SVFLFPPKPK DTLMISRTPE VTCVVVDVSH EDPEVKFNWY

1451 VDGVEVHNAK TKPREEQYNS TYRVVSVLTV LHQDWLNGKE YKCKVSNKAL

1501 PAPIEKTISK AKGQPREPQV YTLPPSRDEL TKNQVSLTCL VKGFYPSDIA

1551 VEWESNGQPE NNYKTTPPVL DSDGSFFLYS KLTVDKSRWQ QGNVFSCSVM

1601 HEALHNHYTQ KSLSLSPGK*
```

pSYN VWF073 nucleotide sequence-(encoding VWFD1D2D′D3-144 AE XTEN-FVIII truncated a2 thrombin site-Fc)

(SEQ ID NO: 174)

```
   1 ATGATTCCTG CCAGATTTGC CGGGGTGCTG CTTGCTCTGG CCCTCATTTT
```

-continued

```
  51 GCCAGGGACC CTTTGTGCAG AAGGAACTCG CGGCAGGTCA TCCACGGCCC
 101 GATGCAGCCT TTTCGGAAGT GACTTCGTCA ACACCTTTGA TGGGAGCATG
 151 TACAGCTTTG CGGGATACTG CAGTTACCTC CTGGCAGGGG GCTGCCAGAA
 201 ACGCTCCTTC TCGATTATTG GGGACTTCCA GAATGGCAAG AGAGTGAGCC
 251 TCTCCGTGTA TCTTGGGGAA TTTTTTGACA TCCATTTGTT TGTCAATGGT
 301 ACCGTGACAC AGGGGGACCA AAGAGTCTCC ATGCCCTATG CCTCCAAAGG
 351 GCTGTATCTA GAAACTGAGG CTGGGTACTA CAAGCTGTCC GGTGAGGCCT
 401 ATGGCTTTGT GGCCAGGATC GATGGCAGCG GCAACTTTCA AGTCCTGCTG
 451 TCAGACAGAT ACTTCAACAA GACCTGCGGG CTGTGTGGCA ACTTTAACAT
 501 CTTTGCTGAA GATGACTTTA TGACCCAAGA AGGGACCTTG ACCTCGGACC
 551 CTTATGACTT TGCCAACTCA TGGGCTCTGA GCAGTGGAGA ACAGTGGTGT
 601 GAACGGGCAT CTCCTCCCAG CAGCTCATGC AACATCTCCT CTGGGGAAAT
 651 GCAGAAGGGC CTGTGGGAGC AGTGCCAGCT TCTGAAGAGC ACCTCGGTGT
 701 TTGCCCGCTG CCACCCTCTG GTGGACCCCG AGCCTTTTGT GGCCCTGTGT
 751 GAGAAGACTT TGTGTGAGTG TGCTGGGGGG CTGGAGTGCG CCTGCCCTGC
 801 CCTCCTGGAG TACGCCCGGA CCTGTGCCCA GGAGGGAATG GTGCTGTACG
 851 GCTGGACCGA CCACAGCGCG TGCAGCCCAG TGTGCCCTGC TGGTATGGAG
 901 TATAGGCAGT GTGTGTCCCC TTGCGCCAGG ACCTGCCAGA GCCTGCACAT
 951 CAATGAAATG TGTCAGGAGC GATGCGTGGA TGGCTGCAGC TGCCCTGAGG
1001 GACAGCTCCT GGATGAAGGC CTCTGCGTGG AGAGCACCGA GTGTCCCTGC
1051 GTGCATTCCG GAAAGCGCTA CCCTCCCGGC ACCTCCCTCT CTCGAGACTG
1101 CAACACCTGC ATTTGCCGAA ACAGCCAGTG GATCTGCAGC AATGAAGAAT
1151 GTCCAGGGGA GTGCCTTGTC ACTGGTCAAT CCCACTTCAA GAGCTTTGAC
1201 AACAGATACT TCACCTTCAG TGGGATCTGC CAGTACCTGC TGGCCCGGGA
1251 TTGCCAGGAC CACTCCTTCT CCATTGTCAT TGAGACTGTC CAGTGTGCTG
1301 ATGACCGCGA CGCTGTGTGC ACCCGCTCCG TCACCGTCCG GCTGCCTGGC
1351 CTGCACAACA GCCTTGTGAA ACTGAAGCAT GGGGCAGGAG TTGCCATGGA
1401 TGGCCAGGAC ATCCAGCTCC CCCTCCTGAA AGGTGACCTC CGCATCCAGC
1451 ATACAGTGAC GGCCTCCGTG CGCCTCAGCT ACGGGGAGGA CCTGCAGATG
1501 GACTGGGATG GCCGCGGGAG GCTGCTGGTG AAGCTGTCCC CCGTCTATGC
1551 CGGGAAGACC TGCGGCCTGT GTGGGAATTA CAATGGCAAC CAGGGCGACG
1601 ACTTCCTTAC CCCCTCTGGG CTGGCGGAGC CCCGGGTGGA GGACTTCGGG
1651 AACGCCTGGA AGCTGCACGG GGACTGCCAG GACCTGCAGA AGCAGCACAG
1701 CGATCCCTGC GCCCTCAACC CGCGCATGAC CAGGTTCTCC GAGGAGGCGT
1751 GCGCGGTCCT GACGTCCCCC ACATTCGAGG CCTGCCATCG TGCCGTCAGC
1801 CCGCTGCCCT ACCTGCGGAA CTGCCGCTAC GACGTGTGCT CCTGCTCGGA
1851 CGGCCGCGAG TGCCTGTGCG GCGCCCTGGC CAGCTATGCC GCGGCCTGCG
1901 CGGGGAGAGG CGTGCGCGTC GCGTGGCGCG AGCCAGGCCG CTGTGAGCTG
1951 AACTGCCCGA AAGGCCAGGT GTACCTGCAG TGCGGGACCC CCTGCAACCT
2001 GACCTGCCGC TCTCTCTCTT ACCCGGATGA GGAATGCAAT GAGGCCTGCC
```

-continued

2051 TGGAGGGCTG CTTCTGCCCC CCAGGGCTCT ACATGGATGA GAGGGGGGAC

2101 TGCGTGCCCA AGGCCCAGTG CCCCTGTTAC TATGACGGTG AGATCTTCCA

2151 GCCAGAAGAC ATCTTCTCAG ACCATCACAC CATGTGCTAC TGTGAGGATG

2201 GCTTCATGCA CTGTACCATG AGTGGAGTCC CCGGAAGCTT GCTGCCTGAC

2251 GCTGTCCTCA GCAGTCCCCT GTCTCATCGC AGCAAAAGGA GCCTATCCTG

2301 TCGGCCCCCC ATGGTCAAGC TGGTGTGTCC CGCTGACAAC CTGCGGGCTG

2351 AAGGGCTCGA GTGTACCAAA ACGTGCCAGA ACTATGACCT GGAGTGCATG

2401 AGCATGGGCT GTGTCTCTGG CTGCCTCTGC CCCCCGGGCA TGGTCCGGCA

2451 TGAGAACAGA TGTGTGGCCC TGGAAAGGTG TCCCTGCTTC CATCAGGGCA

2501 AGGAGTATGC CCCTGGAGAA ACAGTGAAGA TTGGCTGCAA CACTTGTGTC

2551 TGTCGGGACC GGAAGTGGAA CTGCACAGAC CATGTGTGTG ATGCCACGTG

2601 CTCCACGATC GGCATGGCCC ACTACCTCAC CTTCGACGGG CTCAAATACC

2651 TGTTCCCCGG GGAGTGCCAG TACGTTCTGG TGCAGGATTA CTGCGGCAGT

2701 AACCCTGGGA CCTTTCGGAT CCTAGTGGGG AATAAGGGAT GCAGCCACCC

2751 CTCAGTGAAA TGCAAGAAAC GGGTCACCAT CCTGGTGGAG GGAGGAGAGA

2801 TTGAGCTGTT TGACGGGGAG GTGAATGTGA AGAGGCCCAT GAAGGATGAG

2851 ACTCACTTTG AGGTGGTGGA GTCTGGCCGG TACATCATTC TGCTGCTGGG

2901 CAAAGCCCTC TCCGTGGTCT GGGACCGCCA CCTGAGCATC TCCGTGGTCC

2951 TGAAGCAGAC ATACCAGGAG AAAGTGTGTG GCCTGTGTGG GAATTTTGAT

3001 GGCATCCAGA ACAATGACCT CACCAGCAGC AACCTCCAAG TGGAGGAAGA

3051 CCCTGTGGAC TTTGGGAACT CCTGGAAAGT GAGCTCGCAG TGTGCTGACA

3101 CCAGAAAAGT GCCTCTGGAC TCATCCCCTG CCACCTGCCA TAACAACATC

3151 ATGAAGCAGA CGATGGTGGA TTCCTCCTGT AGAATCCTTA CCAGTGACGT

3201 CTTCCAGGAC TGCAACAAGC TGGTGGACCC CGAGCCATAT CTGGATGTCT

3251 GCATTTACGA CACCTGCTCC TGTGAGTCCA TTGGGGACTG CGCCGCATTC

3301 TGCGACACCA TTGCTGCCTA TGCCCACGTG TGTGCCCAGC ATGGCAAGGT

3351 GGTGACCTGG AGGACGGCCA CATTGTGCCC CCAGAGCTGC GAGGAGAGGA

3401 ATCTCCGGGA GAACGGGTAT GAGGCTGAGT GGCGCTATAA CAGCTGTGCA

3451 CCTGCCTGTC AAGTCACGTG TCAGCACCCT GAGCCACTGG CCTGCCCTGT

3501 GCAGTGTGTG GAGGGCTGCC ATGCCCACTG CCCTCCAGGG AAAATCCTGG

3551 ATGAGCTTTT GCAGACCTGC GTTGACCCTG AAGACTGTCC AGTGTGTGAG

3601 GTGGCTGGCC GGCGTTTTGC CTCAGGAAAG AAAGTCACCT TGAATCCCAG

3651 TGACCCTGAG CACTGCCAGA TTTGCCACTG TGATGTTGTC AACCTCACCT

3701 GTGAAGCCTG CCAGGAGCCG GGCGCGCCAA CATCAGAGAG CGCCACCCCT

3751 GAAAGTGGTC CCGGGAGCGA GCCAGCCACA TCTGGGTCGG AAACGCCAGG

3801 CACAAGTGAG TCTGCAACTC CCGAGTCCGG ACCTGGCTCC GAGCCTGCCA

3851 CTAGCGGCTC CGAGACTCCG GGAACTTCCG AGAGCGCTAC ACCAGAAAGC

3901 GGACCCGGAA CCAGTACCGA ACCTAGCGAG GGCTCTGCTC CGGGCAGCCC

3951 AGCCGGCTCT CCTACATCCA CGGAGGAGGG CACTTCCGAA TCCGCCACCC

4001 CGGAGTCAGG GCCAGGATCT GAACCCGCTA CCTCAGGCAG TGAGACGCCA

4051 GGAACGAGCG AGTCCGCTAC ACCGGAGAGT GGGCCAGGGA GCCCTGCTGG

-continued

4101 ATCTCCTACG TCCACTGAGG AAGGGTCACC AGCGGGCTCG CCCACCAGCA

4151 CTGAAGAAGG TGCCTCGAGC GGCGGTGGAG GATCCGGTGG CGGGGGATCC

4201 GGTGGCGGGG GATCCGGTGG CGGGGGATCC GGTGGCGGGG GATCCGGTGG

4251 CGGGGGATCC ATTGAACCAA GAAGCTTCTC TGGCAGCGGA GGCGACAAAA

4301 CTCACACATG CCCACCGTGC CCAGCTCCAG AACTCCTGGG CGGACCGTCA

4351 GTCTTCCTCT TCCCCCCAAA ACCCAAGGAC ACCCTCATGA TCTCCCGGAC

4401 CCCTGAGGTC ACATGCGTGG TGGTGGACGT GAGCCACGAA GACCCTGAGG

4451 TCAAGTTCAA CTGGTACGTG GACGGCGTGG AGGTGCATAA TGCCAAGACA

4501 AAGCCGCGGG AGGAGCAGTA CAACAGCACG TACCGTGTGG TCAGCGTCCT

4551 CACCGTCCTG CACCAGGACT GGCTGAATGG CAAGGAGTAC AAGTGCAAGG

4601 TCTCCAACAA AGCCCTCCCA GCCCCCATCG AGAAAACCAT CTCCAAAGCC

4651 AAAGGGCAGC CCCGAGAACC ACAGGTGTAC ACCCTGCCCC CATCCCGGGA

4701 TGAGCTGACC AAGAACCAGG TCAGCCTGAC CTGCCTGGTC AAAGGCTTCT

4751 ATCCCAGCGA CATCGCCGTG GAGTGGGAGA GCAATGGGCA GCCGGAGAAC

4801 AACTACAAGA CCACGCCTCC CGTGTTGGAC TCCGACGGCT CCTTCTTCCT

4851 CTACAGCAAG CTCACCGTGG ACAAGAGCAG GTGGCAGCAG GGGAACGTCT

4901 TCTCATGCTC CGTGATGCAT GAGGCTCTGC ACAACCACTA CACGCAGAAG

4951 AGCCTCTCCC TGTCTCCGGG TAAATGA pSYN VWF073 protein sequence-(VWFD1D2D′D3-144 AE XTEN-truncated a2 thrombin site-Fc)

(SEQ ID NO: 175)

1 MIPARFAGVL LALALILPGT LCAEGTRGRS STARCSLFGS DFVNTFDGSM

51 YSFAGYCSYL LAGGCQKRSF SIIGDFQNGK RVSLSVYLGE FFDIHLFVNG

101 TVTQGDQRVS MPYASKGLYL ETEAGYYKLS GEAYGFVARI DGSGNFQVLL

151 SDRYFNKTCG LCGNFNIFAE DDFMTQEGTL TSDPYDFANS WALSSGEQWC

201 ERASPPSSSC NISSGEMQKG LWEQCQLLKS TSVFARCHPL VDPEPFVALC

251 EKTLCECAGG LECACPALLE YARTCAQEGM VLYGWTDHSA CSPVCPAGME

301 YRQCVSPCAR TCQSLHINEM CQERCVDGCS CPEGQLLDEG LCVESTECPC

351 VHSGKRYPPG TSLSRDCNTC ICRNSQWICS NEECPGECLV TGQSHFKSFD

401 NRYFTFSGIC QYLLARDCQD HSFSIVIETV QCADDRDAVC TRSVTVRLPG

451 LHNSLVKLKH GAGVAMDGQD IQLPLLKGDL RIQHTVTASV RLSYGEDLQM

501 DWDGRGRLLV KLSPVYAGKT CGLCGNYNGN QGDDFLTPSG LAEPRVEDFG

551 NAWKLHGDCQ DLQKQHSDPC ALNPRMTRFS EEACAVLTSP TFEACHRAVS

601 PLPYLRNCRY DVCSCSDGRE CLCGALASYA AACAGRGVRV AWREPGRCEL

651 NCPKGQVYLQ CGTPCNLTCR SLSYPDEECN EACLEGCFCP PGLYMDERGD

701 CVPKAQCPCY YDGEIFQPED IFSDHHTMCY CEDGFMHCTM SGVPGSLLPD

751 AVLSSPLSHR SKRSLSCRPP MVKLVCPADN LRAEGLECTK TCQNYDLECM

801 SMGCVSGCLC PPGMVRHENR CVALERCPCF HQGKEYAPGE TVKIGCNTCV

851 CRDRKWNCTD HVCDATCSTI GMAHYLTFDG LKYLFPGECQ YVLVQDYCGS

901 NPGTFRILVG NKGCSHPSVK CKKRVTILVE GGEIELFDGE VNVKRPMKDE

951 THFEVVESGR YIILLLGKAL SVVWDRHLSI SVVLKQTYQE KVCGLCGNFD

1001 GIQNNDLTSS NLQVEEDPVD FGNSWKVSSQ CADTRKVPLD SSPATCHNNI

-continued

```
1051 MKQTMVDSSC RILTSDVFQD CNKLVDPEPY LDVCIYDTCS CESIGDCAAF

1101 CDTIAAYAHV CAQHGKVVTW RTATLCPQSC EERNLRENGY EAEWRYNSCA

1151 PACQVTCQHP EPLACPVQCV EGCHAHCPPG KILDELLQTC VDPEDCPVCE

1201 VAGRRFASGK KVTLNPSDPE HCQICHCDVV NLTCEACQEP GAPTSESATP

1251 ESGPGSEPAT SGSETPGTSE SATPESGPGS EPATSGSETP GTSESATPES

1301 GPGTSTEPSE GSAPGSPAGS PTSTEEGTSE SATPESGPGS EPATSGSETP

1351 GTSESATPES GPGSPAGSPT STEEGSPAGS PTSTEEGASS GGGGSGGGGS

1401 GGGGSGGGGS GGGGSGGGGS IEPRSFSGSG GDKTHTCPPC PAPELLGGPS

1451 VFLFPPKPKD TLMISRTPEV TCVVVDVSHE DPEVKFNWYV DGVEVHNAKT

1501 KPREEQYNST YRVVSVLTVL HQDWLNGKEY KCKVSNKALP APIEKTISKA

1551 KGQPREPQVY TLPPSRDELT KNQVSLTCLV KGFYPSDIAV EWESNGQPEN

1601 NYKTTPPVLD SDGSFFLYSK LTVDKSRWQQ GNVFSCSVMH EALHNHYTQK

1651 SLSLSPGK*
```

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are incorporated by reference herein in their entirety.

---

SEQUENCE LISTING

The patent contains a lengthy sequence listing. A copy of the sequence listing is available in electronic form from the USPTO web site (https://seqdata.uspto.gov/docdetail?docId=US12617839B2). An electronic copy of the sequence listing will also be available from the USPTO upon request and payment of the fee set forth in 37 CFR 1.19(b)(3).

---

What is claimed is:

1. A method of treating a disorder caused by a deficiency in Factor VIII comprising administering to a subject in need thereof a therapeutically effective amount of a chimeric protein comprising:

(i) a first polypeptide chain which comprises, from the N-terminus to the C-terminus thereof:

(a) a Factor VIII ("FVIII") protein comprising a N-terminal portion and a C-terminal portion;

wherein the N-terminal portion of the FVIII protein comprises the A1 domain, A2 domain, and a portion of the B domain of full length mature FVIII (SEQ ID NO: 65);

such that the N-terminal portion comprises the amino acid sequence of residues 1 to 745 of SEQ ID NO: 65;

wherein the N-terminal portion is fused to a first XTEN sequence inserted immediately downstream of amino acid 745 of SEQ ID NO: 65; and wherein the C-terminal portion comprises the A3 domain, the C1 domain, and the C2 domain, such that the C-terminal portion comprises residues 1690-2332 of SEQ ID NO: 65;

(b) a first immunoglobulin ("Ig") constant region or a portion thereof, wherein the first XTEN sequence comprises the amino acid sequence of SEQ ID NO: 8; and (ii) a second polypeptide chain which comprises, from the N-terminus to the C-terminus thereof:

(a) a von Willebrand Factor ("VWF") protein comprising a D' domain and a D3 domain of VWF, wherein the VWF protein contains a residue other than cysteine substituted for residues corresponding to residues 1099 and 1142 of SEQ ID NO: 21;

(b) a second XTEN sequence comprising the amino acid sequence of SEQ ID NO: 58, wherein the second XTEN sequence contains less than 288 amino acid residues;

(c) a cleavable linker comprising an a2 region of FVIII which comprises the amino acid sequence of Glu720 to Arg740 corresponding to SEQ ID NO: 65, wherein the a2 region is capable of being cleaved by thrombin; and (d) a second Ig constant region or a portion thereof, wherein the first polypeptide chain is associated with the second polypeptide chain through the first Ig constant region or a portion thereof and the second Ig constant region or a portion thereof.

2. The method of claim 1, wherein the disorder is hemophilia A.

3. The method of claim 2, wherein wherein the first Ig constant region or portion thereof is associated with the second Ig constant region or portion thereof through two disulfide bonds.

4. The method of claim 3, wherein wherein the first Ig constant region or portion thereof is a first Fc region and the second Ig constant region or portion thereof is a second Fc region.

5. The method of claim 4, wherein the cleavable linker is 20 to 50 amino acids long.

6. The method of claim 3, wherein the cleavable linker is about 30 amino acids long.

7. The method of claim 2, wherein the chimeric protein is administered prophylactically.

8. The method of claim 2, wherein the chimeric protein is administered for on-demand treatment.

9. The method of claim 2, wherein the chimeric protein is administered prior to, during, or after surgery.

10. The method of claim 2, wherein the chimeric protein is administered to control an acute bleeding episode.

11. A method of treating a disorder that comprises a deficiency in Factor VIII comprising intravenously administering to a subject in need thereof a therapeutically effective amount of a chimeric protein comprising:

(i) a first polypeptide chain which comprises, from the N-terminus to the C-terminus thereof:

(a) a Factor VIII ("FVIII") protein comprising the amino acid sequence of residues 1 to 745 of SEQ ID NO: 65, fused to a first XTEN sequence inserted immediately downstream of residue 745 of SEQ ID NO: 65, fused to residues 1649 to 2332 of SEQ ID NO: 65, and (b) a first Fc region;

wherein the first XTEN sequence comprises the amino acid sequence of SEQ ID NO: 8; and (ii) a second polypeptide chain which comprises, from the N-terminus to the C-terminus thereof:

(a) a von Willebrand Factor ("VWF") protein comprising a D' domain and a D3 domain of VWF, wherein the VWF protein comprises the amino acid sequence of residues 764 to 1240 of SEQ ID NO: 21 with alanine substitutions at residues 1099 and 1142 of SEQ ID NO: 21, (b) a second XTEN sequence comprising the amino acid sequence of SEQ ID NO: 58, (c) a cleavable linker comprising the amino acid sequence of SEQ ID NO: 88, and (d) a second Fc region;

wherein the first Fc region is associated with the second Fc region through a disulfide bond.

12. A method of treating a disorder that comprises a deficiency in Factor VIII comprising intravenously administering to a subject in need thereof a therapeutically effective amount of a chimeric protein comprising:

(i) a first polypeptide chain which comprises, from the N-terminus to the C-terminus thereof:

(a) a Factor VIII ("FVIII") protein comprising an amino acid sequence that is at least 99% identical to SEQ ID NO: 67 with a first XTEN sequence inserted immediately downstream of the residue corresponding to residue 745 of SEQ ID NO: 67; and (b) a first Fc region;

wherein the first XTEN sequence comprises the amino acid sequence of SEQ ID NO: 8; and (ii) a second polypeptide chain which comprises, from the N-terminus to the C-terminus thereof:

(a) a von Willebrand Factor ("VWF") protein comprising a D' domain and a D3 domain of VWF, wherein the VWF protein contains a residue other than cysteine substituted for residues 1099 and 1142 of SEQ ID NO: 21;

(b) a second XTEN sequence comprising the amino acid sequence of SEQ ID NO: 58, wherein the second XTEN sequence contains less than 288 amino acid residues;

(c) a cleavable linker comprising an a2 region of FVIII which comprises the amino acid sequence of Glu720 to Arg740 corresponding to SEQ ID NO: 65, wherein the a2 region is capable of being cleaved by thrombin; and (d) a second Fc region, wherein the first Fc region is associated with the second Fc region through a disulfide bond.

13. A method of treating a disorder that comprises a deficiency in Factor VIII comprising intravenously administering to a subject in need thereof a therapeutically effective amount of a chimeric protein comprising:

(i) a first polypeptide chain which comprises a Factor VIII ("FVIII") protein fused to a first immunoglobulin ("Ig") constant region or a portion thereof, wherein the FVIII protein comprises the amino acid sequence of residues 1 to 745 of SEQ ID NO: 202, fused to a first XTEN sequence inserted immediately downstream of residue 745 of SEQ ID NO: 202, fused to residues 746 to 1429 of SEQ ID NO: 202; and wherein the first XTEN sequence comprises the amino acid sequence of SEQ ID NO: 8; and (ii) a second polypeptide chain which comprises a von Willebrand Factor ("VWF") protein comprising a D' domain and a D3 domain of VWF fused to a second Ig constant region or a portion thereof by a second XTEN sequence in-between, wherein the VWF protein comprises the amino acid sequence of SEQ ID NO: 201;

wherein the second XTEN sequence comprises the amino acid sequence of SEQ ID NO: 58; and wherein the second XTEN sequence is linked to the second Ig constant region or a portion thereof by a linker comprising the amino acid sequence of SEQ ID NO: 88;

wherein the first polypeptide chain is associated with the second polypeptide chain through the first Ig constant region or a portion thereof and the second Ig constant region or a portion thereof.

14. The method of claim 1, wherein the disorder is Von Willebrand Disease.

15. The method of claim 14, wherein the Von Willebrand Disease is Von Willebrand Disease type 3.

16. The method of claim 2, wherein the C-terminal portion of the FVIII protein comprises an amino acid sequence at least 95% identical to residues 1641 to 2332of SEQ ID NO: 65.

17. The method of claim 16, wherein the VWF protein contains an alanine substitution at residue 1099 and residue 1142 of SEQ ID NO: 21.

18. The method of claim 17, wherein the first Fc region and the second Fc region are the same.

19. The method of claim 18, wherein the first Fc region and the second Fc region are derived from human IgG1.

20. The method of claim 19, wherein the VWF protein consists of the D' domain and the D3 domain.

21. The method of claim 11, wherein the disorder is hemophilia A.

22. The method of claim 11, wherein the disorder is Von Willebrand Disease.

23. The method of claim 22, wherein the Von Willebrand Disease is Von Willebrand Disease type 3.

24. The method of claim 21, wherein the first Fc region is associated with the second Fc region through two disulfide bonds.

25. The method of claim 21, wherein the second XTEN sequence links the VWF protein to the cleavable linker, such that the second polypeptide chain comprises the amino acid sequence of SEQ ID NO: 22.

26. The method of claim 25, wherein the first XTEN sequence is inserted into the FVIII protein such that the first polypeptide chain comprises the amino acid sequence of SEQ ID NO: 2.

27. The method of claim 26, wherein the first polypeptide chain comprises an amino acid sequence at least 99% identical to the amino acid sequence of SEQ ID NO: 173.

28. The method of claim 27, wherein the VWF protein consists of the D' domain and the D3 domain.

29. The method of claim 12, wherein the disorder is hemophilia A.

30. The method of claim 12, wherein the disorder is Von Willebrand Disease.

31. The method of claim 30, wherein the Von Willebrand Disease is Von Willebrand Disease type 3.

32. The method of claim 29, wherein the VWF protein contains an alanine substitution at residue 1099 and residue 1142 of SEQ ID NO: 21.

33. The method of claim 32, wherein the first Fc region and the second Fc region are the same.

34. The method of claim 33, wherein the first Fc region and the second Fc region are derived from human IgG1.

35. The method of claim 34, wherein the VWF protein consists of the D' domain and the D3 domain.

36. The method of claim 33, wherein the cleavable linker comprises an a2 region of FVIII comprising an amino acid sequence at least 90% identical to SEQ ID NO: 106.

37. The method of claim 33, wherein the cleavable linker is 20 to 50 amino acids long.

38. The method of claim 37, wherein the cleavable linker is about 30 amino acids long.

39. The method of claim 13, wherein the disorder is hemophilia A.

40. The method of claim 13, wherein the disorder is Von Willebrand Disease.

41. The method of claim 40, wherein the Von Willebrand Disease is Von Willebrand Disease type 3.

42. The method of claim 39, wherein the first Ig constant region or a portion thereof comprises a first Fc region and the second Ig constant region or a portion thereof comprises a second Fc region.

43. The method of claim 39, wherein the first Ig constant region or a portion thereof is associated with the second Ig constant region or a portion thereof by a covalent bond.

44. The method of claim 39, wherein the FVIII protein comprises a deletion of residues 746-1648 corresponding to native mature human FVIII protein (SEQ ID NO: 65).

45. The method of claim 39, wherein the first Ig constant region or a portion thereof is associated with the second Ig constant region or a portion thereof by a disulfide bond.

46. The method of claim 39, wherein the first polypeptide chain comprises an amino acid sequence at least 99% identical to SEQ ID NO: 173.

47. The method of claim 39, wherein the first polypeptide chain comprises the amino acid sequence of SEQ ID NO: 173.

48. The method of claim 39, wherein the second XTEN sequence is fused to the linker such that the second polypeptide chain comprises the amino acid sequence of SEQ ID NO: 22.

49. The method of claim 39, wherein the second XTEN sequence is linked to the second Ig constant region or a portion thereof by a linker consisting of the amino acid sequence of SEQ ID NO: 88.

50. The method of claim 48, wherein the first XTEN sequence is inserted into the FVIII protein such that the first polypeptide chain comprises the amino acid sequence of SEQ ID NO: 2.

51. The method of claim 42, wherein the first Fc region and the second Fc region are identical.

52. The method of claim 42, wherein the first Fc region and the second Fc region are derived from human IgG1.

53. The method of claim 39, wherein the first Ig constant region or a portion thereof is associated with the second Ig constant region or a portion thereof by two disulfide bonds.

54. The method of claim 39, wherein the VWF protein consists of the D' domain and the D3 domain.

55. A method of treating a disorder that comprises a deficiency in Factor VIII comprising intravenously administering to a subject in need thereof a therapeutically effective amount of a chimeric protein comprising:

(i) a first polypeptide chain which comprises, from the N-terminus to the C-terminus thereof:

(a) a Factor VIII ("FVIII") protein comprising the amino acid sequence of residues 1 to 745 of SEQ ID NO: 65, fused to a first XTEN sequence inserted immediately downstream of residue 745 of SEQ ID NO: 65, fused to residues 1649 to 2332 of SEQ ID NO: 65, and (b) a first Fc region;

wherein the first XTEN sequence comprises the amino acid sequence of SEQ ID NO: 8; and (ii) a second polypeptide chain which comprises, from the N-terminus to the C-terminus thereof:

(a) a von Willebrand Factor ("VWF") protein comprising a D' domain and a D3 domain of VWF, wherein the VWF protein comprises the amino acid sequence of residues 764 to 1240of SEQ ID NO: 21 with alanine substitutions at residues 1099 and 1142 of SEQ ID NO: 21, (b) a second XTEN sequence comprising the amino acid sequence of SEQ ID NO: 58, wherein the second XTEN sequence contains less than 288 amino acid residues;

(c) a cleavable linker comprising an a2 region of FVIII which comprises the amino acid sequence of Glu720 to Arg740 corresponding to SEQ ID NO: 65, wherein the a2 region is capable of being cleaved by thrombin; and (d) a second Fc region;

wherein the first Fc region is associated with the second Fc region through a disulfide bond.

56. The method of claim 55, wherein the disorder is hemophilia A.

57. The method of claim 55, wherein the disorder is Von Willebrand Disease.

58. The method of claim 57, wherein the Von Willebrand Disease is Von Willebrand Disease type 3.

59. The method of claim 56, wherein the first Fc region and the second Fc region are the same.

60. The method of claim 59, wherein the first Fc region and the second Fc region are derived from human IgG1.

61. The method of claim 60, wherein the VWF protein consists of the D' domain and the D3 domain.

62. The method of claim 59, wherein the cleavable linker comprises an a2 region of FVIII comprising an amino acid sequence at least 90% identical to SEQ ID NO: 106.

63. The method of claim 59, wherein the cleavable linker is 20 to 50 amino acids long.

64. The method of claim 63, wherein the cleavable linker is about 30 amino acids long.

65. A method of treating hemophilia A comprising intravenously administering a therapeutically effective amount of a chimeric protein to a subject in need thereof, wherein the chimeric protein comprises:

(i) a first polypeptide chain which comprises, from the N-terminus to the C-terminus thereof:

(a) a Factor VIII ("FVIII") protein comprising the amino acid sequence of residues 1 to 745 of SEQ ID NO: 65, fused to a first XTEN sequence inserted immediately downstream of residue 745 of SEQ ID NO: 65, fused to residues 1649 to 2332 of SEQ ID NO: 65, and (b) a first Fc region;

wherein the first XTEN sequence comprises the amino acid sequence of SEQ ID NO: 8; and (ii) a second polypeptide chain which comprises, from the N-terminus to the C-terminus thereof:

(a) a von Willebrand Factor ("VWF") protein comprising a D' domain and a D3 domain of VWF, wherein the VWF protein comprises the amino acid sequence of residues 764 to 1240 of SEQ ID NO: 21 with alanine substitutions at residues 1099 and 1142 of SEQ ID NO: 21;

(b) a second XTEN sequence comprising the amino acid sequence of SEQ ID NO: 58;

(c) a cleavable linker comprising an a2 region of FVIII which comprises the amino acid sequence of Glu720 to Arg740 corresponding to SEQ ID NO: 65, wherein the a2 region is capable of being cleaved by thrombin; and (d) a second Fc region, wherein the first Fc region is associated with the second Fc region through a disulfide bond, and wherein the chimeric protein is administered prophylactically.

66. A method of treating hemophilia A comprising intravenously administering a therapeutically effective amount of a chimeric protein to a subject in need thereof, wherein the chimeric protein comprises:

(i) a first polypeptide chain which comprises from the N-terminus to the C-terminus thereof: a Factor VIII ("FVIII") protein and a first Fc region;

wherein the FVIII protein comprises residues 1 to 745 and 1649 to 2332 of SEQ ID NO: 65with a first XTEN sequence inserted immediately downstream of residue 745; and wherein the first XTEN sequence consists of at least about 288 amino acids and comprises an amino acid sequence of SEQ ID NO: 28, SEQ ID NO: 29, SEQ ID NO: 30, SEQ ID NO: 31 or any combination thereof, and (ii) a second polypeptide chain which comprises from the N-terminus to the C-terminus thereof:

a von Willebrand Factor ("VWF") protein comprising a D' domain and a D3 domain of VWF, a second XTEN sequence, a cleavable linker, and a second Fc region, wherein the D' domain and D3 domain comprises the amino acid sequence of residues 764 to 1240 of SEQ ID NO: 21 with alanine substitutions at the residues that correspond to positions 1099 and 1142 of SEQ ID NO: 21, wherein the second XTEN sequence consists of at least about 144 amino acids and less than 288 amino acids and comprises an amino acid sequence of SEQ ID NO: 28, SEQ ID NO: 29, SEQ ID NO: 30, SEQ ID NO: 31 or any combination thereof, wherein the cleavable linker comprises an a2 region of FVIII which comprises the amino acid sequence of SEQ ID NO: 194, wherein the a2 region is capable of being cleaved by thrombin, wherein the first Fc region is associated with the second Fc region through a disulfide bond.

67. The method of claim 66, wherein the cleavable linker is 30 to 35 amino acids long.

68. The method of claim 66, wherein the cleavable linker is about 30 amino acids long.

69. The method of claim 66, herein the first Fc region is associated with the second Fc region through two disulfide bonds.

70. The method of claim 69, wherein the first Fc region and the second Fc region are the same, and wherein the first Fc region and the second Fc region are derived from human IgG1.

71. The method of claim 70, wherein the VWF protein consists of the D' domain and the D3 domain.

72. The method of claim 66, wherein the chimeric protein is administered prophylactically.

73. The method of claim 65, wherein the cleavable linker comprises the amino acid sequence of SEQ ID NO: 88.

74. The method of claim 66, wherein the cleavable linker comprises the amino acid sequence of SEQ ID NO: 88.

75. The method of claim 1 , wherein the cleavable linker comprises the amino acid sequence of SEQ ID NO: 88.

76. The method of claim 12, wherein the cleavable linker comprises the amino acid sequence of SEQ ID NO: 88.

77. The method of claim 66, wherein the first XTEN sequence consists of about 288 amino acids.

78. The method of claim 77, wherein the first XTEN sequence comprises the amino acid sequence of SEQ ID NO: 8.

79. The method of claim 66, wherein the second XTEN consists of about 144 amino acids.

80. The method of claim 79, wherein the second XTEN comprises the amino acid sequence of SEQ ID NO: 58.

81. A method of administering a chimeric protein to a subject who has hemophilia A, comprising intravenously administering about 0.1 to 400,000 μg/kg of the chimeric protein to the subject, wherein the chimeric protein comprises:

(i) a first polypeptide chain which comprises, from the N-terminus to the C-terminus thereof:

(a) a Factor VIII ("FVIII") protein comprising a N-terminal portion and a C-terminal portion;

wherein the N-terminal portion of the FVIII protein comprises the A1domain, A2 domain, and a portion of the B domain of full length mature FVIII (SEQ ID NO: 65)

such that the N-terminal portion comprises the amino acid sequence of residues 1 to 745 of SEQ ID NO: 65;

wherein the N-terminal portion is fused to a first XTEN sequence inserted immediately downstream of amino acid 745 of SEQ ID NO: 65; and wherein the C-terminal portion comprises the A3 domain, the C1 domain, and the C2 domain, such that the C-terminal portion comprises residues 1690-2332 of SEQ ID NO: 65;

(b) a first immunoglobulin ("Ig") constant region or a portion thereof, wherein the first XTEN sequence comprises the amino acid sequence of SEQ ID NO: 8; and (ii) a second polypeptide chain which comprises, from the N-terminus to the C-terminus thereof:

(a) a von Willebrand Factor ("VWF") protein comprising a D' domain and a D3 domain of VWF, wherein the VWF protein contains a residue other than cysteine substituted for residues corresponding to residues 1099 and 1142 of SEQ ID NO: 21;

(b) a second XTEN sequence comprising the amino acid sequence of SEQ ID NO: 58, wherein the second XTEN sequence contains less than 288 amino acid residues;

(c) a cleavable linker comprising an a2 region of FVIII which comprises the amino acid sequence of Glu720 to Arg740 corresponding to SEQ ID NO: 65, wherein the a2 region is capable of being cleaved by thrombin; and (d) a second Ig constant region or a portion thereof, wherein the first polypeptide chain is associated with the second polypeptide chain through the first Ig constant region or a portion thereof and the second Ig constant region or a portion thereof.

82. The method of claim 81, wherein wherein the first Ig constant region or portion thereof is associated with the second Ig constant region or portion thereof through two disulfide bonds.

83. The method of claim 82, wherein wherein the first Ig constant region or portion thereof is a first Fc region and the second Ig constant region or portion thereof is a second Fc region.

84. The method of claim 83, wherein the cleavable linker is 20 to 50 amino acids long.

85. The method of claim 84, wherein the cleavable linker is about 30 amino acids long.

86. The method of claim 81, wherein the chimeric protein is administered prophylactically.

87. The method of claim 81, wherein the chimeric protein is administered for on-demand treatment.

88. The method of claim 81, wherein the chimeric protein is administered prior to, during, or after surgery.

89. The method of claim 81, wherein the chimeric protein is administered to control an acute bleeding episode.

90. A method of administering a chimeric protein to a subject who has hemophilia A, comprising intravenously administering about 0.1 to 400,000 μg/kg of the chimeric protein to the subject, wherein the chimeric protein comprises:

(i) a first polypeptide chain which comprises, from the N-terminus to the C-terminus thereof:

(a) a Factor VIII ("FVIII") protein comprising the amino acid sequence of residues 1 to 745 of SEQ ID NO: 65, fused to a first XTEN sequence inserted immediately downstream of residue 745 of SEQ ID NO: 65, fused to residues 1649 to 2332 of SEQ ID NO: 65, and (b) a first Fc region;

wherein the first XTEN sequence comprises the amino acid sequence of SEQ ID NO: 8; and (ii) a second polypeptide chain which comprises, from the N-terminus to the C-terminus thereof:

(a) a von Willebrand Factor ("VWF") protein comprising a D' domain and a D3 domain of VWF, wherein the VWF protein comprises the amino acid sequence of residues 764 to 1240 of SEQ ID NO: 21 with alanine substitutions at residues 1099 and 1142 of SEQ ID NO: 21, (b) a second XTEN sequence comprising the amino acid sequence of SEQ ID NO: 58, (c) a cleavable linker comprising the amino acid sequence of SEQ ID NO: 88, and (d) a second Fc region;

wherein the first Fc region is associated with the second Fc region through a disulfide bond.

91. A method of administering a chimeric protein to a subject who has hemophilia A, comprising intravenously administering about 0.1 to 400,000 μg/kg of the chimeric protein to the subject, wherein the chimeric protein comprises:

(i) a first polypeptide chain which comprises, from the N-terminus to the C-terminus thereof:

(a) a Factor VIII ("FVIII") protein comprising an amino acid sequence that is at least 99% identical to SEQ ID NO: 67 with a first XTEN sequence inserted immediately downstream of the residue corresponding to residue 745 of SEQ ID NO: 67; and (b) a first Fc region;

wherein the first XTEN sequence comprises the amino acid sequence of SEQ ID NO: 8; and (ii) a second polypeptide chain which comprises, from the N-terminus to the C-terminus thereof:

(a) a von Willebrand Factor ("VWF") protein comprising a D' domain and a D3 domain of VWF, wherein the VWF protein contains a residue other than cysteine substituted for residues 1099 and 1142 of SEQ ID NO: 21;

(b) a second XTEN sequence comprising the amino acid sequence of SEQ ID NO: 58, wherein the second XTEN sequence contains less than 288 amino acid residues;

(c) a cleavable linker comprising an a2 region of FVIII which comprises the amino acid sequence of Glu720 to Arg740 corresponding to SEQ ID NO: 65, wherein the a2 region is capable of being cleaved by thrombin; and (d) a second Fc region, wherein the first Fc region is associated with the second Fc region through a disulfide bond.

92. A method of administering a chimeric protein to a subject who has hemophilia A, comprising intravenously administering about 0.1 to 400,000 μg/kg of the chimeric protein to the subject, wherein the chimeric protein comprises:

(i) a first polypeptide chain which comprises a Factor VIII ("FVIII") protein fused to a first immunoglobulin ("Ig") constant region or a portion thereof,
 wherein the FVIII protein comprises the amino acid sequence of residues 1 to 745 of SEQ ID NO: 202, fused to a first XTEN sequence inserted immediately downstream of residue 745 of SEQ ID NO: 202, fused to residues 746 to 1429 of SEQ ID NO: 202; and wherein the first XTEN sequence comprises the amino acid sequence of SEQ ID NO: 8; and (ii) a second polypeptide chain which comprises a von Willebrand Factor ("VWF") protein comprising a D' domain and a D3 domain of VWF fused to a second Ig constant region or a portion thereof by a second XTEN sequence in-between,
 wherein the VWF protein comprises the amino acid sequence of SEQ ID NO: 201;
 wherein the second XTEN sequence comprises the amino acid sequence of SEQ ID NO: 58; and
 wherein the second XTEN sequence is linked to the second Ig constant region or a portion thereof by a linker comprising the amino acid sequence of SEQ ID NO: 88; wherein the first polypeptide chain is associated with the second polypeptide chain through the first Ig constant region or a portion thereof and the second Ig constant region or a portion thereof.

93. The method of claim 81, wherein the C-terminal portion of the FVIII protein comprises an amino acid sequence at least 95% identical to residues 1641 to 2332 of SEQ ID NO: 65.

94. The method of claim 93, wherein the VWF protein contains an alanine substitution at residue 1099 and residue 1142 of SEQ ID NO: 21.

95. The method of claim 94, wherein the first Fc region and the second Fc region are the same.

96. The method of claim 95, wherein the first Fc region and the second Fc region are derived from human IgG1.

97. The method of claim 96, wherein the VWF protein consists of the D' domain and the D3 domain.

98. The method of claim 81, wherein the first Fc region is associated with the second Fc region through two disulfide bonds.

99. The method of claim 81, wherein the second XTEN sequence is fused to the linker such that the second polypeptide chain comprises the amino acid sequence of SEQ ID NO: 22.

100. The method of claim 99, wherein the first XTEN sequence is inserted into the FVIII protein such that the first polypeptide chain comprises the amino acid sequence of SEQ ID NO: 2.

101. The method of claim 100, wherein the first polypeptide chain comprises an amino acid sequence at least 99% identical to the amino acid sequence of SEQ ID NO: 173.

102. The method of claim 101, wherein the VWF protein consists of the D' domain and the D3 domain.

103. The method of claim 101, wherein the VWF protein contains an alanine substitution at residue 1099 and residue 1142 of SEQ ID NO: 21.

104. The method of claim 103, wherein the first Fc region and the second Fc region are the same.

105. The method of claim 104, wherein the first Fc region and the second Fc region are derived from human IgG1.

106. The method of claim 105, wherein the VWF protein consists of the D' domain and the D3 domain.

107. The method of claim 104, wherein the cleavable linker comprises an a2 region of FVIII comprising an amino acid sequence at least 90% identical to SEQ ID NO: 106.

108. The method of claim 104, wherein the cleavable linker is 20 to 50 amino acids long.

109. The method of claim 108, wherein the cleavable linker is about 30 amino acids long.

110. The method of claim 92, wherein the first Ig constant region or a portion thereof comprises a first Fc region and the second Ig constant region or a portion thereof comprises a second Fc region.

111. The method of claim 92, wherein the first Ig constant region or a portion thereof is associated with the second Ig constant region or a portion thereof by a covalent bond.

112. The method of claim 92, wherein the FVIII protein comprises a deletion of residues 746-1648 corresponding to native mature human FVIII protein (SEQ ID NO: 65).

113. The method of claim 92, wherein the first Ig constant region or a portion thereof is associated with the second Ig constant region or a portion thereof by a disulfide bond.

114. The method of claim 92, wherein the first polypeptide chain comprises an amino acid sequence at least 99% identical to SEQ ID NO: 173.

115. The method of claim 92, wherein the first polypeptide chain comprises the amino acid sequence of SEQ ID NO: 173.

116. The method of claim 92, wherein the second XTEN sequence is fused to the linker such that the second polypeptide chain comprises the amino acid sequence of SEQ ID NO: 22.

117. The method of claim 92, wherein the second XTEN sequence is linked to the second Ig constant region or a portion thereof by a linker consisting of the amino acid sequence of SEQ ID NO: 88.

118. The method of claim 116, wherein the first XTEN sequence is inserted into the FVIII protein such that the first polypeptide chain comprises the amino acid sequence of SEQ ID NO: 2.

119. The method of claim 113, wherein the first Fc region and the second Fc region are the same.

120. The method of claim 113, wherein the first Fc region and the second Fc region are derived from human IgG1.

121. The method of claim 92, wherein the first Ig constant region or a portion thereof is associated with the second Ig constant region or a portion thereof by two disulfide bonds.

122. The method of claim 92, wherein the VWF protein consists of the D' domain and the D3 domain.

123. A method of administering a chimeric protein to a subject who has hemophilia A, comprising intravenously administering about 0.1 to 400,000 μg/kg of the chimeric protein to the subject, wherein the chimeric protein comprises:

(i) a first polypeptide chain which comprises, from the N-terminus to the C-terminus thereof:
 (a) a Factor VIII ("FVIII") protein comprising the amino acid sequence of residues 1 to 745 of SEQ ID NO: 65, fused to a first XTEN sequence inserted immediately downstream of residue 745 of SEQ ID NO: 65, fused to residues 1649 to 2332 of SEQ ID NO: 65, and
 (b) a first Fc region;
 wherein the first XTEN sequence comprises the amino acid sequence of SEQ ID NO: 8; and (ii) a second polypeptide chain which comprises, from the N-terminus to the C-terminus thereof:

(a) a von Willebrand Factor ("VWF") protein comprising a D' domain and a D3 domain of VWF, wherein the VWF protein comprises the amino acid sequence of residues 764 to 1240 of SEQ ID NO: 21 with alanine substitutions at residues 1099 and 1142 of SEQ ID NO: 21, (b) a second XTEN sequence comprising the amino acid sequence of SEQ ID NO: 58, wherein the second XTEN sequence contains less than 288 amino acid residues;

(c) a cleavable linker comprising an a2 region of FVIII which comprises the amino acid sequence of Glu720 to Arg740 corresponding to SEQ ID NO: 65, wherein the a2 region is capable of being cleaved by thrombin; and (d) a second Fc region;

wherein the first Fc region is associated with the second Fc region through a disulfide bond.

124. The method of claim 123, wherein the first Fc region and the second Fc region are the same.

125. The method of claim 124, wherein the first Fc region and the second Fc region are derived from human IgG1.

126. The method of claim 125, wherein the VWF protein consists of the D' domain and the D3 domain.

127. The method of claim 124, wherein the cleavable linker comprises an a2 region of FVIII comprising an amino acid sequence at least 90% identical to SEQ ID NO: 106.

128. The method of claim 124, wherein the cleavable linker is 20 to 50 amino acids long.

129. The method of claim 128, wherein the cleavable linker is about 30 amino acids long.

130. A method of administering a chimeric protein to a subject who has hemophilia A, comprising intravenously administering about 0.1 to 400,000 μg/kg of the chimeric protein to the subject, wherein the chimeric protein comprises:

(i) a first polypeptide chain which comprises, from the N-terminus to the C-terminus thereof:

(a) a Factor VIII ("FVIII") protein comprising the amino acid sequence of residues 1 to 745 of SEQ ID NO: 65, fused to a first XTEN sequence inserted immediately downstream of residue 745 of SEQ ID NO: 65, fused to residues 1649 to 2332 of SEQ ID NO: 65, and (b) a first Fc region;

wherein the first XTEN sequence comprises the amino acid sequence of SEQ ID NO: 8; and (ii) a second polypeptide chain which comprises, from the N-terminus to the C-terminus thereof:

(a) a von Willebrand Factor ("VWF") protein comprising a D' domain and a D3 domain of VWF, wherein the VWF protein comprises the amino acid sequence of residues 764 to 1240 of SEQ ID NO: 21 with alanine substitutions at residues 1099 and 1142 of SEQ ID NO: 21;

(b) a second XTEN sequence comprising the amino acid sequence of SEQ ID NO: 58;

(c) a cleavable linker comprising an a2 region of FVIII which comprises the amino acid sequence of Glu720 to Arg740 corresponding to SEQ ID NO: 65, wherein the a2 region is capable of being cleaved by thrombin; and (d) a second Fc region, wherein the first Fc region is associated with the second Fc region through a disulfide bond, and wherein the chimeric protein is administered prophylactically.

131. A method of administering a chimeric protein to a subject who has hemophilia A, comprising intravenously administering about 0.1 to 400,000 μg/kg of the chimeric protein to the subject, wherein the chimeric protein comprises:

(i) a first polypeptide chain which comprises from the N-terminus to the C-terminus thereof: a Factor VIII ("FVIII") protein and a first Fc region;

wherein the FVIII protein comprises residues 1 to 745 and 1649 to 2332 of SEQ ID NO: 65 with a first XTEN sequence inserted immediately downstream of residue 745; and wherein the first XTEN sequence consists of at least about 288 amino acids and comprises an amino acid sequence of SEQ ID NO: 28, SEQ ID NO: 29, SEQ ID NO: 30, SEQ ID NO: 31 or any combination thereof, and (ii) a second polypeptide chain which comprises from the N-terminus to the C-terminus thereof: a von Willebrand Factor ("VWF") protein comprising a D' domain and a D3 domain of VWF, a second XTEN sequence, a cleavable linker, and a second Fc region, wherein the D' domain and D3 domain comprises the amino acid sequence of residues 764 to 1240 of SEQ ID NO: 21 with alanine substitutions at the residues that correspond to positions 1099 and 1142 of SEQ ID NO: 21, wherein the second XTEN sequence consists of at least about 144 amino acids and less than 288 amino acids and comprises an amino acid sequence of SEQ ID NO: 28, SEQ ID NO: 29, SEQ ID NO: 30, SEQ ID NO: 31 or any combination thereof, wherein the cleavable linker comprises an a2 region of FVIII which comprises the amino acid sequence of SEQ ID NO: 194, wherein the a2 region is capable of being cleaved by thrombin, wherein the first Fc region is associated with the second Fc region through a disulfide bond.

132. The method of claim 131, wherein the cleavable linker is 30 to 35 amino acids long.

133. The method of claim 131, wherein the cleavable linker is about 30 amino acids long.

134. The method of claim 131, herein the first Fc region is associated with the second Fc region through two disulfide bonds.

135. The method of claim 134, wherein the first Fc region and the second Fc region are the same, and wherein the first Fc region and the second Fc region are derived from human IgG1.

136. The method of claim 135, wherein the VWF protein consists of the D' domain and the D3 domain.

137. The method of claim 131, wherein the chimeric protein is administered prophylactically.

138. The method of claim 130, wherein the cleavable linker comprises the amino acid sequence of SEQ ID NO: 88.

139. The method of claim 131, wherein the cleavable linker comprises the amino acid sequence of SEQ ID NO: 88.

140. The method of claim 81, wherein the cleavable linker comprises the amino acid sequence of SEQ ID NO: 88.

141. The method of claim 91, wherein the cleavable linker comprises the amino acid sequence of SEQ ID NO: 88.

142. The method of claim 131, wherein the first XTEN sequence consists of about 288 amino acids.

143. The method of claim 142, wherein the first XTEN sequence comprises the amino acid sequence of SEQ ID NO: 8.

144. The method of claim 131, wherein the second XTEN consists of about 144 amino acids.

145. The method of claim 144, wherein the second XTEN comprises the amino acid sequence of SEQ ID NO: 58.

146. The method of claim 81, comprising administering about 0.1 to 100,000 μg/kg of the chimeric protein to the subject.

147. The method of claim 81, comprising administering about 1,000 to 400,000 μg/kg of the chimeric protein to the subject.

148. The method of claim 90, comprising administering about 0.1 to 100,000 μg/kg of the chimeric protein to the subject.

149. The method of claim 90, comprising administering about 1,000 to 400,000 μg/kg of the chimeric protein to the subject.

150. The method of claim 91, comprising administering about 0.1 to 100,000 μg/kg of the chimeric protein to the subject.

151. The method of claim 91, comprising administering about 1,000 to 400,000 μg/kg of the chimeric protein to the subject.

152. The method of claim 92, comprising administering about 0.1 to 100,000 μg/kg of the chimeric protein to the subject.

153. The method of claim 92, comprising administering about 1,000 to 400,000 μg/kg of the chimeric protein to the subject.

154. The method of claim 123, comprising administering about 0.1 to 100,000 μg/kg of the chimeric protein to the subject.

155. The method of claim 123, comprising administering about 1,000 to 400,000 μg/kg of the chimeric protein to the subject.

156. The method of claim 130, comprising administering about 0.1 to 100,000 μg/kg of the chimeric protein to the subject.

157. The method of claim 130, comprising administering about 1,000 to 400,000 μg/kg of the chimeric protein to the subject.

158. The method of claim 131, comprising administering about 0.1 to 100,000 μg/kg of the chimeric protein to the subject.

159. The method of claim 131, comprising administering about 1,000 to 400,000 μg/kg of the chimeric protein to the subject.

160. The method of claim 1, wherein the VWF protein contains an alanine substitution at residue 1099 and residue 1142 of SEQ ID NO: 21.

161. The method of claim 81, wherein the VWF protein contains an alanine substitution at residue 1099 and residue 1142 of SEQ ID NO: 21.

* * * * *